United States Patent [19]

Daggett et al.

[11] Patent Number: 5,849,895
[45] Date of Patent: Dec. 15, 1998

[54] HUMAN N-METHYL-D-ASPARTATE RECEPTOR SUBUNITS, NUCLEIC ACIDS ENCODING SAME AND USES THEREFOR

[75] Inventors: Lorrie P. Daggett; Chin-Chun Lu, both of San Diego, Calif.

[73] Assignee: SIBIA Neurosciences, Inc., La Jolla, Calif.

[21] Appl. No.: 231,193

[22] Filed: Apr. 20, 1994

Related U.S. Application Data

[60] Division of Ser. No. 231,193, Apr. 20, 1994, and a continuation-in-part of Ser. No. 52,449, Apr. 20, 1993, abandoned.

[51] Int. Cl.⁶ .............................. C12N 15/12; C12N 5/10
[52] U.S. Cl. .................... 536/23.5; 435/69.1; 435/752.3; 435/320.1
[58] Field of Search ............................... 435/69.1, 252.3, 435/320.1; 530/350, 23.5

[56] References Cited

U.S. PATENT DOCUMENTS

| | | | |
|---|---|---|---|
| 4,837,148 | 6/1989 | Cregg | 435/172.3 |
| 4,855,231 | 8/1989 | Stroman et al. | 435/68 |
| 4,882,279 | 11/1989 | Cregg | 435/68 |
| 4,929,555 | 5/1990 | Cregg et al. | 435/172.3 |
| 5,024,939 | 6/1991 | Gorman | 435/69.1 |
| 5,202,257 | 4/1993 | Heinemann et al. | 435/252.3 |
| 5,401,629 | 3/1995 | Harpold et al. | 435/6 |
| 5,403,484 | 4/1995 | Ladner et al. | 435/235.1 |
| 5,436,128 | 7/1995 | Harpold et al. | 435/6 |

FOREIGN PATENT DOCUMENTS

| | | |
|---|---|---|
| 0 600 278 A2 | 6/1994 | European Pat. Off. . |
| 0600278 | 6/1994 | European Pat. Off. . |
| 0606734 | 7/1994 | European Pat. Off. . |
| 0674003 | 9/1995 | European Pat. Off. . |
| 6014783 | 1/1994 | Japan . |
| 9223769 | 11/1992 | United Kingdom . |
| 9307026 | 4/1993 | United Kingdom . |
| 2291647 | 1/1996 | United Kingdom . |
| 9106648 | 5/1991 | WIPO . |
| 9313423 | 7/1993 | WIPO . |
| 9323536 | 11/1993 | WIPO . |
| WO 93/23536 | 11/1993 | WIPO . |
| 9324629 | 12/1993 | WIPO . |
| 9325679 | 12/1993 | WIPO . |
| WO 93/25679 | 12/1993 | WIPO . |
| 9401094 | 1/1994 | WIPO . |
| 9404698 | 3/1994 | WIPO . |
| 9406428 | 3/1994 | WIPO . |
| 9411501 | 5/1994 | WIPO . |
| WO 94/11501 | 5/1994 | WIPO . |
| 9526401 | 10/1995 | WIPO . |

OTHER PUBLICATIONS

Abbott, NMDA receptor cloned, *Trends Pharmacol. Sci.* 12:449 (1991).

Abbott, NMDA receptor subunit cloned, *Trends Pharmacol. Sci.* 12:334 (1991).

Abe et al., Molecular characterization of a novel metabotropic glutamate receptor mGluR5 coupled to inositol phosphate/$Ca^{2+}$ signal transduction, *J. Biol. Chem.* 267:13361–13368 (1992).

Albin et al., Abnormalities of striatal projection neurons and N–methyl–D–aspartate receptors in presymptomatic Huntington's Disease, *N. Engl. J. Med.* 322(18):1293–1298 (1990).

Bahouth et al., Immunological approaches for probing receptor structure and function, *Trends Pharmacol. Sci.* 12:338–343 (1991).

Barnard, Will the real NMDA receptor please stand up? *Trends Pharmacol. Sci.* 13:11–12 (1992).

Beal, Mechanisms of excitotoxicity in neurologic diseases, *FASEB J.* 6:3338–3344 (1992).

Ben–Ari et al., Protein kinase C modulation of NMDA currents: an important link for LTP induction, *Trends Neurosci.* 15:333–339 (1992).

Black et al., N–methyl–D–aspartate–or glutamate–mediated toxicity in cultured rat cortical rat cortical neurons is antagonized by FPL 15896AR, *J. Neurochem.* 65:2170–2177 (1995).

Bottaro et al, Identification of the hepatocyte growth factor receptor as the c–met proto–oncogene product, *Science* 251:802–804 (1991).

Bradford, A rapid and sensitive method for the quantitation of microgram quantities of protein utilizing the principle of protein–dye binding, *Anal. Biochem.* 72:248 (1976).

(List continued on next page.)

*Primary Examiner*—John Ulm
*Attorney, Agent, or Firm*—Stephanie L. Seidman; Brown Martin Haller & McClain

[57] ABSTRACT

In accordance with the present invention, there are provided nucleic acids encoding human NMDA receptor protein subunits and the proteins encoded thereby. The NMDA receptor subunits of the invention comprise components of NMDA receptors that have cation-selective channels and bind glutamate and NMDA. In one aspect of the invention, the nucleic acids encode NMDAR1 and NMDAR2 subunits of human NMDA receptors. In a preferred embodiment, the invention nucleic acids encode NMDAR1, NMDAR2A, NMDAR2B, NMDAR2C and NMDAR2D subunits of human NMDA receptors. In addition to being useful for the production of NMDA receptor subunit proteins, these nucleic acids are also useful as probes, thus enabling those skilled in the art, without undue experimentation, to identify and isolate related human receptor subunits. Functional glutamate receptors can be assembled, in accordance with the present invention, from a plurality of one type of NMDA receptor subunit protein (homomeric) or from a mixture of two or more types of subunit proteins (heteromeric). In addition to disclosing novel NMDA receptor protein subunits, the present invention also comprises methods for using such receptor subunits to identify and characterize compounds which affect the function of such receptors, e.g., agonists, antagonists, and modulators of glutamate receptor function. The invention also comprises methods for determining whether unknown protein(s) are functional as NMDA receptor subunits.

25 Claims, 9 Drawing Sheets

OTHER PUBLICATIONS

Bristow et al., The glycine/NMDA receptor antagonist R–(+)–HA–966, blocks actvation of the mesolimbic dopaminergic system induced by phencyclidine and dizcilpine (MK–801) in rodents, *Br. J. Pharmacol.* 108:1156–1163 (1993).

Choi, Calcium–mediated neurotoxicity: Relationship to specific channel types and role in ischemic damage, *Trends Neurosci.* 11(10):465469 (1988).

Choi, Glutamate neurotoxicity and diseases of the nervous system, *Neuron* 1:623–634 (1988).

Ciba–Geigy, Unveils Research Agreement with SIBIA of U.S., *The Wall Street Journal* (Sep. 17, 1992).

Coyle et al., Oxidative stress, glutamate, and neurodegenerative disorders, *Science* 262:689–695 (1993).

Daggett et al., Cloning and functional characterization of three splice variants of the human NMDAR1 receptor, *Biophys J.*, 36(2):447 (1994).

Dascal, The use of Xenopus oocytes for the study of ion channels, *CRC Critical Reviews in Biochemistry* 22(4)317–387 (1987).

Donnelly and Pallotta, Single–channel currents from diethylpyrocarbonate–modified NMDA receptors in cultured rat brain cortical neurons, *J. Gen. Physiol.* 105:837–859 (1995).

Durand et al., Cloning of an apparent splice variant of the rat N–methyl–D–aspartate receptor NMDAR1 with altered sensitivity to polyamines and activators of protein kinase C, *Proc. Natl. Acad. Sci. USA* 89:9359–9363 (1992).

Egebjerg et al., Intron sequence directs RNA editing of the glutamate receptor subunit GluR2 coding sequence, *Proc. Natl. Acad. Sci. USA* 91:10270–10274 (1994).

Felder et al., A transfected m1 muscarinic acetylcholine receptor stimulates adenylate cyclase via phosphatidylinisitol hydrolysis, *J. Biol. Chem.* 264:20356–20362 (1989).

Fisher and Aronson, Characterization of the cDNA and genomic sequence of a G protein γ subunit ($γ_5$), *Mol. Cell. Biol.* 12:1585 (1992).

Foldes et al., Cloning and sequence analysis of cDNAs encoding human hippocampus N–methyl–D–aspartate receptor subunits: Evidence for alternative splicing, *Gene* 131:293–298 (1993).

Gautam et al., A G protein gamma subunit shares homology with ras proteins, *Science* 244:971 (1989).

Gautam et al., G protein diversity is increased by associations with a variety of γ subunits, *Proc. Natl. Acad. Sci. USA* 87:7973 (1990).

Gereau and Conn, Multiple presynaptic metabotropic glutamate receptors modulate excitory and inhibitory synaptic transmission in hippocampal area CA1, *J. Neurosci* 15(10):6879–6889 (1995).

Greenamyre et al., Synaptic localization of striatal NMDA, quisqualate and kainate receptors, *Neurosci. Lttrs.* 101:133–137 (1989).

Grimwood et al., Interactions between the glutamate and glycine recognition sites of the N–methyl–D–aspartate receptor from rat brain, as revealed from radioligand binding studies, *J. Neurochem.* 60(5):1729–1738 (1993).

Gubler et al., A simple and very efficient method for generating cDNA libraries, *Gene* 25:263–269 (1983).

Gunasekar et al., NMDA receptor activation produces concurrent generation of nitric oxide and reactive oxygen species: Implication for cell death, *J. Neurochem.* 65:2016–2021 (1995).

Gundersen et al., Glutamate and kainate receptors induced by rat brain messenger RNA in Xenopus oocytes, *Proc. R. Soc. London* Ser. 221:127 (1984).

Hess et al., Cloning, functional expression, and pharmacological characterization of human NMDAR1/NMDAR2 heteromeric receptors, *Biophys J.*, 36(2):446 (1994) (abstract and poster).

Hess et al., Biophysical properties of human NMDA receptors stably expressed in mammalian cells, *Soc. Neurosci. Abst.* 21:1–3 (1995).

Hoffman, NMDA receptor cloned—twice! *Science* 254:801–802 (1991).

Hollman et al., Zinc potentiates agonist–induced currents at certain splice variants of the NMDA receptor, *Neuron* 10:943–954 (1993).

Hollman et al., Cloned glutamate receptors, *Annu. Rev. Neurosci.* 17:31–108 (1994).

Hurley et al., Isolation and characterization of a cDNA clone for the δ subunit of bovine retinal transducin, *Proc. Natl. Acad. Sci. USA* 81:6948 (1984).

Ishii et al., Molecular characterization of the family of the N–methyl–D–aspartate receptor subunits, *J. Biol. Chem.* 268(4):2836–2843 (1993).

Ito et al., Chacterization of prostaglandin $E_2$–induced $Ca^{2+}$ mobilization in single bovine adrenal chromaffin cells by digital image microscopy, *J. Neurochem.* 56:531–540 (1991).

Jones et al., Chacterization of the binding of radioligands to the N–methyl–D–aspartate, phencyclidine, and glycine receptors in buffy coat membranes, *J. Pharmacol. Meth.* 21:61 (1989).

Kantak et al., Effects of N–methyl–D–aspartate antagonists in rats discriminating different doses of cocaine: Comparisons with direct and indirect dopamine agonists, *J. Pharmacol. Exper. Therap.* 274:657–665 (1995).

Karp et al., Molecular cloning and chromosomal localization of the key subunit of the human N–methyl–D–aspartate receptor, *J. Biol. Chem.* 268:3728–3733 (1993).

Kemp et al., Protein kinase recognition sequence motifs, *Trends Biochem. Sci.* 15:342–346 (1990).

Kishimoto et al. Studies on the phosphorylation of myelin basic protein by protein kinase C and adenosine 3':5'–monophosphate–dependent protein kinase, *J. Biol. Chem.* 260:12492–12499 (1985).

Kisselev et al., Receptor–G protein coupling is established by a conformational switch in the βγ complex, *Proc. Natl. Acad. Sci. USA* 92:9102–9106 (1995).

Kleuss et al., Selectivity in signal transduction determined by γ subunits of heterotrimeric G proteins, *Science* 259:832 (1993).

Köhr et al., NMDA receptor Channels: Subunit–specific potentiation by reducing agents, *Neuron* 12:1031–1040 (1994).

Kozak, Structural features in eukaryotic mRNAs that modulate the initiation of translation, *J. Biol. Chem.* 266:19867–19870 (1991).

Krieg and Melton, Functional messenger RNAs are produced by SP6 in vitro transcription of cloned cDNAs, *Nucleic Acids Research* 12:7057–7070 (1984).

Kumar et al., Cloning of cDNA of the glutamate–binding subunit of an NMDA receptor complex, *Nature* 354:70–73 (1991).

Kutsuwada et al., Molecular diversity of the NMDA receptor channel, *Nature* 358:36–41 (1992).

Kyte and Doolittle, A simple method for displaying the hydropathic chacter of a protein, *J. Mol. Biol.* 157:105 (1982).

Landwehrmeyer et al., NMDA receptor subunit mRNA expression by projection neurons and interneurons in rat striatum, *J. Neurosci.* 15(7): 5297–5307 (1995).

Le Bourdellès et al., Cloning, functional coexpression, and pharmacological characterisation of human cDNAs encoding NMDA receptor NR1 and NR2A subunits, *J. Neurochem.* 62:2091–2098 (1994).

Linder and Gilman, G proteins, *Scientific American* 267:56–65 (1992).

Liu et al., Mutational analysis of the relative orientation of transmembrane helices I and VII in G protein–coupled receptors, *J. Biol. Chem.* 270(3):19532–19539 (1995).

Lynch et al., Pharmacological chacterization of heterodimeric NMDA receptors of NR1a and 2B subunits: Differences with receptors formed from NR 1a and 2A, *J. Neurochem.* 64:1462–1468 (1995).

Masu et al., Sequence and expression of a metabotropic glutamate receptor, *Nature* 349:760–765 (1991).

Mayer, NMDA receptors cloned at last, *Nature* 354:16–17 (1991).

Meguro et al., Functional characterization of a heteromeric NMDA receptor channel expressed from cloned cDNAs, *Nature* 357:70–74 (1992).

Meldrum, Possible therapeutic applications of antagonists of excitatory amino acid neurotransmitters, *Clin. Sci.* 68:113–122 (1985).

Meldrum et al., Excitatory amino acid neurotoxicity and neurodegenerative disease, *Trends Pharmacol. Sci.* 11:379–387 (1990).

Minakami et al., The expression of two splice variants of metabotropic glutamate receptor subtype 5 in the rat brain and neuronal cells during development, *J. Neurochem.* 65:1536–1542 (1995).

Monaghan et al., The excitory amino acid receptors: Their classes, pharmacology, and distinct properties in the function of the central nervous system, *Ann. Rev. Pharmacol. Toxicol.* 29:365–402 (1980).

Monyer et al., Heteromeric NMDA receptors: Molecular and functional distinction of subtypes, *Science* 256:1217–1221 (1992).

Monyer et al., Developmental and regional expression in the rat brain and functional properties of four NMDA receptors, *Neuron* 12:529–540 (1994).

Moriyoshi et al., Molecular cloning and characterization of the rat NMDA receptor, *Nature* 354:31–37 (1991).

Nakajima et al., Direct linkage of three tachykinin receptors to stimulation of both phosphatidylinositol hydrolysis and cyclic AMP cascades in transfected Chinese hamster ovary cells, *J. Biol. Chem.* 267:2437–2442 (1992).

Nakanishi, Molecular diversity of glutamate receptors and implications for brain function, *Science* 258:597–602 (1992).

Nicoletti et al., The activation of inositol phospholipid metabolism as a signal–transducing system for excitory amino acids in primary cultures of cerebellar granule cells, *J. Neurosci.* 6:1905 (1986).

SIBIA/Ciba–Geigy agreement, *UCSD Connect* (Sep. 16, 1992).

Ogita et al., A possible role of glutathione as an endogenous agonist at the N–methyl–D–aspartate recognition domain in rat brain, *J. Neurochem.* 64:1088–1096 (1995).

Other News to Note, *BioWorld Today*, 6 (Apr. 15, 1994).

O'Connor et al., Tetanically induced LTP involves a similar increase in the AMPA and NMDA receptor components of the excitory postsynaptic current: Investigations of the involvement of mGlu receptors, *J. Neurosci.* 15(3):2013–2020 (1995).

Paoletti and Ascher, Mechanosensitivity of NMDA receptors in cultured mouse central neurons, *Neuron* 13:645–655 (1995).

Pin et al., Alternative splicing generates metabotropic glutamate receptors inducing different patterns of calcium release in Xenopus oocytes, *Neurobiology* 89:10331–10335 (1992).

Planells–Cases et al., Molecular cloning, functional expression, and pharmacological characterization of a N–methyl––D–aspartate receptor subunit from human brain, *Proc. Natl. Acad. Sci. USA* 90:5057–5071 (1993).

Potter, Sibia to collaborate with Ciba–Geigy, *BioWorld Today* 3:1 (Sep. 17, 1992).

Rueter et al., Glutamate receptor RNA editing in vitro by enzymatic conversion of adenosine to inosine, *Science* 267:1491–1494 (1995).

Sakurada et al., Alteration of $Ca^{2+}$ permeability and sensitivity of $Mg^{2+}$ and channel blockers by a single amino acid substitution in the N–methyl–D–aspartate, *J. Biol. Chem.* 268(1):410–415 (1993).

Sambrook et al., *Molecular Cloning. A Laboratory Manual*, 2d Ed., Cold Spring Harbor Laboratory Press (1989).

Sanes et al., Use of a recombinant retrovirus to study post–implantation cell lineage in mouse embryos, *EMBO J.* 5(12):3133–3142 (1986).

Sanner et al., NMDA receptor blockade rescues Clarke's and red nucleus neurons after spinal hemisection, *J. Neurosci.* 14(11):6472–6480 (1995).

Schoepp et al., 1S,3R–ACPD–sensitive (metabotropic [$^3$H] glutamate receptor binding in membranes, *Neurosci. Lett.* 145:100 (1992).

Sills et al., [$^3$H]CGP 39653: a new N–methyl–D–aspartate antagonist radioligand with low nanomolar affinity in rat brain, *Eur. J. Pharmacol.* 192:19 (1991).

Simon et al., Diversity of G proteins in signal transduction, *Science* 252:802 (1991).

Singaram et al., Dopaminergic defect of enteric nervous system in Parkinson's disease patients with chronic constipation, *Lancet* 346:861–864 (1995).

Sladeczek et al., Glutamate stimulates inositol phosphate formation in striatial neurones, *Nature* 317:717 (1985).

Smirnova et al., Cloning a complementary DNA fragment of human brain kainate receptor, *Dokl. Akad. Nauk SSSR* 309(3):745–748 (1989).

Smirnova et al., Characterization of a presynaptic glutamate receptor, *Science* 262:430–433 (1993).

Smirnova et al., Transsynaptic expression of a presynaptic glutamate receptor during hippocampal long–term potentiation, *Science* 262:433–436 (1993).

Sommer et al., Glutamate receptor channels: novel properties and new clones, *Trends Pharmacol. Sci* 13:291 296 (1992).

Steiner et al., Radioimmunoassay for cyclic nucleotides, *J. Biol. Chem.* 247:1106–1113 (1972).

Stillman et al., Replication and supercoiling of simian virus 40DNA in cell extracts from human cells, *Mol. Cell. Biol.* 5:2051–2060 (1985).

Stühmer, Electrophysiological recording from Xenopus oocytes, *Meth. Enzymol.* 207:319–339 (1992).

Sugihara et al., Structures and properties of seven isoforms of the NMDA receptor generated by alternative splicing, *Biochem. Biophys. Res. Commun.* 185(3):826–832 (1992).

Sugiyama et al., A new type of glutamate receptor linked to inositol phospholipid metabolism, *Nature* 325:531 (1987).

Sullivan et al., Identification of two cysteine residues that are required for redox modulation of the NMDA subtype of glutamate receptor, *Neuron* 13:929–936 (1994).

Takano et al., Chromosomal localization of the $\epsilon1$, $\epsilon3$ and $\zeta1$ subunit genes of the human NMDA receptor channel, *Biochem. Biophys. Res. Commun.* 197(2):922–926 (1993).

Tamir et al., G–protein $\beta\gamma$ forms: Identitiy of $\beta$ and diversity of $\gamma$ subunits, *Biochemistry* 30:3929 (1991).

Tanabe et al., A family of metabotropic glutamate receptors, *Neuron* 8:169–179 (1992).

Tingley et al., Regulation of NMDA receptor phosphorylation by alternative splicing of the C–terminal domain, *Nature* 364:70–73 (1993).

Ulas et al., Selective increase of NMDA–sensitive glutamate binding in the striatum of Parkinson's disease, Alzheimer's disaease, and mixed Parkinson's disease/ Alzheimer's disease patients: An autoradiographic study, *J. Neurosci.* 14(11):6317–6324 (1994).

Urlaub et al., Effect of gamma rays at the dihydrofolate reductase locus: Deletions and Inversions, *Somatic Cell and Mol. Genetics* 12(6):555–566 (1986.

Varney et al., Stable expression and characterization of recombinant human dimeric NMDA receptor subtypes 1A/2A and 1A/2B in mammalian cells, *Soc. Neurosci. Abstr.* (1995).

Vornov et al., Enhancement of NMDA receptor–mediated neurotoxicity in the hippocampal slice by depolarization and ischemia, *Brain Res.* 555:99–106 (1991).

Waechter and Baserga, Effect of methylation on expression of microinjected genes, *Proc. Natl. Acad. Sci. USA* 79:1106–1110 (1982).

Wafford et al., Preferential co–assembly of recombinant NMDA receptors composed of three different subunits, *NeuroReport* 4(12):1347–1349 (1993).

Wahlestedt et al., Antisense oligodeoxynucleotides to NMDA–R1 receptor channel protect cortical neurons from excitotoxicity and reduce focal ischaemic infarctions, *Nature* 363:260–263 (1993).

Wenzel et al., Distribution of NMDA receptor subunit proteins NR2A, 2B, 2C, and 2D in rat brain, *NeuroReport* 7:45–48 (1995).

Wigler et al., DNA–mediated transfer of the adenine phosphoribosyltransferase locus into mammalian cells, *Proc. Natl. Acad. Sci. USA* 76:1373–1376 (1979).

Wong et al., The anticonvulsant MK–801 is a potent N–methyl–D–aspartate antagonist, *Proc. Natl. Acad. Sci. USA* 83:7104 (1986).

Yakel et al., Identification of a $Ca^{2+}$/calmodulin protein kinase II regulatory phosphorylation site in N–methyl–D–aspartate glutamate receptors, *Proc. Natl. Acad. Sci. USA* 92:1376–1380 (1995).

Young et al., NMDA receptor losses in putamen from patients with Huntington's Disease, *Science* 241:981–983 (1988).

Younkin et al., Inducible expression of neuronal glutamate receptor channels in the NT2 human cell line, *Proc. Natl. Acad. Sci. USA* 90:2174–2178 (1993).

Zeevalk et al., Chemically induced hypoglycemia and anoxia: Relationship to glutamate receptor–mediated toxicity in retina, *J. Pharmacol. Exp. Thera.* 253(3):1285–1292 (1990).

Zeevalk et al., Mechanisms underlying initiation of excitotoxicity associated with metabolic inhibition, *J. Pharmacol. Exp. Thera.* 257(2):870–878 (1991).

Zhang et al., Spermine potentiation of recombinant N–methyl–D–aspartate receptors is affected by subunit composition, *Proc. Natl. Acad. Sci. USA* 91:10883–10887 (1994).

Zipser et al., Mapping function domains in the promoter region of the herpes thymidine kinase gene, *Proc. Natl. Acad. Sci. USA* 78(10):6276–6280 (1981).

Stumpo, D. et al., Identification of c–fos sequences involved in induction by insulin and phorbol esters, *J. Biol. Chem.* 263(4):1611 (1988).

Yamazaki, M. et al., Cloning expression and modulation of a mouse NMDA receptor subunit *FEBS Letters* 300(1):39 (1992).

Daggett et al., "Cloning and Functional Characterization of Three Splice Variants of the Human NDMAR1 Receptor" *Biophysical Journal*, 66(2):Part 2 of 2 (1994).

Grenningloh et al., "Alpha subunit variants of the human glycine receptor: primary structures, functional expression and chromosomal localization of the corresponding genes" *EMBO J.* 9(3):771–776 (1990).

Hess et al., "Cloning, Functional Expression, and Pharmacological Characterization of Human NMDAR1/NMDAR2 Heteromeric Receptors" *Biophysical Journal*, 66(2):Part 2 of 2 (1994).

Meldrum and Garthwaite, "Excitatory amino acid neurotoxicity and neurodegenerative disease", *TIPS* 11:379–387 (1990).

Puckett et al., "Molecular cloning and chromosomal localization of one of the human glutamate receptor genes" *Proc. Natl. Acad. Sci. USA* 88:7557–7561 (1991).

Schofield et al., "Sequence and expression of human $GABA_A$ receptor $\alpha1$ and $\beta1$ subunits" *FEBS Letters* 244(2):361–364 (1989).

Smirnova et al., "Isolation and study of cDNA coding for the synthesis of glutamate receptors of human brain" *Dol. Akad. Nauk SSSR* 303(3):756–759 (1988).

Karp et al, *J. Biol. Chem.* 268(5):3728–3733, 15 Feb. 1993.

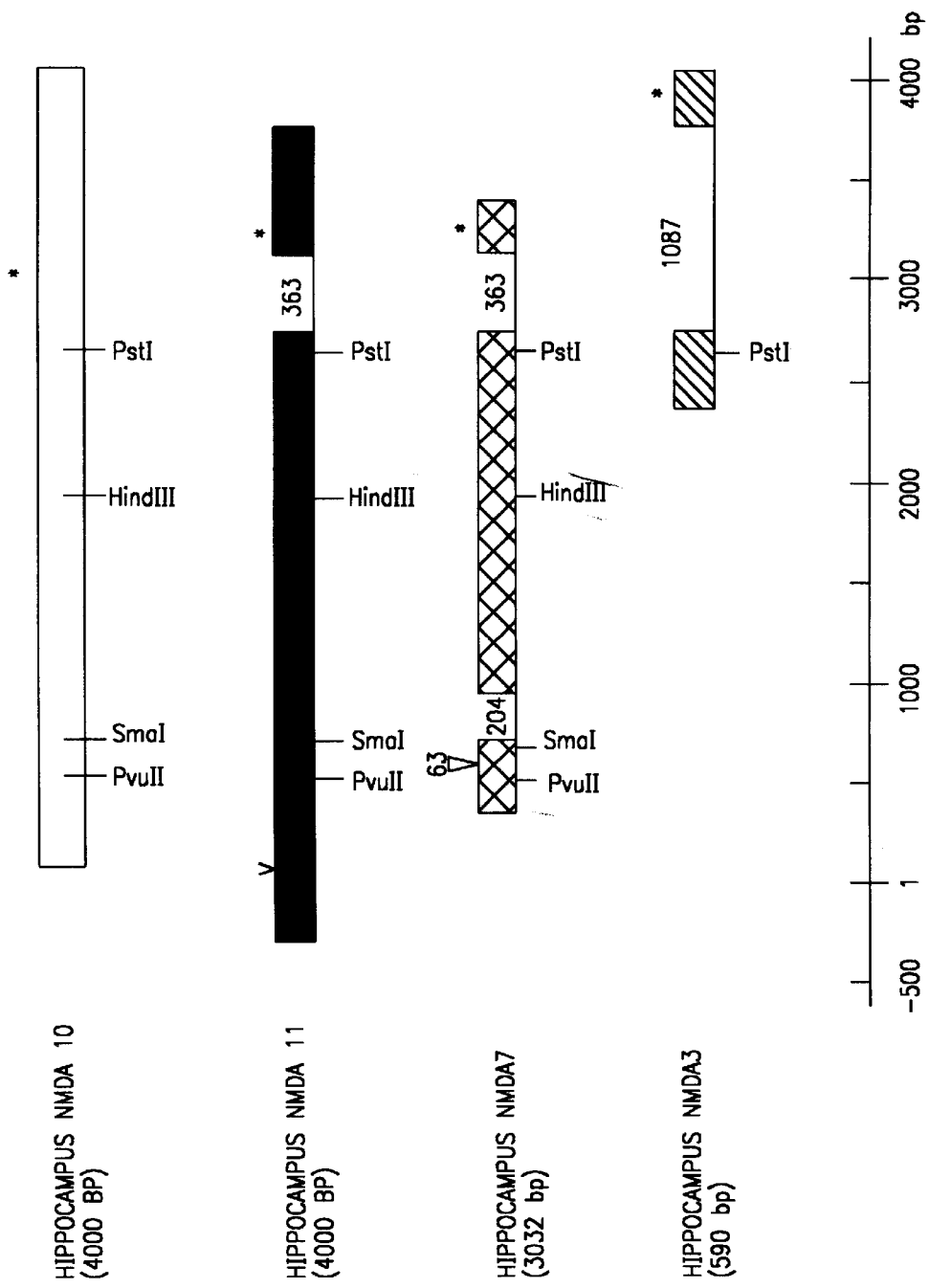

```
    1  CAAGCCGGGC GTTCGGAGCT GTGCCCGGCC CCGCTTCAGC ACCGCGGACA GCGCCCGGCC CGTGGGGCTG AGCGCCGAGC CCCCGCGCAC GCTTCAGCCC
  101  CCCTTCCCTC GGCCGACGTC CCGGGACCGC CGCTCCGGGG GAGACGTGGC GTCCGCAGCC GGCGAGGCCA GGACGGCCCG GAAGCCCCGC
                                                                                                           -START
  201  GGGGGATGCG CCGAGGGCCC CCGGTTCGCG CCGGCGCGAC CCGGCAGAG  CCAGGCCCGC GGCCCGAGCC CATGAGCACC ATGGCCTGC  CCTGCTGTTC
  301  TCCTGCTCCG TCGCCCGTGC CGCGTGCGAC CCCAAGATCG TCAACATTGG CGCGGTGCTG AGCACGCGGA AGCACGAGCA GATGTTCCGC GAGGCCGTGA
  401  ACCAGGCCAA CAAGCGGCAC GGCTCCTGGA AGATTCAGCT CAATGCCACC CCACTTCACT CCACTTCACT CGCCATCCAG ACAAGCCCAA ATGGCTCTGT CGGTGTGCGA
  501  GGAACTTCATC TCCAGCCAGG TCTACGCCAT CCTAGTTAGC CCCCCAACGA CCCACCCCTG TCTCCTACAC AGCCGGCTTC
  601  TACCGCATAC CCGTGCTGGG GCTGACCACC CGCATGTCCA TCTACTCGGA CAAGAGCATC CACCTGAGCT TCCTGCCGCC TACTCCCACC
  701  AGTCCAGCGT GTGGTTTGAG ATGATGCGTG TCTACAGCTG GAACCACATC ATCCTGCTGG TCAGCGACGA CCACGAGGGC CGGGCGGGTC AGAAACGCCT
                                                     Pvu II
                                                     63 bp INSERT
  801  GGAGACGCTG CTGGAGGAGC GTGAGTCCAA GGCAGAGAAG GTGCTGCAGT TTGACCCAGG GACCAAGAAC GTGACGGCCC TGCTGATGGA GGGGAAAGAG
  901  CTGGAGGCCC GGGTCATCAT CCTTTCTGCC AGCGGAGGAC ATGCTGCCAC TGTATACCGC GCAGCCGCGA TGCTGAACAT GACGGCTCC GGGTACGTGT
               Sma I                                                                                                                    204 bp
                                                                                                                                       DELETION
 1001  CTGGAGGCCC CGAGCGGAG ATCTGGGGAC ACGCCCTGCG CTAGGCCCCA GACGGCATCC TCGGGCTGCA GCTCATCAAC GGCAAGAACG AGTCGGCCCA
            Bgl II
 1101  CATCAGCGAC GCCGTGGGCG TGGTGGCCCA GGCCGTGCAC CATCACCGAC AGAAGGAGAA CATCACCGAC CCGCCGCGGG GCTGCTGGG CAACACCAAC
 1201  ATCTGGAAGA CCGGGCCGCT CTTCAAGAGA GTGCTGATGT CTTCCAAGTA TGCGGATGGG GTGACTGGTC GCGTGGAGTT CAATGAGGAT GGGGACCGGA
 1301  AGTTCGCCAA CTACAGCATC ATGAACCTGC AGAACCGCAA GCTGGTGCAA GTGGGCATCT ACAATGGCAC CCACGTCATC CCTAATGACA GGAAGATCAT
 1401  CTGGCCAGGC GGAGAGACAG AGAAGCCTCG AGGGTACCAG ATGTCCACCA GACTGAAGAT TGTGACGATC CACCAGGAGC CCTTCGTGTA CGTCAAGCCC
                                              Kpn I
 1501  ACGGCTGAGTG ATGGGACATG CAAGGAGGAG TTCACAGTCA ACGGCGACCC AGTCAAGAAG GTGATCTGCA CCGGGCCCAA CGACACGTCG CCGGGCAGCC
 1601  CCGCCACAC GGTGCCTCAG TGTTGCTACG GCTTTTGCAT CGACCTGCTC ATCAGCCTCC CACGGACCAT GAACTTCACC TACGAGGTGC ACCTGGTGGC
```

| | | | | | | | |
|---|---|---|---|---|---|---|---|
| 1701 | AGATGGCAAG | TTCGGCACAC | AGGAGCGGGT | GAACAACAGC | AACAAGAAGG | AGTGGAATGG | GATGATGGGC | GAGCTGCTCA | GCGGGCAGGC | AGACATGATC |
| 1801 | GTGGCGCCGC | TAACCATAAA | CAACGAGCGC | GCGCAGTACA | TCGAGTTTTC | CAAGCCCTTC | AAGTACCAGG | GCCTGACTAT | TCTGGTCAAG | AAGGAGATTC |
| 1901 | CCCGGAGCAC | GCTGGACTCG | TTCATGCAGC | CGTTCCAGAG | CACACTGGTG | CTGCTGGTGG | GGCTGTCGGT | GCACGTGGTG | GCCGTGATGC | TGTACCTGCT |
| 2001 | GGACCGCTTC | AGCCCCTTCG | GCCGGTTCAA | GGTGAACAGC | AGGAGGACGC | ACTGACCCTG | TCCTCGGCCA | TGGTGTGGG | CCGGCTTTGC | CATGATCATC | GTGGCCTCCT |
| 2101 | CTGCTCAACT | CCGGCATCGG | GGAAGGCGCC | CCCAGAAGCT | TCTCAGCGCG | GGAGGAGCGC | TCGGCTGAGG | AACCCCTCGG | ACAAGTTTAT |
| 2201 | ACACCGCCAA | CCTGGGTGC | TTCCTGGTGC | GCTCGTGGA | TATCTACTTC | CGGCGCCAGG | TGGAGCTGAG | CACCATGTAC | CGGCATATGG | AGAAGCACAA | CTACGAGAGT |
| 2301 | CTACGCCACG | GTGAAGCAGA | GCTCCATCAG | AACAAGCTGC | CGTGAGAGAC | CTGGGACTCG | GCGGTGCTGG | AGTTCGAGGC | CTCGCAGAAG | TGCGACCTGG |
| 2401 | GCGGCGGAGG | CCATCCAGGC | CGTGAGAGAC | ATGCCTTCAT | AGGCATGCGC | AGGACACAGCC | CCTGGAAGCA | GAACGTCTCC | CTGTCCATCC | TCAAGTCCA |
| 2501 | TGACGACTGG | AGAGCTGTTT | TTCCGCTCGG | GCTTCGGACA | GACGTGGGTT | CGGTATCAGG | AATGTGACTC | GCGCAGCAAC | GCCCCTGCGA | CCCTTACTTT | TGAGAACATG |
| 2601 | CGAGAATGGC | TTCATGGAAG | ACCTGGACAA | GACGTGGGTT | CGGTATCAGG | AATGTGACTC | GCGCAGCAAC | GCCCCTGCGA | CCCTTACTTT | TGAGAACATG |
| 2701 | GCCGGGGTCT | TCATGCTGGT | AGTCTGGGGC | ATCGTGGCCG | GGATCTTCCT | GATTTTCATC | ACAAGCGGCA | CAAGGGATGCT | CGCCGGAAGC |
| 2801 | AGATGCAGCT | GGCCTTTGCC | GCCGTTAACG | TGTGGCGGAA | GAACCTGACG | GATAGAAAGA | GTGGTAGAGC | AGAGCCTGAC | AAGCCACATT |
| 2901 | TAGGCTATC | ACCTCCACCC | TGGCTTCCAG | AGGGAGGAGG | CCAGCTGCA | GCTGTGTTCC | CGTCATAGGG | AGAGCTGAGG GGTGGACGCG | GTGCTTTGCA | AAACCAAAAA |
| 3001 | GACACAGTGC | TGCCGCGACG | CGCTATTGAG | AGGGAGGAGG | CCAGCTGCA | GCGGCCCGGC | CCACGAGCA | CCCCGGGGTC | CTCCCCGCCC | GCCCTCCTCT |
| 3101 | GCCCCCTCCC | CCGCAGACAG | ACAGACAGAC | GGACGGGACA | GCGGCCCGGC | GCCCCCCGCGC | CCACCCCGC | CCACGAGCA | CCCCGGGGTC | GGGGAGGAG | CACCCCCAGC |
| 3201 | CTCCCCAGG | CTGCCTGC | CCGCCCGCCG | GTTGCCGGTCC | TGGCCGGTCC | ACCCCGTCC | GGCCCCGCGC | GTGCCCCAG | CGTGGGCTA | ACGGGCGCCT |
| 3301 | TGTCTGTGTA | TTTCTATTTT | GCAGCAGTAC | CATCCCACTG | ATATCACGGG | CCCGCTCAAC | CCCGGCTCAG | CCTCGGTCAG | CACCGTGGTG | TGAGGCCCCC |

363 bp DELETION

```
3401    GGAGGGCGCCC ACCTGCCCAG TTAGCCCGGC CAAGGACACT GATGGGTCCT GCTGCTCGGG AAGGCCTGAG GGAAGCCCAC CCGCCCCAGA GACTGCCCAC
3501    CCTGGGCCTC CCGTCCGTCC GCCCGCCCAC CCCGCTGCCT GGCGGGCAGC CCCTGCTGGA CCAAGGTGCG GACCGGAGCG GCTGAGGACG GGGCAGAGCT
3601    GAGTCGGCTG GGCAGGGCCG CAGGGGCTC CGGGGGCGTC CGGCAGAGGC AGGCCCCTGG GGTCTCTGAG CAGTGGGGAG CGGGGGCTAA CTGCCCCCAG GCGGAGGGGC
3701    TTGGAGCAGA GACGGCAGCC CCATCCTTCC CGCAGCACCA GCCTGAGCCA CAGTGGGGCC CATGGCCCCA GCTGGCTGGG TCGCCCCTCC TCGGGCGCCT
3801    GCGCTCCTCT GCAGCCTGAG CTCCACCCTC CTGACTTCTT GCGGCACCGC CCCTGTCTGC CCCTTGACGC CACACGCCGG GGCTGGCGCT
3901    GCCCTCCCCC ACGGCCGTCC AGCTGGCAGC GCCTCCCGCC GCCTCCTCCA GAATCGAGAG GGCTGAGCCC CTCCTCTCCT
4001    CGTCCGGCCT GCAGCACAGA AGGGGCCTC CCCGGGGGTC GGCTCGGGAC TGTCTTCAAC CCTGCCCTGC ACCTTGGGCA CGGGAGAGCG
4101    CCACCCGCCC GCCCCCGCCC TCGCTCCGGG TGCGTGACCG GCCCGCCACC TTGTACAGAA CCAGCACTCC CAGGGCCCGA GCGCGTGCCT TCCCCGTGCG
4201    CAGCCGGCGCT CTGCCCCTCC GTCCCCAGGG TGCAGGCGCG CACCGCCCAA CCCCCACCTC CGGGTGTATG CAGTGGTGAT GCCTAAAGGA ATGTCACG
```

—1087 bp DELETION

FIG. 3C

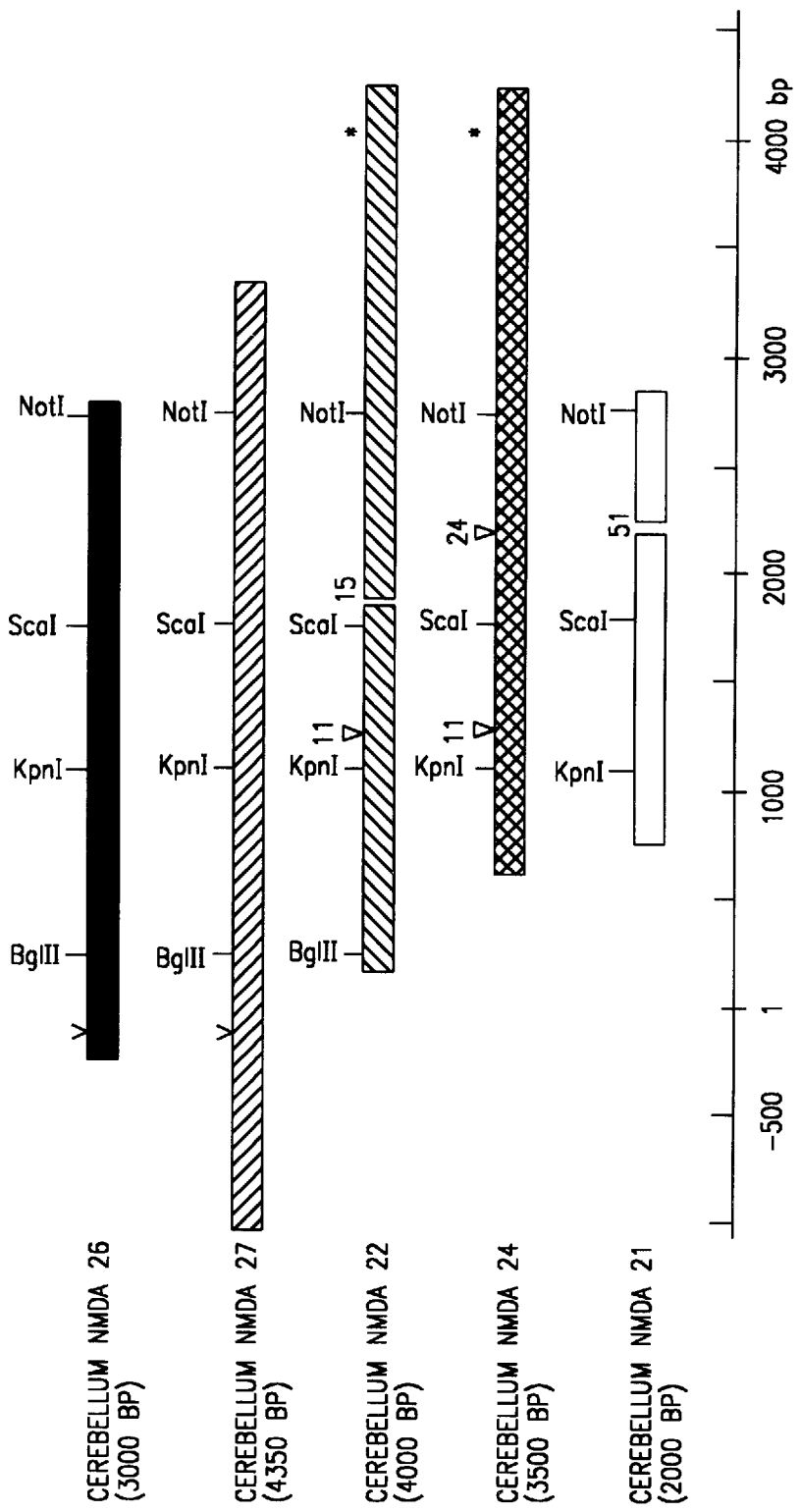

SEQUENCE LISTING ( 1 ) GENERAL INFORMATION:

( i i i ) NUMBER OF SEQUENCES: 63

( 2 ) INFORMATION FOR SEQ ID NO:1:

( i ) SEQUENCE CHARACTERISTICS:
        ( A ) LENGTH: 4298 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..3078

( x i ) SEQUENCE DESCRIPTION: SEQ ID NO:1:

```
CAAGCCGGGC GTTCGGAGCT GTGCCCGGCC CCGCTTCAGC ACCGCGGACA GCGCCGGCCG        60

CGTGGGGCTG AGCGCCGAGC CCCCGCGCAC GCTTCAGCCC CCCTTCCCTC GGCCGACGTC       120

CCGGGACCGC CGCTCCGGGG GAGACGTGGC GTCCGCAGCC CGCGGGGCCG GGCGAGCGCA       180

GGACGGCCCG GAAGCCCCGC GGGGGATGCG CCGAGGGCCC CGCGTTCGCG CCGCGCAGAG       240

CCAGGCCCGC GGCCCGAGCC C ATG AGC ACC ATG CGC CTG CTG ACG CTC GCC        291
                         Met Ser Thr Met Arg Leu Leu Thr Leu Ala
                          1               5                    10

CTG CTG TTC TCC TGC TCC GTC GCC CGT GCC GCG TGC GAC CCC AAG ATC        339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC        387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT        435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG        483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC        531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT        579
Leu Val Ser His Pro Pro Thr Pro Asn Asp His Phe Thr Pro Thr Pro
                95                  100                 105

GTC TCC TAC ACA GCC GGC TTC TAC CGC ATA CCC GTG CTG GGG CTG ACC        627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG        675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG        723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC        771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG        819
```

-continued

```
His Glu Gly Arg Ala Ala Gln Lys Arg Leu Glu Thr Leu Leu Glu Glu
            175                 180                 185

CGT GAG TCC AAG GCA GAG AAG GTG CTG CAG TTT GAC CCA GGG ACC AAG         867
Arg Glu Ser Lys Ala Glu Lys Val Leu Gln Phe Asp Pro Gly Thr Lys
            190                 195                 200

AAC GTG ACG GCC CTG CTG ATG GAG GCG AAA GAG CTG GAG GCC CGG GTC         915
Asn Val Thr Ala Leu Leu Met Glu Ala Lys Glu Leu Glu Ala Arg Val
            205                 210                 215

ATC ATC CTT TCT GCC AGC GAG GAC GAT GCT GCC ACT GTA TAC CGC GCA         963
Ile Ile Leu Ser Ala Ser Glu Asp Asp Ala Ala Thr Val Tyr Arg Ala
            220                 225                 230

GCC GCG ATG CTG AAC ATG ACG GGC TCC GGG TAC GTG TGG CTG GTC GGC        1011
Ala Ala Met Leu Asn Met Thr Gly Ser Gly Tyr Val Trp Leu Val Gly
235                 240                 245                 250

GAG CGC GAG ATC TCG GGG AAC GCC CTG CGC TAC GCC CCA GAC GGC ATC        1059
Glu Arg Glu Ile Ser Gly Asn Ala Leu Arg Tyr Ala Pro Asp Gly Ile
            255                 260                 265

CTC GGG CTG CAG CTC ATC AAC GGC AAG AAC GAG TCG GCC CAC ATC AGC        1107
Leu Gly Leu Gln Leu Ile Asn Gly Lys Asn Glu Ser Ala His Ile Ser
            270                 275                 280

GAC GCC GTG GGC GTG GTG GCC CAG GCC GTG CAC GAG CTC CTC GAG AAG        1155
Asp Ala Val Gly Val Val Ala Gln Ala Val His Glu Leu Leu Glu Lys
            285                 290                 295

GAG AAC ATC ACC GAC CCG CCG CGG GGC TGC GTG GGC AAC ACC AAC ATC        1203
Glu Asn Ile Thr Asp Pro Pro Arg Gly Cys Val Gly Asn Thr Asn Ile
300                 305                 310

TGG AAG ACC GGG CCG CTC TTC AAG AGA GTG CTG ATG TCT TCC AAG TAT        1251
Trp Lys Thr Gly Pro Leu Phe Lys Arg Val Leu Met Ser Ser Lys Tyr
315                 320                 325                 330

GCG GAT GGG GTG ACT GGT CGC GTG GAG TTC AAT GAG GAT GGG GAC CGG        1299
Ala Asp Gly Val Thr Gly Arg Val Glu Phe Asn Glu Asp Gly Asp Arg
                        335                 340                 345

AAG TTC GCC AAC TAC AGC ATC ATG AAC CTG CAG AAC CGC AAG CTG GTG        1347
Lys Phe Ala Asn Tyr Ser Ile Met Asn Leu Gln Asn Arg Lys Leu Val
            350                 355                 360

CAA GTG GGC ATC TAC AAT GGC ACC CAC GTC ATC CCT AAT GAC AGG AAG        1395
Gln Val Gly Ile Tyr Asn Gly Thr His Val Ile Pro Asn Asp Arg Lys
            365                 370                 375

ATC ATC TGG CCA GGC GGA GAG ACA GAG AAG CCT CGA GGG TAC CAG ATG        1443
Ile Ile Trp Pro Gly Gly Glu Thr Glu Lys Pro Arg Gly Tyr Gln Met
            380                 385                 390

TCC ACC AGA CTG AAG ATT GTG ACG ATC CAC CAG GAG CCC TTC GTG TAC        1491
Ser Thr Arg Leu Lys Ile Val Thr Ile His Gln Glu Pro Phe Val Tyr
395                 400                 405                 410

GTC AAG CCC ACG CTG AGT GAT GGG ACA TGC AAG GAG GAG TTC ACA GTC        1539
Val Lys Pro Thr Leu Ser Asp Gly Thr Cys Lys Glu Glu Phe Thr Val
                        415                 420                 425

AAC GGC GAC CCA GTC AAG AAG GTG ATC TGC ACC GGG CCC AAC GAC ACG        1587
Asn Gly Asp Pro Val Lys Lys Val Ile Cys Thr Gly Pro Asn Asp Thr
            430                 435                 440

TCG CCG GGC AGC CCC CGC CAC ACG GTG CCT CAG TGT TGC TAC GGC TTT        1635
Ser Pro Gly Ser Pro Arg His Thr Val Pro Gln Cys Cys Tyr Gly Phe
            445                 450                 455

TGC ATC GAC CTG CTC ATC AAG CTG GCA CGG ACC ATG AAC TTC ACC TAC        1683
Cys Ile Asp Leu Leu Ile Lys Leu Ala Arg Thr Met Asn Phe Thr Tyr
            460                 465                 470

GAG GTG CAC CTG GTG GCA GAT GGC AAG TTC GGC ACA CAG GAG CGG GTG        1731
Glu Val His Leu Val Ala Asp Gly Lys Phe Gly Thr Gln Glu Arg Val
475                 480                 485                 490

AAC AAC AGC AAC AAG AAG GAG TGG AAT GGG ATG ATG GGC GAG CTG CTC        1779
```

```
Asn Asn Ser Asn Lys Lys Glu Trp Asn Gly Met Met Gly Glu Leu Leu
            495             500                 505

AGC GGG CAG GCA GAC ATG ATC GTG GCG CCG CTA ACC ATA AAC AAC GAG    1827
Ser Gly Gln Ala Asp Met Ile Val Ala Pro Leu Thr Ile Asn Asn Glu
        510             515                 520

CGC GCG CAG TAC ATC GAG TTT TCC AAG CCC TTC AAG TAC CAG GGC CTG    1875
Arg Ala Gln Tyr Ile Glu Phe Ser Lys Pro Phe Lys Tyr Gln Gly Leu
        525             530                 535

ACT ATT CTG GTC AAG AAG GAG ATT CCC CGG AGC ACG CTG GAC TCG TTC    1923
Thr Ile Leu Val Lys Lys Glu Ile Pro Arg Ser Thr Leu Asp Ser Phe
        540             545                 550

ATG CAG CCG TTC CAG AGC ACA CTG TGG CTG CTG GTG GGC CTG TCG GTG    1971
Met Gln Pro Phe Gln Ser Thr Leu Trp Leu Leu Val Gly Leu Ser Val
555         560             565                     570

CAC GTG GTG GCC GTG ATG CTG TAC CTG CTG GAC CGC TTC AGC CCC TTC    2019
His Val Val Ala Val Met Leu Tyr Leu Leu Asp Arg Phe Ser Pro Phe
                575             580                 585

GGC CGG TTC AAG GTG AAC AGC GAG GAG GAG GAG GAG GAC GCA CTG ACC    2067
Gly Arg Phe Lys Val Asn Ser Glu Glu Glu Glu Glu Asp Ala Leu Thr
            590             595                 600

CTG TCC TCG GCC ATG TGG TTC TCC TGG GGC GTC CTG CTC AAC TCC GGC    2115
Leu Ser Ser Ala Met Trp Phe Ser Trp Gly Val Leu Leu Asn Ser Gly
        605             610                 615

ATC GGG GAA GGC GCC CCC AGA AGC TTC TCA GCG CGC ATC CTG GGC ATG    2163
Ile Gly Glu Gly Ala Pro Arg Ser Phe Ser Ala Arg Ile Leu Gly Met
        620             625                 630

GTG TGG GCC GGC TTT GCC ATG ATC ATC GTG GCC TCC TAC ACC GCC AAC    2211
Val Trp Ala Gly Phe Ala Met Ile Ile Val Ala Ser Tyr Thr Ala Asn
635         640             645                     650

CTG GCG GCC TTC CTG GTG CTG GAC CGG CCG GAG GAG CGC ATC ACG GGC    2259
Leu Ala Ala Phe Leu Val Leu Asp Arg Pro Glu Glu Arg Ile Thr Gly
                655             660                 665

ATC AAC GAC CCT CGG CTG AGG AAC CCC TCG GAC AAG TTT ATC TAC GCC    2307
Ile Asn Asp Pro Arg Leu Arg Asn Pro Ser Asp Lys Phe Ile Tyr Ala
            670             675                 680

ACG GTG AAG CAG AGC TCC GTG GAT ATC TAC TTC CGG CGC CAG GTG GAG    2355
Thr Val Lys Gln Ser Ser Val Asp Ile Tyr Phe Arg Arg Gln Val Glu
        685             690                 695

CTG AGC ACC ATG TAC CGG CAT ATG GAG AAG CAC AAC TAC GAG AGT GCG    2403
Leu Ser Thr Met Tyr Arg His Met Glu Lys His Asn Tyr Glu Ser Ala
700         705             710

GCG GAG GCC ATC CAG GCC GTG AGA GAC AAC AAG CTG CAT GCC TTC ATC    2451
Ala Glu Ala Ile Gln Ala Val Arg Asp Asn Lys Leu His Ala Phe Ile
715             720             725                 730

TGG GAC TCG GCG GTG CTG GAG TTC GAG GCC TCG CAG AAG TGC GAC CTG    2499
Trp Asp Ser Ala Val Leu Glu Phe Glu Ala Ser Gln Lys Cys Asp Leu
                735             740                 745

GTG ACG ACT GGA GAG CTG TTT TTC CGC TCG GGC TTC GGC ATA GGC ATG    2547
Val Thr Thr Gly Glu Leu Phe Phe Arg Ser Gly Phe Gly Ile Gly Met
        750             755                 760

CGC AAA GAC AGC CCC TGG AAG CAG AAC GTC TCC CTG TCC ATC CTC AAG    2595
Arg Lys Asp Ser Pro Trp Lys Gln Asn Val Ser Leu Ser Ile Leu Lys
        765             770                 775

TCC CAC GAG AAT GGC TTC ATG GAA GAC CTG GAC AAG ACG TGG GTT CGG    2643
Ser His Glu Asn Gly Phe Met Glu Asp Leu Asp Lys Thr Trp Val Arg
        780             785                 790

TAT CAG GAA TGT GAC TCG CGC AGC AAC GCC CCT GCG ACC CTT ACT TTT    2691
Tyr Gln Glu Cys Asp Ser Arg Ser Asn Ala Pro Ala Thr Leu Thr Phe
795             800             805                 810

GAG AAC ATG GCC GGG GTC TTC ATG CTG GTA GCT GGG GGC ATC GTG GCC    2739
```

| | | | | | | | | | | | | | | | |
|---|---|---|---|---|---|---|---|---|---|---|---|---|---|---|---|
|Glu|Asn|Met|Ala|Gly|Val|Phe|Met|Leu|Val|Ala|Gly|Gly|Ile|Val|Ala|
| | | |  |815| | | |820| | | | |825| | |

```
GGG ATC TTC CTG ATT TTC ATC GAG ATT GCC TAC AAG CGG CAC AAG GAT      2787
Gly Ile Phe Leu Ile Phe Ile Glu Ile Ala Tyr Lys Arg His Lys Asp
            830             835                 840

GCT CGC CGG AAG CAG ATG CAG CTG GCC TTT GCC GCC GTT AAC GTG TGG      2835
Ala Arg Arg Lys Gln Met Gln Leu Ala Phe Ala Ala Val Asn Val Trp
        845                 850                 855

CGG AAG AAC CTG CAG GAT AGA AAG AGT GGT AGA GCA GAG CCT GAC CCT      2883
Arg Lys Asn Leu Gln Asp Arg Lys Ser Gly Arg Ala Glu Pro Asp Pro
    860                 865                 870

AAA AAG AAA GCC ACA TTT AGG GCT ATC ACC TCC ACC CTG GCT TCC AGC      2931
Lys Lys Lys Ala Thr Phe Arg Ala Ile Thr Ser Thr Leu Ala Ser Ser
875             880                 885                 890

TTC AAG AGG CGT AGG TCC TCC AAA GAC ACG AGC ACC GGG GGT GGA CGC      2979
Phe Lys Arg Arg Arg Ser Ser Lys Asp Thr Ser Thr Gly Gly Gly Arg
                895                 900                 905

GGT GCT TTG CAA AAC CAA AAA GAC ACA GTG CTG CCG CGA CGC GCT ATT      3027
Gly Ala Leu Gln Asn Gln Lys Asp Thr Val Leu Pro Arg Arg Ala Ile
            910                 915                 920

GAG AGG GAG GAG GGC CAG CTG CAG CTG TGT TCC CGT CAT AGG GAG AGC      3075
Glu Arg Glu Glu Gly Gln Leu Gln Leu Cys Ser Arg His Arg Glu Ser
        925                 930                 935
```

| | | | | |
|---|---|---|---|---|
|TGAGACTCCC|CGCCCGCCCT|CCTCTGCCCC|CTCCCCCGCA|GACAGACAGA CAGACGGACG|3135|
|GGACAGCGGC|CCGGCCCACG|CAGAGCCCCG|GAGCACCACG|GGGTCGGGGG AGGAGCACCC|3195|
|CCAGCCTCCC|CCAGGCTGCG|CCTGCCCGCC|CGCCGGTTGG|CCGGCTGGCC GGTCCACCCC|3255|
|GTCCGGCCC|CGCGCGTGCC|CCCAGCGTGG|GGCTAACGGG|CGCCTTGTCT GTGTATTTCT|3315|
|ATTTTGCAGC|AGTACCATCC|CACTGATATC|ACGGGCCCGC|TCAACCTCTC AGATCCCTCG|3375|
|GTCAGCACCG|TGGTGTGAGG|CCCCCGGAGG|CGCCCACCTG|CCCAGTTAGC CCGGCCAAGG|3435|
|ACACTGATGG|GTCCTGCTGC|TCGGGAAGGC|CTGAGGGAAG|CCCACCCGCC CCAGAGACTG|3495|
|CCCACCCTGG|GCCTCCCGTC|CGTCCGCCCG|CCCACCCCGC|TGCCTGGCGG GCAGCCCCTG|3555|
|CTGGACCAAG|GTGCGGACCG|GAGCGGCTGA|GGACGGGGCA|GAGCTGAGTC GGCTGGGCAG|3615|
|GGCCGCAGGG|CGCTCCGGCA|GAGGCAGGCC|CCTGGGGTCT|CTGAGCAGTG GGGAGCGGGG|3675|
|GCTAACTGCC|CCCAGGCGGA|GGGGCTTGGA|GCAGAGACGG|CAGCCCATC CTTCCCGCAG|3735|
|CACCAGCCTG|AGCCACAGTG|GGGCCCATGG|CCCCAGCTGG|CTGGGTCGCC CCTCCTCGGG|3795|
|CGCCTGCGCT|CCTCTGCAGC|CTGAGCTCCA|CCCTCCCCTC|TTCTTGCGGC ACCGCCCACC|3855|
|AAACACCCCG|TCTGCCCCTT|GACGCCACAC|GCCGGGGCTG|GCGCTGCCCT CCCCACGGC|3915|
|CGTCCCTGAC|TTCCAGCTG|GCAGCGCCTC|CCGCCGCCTC|GGGCCGCCTC CTCCAGAATC|3975|
|GAGAGGGCTG|AGCCCCTCCT|CTCCTCGTCC|GGCCTGCAGC|ACAGAAGGGG GCCTCCCCGG|4035|
|GGGTCCCCGG|ACGCTGGCTC|GGGACTGTCT|TCAACCCTGC|CCTGCACCTT GGGCACGGGA|4095|
|GAGCGCCACC|CGCCCGCCCC|CGCCCTCGCT|CCGGGTGCGT|GACCGGCCCG CCACCTTGTA|4155|
|CAGAACCAGC|ACTCCCAGGG|CCCGAGCGCG|TGCCTTCCCC|GTGCGCAGCC GCGCTCTGCC|4215|
|CCTCCGTCCC|CAGGGTGCAG|GCGCGCACCG|CCCAACCCCC|ACCTCCGGT GTATGCAGTG|4275|
|GTGATGCCTA|AAGGAATGTC|ACG| | |4298|

( 2 ) INFORMATION FOR SEQ ID NO:2:

( i ) SEQUENCE CHARACTERISTICS:
        ( A ) LENGTH: 938 amino acids
        ( B ) TYPE: amino acid
        ( D ) TOPOLOGY: linear (i i) MOLECULE TYPE: protein (x i) SEQUENCE DESCRIPTION: SEQ ID NO:2:

| Met | Ser | Thr | Met | Arg | Leu | Leu | Thr | Leu | Ala | Leu | Leu | Phe | Ser | Cys | Ser |
|---|---|---|---|---|---|---|---|---|---|---|---|---|---|---|---|
| 1 | | | | 5 | | | | | 10 | | | | | 15 | |

| Val | Ala | Arg | Ala | Ala | Cys | Asp | Pro | Lys | Ile | Val | Asn | Ile | Gly | Ala | Val |
|---|---|---|---|---|---|---|---|---|---|---|---|---|---|---|---|
| | | | 20 | | | | 25 | | | | | 30 | | | |

| Leu | Ser | Thr | Arg | Lys | His | Glu | Gln | Met | Phe | Arg | Glu | Ala | Val | Asn | Gln |
|---|---|---|---|---|---|---|---|---|---|---|---|---|---|---|---|
| | | 35 | | | | | 40 | | | | | 45 | | | |

| Ala | Asn | Lys | Arg | His | Gly | Ser | Trp | Lys | Ile | Gln | Leu | Asn | Ala | Thr | Ser |
|---|---|---|---|---|---|---|---|---|---|---|---|---|---|---|---|
| | 50 | | | | | 55 | | | | | | 60 | | | |

| Val | Thr | His | Lys | Pro | Asn | Ala | Ile | Gln | Met | Ala | Leu | Ser | Val | Cys | Glu |
|---|---|---|---|---|---|---|---|---|---|---|---|---|---|---|---|
| 65 | | | | | 70 | | | | | 75 | | | | | 80 |

| Asp | Leu | Ile | Ser | Ser | Gln | Val | Tyr | Ala | Ile | Leu | Val | Ser | His | Pro | Pro |
|---|---|---|---|---|---|---|---|---|---|---|---|---|---|---|---|
| | | | | 85 | | | | | 90 | | | | | 95 | |

| Thr | Pro | Asn | Asp | His | Phe | Thr | Pro | Thr | Pro | Val | Ser | Tyr | Thr | Ala | Gly |
|---|---|---|---|---|---|---|---|---|---|---|---|---|---|---|---|
| | | | 100 | | | | 105 | | | | | 110 | | | |

| Phe | Tyr | Arg | Ile | Pro | Val | Leu | Gly | Leu | Thr | Thr | Arg | Met | Ser | Ile | Tyr |
|---|---|---|---|---|---|---|---|---|---|---|---|---|---|---|---|
| | | 115 | | | | | 120 | | | | | 125 | | | |

| Ser | Asp | Lys | Ser | Ile | His | Leu | Ser | Phe | Leu | Arg | Thr | Val | Pro | Pro | Tyr |
|---|---|---|---|---|---|---|---|---|---|---|---|---|---|---|---|
| | 130 | | | | | 135 | | | | | 140 | | | | |

| Ser | His | Gln | Ser | Ser | Val | Trp | Phe | Glu | Met | Met | Arg | Val | Tyr | Ser | Trp |
|---|---|---|---|---|---|---|---|---|---|---|---|---|---|---|---|
| 145 | | | | | 150 | | | | | 155 | | | | | 160 |

| Asn | His | Ile | Ile | Leu | Leu | Val | Ser | Asp | Asp | His | Glu | Gly | Arg | Ala | Ala |
|---|---|---|---|---|---|---|---|---|---|---|---|---|---|---|---|
| | | | | 165 | | | | | 170 | | | | | 175 | |

| Gln | Lys | Arg | Leu | Glu | Thr | Leu | Leu | Glu | Glu | Arg | Glu | Ser | Lys | Ala | Glu |
|---|---|---|---|---|---|---|---|---|---|---|---|---|---|---|---|
| | | | 180 | | | | | 185 | | | | | 190 | | |

| Lys | Val | Leu | Gln | Phe | Asp | Pro | Gly | Thr | Lys | Asn | Val | Thr | Ala | Leu | Leu |
|---|---|---|---|---|---|---|---|---|---|---|---|---|---|---|---|
| | | | 195 | | | | | 200 | | | | | 205 | | |

| Met | Glu | Ala | Lys | Glu | Leu | Glu | Ala | Arg | Val | Ile | Ile | Leu | Ser | Ala | Ser |
|---|---|---|---|---|---|---|---|---|---|---|---|---|---|---|---|
| | 210 | | | | | 215 | | | | | 220 | | | | |

| Glu | Asp | Asp | Ala | Ala | Thr | Val | Tyr | Arg | Ala | Ala | Ala | Met | Leu | Asn | Met |
|---|---|---|---|---|---|---|---|---|---|---|---|---|---|---|---|
| 225 | | | | | 230 | | | | | 235 | | | | | 240 |

| Thr | Gly | Ser | Gly | Tyr | Val | Trp | Leu | Val | Gly | Glu | Arg | Glu | Ile | Ser | Gly |
|---|---|---|---|---|---|---|---|---|---|---|---|---|---|---|---|
| | | | | 245 | | | | | 250 | | | | | 255 | |

| Asn | Ala | Leu | Arg | Tyr | Ala | Pro | Asp | Gly | Ile | Leu | Gly | Leu | Gln | Leu | Ile |
|---|---|---|---|---|---|---|---|---|---|---|---|---|---|---|---|
| | | | 260 | | | | | 265 | | | | | 270 | | |

| Asn | Gly | Lys | Asn | Glu | Ser | Ala | His | Ile | Ser | Asp | Ala | Val | Gly | Val | Val |
|---|---|---|---|---|---|---|---|---|---|---|---|---|---|---|---|
| | | 275 | | | | | 280 | | | | | 285 | | | |

| Ala | Gln | Ala | Val | His | Glu | Leu | Leu | Glu | Lys | Glu | Asn | Ile | Thr | Asp | Pro |
|---|---|---|---|---|---|---|---|---|---|---|---|---|---|---|---|
| | 290 | | | | | 295 | | | | | 300 | | | | |

| Pro | Arg | Gly | Cys | Val | Gly | Asn | Thr | Asn | Ile | Trp | Lys | Thr | Gly | Pro | Leu |
|---|---|---|---|---|---|---|---|---|---|---|---|---|---|---|---|
| 305 | | | | | 310 | | | | | 315 | | | | | 320 |

| Phe | Lys | Arg | Val | Leu | Met | Ser | Ser | Lys | Tyr | Ala | Asp | Gly | Val | Thr | Gly |
|---|---|---|---|---|---|---|---|---|---|---|---|---|---|---|---|
| | | | | 325 | | | | | 330 | | | | | 335 | |

| Arg | Val | Glu | Phe | Asn | Glu | Asp | Gly | Asp | Arg | Lys | Phe | Ala | Asn | Tyr | Ser |
|---|---|---|---|---|---|---|---|---|---|---|---|---|---|---|---|
| | | | 340 | | | | | 345 | | | | | 350 | | |

| Ile | Met | Asn | Leu | Gln | Asn | Arg | Lys | Leu | Val | Gln | Val | Gly | Ile | Tyr | Asn |
|---|---|---|---|---|---|---|---|---|---|---|---|---|---|---|---|
| | | 355 | | | | | 360 | | | | | 365 | | | |

| Gly | Thr | His | Val | Ile | Pro | Asn | Asp | Arg | Lys | Ile | Ile | Trp | Pro | Gly | Gly |
|---|---|---|---|---|---|---|---|---|---|---|---|---|---|---|---|
| | 370 | | | | | 375 | | | | | 380 | | | | |

| Glu | Thr | Glu | Lys | Pro | Arg | Gly | Tyr | Gln | Met | Ser | Thr | Arg | Leu | Lys | Ile |
|---|---|---|---|---|---|---|---|---|---|---|---|---|---|---|---|
| 385 | | | | | 390 | | | | | 395 | | | | | 400 |

| | | | | | | | | | | | | | | |
|---|---|---|---|---|---|---|---|---|---|---|---|---|---|---|
| Val | Thr | Ile | His | Gln | Glu | Pro | Phe | Val | Tyr | Val | Lys | Pro | Thr | Leu | Ser |
| | | | | 405 | | | | 410 | | | | | | 415 | |
| Asp | Gly | Thr | Cys | Lys | Glu | Glu | Phe | Thr | Val | Asn | Gly | Asp | Pro | Val | Lys |
| | | | 420 | | | | 425 | | | | | 430 | | | |
| Lys | Val | Ile | Cys | Thr | Gly | Pro | Asn | Asp | Thr | Ser | Pro | Gly | Ser | Pro | Arg |
| | | 435 | | | | | 440 | | | | | 445 | | | |
| His | Thr | Val | Pro | Gln | Cys | Cys | Tyr | Gly | Phe | Cys | Ile | Asp | Leu | Leu | Ile |
| | 450 | | | | | 455 | | | | | 460 | | | | |
| Lys | Leu | Ala | Arg | Thr | Met | Asn | Phe | Thr | Tyr | Glu | Val | His | Leu | Val | Ala |
| 465 | | | | | 470 | | | | 475 | | | | | | 480 |
| Asp | Gly | Lys | Phe | Gly | Thr | Gln | Glu | Arg | Val | Asn | Asn | Ser | Asn | Lys | Lys |
| | | | | 485 | | | | 490 | | | | | | 495 | |
| Glu | Trp | Asn | Gly | Met | Met | Gly | Glu | Leu | Leu | Ser | Gly | Gln | Ala | Asp | Met |
| | | | 500 | | | | | 505 | | | | | 510 | | |
| Ile | Val | Ala | Pro | Leu | Thr | Ile | Asn | Asn | Glu | Arg | Ala | Gln | Tyr | Ile | Glu |
| | | 515 | | | | | 520 | | | | | 525 | | | |
| Phe | Ser | Lys | Pro | Phe | Lys | Tyr | Gln | Gly | Leu | Thr | Ile | Leu | Val | Lys | Lys |
| | 530 | | | | | 535 | | | | | 540 | | | | |
| Glu | Ile | Pro | Arg | Ser | Thr | Leu | Asp | Ser | Phe | Met | Gln | Pro | Phe | Gln | Ser |
| 545 | | | | | 550 | | | | | 555 | | | | | 560 |
| Thr | Leu | Trp | Leu | Leu | Val | Gly | Leu | Ser | Val | His | Val | Val | Ala | Val | Met |
| | | | | 565 | | | | | 570 | | | | | 575 | |
| Leu | Tyr | Leu | Leu | Asp | Arg | Phe | Ser | Pro | Phe | Gly | Arg | Phe | Lys | Val | Asn |
| | | | 580 | | | | | 585 | | | | | 590 | | |
| Ser | Glu | Glu | Glu | Glu | Glu | Asp | Ala | Leu | Thr | Leu | Ser | Ser | Ala | Met | Trp |
| | | | 595 | | | | | 600 | | | | 605 | | | |
| Phe | Ser | Trp | Gly | Val | Leu | Leu | Asn | Ser | Gly | Ile | Gly | Glu | Gly | Ala | Pro |
| | | 610 | | | | | 615 | | | | | 620 | | | |
| Arg | Ser | Phe | Ser | Ala | Arg | Ile | Leu | Gly | Met | Val | Trp | Ala | Gly | Phe | Ala |
| 625 | | | | | 630 | | | | | 635 | | | | | 640 |
| Met | Ile | Ile | Val | Ala | Ser | Tyr | Thr | Ala | Asn | Leu | Ala | Ala | Phe | Leu | Val |
| | | | | 645 | | | | | 650 | | | | | 655 | |
| Leu | Asp | Arg | Pro | Glu | Glu | Arg | Ile | Thr | Gly | Ile | Asn | Asp | Pro | Arg | Leu |
| | | | 660 | | | | | 665 | | | | | 670 | | |
| Arg | Asn | Pro | Ser | Asp | Lys | Phe | Ile | Tyr | Ala | Thr | Val | Lys | Gln | Ser | Ser |
| | | 675 | | | | | 680 | | | | | 685 | | | |
| Val | Asp | Ile | Tyr | Phe | Arg | Arg | Gln | Val | Glu | Leu | Ser | Thr | Met | Tyr | Arg |
| | 690 | | | | | 695 | | | | | 700 | | | | |
| His | Met | Glu | Lys | His | Asn | Tyr | Glu | Ser | Ala | Ala | Glu | Ala | Ile | Gln | Ala |
| 705 | | | | | 710 | | | | | 715 | | | | | 720 |
| Val | Arg | Asp | Asn | Lys | Leu | His | Ala | Phe | Ile | Trp | Asp | Ser | Ala | Val | Leu |
| | | | | 725 | | | | | 730 | | | | | 735 | |
| Glu | Phe | Glu | Ala | Ser | Gln | Lys | Cys | Asp | Leu | Val | Thr | Thr | Gly | Glu | Leu |
| | | | 740 | | | | 745 | | | | | 750 | | | |
| Phe | Phe | Arg | Ser | Gly | Phe | Gly | Ile | Gly | Met | Arg | Lys | Asp | Ser | Pro | Trp |
| | | 755 | | | | 760 | | | | | 765 | | | | |
| Lys | Gln | Asn | Val | Ser | Leu | Ser | Ile | Leu | Lys | Ser | His | Glu | Asn | Gly | Phe |
| | 770 | | | | | 775 | | | | | 780 | | | | |
| Met | Glu | Asp | Leu | Asp | Lys | Thr | Trp | Val | Arg | Tyr | Gln | Glu | Cys | Asp | Ser |
| 785 | | | | | 790 | | | | | 795 | | | | | 800 |
| Arg | Ser | Asn | Ala | Pro | Ala | Thr | Leu | Thr | Phe | Glu | Asn | Met | Ala | Gly | Val |
| | | | | 805 | | | | | 810 | | | | | 815 | |
| Phe | Met | Leu | Val | Ala | Gly | Gly | Ile | Val | Ala | Gly | Ile | Phe | Leu | Ile | Phe |
| | | | 820 | | | | | 825 | | | | | 830 | | |

| Ile | Glu | Ile | Ala | Tyr | Lys | Arg | His | Lys | Asp | Ala | Arg | Arg | Lys | Gln | Met |
|||835|||||840||||845||||

| Gln | Leu | Ala | Phe | Ala | Ala | Val | Asn | Val | Trp | Arg | Lys | Asn | Leu | Gln | Asp |
||850|||||855||||860|||||

| Arg | Lys | Ser | Gly | Arg | Ala | Glu | Pro | Asp | Pro | Lys | Lys | Lys | Ala | Thr | Phe |
|865||||870||||875||||||880|

| Arg | Ala | Ile | Thr | Ser | Thr | Leu | Ala | Ser | Ser | Phe | Lys | Arg | Arg | Arg | Ser |
|||||885||||890|||||895||

| Ser | Lys | Asp | Thr | Ser | Thr | Gly | Gly | Gly | Arg | Gly | Ala | Leu | Gln | Asn | Gln |
||||900|||||905||||910|||

| Lys | Asp | Thr | Val | Leu | Pro | Arg | Arg | Ala | Ile | Glu | Arg | Glu | Glu | Gly | Gln |
|||915||||920|||||925|||

| Leu | Gln | Leu | Cys | Ser | Arg | His | Arg | Glu | Ser |
||930||||935||||

(2) INFORMATION FOR SEQ ID NO:3:

(i) SEQUENCE CHARACTERISTICS:
        (A) LENGTH: 63 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 1..63

(xi) SEQUENCE DESCRIPTION: SEQ ID NO:3:

| AGT | AAA | AAA | AGG | AAC | TAT | GAA | AAC | CTC | GAC | CAA | CTG | TCC | TAT | GAC | AAC | 48 |
| Ser | Lys | Lys | Arg | Asn | Tyr | Glu | Asn | Leu | Asp | Gln | Leu | Ser | Tyr | Asp | Asn | |
| 1 | | | | 5 | | | | 10 | | | | | | 15 | | |

| AAG | CGC | GGA | CCC | AAG | | | | | | | | | | | | 63 |
| Lys | Arg | Gly | Pro | Lys | | | | | | | | | | | | |
| | | | | 20 | | | | | | | | | | | | |

(2) INFORMATION FOR SEQ ID NO:4:

(i) SEQUENCE CHARACTERISTICS:
        (A) LENGTH: 21 amino acids
        (B) TYPE: amino acid
        (D) TOPOLOGY: linear (ii) MOLECULE TYPE: protein (xi) SEQUENCE DESCRIPTION: SEQ ID NO:4:

| Ser | Lys | Lys | Arg | Asn | Tyr | Glu | Asn | Leu | Asp | Gln | Leu | Ser | Tyr | Asp | Asn |
| 1 | | | | 5 | | | | 10 | | | | | | 15 | |

| Lys | Arg | Gly | Pro | Lys |
| | | | | 20 |

(2) INFORMATION FOR SEQ ID NO:5:

(i) SEQUENCE CHARACTERISTICS:
        (A) LENGTH: 4068 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 189..3899

( x i ) SEQUENCE DESCRIPTION: SEQ ID NO:5:

```
CCCTTAATAA GATTTGCTAC GTACACTCGA GCCATCGCGA GTGTCCTTGA GCCGCGGGTG         60

ACGGTGGCTC TCGCTGCTCG CGCCCCCTCC TCCCGCGGGG GGAGCCTGAT GCCACGTTCC        120

CTATGAATTA TTTATCGCCG GCCTAAAAAT ACCCCGAACT TCACAGCCCG AGTGACCCTC        180

CGGTGGAC ATG GGT GGG GCC CTG GGG CCG GCC CTG TTG CTC ACC TCG CTC        230
         Met Gly Gly Ala Leu Gly Pro Ala Leu Leu Leu Thr Ser Leu
          1               5                      10

TTC GGT GCC TGG GCA GGG CTG GGT CCG GGG CAG GGC GAG CAG GGC ATG        278
Phe Gly Ala Trp Ala Gly Leu Gly Pro Gly Gln Gly Glu Gln Gly Met
 15              20                  25                       30

ACG GTG GCC GTG GTG TTT AGC AGC TCA GGG CCG CCC CAG GCC CAG TTC        326
Thr Val Ala Val Val Phe Ser Ser Ser Gly Pro Pro Gln Ala Gln Phe
                 35                  40                  45

CGT GTC CGC CTC ACC CCC CAG AGC TTC CTG GAC CTA CCC CTG GAG ATC        374
Arg Val Arg Leu Thr Pro Gln Ser Phe Leu Asp Leu Pro Leu Glu Ile
             50                  55                  60

CAG CCG CTC ACA GTT GGG GTC AAC ACC ACC AAC CCC AGC AGC CTC CTC        422
Gln Pro Leu Thr Val Gly Val Asn Thr Thr Asn Pro Ser Ser Leu Leu
         65                  70                  75

ACC CAG ATC TGC GGC CTC CTG GGT GCT GCC CAC GTC CAC GGC ATT GTC        470
Thr Gln Ile Cys Gly Leu Leu Gly Ala Ala His Val His Gly Ile Val
     80                  85                  90

TTT GAG GAC AAC GTG GAC ACC GAG GCG GTG GCC CAG ATC CTT GAC TTC        518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT        566
Ile Ser Ser Gln Thr His Val Pro Ile Leu Ser Ile Ser Gly Gly Ser
                 115                 120                 125

GCT GTG GTC CTC ACC CCC AAG GAG CCG GGC TCC GCC TTC CTG CAG CTG        614
Ala Val Val Leu Thr Pro Lys Glu Pro Gly Ser Ala Phe Leu Gln Leu
             130                 135                 140

GGC GTG TCC CTG GAG CAG CAG CTG CAG GTG CTG TTC AAG GTG CTG GAA        662
Gly Val Ser Leu Glu Gln Gln Leu Gln Val Leu Phe Lys Val Leu Glu
         145                 150                 155

GAG TAC GAC TGG AGC GCC TTC GCC GTC ATC ACC AGC CTG CAC CCG GGC        710
Glu Tyr Asp Trp Ser Ala Phe Ala Val Ile Thr Ser Leu His Pro Gly
     160                 165                 170

CAC GCG CTC TTC CTG GAG GGC GTG CGC GCC GTC GCC GAC GCC AGC CAC        758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA        806
Val Ser Trp Arg Leu Leu Asp Val Val Thr Leu Glu Leu Asp Pro Gly
                 195                 200                 205

GGG CCG CGC GCG CGC ACG CAG CGC CTG CTG CGC CAG CTC GAC GCG CCC        854
Gly Pro Arg Ala Arg Thr Gln Arg Leu Leu Arg Gln Leu Asp Ala Pro
             210                 215                 220

GTG TTT GTG GCC TAC TGC TCG CGC GAG GAG GCC GAG GTG CTC TTC GCC        902
Val Phe Val Ala Tyr Cys Ser Arg Glu Glu Ala Glu Val Leu Phe Ala
         225                 230                 235

GAG GCG GCG CAG GCC GGT CTG GTG GGG CCC GGC CAC GTG TGG CTG GTG        950
Glu Ala Ala Gln Ala Gly Leu Val Gly Pro Gly His Val Trp Leu Val
     240                 245                 250

CCC AAC CTG GCG CTG GGC AGC ACC GAT GCG CCC CCC GCC ACC TTC CCC        998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC       1046
Val Gly Leu Ile Ser Val Val Thr Glu Ser Trp Arg Leu Ser Leu Arg
                 275                 280                 285
```

```
CAG  AAG  GTG  CGC  GAC  GGC  GTG  GCC  ATT  CTG  GCC  CTG  GGC  GCC  CAC  AGC      1094
Gln  Lys  Val  Arg  Asp  Gly  Val  Ala  Ile  Leu  Ala  Leu  Gly  Ala  His  Ser
               290                 295                 300

TAC  TGG  CGC  CAG  CAT  GGA  ACC  CTG  CCA  GCC  CCG  GCC  GGG  GAC  TGC  CGT      1142
Tyr  Trp  Arg  Gln  His  Gly  Thr  Leu  Pro  Ala  Pro  Ala  Gly  Asp  Cys  Arg
          305                 310                 315

GTT  CAC  CCT  GGG  CCC  GTC  AGC  CCT  GCC  CGG  GAG  GCC  TTC  TAC  AGG  CAC      1190
Val  His  Pro  Gly  Pro  Val  Ser  Pro  Ala  Arg  Glu  Ala  Phe  Tyr  Arg  His
     320                 325                 330

CTA  CTG  AAT  GTC  ACC  TGG  GAG  GGC  CGA  GAC  TTC  TCC  TTC  AGC  CCT  GGT      1238
Leu  Leu  Asn  Val  Thr  Trp  Glu  Gly  Arg  Asp  Phe  Ser  Phe  Ser  Pro  Gly
335            340                 345                 350

GGG  TAC  CTG  GTC  CAG  CCC  ACC  ATG  GTG  GTG  ATC  GCC  CTC  AAC  CGG  CAC      1286
Gly  Tyr  Leu  Val  Gln  Pro  Thr  Met  Val  Val  Ile  Ala  Leu  Asn  Arg  His
               355                 360                 365

CGC  CTC  TGG  GAG  ATG  GTG  GGG  CGC  TGG  GAG  CAT  GGC  GTC  CTA  TAC  ATG      1334
Arg  Leu  Trp  Glu  Met  Val  Gly  Arg  Trp  Glu  His  Gly  Val  Leu  Tyr  Met
          370                 375                 380

AAG  TAC  CCC  GTG  TGG  CCT  CGC  TAC  AGT  GCC  TCT  CTG  CAG  CCT  GTG  GTG      1382
Lys  Tyr  Pro  Val  Trp  Pro  Arg  Tyr  Ser  Ala  Ser  Leu  Gln  Pro  Val  Val
     385                 390                 395

GAC  AGT  CGG  CAC  CTG  ACG  GTG  GCC  ACG  CTG  GAA  GAG  CGG  CCC  TTT  GTC      1430
Asp  Ser  Arg  His  Leu  Thr  Val  Ala  Thr  Leu  Glu  Glu  Arg  Pro  Phe  Val
400            405                 410

ATC  GTG  GAG  AGC  CCT  GAC  CCT  GGC  ACA  GGA  GGC  TGT  GTC  CCC  AAC  ACC      1478
Ile  Val  Glu  Ser  Pro  Asp  Pro  Gly  Thr  Gly  Gly  Cys  Val  Pro  Asn  Thr
415            420                 425                 430

GTG  CCC  TGC  CGC  AGG  CAG  AGC  AAC  CAC  ACC  TTC  AGC  AGC  GGG  GAC  GTG      1526
Val  Pro  Cys  Arg  Arg  Gln  Ser  Asn  His  Thr  Phe  Ser  Ser  Gly  Asp  Val
               435                 440                 445

GCC  CCC  TAC  ACC  AAG  CTC  TGC  TGT  AAG  GGA  TTC  TGC  ATC  GAC  ATC  CTC      1574
Ala  Pro  Tyr  Thr  Lys  Leu  Cys  Cys  Lys  Gly  Phe  Cys  Ile  Asp  Ile  Leu
          450                 455                 460

AAG  AAG  CTG  GCC  AGA  GTG  GTC  AAA  TTC  TCC  TAC  GAC  CTG  TAC  CTG  GTG      1622
Lys  Lys  Leu  Ala  Arg  Val  Val  Lys  Phe  Ser  Tyr  Asp  Leu  Tyr  Leu  Val
     465                 470                 475

ACC  AAC  GGC  AAG  CAT  GGC  AAG  CGG  GTG  CGC  GGC  GTA  TGG  AAC  GGC  ATG      1670
Thr  Asn  Gly  Lys  His  Gly  Lys  Arg  Val  Arg  Gly  Val  Trp  Asn  Gly  Met
480            485                 490

ATT  GGG  GAG  GTG  TAC  TAC  AAG  CGG  GCA  GAC  ATG  GCC  ATC  GGC  TCC  CTC      1718
Ile  Gly  Glu  Val  Tyr  Tyr  Lys  Arg  Ala  Asp  Met  Ala  Ile  Gly  Ser  Leu
495            500                 505                 510

ACC  ATC  AAT  GAG  GAA  CGC  TCC  GAG  ATC  GTA  GAC  TTC  TCT  GTA  CCC  TTT      1766
Thr  Ile  Asn  Glu  Glu  Arg  Ser  Glu  Ile  Val  Asp  Phe  Ser  Val  Pro  Phe
               515                 520                 525

GTG  GAG  ACG  GGC  ATC  AGT  GTG  ATG  GTG  GCT  CGC  AGC  AAT  GGC  ACC  GTC      1814
Val  Glu  Thr  Gly  Ile  Ser  Val  Met  Val  Ala  Arg  Ser  Asn  Gly  Thr  Val
               530                 535                 540

TCC  CCC  TCG  GCC  TTC  TTG  GAG  CCA  TAT  AGC  CCT  GCA  GTG  TGG  GTG  ATG      1862
Ser  Pro  Ser  Ala  Phe  Leu  Glu  Pro  Tyr  Ser  Pro  Ala  Val  Trp  Val  Met
          545                 550                 555

ATG  TTT  GTC  ATG  TGC  CTC  ACT  GTG  GTG  GCC  ATC  ACC  GTC  TTC  ATG  TTC      1910
Met  Phe  Val  Met  Cys  Leu  Thr  Val  Val  Ala  Ile  Thr  Val  Phe  Met  Phe
     560                 565                 570

GAG  TAC  TTC  AGC  CCT  GTC  AGC  TAC  AAC  CAG  AAC  CTC  ACC  AGA  GGC  AAG      1958
Glu  Tyr  Phe  Ser  Pro  Val  Ser  Tyr  Asn  Gln  Asn  Leu  Thr  Arg  Gly  Lys
575            580                 585                 590

AAG  TCC  GGG  GGC  CCA  GCT  TTC  ACT  ATC  GGC  AAG  TCC  GTG  TGG  CTG  CTG      2006
Lys  Ser  Gly  Gly  Pro  Ala  Phe  Thr  Ile  Gly  Lys  Ser  Val  Trp  Leu  Leu
               595                 600                 605
```

| | | | | | | | | | | | | | | | | |
|---|---|---|---|---|---|---|---|---|---|---|---|---|---|---|---|---|
| TGG | GCG | CTG | GTC | TTC | AAC | AAC | TCA | GTG | CCC | ATC | GAG | AAC | CCG | CGG | GGC | 2054 |
| Trp | Ala | Leu | Val<br>610 | Phe | Asn | Asn | Ser | Val<br>615 | Pro | Ile | Glu | Asn | Pro<br>620 | Arg | Gly | |
| ACC | ACC | AGC | AAG | ATC | ATG | GTT | CTG | GTC | TGG | GCC | TTC | TTT | GCT | GTC | ATC | 2102 |
| Thr | Thr | Ser<br>625 | Lys | Ile | Met | Val | Leu<br>630 | Val | Trp | Ala | Phe | Phe<br>635 | Ala | Val | Ile | |
| TTC | CTC | GCC | AGA | TAC | ACG | GCC | AAC | CTG | GCC | GCC | TTC | ATG | ATC | CAA | GAG | 2150 |
| Phe | Leu<br>640 | Ala | Arg | Tyr | Thr | Ala<br>645 | Asn | Leu | Ala | Ala | Phe<br>650 | Met | Ile | Gln | Glu | |
| CAA | TAC | ATC | GAC | ACT | GTG | TCG | GGC | CTC | AGT | GAC | AAG | AAG | TTT | CAG | CGG | 2198 |
| Gln<br>655 | Tyr | Ile | Asp | Thr | Val<br>660 | Ser | Gly | Leu | Ser | Asp<br>665 | Lys | Lys | Phe | Gln | Arg<br>670 | |
| CCT | CAA | GAT | CAG | TAC | CCA | CCT | TTC | CGC | TTC | GGC | ACG | GTG | CCC | AAC | GGC | 2246 |
| Pro | Gln | Asp | Gln | Tyr<br>675 | Pro | Pro | Phe | Arg | Phe<br>680 | Gly | Thr | Val | Pro | Asn<br>685 | Gly | |
| AGC | ACG | GAG | CGG | AAC | ATC | CGC | AGT | AAC | TAC | CGT | GAC | ATG | CAC | ACC | CAC | 2294 |
| Ser | Thr | Glu | Arg<br>690 | Asn | Ile | Arg | Ser | Asn<br>695 | Tyr | Arg | Asp | Met | His<br>700 | Thr | His | |
| ATG | GTC | AAG | TTC | AAC | CAG | CGC | TCG | GTG | GAG | GAC | GCG | CTC | ACC | AGC | CTC | 2342 |
| Met | Val | Lys<br>705 | Phe | Asn | Gln | Arg | Ser<br>710 | Val | Glu | Asp | Ala | Leu<br>715 | Thr | Ser | Leu | |
| AAG | ATG | GGG | AAG | CTG | GAT | GCC | TTC | ATC | TAT | GAT | GCT | GCT | GTC | CTC | AAC | 2390 |
| Lys | Met<br>720 | Gly | Lys | Leu | Asp | Ala<br>725 | Phe | Ile | Tyr | Asp | Ala<br>730 | Ala | Val | Leu | Asn | |
| TAC | ATG | GCA | GGC | AAG | GAC | GAG | GGC | TGC | AAG | CTG | GTC | ACC | ATT | GGG | TCT | 2438 |
| Tyr<br>735 | Met | Ala | Gly | Lys | Asp<br>740 | Glu | Gly | Cys | Lys | Leu<br>745 | Val | Thr | Ile | Gly | Ser<br>750 | |
| GGC | AAG | GTC | TTT | GCT | ACC | ACT | GGC | TAC | GGC | ATC | GCC | ATG | CAG | AAG | GAC | 2486 |
| Gly | Lys | Val | Phe | Ala<br>755 | Thr | Thr | Gly | Tyr | Gly<br>760 | Ile | Ala | Met | Gln | Lys<br>765 | Asp | |
| TCC | CAC | TGG | AAG | CGG | GCC | ATA | GAC | CTG | GCG | CTC | TTG | CAG | TTC | CTG | GGG | 2534 |
| Ser | His | Trp<br>770 | Lys | Arg | Ala | Ile | Asp<br>775 | Leu | Ala | Leu | Leu | Gln<br>780 | Phe | Leu | Gly | |
| GAC | GGA | GAG | ACA | CAG | AAA | CTG | GAG | ACA | GTG | TGG | CTC | TCA | GGG | ATC | TGC | 2582 |
| Asp | Gly | Glu<br>785 | Thr | Gln | Lys | Leu | Glu<br>790 | Thr | Val | Trp | Leu | Ser<br>795 | Gly | Ile | Cys | |
| CAG | AAT | GAG | AAG | AAC | GAG | GTG | ATG | AGC | AGC | AAG | CTG | GAC | ATC | GAC | AAC | 2630 |
| Gln | Asn | Glu<br>800 | Lys | Asn | Glu | Val | Met<br>805 | Ser | Ser | Lys | Leu | Asp<br>810 | Ile | Asp | Asn | |
| ATG | GGA | GGC | GTC | TTC | TAC | ATG | CTG | CTG | GTG | GCC | ATG | GGG | CTG | GCC | CTG | 2678 |
| Met | Gly | Gly | Val | Phe | Tyr<br>820 | Met | Leu | Leu | Val | Ala<br>825 | Met | Gly | Leu | Ala | Leu<br>830 | |
| Met<br>815 | | | | | | | | | | | | | | | | |
| CTG | GTC | TTC | GCC | TGG | GAG | CAC | CTG | GTC | TAC | TGG | AAG | CTG | CGC | CAC | TCG | 2726 |
| Leu | Val | Phe | Ala | Trp<br>835 | Glu | His | Leu | Val | Tyr<br>840 | Trp | Lys | Leu | Arg | His<br>845 | Ser | |
| GTG | CCC | AAC | TCA | TCC | CAG | CTG | GAC | TTC | CTG | CTG | GCT | TTC | AGC | AGG | GGC | 2774 |
| Val | Pro | Asn | Ser<br>850 | Ser | Gln | Leu | Asp | Phe<br>855 | Leu | Leu | Ala | Phe | Ser<br>860 | Arg | Gly | |
| ATC | TAC | AGC | TGC | TTC | AGC | GGG | GTG | CAG | AGC | CTC | GCC | AGC | CCA | CCG | CGG | 2822 |
| Ile | Tyr | Ser<br>865 | Cys | Phe | Ser | Gly | Val<br>870 | Gln | Ser | Leu | Ala | Ser<br>875 | Pro | Pro | Arg | |
| CAG | GCC | AGC | CCG | GAC | CTC | ACG | GCC | AGC | TCG | GCC | CAG | GCC | AGC | GTG | CTC | 2870 |
| Gln | Ala | Ser<br>880 | Pro | Asp | Leu | Thr | Ala<br>885 | Ser | Ser | Ala | Gln | Ala<br>890 | Ser | Val | Leu | |
| AAG | ATT | CTG | CAG | GCA | GCC | CGC | GAC | ATG | GTG | ACC | ACG | GCG | GGC | GTA | AGC | 2918 |
| Lys | Ile | Leu | Gln<br>895 | Ala | Ala | Arg | Asp | Met<br>900 | Val | Thr | Thr | Ala | Gly<br>905 | Val | Ser<br>910 | |
| AAC | TCC | CTG | GAC | CGC | GCC | ACT | CGC | ACC | ATC | GAG | AAT | TGG | GGT | GGC | GGC | 2966 |
| Asn | Ser | Leu | Asp | Arg<br>915 | Ala | Thr | Arg | Thr | Ile<br>920 | Glu | Asn | Trp | Gly | Gly<br>925 | Gly | |

| | | | | | | | | | | | | | | | | |
|---|---|---|---|---|---|---|---|---|---|---|---|---|---|---|---|---|
| CGC | CGT | GCG | CCC | CCA | CCG | TCC | CCC | TGC | CCG | ACC | CCG | CGG | TCT | GGC | CCC | 3014 |
| Arg | Arg | Ala | Pro | Pro | Pro | Ser | Pro | Cys | Pro | Thr | Pro | Arg | Ser | Gly | Pro | |
| | | | 930 | | | | 935 | | | | | 940 | | | | |
| AGC | CCA | TGC | CTG | CCC | ACC | CCC | GAC | CCG | CCC | CCA | GAG | CCG | AGC | CCC | ACG | 3062 |
| Ser | Pro | Cys | Leu | Pro | Thr | Pro | Asp | Pro | Pro | Pro | Glu | Pro | Ser | Pro | Thr | |
| | 945 | | | | | 950 | | | | | 955 | | | | | |
| GGC | TGG | GGA | CCG | CCA | GAC | GGG | GGT | CGC | GCG | GCG | CTT | GTG | CGC | AGG | GCT | 3110 |
| Gly | Trp | Gly | Pro | Pro | Asp | Gly | Gly | Arg | Ala | Ala | Leu | Val | Arg | Arg | Ala | |
| | 960 | | | | 965 | | | | | 970 | | | | | | |
| CCG | CAG | CCC | CCG | GGC | CGC | CCC | CGA | CCG | GGG | CCG | CCC | CTG | TCC | GAC | | 3158 |
| Pro | Gln | Pro | Pro | Gly | Arg | Pro | Pro | Thr | Pro | Gly | Pro | Pro | Leu | Ser | Asp | |
| 975 | | | | | 980 | | | | | 985 | | | | | 990 | |
| GTC | TCC | CGA | GTG | TCG | CGC | CGC | CCA | GCC | TGG | GAG | GCG | CGG | TGG | CCG | GTG | 3206 |
| Val | Ser | Arg | Val | Ser | Arg | Arg | Pro | Ala | Trp | Glu | Ala | Arg | Trp | Pro | Val | |
| | | | | 995 | | | | | 1000 | | | | | 1005 | | |
| CGG | ACC | GGG | CAC | TGC | GGG | AGG | CAC | CTC | TCG | GCC | TCC | GAG | CGG | CCC | CTG | 3254 |
| Arg | Thr | Gly | His | Cys | Gly | Arg | His | Leu | Ser | Ala | Ser | Glu | Arg | Pro | Leu | |
| | | 1010 | | | | | 1015 | | | | | 1020 | | | | |
| TCG | CCC | GCG | CGC | TGT | CAC | TAC | AGC | TCC | TTT | CCT | CGA | GCC | GAC | CGA | TCC | 3302 |
| Ser | Pro | Ala | Arg | Cys | His | Tyr | Ser | Ser | Phe | Pro | Arg | Ala | Asp | Arg | Ser | |
| | | 1025 | | | | | 1030 | | | | | 1035 | | | | |
| GGC | CGC | CCC | TTC | CTC | CCG | CTC | TTC | CCG | GAG | CCC | CCG | GAG | CTG | GAG | GAC | 3350 |
| Gly | Arg | Pro | Phe | Leu | Pro | Leu | Phe | Pro | Glu | Pro | Pro | Glu | Leu | Glu | Asp | |
| | 1040 | | | | | 1045 | | | | | 1050 | | | | | |
| CTG | CCG | CTG | CTC | GGT | CCG | GAG | CAG | CTG | GCC | CGG | CGG | GAG | GCC | CTG | CTG | 3398 |
| Leu | Pro | Leu | Leu | Gly | Pro | Glu | Gln | Leu | Ala | Arg | Arg | Glu | Ala | Leu | Leu | |
| 1055 | | | | | 1060 | | | | | 1065 | | | | | 1070 | |
| AAC | GCG | GCC | TGG | GCC | CGG | GGC | TCG | CGC | CCG | AGT | CAC | GCT | TCC | CTG | CCC | 3446 |
| Asn | Ala | Ala | Trp | Ala | Arg | Gly | Ser | Arg | Pro | Ser | His | Ala | Ser | Leu | Pro | |
| | | | 1075 | | | | | 1080 | | | | | 1085 | | | |
| AGC | TCC | GTG | GCC | GAG | GCC | TTC | GCT | CGG | CCC | AGC | TCG | CTG | CCC | GCT | GGG | 3494 |
| Ser | Ser | Val | Ala | Glu | Ala | Phe | Ala | Arg | Pro | Ser | Ser | Leu | Pro | Ala | Gly | |
| | | | 1090 | | | | | 1095 | | | | | 1100 | | | |
| TGC | ACC | GGC | CCC | GCC | TGC | GCC | CGC | CCC | GAC | GGC | CAC | TCG | GCC | TGC | AGG | 3542 |
| Cys | Thr | Gly | Pro | Ala | Cys | Ala | Arg | Pro | Asp | Gly | His | Ser | Ala | Cys | Arg | |
| | | 1105 | | | | | 1110 | | | | | 1115 | | | | |
| CGC | TTG | GCG | CAG | GCG | CAG | TCG | ATG | TGC | TTG | CCG | ATC | TAC | CGG | GAG | GCC | 3590 |
| Arg | Leu | Ala | Gln | Ala | Gln | Ser | Met | Cys | Leu | Pro | Ile | Tyr | Arg | Glu | Ala | |
| | 1120 | | | | | 1125 | | | | | 1130 | | | | | |
| TGC | CAG | GAG | GGC | GAG | CAG | GCA | GGG | GCC | CCC | GCC | TGG | CAG | CAC | AGA | CAG | 3638 |
| Cys | Gln | Glu | Gly | Glu | Gln | Ala | Gly | Ala | Pro | Ala | Trp | Gln | His | Arg | Gln | |
| 1135 | | | | | 1140 | | | | | 1145 | | | | | 1150 | |
| CAC | GTC | TGC | CTG | CAC | GCC | CAC | GCC | CAC | CTG | CCA | TTG | TGC | TGG | GGG | GCT | 3686 |
| His | Val | Cys | Leu | His | Ala | His | Ala | His | Leu | Pro | Leu | Cys | Trp | Gly | Ala | |
| | | | | 1155 | | | | 1160 | | | | | 1165 | | | |
| GTC | TGT | CCT | CAC | CTT | CCA | CCC | TGT | GAC | AGC | CAC | GGC | TCC | TGG | CTC | TCC | 3734 |
| Val | Cys | Pro | His | Leu | Pro | Pro | Cys | Asp | Ser | His | Gly | Ser | Trp | Leu | Ser | |
| | | | 1170 | | | | 1175 | | | | | 1180 | | | | |
| GGC | GCC | TGG | GGG | CCT | CTG | GGG | CAC | AGC | GGC | AGG | ACT | CTG | GGG | CTG | GGC | 3782 |
| Gly | Ala | Trp | Gly | Pro | Leu | Gly | His | Ser | Gly | Arg | Thr | Leu | Gly | Leu | Gly | |
| | | | 1185 | | | | | 1190 | | | | | 1195 | | | |
| ACA | GGC | TAC | AGA | GAC | AGT | GGG | GGA | CTG | GAC | GAG | ATC | AGC | AGT | GTA | GCC | 3830 |
| Thr | Gly | Tyr | Arg | Asp | Ser | Gly | Gly | Leu | Asp | Glu | Ile | Ser | Ser | Val | Ala | |
| | | | 1200 | | | | | 1205 | | | | | 1210 | | | |
| CGT | GGG | ACG | CAA | GGC | TTC | CCG | GGA | CCC | TGC | ACC | TGG | AGA | CGG | ATC | TCC | 3878 |
| Arg | Gly | Thr | Gln | Gly | Phe | Pro | Gly | Pro | Cys | Thr | Trp | Arg | Arg | Ile | Ser | |
| 1215 | | | | | 1220 | | | | | 1225 | | | | | 1230 | |
| AGT | CTG | GAG | TCA | GAA | GTG | TGAGTTATCA GCCACTCAGG CTCCGAGCCA | | | | | | | | | | 3926 |
| Ser | Leu | Glu | Ser | Glu | Val | | | | | | | | | | | |
| | | | 1235 | | | | | | | | | | | | | |

```
GCTGGATTCT CTGCCTGCCA CTGTCAGGGT TAAGCGGCAG GCAGGATTGG CCCTTCTCTG     3986

GCTTCTACCA TGAAATCCTG GCCATGGCAC CCCAGTGACA GATGATGTCT TCCATGGTCA     4046

TCAGTGACCT CAGCTAGCCT CA                                              4068
```

( 2 ) INFORMATION FOR SEQ ID NO:6:

( i ) SEQUENCE CHARACTERISTICS:
        ( A ) LENGTH: 1236 amino acids
        ( B ) TYPE: amino acid
        ( D ) TOPOLOGY: linear ( i i ) MOLECULE TYPE: protein ( x i ) SEQUENCE DESCRIPTION: SEQ ID NO:6:

```
Met Gly Gly Ala Leu Gly Pro Ala Leu Leu Thr Ser Leu Phe Gly
 1               5                  10                  15

Ala Trp Ala Gly Leu Gly Pro Gly Gln Gly Glu Gln Gly Met Thr Val
                20                  25                  30

Ala Val Val Phe Ser Ser Ser Gly Pro Pro Gln Ala Gln Phe Arg Val
                35                  40                  45

Arg Leu Thr Pro Gln Ser Phe Leu Asp Leu Pro Leu Glu Ile Gln Pro
        50                  55                  60

Leu Thr Val Gly Val Asn Thr Thr Asn Pro Ser Ser Leu Leu Thr Gln
65                  70                  75                  80

Ile Cys Gly Leu Leu Gly Ala Ala His Val His Gly Ile Val Phe Glu
                85                  90                  95

Asp Asn Val Asp Thr Glu Ala Val Ala Gln Ile Leu Asp Phe Ile Ser
                100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
                180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
                260                 265                 270

Leu Ile Ser Val Val Thr Glu Ser Trp Arg Leu Ser Leu Arg Gln Lys
        275                 280                 285

Val Arg Asp Gly Val Ala Ile Leu Ala Leu Gly Ala His Ser Tyr Trp
290                 295                 300

Arg Gln His Gly Thr Leu Pro Ala Pro Ala Gly Asp Cys Arg Val His
305                 310                 315                 320

Pro Gly Pro Val Ser Pro Ala Arg Glu Ala Phe Tyr Arg His Leu Leu
                325                 330                 335
```

```
Asn  Val  Thr  Trp  Glu  Gly  Arg  Asp  Phe  Ser  Phe  Ser  Pro  Gly  Gly  Tyr
               340                 345                           350

Leu  Val  Gln  Pro  Thr  Met  Val  Val  Ile  Ala  Leu  Asn  Arg  His  Arg  Leu
          355                 360                      365

Trp  Glu  Met  Val  Gly  Arg  Trp  Glu  His  Gly  Val  Leu  Tyr  Met  Lys  Tyr
     370                      375                      380

Pro  Val  Trp  Pro  Arg  Tyr  Ser  Ala  Ser  Leu  Gln  Pro  Val  Val  Asp  Ser
385                      390                      395                      400

Arg  His  Leu  Thr  Val  Ala  Thr  Leu  Glu  Glu  Arg  Pro  Phe  Val  Ile  Val
               405                      410                           415

Glu  Ser  Pro  Asp  Pro  Gly  Thr  Gly  Gly  Cys  Val  Pro  Asn  Thr  Val  Pro
               420                 425                      430

Cys  Arg  Arg  Gln  Ser  Asn  His  Thr  Phe  Ser  Ser  Gly  Asp  Val  Ala  Pro
          435                      440                      445

Tyr  Thr  Lys  Leu  Cys  Cys  Lys  Gly  Phe  Cys  Ile  Asp  Ile  Leu  Lys  Lys
     450                 455                      460

Leu  Ala  Arg  Val  Val  Lys  Phe  Ser  Tyr  Asp  Leu  Tyr  Leu  Val  Thr  Asn
465                      470                 475                           480

Gly  Lys  His  Gly  Lys  Arg  Val  Arg  Gly  Val  Trp  Asn  Gly  Met  Ile  Gly
                    485                      490                      495

Glu  Val  Tyr  Tyr  Lys  Arg  Ala  Asp  Met  Ala  Ile  Gly  Ser  Leu  Thr  Ile
               500                      505                      510

Asn  Glu  Glu  Arg  Ser  Glu  Ile  Val  Asp  Phe  Ser  Val  Pro  Phe  Val  Glu
          515                 520                      525

Thr  Gly  Ile  Ser  Val  Met  Val  Ala  Arg  Ser  Asn  Gly  Thr  Val  Ser  Pro
     530                 535                      540

Ser  Ala  Phe  Leu  Glu  Pro  Tyr  Ser  Pro  Ala  Val  Trp  Val  Met  Met  Phe
545                      550                      555                      560

Val  Met  Cys  Leu  Thr  Val  Val  Ala  Ile  Thr  Val  Phe  Met  Phe  Glu  Tyr
               565                      570                      575

Phe  Ser  Pro  Val  Ser  Tyr  Asn  Gln  Asn  Leu  Thr  Arg  Gly  Lys  Lys  Ser
               580                      585                 590

Gly  Gly  Pro  Ala  Phe  Thr  Ile  Gly  Lys  Ser  Val  Trp  Leu  Leu  Trp  Ala
          595                      600                 605

Leu  Val  Phe  Asn  Asn  Ser  Val  Pro  Ile  Glu  Asn  Pro  Arg  Gly  Thr  Thr
     610                      615                 620

Ser  Lys  Ile  Met  Val  Leu  Val  Trp  Ala  Phe  Phe  Ala  Val  Ile  Phe  Leu
625                 630                      635                           640

Ala  Arg  Tyr  Thr  Ala  Asn  Leu  Ala  Ala  Phe  Met  Ile  Gln  Glu  Gln  Tyr
               645                      650                      655

Ile  Asp  Thr  Val  Ser  Gly  Leu  Ser  Asp  Lys  Lys  Phe  Gln  Arg  Pro  Gln
               660                      665                 670

Asp  Gln  Tyr  Pro  Pro  Phe  Arg  Phe  Gly  Thr  Val  Pro  Asn  Gly  Ser  Thr
          675                      680                      685

Glu  Arg  Asn  Ile  Arg  Ser  Asn  Tyr  Arg  Asp  Met  His  Thr  His  Met  Val
     690                      695                 700

Lys  Phe  Asn  Gln  Arg  Ser  Val  Glu  Asp  Ala  Leu  Thr  Ser  Leu  Lys  Met
705                      710                      715                      720

Gly  Lys  Leu  Asp  Ala  Phe  Ile  Tyr  Asp  Ala  Ala  Val  Leu  Asn  Tyr  Met
               725                      730                      735

Ala  Gly  Lys  Asp  Glu  Gly  Cys  Lys  Leu  Val  Thr  Ile  Gly  Ser  Gly  Lys
               740                      745                      750

Val  Phe  Ala  Thr  Thr  Gly  Tyr  Gly  Ile  Ala  Met  Gln  Lys  Asp  Ser  His
               755                      760                      765
```

```
Trp  Lys  Arg  Ala  Ile  Asp  Leu  Ala  Leu  Leu  Gln  Phe  Leu  Gly  Asp  Gly
     770                 775                           780

Glu  Thr  Gln  Lys  Leu  Glu  Thr  Val  Trp  Leu  Ser  Gly  Ile  Cys  Gln  Asn
     785                 790                 795                           800

Glu  Lys  Asn  Glu  Val  Met  Ser  Ser  Lys  Leu  Asp  Ile  Asp  Asn  Met  Gly
                         805                 810                          815

Gly  Val  Phe  Tyr  Met  Leu  Leu  Val  Ala  Met  Gly  Leu  Ala  Leu  Leu  Val
                    820                      825                 830

Phe  Ala  Trp  Glu  His  Leu  Val  Tyr  Trp  Lys  Leu  Arg  His  Ser  Val  Pro
               835                 840                      845

Asn  Ser  Ser  Gln  Leu  Asp  Phe  Leu  Leu  Ala  Phe  Ser  Arg  Gly  Ile  Tyr
     850                      855                      860

Ser  Cys  Phe  Ser  Gly  Val  Gln  Ser  Leu  Ala  Ser  Pro  Pro  Arg  Gln  Ala
865                      870                 875                           880

Ser  Pro  Asp  Leu  Thr  Ala  Ser  Ser  Ala  Gln  Ala  Ser  Val  Leu  Lys  Ile
                    885                      890                      895

Leu  Gln  Ala  Ala  Arg  Asp  Met  Val  Thr  Thr  Ala  Gly  Val  Ser  Asn  Ser
               900                      905                      910

Leu  Asp  Arg  Ala  Thr  Arg  Thr  Ile  Glu  Asn  Trp  Gly  Gly  Arg  Arg
          915                      920                      925

Ala  Pro  Pro  Pro  Ser  Pro  Cys  Pro  Thr  Pro  Arg  Ser  Gly  Pro  Ser  Pro
930                      935                      940

Cys  Leu  Pro  Thr  Pro  Asp  Pro  Pro  Glu  Pro  Ser  Pro  Thr  Gly  Trp
945                      950                 955                          960

Gly  Pro  Pro  Asp  Gly  Gly  Arg  Ala  Ala  Leu  Val  Arg  Arg  Ala  Pro  Gln
                    965                      970                      975

Pro  Pro  Gly  Arg  Pro  Pro  Thr  Pro  Gly  Pro  Pro  Leu  Ser  Asp  Val  Ser
               980                      985                      990

Arg  Val  Ser  Arg  Arg  Pro  Ala  Trp  Glu  Ala  Arg  Trp  Pro  Val  Arg  Thr
          995                      1000                     1005

Gly  His  Cys  Gly  Arg  His  Leu  Ser  Ala  Ser  Glu  Arg  Pro  Leu  Ser  Pro
     1010                     1015                     1020

Ala  Arg  Cys  His  Tyr  Ser  Ser  Phe  Pro  Arg  Ala  Asp  Arg  Ser  Gly  Arg
1025                     1030                     1035                     1040

Pro  Phe  Leu  Pro  Leu  Phe  Pro  Glu  Pro  Pro  Glu  Leu  Glu  Asp  Leu  Pro
                    1045                     1050                     1055

Leu  Leu  Gly  Pro  Glu  Gln  Leu  Ala  Arg  Arg  Glu  Ala  Leu  Leu  Asn  Ala
                    1060                     1065                     1070

Ala  Trp  Ala  Arg  Gly  Ser  Arg  Pro  Ser  His  Ala  Ser  Leu  Pro  Ser  Ser
               1075                     1080                     1085

Val  Ala  Glu  Ala  Phe  Ala  Arg  Pro  Ser  Ser  Leu  Pro  Ala  Gly  Cys  Thr
     1090                     1095                     1100

Gly  Pro  Ala  Cys  Ala  Arg  Pro  Asp  Gly  His  Ser  Ala  Cys  Arg  Arg  Leu
1105                     1110                     1115                     1120

Ala  Gln  Ala  Gln  Ser  Met  Cys  Leu  Pro  Ile  Tyr  Arg  Glu  Ala  Cys  Gln
                    1125                     1130                     1135

Glu  Gly  Glu  Gln  Ala  Gly  Ala  Pro  Ala  Trp  Gln  His  Arg  Gln  His  Val
                    1140                     1145                     1150

Cys  Leu  His  Ala  His  Ala  His  Leu  Pro  Leu  Cys  Trp  Gly  Ala  Val  Cys
          1155                     1160                     1165

Pro  His  Leu  Pro  Pro  Cys  Asp  Ser  His  Gly  Ser  Trp  Leu  Ser  Gly  Ala
     1170                     1175                     1180

Trp  Gly  Pro  Leu  Gly  His  Ser  Gly  Arg  Thr  Leu  Gly  Leu  Gly  Thr  Gly
1185                     1190                     1195                     1200
```

```
Tyr Arg Asp Ser Gly Gly Leu Asp Glu Ile Ser Ser Val Ala Arg Gly
            1205                1210                1215

Thr Gln Gly Phe Pro Gly Pro Cys Thr Trp Arg Arg Ile Ser Ser Leu
            1220                1225                1230

Glu Ser Glu Val
        1235
```

(2) INFORMATION FOR SEQ ID NO:7:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 2..22

(xi) SEQUENCE DESCRIPTION: SEQ ID NO:7:

```
C TCT GAG GCT CAG CCT GTC CCC AG                               24
  Ser Glu Ala Gln Pro Val Pro
   1               5
```

(2) INFORMATION FOR SEQ ID NO:8:

(i) SEQUENCE CHARACTERISTICS:
        (A) LENGTH: 7 amino acids
        (B) TYPE: amino acid
        (D) TOPOLOGY: linear (ii) MOLECULE TYPE: protein (xi) SEQUENCE DESCRIPTION: SEQ ID NO:8:

```
Ser Glu Ala Gln Pro Val Pro
 1               5
```

(2) INFORMATION FOR SEQ ID NO:9:

(i) SEQUENCE CHARACTERISTICS:
        (A) LENGTH: 11 base pairs
        (B) TYPE: nucleic acid
        (C) STRANDEDNESS: unknown
        (D) TOPOLOGY: unknown (ii) MOLECULE TYPE: cDNA (xi) SEQUENCE DESCRIPTION: SEQ ID NO:9:

```
AGAAGGGGGT G                                                   11
```

(2) INFORMATION FOR SEQ ID NO:10:

(i) SEQUENCE CHARACTERISTICS:
        (A) LENGTH: 4808 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 311..4705

(xi) SEQUENCE DESCRIPTION: SEQ ID NO:10:

```
ATCATGGGAC CGGGTGAGCG CTGAGAATCG CGGCCGCAGC CATCAGCCCT GGAGATGACC    60
```

```
AGGAGCGGCC ACTGCTGAGA ACTATGTGGA GAGAGGCTGC GAGCCCTGCT GCAGAGCCTC      120

CGGCTGGGAT AGCCGCCCCC CGTGGGGGCG ATGCGGACAG CGCGGGACAG CCAGGGGAGC      180

GCGCTGGGGC CGCAGCATGC GGAACCCGC TAAACCCGGT GGCTGCTGAG GCGGCCGAGA       240

TGCTCGTGCG CGCAGCGCGC CCCACTGCAT CCTCGACCTT CTCGGGCTAC AGGGACCGTC     300

AGTGGCGACT ATG GGC AGA GTG GGC TAT TGG ACC CTG CTG GTG CTG CCG        349
           Met Gly Arg Val Gly Tyr Trp Thr Leu Leu Val Leu Pro
            1               5                  10

GCC CTT CTG GTC TGG CGC GGT CCG GCG CCG AGC GCG GCG GCG GAG AAG        397
Ala Leu Leu Val Trp Arg Gly Pro Ala Pro Ser Ala Ala Ala Glu Lys
     15               20                  25

GGT CCC CCC GCG CTA AAT ATT GCG GTG ATG CTG GGT CAC AGC CAC GAC        445
Gly Pro Pro Ala Leu Asn Ile Ala Val Met Leu Gly His Ser His Asp
 30              35                   40                       45

GTG ACA GAG CGC GAA CTT CGA ACA CTG TGG GGC CCC GAG CAG GCG GCG        493
Val Thr Glu Arg Glu Leu Arg Thr Leu Trp Gly Pro Glu Gln Ala Ala
                  50                   55                   60

GGG CTG CCC CTG GAC GTG AAC GTG GTA GCT CTG CTG ATG AAC CGC ACC        541
Gly Leu Pro Leu Asp Val Asn Val Val Ala Leu Leu Met Asn Arg Thr
             65                   70                   75

GAC CCC AAG AGC CTC ATC ACG CAC GTG TGC GAC CTC ATG TCC GGG GCA        589
Asp Pro Lys Ser Leu Ile Thr His Val Cys Asp Leu Met Ser Gly Ala
         80                   85                   90

CGC ATC CAC GGC CTC GTG TTT GGG GAC GAC ACG GAC CAG GAG GCC GTA        637
Arg Ile His Gly Leu Val Phe Gly Asp Asp Thr Asp Gln Glu Ala Val
     95                  100                 105

GCC CAG ATG CTG GAT TTT ATC TCC TCC CAC ACC TTC GTC CCC ATC TTG        685
Ala Gln Met Leu Asp Phe Ile Ser Ser His Thr Phe Val Pro Ile Leu
110                 115                 120                 125

GGC ATT CAT GGG GGC GCA TCT ATG ATC ATG GCT GAC AAG GAT CCG ACG        733
Gly Ile His Gly Gly Ala Ser Met Ile Met Ala Asp Lys Asp Pro Thr
                130                 135                 140

TCT ACC TTC TTC CAG TTT GGA GCG TCC ATC CAG CAG CAA GCC ACG GTC        781
Ser Thr Phe Phe Gln Phe Gly Ala Ser Ile Gln Gln Gln Ala Thr Val
             145                 150                 155

ATG CTG AAG ATC ATG CAG GAT TAT GAC TGG CAT GTC TTC TCC CTG GTG        829
Met Leu Lys Ile Met Gln Asp Tyr Asp Trp His Val Phe Ser Leu Val
         160                 165                 170

ACC ACT ATC TTC CCT GGC TAC AGG GAA TTC ATC AGC TTC GTC AAG ACC        877
Thr Thr Ile Phe Pro Gly Tyr Arg Glu Phe Ile Ser Phe Val Lys Thr
175                 180                 185

ACA GTG GAC AAC AGC TTT GTG GGC TGG GAC ATG CAG AAT GTG ATC ACA        925
Thr Val Asp Asn Ser Phe Val Gly Trp Asp Met Gln Asn Val Ile Thr
190                 195                 200                 205

CTG GAC ACT TCC TTT GAG GAT GCA AAG ACA CAA GTC CAG CTG AAG AAG        973
Leu Asp Thr Ser Phe Glu Asp Ala Lys Thr Gln Val Gln Leu Lys Lys
                210                 215                 220

ATC CAC TCT TCT GTC ATC TTG CTC TAC TGT TCC AAA GAC GAG GCT GTT       1021
Ile His Ser Ser Val Ile Leu Leu Tyr Cys Ser Lys Asp Glu Ala Val
             225                 230                 235

CTC ATT CTG AGT GAG GCC CGC TCC CTT GGC CTC ACC GGG TAT GAT TTC       1069
Leu Ile Leu Ser Glu Ala Arg Ser Leu Gly Leu Thr Gly Tyr Asp Phe
         240                 245                 250

TTC TGG ATT GTC CCC AGC TTG GTC TCT GGG AAC ACG GAG CTC ATC CCA       1117
Phe Trp Ile Val Pro Ser Leu Val Ser Gly Asn Thr Glu Leu Ile Pro
     255                 260                 265

AAA GAG TTT CCA TCG GGA CTC ATT TCT GTC TCC TAC GAT GAC TGG GAC       1165
Lys Glu Phe Pro Ser Gly Leu Ile Ser Val Ser Tyr Asp Asp Trp Asp
270                 275                 280                 285
```

| | | | | | | | | | | | | | | | | |
|---|---|---|---|---|---|---|---|---|---|---|---|---|---|---|---|---|
| TAC | AGC | CTG | GAG | GCG | AGA | GTG | AGG | GAC | GGC | ATT | GGC | ATC | CTA | ACC | ACC | 1213 |
| Tyr | Ser | Leu | Glu | Ala | Arg | Val | Arg | Asp | Gly | Ile | Gly | Ile | Leu | Thr | Thr | |
| | | | | 290 | | | | 295 | | | | | | 300 | | |
| GCT | GCA | TCT | TCT | ATG | CTG | GAG | AAG | TTC | TCC | TAC | ATC | CCC | GAG | GCC | AAG | 1261 |
| Ala | Ala | Ser | Ser | Met | Leu | Glu | Lys | Phe | Ser | Tyr | Ile | Pro | Glu | Ala | Lys | |
| | | | 305 | | | | 310 | | | | | 315 | | | | |
| GCC | AGC | TGC | TAC | GGG | CAG | ATG | GAG | AGG | CCA | GAG | GTC | CCG | ATG | CAC | ACC | 1309 |
| Ala | Ser | Cys | Tyr | Gly | Gln | Met | Glu | Arg | Pro | Glu | Val | Pro | Met | His | Thr | |
| | | 320 | | | | 325 | | | | | 330 | | | | | |
| TTG | CAC | CCA | TTT | ATG | GTC | AAT | GTT | ACA | TGG | GAT | GGC | AAA | GAC | TTA | TCC | 1357 |
| Leu | His | Pro | Phe | Met | Val | Asn | Val | Thr | Trp | Asp | Gly | Lys | Asp | Leu | Ser | |
| | 335 | | | | | 340 | | | | | 345 | | | | | |
| TTC | ACT | GAG | GAA | GGC | TAC | CAG | GTG | CAC | CCC | AGG | CTG | GTG | GTG | ATT | GTG | 1405 |
| Phe | Thr | Glu | Glu | Gly | Tyr | Gln | Val | His | Pro | Arg | Leu | Val | Val | Ile | Val | |
| 350 | | | | | 355 | | | | | 360 | | | | | 365 | |
| CTG | AAC | AAA | GAC | CGG | GAA | TGG | GAA | AAG | GTG | GGC | AAG | TGG | GAG | AAC | CAT | 1453 |
| Leu | Asn | Lys | Asp | Arg | Glu | Trp | Glu | Lys | Val | Gly | Lys | Trp | Glu | Asn | His | |
| | | | | 370 | | | | 375 | | | | | 380 | | | |
| ACG | CTG | AGC | CTG | AGG | CAC | GCC | GTG | TGG | CCC | AGG | TAC | AAG | TCC | TTC | TCC | 1501 |
| Thr | Leu | Ser | Leu | Arg | His | Ala | Val | Trp | Pro | Arg | Tyr | Lys | Ser | Phe | Ser | |
| | | | 385 | | | | 390 | | | | | 395 | | | | |
| GAC | TGT | GAG | CCG | GAT | GAC | AAC | CAT | CTC | AGC | ATC | GTC | ACC | CTG | GAG | GAG | 1549 |
| Asp | Cys | Glu | Pro | Asp | Asp | Asn | His | Leu | Ser | Ile | Val | Thr | Leu | Glu | Glu | |
| | | 400 | | | | 405 | | | | | 410 | | | | | |
| GCC | CCA | TTC | GTC | ATC | GTG | GAA | GAC | ATA | GAC | CCC | CTG | ACC | GAG | ACG | TGT | 1597 |
| Ala | Pro | Phe | Val | Ile | Val | Glu | Asp | Ile | Asp | Pro | Leu | Thr | Glu | Thr | Cys | |
| | 415 | | | | | 420 | | | | | 425 | | | | | |
| GTG | AGG | AAC | ACC | GTG | CCA | TGT | CGG | AAG | TTC | GTC | AAA | ATC | AAC | AAT | TCA | 1645 |
| Val | Arg | Asn | Thr | Val | Pro | Cys | Arg | Lys | Phe | Val | Lys | Ile | Asn | Asn | Ser | |
| 430 | | | | | 435 | | | | | 440 | | | | | 445 | |
| ACC | AAT | GAG | GGG | ATG | AAT | GTG | AAG | AAA | TGC | TGC | AAG | GGG | TTC | TGC | ATT | 1693 |
| Thr | Asn | Glu | Gly | Met | Asn | Val | Lys | Lys | Cys | Cys | Lys | Gly | Phe | Cys | Ile | |
| | | | | 450 | | | | 455 | | | | | 460 | | | |
| GAT | ATT | CTG | AAG | AAG | CTT | TCC | AGA | ACT | GTG | AAG | TTT | ACT | TAC | GAC | CTC | 1741 |
| Asp | Ile | Leu | Lys | Lys | Leu | Ser | Arg | Thr | Val | Lys | Phe | Thr | Tyr | Asp | Leu | |
| | | | 465 | | | | 470 | | | | | 475 | | | | |
| TAT | CTG | GTG | ACC | AAT | GGG | AAG | CAT | GGC | AAG | AAA | GTT | AAC | AAT | GTG | TGG | 1789 |
| Tyr | Leu | Val | Thr | Asn | Gly | Lys | His | Gly | Lys | Lys | Val | Asn | Asn | Val | Trp | |
| | | 480 | | | | 485 | | | | | 490 | | | | | |
| AAT | GGA | ATG | ATC | GGT | GAA | GTG | GTC | TAT | CAA | CGG | GCA | GTC | ATG | GCA | GTT | 1837 |
| Asn | Gly | Met | Ile | Gly | Glu | Val | Val | Tyr | Gln | Arg | Ala | Val | Met | Ala | Val | |
| | 495 | | | | | 500 | | | | | 505 | | | | | |
| GGC | TCG | CTC | ACC | ATC | AAT | GAG | GAA | CGT | TCT | GAA | GTG | GTG | GAC | TTC | TCT | 1885 |
| Gly | Ser | Leu | Thr | Ile | Asn | Glu | Glu | Arg | Ser | Glu | Val | Val | Asp | Phe | Ser | |
| 510 | | | | | 515 | | | | | 520 | | | | | 525 | |
| GTG | CCC | TTT | GTG | GAA | ACG | GGA | ATC | AGT | GTC | ATG | GTT | TCA | AGA | AGT | AAT | 1933 |
| Val | Pro | Phe | Val | Glu | Thr | Gly | Ile | Ser | Val | Met | Val | Ser | Arg | Ser | Asn | |
| | | | | 530 | | | | 535 | | | | | 540 | | | |
| GGC | ACC | GTC | TCA | CCT | TCT | GCT | TTT | CTA | GAA | CCA | TTC | AGC | GCC | TCT | GTC | 1981 |
| Gly | Thr | Val | Ser | Pro | Ser | Ala | Phe | Leu | Glu | Pro | Phe | Ser | Ala | Ser | Val | |
| | | | 545 | | | | 550 | | | | | 555 | | | | |
| TGG | GTG | ATG | ATG | TTT | GTG | ATG | CTG | CTC | ATT | GTT | TCT | GCC | ATA | GCT | GTT | 2029 |
| Trp | Val | Met | Met | Phe | Val | Met | Leu | Leu | Ile | Val | Ser | Ala | Ile | Ala | Val | |
| | | | 560 | | | | 565 | | | | | 570 | | | | |
| TGG | GTC | TTG | GAT | TAC | TCC | AGC | CCT | GTT | GGA | TAC | AAC | AGA | AAC | TTA | GCC | 2077 |
| Trp | Val | Leu | Asp | Tyr | Ser | Ser | Pro | Val | Gly | Tyr | Asn | Arg | Asn | Leu | Ala | |
| | | 575 | | | | 580 | | | | | 585 | | | | | |
| AAA | GGG | AAA | GCA | CCC | CAT | GGG | CCT | TCT | TTT | ACA | ATT | GGA | AAA | GCT | ATA | 2125 |
| Lys | Gly | Lys | Ala | Pro | His | Gly | Pro | Ser | Phe | Thr | Ile | Gly | Lys | Ala | Ile | |
| | 590 | | | | | 595 | | | | | 600 | | | | | 605 |

| | | | | | | | | | | | | | | | | |
|---|---|---|---|---|---|---|---|---|---|---|---|---|---|---|---|---|
| TGG | CTT | CTT | TGG | GGC | CTG | GTG | TTC | AAT | AAC | TCC | GTG | CCT | GTC | CAG | AAT | 2173 |
| Trp | Leu | Leu | Trp | Gly 610 | Leu | Val | Phe | Asn | Asn 615 | Ser | Val | Pro | Val | Gln 620 | Asn | |
| CCT | AAA | GGG | ACC | ACC | AGC | AAG | ATC | ATG | GTA | TCT | GTA | TGG | GCC | TTC | TTC | 2221 |
| Pro | Lys | Gly | Thr 625 | Thr | Ser | Lys | Ile | Met 630 | Val | Ser | Val | Trp | Ala 635 | Phe | Phe | |
| GCT | GTC | ATA | TTC | CTG | GCT | AGC | TAC | ACA | GCC | AAT | CTG | GCT | GCC | TTC | ATG | 2269 |
| Ala | Val | Ile 640 | Phe | Leu | Ala | Ser | Tyr 645 | Thr | Ala | Asn | Leu | Ala 650 | Ala | Phe | Met | |
| ATC | CAA | GAG | GAA | TTT | GTG | GAC | CAA | GTG | ACC | GGC | CTC | AGT | GAC | AAA | AAG | 2317 |
| Ile | Gln | Glu 655 | Glu | Phe | Val | Asp | Gln 660 | Val | Thr | Gly | Leu | Ser 665 | Asp | Lys | Lys | |
| TTT | CAG | AGA | CCT | CAT | GAC | TAT | TCC | CCA | CCT | TTT | CGA | TTT | GGG | ACA | GTG | 2365 |
| Phe 670 | Gln | Arg | Pro | His | Asp 675 | Tyr | Ser | Pro | Pro | Phe 680 | Arg | Phe | Gly | Thr | Val 685 | |
| CCT | AAT | GGA | AGC | ACG | GAG | AGA | AAC | ATT | CGG | AAT | AAC | TAT | CCC | TAC | ATG | 2413 |
| Pro | Asn | Gly | Ser | Thr 690 | Glu | Arg | Asn | Ile | Arg 695 | Asn | Asn | Tyr | Pro | Tyr 700 | Met | |
| CAT | CAG | TAC | ATG | ACC | AAA | TTT | AAT | CAG | AAA | GGA | GTA | GAG | GAC | GCC | TTG | 2461 |
| His | Gln | Tyr | Met 705 | Thr | Lys | Phe | Asn | Gln 710 | Lys | Gly | Val | Glu | Asp 715 | Ala | Leu | |
| GTC | AGC | CTG | AAA | ACG | GGG | AAG | CTG | GAC | GCT | TTC | ATC | TAC | GAT | GCC | GCA | 2509 |
| Val | Ser | Leu | Lys 720 | Thr | Gly | Lys | Leu | Asp 725 | Ala | Phe | Ile | Tyr | Asp 730 | Ala | Ala | |
| GTC | TTG | AAT | TAC | AAG | GCT | GGG | AGG | GAT | GAA | GGC | TGC | AAG | CTG | GTG | ACC | 2557 |
| Val | Leu | Asn 735 | Tyr | Lys | Ala | Gly | Arg 740 | Asp | Glu | Gly | Cys | Lys 745 | Leu | Val | Thr | |
| ATC | GGG | AGT | GGG | TAC | ATC | TTT | GCC | ACC | ACC | GGT | TAT | GGA | ATT | GCC | CTT | 2605 |
| Ile | Gly | Ser | Gly | Tyr | Ile | Phe | Ala | Thr | Thr | Gly | Tyr | Gly | Ile | Ala | Leu | |
| 750 | | | | | 755 | | | | | 760 | | | | | 765 | |
| CAG | AAA | GGC | TCT | CCT | TGG | AAG | AGG | CAG | ATC | GAC | CTG | GCC | TTG | CTT | CAG | 2653 |
| Gln | Lys | Gly | Ser | Pro 770 | Trp | Lys | Arg | Gln | Ile 775 | Asp | Leu | Ala | Leu | Leu 780 | Gln | |
| TTT | GTG | GGT | GAT | GGT | GAG | ATG | GAG | GAG | CTG | GAG | ACC | CTG | TGG | CTC | ACT | 2701 |
| Phe | Val | Gly | Asp 785 | Gly | Glu | Met | Glu | Glu 790 | Leu | Glu | Thr | Leu | Trp 795 | Leu | Thr | |
| GGG | ATC | TGC | CAC | AAC | GAG | AAG | AAC | GAG | GTG | ATG | AGC | AGC | CAG | CTG | GAC | 2749 |
| Gly | Ile | Cys 800 | His | Asn | Glu | Lys | Asn 805 | Glu | Val | Met | Ser | Ser 810 | Gln | Leu | Asp | |
| ATT | GAC | AAC | ATG | GCG | GGC | GTA | TTC | TAC | ATG | CTG | GCT | GCC | GCC | ATG | GCC | 2797 |
| Ile | Asp | Asn | Met | Ala | Gly | Val | Phe | Tyr | Met | Leu | Ala | Ala | Ala | Met | Ala | |
| 815 | | | | | 820 | | | | | 825 | | | | | | |
| CTT | AGC | CTC | ATC | ACC | TTC | ATC | TGG | GAG | CAC | CTC | TTC | TAC | TGG | AAG | CTG | 2845 |
| Leu 830 | Ser | Leu | Ile | Thr | Phe 835 | Ile | Trp | Glu | His | Leu 840 | Phe | Tyr | Trp | Lys | Leu 845 | |
| CGC | TTC | TGT | TTC | ACG | GGC | GTG | TGC | TCC | GAC | CGG | CCT | GGG | TTG | CTC | TTC | 2893 |
| Arg | Phe | Cys | Phe | Thr 850 | Gly | Val | Cys | Ser | Asp 855 | Arg | Pro | Gly | Leu | Leu 860 | Phe | |
| TCC | ATC | AGC | AGG | GGC | ATC | TAC | AGC | TGC | ATT | CAT | GGA | GTG | CAC | ATT | GAA | 2941 |
| Ser | Ile | Ser | Arg 865 | Gly | Ile | Tyr | Ser | Cys 870 | Ile | His | Gly | Val | His 875 | Ile | Glu | |
| GAA | AAG | AAG | AAG | TCT | CCA | GAC | TTC | AAT | CTG | ACG | GGA | TCC | CAG | AGC | AAC | 2989 |
| Glu | Lys | Lys | Lys 880 | Ser | Pro | Asp | Phe | Asn 885 | Leu | Thr | Gly | Ser | Gln 890 | Ser | Asn | |
| ATG | TTA | AAA | CTC | CTC | CGG | TCA | GCC | AAA | AAC | ATT | TCC | AGC | ATG | TCC | AAC | 3037 |
| Met | Leu | Lys | Leu | Leu | Arg | Ser | Ala | Lys | Asn | Ile | Ser | Ser | Met | Ser | Asn | |
| | | 895 | | | | 900 | | | | | 905 | | | | | |
| ATG | AAC | TCC | TCA | AGA | ATG | GAC | TCA | CCC | AAA | AGA | GCT | GCT | GAC | TTC | ATC | 3085 |
| Met | Asn | Ser | Ser | Arg | Met | Asp | Ser | Pro | Lys | Arg | Ala | Ala | Asp | Phe | Ile | |
| 910 | | | | | 915 | | | | | 920 | | | | | 925 | |

| | | | | | | | | | | | | | | | | |
|---|---|---|---|---|---|---|---|---|---|---|---|---|---|---|---|---|
| CAA | AGA | GGT | TCC | CTC | ATC | ATG | GAC | ATG | GTT | TCA | GAT | AAG | GGG | AAT | TTG | 3133 |
| Gln | Arg | Gly | Ser | Leu | Ile | Met | Asp | Met | Val | Ser | Asp | Lys | Gly | Asn | Leu | |
| | | | | 930 | | | | 935 | | | | | | 940 | | |
| ATG | TAC | TCA | GAC | AAC | AGG | TCC | TTT | CAG | GGG | AAA | GAG | AGC | ATT | TTT | GGA | 3181 |
| Met | Tyr | Ser | Asp | Asn | Arg | Ser | Phe | Gln | Gly | Lys | Glu | Ser | Ile | Phe | Gly | |
| | | | 945 | | | | | 950 | | | | | 955 | | | |
| GAC | AAC | ATG | AAC | GAA | CTC | CAA | ACA | TTT | GTG | GCC | AAC | CGG | CAG | AAG | GAT | 3229 |
| Asp | Asn | Met | Asn | Glu | Leu | Gln | Thr | Phe | Val | Ala | Asn | Arg | Gln | Lys | Asp | |
| | | 960 | | | | | 965 | | | | | 970 | | | | |
| AAC | CTC | AAT | AAC | TAT | GTA | TTC | CAG | GGA | CAA | CAT | CCT | CTT | ACT | CTC | AAT | 3277 |
| Asn | Leu | Asn | Asn | Tyr | Val | Phe | Gln | Gly | Gln | His | Pro | Leu | Thr | Leu | Asn | |
| | 975 | | | | | 980 | | | | | 985 | | | | | |
| GAG | TCC | AAC | CCT | AAC | ACG | GTG | GAG | GTG | GCC | GTG | AGC | ACA | GAA | TCC | AAA | 3325 |
| Glu | Ser | Asn | Pro | Asn | Thr | Val | Glu | Val | Ala | Val | Ser | Thr | Glu | Ser | Lys | |
| 990 | | | | | 995 | | | | | 1000 | | | | | 1005 | |
| GCG | AAC | TCT | AGA | CCC | CGG | CAG | CTG | TGG | AAG | AAA | TCC | GTG | GAT | TCC | ATA | 3373 |
| Ala | Asn | Ser | Arg | Pro | Arg | Gln | Leu | Trp | Lys | Lys | Ser | Val | Asp | Ser | Ile | |
| | | | | 1010 | | | | | 1015 | | | | | 1020 | | |
| CGC | CAG | GAT | TCA | CTA | TCC | CAG | AAT | CCA | GTC | TCC | CAG | AGG | GAT | GAG | GCA | 3421 |
| Arg | Gln | Asp | Ser | Leu | Ser | Gln | Asn | Pro | Val | Ser | Gln | Arg | Asp | Glu | Ala | |
| | | | | 1025 | | | | | 1030 | | | | | 1035 | | |
| ACA | GCA | GAG | AAT | AGG | ACC | CAC | TCC | CTA | AAG | AGC | CCT | AGG | TAT | CTT | CCA | 3469 |
| Thr | Ala | Glu | Asn | Arg | Thr | His | Ser | Leu | Lys | Ser | Pro | Arg | Tyr | Leu | Pro | |
| | | | | 1040 | | | | | 1045 | | | | | 1050 | | |
| GAA | GAG | ATG | GCC | CAC | TCT | GAC | ATT | TCA | GAA | ACG | TCA | AAT | CGG | GCC | ACG | 3517 |
| Glu | Glu | Met | Ala | His | Ser | Asp | Ile | Ser | Glu | Thr | Ser | Asn | Arg | Ala | Thr | |
| | | | | 1055 | | | | | 1060 | | | | | 1065 | | |
| TGC | CAC | AGG | GAA | CCT | GAC | AAC | AGT | AAG | AAC | CAC | AAA | ACC | AAG | GAC | AAC | 3565 |
| Cys | His | Arg | Glu | Pro | Asp | Asn | Ser | Lys | Asn | His | Lys | Thr | Lys | Asp | Asn | |
| 1070 | | | | | 1075 | | | | | 1080 | | | | | 1085 | |
| TTT | AAA | AGG | TCA | GTG | GCC | TCC | AAA | TAC | CCC | AAG | GAC | TGT | AGT | GAG | GTC | 3613 |
| Phe | Lys | Arg | Ser | Val | Ala | Ser | Lys | Tyr | Pro | Lys | Asp | Cys | Ser | Glu | Val | |
| | | | | 1090 | | | | | 1095 | | | | | 1100 | | |
| GAG | CGC | ACC | TAC | CTG | AAA | ACC | AAA | TCA | AGC | TCC | CCT | AGA | GAC | AAG | ATC | 3661 |
| Glu | Arg | Thr | Tyr | Leu | Lys | Thr | Lys | Ser | Ser | Ser | Pro | Arg | Asp | Lys | Ile | |
| | | | | 1105 | | | | | 1110 | | | | | 1115 | | |
| TAC | ACT | ATA | GAT | GGT | GAG | AAG | GAG | CCT | GGT | TTC | CAC | TTA | GAT | CCA | CCC | 3709 |
| Tyr | Thr | Ile | Asp | Gly | Glu | Lys | Glu | Pro | Gly | Phe | His | Leu | Asp | Pro | Pro | |
| | | | | 1120 | | | | | 1125 | | | | | 1130 | | |
| CAG | TTT | GTT | GAA | AAT | GTG | ACC | CTG | CCC | GAG | AAC | GTG | GAC | TTC | CCG | GAC | 3757 |
| Gln | Phe | Val | Glu | Asn | Val | Thr | Leu | Pro | Glu | Asn | Val | Asp | Phe | Pro | Asp | |
| | | | | 1135 | | | | | 1140 | | | | | 1145 | | |
| CCC | TAC | CAG | GAT | CCC | AGT | GAA | AAC | TTC | CGC | AAG | GGG | GAC | TCC | ACG | CTG | 3805 |
| Pro | Tyr | Gln | Asp | Pro | Ser | Glu | Asn | Phe | Arg | Lys | Gly | Asp | Ser | Thr | Leu | |
| 1150 | | | | | 1155 | | | | | 1160 | | | | | 1165 | |
| CCA | ATG | AAC | CGG | AAC | CCC | TTG | CAT | AAT | GAA | GAG | GGG | CTT | TCC | AAC | AAC | 3853 |
| Pro | Met | Asn | Arg | Asn | Pro | Leu | His | Asn | Glu | Glu | Gly | Leu | Ser | Asn | Asn | |
| | | | | 1170 | | | | | 1175 | | | | | 1180 | | |
| GAC | CAG | TAT | AAA | CTC | TAC | TCC | AAG | CAC | TTC | ACC | TTG | AAA | GAC | AAG | GGT | 3901 |
| Asp | Gln | Tyr | Lys | Leu | Tyr | Ser | Lys | His | Phe | Thr | Leu | Lys | Asp | Lys | Gly | |
| | | | | 1185 | | | | | 1190 | | | | | 1195 | | |
| TCC | CCG | CAC | AGT | GAG | ACC | AGC | GAG | CGA | TAC | CGG | CAG | AAC | TCC | ACG | CAC | 3949 |
| Ser | Pro | His | Ser | Glu | Thr | Ser | Glu | Arg | Tyr | Arg | Gln | Asn | Ser | Thr | His | |
| | | | | 1200 | | | | | 1205 | | | | | 1210 | | |
| TGC | AGA | AGC | TGC | CTT | TCC | AAC | ATG | CCC | ACC | TAT | TCA | GGC | CAC | TTC | ACC | 3997 |
| Cys | Arg | Ser | Cys | Leu | Ser | Asn | Met | Pro | Thr | Tyr | Ser | Gly | His | Phe | Thr | |
| | | 1215 | | | | | 1220 | | | | | 1225 | | | | |
| ATG | AGG | TCC | CCC | TTC | AAG | TGC | GAT | GCC | TGC | CTG | CGG | ATG | GGG | AAC | CTC | 4045 |
| Met | Arg | Ser | Pro | Phe | Lys | Cys | Asp | Ala | Cys | Leu | Arg | Met | Gly | Asn | Leu | |
| | | 1230 | | | | | 1235 | | | | | 1240 | | | | 1245 |

```
TAT GAC ATC GAT GAA GAC CAG ATG CTT CAG GAG ACA GGT AAC CCA GCC      4093
Tyr Asp Ile Asp Glu Asp Gln Met Leu Gln Glu Thr Gly Asn Pro Ala
            1250                1255                1260

ACC GGG GAG CAG GTC TAC CAG CAG GAC TGG GCA CAG AAC AAT GCC CTT      4141
Thr Gly Glu Gln Val Tyr Gln Gln Asp Trp Ala Gln Asn Asn Ala Leu
            1265                1270                1275

CAA TTA CAA AAG AAC AAG CTA AGG ATT AGC CGT CAG CAT TCC TAC GAT      4189
Gln Leu Gln Lys Asn Lys Leu Arg Ile Ser Arg Gln His Ser Tyr Asp
            1280                1285                1290

AAC ATT GTC GAC AAA CCT AGG GAG CTA GAC CTT AGC AGG CCC TCC CGG      4237
Asn Ile Val Asp Lys Pro Arg Glu Leu Asp Leu Ser Arg Pro Ser Arg
    1295                1300                1305

AGC ATA AGC CTC AAG GAC AGG GAA CGG CTT CTG GAG GGA AAT TTT TAC      4285
Ser Ile Ser Leu Lys Asp Arg Glu Arg Leu Leu Glu Gly Asn Phe Tyr
1310                1315                1320                1325

GGC AGC CTG TTT AGT GTC CCC TCA AGC AAA CTC TCG GGG AAA AAA AGC      4333
Gly Ser Leu Phe Ser Val Pro Ser Ser Lys Leu Ser Gly Lys Lys Ser
                1330                1335                1340

TCC CTT TTC CCC CAA GGT CTG GAG GAC AGC AAG AGG AGC AAG TCT CTC      4381
Ser Leu Phe Pro Gln Gly Leu Glu Asp Ser Lys Arg Ser Lys Ser Leu
            1345                1350                1355

TTG CCA GAC CAC ACC TCC GAT AAC CCT TTC CTC CAC TCC CAC AGG GAT      4429
Leu Pro Asp His Thr Ser Asp Asn Pro Phe Leu His Ser His Arg Asp
            1360                1365                1370

GAC CAA CGC TTG GTT ATT GGG AGA TGC CCC TCG GAC CCT TAC AAA CAC      4477
Asp Gln Arg Leu Val Ile Gly Arg Cys Pro Ser Asp Pro Tyr Lys His
    1375                1380                1385

TCG TTG CCA TCC CAG GCG GTG AAT GAC AGC TAT CTT CGG TCG TCC TTG      4525
Ser Leu Pro Ser Gln Ala Val Asn Asp Ser Tyr Leu Arg Ser Ser Leu
1390                1395                1400                1405

AGG TCA ACG GCA TCG TAC TGT TCC AGG GAC AGT CGG GGC CAC AAT GAT      4573
Arg Ser Thr Ala Ser Tyr Cys Ser Arg Asp Ser Arg Gly His Asn Asp
            1410                1415                1420

GTG TAT ATT TCG GAG CAT GTT ATG CCT TAT GCT GCA AAT AAG AAT AAT      4621
Val Tyr Ile Ser Glu His Val Met Pro Tyr Ala Ala Asn Lys Asn Asn
            1425                1430                1435

ATG TAC TCT ACC CCC AGG GTT TTA AAT TCC TGC AGC AAT AGA CGC GTG      4669
Met Tyr Ser Thr Pro Arg Val Leu Asn Ser Cys Ser Asn Arg Arg Val
            1440                1445                1450

TAC AAG GAA ATG CCT AGT ATC GAA TCT GAT GTT TAAAAATCTT CCATTAATGT    4722
Tyr Lys Glu Met Pro Ser Ile Glu Ser Asp Val
            1455                1460             146

TTTATCTATA GGGAAATACA CGTAATGGCC AATGTTCTGG AGGGTAAATG TTGGATGTCC    4782

AATAGTGCCC TGCTAAGAGG AAGGAG                                         4808
```

( 2 ) INFORMATION FOR SEQ ID NO:11:

( i ) SEQUENCE CHARACTERISTICS:
        ( A ) LENGTH: 1464 amino acids
        ( B ) TYPE: amino acid
        ( D ) TOPOLOGY: linear ( i i ) MOLECULE TYPE: protein ( x i ) SEQUENCE DESCRIPTION: SEQ ID NO:11:

```
Met Gly Arg Val Gly Tyr Trp Thr Leu Leu Val Leu Pro Ala Leu Leu
 1               5                  10                  15

Val Trp Arg Gly Pro Ala Pro Ser Ala Ala Ala Glu Lys Gly Pro Pro
                20                  25                  30

Ala Leu Asn Ile Ala Val Met Leu Gly His Ser His Asp Val Thr Glu
            35                  40                  45
```

-continued

| | | | | | | | | | | | | | | |
|---|---|---|---|---|---|---|---|---|---|---|---|---|---|---|
| Arg | Glu | Leu | Arg | Thr | Leu | Trp | Gly | Pro | Glu | Gln | Ala | Ala | Gly | Leu | Pro |
| | 50 | | | | | 55 | | | | | 60 | | | | |
| Leu | Asp | Val | Asn | Val | Val | Ala | Leu | Leu | Met | Asn | Arg | Thr | Asp | Pro | Lys |
| 65 | | | | | 70 | | | | | 75 | | | | | 80 |
| Ser | Leu | Ile | Thr | His | Val | Cys | Asp | Leu | Met | Ser | Gly | Ala | Arg | Ile | His |
| | | | | 85 | | | | | 90 | | | | | 95 | |
| Gly | Leu | Val | Phe | Gly | Asp | Thr | Asp | Gln | Glu | Ala | Val | Ala | Gln | Met |
| | | | 100 | | | | | 105 | | | | | 110 | |
| Leu | Asp | Phe | Ile | Ser | Ser | His | Thr | Phe | Val | Pro | Ile | Leu | Gly | Ile | His |
| | | | 115 | | | | 120 | | | | | 125 | | | |
| Gly | Gly | Ala | Ser | Met | Ile | Met | Ala | Asp | Lys | Asp | Pro | Thr | Ser | Thr | Phe |
| | 130 | | | | | 135 | | | | | 140 | | | | |
| Phe | Gln | Phe | Gly | Ala | Ser | Ile | Gln | Gln | Gln | Ala | Thr | Val | Met | Leu | Lys |
| 145 | | | | | 150 | | | | | 155 | | | | | 160 |
| Ile | Met | Gln | Asp | Tyr | Asp | Trp | His | Val | Phe | Ser | Leu | Val | Thr | Thr | Ile |
| | | | | 165 | | | | | 170 | | | | | 175 | |
| Phe | Pro | Gly | Tyr | Arg | Glu | Phe | Ile | Ser | Phe | Val | Lys | Thr | Thr | Val | Asp |
| | | | 180 | | | | | 185 | | | | | 190 | | |
| Asn | Ser | Phe | Val | Gly | Trp | Asp | Met | Gln | Asn | Val | Ile | Thr | Leu | Asp | Thr |
| | | 195 | | | | | 200 | | | | | 205 | | | |
| Ser | Phe | Glu | Asp | Ala | Lys | Thr | Gln | Val | Gln | Leu | Lys | Lys | Ile | His | Ser |
| | 210 | | | | | 215 | | | | | 220 | | | | |
| Ser | Val | Ile | Leu | Leu | Tyr | Cys | Ser | Lys | Asp | Glu | Ala | Val | Leu | Ile | Leu |
| 225 | | | | | 230 | | | | | 235 | | | | | 240 |
| Ser | Glu | Ala | Arg | Ser | Leu | Gly | Leu | Thr | Gly | Tyr | Asp | Phe | Phe | Trp | Ile |
| | | | | 245 | | | | | 250 | | | | | 255 | |
| Val | Pro | Ser | Leu | Val | Ser | Gly | Asn | Thr | Glu | Leu | Ile | Pro | Lys | Glu | Phe |
| | | | 260 | | | | | 265 | | | | | 270 | | |
| Pro | Ser | Gly | Leu | Ile | Ser | Val | Ser | Tyr | Asp | Asp | Trp | Asp | Tyr | Ser | Leu |
| | | 275 | | | | | 280 | | | | | 285 | | | |
| Glu | Ala | Arg | Val | Arg | Asp | Gly | Ile | Gly | Ile | Leu | Thr | Thr | Ala | Ala | Ser |
| | 290 | | | | | 295 | | | | | 300 | | | | |
| Ser | Met | Leu | Glu | Lys | Phe | Ser | Tyr | Ile | Pro | Glu | Ala | Lys | Ala | Ser | Cys |
| 305 | | | | | 310 | | | | | 315 | | | | | 320 |
| Tyr | Gly | Gln | Met | Glu | Arg | Pro | Glu | Val | Pro | Met | His | Thr | Leu | His | Pro |
| | | | | 325 | | | | | 330 | | | | | 335 | |
| Phe | Met | Val | Asn | Val | Thr | Trp | Asp | Gly | Lys | Asp | Leu | Ser | Phe | Thr | Glu |
| | | | 340 | | | | | 345 | | | | | 350 | | |
| Glu | Gly | Tyr | Gln | Val | His | Pro | Arg | Leu | Val | Val | Ile | Val | Leu | Asn | Lys |
| | | 355 | | | | | 360 | | | | | 365 | | | |
| Asp | Arg | Glu | Trp | Glu | Lys | Val | Gly | Lys | Trp | Glu | Asn | His | Thr | Leu | Ser |
| | 370 | | | | | 375 | | | | | 380 | | | | |
| Leu | Arg | His | Ala | Val | Trp | Pro | Arg | Tyr | Lys | Ser | Phe | Ser | Asp | Cys | Glu |
| 385 | | | | | 390 | | | | | 395 | | | | | 400 |
| Pro | Asp | Asp | Asn | His | Leu | Ser | Ile | Val | Thr | Leu | Glu | Glu | Ala | Pro | Phe |
| | | | | 405 | | | | | 410 | | | | | 415 | |
| Val | Ile | Val | Glu | Asp | Ile | Asp | Pro | Leu | Thr | Glu | Thr | Cys | Val | Arg | Asn |
| | | | 420 | | | | | 425 | | | | | 430 | | |
| Thr | Val | Pro | Cys | Arg | Lys | Phe | Val | Lys | Ile | Asn | Asn | Ser | Thr | Asn | Glu |
| | | 435 | | | | | 440 | | | | | 445 | | | |
| Gly | Met | Asn | Val | Lys | Lys | Cys | Cys | Lys | Gly | Phe | Cys | Ile | Asp | Ile | Leu |
| | 450 | | | | | 455 | | | | | 460 | | | | |
| Lys | Lys | Leu | Ser | Arg | Thr | Val | Lys | Phe | Thr | Tyr | Asp | Leu | Tyr | Leu | Val |

```
              465                     470                    475                    480
Thr  Asn  Gly  Lys  His  Gly  Lys  Lys  Val  Asn  Val  Trp  Asn  Gly  Met
                    485                   490                   495

Ile  Gly  Glu  Val  Val  Tyr  Gln  Arg  Ala  Val  Met  Ala  Val  Gly  Ser  Leu
               500                   505                   510

Thr  Ile  Asn  Glu  Glu  Arg  Ser  Glu  Val  Val  Asp  Phe  Ser  Val  Pro  Phe
               515                   520                   525

Val  Glu  Thr  Gly  Ile  Ser  Val  Met  Val  Ser  Arg  Ser  Asn  Gly  Thr  Val
               530                   535                   540

Ser  Pro  Ser  Ala  Phe  Leu  Glu  Pro  Phe  Ser  Ala  Ser  Val  Trp  Val  Met
545                      550                   555                        560

Met  Phe  Val  Met  Leu  Leu  Ile  Val  Ser  Ala  Ile  Ala  Val  Trp  Val  Leu
                    565                   570                   575

Asp  Tyr  Ser  Ser  Pro  Val  Gly  Tyr  Asn  Arg  Asn  Leu  Ala  Lys  Gly  Lys
               580                   585                   590

Ala  Pro  His  Gly  Pro  Ser  Phe  Thr  Ile  Gly  Lys  Ala  Ile  Trp  Leu  Leu
               595                   600                   605

Trp  Gly  Leu  Val  Phe  Asn  Asn  Ser  Val  Pro  Val  Gln  Asn  Pro  Lys  Gly
     610                   615                   620

Thr  Thr  Ser  Lys  Ile  Met  Val  Ser  Val  Trp  Ala  Phe  Phe  Ala  Val  Ile
625                      630                   635                        640

Phe  Leu  Ala  Ser  Tyr  Thr  Ala  Asn  Leu  Ala  Ala  Phe  Met  Ile  Gln  Glu
                    645                   650                   655

Glu  Phe  Val  Asp  Gln  Val  Thr  Gly  Leu  Ser  Asp  Lys  Lys  Phe  Gln  Arg
               660                   665                   670

Pro  His  Asp  Tyr  Ser  Pro  Pro  Phe  Arg  Phe  Gly  Thr  Val  Pro  Asn  Gly
               675                   680                   685

Ser  Thr  Glu  Arg  Asn  Ile  Arg  Asn  Asn  Tyr  Pro  Tyr  Met  His  Gln  Tyr
     690                   695                   700

Met  Thr  Lys  Phe  Asn  Gln  Lys  Gly  Val  Glu  Asp  Ala  Leu  Val  Ser  Leu
705                      710                   715                        720

Lys  Thr  Gly  Lys  Leu  Asp  Ala  Phe  Ile  Tyr  Asp  Ala  Ala  Val  Leu  Asn
                    725                   730                   735

Tyr  Lys  Ala  Gly  Arg  Asp  Glu  Gly  Cys  Lys  Leu  Val  Thr  Ile  Gly  Ser
               740                   745                   750

Gly  Tyr  Ile  Phe  Ala  Thr  Thr  Gly  Tyr  Gly  Ile  Ala  Leu  Gln  Lys  Gly
               755                   760                   765

Ser  Pro  Trp  Lys  Arg  Gln  Ile  Asp  Leu  Ala  Leu  Leu  Gln  Phe  Val  Gly
     770                   775                   780

Asp  Gly  Glu  Met  Glu  Glu  Leu  Glu  Thr  Leu  Trp  Leu  Thr  Gly  Ile  Cys
785                      790                   795                        800

His  Asn  Glu  Lys  Asn  Glu  Val  Met  Ser  Ser  Gln  Leu  Asp  Ile  Asp  Asn
                    805                   810                   815

Met  Ala  Gly  Val  Phe  Tyr  Met  Leu  Ala  Ala  Ala  Met  Ala  Leu  Ser  Leu
               820                   825                   830

Ile  Thr  Phe  Ile  Trp  Glu  His  Leu  Phe  Tyr  Trp  Lys  Leu  Arg  Phe  Cys
               835                   840                   845

Phe  Thr  Gly  Val  Cys  Ser  Asp  Arg  Pro  Gly  Leu  Leu  Phe  Ser  Ile  Ser
850                      855                   860

Arg  Gly  Ile  Tyr  Ser  Cys  Ile  His  Gly  Val  His  Ile  Glu  Glu  Lys  Lys
865                      870                   875                        880

Lys  Ser  Pro  Asp  Phe  Asn  Leu  Thr  Gly  Ser  Gln  Ser  Asn  Met  Leu  Lys
               885                   890                   895
```

```
Leu Leu Arg Ser Ala Lys Asn Ile Ser Ser Met Ser Asn Met Asn Ser
            900                 905                 910
Ser Arg Met Asp Ser Pro Lys Arg Ala Ala Asp Phe Ile Gln Arg Gly
            915                 920                 925
Ser Leu Ile Met Asp Met Val Ser Asp Lys Gly Asn Leu Met Tyr Ser
            930                 935                 940
Asp Asn Arg Ser Phe Gln Gly Lys Glu Ser Ile Phe Gly Asp Asn Met
945                 950                 955                 960
Asn Glu Leu Gln Thr Phe Val Ala Asn Arg Gln Lys Asp Asn Leu Asn
                965                 970                 975
Asn Tyr Val Phe Gln Gly Gln His Pro Leu Thr Leu Asn Glu Ser Asn
            980                 985                 990
Pro Asn Thr Val Glu Val Ala Val Ser Thr Glu Ser Lys Ala Asn Ser
            995                1000                1005
Arg Pro Arg Gln Leu Trp Lys Lys Ser Val Asp Ser Ile Arg Gln Asp
           1010                1015                1020
Ser Leu Ser Gln Asn Pro Val Ser Gln Arg Asp Glu Ala Thr Ala Glu
           1025                1030                1035                1040
Asn Arg Thr His Ser Leu Lys Ser Pro Arg Tyr Leu Pro Glu Glu Met
                1045                1050                1055
Ala His Ser Asp Ile Ser Glu Thr Ser Asn Arg Ala Thr Cys His Arg
                1060                1065                1070
Glu Pro Asp Asn Ser Lys Asn His Lys Thr Lys Asp Asn Phe Lys Arg
           1075                1080                1085
Ser Val Ala Ser Lys Tyr Pro Lys Asp Cys Ser Glu Val Glu Arg Thr
           1090                1095                1100
Tyr Leu Lys Thr Lys Ser Ser Ser Pro Arg Asp Lys Ile Tyr Thr Ile
1105                1110                1115                1120
Asp Gly Glu Lys Glu Pro Gly Phe His Leu Asp Pro Gln Phe Val
                1125                1130                1135
Glu Asn Val Thr Leu Pro Glu Asn Val Asp Phe Pro Asp Pro Tyr Gln
                1140                1145                1150
Asp Pro Ser Glu Asn Phe Arg Lys Gly Asp Ser Thr Leu Pro Met Asn
           1155                1160                1165
Arg Asn Pro Leu His Asn Glu Glu Gly Leu Ser Asn Asn Asp Gln Tyr
1170                1175                1180
Lys Leu Tyr Ser Lys His Phe Thr Leu Lys Asp Lys Gly Ser Pro His
1185                1190                1195                1200
Ser Glu Thr Ser Glu Arg Tyr Arg Gln Asn Ser Thr His Cys Arg Ser
                1205                1210                1215
Cys Leu Ser Asn Met Pro Thr Tyr Ser Gly His Phe Thr Met Arg Ser
                1220                1225                1230
Pro Phe Lys Cys Asp Ala Cys Leu Arg Met Gly Asn Leu Tyr Asp Ile
           1235                1240                1245
Asp Glu Asp Gln Met Leu Gln Glu Thr Gly Asn Pro Ala Thr Gly Glu
1250                1255                1260
Gln Val Tyr Gln Gln Asp Trp Ala Gln Asn Asn Ala Leu Gln Leu Gln
1265                1270                1275                1280
Lys Asn Lys Leu Arg Ile Ser Arg Gln His Ser Tyr Asp Asn Ile Val
                1285                1290                1295
Asp Lys Pro Arg Glu Leu Asp Leu Ser Arg Pro Ser Arg Ser Ile Ser
           1300                1305                1310
Leu Lys Asp Arg Glu Arg Leu Leu Glu Gly Asn Phe Tyr Gly Ser Leu
           1315                1320                1325
```

```
Phe  Ser  Val  Pro  Ser  Ser  Lys  Leu  Ser  Gly  Lys  Lys  Ser  Ser  Leu  Phe
          1330                 1335                1340

Pro  Gln  Gly  Leu  Glu  Asp  Ser  Lys  Arg  Ser  Lys  Ser  Leu  Leu  Pro  Asp
1345                     1350                1355                          1360

His  Thr  Ser  Asp  Asn  Pro  Phe  Leu  His  Ser  His  Arg  Asp  Asp  Gln  Arg
                    1365                     1370                     1375

Leu  Val  Ile  Gly  Arg  Cys  Pro  Ser  Asp  Pro  Tyr  Lys  His  Ser  Leu  Pro
               1380                     1385                     1390

Ser  Gln  Ala  Val  Asn  Asp  Ser  Tyr  Leu  Arg  Ser  Ser  Leu  Arg  Ser  Thr
               1395                     1400                     1405

Ala  Ser  Tyr  Cys  Ser  Arg  Asp  Ser  Arg  Gly  His  Asn  Asp  Val  Tyr  Ile
          1410                 1415                     1420

Ser  Glu  His  Val  Met  Pro  Tyr  Ala  Ala  Asn  Lys  Asn  Asn  Met  Tyr  Ser
1425                     1430                     1435                     1440

Thr  Pro  Arg  Val  Leu  Asn  Ser  Cys  Ser  Asn  Arg  Arg  Val  Tyr  Lys  Glu
                    1445                     1450                     1455

Met  Pro  Ser  Ile  Glu  Ser  Asp  Val
               1460
```

(2) INFORMATION FOR SEQ ID NO:12:

(i) SEQUENCE CHARACTERISTICS:
        (A) LENGTH: 74 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:12:

```
CGAGGGAGGC  GGCCGGCGCG  GACTCTCTTC  GCGGGCGCAG  CGCCCCTTCC  CCCTCGGACC        60

CTCCGGTGGA  CATG                                                              74
```

(2) INFORMATION FOR SEQ ID NO:13:

(i) SEQUENCE CHARACTERISTICS:
        (A) LENGTH: 3155 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 262..3030

(xi) SEQUENCE DESCRIPTION: SEQ ID NO:13:

```
CAAGCCGGGC  GTTCGGAGCT  GTGCCCGGCC  CCGCTTCAGC  ACCGCGGACA  GCGCCGGCCG        60

CGTGGGGCTG  AGCGCCGAGC  CCCCGCGCAC  GCTTCAGCCC  CCCTTCCCTC  GGCCGACGTC       120

CCGGGACCGC  CGCTCCGGGG  GAGACGTGGC  GTCCGCAGCC  CGCGGGCCG   GGCGAGCGCA       180

GGACGGCCCG  GAAGCCCCGC  GGGGGATGCG  CCGAGGGCCC  CGCGTTCGCG  CCGCGCAGAG       240

CCAGGCCCGC  GGCCCGAGCC  C  ATG  AGC  ACC  ATG  CGC  CTG  CTG  ACG  CTC  GCC   291
              Met  Ser  Thr  Met  Arg  Leu  Leu  Thr  Leu  Ala
                1                  5                        10

CTG  CTG  TTC  TCC  TGC  TCC  GTC  GCC  CGT  GCC  GCG  TGC  GAC  CCC  AAG  ATC   339
Leu  Leu  Phe  Ser  Cys  Ser  Val  Ala  Arg  Ala  Ala  Cys  Asp  Pro  Lys  Ile
               15                      20                      25

GTC  AAC  ATT  GGC  GCG  GTG  CTG  AGC  ACG  CGG  AAG  CAC  GAG  CAG  ATG  TTC   387
Val  Asn  Ile  Gly  Ala  Val  Leu  Ser  Thr  Arg  Lys  His  Glu  Gln  Met  Phe
```

-continued

| | | | 30 | | | | 35 | | | | 40 | | | | |
|---|---|---|---|---|---|---|---|---|---|---|---|---|---|---|---|
| CGC | GAG | GCC | GTG | AAC | CAG | GCC | AAC | AAG | CGG | CAC | GGC | TCC | TGG | AAG | ATT | 435
| Arg | Glu | Ala | Val | Asn | Gln | Ala | Asn | Lys | Arg | His | Gly | Ser | Trp | Lys | Ile |
| | | | 45 | | | | 50 | | | | 55 | | | | |

| CAG | CTC | AAT | GCC | ACC | TCC | GTC | ACG | CAC | AAG | CCC | AAC | GCC | ATC | CAG | ATG | 483
| Gln | Leu | Asn | Ala | Thr | Ser | Val | Thr | His | Lys | Pro | Asn | Ala | Ile | Gln | Met |
| | 60 | | | | 65 | | | | 70 | | | | | | |

| GCT | CTG | TCG | GTG | TGC | GAG | GAC | CTC | ATC | TCC | AGC | CAG | GTC | TAC | GCC | ATC | 531
| Ala | Leu | Ser | Val | Cys | Glu | Asp | Leu | Ile | Ser | Ser | Gln | Val | Tyr | Ala | Ile |
| 75 | | | | 80 | | | | 85 | | | | | | | 90 |

| CTA | GTT | AGC | CAT | CCA | CCT | ACC | CCC | AAC | GAC | CAC | TTC | ACT | CCC | ACC | CCT | 579
| Leu | Val | Ser | His | Pro | Pro | Thr | Pro | Asn | Asp | His | Phe | Thr | Pro | Thr | Pro |
| | | | | 95 | | | | | 100 | | | | | 105 | |

| GTC | TCC | TAC | ACA | GCC | GGC | TTC | TAC | CGC | ATA | CCC | GTG | CTG | GGG | CTG | ACC | 627
| Val | Ser | Tyr | Thr | Ala | Gly | Phe | Tyr | Arg | Ile | Pro | Val | Leu | Gly | Leu | Thr |
| | | | 110 | | | | | 115 | | | | | 120 | | |

| ACC | CGC | ATG | TCC | ATC | TAC | TCG | GAC | AAG | AGC | ATC | CAC | CTG | AGC | TTC | CTG | 675
| Thr | Arg | Met | Ser | Ile | Tyr | Ser | Asp | Lys | Ser | Ile | His | Leu | Ser | Phe | Leu |
| | | 125 | | | | | 130 | | | | | 135 | | | |

| CGC | ACC | GTG | CCG | CCC | TAC | TCC | CAC | CAG | TCC | AGC | GTG | TGG | TTT | GAG | ATG | 723
| Arg | Thr | Val | Pro | Pro | Tyr | Ser | His | Gln | Ser | Ser | Val | Trp | Phe | Glu | Met |
| 140 | | | | | 145 | | | | | 150 | | | | | |

| ATG | CGT | GTC | TAC | AGC | TGG | AAC | CAC | ATC | ATC | CTG | CTG | GTC | AGC | GAC | GAC | 771
| Met | Arg | Val | Tyr | Ser | Trp | Asn | His | Ile | Ile | Leu | Leu | Val | Ser | Asp | Asp |
| 155 | | | | | 160 | | | | | 165 | | | | | 170 |

| CAC | GAG | GGC | CGG | GCG | GCT | CAG | AAA | CGC | CTG | GAG | ACG | CTG | CTG | GAG | GAG | 819
| His | Glu | Gly | Arg | Ala | Ala | Gln | Lys | Arg | Leu | Glu | Thr | Leu | Leu | Glu | Glu |
| | | | | 175 | | | | | 180 | | | | | 185 | |

| CGT | GAG | TCC | AAG | GCA | GAG | AAG | GTG | CTG | CAG | TTT | GAC | CCA | GGG | ACC | AAG | 867
| Arg | Glu | Ser | Lys | Ala | Glu | Lys | Val | Leu | Gln | Phe | Asp | Pro | Gly | Thr | Lys |
| | | | 190 | | | | | 195 | | | | | 200 | | |

| AAC | GTG | ACG | GCC | CTG | CTG | ATG | GAG | GCG | AAA | GAG | CTG | GAG | GCC | CGG | GTC | 915
| Asn | Val | Thr | Ala | Leu | Leu | Met | Glu | Ala | Lys | Glu | Leu | Glu | Ala | Arg | Val |
| | | 205 | | | | | 210 | | | | | 215 | | | |

| ATC | ATC | CTT | TCT | GCC | AGC | GAG | GAC | GAT | GCT | GCC | ACT | GTA | TAC | CGC | GCA | 963
| Ile | Ile | Leu | Ser | Ala | Ser | Glu | Asp | Asp | Ala | Ala | Thr | Val | Tyr | Arg | Ala |
| 220 | | | | | 225 | | | | | 230 | | | | | |

| GCC | GCG | ATG | CTG | AAC | ATG | ACG | GGC | TCC | GGG | TAC | GTG | TGG | CTG | GTC | GGC | 1011
| Ala | Ala | Met | Leu | Asn | Met | Thr | Gly | Ser | Gly | Tyr | Val | Trp | Leu | Val | Gly |
| 235 | | | | 240 | | | | | 245 | | | | | | 250 |

| GAG | CGC | GAG | ATC | TCG | GGG | AAC | GCC | CTG | CGC | TAC | GCC | CCA | GAC | GGC | ATC | 1059
| Glu | Arg | Glu | Ile | Ser | Gly | Asn | Ala | Leu | Arg | Tyr | Ala | Pro | Asp | Gly | Ile |
| | | | | 255 | | | | | 260 | | | | | 265 | |

| CTC | GGG | CTG | CAG | CTC | ATC | AAC | GGC | AAG | AAC | GAG | TCG | GCC | CAC | ATC | AGC | 1107
| Leu | Gly | Leu | Gln | Leu | Ile | Asn | Gly | Lys | Asn | Glu | Ser | Ala | His | Ile | Ser |
| | | | 270 | | | | | 275 | | | | | 280 | | |

| GAC | GCC | GTG | GGC | GTG | GTG | GCC | CAG | GCC | GTG | CAC | GAG | CTC | CTC | GAG | AAG | 1155
| Asp | Ala | Val | Gly | Val | Val | Ala | Gln | Ala | Val | His | Glu | Leu | Leu | Glu | Lys |
| | | | 285 | | | | | 290 | | | | | 295 | | |

| GAG | AAC | ATC | ACC | GAC | CCG | CCG | CGG | GGC | TGC | GTG | GGC | AAC | ACC | AAC | ATC | 1203
| Glu | Asn | Ile | Thr | Asp | Pro | Pro | Arg | Gly | Cys | Val | Gly | Asn | Thr | Asn | Ile |
| | | 300 | | | | | 305 | | | | | 310 | | | |

| TGG | AAG | ACC | GGG | CCG | CTC | TTC | AAG | AGA | GTG | CTG | ATG | TCT | TCC | AAG | TAT | 1251
| Trp | Lys | Thr | Gly | Pro | Leu | Phe | Lys | Arg | Val | Leu | Met | Ser | Ser | Lys | Tyr |
| 315 | | | | | 320 | | | | | 325 | | | | | 330 |

| GCG | GAT | GGG | GTG | ACT | GGT | CGC | GTG | GAG | TTC | AAT | GAG | GAT | GGG | GAC | CGG | 1299
| Ala | Asp | Gly | Val | Thr | Gly | Arg | Val | Glu | Phe | Asn | Glu | Asp | Gly | Asp | Arg |
| | | | | 335 | | | | | 340 | | | | | 345 | |

| AAG | TTC | GCC | AAC | TAC | AGC | ATC | ATG | AAC | CTG | CAG | AAC | CGC | AAG | CTG | GTG | 1347
| Lys | Phe | Ala | Asn | Tyr | Ser | Ile | Met | Asn | Leu | Gln | Asn | Arg | Lys | Leu | Val |

```
            350                          355                          360
CAA GTG GGC ATC TAC AAT GGC ACC CAC GTC ATC CCT AAT GAC AGG AAG        1395
Gln Val Gly Ile Tyr Asn Gly Thr His Val Ile Pro Asn Asp Arg Lys
        365                      370                      375

ATC ATC TGG CCA GGC GGA GAG ACA GAG AAG CCT CGA GGG TAC CAG ATG        1443
Ile Ile Trp Pro Gly Gly Glu Thr Glu Lys Pro Arg Gly Tyr Gln Met
        380                      385                      390

TCC ACC AGA CTG AAG ATT GTG ACG ATC CAC CAG GAG CCC TTC GTG TAC        1491
Ser Thr Arg Leu Lys Ile Val Thr Ile His Gln Glu Pro Phe Val Tyr
395                      400                      405                      410

GTC AAG CCC ACG CTG AGT GAT GGG ACA TGC AAG GAG GAG TTC ACA GTC        1539
Val Lys Pro Thr Leu Ser Asp Gly Thr Cys Lys Glu Glu Phe Thr Val
                         415                      420                      425

AAC GGC GAC CCA GTC AAG AAG GTG ATC TGC ACC GGG CCC AAC GAC ACG        1587
Asn Gly Asp Pro Val Lys Lys Val Ile Cys Thr Gly Pro Asn Asp Thr
                 430                      435                      440

TCG CCG GGC AGC CCC CGC CAC ACG GTG CCT CAG TGT TGC TAC GGC TTT        1635
Ser Pro Gly Ser Pro Arg His Thr Val Pro Gln Cys Cys Tyr Gly Phe
             445                      450                      455

TGC ATC GAC CTG CTC ATC AAG CTG GCA CGG ACC ATG AAC TTC ACC TAC        1683
Cys Ile Asp Leu Leu Ile Lys Leu Ala Arg Thr Met Asn Phe Thr Tyr
460                      465                      470

GAG GTG CAC CTG GTG GCA GAT GGC AAG TTC GGC ACA CAG GAG CGG GTG        1731
Glu Val His Leu Val Ala Asp Gly Lys Phe Gly Thr Gln Glu Arg Val
475                      480                      485                      490

AAC AAC AGC AAC AAG AAG GAG TGG AAT GGG ATG ATG GGC GAG CTG CTC        1779
Asn Asn Ser Asn Lys Lys Glu Trp Asn Gly Met Met Gly Glu Leu Leu
                 495                      500                      505

AGC GGG CAG GCA GAC ATG ATC GTG GCG CCG CTA ACC ATA AAC AAC GAG        1827
Ser Gly Gln Ala Asp Met Ile Val Ala Pro Leu Thr Ile Asn Asn Glu
             510                      515                      520

CGC GCG CAG TAC ATC GAG TTT TCC AAG CCC TTC AAG TAC CAG GGC CTG        1875
Arg Ala Gln Tyr Ile Glu Phe Ser Lys Pro Phe Lys Tyr Gln Gly Leu
         525                      530                      535

ACT ATT CTG GTC AAG AAG GAG ATT CCC CGG AGC ACG CTG GAC TCG TTC        1923
Thr Ile Leu Val Lys Lys Glu Ile Pro Arg Ser Thr Leu Asp Ser Phe
540                      545                      550

ATG CAG CCG TTC CAG AGC ACA CTG TGG CTG CTG GTG GGG CTG TCG GTG        1971
Met Gln Pro Phe Gln Ser Thr Leu Trp Leu Leu Val Gly Leu Ser Val
555                      560                      565                      570

CAC GTG GTG GCC GTG ATG CTG TAC CTG CTG GAC CGC TTC AGC CCC TTC        2019
His Val Val Ala Val Met Leu Tyr Leu Leu Asp Arg Phe Ser Pro Phe
                 575                      580                      585

GGC CGG TTC AAG GTG AAC AGC GAG GAG GAG GAG GAG GAC GCA CTG ACC        2067
Gly Arg Phe Lys Val Asn Ser Glu Glu Glu Glu Glu Asp Ala Leu Thr
             590                      595                      600

CTG TCC TCG GCC ATG TGG TTC TCC TGG GGC GTC CTG CTC AAC TCC GGC        2115
Leu Ser Ser Ala Met Trp Phe Ser Trp Gly Val Leu Leu Asn Ser Gly
         605                      610                      615

ATC GGG GAA GGC GCC CCC AGA AGC TTC TCA GCG CGC ATC CTG GGC ATG        2163
Ile Gly Glu Gly Ala Pro Arg Ser Phe Ser Ala Arg Ile Leu Gly Met
620                      625                      630

GTG TGG GCC GGC TTT GCC ATG ATC ATC GTG GCC TCC TAC ACC GCC AAC        2211
Val Trp Ala Gly Phe Ala Met Ile Ile Val Ala Ser Tyr Thr Ala Asn
635                      640                      645                      650

CTG GCG GCC TTC CTG GTG CTG GAC CGG CCG GAG GAG CGC ATC ACG GGC        2259
Leu Ala Ala Phe Leu Val Leu Asp Arg Pro Glu Glu Arg Ile Thr Gly
                 655                      660                      665

ATC AAC GAC CCT CGG CTG AGG AAC CCC TCG GAC AAG TTT ATC TAC GCC        2307
Ile Asn Asp Pro Arg Leu Arg Asn Pro Ser Asp Lys Phe Ile Tyr Ala
```

|   |   |   |   |   | 670 |   |   |   |   | 675 |   |   |   |   | 680 |   |   |   |      |
|---|---|---|---|---|---|---|---|---|---|---|---|---|---|---|---|---|---|---|------|
|ACG|GTG|AAG|CAG|AGC|TCC|GTG|GAT|ATC|TAC|TTC|CGG|CGC|CAG|GTG|GAG|   |   |   | 2355 |
|Thr|Val|Lys|Gln|Ser|Ser|Val|Asp|Ile|Tyr|Phe|Arg|Arg|Gln|Val|Glu|   |   |   |      |
|   |   |685|   |   |   |   |690|   |   |   |   |695|   |   |   |   |   |   |      |
|CTG|AGC|ACC|ATG|TAC|CGG|CAT|ATG|GAG|AAG|CAC|AAC|TAC|GAG|AGT|GCG|   |   |   | 2403 |
|Leu|Ser|Thr|Met|Tyr|Arg|His|Met|Glu|Lys|His|Asn|Tyr|Glu|Ser|Ala|   |   |   |      |
|   |700|   |   |   |   |705|   |   |   |   |710|   |   |   |   |   |   |   |      |
|GCG|GAG|GCC|ATC|CAG|GCC|GTG|AGA|GAC|AAC|AAG|CTG|CAT|GCC|TTC|ATC|   |   |   | 2451 |
|Ala|Glu|Ala|Ile|Gln|Ala|Val|Arg|Asp|Asn|Lys|Leu|His|Ala|Phe|Ile|   |   |   |      |
|715|   |   |   |   |720|   |   |   |   |725|   |   |   |   |730|   |   |   |      |
|TGG|GAC|TCG|GCG|GTG|CTG|GAG|TTC|GAG|GCC|TCG|CAG|AAG|TGC|GAC|CTG|   |   |   | 2499 |
|Trp|Asp|Ser|Ala|Val|Leu|Glu|Phe|Glu|Ala|Ser|Gln|Lys|Cys|Asp|Leu|   |   |   |      |
|   |   |   |   |735|   |   |   |   |740|   |   |   |   |745|   |   |   |   |      |
|GTG|ACG|ACT|GGA|GAG|CTG|TTT|TTC|CGC|TCG|GGC|TTC|GGC|ATA|GGC|ATG|   |   |   | 2547 |
|Val|Thr|Thr|Gly|Glu|Leu|Phe|Phe|Arg|Ser|Gly|Phe|Gly|Ile|Gly|Met|   |   |   |      |
|   |   |   |750|   |   |   |   |755|   |   |   |   |760|   |   |   |   |   |      |
|CGC|AAA|GAC|AGC|CCC|TGG|AAG|CAG|AAC|GTC|TCC|CTG|TCC|ATC|CTC|AAG|   |   |   | 2595 |
|Arg|Lys|Asp|Ser|Pro|Trp|Lys|Gln|Asn|Val|Ser|Leu|Ser|Ile|Leu|Lys|   |   |   |      |
|   |   |765|   |   |   |   |770|   |   |   |   |775|   |   |   |   |   |   |      |
|TCC|CAC|GAG|AAT|GGC|TTC|ATG|GAA|GAC|CTG|GAC|AAG|ACG|TGG|GTT|CGG|   |   |   | 2643 |
|Ser|His|Glu|Asn|Gly|Phe|Met|Glu|Asp|Leu|Asp|Lys|Thr|Trp|Val|Arg|   |   |   |      |
|   |780|   |   |   |   |785|   |   |   |   |790|   |   |   |   |   |   |   |      |
|TAT|CAG|GAA|TGT|GAC|TCG|CGC|AGC|AAC|GCC|CCT|GCG|ACC|CTT|ACT|TTT|   |   |   | 2691 |
|Tyr|Gln|Glu|Cys|Asp|Ser|Arg|Ser|Asn|Ala|Pro|Ala|Thr|Leu|Thr|Phe|   |   |   |      |
|795|   |   |   |   |800|   |   |   |   |805|   |   |   |   |810|   |   |   |      |
|GAG|AAC|ATG|GCC|GGG|GTC|TTC|ATG|CTG|GTA|GCT|GGG|GGC|ATC|GTG|GCC|   |   |   | 2739 |
|Glu|Asn|Met|Ala|Gly|Val|Phe|Met|Leu|Val|Ala|Gly|Gly|Ile|Val|Ala|   |   |   |      |
|   |   |   |   |815|   |   |   |   |820|   |   |   |   |825|   |   |   |   |      |
|GGG|ATC|TTC|CTG|ATT|TTC|ATC|GAG|ATT|GCC|TAC|AAG|CGG|CAC|AAG|GAT|   |   |   | 2787 |
|Gly|Ile|Phe|Leu|Ile|Phe|Ile|Glu|Ile|Ala|Tyr|Lys|Arg|His|Lys|Asp|   |   |   |      |
|   |   |   |830|   |   |   |   |835|   |   |   |   |840|   |   |   |   |   |      |
|GCT|CGC|CGG|AAG|CAG|ATG|CAG|CTG|GCC|TTT|GCC|GCC|GTT|AAC|GTG|TGG|   |   |   | 2835 |
|Ala|Arg|Arg|Lys|Gln|Met|Gln|Leu|Ala|Phe|Ala|Ala|Val|Asn|Val|Trp|   |   |   |      |
|   |   |845|   |   |   |   |850|   |   |   |   |855|   |   |   |   |   |   |      |
|CGG|AAG|AAC|CTG|CAG|GAT|AGA|AAG|AGT|GGT|AGA|GCA|GAG|CCT|GAC|CCT|   |   |   | 2883 |
|Arg|Lys|Asn|Leu|Gln|Asp|Arg|Lys|Ser|Gly|Arg|Ala|Glu|Pro|Asp|Pro|   |   |   |      |
|   |860|   |   |   |   |865|   |   |   |   |870|   |   |   |   |   |   |   |      |
|AAA|AAG|AAA|GCC|ACA|TTT|AGG|GCT|ATC|ACC|TCC|ACC|CTG|GCT|TCC|AGC|   |   |   | 2931 |
|Lys|Lys|Lys|Ala|Thr|Phe|Arg|Ala|Ile|Thr|Ser|Thr|Leu|Ala|Ser|Ser|   |   |   |      |
|875|   |   |   |   |880|   |   |   |   |885|   |   |   |   |890|   |   |   |      |
|TTC|AAG|AGG|CGT|AGG|TCC|TCC|AAA|GAC|ACG|CAG|TAC|CAT|CCC|ACT|GAT|   |   |   | 2979 |
|Phe|Lys|Arg|Arg|Arg|Ser|Ser|Lys|Asp|Thr|Gln|Tyr|His|Pro|Thr|Asp|   |   |   |      |
|   |   |   |   |895|   |   |   |   |900|   |   |   |   |905|   |   |   |   |      |
|ATC|ACG|GGC|CCG|CTC|AAC|CTC|TCA|GAT|CCC|TCG|GTC|AGC|ACC|GTG|GTG|   |   |   | 3027 |
|Ile|Thr|Gly|Pro|Leu|Asn|Leu|Ser|Asp|Pro|Ser|Val|Ser|Thr|Val|Val|   |   |   |      |
|   |   |   |910|   |   |   |   |915|   |   |   |   |920|   |   |   |   |   |      |

TGAGGCCCCC GGAGGCGCCC ACCTGCCCAG TTAGCCCGGC CAAGGACACT GATGGGTCCT         3087

GCTGCTCGGG AAGGCCTGAG GGAAGCCCAC CCGCCCAGA GACTGCCCAC CCTGGGCCTC         3147

CCGTCCGT                                                                 3155

( 2 ) INFORMATION FOR SEQ ID NO:14:

( i ) SEQUENCE CHARACTERISTICS:
        ( A ) LENGTH: 922 amino acids
        ( B ) TYPE: amino acid
        ( D ) TOPOLOGY: linear ( i i ) MOLECULE TYPE: protein ( x i ) SEQUENCE DESCRIPTION: SEQ ID NO:14:

| | | | | | | | | | | | | | | |
|---|---|---|---|---|---|---|---|---|---|---|---|---|---|---|
|Met|Ser|Thr|Met|Arg|Leu|Leu|Thr|Leu|Ala|Leu|Leu|Phe|Ser|Cys|Ser|
|1| | | |5| | | | |10| | | | |15|
|Val|Ala|Arg|Ala|Ala|Cys|Asp|Pro|Lys|Ile|Val|Asn|Ile|Gly|Ala|Val|
| | | |20| | | |25| | | | |30| | |
|Leu|Ser|Thr|Arg|Lys|His|Glu|Gln|Met|Phe|Arg|Glu|Ala|Val|Asn|Gln|
| | |35| | | | |40| | | | |45| | |
|Ala|Asn|Lys|Arg|His|Gly|Ser|Trp|Lys|Ile|Gln|Leu|Asn|Ala|Thr|Ser|
| |50| | | | |55| | | | |60| | | |
|Val|Thr|His|Lys|Pro|Asn|Ala|Ile|Gln|Met|Ala|Leu|Ser|Val|Cys|Glu|
|65| | | | |70| | | | |75| | | | |80|
|Asp|Leu|Ile|Ser|Ser|Gln|Val|Tyr|Ala|Ile|Leu|Val|Ser|His|Pro|Pro|
| | | | |85| | | | |90| | | | |95| |
|Thr|Pro|Asn|Asp|His|Phe|Thr|Pro|Thr|Pro|Val|Ser|Tyr|Thr|Ala|Gly|
| | | |100| | | |105| | | | |110| | |
|Phe|Tyr|Arg|Ile|Pro|Val|Leu|Gly|Leu|Thr|Thr|Arg|Met|Ser|Ile|Tyr|
| | |115| | | |120| | | | |125| | | |
|Ser|Asp|Lys|Ser|Ile|His|Leu|Ser|Phe|Leu|Arg|Thr|Val|Pro|Pro|Tyr|
| |130| | | |135| | | | |140| | | | |
|Ser|His|Gln|Ser|Ser|Val|Trp|Phe|Glu|Met|Met|Arg|Val|Tyr|Ser|Trp|
|145| | | |150| | | | |155| | | | |160|
|Asn|His|Ile|Ile|Leu|Leu|Val|Ser|Asp|Asp|His|Glu|Gly|Arg|Ala|Ala|
| | | |165| | | | |170| | | | |175| | |
|Gln|Lys|Arg|Leu|Glu|Thr|Leu|Leu|Glu|Glu|Arg|Glu|Ser|Lys|Ala|Glu|
| | | |180| | | | |185| | | | |190| | |
|Lys|Val|Leu|Gln|Phe|Asp|Pro|Gly|Thr|Lys|Asn|Val|Thr|Ala|Leu|Leu|
| | |195| | | |200| | | | |205| | | |
|Met|Glu|Ala|Lys|Glu|Leu|Glu|Ala|Arg|Val|Ile|Ile|Leu|Ser|Ala|Ser|
| |210| | | |215| | | | |220| | | | |
|Glu|Asp|Asp|Ala|Ala|Thr|Val|Tyr|Arg|Ala|Ala|Ala|Met|Leu|Asn|Met|
|225| | | |230| | | | |235| | | | |240|
|Thr|Gly|Ser|Gly|Tyr|Val|Trp|Leu|Val|Gly|Glu|Arg|Glu|Ile|Ser|Gly|
| | | |245| | | | |250| | | | |255| |
|Asn|Ala|Leu|Arg|Tyr|Ala|Pro|Asp|Gly|Ile|Leu|Gly|Leu|Gln|Leu|Ile|
| | |260| | | |265| | | | |270| | | |
|Asn|Gly|Lys|Asn|Glu|Ser|Ala|His|Ile|Ser|Asp|Ala|Val|Gly|Val|Val|
| |275| | | | |280| | | | |285| | | |
|Ala|Gln|Ala|Val|His|Glu|Leu|Leu|Glu|Lys|Glu|Asn|Ile|Thr|Asp|Pro|
|290| | | | |295| | | | |300| | | | |
|Pro|Arg|Gly|Cys|Val|Gly|Asn|Thr|Asn|Ile|Trp|Lys|Thr|Gly|Pro|Leu|
|305| | | |310| | | |315| | | | |320|
|Phe|Lys|Arg|Val|Leu|Met|Ser|Ser|Lys|Tyr|Ala|Asp|Gly|Val|Thr|Gly|
| | | |325| | | | |330| | | | |335| |
|Arg|Val|Glu|Phe|Asn|Glu|Asp|Gly|Asp|Arg|Lys|Phe|Ala|Asn|Tyr|Ser|
| | |340| | | |345| | | | |350| | | |
|Ile|Met|Asn|Leu|Gln|Asn|Arg|Lys|Leu|Val|Gln|Val|Gly|Ile|Tyr|Asn|
| |355| | | | |360| | | | |365| | | |
|Gly|Thr|His|Val|Ile|Pro|Asn|Asp|Arg|Lys|Ile|Ile|Trp|Pro|Gly|Gly|
|370| | | | |375| | | | |380| | | | |
|Glu|Thr|Glu|Lys|Pro|Arg|Gly|Tyr|Gln|Met|Ser|Thr|Arg|Leu|Lys|Ile|
|385| | | |390| | | | |395| | | | |400|
|Val|Thr|Ile|His|Gln|Glu|Pro|Phe|Val|Tyr|Val|Lys|Pro|Thr|Leu|Ser|
| | | |405| | | |410| | | | |415| | |
|Asp|Gly|Thr|Cys|Lys|Glu|Glu|Phe|Thr|Val|Asn|Gly|Asp|Pro|Val|Lys|
| | |420| | | |425| | | | |430| | | |

```
Lys  Val  Ile  Cys  Thr  Gly  Pro  Asn  Asp  Thr  Ser  Pro  Gly  Ser  Pro  Arg
          435                     440                     445

His  Thr  Val  Pro  Gln  Cys  Cys  Tyr  Gly  Phe  Cys  Ile  Asp  Leu  Leu  Ile
     450                     455                     460

Lys  Leu  Ala  Arg  Thr  Met  Asn  Phe  Thr  Tyr  Glu  Val  His  Leu  Val  Ala
465                      470                     475                          480

Asp  Gly  Lys  Phe  Gly  Thr  Gln  Glu  Arg  Val  Asn  Asn  Ser  Asn  Lys  Lys
                    485                     490                          495

Glu  Trp  Asn  Gly  Met  Met  Gly  Glu  Leu  Leu  Ser  Gly  Gln  Ala  Asp  Met
               500                     505                     510

Ile  Val  Ala  Pro  Leu  Thr  Ile  Asn  Asn  Glu  Arg  Ala  Gln  Tyr  Ile  Glu
               515                     520                     525

Phe  Ser  Lys  Pro  Phe  Lys  Tyr  Gln  Gly  Leu  Thr  Ile  Leu  Val  Lys  Lys
          530                     535                     540

Glu  Ile  Pro  Arg  Ser  Thr  Leu  Asp  Ser  Phe  Met  Gln  Pro  Phe  Gln  Ser
545                      550                     555                          560

Thr  Leu  Trp  Leu  Leu  Val  Gly  Leu  Ser  Val  His  Val  Val  Ala  Val  Met
                    565                     570                     575

Leu  Tyr  Leu  Leu  Asp  Arg  Phe  Ser  Pro  Phe  Gly  Arg  Phe  Lys  Val  Asn
               580                     585                     590

Ser  Glu  Glu  Glu  Glu  Asp  Ala  Leu  Thr  Leu  Ser  Ser  Ala  Met  Trp
          595                     600                     605

Phe  Ser  Trp  Gly  Val  Leu  Leu  Asn  Ser  Gly  Ile  Gly  Glu  Gly  Ala  Pro
          610                     615                     620

Arg  Ser  Phe  Ser  Ala  Arg  Ile  Leu  Gly  Met  Val  Trp  Ala  Gly  Phe  Ala
625                      630                     635                          640

Met  Ile  Ile  Val  Ala  Ser  Tyr  Thr  Ala  Asn  Leu  Ala  Ala  Phe  Leu  Val
               645                     650                     655

Leu  Asp  Arg  Pro  Glu  Glu  Arg  Ile  Thr  Gly  Ile  Asn  Asp  Pro  Arg  Leu
               660                     665                     670

Arg  Asn  Pro  Ser  Asp  Lys  Phe  Ile  Tyr  Ala  Thr  Val  Lys  Gln  Ser  Ser
          675                     680                     685

Val  Asp  Ile  Tyr  Phe  Arg  Arg  Gln  Val  Glu  Leu  Ser  Thr  Met  Tyr  Arg
     690                     695                     700

His  Met  Glu  Lys  His  Asn  Tyr  Glu  Ser  Ala  Ala  Glu  Ala  Ile  Gln  Ala
705                      710                     715                          720

Val  Arg  Asp  Asn  Lys  Leu  His  Ala  Phe  Ile  Trp  Asp  Ser  Ala  Val  Leu
               725                     730                     735

Glu  Phe  Glu  Ala  Ser  Gln  Lys  Cys  Asp  Leu  Val  Thr  Thr  Gly  Glu  Leu
               740                     745                     750

Phe  Phe  Arg  Ser  Gly  Phe  Gly  Ile  Gly  Met  Arg  Lys  Asp  Ser  Pro  Trp
          755                     760                     765

Lys  Gln  Asn  Val  Ser  Leu  Ser  Ile  Leu  Lys  Ser  His  Glu  Asn  Gly  Phe
     770                     775                     780

Met  Glu  Asp  Leu  Asp  Lys  Thr  Trp  Val  Arg  Tyr  Gln  Glu  Cys  Asp  Ser
785                      790                     795                          800

Arg  Ser  Asn  Ala  Pro  Ala  Thr  Leu  Thr  Phe  Glu  Asn  Met  Ala  Gly  Val
               805                     810                     815

Phe  Met  Leu  Val  Ala  Gly  Gly  Ile  Val  Ala  Gly  Ile  Phe  Leu  Ile  Phe
               820                     825                     830

Ile  Glu  Ile  Ala  Tyr  Lys  Arg  His  Lys  Asp  Ala  Arg  Arg  Lys  Gln  Met
          835                     840                     845

Gln  Leu  Ala  Phe  Ala  Ala  Val  Asn  Val  Trp  Arg  Lys  Asn  Leu  Gln  Asp
```

```
                        850                             855                             860
Arg  Lys  Ser  Gly  Arg  Ala  Glu  Pro  Asp  Pro  Lys  Lys  Lys  Ala  Thr  Phe
865                      870                           875                           880

Arg  Ala  Ile  Thr  Ser  Thr  Leu  Ala  Ser  Ser  Phe  Lys  Arg  Arg  Arg  Ser
               885                      890                           895

Ser  Lys  Asp  Thr  Gln  Tyr  His  Pro  Thr  Asp  Ile  Thr  Gly  Pro  Leu  Asn
               900                      905                      910

Leu  Ser  Asp  Pro  Ser  Val  Ser  Thr  Val  Val
               915                      920
```

( 2 ) INFORMATION FOR SEQ ID NO:15:

( i ) SEQUENCE CHARACTERISTICS:
        ( A ) LENGTH: 2540 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 1..2334

( x i ) SEQUENCE DESCRIPTION: SEQ ID NO:15:

```
AAC  GAC  CAC  TTC  ACT  CCC  ACC  CCT  GTC  TCC  TAC  ACA  GCC  GGC  TTC  TAC       48
Asn  Asp  His  Phe  Thr  Pro  Thr  Pro  Val  Ser  Tyr  Thr  Ala  Gly  Phe  Tyr
 1                        5                        10                       15

CGC  ATA  CCC  GTG  CTG  GGG  CTG  ACC  ACC  CGC  ATG  TCC  ATC  TAC  TCG  GAC       96
Arg  Ile  Pro  Val  Leu  Gly  Leu  Thr  Thr  Arg  Met  Ser  Ile  Tyr  Ser  Asp
                20                        25                       30

AAG  AGC  ATC  CAC  CTG  AGC  TTC  CTG  CGC  ACC  GTG  CCG  CCC  TAC  TCC  CAC      144
Lys  Ser  Ile  His  Leu  Ser  Phe  Leu  Arg  Thr  Val  Pro  Pro  Tyr  Ser  His
           35                        40                       45

CAG  TCC  AGC  GTG  TGG  TTT  GAG  ATG  ATG  CGT  GTC  TAC  AGC  TGG  AAC  CAC      192
Gln  Ser  Ser  Val  Trp  Phe  Glu  Met  Met  Arg  Val  Tyr  Ser  Trp  Asn  His
           50                        55                       60

ATC  ATC  CTG  CTG  GTC  AGC  GAC  GAC  CAC  GAG  GGC  CGG  GCG  GCT  CAG  AAA      240
Ile  Ile  Leu  Leu  Val  Ser  Asp  Asp  His  Glu  Gly  Arg  Ala  Ala  Gln  Lys
 65                       70                       75                       80

CGC  CTG  GAG  ACG  CTG  CTG  GAG  GAG  CGT  GAG  TCC  AAG  AGT  AAA  AAA  AGG      288
Arg  Leu  Glu  Thr  Leu  Leu  Glu  Glu  Arg  Glu  Ser  Lys  Ser  Lys  Lys  Arg
                85                       90                       95

AAC  TAT  GAA  AAC  CTC  GAC  CAA  CTG  TCC  TAT  GAC  AAC  AAG  CGC  GGA  CCC      336
Asn  Tyr  Glu  Asn  Leu  Asp  Gln  Leu  Ser  Tyr  Asp  Asn  Lys  Arg  Gly  Pro
                100                      105                      110

AAG  GCA  GAG  AAG  GTG  CTG  CAG  TTT  GAC  CCA  GGG  ACC  AAG  AAC  GTG  ACG      384
Lys  Ala  Glu  Lys  Val  Leu  Gln  Phe  Asp  Pro  Gly  Thr  Lys  Asn  Val  Thr
          115                       120                      125

GCC  CTG  CTG  ATG  GAG  GCG  AAA  GAG  CTG  GAG  GCC  CGG  GTC  ATC  ATC  CTT      432
Ala  Leu  Leu  Met  Glu  Ala  Lys  Glu  Leu  Glu  Ala  Arg  Val  Ile  Ile  Leu
          130                       135                      140

TCT  GCC  AGC  GAG  GAC  GAT  GCT  GCC  ACT  GTA  TAC  CGC  GCA  GCC  GCG  ATG      480
Ser  Ala  Ser  Glu  Asp  Asp  Ala  Ala  Thr  Val  Tyr  Arg  Ala  Ala  Ala  Met
145                       150                      155                      160

CTG  AAC  ATG  ACG  GGC  AAC  ACC  AAC  ATC  TGG  AAG  ACC  GGG  CCG  CTC  TTC      528
Leu  Asn  Met  Thr  Gly  Asn  Thr  Asn  Ile  Trp  Lys  Thr  Gly  Pro  Leu  Phe
                     165                      170                      175

AAG  AGA  GTG  CTG  ATG  TCT  TCC  AAG  TAT  GCG  GAT  GGG  GTG  ACT  GGT  CGC      576
Lys  Arg  Val  Leu  Met  Ser  Ser  Lys  Tyr  Ala  Asp  Gly  Val  Thr  Gly  Arg
                     180                      185                      190

GTG  GAG  TTC  AAT  GAG  GAT  GGG  GAC  CGG  AAG  TTC  GCC  AAC  TAC  AGC  ATC      624
```

|     |     |     |     |     |     |     |     |     |     |     |     |     |     |     |     |      |
|-----|-----|-----|-----|-----|-----|-----|-----|-----|-----|-----|-----|-----|-----|-----|-----|------|
| Val | Glu | Phe | Asn | Glu | Asp | Gly | Asp | Arg | Lys | Phe | Ala | Asn | Tyr | Ser | Ile |      |
|     | 195 |     |     |     |     | 200 |     |     |     |     | 205 |     |     |     |     |      |
| ATG | AAC | CTG | CAG | AAC | CGC | AAG | CTG | GTG | CAA | GTG | GGC | ATC | TAC | AAT | GGC | 672  |
| Met | Asn | Leu | Gln | Asn | Arg | Lys | Leu | Val | Gln | Val | Gly | Ile | Tyr | Asn | Gly |      |
|     | 210 |     |     |     | 215 |     |     |     |     | 220 |     |     |     |     |     |      |
| ACC | CAC | GTC | ATC | CCT | AAT | GAC | AGG | AAG | ATC | ATC | TGG | CCA | GGC | GGA | GAG | 720  |
| Thr | His | Val | Ile | Pro | Asn | Asp | Arg | Lys | Ile | Ile | Trp | Pro | Gly | Gly | Glu |      |
| 225 |     |     |     |     | 230 |     |     |     |     | 235 |     |     |     |     | 240 |      |
| ACA | GAG | AAG | CCT | CGA | GGG | TAC | CAG | ATG | TCC | ACC | AGA | CTG | AAG | ATT | GTG | 768  |
| Thr | Glu | Lys | Pro | Arg | Gly | Tyr | Gln | Met | Ser | Thr | Arg | Leu | Lys | Ile | Val |      |
|     |     |     |     | 245 |     |     |     |     | 250 |     |     |     |     | 255 |     |      |
| ACG | ATC | CAC | CAG | GAG | CCC | TTC | GTG | TAC | GTC | AAG | CCC | ACG | CTG | AGT | GAT | 816  |
| Thr | Ile | His | Gln | Glu | Pro | Phe | Val | Tyr | Val | Lys | Pro | Thr | Leu | Ser | Asp |      |
|     |     |     | 260 |     |     |     |     | 265 |     |     |     |     | 270 |     |     |      |
| GGG | ACA | TGC | AAG | GAG | GAG | TTC | ACA | GTC | AAC | GGC | GAC | CCA | GTC | AAG | AAG | 864  |
| Gly | Thr | Cys | Lys | Glu | Glu | Phe | Thr | Val | Asn | Gly | Asp | Pro | Val | Lys | Lys |      |
|     |     | 275 |     |     |     |     | 280 |     |     |     |     | 285 |     |     |     |      |
| GTG | ATC | TGC | ACC | GGG | CCC | AAC | GAC | ACG | TCG | CCG | GGC | AGC | CCC | CGC | CAC | 912  |
| Val | Ile | Cys | Thr | Gly | Pro | Asn | Asp | Thr | Ser | Pro | Gly | Ser | Pro | Arg | His |      |
|     | 290 |     |     |     |     | 295 |     |     |     |     | 300 |     |     |     |     |      |
| ACG | GTG | CCT | CAG | TGT | TGC | TAC | GGC | TTT | TGC | ATC | GAC | CTG | CTC | ATC | AAG | 960  |
| Thr | Val | Pro | Gln | Cys | Cys | Tyr | Gly | Phe | Cys | Ile | Asp | Leu | Leu | Ile | Lys |      |
| 305 |     |     |     |     | 310 |     |     |     |     | 315 |     |     |     |     | 320 |      |
| CTG | GCA | CGG | ACC | ATG | AAC | TTC | ACC | TAC | GAG | GTG | CAC | CTG | GTG | GCA | GAT | 1008 |
| Leu | Ala | Arg | Thr | Met | Asn | Phe | Thr | Tyr | Glu | Val | His | Leu | Val | Ala | Asp |      |
|     |     |     |     | 325 |     |     |     |     | 330 |     |     |     |     | 335 |     |      |
| GGC | AAG | TTC | GGC | ACA | CAG | GAG | CGG | GTG | AAC | AAC | AGC | AAC | AAG | AAG | GAG | 1056 |
| Gly | Lys | Phe | Gly | Thr | Gln | Glu | Arg | Val | Asn | Asn | Ser | Asn | Lys | Lys | Glu |      |
|     |     |     | 340 |     |     |     |     | 345 |     |     |     |     | 350 |     |     |      |
| TGG | AAT | GGG | ATG | ATG | GGC | GAG | CTG | CTC | AGC | GGG | CAG | GCA | GAC | ATG | ATC | 1104 |
| Trp | Asn | Gly | Met | Met | Gly | Glu | Leu | Leu | Ser | Gly | Gln | Ala | Asp | Met | Ile |      |
|     |     | 355 |     |     |     |     | 360 |     |     |     |     | 365 |     |     |     |      |
| GTG | GCG | CCG | CTA | ACC | ATA | AAC | AAC | GAG | CGC | GCG | CAG | TAC | ATC | GAG | TTT | 1152 |
| Val | Ala | Pro | Leu | Thr | Ile | Asn | Asn | Glu | Arg | Ala | Gln | Tyr | Ile | Glu | Phe |      |
|     | 370 |     |     |     |     | 375 |     |     |     |     | 380 |     |     |     |     |      |
| TCC | AAG | CCC | TTC | AAG | TAC | CAG | GGC | CTG | ACT | ATT | CTG | GTC | AAG | AAG | GAG | 1200 |
| Ser | Lys | Pro | Phe | Lys | Tyr | Gln | Gly | Leu | Thr | Ile | Leu | Val | Lys | Lys | Glu |      |
| 385 |     |     |     |     | 390 |     |     |     |     | 395 |     |     |     |     | 400 |      |
| ATT | CCC | CGG | AGC | ACG | CTG | GAC | TCG | TTC | ATG | CAG | CCG | TTC | CAG | AGC | ACA | 1248 |
| Ile | Pro | Arg | Ser | Thr | Leu | Asp | Ser | Phe | Met | Gln | Pro | Phe | Gln | Ser | Thr |      |
|     |     |     |     | 405 |     |     |     |     | 410 |     |     |     |     | 415 |     |      |
| CTG | TGG | CTG | CTG | GTG | GGG | CTG | TCG | GTG | CAC | GTG | GTG | GCC | GTG | ATG | CTG | 1296 |
| Leu | Trp | Leu | Leu | Val | Gly | Leu | Ser | Val | His | Val | Val | Ala | Val | Met | Leu |      |
|     |     |     | 420 |     |     |     |     | 425 |     |     |     |     | 430 |     |     |      |
| TAC | CTG | CTG | GAC | CGC | TTC | AGC | CCC | TTC | GGC | CGG | TTC | AAG | GTG | AAC | AGC | 1344 |
| Tyr | Leu | Leu | Asp | Arg | Phe | Ser | Pro | Phe | Gly | Arg | Phe | Lys | Val | Asn | Ser |      |
|     |     | 435 |     |     |     |     | 440 |     |     |     |     | 445 |     |     |     |      |
| GAG | GAG | GAG | GAG | GAG | GAC | GCA | CTG | ACC | CTG | TCC | TCG | GCC | ATG | TGG | TTC | 1392 |
| Glu | Glu | Glu | Glu | Glu | Asp | Ala | Leu | Thr | Leu | Ser | Ser | Ala | Met | Trp | Phe |      |
|     | 450 |     |     |     |     | 455 |     |     |     |     | 460 |     |     |     |     |      |
| TCC | TGG | GGC | GTC | CTG | CTC | AAC | TCC | GGC | ATC | GGG | GAA | GGC | GCC | CCC | AGA | 1440 |
| Ser | Trp | Gly | Val | Leu | Leu | Asn | Ser | Gly | Ile | Gly | Glu | Gly | Ala | Pro | Arg |      |
| 465 |     |     |     |     | 470 |     |     |     |     | 475 |     |     |     |     | 480 |      |
| AGC | TTC | TCA | GCG | CGC | ATC | CTG | GGC | ATG | GTG | TGG | GCC | GGC | TTT | GCC | ATG | 1488 |
| Ser | Phe | Ser | Ala | Arg | Ile | Leu | Gly | Met | Val | Trp | Ala | Gly | Phe | Ala | Met |      |
|     |     |     |     | 485 |     |     |     |     | 490 |     |     |     |     | 495 |     |      |
| ATC | ATC | GTG | GCC | TCC | TAC | ACC | GCC | AAC | CTG | GCG | GCC | TTC | CTG | GTG | CTG | 1536 |
| Ile | Ile | Val | Ala | Ser | Tyr | Thr | Ala | Asn | Leu | Ala | Ala | Phe | Leu | Val | Leu |      |
|     |     |     | 500 |     |     |     |     | 505 |     |     |     |     | 510 |     |     |      |
| GAC | CGG | CCG | GAG | GAG | CGC | ATC | ACG | GGC | ATC | AAC | GAC | CCT | CGG | CTG | AGG | 1584 |

| | | | | | | | | | | | | | | | |
|---|---|---|---|---|---|---|---|---|---|---|---|---|---|---|---|
| Asp | Arg | Pro | Glu | Glu | Arg | Ile | Thr | Gly | Ile | Asn | Asp | Pro | Arg | Leu | Arg |
| | | 515 | | | | | 520 | | | | | 525 | | | |

```
AAC  CCC  TCG  GAC  AAG  TTT  ATC  TAC  GCC  ACG  GTG  AAG  CAG  AGC  TCC  GTG    1632
Asn  Pro  Ser  Asp  Lys  Phe  Ile  Tyr  Ala  Thr  Val  Lys  Gln  Ser  Ser  Val
     530                 535                      540

GAT  ATC  TAC  TTC  CGG  CGC  CAG  GTG  GAG  CTG  AGC  ACC  ATG  TAC  CGG  CAT    1680
Asp  Ile  Tyr  Phe  Arg  Arg  Gln  Val  Glu  Leu  Ser  Thr  Met  Tyr  Arg  His
545                      550                 555                           560

ATG  GAG  AAG  CAC  AAC  TAC  GAG  AGT  GCG  GCG  GAG  GCC  ATC  CAG  GCC  GTG    1728
Met  Glu  Lys  His  Asn  Tyr  Glu  Ser  Ala  Ala  Glu  Ala  Ile  Gln  Ala  Val
                    565                      570                      575

AGA  GAC  AAC  AAG  CTG  CAT  GCC  TTC  ATC  TGG  GAC  TCG  GCG  GTG  CTG  GAG    1776
Arg  Asp  Asn  Lys  Leu  His  Ala  Phe  Ile  Trp  Asp  Ser  Ala  Val  Leu  Glu
                    580                      585                 590

TTC  GAG  GCC  TCG  CAG  AAG  TGC  GAC  CTG  GTG  ACG  ACT  GGA  GAG  CTG  TTT    1824
Phe  Glu  Ala  Ser  Gln  Lys  Cys  Asp  Leu  Val  Thr  Thr  Gly  Glu  Leu  Phe
          595                      600                      605

TTC  CGC  TCG  GGC  TTC  GGC  ATA  GGC  ATG  CGC  AAA  GAC  AGC  CCC  TGG  AAG    1872
Phe  Arg  Ser  Gly  Phe  Gly  Ile  Gly  Met  Arg  Lys  Asp  Ser  Pro  Trp  Lys
     610                      615                      620

CAG  AAC  GTC  TCC  CTG  TCC  ATC  CTC  AAG  TCC  CAC  GAG  AAT  GGC  TTC  ATG    1920
Gln  Asn  Val  Ser  Leu  Ser  Ile  Leu  Lys  Ser  His  Glu  Asn  Gly  Phe  Met
625                      630                      635                      640

GAA  GAC  CTG  GAC  AAG  ACG  TGG  GTT  CGG  TAT  CAG  GAA  TGT  GAC  TCG  CGC    1968
Glu  Asp  Leu  Asp  Lys  Thr  Trp  Val  Arg  Tyr  Gln  Glu  Cys  Asp  Ser  Arg
                    645                      650                      655

AGC  AAC  GCC  CCT  GCG  ACC  CTT  ACT  TTT  GAG  AAC  ATG  GCC  GGG  GTC  TTC    2016
Ser  Asn  Ala  Pro  Ala  Thr  Leu  Thr  Phe  Glu  Asn  Met  Ala  Gly  Val  Phe
               660                      665                      670

ATG  CTG  GTA  GCT  GGG  GGC  ATC  GTG  GCC  GGG  ATC  TTC  CTG  ATT  TTC  ATC    2064
Met  Leu  Val  Ala  Gly  Gly  Ile  Val  Ala  Gly  Ile  Phe  Leu  Ile  Phe  Ile
          675                      680                      685

GAG  ATT  GCC  TAC  AAG  CGG  CAC  AAG  GAT  GCT  CGC  CGG  AAG  CAG  ATG  CAG    2112
Glu  Ile  Ala  Tyr  Lys  Arg  His  Lys  Asp  Ala  Arg  Arg  Lys  Gln  Met  Gln
     690                      695                      700

CTG  GCC  TTT  GCC  GCC  GTT  AAC  GTG  TGG  CGG  AAG  AAC  CTG  CAG  GAT  AGA    2160
Leu  Ala  Phe  Ala  Ala  Val  Asn  Val  Trp  Arg  Lys  Asn  Leu  Gln  Asp  Arg
705                      710                      715                      720

AAG  AGT  GGT  AGA  GCA  GAG  CCT  GAC  CCT  AAA  AAG  AAA  GCC  ACA  TTT  AGG    2208
Lys  Ser  Gly  Arg  Ala  Glu  Pro  Asp  Pro  Lys  Lys  Lys  Ala  Thr  Phe  Arg
                    725                      730                      735

GCT  ATC  ACC  TCC  ACC  CTG  GCT  TCC  AGC  TTC  AAG  AGG  CGT  AGG  TCC  TCC    2256
Ala  Ile  Thr  Ser  Thr  Leu  Ala  Ser  Ser  Phe  Lys  Arg  Arg  Arg  Ser  Ser
               740                      745                      750

AAA  GAC  ACG  CAG  TAC  CAT  CCC  ACT  GAT  ATC  ACG  GGC  CCG  CTC  AAC  CTC    2304
Lys  Asp  Thr  Gln  Tyr  His  Pro  Thr  Asp  Ile  Thr  Gly  Pro  Leu  Asn  Leu
          755                      760                      765

TCA  GAT  CCC  TCG  GTC  AGC  ACC  GTG  GTG  TGAGGCCCCC  GGAGGCGCCC                2351
Ser  Asp  Pro  Ser  Val  Ser  Thr  Val  Val
          770                      775

ACCTGCCCAG   TTAGCCCGGC   CAAGGACACT   GATGGGTCCT   GCTGCTCGGG   AAGGCCTGAG        2411

GGAAGCCCAC   CCGCCCCAGA   GACTGCCCAC   CCTGGGCCTC   CCGTCCGTCC   GCCCGCCCAC        2471

CCCGCTGCCT   GGCGGGCAGC   CCCTGCTGGA   CCAAGGTGCG   GACCGGAGCG   GCTGAGGACG        2531

GGGCAGAGC                                                                          2540
```

( 2 ) INFORMATION FOR SEQ ID NO:16:

( i ) SEQUENCE CHARACTERISTICS:
        ( A ) LENGTH: 777 amino acids (B) TYPE: amino acid
(D) TOPOLOGY: linear (ii) MOLECULE TYPE: protein (xi) SEQUENCE DESCRIPTION: SEQ ID NO:16:

```
Asn  Asp  His  Phe  Thr  Pro  Thr  Pro  Val  Ser  Tyr  Thr  Ala  Gly  Phe  Tyr
 1              5                   10                            15

Arg  Ile  Pro  Val  Leu  Gly  Leu  Thr  Thr  Arg  Met  Ser  Ile  Tyr  Ser  Asp
              20                        25                        30

Lys  Ser  Ile  His  Leu  Ser  Phe  Leu  Arg  Thr  Val  Pro  Pro  Tyr  Ser  His
               35                        40                   45

Gln  Ser  Ser  Val  Trp  Phe  Glu  Met  Met  Arg  Val  Tyr  Ser  Trp  Asn  His
      50                        55                        60

Ile  Ile  Leu  Leu  Val  Ser  Asp  Asp  His  Glu  Gly  Arg  Ala  Ala  Gln  Lys
 65                        70                   75                            80

Arg  Leu  Glu  Thr  Leu  Leu  Glu  Glu  Arg  Glu  Ser  Lys  Ser  Lys  Lys  Arg
                    85                        90                        95

Asn  Tyr  Glu  Asn  Leu  Asp  Gln  Leu  Ser  Tyr  Asp  Asn  Lys  Arg  Gly  Pro
               100                      105                      110

Lys  Ala  Glu  Lys  Val  Leu  Gln  Phe  Asp  Pro  Gly  Thr  Lys  Asn  Val  Thr
               115                      120                      125

Ala  Leu  Leu  Met  Glu  Ala  Lys  Glu  Leu  Glu  Ala  Arg  Val  Ile  Ile  Leu
     130                      135                      140

Ser  Ala  Ser  Glu  Asp  Asp  Ala  Ala  Thr  Val  Tyr  Arg  Ala  Ala  Ala  Met
145                           150                      155                      160

Leu  Asn  Met  Thr  Gly  Asn  Thr  Asn  Ile  Trp  Lys  Thr  Gly  Pro  Leu  Phe
                    165                      170                      175

Lys  Arg  Val  Leu  Met  Ser  Ser  Lys  Tyr  Ala  Asp  Gly  Val  Thr  Gly  Arg
               180                      185                      190

Val  Glu  Phe  Asn  Glu  Asp  Gly  Asp  Arg  Lys  Phe  Ala  Asn  Tyr  Ser  Ile
          195                      200                      205

Met  Asn  Leu  Gln  Asn  Arg  Lys  Leu  Val  Gln  Val  Gly  Ile  Tyr  Asn  Gly
     210                      215                      220

Thr  His  Val  Ile  Pro  Asn  Asp  Arg  Lys  Ile  Ile  Trp  Pro  Gly  Gly  Glu
225                           230                      235                      240

Thr  Glu  Lys  Pro  Arg  Gly  Tyr  Gln  Met  Ser  Thr  Arg  Leu  Lys  Ile  Val
               245                      250                      255

Thr  Ile  His  Gln  Glu  Pro  Phe  Val  Tyr  Val  Lys  Pro  Thr  Leu  Ser  Asp
               260                      265                      270

Gly  Thr  Cys  Lys  Glu  Glu  Phe  Thr  Val  Asn  Gly  Asp  Pro  Val  Lys  Lys
               275                      280                      285

Val  Ile  Cys  Thr  Gly  Pro  Asn  Asp  Thr  Ser  Pro  Gly  Ser  Pro  Arg  His
     290                      295                      300

Thr  Val  Pro  Gln  Cys  Cys  Tyr  Gly  Phe  Cys  Ile  Asp  Leu  Leu  Ile  Lys
305                           310                      315                      320

Leu  Ala  Arg  Thr  Met  Asn  Phe  Thr  Tyr  Glu  Val  His  Leu  Val  Ala  Asp
                    325                      330                      335

Gly  Lys  Phe  Gly  Thr  Gln  Glu  Arg  Val  Asn  Asn  Ser  Asn  Lys  Lys  Glu
               340                      345                      350

Trp  Asn  Gly  Met  Met  Gly  Glu  Leu  Leu  Ser  Gly  Gln  Ala  Asp  Met  Ile
               355                      360                      365

Val  Ala  Pro  Leu  Thr  Ile  Asn  Asn  Glu  Arg  Ala  Gln  Tyr  Ile  Glu  Phe
     370                      375                      380

Ser  Lys  Pro  Phe  Lys  Tyr  Gln  Gly  Leu  Thr  Ile  Leu  Val  Lys  Lys  Glu
```

```
385                      390                      395                      400

Ile  Pro  Arg  Ser  Thr  Leu  Asp  Ser  Phe  Met  Gln  Pro  Phe  Gln  Ser  Thr
                    405                      410                      415

Leu  Trp  Leu  Leu  Val  Gly  Leu  Ser  Val  His  Val  Val  Ala  Val  Met  Leu
               420                      425                      430

Tyr  Leu  Leu  Asp  Arg  Phe  Ser  Pro  Phe  Gly  Arg  Phe  Lys  Val  Asn  Ser
               435                      440                      445

Glu  Glu  Glu  Glu  Glu  Asp  Ala  Leu  Thr  Leu  Ser  Ser  Ala  Met  Trp  Phe
     450                      455                      460

Ser  Trp  Gly  Val  Leu  Leu  Asn  Ser  Gly  Ile  Gly  Glu  Gly  Ala  Pro  Arg
465                      470                      475                      480

Ser  Phe  Ser  Ala  Arg  Ile  Leu  Gly  Met  Val  Trp  Ala  Gly  Phe  Ala  Met
                    485                      490                      495

Ile  Ile  Val  Ala  Ser  Tyr  Thr  Ala  Asn  Leu  Ala  Ala  Phe  Leu  Val  Leu
               500                      505                      510

Asp  Arg  Pro  Glu  Glu  Arg  Ile  Thr  Gly  Ile  Asn  Asp  Pro  Arg  Leu  Arg
               515                      520                      525

Asn  Pro  Ser  Asp  Lys  Phe  Ile  Tyr  Ala  Thr  Val  Lys  Gln  Ser  Ser  Val
               530                      535                      540

Asp  Ile  Tyr  Phe  Arg  Arg  Gln  Val  Glu  Leu  Ser  Thr  Met  Tyr  Arg  His
545                      550                      555                      560

Met  Glu  Lys  His  Asn  Tyr  Glu  Ser  Ala  Ala  Glu  Ala  Ile  Gln  Ala  Val
                    565                      570                      575

Arg  Asp  Asn  Lys  Leu  His  Ala  Phe  Ile  Trp  Asp  Ser  Ala  Val  Leu  Glu
               580                      585                      590

Phe  Glu  Ala  Ser  Gln  Lys  Cys  Asp  Leu  Val  Thr  Thr  Gly  Glu  Leu  Phe
               595                      600                      605

Phe  Arg  Ser  Gly  Phe  Gly  Ile  Gly  Met  Arg  Lys  Asp  Ser  Pro  Trp  Lys
     610                      615                      620

Gln  Asn  Val  Ser  Leu  Ser  Ile  Leu  Lys  Ser  His  Glu  Asn  Gly  Phe  Met
625                      630                      635                      640

Glu  Asp  Leu  Asp  Lys  Thr  Trp  Val  Arg  Tyr  Gln  Glu  Cys  Asp  Ser  Arg
                    645                      650                      655

Ser  Asn  Ala  Pro  Ala  Thr  Leu  Thr  Phe  Glu  Asn  Met  Ala  Gly  Val  Phe
               660                      665                      670

Met  Leu  Val  Ala  Gly  Gly  Ile  Val  Ala  Gly  Ile  Phe  Leu  Ile  Phe  Ile
               675                      680                      685

Glu  Ile  Ala  Tyr  Lys  Arg  His  Lys  Asp  Ala  Arg  Arg  Lys  Gln  Met  Gln
     690                      695                      700

Leu  Ala  Phe  Ala  Ala  Val  Asn  Val  Trp  Arg  Lys  Asn  Leu  Gln  Asp  Arg
705                      710                      715                      720

Lys  Ser  Gly  Arg  Ala  Glu  Pro  Asp  Pro  Lys  Lys  Lys  Ala  Thr  Phe  Arg
                    725                      730                      735

Ala  Ile  Thr  Ser  Thr  Leu  Ala  Ser  Ser  Phe  Lys  Arg  Arg  Arg  Ser  Ser
               740                      745                      750

Lys  Asp  Thr  Gln  Tyr  His  Pro  Thr  Asp  Ile  Thr  Gly  Pro  Leu  Asn  Leu
               755                      760                      765

Ser  Asp  Pro  Ser  Val  Ser  Thr  Val  Val
               770                      775
```

( 2 ) INFORMATION FOR SEQ ID NO:17:

( i ) SEQUENCE CHARACTERISTICS:
        ( A ) LENGTH: 595 base pairs
        ( B ) TYPE: nucleic acid ( C ) STRANDEDNESS: both
( D ) TOPOLOGY: both ( i i ) MOLECULE TYPE: cDNA ( i x ) FEATURE:
( A ) NAME/KEY: CDS
( B ) LOCATION: 1..576

( x i ) SEQUENCE DESCRIPTION: SEQ ID NO:17:

| GAA | GAC | CTG | GAC | AAG | ACG | TGG | GTT | CGG | TAT | CAG | GAA | TGT | GAC | TCG | CGC | 48 |
|---|---|---|---|---|---|---|---|---|---|---|---|---|---|---|---|---|
| Glu | Asp | Leu | Asp | Lys | Thr | Trp | Val | Arg | Tyr | Gln | Glu | Cys | Asp | Ser | Arg | |
| 1 | | | | 5 | | | | | 10 | | | | | 15 | | |

| AGC | AAC | GCC | CCT | GCG | ACC | CTT | ACT | TTT | GAG | AAC | ATG | GCC | GGG | GTC | TTC | 96 |
|---|---|---|---|---|---|---|---|---|---|---|---|---|---|---|---|---|
| Ser | Asn | Ala | Pro | Ala | Thr | Leu | Thr | Phe | Glu | Asn | Met | Ala | Gly | Val | Phe | |
| | | | 20 | | | | | 25 | | | | | 30 | | | |

| ATG | CTG | GTA | GCT | GGG | GGC | ATC | GTG | GCC | GGG | ATC | TTC | CTG | ATT | TTC | ATC | 144 |
|---|---|---|---|---|---|---|---|---|---|---|---|---|---|---|---|---|
| Met | Leu | Val | Ala | Gly | Gly | Ile | Val | Ala | Gly | Ile | Phe | Leu | Ile | Phe | Ile | |
| | | | 35 | | | | | 40 | | | | | 45 | | | |

| GAG | ATT | GCC | TAC | AAG | CGG | CAC | AAG | GAT | GCT | CGC | CGG | AAG | CAG | ATG | CAG | 192 |
|---|---|---|---|---|---|---|---|---|---|---|---|---|---|---|---|---|
| Glu | Ile | Ala | Tyr | Lys | Arg | His | Lys | Asp | Ala | Arg | Arg | Lys | Gln | Met | Gln | |
| | 50 | | | | | 55 | | | | | 60 | | | | | |

| CTG | GCC | TTT | GCC | GCC | GTT | AAC | GTG | TGG | CGG | AAG | AAC | CTG | CAG | GAT | AGA | 240 |
|---|---|---|---|---|---|---|---|---|---|---|---|---|---|---|---|---|
| Leu | Ala | Phe | Ala | Ala | Val | Asn | Val | Trp | Arg | Lys | Asn | Leu | Gln | Asp | Arg | |
| 65 | | | | | 70 | | | | | 75 | | | | | 80 | |

| AAG | AGT | GGT | AGA | GCA | GAG | CCT | GAC | CCT | AAA | AAG | AAA | GCC | ACA | TTT | AGG | 288 |
|---|---|---|---|---|---|---|---|---|---|---|---|---|---|---|---|---|
| Lys | Ser | Gly | Arg | Ala | Glu | Pro | Asp | Pro | Lys | Lys | Lys | Ala | Thr | Phe | Arg | |
| | | | | 85 | | | | | 90 | | | | | 95 | | |

| GCT | ATC | ACC | TCC | ACC | CTG | GCT | TCC | AGC | TTC | AAG | AGG | CGT | AGG | TCC | TCC | 336 |
|---|---|---|---|---|---|---|---|---|---|---|---|---|---|---|---|---|
| Ala | Ile | Thr | Ser | Thr | Leu | Ala | Ser | Ser | Phe | Lys | Arg | Arg | Arg | Ser | Ser | |
| | | | 100 | | | | | 105 | | | | | 110 | | | |

| AAA | GAC | ACG | CTG | GCT | CGG | GAC | TGT | CTT | CAA | CCC | TGC | CCT | GCA | CCT | TGG | 384 |
|---|---|---|---|---|---|---|---|---|---|---|---|---|---|---|---|---|
| Lys | Asp | Thr | Leu | Ala | Arg | Asp | Cys | Leu | Gln | Pro | Cys | Pro | Ala | Pro | Trp | |
| | | 115 | | | | | 120 | | | | | 125 | | | | |

| GCA | CGG | GAG | AGC | GCC | ACC | CGC | CCG | CCC | CCG | CCC | TCG | CTC | CGG | GTG | CGT | 432 |
|---|---|---|---|---|---|---|---|---|---|---|---|---|---|---|---|---|
| Ala | Arg | Glu | Ser | Ala | Thr | Arg | Pro | Pro | Pro | Pro | Ser | Leu | Arg | Val | Arg | |
| | 130 | | | | | 135 | | | | | 140 | | | | | |

| GAC | CGG | CCC | GCC | ACC | TTG | TAC | AGA | ACC | AGC | ACT | CCC | AGG | GCC | CGA | GCG | 480 |
|---|---|---|---|---|---|---|---|---|---|---|---|---|---|---|---|---|
| Asp | Arg | Pro | Ala | Thr | Leu | Tyr | Arg | Thr | Ser | Thr | Pro | Arg | Ala | Arg | Ala | |
| 145 | | | | | 150 | | | | | 155 | | | | | 160 | |

| CGT | GCC | TTC | CCC | GTG | CGC | AGC | CGC | GCT | CTG | CCC | CTC | CGT | CCC | CAG | GGT | 528 |
|---|---|---|---|---|---|---|---|---|---|---|---|---|---|---|---|---|
| Arg | Ala | Phe | Pro | Val | Arg | Ser | Arg | Ala | Leu | Pro | Leu | Arg | Pro | Gln | Gly | |
| | | | | 165 | | | | | 170 | | | | | 175 | | |

| GCA | GGC | GCG | CAC | CGC | CCA | ACC | CCC | ACC | TCC | CGG | TGT | ATG | | | | |
|---|---|---|---|---|---|---|---|---|---|---|---|---|---|---|---|---|
| Ala | Gly | Ala | His | Arg | Pro | Thr | Pro | Thr | Ser | Arg | Cys | Met | | | | |
| | | | 180 | | | | | 185 | | | | | | | | |

| | | | | | | | | | | | | CAG | TGG | TGATGCCTA | | 583 |
|---|---|---|---|---|---|---|---|---|---|---|---|---|---|---|---|---|
| | | | | | | | | | | | | Gln | Trp | | | |
| | | | | | | | | | | | | 190 | | | | |

AGGAATGTCA CG    595

( 2 ) INFORMATION FOR SEQ ID NO:18:

( i ) SEQUENCE CHARACTERISTICS:
( A ) LENGTH: 191 amino acids
( B ) TYPE: amino acid
( D ) TOPOLOGY: linear ( i i ) MOLECULE TYPE: protein ( x i ) SEQUENCE DESCRIPTION: SEQ ID NO:18:

| Glu | Asp | Leu | Asp | Lys | Thr | Trp | Val | Arg | Tyr | Gln | Glu | Cys | Asp | Ser | Arg |
|---|---|---|---|---|---|---|---|---|---|---|---|---|---|---|---|
| 1 | | | | 5 | | | | | 10 | | | | | 15 | |

| | | | | | | | | | | | | | | |
|---|---|---|---|---|---|---|---|---|---|---|---|---|---|---|
| Ser | Asn | Ala | Pro<br>20 | Ala | Thr | Leu | Thr | Phe<br>25 | Glu | Asn | Met | Ala | Gly<br>30 | Val | Phe |
| Met | Leu | Val<br>35 | Ala | Gly | Gly | Ile | Val<br>40 | Ala | Gly | Ile | Phe | Leu<br>45 | Ile | Phe | Ile |
| Glu | Ile<br>50 | Ala | Tyr | Lys | Arg | His<br>55 | Lys | Asp | Ala | Arg | Arg<br>60 | Lys | Gln | Met | Gln |
| Leu<br>65 | Ala | Phe | Ala | Ala | Val<br>70 | Asn | Val | Trp | Arg | Lys<br>75 | Asn | Leu | Gln | Asp | Arg<br>80 |
| Lys | Ser | Gly | Arg | Ala<br>85 | Glu | Pro | Asp | Pro | Lys<br>90 | Lys | Lys | Ala | Thr | Phe<br>95 | Arg |
| Ala | Ile | Thr | Ser<br>100 | Thr | Leu | Ala | Ser | Ser<br>105 | Phe | Lys | Arg | Arg | Ser<br>110 | Ser | Ser |
| Lys | Asp | Thr<br>115 | Leu | Ala | Arg | Asp | Cys<br>120 | Leu | Gln | Pro | Cys | Pro<br>125 | Ala | Pro | Trp |
| Ala | Arg<br>130 | Glu | Ser | Ala | Thr | Arg<br>135 | Pro | Pro | Pro | Pro | Ser<br>140 | Leu | Arg | Val | Arg |
| Asp<br>145 | Arg | Pro | Ala | Thr | Leu<br>150 | Tyr | Arg | Thr | Ser | Thr<br>155 | Pro | Arg | Ala | Arg | Ala<br>160 |
| Arg | Ala | Phe | Pro | Val<br>165 | Arg | Ser | Arg | Ala | Leu<br>170 | Pro | Leu | Arg | Pro | Gln<br>175 | Gly |
| Ala | Gly | Ala | His<br>180 | Arg | Pro | Thr | Pro | Thr<br>185 | Ser | Arg | Cys | Met | Gln<br>190 | Trp | |

( 2 ) INFORMATION FOR SEQ ID NO:19:

( i ) SEQUENCE CHARACTERISTICS:
        ( A ) LENGTH: 3935 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..3030

( x i ) SEQUENCE DESCRIPTION: SEQ ID NO:19:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GCGAGCGCA      180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC       291
                       Met Ser Thr Met Arg Leu Leu Thr Leu Ala
                         1               5                  10

CTG CTG TTC TCC TGC TCC GTC GCC CGT GCC GCG TGC GAC CCC AAG ATC       339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC       387
Val Asn Ile Gly Ala Val Leu Ser Thr Arg Lys His Glu Gln Met Phe
            30                  35                  40

CGC GAG GCC GTG AAC CAG GCC AAC AAG CGG CAC GGC TCC TGG AAG ATT       435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG       483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC       531
```

| | | | | | | | | | | | | | | | | |
|---|---|---|---|---|---|---|---|---|---|---|---|---|---|---|---|---|
| Ala | Leu | Ser | Val | Cys | Glu | Asp | Leu | Ile | Ser | Ser | Gln | Val | Tyr | Ala | Ile | |
| 75 | | | | | 80 | | | | | 85 | | | | | 90 | |
| CTA | GTT | AGC | CAT | CCA | CCT | ACC | CCC | AAC | GAC | CAC | TTC | ACT | CCC | ACC | CCT | 579 |
| Leu | Val | Ser | His | Pro | Pro | Thr | Pro | Asn | Asp | His | Phe | Thr | Pro | Thr | Pro | |
| | | | | 95 | | | | 100 | | | | | | 105 | | |
| GTC | TCC | TAC | ACA | GCC | GGC | TTC | TAC | CGC | ATA | CCC | GTG | CTG | GGG | CTG | ACC | 627 |
| Val | Ser | Tyr | Thr | Ala | Gly | Phe | Tyr | Arg | Ile | Pro | Val | Leu | Gly | Leu | Thr | |
| | | | 110 | | | | | 115 | | | | | 120 | | | |
| ACC | CGC | ATG | TCC | ATC | TAC | TCG | GAC | AAG | AGC | ATC | CAC | CTG | AGC | TTC | CTG | 675 |
| Thr | Arg | Met | Ser | Ile | Tyr | Ser | Asp | Lys | Ser | Ile | His | Leu | Ser | Phe | Leu | |
| | | 125 | | | | | 130 | | | | | 135 | | | | |
| CGC | ACC | GTG | CCG | CCC | TAC | TCC | CAC | CAG | TCC | AGC | GTG | TGG | TTT | GAG | ATG | 723 |
| Arg | Thr | Val | Pro | Pro | Tyr | Ser | His | Gln | Ser | Ser | Val | Trp | Phe | Glu | Met | |
| | 140 | | | | | 145 | | | | | 150 | | | | | |
| ATG | CGT | GTC | TAC | AGC | TGG | AAC | CAC | ATC | ATC | CTG | CTG | GTC | AGC | GAC | GAC | 771 |
| Met | Arg | Val | Tyr | Ser | Trp | Asn | His | Ile | Ile | Leu | Leu | Val | Ser | Asp | Asp | |
| 155 | | | | | 160 | | | | | 165 | | | | | 170 | |
| CAC | GAG | GGC | CGG | GCG | GCT | CAG | AAA | CGC | CTG | GAG | ACG | CTG | CTG | GAG | GAG | 819 |
| His | Glu | Gly | Arg | Ala | Ala | Gln | Lys | Arg | Leu | Glu | Thr | Leu | Leu | Glu | Glu | |
| | | | 175 | | | | | 180 | | | | | 185 | | | |
| CGT | GAG | TCC | AAG | GCA | GAG | AAG | GTG | CTG | CAG | TTT | GAC | CCA | GGG | ACC | AAG | 867 |
| Arg | Glu | Ser | Lys | Ala | Glu | Lys | Val | Leu | Gln | Phe | Asp | Pro | Gly | Thr | Lys | |
| | | | 190 | | | | | 195 | | | | | 200 | | | |
| AAC | GTG | ACG | GCC | CTG | CTG | ATG | GAG | GCG | AAA | GAG | CTG | GAG | GCC | CGG | GTC | 915 |
| Asn | Val | Thr | Ala | Leu | Leu | Met | Glu | Ala | Lys | Glu | Leu | Glu | Ala | Arg | Val | |
| | | 205 | | | | | 210 | | | | | 215 | | | | |
| ATC | ATC | CTT | TCT | GCC | AGC | GAG | GAC | GAT | GCT | GCC | ACT | GTA | TAC | CGC | GCA | 963 |
| Ile | Ile | Leu | Ser | Ala | Ser | Glu | Asp | Asp | Ala | Ala | Thr | Val | Tyr | Arg | Ala | |
| | 220 | | | | | 225 | | | | | 230 | | | | | |
| GCC | GCG | ATG | CTG | AAC | ATG | ACG | GGC | TCC | GGG | TAC | GTG | TGG | CTG | GTC | GGC | 1011 |
| Ala | Ala | Met | Leu | Asn | Met | Thr | Gly | Ser | Gly | Tyr | Val | Trp | Leu | Val | Gly | |
| 235 | | | | | 240 | | | | | 245 | | | | | 250 | |
| GAG | CGC | GAG | ATC | TCG | GGG | AAC | GCC | CTG | CGC | TAC | GCC | CCA | GAC | GGC | ATC | 1059 |
| Glu | Arg | Glu | Ile | Ser | Gly | Asn | Ala | Leu | Arg | Tyr | Ala | Pro | Asp | Gly | Ile | |
| | | | | 255 | | | | | 260 | | | | | 265 | | |
| CTC | GGG | CTG | CAG | CTC | ATC | AAC | GGC | AAG | AAC | GAG | TCG | GCC | CAC | ATC | AGC | 1107 |
| Leu | Gly | Leu | Gln | Leu | Ile | Asn | Gly | Lys | Asn | Glu | Ser | Ala | His | Ile | Ser | |
| | | | 270 | | | | | 275 | | | | | 280 | | | |
| GAC | GCC | GTG | GGC | GTG | GTG | GCC | CAG | GCC | GTG | CAC | GAG | CTC | CTC | GAG | AAG | 1155 |
| Asp | Ala | Val | Gly | Val | Val | Ala | Gln | Ala | Val | His | Glu | Leu | Leu | Glu | Lys | |
| | | | 285 | | | | | 290 | | | | | 295 | | | |
| GAG | AAC | ATC | ACC | GAC | CCG | CCG | CGG | GGC | TGC | GTG | GGC | AAC | ACC | AAC | ATC | 1203 |
| Glu | Asn | Ile | Thr | Asp | Pro | Pro | Arg | Gly | Cys | Val | Gly | Asn | Thr | Asn | Ile | |
| | | 300 | | | | | 305 | | | | | 310 | | | | |
| TGG | AAG | ACC | GGG | CCG | CTC | TTC | AAG | AGA | GTG | CTG | ATG | TCT | TCC | AAG | TAT | 1251 |
| Trp | Lys | Thr | Gly | Pro | Leu | Phe | Lys | Arg | Val | Leu | Met | Ser | Ser | Lys | Tyr | |
| 315 | | | | | 320 | | | | | 325 | | | | | 330 | |
| GCG | GAT | GGG | GTG | ACT | GGT | CGC | GTG | GAG | TTC | AAT | GAG | GAT | GGG | GAC | CGG | 1299 |
| Ala | Asp | Gly | Val | Thr | Gly | Arg | Val | Glu | Phe | Asn | Glu | Asp | Gly | Asp | Arg | |
| | | | | 335 | | | | | 340 | | | | | 345 | | |
| AAG | TTC | GCC | AAC | TAC | AGC | ATC | ATG | AAC | CTG | CAG | AAC | CGC | AAG | CTG | GTG | 1347 |
| Lys | Phe | Ala | Asn | Tyr | Ser | Ile | Met | Asn | Leu | Gln | Asn | Arg | Lys | Leu | Val | |
| | | | 350 | | | | | 355 | | | | | 360 | | | |
| CAA | GTG | GGC | ATC | TAC | AAT | GGC | ACC | CAC | GTC | ATC | CCT | AAT | GAC | AGG | AAG | 1395 |
| Gln | Val | Gly | Ile | Tyr | Asn | Gly | Thr | His | Val | Ile | Pro | Asn | Asp | Arg | Lys | |
| | | 365 | | | | | 370 | | | | | 375 | | | | |
| ATC | ATC | TGG | CCA | GGC | GGA | GAG | ACA | GAG | AAG | CCT | CGA | GGG | TAC | CAG | ATG | 1443 |
| Ile | Ile | Trp | Pro | Gly | Gly | Glu | Thr | Glu | Lys | Pro | Arg | Gly | Tyr | Gln | Met | |
| | | 380 | | | | | 385 | | | | | 390 | | | | |
| TCC | ACC | AGA | CTG | AAG | ATT | GTG | ACG | ATC | CAC | CAG | GAG | CCC | TTC | GTG | TAC | 1491 |

| | | | | | | | | | | | | | | | | |
|---|---|---|---|---|---|---|---|---|---|---|---|---|---|---|---|---|
| Ser 395 | Thr | Arg | Leu | Lys | Ile 400 | Val | Thr | Ile | His | Gln 405 | Glu | Pro | Phe | Val | Tyr 410 | |
| GTC Val | AAG Lys | CCC Pro | ACG Thr | CTG Leu 415 | AGT Ser | GAT Asp | GGG Gly | ACA Thr | TGC Cys 420 | AAG Lys | GAG Glu | GAG Glu | TTC Phe | ACA Thr 425 | GTC Val | 1539 |
| AAC Asn | GGC Gly | GAC Asp | CCA Pro 430 | GTC Val | AAG Lys | AAG Lys | GTG Val | ATC Ile 435 | TGC Cys | ACC Thr | GGG Gly | CCC Pro | AAC Asn 440 | GAC Asp | ACG Thr | 1587 |
| TCG Ser | CCG Pro | GGC Gly | AGC Ser 445 | CCC Pro | CGC Arg | CAC His | ACG Thr 450 | GTG Val | CCT Pro | CAG Gln | TGT Cys | TGC Cys 455 | TAC Tyr | GGC Gly | TTT Phe | 1635 |
| TGC Cys | ATC Ile 460 | GAC Asp | CTG Leu | CTC Leu | ATC Ile | AAG Lys 465 | CTG Leu | GCA Ala | CGG Arg | ACC Thr | ATG Met 470 | AAC Asn | TTC Phe | ACC Thr | TAC Tyr | 1683 |
| GAG Glu 475 | GTG Val | CAC His | CTG Leu | GTG Val | GCA Ala 480 | GAT Asp | GGC Gly | AAG Lys | TTC Phe | GGC Gly 485 | ACA Thr | CAG Gln | GAG Glu | CGG Arg | GTG Val 490 | 1731 |
| AAC Asn | AAC Asn | AGC Ser | AAC Asn | AAG Lys 495 | AAG Lys | GAG Glu | TGG Trp | AAT Asn | GGG Gly 500 | ATG Met | ATG Met | GGC Gly | GAG Glu | CTG Leu 505 | CTC Leu | 1779 |
| AGC Ser | GGG Gly | CAG Gln | GCA Ala | GAC Asp 510 | ATG Met | ATC Ile | GTG Val | GCG Ala | CCG Pro 515 | CTA Leu | ACC Thr | ATA Ile | AAC Asn | AAC Asn 520 | GAG Glu | 1827 |
| CGC Arg | GCG Ala | CAG Gln | TAC Tyr 525 | ATC Ile | GAG Glu | TTT Phe | TCC Ser 530 | AAG Lys | CCC Pro | TTC Phe | AAG Lys | TAC Tyr 535 | CAG Gln | GGC Gly | CTG Leu | 1875 |
| ACT Thr | ATT Ile 540 | CTG Leu | GTC Val | AAG Lys | AAG Lys | GAG Glu 545 | ATT Ile | CCC Pro | CGG Arg | AGC Ser | ACG Thr 550 | CTG Leu | GAC Asp | TCG Ser | TTC Phe | 1923 |
| ATG Met 555 | CAG Gln | CCG Pro | TTC Phe | CAG Gln | AGC Ser 560 | ACA Thr | CTG Leu | TGG Trp | CTG Leu | CTG Leu 565 | GTG Val | GGG Gly | CTG Leu | TCG Ser | GTG Val 570 | 1971 |
| CAC His | GTG Val | GTG Val | GCC Ala | GTG Val 575 | ATG Met | CTG Leu | TAC Tyr | CTG Leu | CTG Leu 580 | GAC Asp | CGC Arg | TTC Phe | AGC Ser | CCC Pro 585 | TTC Phe | 2019 |
| GGC Gly | CGG Arg | TTC Phe | AAG Lys 590 | GTG Val | AAC Asn | AGC Ser | GAG Glu | GAG Glu 595 | GAG Glu | GAG Glu | GAG Glu | GAC Asp | GCA Ala 600 | CTG Leu | ACC Thr | 2067 |
| CTG Leu | TCC Ser | TCG Ser 605 | GCC Ala | ATG Met | TGG Trp | TTC Phe | TCC Ser 610 | TGG Trp | GGC Gly | GTC Val | CTG Leu | CTC Leu 615 | AAC Asn | TCC Ser | GGC Gly | 2115 |
| ATC Ile | GGG Gly | GAA Glu 620 | GGC Gly | GCC Ala | CCC Pro | AGA Arg | AGC Ser 625 | TTC Phe | TCA Ser | GCG Ala | CGC Arg | ATC Ile 630 | CTG Leu | GGC Gly | ATG Met | 2163 |
| GTG Val | TGG Trp 635 | GCC Ala | GGC Gly | TTT Phe | GCC Ala | ATG Met 640 | ATC Ile | ATC Ile | GTG Val | GCC Ala | TCC Ser 645 | TAC Tyr | ACC Thr | GCC Ala | AAC Asn 650 | 2211 |
| CTG Leu | GCG Ala | GCC Ala | TTC Phe | CTG Leu 655 | GTG Val | CTG Leu | GAC Asp | CGG Arg | CCG Pro 660 | GAG Glu | GAG Glu | CGC Arg | ATC Ile | ACG Thr 665 | GGC Gly | 2259 |
| ATC Ile | AAC Asn | GAC Asp | CCT Pro 670 | CGG Arg | CTG Leu | AGG Arg | AAC Asn | CCC Pro 675 | TCG Ser | GAC Asp | AAG Lys | TTT Phe | ATC Ile 680 | TAC Tyr | GCC Ala | 2307 |
| ACG Thr | GTG Val | AAG Lys 685 | CAG Gln | AGC Ser | TCC Ser | GTG Val | GAT Asp 690 | ATC Ile | TAC Tyr | TTC Phe | CGG Arg | CGC Arg 695 | CAG Gln | GTG Val | GAG Glu | 2355 |
| CTG Leu | AGC Ser 700 | ACC Thr | ATG Met | TAC Tyr | CGG Arg | CAT His 705 | ATG Met | GAG Glu | AAG Lys | CAC His | AAC Asn 710 | TAC Tyr | GAG Glu | AGT Ser | GCG Ala | 2403 |
| GCG Ala | GAG Glu | GCC Ala | ATC Ile | CAG Gln | GCC Ala | GTG Val | AGA Arg | GAC Asp | AAC Asn | AAG Lys | CTG Leu | CAT His | GCC Ala | TTC Phe | ATC Ile | 2451 |

| | | | | | | | | | | | | | | | | |
|---|---|---|---|---|---|---|---|---|---|---|---|---|---|---|---|---|
| Ala | Glu | Ala | Ile | Gln | Ala | Val | Arg | Asp | Asn | Lys | Leu | His | Ala | Phe | Ile | |
| 715 | | | | 720 | | | | | 725 | | | | | | 730 | |

```
TGG  GAC  TCG  GCG  GTG  CTG  GAG  TTC  GAG  GCC  TCG  CAG  AAG  TGC  GAC  CTG    2499
Trp  Asp  Ser  Ala  Val  Leu  Glu  Phe  Glu  Ala  Ser  Gln  Lys  Cys  Asp  Leu
               735                     740                         745

GTG  ACG  ACT  GGA  GAG  CTG  TTT  TTC  CGC  TCG  GGC  TTC  GGC  ATA  GGC  ATG    2547
Val  Thr  Thr  Gly  Glu  Leu  Phe  Phe  Arg  Ser  Gly  Phe  Gly  Ile  Gly  Met
               750                     755                         760

CGC  AAA  GAC  AGC  CCC  TGG  AAG  CAG  AAC  GTC  TCC  CTG  TCC  ATC  CTC  AAG    2595
Arg  Lys  Asp  Ser  Pro  Trp  Lys  Gln  Asn  Val  Ser  Leu  Ser  Ile  Leu  Lys
               765                     770                         775

TCC  CAC  GAG  AAT  GGC  TTC  ATG  GAA  GAC  CTG  GAC  AAG  ACG  TGG  GTT  CGG    2643
Ser  His  Glu  Asn  Gly  Phe  Met  Glu  Asp  Leu  Asp  Lys  Thr  Trp  Val  Arg
               780                     785                         790

TAT  CAG  GAA  TGT  GAC  TCG  CGC  AGC  AAC  GCC  CCT  GCG  ACC  CTT  ACT  TTT    2691
Tyr  Gln  Glu  Cys  Asp  Ser  Arg  Ser  Asn  Ala  Pro  Ala  Thr  Leu  Thr  Phe
795                     800                     805                         810

GAG  AAC  ATG  GCC  GGG  GTC  TTC  ATG  CTG  GTA  GCT  GGG  GGC  ATC  GTG  GCC    2739
Glu  Asn  Met  Ala  Gly  Val  Phe  Met  Leu  Val  Ala  Gly  Gly  Ile  Val  Ala
               815                     820                         825

GGG  ATC  TTC  CTG  ATT  TTC  ATC  GAG  ATT  GCC  TAC  AAG  CGG  CAC  AAG  GAT    2787
Gly  Ile  Phe  Leu  Ile  Phe  Ile  Glu  Ile  Ala  Tyr  Lys  Arg  His  Lys  Asp
               830                     835                         840

GCT  CGC  CGG  AAG  CAG  ATG  CAG  CTG  GCC  TTT  GCC  GCC  GTT  AAC  GTG  TGG    2835
Ala  Arg  Arg  Lys  Gln  Met  Gln  Leu  Ala  Phe  Ala  Ala  Val  Asn  Val  Trp
               845                     850                         855

CGG  AAG  AAC  CTG  CAG  GAT  AGA  AAG  AGT  GGT  AGA  GCA  GAG  CCT  GAC  CCT    2883
Arg  Lys  Asn  Leu  Gln  Asp  Arg  Lys  Ser  Gly  Arg  Ala  Glu  Pro  Asp  Pro
     860                     865                     870

AAA  AAG  AAA  GCC  ACA  TTT  AGG  GCT  ATC  ACC  TCC  ACC  CTG  GCT  TCC  AGC    2931
Lys  Lys  Lys  Ala  Thr  Phe  Arg  Ala  Ile  Thr  Ser  Thr  Leu  Ala  Ser  Ser
875                     880                     885                         890

TTC  AAG  AGG  CGT  AGG  TCC  TCC  AAA  GAC  ACG  CAG  TAC  CAT  CCC  ACT  GAT    2979
Phe  Lys  Arg  Arg  Arg  Ser  Ser  Lys  Asp  Thr  Gln  Tyr  His  Pro  Thr  Asp
               895                     900                         905

ATC  ACG  GGC  CCG  CTC  AAC  CTC  TCA  GAT  CCC  TCG  GTC  AGC  ACC  GTG  GTG    3027
Ile  Thr  Gly  Pro  Leu  Asn  Leu  Ser  Asp  Pro  Ser  Val  Ser  Thr  Val  Val
               910                     915                         920
```

```
TGAGGCCCCC  GGAGGCGCCC  ACCTGCCCAG  TTAGCCCGGC  CAAGGACACT  GATGGGTCCT    3087
GCTGCTCGGG  AAGGCCTGAG  GGAAGCCCAC  CCGCCCCAGA  GACTGCCCAC  CCTGGGCCTC    3147
CCGTCCGTCC  GCCCGCCCAC  CCCGCTGCCT  GGCGGGCAGC  CCTGCTGGA   CCAAGGTGCG    3207
GACCGGAGCG  GCTGAGGACG  GGGCAGAGCT  GAGTCGGCTG  GCAGGGCCG   CAGGGCGCTC    3267
CGGCAGAGGC  AGGCCCTGG   GGTCTCTGAG  CAGTGGGGAG  CGGGGGCTAA  CTGCCCCCAG    3327
GCGGAGGGGC  TTGGAGCAGA  GACGGCAGCC  CCATCCTTCC  CGCAGCACCA  GCCTGAGCCA    3387
CAGTGGGGCC  CATGGCCCCA  GCTGGCTGGG  TCGCCCCTCC  TCGGGCGCCT  GCGCTCCTCT    3447
GCAGCCTGAG  CTCCACCCTC  CCCTCTTCTT  GCGGCACCGC  CCACCAAACA  CCCCGTCTGC    3507
CCCTTGACGC  CACACGCCGG  GGCTGGCGCT  GCCCTCCCCC  ACGGCCGTCC  CTGACTTCCC    3567
AGCTGGCAGC  GCCTCCCGCC  GCCTCGGGCC  GCCTCCTCCA  GAATCGAGAG  GCTGAGCCC    3627
CTCCTCTCCT  CGTCCGGCCT  GCAGCACAGA  AGGGGCCTC   CCGGGGGTC   CCCGGACGCT    3687
GGCTCGGGAC  TGTCTTCAAC  CCTGCCCTGC  ACCTTGGGCA  CGGGAGAGCG  CCACCCGCCC    3747
GCCCCGCCC   TCGCTCCGGG  TGCGTGACCG  GCCCGCCACC  TTGTACAGAA  CCAGCACTCC    3807
CAGGGCCCGA  GCGCGTGCCT  TCCCCGTGCG  CAGCCGCGCT  CTGCCCCTCC  GTCCCCAGGG    3867
TGCAGGCGCG  CACCGCCCAA  CCCCCACCTC  CCGGTGTATG  CAGTGGTGAT  GCCTAAAGGA    3927
```

ATGTCACG                                                                                           3935

(2) INFORMATION FOR SEQ ID NO:20:

(i) SEQUENCE CHARACTERISTICS:
        (A) LENGTH: 922 amino acids
        (B) TYPE: amino acid
        (D) TOPOLOGY: linear (ii) MOLECULE TYPE: protein (xi) SEQUENCE DESCRIPTION: SEQ ID NO:20:

| Met | Ser | Thr | Met | Arg | Leu | Leu | Thr | Leu | Ala | Leu | Leu | Phe | Ser | Cys | Ser |
|---|---|---|---|---|---|---|---|---|---|---|---|---|---|---|---|
| 1 | | | | 5 | | | | | 10 | | | | | 15 | |
| Val | Ala | Arg | Ala | Ala | Cys | Asp | Pro | Lys | Ile | Val | Asn | Ile | Gly | Ala | Val |
| | | | 20 | | | | | 25 | | | | | 30 | | |
| Leu | Ser | Thr | Arg | Lys | His | Glu | Gln | Met | Phe | Arg | Glu | Ala | Val | Asn | Gln |
| | | | 35 | | | | 40 | | | | | 45 | | | |
| Ala | Asn | Lys | Arg | His | Gly | Ser | Trp | Lys | Ile | Gln | Leu | Asn | Ala | Thr | Ser |
| | 50 | | | | | 55 | | | | | 60 | | | | |
| Val | Thr | His | Lys | Pro | Asn | Ala | Ile | Gln | Met | Ala | Leu | Ser | Val | Cys | Glu |
| 65 | | | | | 70 | | | | 75 | | | | | | 80 |
| Asp | Leu | Ile | Ser | Ser | Gln | Val | Tyr | Ala | Ile | Leu | Val | Ser | His | Pro | Pro |
| | | | | 85 | | | | | 90 | | | | | 95 | |
| Thr | Pro | Asn | Asp | His | Phe | Thr | Pro | Thr | Pro | Val | Ser | Tyr | Thr | Ala | Gly |
| | | | 100 | | | | | 105 | | | | | 110 | | |
| Phe | Tyr | Arg | Ile | Pro | Val | Leu | Gly | Leu | Thr | Thr | Arg | Met | Ser | Ile | Tyr |
| | | | 115 | | | | | 120 | | | | | 125 | | |
| Ser | Asp | Lys | Ser | Ile | His | Leu | Ser | Phe | Leu | Arg | Thr | Val | Pro | Pro | Tyr |
| | | | 130 | | | | | 135 | | | | | 140 | | |
| Ser | His | Gln | Ser | Ser | Val | Trp | Phe | Glu | Met | Met | Arg | Val | Tyr | Ser | Trp |
| 145 | | | | | 150 | | | | | 155 | | | | | 160 |
| Asn | His | Ile | Ile | Leu | Leu | Val | Ser | Asp | Asp | His | Glu | Gly | Arg | Ala | Ala |
| | | | | 165 | | | | | 170 | | | | | 175 | |
| Gln | Lys | Arg | Leu | Glu | Thr | Leu | Leu | Glu | Glu | Arg | Glu | Ser | Lys | Ala | Glu |
| | | | 180 | | | | | 185 | | | | | 190 | | |
| Lys | Val | Leu | Gln | Phe | Asp | Pro | Gly | Thr | Lys | Asn | Val | Thr | Ala | Leu | Leu |
| | | | 195 | | | | | 200 | | | | | 205 | | |
| Met | Glu | Ala | Lys | Glu | Leu | Glu | Ala | Arg | Val | Ile | Ile | Leu | Ser | Ala | Ser |
| | 210 | | | | | 215 | | | | | 220 | | | | |
| Glu | Asp | Asp | Ala | Ala | Thr | Val | Tyr | Arg | Ala | Ala | Ala | Met | Leu | Asn | Met |
| 225 | | | | | 230 | | | | | 235 | | | | | 240 |
| Thr | Gly | Ser | Gly | Tyr | Val | Trp | Leu | Val | Gly | Glu | Arg | Glu | Ile | Ser | Gly |
| | | | | 245 | | | | | 250 | | | | | 255 | |
| Asn | Ala | Leu | Arg | Tyr | Ala | Pro | Asp | Gly | Ile | Leu | Gly | Leu | Gln | Leu | Ile |
| | | | 260 | | | | | 265 | | | | | 270 | | |
| Asn | Gly | Lys | Asn | Glu | Ser | Ala | His | Ile | Ser | Asp | Ala | Val | Gly | Val | Val |
| | | | 275 | | | | | 280 | | | | | 285 | | |
| Ala | Gln | Ala | Val | His | Glu | Leu | Leu | Glu | Lys | Glu | Asn | Ile | Thr | Asp | Pro |
| | | 290 | | | | | 295 | | | | | 300 | | | |
| Pro | Arg | Gly | Cys | Val | Gly | Asn | Thr | Asn | Ile | Trp | Lys | Thr | Gly | Pro | Leu |
| 305 | | | | | 310 | | | | | 315 | | | | | 320 |
| Phe | Lys | Arg | Val | Leu | Met | Ser | Ser | Lys | Tyr | Ala | Asp | Gly | Val | Thr | Gly |
| | | | | 325 | | | | | 330 | | | | | 335 | |
| Arg | Val | Glu | Phe | Asn | Glu | Asp | Gly | Asp | Arg | Lys | Phe | Ala | Asn | Tyr | Ser |
| | | | 340 | | | | | 345 | | | | | 350 | | |

```
Ile  Met  Asn  Leu  Gln  Asn  Arg  Lys  Leu  Val  Gln  Val  Gly  Ile  Tyr  Asn
          355                 360                      365

Gly  Thr  His  Val  Ile  Pro  Asn  Asp  Arg  Lys  Ile  Ile  Trp  Pro  Gly  Gly
          370                 375                      380

Glu  Thr  Glu  Lys  Pro  Arg  Gly  Tyr  Gln  Met  Ser  Thr  Arg  Leu  Lys  Ile
385                      390                 395                           400

Val  Thr  Ile  His  Gln  Glu  Pro  Phe  Val  Tyr  Val  Lys  Pro  Thr  Leu  Ser
                    405                      410                      415

Asp  Gly  Thr  Cys  Lys  Glu  Glu  Phe  Thr  Val  Asn  Gly  Asp  Pro  Val  Lys
                    420                 425                      430

Lys  Val  Ile  Cys  Thr  Gly  Pro  Asn  Asp  Thr  Ser  Pro  Gly  Ser  Pro  Arg
                    435                 440                      445

His  Thr  Val  Pro  Gln  Cys  Cys  Tyr  Gly  Phe  Cys  Ile  Asp  Leu  Leu  Ile
          450                 455                      460

Lys  Leu  Ala  Arg  Thr  Met  Asn  Phe  Thr  Tyr  Glu  Val  His  Leu  Val  Ala
465                      470                 475                           480

Asp  Gly  Lys  Phe  Gly  Thr  Gln  Glu  Arg  Val  Asn  Asn  Ser  Asn  Lys  Lys
                    485                      490                      495

Glu  Trp  Asn  Gly  Met  Met  Gly  Glu  Leu  Leu  Ser  Gly  Gln  Ala  Asp  Met
                    500                      505                      510

Ile  Val  Ala  Pro  Leu  Thr  Ile  Asn  Asn  Glu  Arg  Ala  Gln  Tyr  Ile  Glu
                    515                      520                      525

Phe  Ser  Lys  Pro  Phe  Lys  Tyr  Gln  Gly  Leu  Thr  Ile  Leu  Val  Lys  Lys
          530                 535                      540

Glu  Ile  Pro  Arg  Ser  Thr  Leu  Asp  Ser  Phe  Met  Gln  Pro  Phe  Gln  Ser
545                      550                 555                           560

Thr  Leu  Trp  Leu  Leu  Val  Gly  Leu  Ser  Val  His  Val  Val  Ala  Val  Met
                    565                      570                      575

Leu  Tyr  Leu  Leu  Asp  Arg  Phe  Ser  Pro  Phe  Gly  Arg  Phe  Lys  Val  Asn
                    580                      585                      590

Ser  Glu  Glu  Glu  Glu  Glu  Asp  Ala  Leu  Thr  Leu  Ser  Ser  Ala  Met  Trp
          595                      600                      605

Phe  Ser  Trp  Gly  Val  Leu  Leu  Asn  Ser  Gly  Ile  Gly  Glu  Gly  Ala  Pro
     610                      615                      620

Arg  Ser  Phe  Ser  Ala  Arg  Ile  Leu  Gly  Met  Val  Trp  Ala  Gly  Phe  Ala
625                      630                 635                           640

Met  Ile  Ile  Val  Ala  Ser  Tyr  Thr  Ala  Asn  Leu  Ala  Ala  Phe  Leu  Val
                    645                      650                      655

Leu  Asp  Arg  Pro  Glu  Glu  Arg  Ile  Thr  Gly  Ile  Asn  Asp  Pro  Arg  Leu
                    660                      665                      670

Arg  Asn  Pro  Ser  Asp  Lys  Phe  Ile  Tyr  Ala  Thr  Val  Lys  Gln  Ser  Ser
                    675                      680                      685

Val  Asp  Ile  Tyr  Phe  Arg  Arg  Gln  Val  Glu  Leu  Ser  Thr  Met  Tyr  Arg
                    690                      695                      700

His  Met  Glu  Lys  His  Asn  Tyr  Glu  Ser  Ala  Ala  Glu  Ala  Ile  Gln  Ala
705                      710                      715                      720

Val  Arg  Asp  Asn  Lys  Leu  His  Ala  Phe  Ile  Trp  Asp  Ser  Ala  Val  Leu
                    725                      730                      735

Glu  Phe  Glu  Ala  Ser  Gln  Lys  Cys  Asp  Leu  Val  Thr  Thr  Gly  Glu  Leu
                    740                      745                      750

Phe  Phe  Arg  Ser  Gly  Phe  Gly  Ile  Gly  Met  Arg  Lys  Asp  Ser  Pro  Trp
                    755                      760                      765

Lys  Gln  Asn  Val  Ser  Leu  Ser  Ile  Leu  Lys  Ser  His  Glu  Asn  Gly  Phe
```

|  |  |  |  |  | 770 |  |  |  |  | 775 |  |  |  |  | 780 |  |
|---|---|---|---|---|---|---|---|---|---|---|---|---|---|---|---|---|

Met Glu Asp Leu Asp Lys Thr Trp Val Arg Tyr Gln Glu Cys Asp Ser
785                     790                     795                     800

Arg Ser Asn Ala Pro Ala Thr Leu Thr Phe Glu Asn Met Ala Gly Val
                    805                 810                     815

Phe Met Leu Val Ala Gly Gly Ile Val Ala Gly Ile Phe Leu Ile Phe
                820                 825                 830

Ile Glu Ile Ala Tyr Lys Arg His Lys Asp Ala Arg Arg Lys Gln Met
            835                 840                 845

Gln Leu Ala Phe Ala Ala Val Asn Val Trp Arg Lys Asn Leu Gln Asp
        850                 855                 860

Arg Lys Ser Gly Arg Ala Glu Pro Asp Pro Lys Lys Lys Ala Thr Phe
865                 870                 875                 880

Arg Ala Ile Thr Ser Thr Leu Ala Ser Ser Phe Lys Arg Arg Arg Ser
                885                 890                 895

Ser Lys Asp Thr Gln Tyr His Pro Thr Asp Ile Thr Gly Pro Leu Asn
            900                 905                 910

Leu Ser Asp Pro Ser Val Ser Thr Val Val
        915                 920

(2) INFORMATION FOR SEQ ID NO:21:

(i) SEQUENCE CHARACTERISTICS:
      (A) LENGTH: 3211 base pairs
      (B) TYPE: nucleic acid
      (C) STRANDEDNESS: both
      (D) TOPOLOGY: both (ii) MOLECULE TYPE: cDNA (ix) FEATURE:
      (A) NAME/KEY: CDS
      (B) LOCATION: 262..3192

(xi) SEQUENCE DESCRIPTION: SEQ ID NO:21:

```
CAAGCCGGGC GTTCGGAGCT GTGCCCGGCC CCGCTTCAGC ACCGCGGACA GCGCCGGCCG        60

CGTGGGGCTG AGCGCCGAGC CCCCGCGCAC GCTTCAGCCC CCCTTCCCTC GGCCGACGTC       120

CCGGGACCGC CGCTCCGGGG GAGACGTGGC GTCCGCAGCC CGCGGGGCCG GGCGAGCGCA       180

GGACGGCCCG GAAGCCCCGC GGGGGATGCG CCGAGGGCCC CGCGTTCGCG CCGCGCAGAG       240

CCAGGCCCGC GGCCCGAGCC C ATG AGC ACC ATG CGC CTG CTG ACG CTC GCC        291
                        Met Ser Thr Met Arg Leu Leu Thr Leu Ala
                         1               5                   10

CTG CTG TTC TCC TGC TCC GTC GCC CGT GCC GCG TGC GAC CCC AAG ATC        339
Leu Leu Phe Ser Cys Ser Val Ala Arg Ala Ala Cys Asp Pro Lys Ile
            15                  20                  25

GTC AAC ATT GGC GCG GTG CTG AGC ACG CGG AAG CAC GAG CAG ATG TTC        387
Val Asn Ile Gly Ala Val Leu Ser Thr Arg Lys His Glu Gln Met Phe
                30                  35                  40

CGC GAG GCC GTG AAC CAG GCC AAC AAG CGG CAC GGC TCC TGG AAG ATT        435
Arg Glu Ala Val Asn Gln Ala Asn Lys Arg His Gly Ser Trp Lys Ile
            45                  50                  55

CAG CTC AAT GCC ACC TCC GTC ACG CAC AAG CCC AAC GCC ATC CAG ATG        483
Gln Leu Asn Ala Thr Ser Val Thr His Lys Pro Asn Ala Ile Gln Met
        60                  65                  70

GCT CTG TCG GTG TGC GAG GAC CTC ATC TCC AGC CAG GTC TAC GCC ATC        531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT        579
Leu Val Ser His Pro Pro Thr Pro Asn Asp His Phe Thr Pro Thr Pro
```

-continued

```
              95                              100                             105
GTC  TCC  TAC  ACA  GCC  GGC  TTC  TAC  CGC  ATA  CCC  GTG  CTG  GGG  CTG  ACC        627
Val  Ser  Tyr  Thr  Ala  Gly  Phe  Tyr  Arg  Ile  Pro  Val  Leu  Gly  Leu  Thr
               110                         115                         120

ACC  CGC  ATG  TCC  ATC  TAC  TCG  GAC  AAG  AGC  ATC  CAC  CTG  AGC  TTC  CTG        675
Thr  Arg  Met  Ser  Ile  Tyr  Ser  Asp  Lys  Ser  Ile  His  Leu  Ser  Phe  Leu
               125                         130                         135

CGC  ACC  GTG  CCG  CCC  TAC  TCC  CAC  CAG  TCC  AGC  GTG  TGG  TTT  GAG  ATG        723
Arg  Thr  Val  Pro  Pro  Tyr  Ser  His  Gln  Ser  Ser  Val  Trp  Phe  Glu  Met
               140                         145                         150

ATG  CGT  GTC  TAC  AGC  TGG  AAC  CAC  ATC  ATC  CTG  CTG  GTC  AGC  GAC  GAC        771
Met  Arg  Val  Tyr  Ser  Trp  Asn  His  Ile  Ile  Leu  Leu  Val  Ser  Asp  Asp
155                      160                         165                         170

CAC  GAG  GGC  CGG  GCG  GCT  CAG  AAA  CGC  CTG  GAG  ACG  CTG  CTG  GAG  GAG        819
His  Glu  Gly  Arg  Ala  Ala  Gln  Lys  Arg  Leu  Glu  Thr  Leu  Leu  Glu  Glu
                         175                         180                         185

CGT  GAG  TCC  AAG  GCA  GAG  AAG  GTG  CTG  CAG  TTT  GAC  CCA  GGG  ACC  AAG        867
Arg  Glu  Ser  Lys  Ala  Glu  Lys  Val  Leu  Gln  Phe  Asp  Pro  Gly  Thr  Lys
                    190                         195                         200

AAC  GTG  ACG  GCC  CTG  CTG  ATG  GAG  GCG  AAA  GAG  CTG  GAG  GCC  CGG  GTC        915
Asn  Val  Thr  Ala  Leu  Leu  Met  Glu  Ala  Lys  Glu  Leu  Glu  Ala  Arg  Val
               205                         210                         215

ATC  ATC  CTT  TCT  GCC  AGC  GAG  GAC  GAT  GCT  GCC  ACT  GTA  TAC  CGC  GCA        963
Ile  Ile  Leu  Ser  Ala  Ser  Glu  Asp  Asp  Ala  Ala  Thr  Val  Tyr  Arg  Ala
220                      225                         230

GCC  GCG  ATG  CTG  AAC  ATG  ACG  GGC  TCC  GGG  TAC  GTG  TGG  CTG  GTC  GGC       1011
Ala  Ala  Met  Leu  Asn  Met  Thr  Gly  Ser  Gly  Tyr  Val  Trp  Leu  Val  Gly
235                      240                         245                         250

GAG  CGC  GAG  ATC  TCG  GGG  AAC  GCC  CTG  CGC  TAC  GCC  CCA  GAC  GGC  ATC       1059
Glu  Arg  Glu  Ile  Ser  Gly  Asn  Ala  Leu  Arg  Tyr  Ala  Pro  Asp  Gly  Ile
                    255                         260                         265

CTC  GGG  CTG  CAG  CTC  ATC  AAC  GGC  AAG  AAC  GAG  TCG  GCC  CAC  ATC  AGC       1107
Leu  Gly  Leu  Gln  Leu  Ile  Asn  Gly  Lys  Asn  Glu  Ser  Ala  His  Ile  Ser
               270                         275                         280

GAC  GCC  GTG  GGC  GTG  GTG  GCC  CAG  GCC  GTG  CAC  GAG  CTC  CTC  GAG  AAG       1155
Asp  Ala  Val  Gly  Val  Val  Ala  Gln  Ala  Val  His  Glu  Leu  Leu  Glu  Lys
               285                         290                         295

GAG  AAC  ATC  ACC  GAC  CCG  CCG  CGG  GGC  TGC  GTG  GGC  AAC  ACC  AAC  ATC       1203
Glu  Asn  Ile  Thr  Asp  Pro  Pro  Arg  Gly  Cys  Val  Gly  Asn  Thr  Asn  Ile
300                      305                         310

TGG  AAG  ACC  GGG  CCG  CTC  TTC  AAG  AGA  GTG  CTG  ATG  TCT  TCC  AAG  TAT       1251
Trp  Lys  Thr  Gly  Pro  Leu  Phe  Lys  Arg  Val  Leu  Met  Ser  Ser  Lys  Tyr
315                      320                         325                         330

GCG  GAT  GGG  GTG  ACT  GGT  CGC  GTG  GAG  TTC  AAT  GAG  GAT  GGG  GAC  CGG       1299
Ala  Asp  Gly  Val  Thr  Gly  Arg  Val  Glu  Phe  Asn  Glu  Asp  Gly  Asp  Arg
                    335                         340                         345

AAG  TTC  GCC  AAC  TAC  AGC  ATC  ATG  AAC  CTG  CAG  AAC  CGC  AAG  CTG  GTG       1347
Lys  Phe  Ala  Asn  Tyr  Ser  Ile  Met  Asn  Leu  Gln  Asn  Arg  Lys  Leu  Val
               350                         355                         360

CAA  GTG  GGC  ATC  TAC  AAT  GGC  ACC  CAC  GTC  ATC  CCT  AAT  GAC  AGG  AAG       1395
Gln  Val  Gly  Ile  Tyr  Asn  Gly  Thr  His  Val  Ile  Pro  Asn  Asp  Arg  Lys
               365                         370                         375

ATC  ATC  TGG  CCA  GGC  GGA  GAG  ACA  GAG  AAG  CCT  CGA  GGG  TAC  CAG  ATG       1443
Ile  Ile  Trp  Pro  Gly  Gly  Glu  Thr  Glu  Lys  Pro  Arg  Gly  Tyr  Gln  Met
380                      385                         390

TCC  ACC  AGA  CTG  AAG  ATT  GTG  ACG  ATC  CAC  CAG  GAG  CCC  TTC  GTG  TAC       1491
Ser  Thr  Arg  Leu  Lys  Ile  Val  Thr  Ile  His  Gln  Glu  Pro  Phe  Val  Tyr
395                      400                         405                         410

GTC  AAG  CCC  ACG  CTG  AGT  GAT  GGG  ACA  TGC  AAG  GAG  GAG  TTC  ACA  GTC       1539
Val  Lys  Pro  Thr  Leu  Ser  Asp  Gly  Thr  Cys  Lys  Glu  Glu  Phe  Thr  Val
```

-continued

```
                        415                                         420                                         425
AAC  GGC  GAC  CCA  GTC  AAG  AAG  GTG  ATC  TGC  ACC  GGG  CCC  AAC  GAC  ACG    1587
Asn  Gly  Asp  Pro  Val  Lys  Lys  Val  Ile  Cys  Thr  Gly  Pro  Asn  Asp  Thr
               430                      435                      440

TCG  CCG  GGC  AGC  CCC  CGC  CAC  ACG  GTG  CCT  CAG  TGT  TGC  TAC  GGC  TTT    1635
Ser  Pro  Gly  Ser  Pro  Arg  His  Thr  Val  Pro  Gln  Cys  Cys  Tyr  Gly  Phe
               445                      450                      455

TGC  ATC  GAC  CTG  CTC  ATC  AAG  CTG  GCA  CGG  ACC  ATG  AAC  TTC  ACC  TAC    1683
Cys  Ile  Asp  Leu  Leu  Ile  Lys  Leu  Ala  Arg  Thr  Met  Asn  Phe  Thr  Tyr
     460                      465                      470

GAG  GTG  CAC  CTG  GTG  GCA  GAT  GGC  AAG  TTC  GGC  ACA  CAG  GAG  CGG  GTG    1731
Glu  Val  His  Leu  Val  Ala  Asp  Gly  Lys  Phe  Gly  Thr  Gln  Glu  Arg  Val
475                      480                      485                      490

AAC  AAC  AGC  AAC  AAG  AAG  GAG  TGG  AAT  GGG  ATG  ATG  GGC  GAG  CTG  CTC    1779
Asn  Asn  Ser  Asn  Lys  Lys  Glu  Trp  Asn  Gly  Met  Met  Gly  Glu  Leu  Leu
                    495                      500                      505

AGC  GGG  CAG  GCA  GAC  ATG  ATC  GTG  GCG  CCG  CTA  ACC  ATA  AAC  AAC  GAG    1827
Ser  Gly  Gln  Ala  Asp  Met  Ile  Val  Ala  Pro  Leu  Thr  Ile  Asn  Asn  Glu
               510                      515                      520

CGC  GCG  CAG  TAC  ATC  GAG  TTT  TCC  AAG  CCC  TTC  AAG  TAC  CAG  GGC  CTG    1875
Arg  Ala  Gln  Tyr  Ile  Glu  Phe  Ser  Lys  Pro  Phe  Lys  Tyr  Gln  Gly  Leu
          525                      530                      535

ACT  ATT  CTG  GTC  AAG  AAG  GAG  ATT  CCC  CGG  AGC  ACG  CTG  GAC  TCG  TTC    1923
Thr  Ile  Leu  Val  Lys  Lys  Glu  Ile  Pro  Arg  Ser  Thr  Leu  Asp  Ser  Phe
540                      545                      550

ATG  CAG  CCG  TTC  CAG  AGC  ACA  CTG  TGG  CTG  CTG  GTG  GGG  CTG  TCG  GTG    1971
Met  Gln  Pro  Phe  Gln  Ser  Thr  Leu  Trp  Leu  Leu  Val  Gly  Leu  Ser  Val
555                      560                      565                      570

CAC  GTG  GTG  GCC  GTG  ATG  CTG  TAC  CTG  CTG  GAC  CGC  TTC  AGC  CCC  TTC    2019
His  Val  Val  Ala  Val  Met  Leu  Tyr  Leu  Leu  Asp  Arg  Phe  Ser  Pro  Phe
                    575                      580                      585

GGC  CGG  TTC  AAG  GTG  AAC  AGC  GAG  GAG  GAG  GAG  GAG  GAC  GCA  CTG  ACC    2067
Gly  Arg  Phe  Lys  Val  Asn  Ser  Glu  Glu  Glu  Glu  Glu  Asp  Ala  Leu  Thr
               590                      595                      600

CTG  TCC  TCG  GCC  ATG  TGG  TTC  TCC  TGG  GGC  GTC  CTG  CTC  AAC  TCC  GGC    2115
Leu  Ser  Ser  Ala  Met  Trp  Phe  Ser  Trp  Gly  Val  Leu  Leu  Asn  Ser  Gly
          605                      610                      615

ATC  GGG  GAA  GGC  GCC  CCC  AGA  AGC  TTC  TCA  GCG  CGC  ATC  CTG  GGC  ATG    2163
Ile  Gly  Glu  Gly  Ala  Pro  Arg  Ser  Phe  Ser  Ala  Arg  Ile  Leu  Gly  Met
620                      625                      630

GTG  TGG  GCC  GGC  TTT  GCC  ATG  ATC  ATC  GTG  GCC  TCC  TAC  ACC  GCC  AAC    2211
Val  Trp  Ala  Gly  Phe  Ala  Met  Ile  Ile  Val  Ala  Ser  Tyr  Thr  Ala  Asn
635                      640                      645                      650

CTG  GCG  GCC  TTC  CTG  GTG  CTG  GAC  CGG  CCG  GAG  GAG  CGC  ATC  ACG  GGC    2259
Leu  Ala  Ala  Phe  Leu  Val  Leu  Asp  Arg  Pro  Glu  Glu  Arg  Ile  Thr  Gly
               655                      660                      665

ATC  AAC  GAC  CCT  CGG  CTG  AGG  AAC  CCC  TCG  GAC  AAG  TTT  ATC  TAC  GCC    2307
Ile  Asn  Asp  Pro  Arg  Leu  Arg  Asn  Pro  Ser  Asp  Lys  Phe  Ile  Tyr  Ala
          670                      675                      680

ACG  GTG  AAG  CAG  AGC  TCC  GTG  GAT  ATC  TAC  TTC  CGG  CGC  CAG  GTG  GAG    2355
Thr  Val  Lys  Gln  Ser  Ser  Val  Asp  Ile  Tyr  Phe  Arg  Arg  Gln  Val  Glu
               685                      690                      695

CTG  AGC  ACC  ATG  TAC  CGG  CAT  ATG  GAG  AAG  CAC  AAC  TAC  GAG  AGT  GCG    2403
Leu  Ser  Thr  Met  Tyr  Arg  His  Met  Glu  Lys  His  Asn  Tyr  Glu  Ser  Ala
     700                      705                      710

GCG  GAG  GCC  ATC  CAG  GCC  GTG  AGA  GAC  AAC  AAG  CTG  CAT  GCC  TTC  ATC    2451
Ala  Glu  Ala  Ile  Gln  Ala  Val  Arg  Asp  Asn  Lys  Leu  His  Ala  Phe  Ile
715                      720                      725                      730

TGG  GAC  TCG  GCG  GTG  CTG  GAG  TTC  GAG  GCC  TCG  CAG  AAG  TGC  GAC  CTG    2499
Trp  Asp  Ser  Ala  Val  Leu  Glu  Phe  Glu  Ala  Ser  Gln  Lys  Cys  Asp  Leu
```

-continued

```
                                 735                            740                           745
GTG  ACG  ACT  GGA  GAG  CTG  TTT  TTC  CGC  TCG  GGC  TTC  GGC  ATA  GGC  ATG        2547
Val  Thr  Thr  Gly  Glu  Leu  Phe  Phe  Arg  Ser  Gly  Phe  Gly  Ile  Gly  Met
               750                            755                           760

CGC  AAA  GAC  AGC  CCC  TGG  AAG  CAG  AAC  GTC  TCC  CTG  TCC  ATC  CTC  AAG        2595
Arg  Lys  Asp  Ser  Pro  Trp  Lys  Gln  Asn  Val  Ser  Leu  Ser  Ile  Leu  Lys
          765                            770                           775

TCC  CAC  GAG  AAT  GGC  TTC  ATG  GAA  GAC  CTG  GAC  AAG  ACG  TGG  GTT  CGG        2643
Ser  His  Glu  Asn  Gly  Phe  Met  Glu  Asp  Leu  Asp  Lys  Thr  Trp  Val  Arg
     780                            785                           790

TAT  CAG  GAA  TGT  GAC  TCG  CGC  AGC  AAC  GCC  CCT  GCG  ACC  CTT  ACT  TTT        2691
Tyr  Gln  Glu  Cys  Asp  Ser  Arg  Ser  Asn  Ala  Pro  Ala  Thr  Leu  Thr  Phe
795                            800                           805                      810

GAG  AAC  ATG  GCC  GGG  GTC  TTC  ATG  CTG  GTA  GCT  GGG  GGC  ATC  GTG  GCC        2739
Glu  Asn  Met  Ala  Gly  Val  Phe  Met  Leu  Val  Ala  Gly  Gly  Ile  Val  Ala
                    815                            820                      825

GGG  ATC  TTC  CTG  ATT  TTC  ATC  GAG  ATT  GCC  TAC  AAG  CGG  CAC  AAG  GAT        2787
Gly  Ile  Phe  Leu  Ile  Phe  Ile  Glu  Ile  Ala  Tyr  Lys  Arg  His  Lys  Asp
               830                            835                      840

GCT  CGC  CGG  AAG  CAG  ATG  CAG  CTG  GCC  TTT  GCC  GCC  GTT  AAC  GTG  TGG        2835
Ala  Arg  Arg  Lys  Gln  Met  Gln  Leu  Ala  Phe  Ala  Ala  Val  Asn  Val  Trp
          845                            850                      855

CGG  AAG  AAC  CTG  CAG  GAT  AGA  AAG  AGT  GGT  AGA  GCA  GAG  CCT  GAC  CCT        2883
Arg  Lys  Asn  Leu  Gln  Asp  Arg  Lys  Ser  Gly  Arg  Ala  Glu  Pro  Asp  Pro
     860                            865                           870

AAA  AAG  AAA  GCC  ACA  TTT  AGG  GCT  ATC  ACC  TCC  ACC  CTG  GCT  TCC  AGC        2931
Lys  Lys  Lys  Ala  Thr  Phe  Arg  Ala  Ile  Thr  Ser  Thr  Leu  Ala  Ser  Ser
875                            880                           885                      890

TTC  AAG  AGG  CGT  AGG  TCC  TCC  AAA  GAC  ACG  CTG  GCT  CGG  GAC  TGT  CTT        2979
Phe  Lys  Arg  Arg  Arg  Ser  Ser  Lys  Asp  Thr  Leu  Ala  Arg  Asp  Cys  Leu
                    895                            900                      905

CAA  CCC  TGC  CCT  GCA  CCT  TGG  GCA  CGG  GAG  AGC  GCC  ACC  CGC  CCG  CCC        3027
Gln  Pro  Cys  Pro  Ala  Pro  Trp  Ala  Arg  Glu  Ser  Ala  Thr  Arg  Pro  Pro
               910                            915                      920

CCG  CCC  TCG  CTC  CGG  GTG  CGT  GAC  CGG  CCC  GCC  ACC  TTG  TAC  AGA  ACC        3075
Pro  Pro  Ser  Leu  Arg  Val  Arg  Asp  Arg  Pro  Ala  Thr  Leu  Tyr  Arg  Thr
          925                            930                           935

AGC  ACT  CCC  AGG  GCC  CGA  GCG  CGT  GCC  TTC  CCC  GTG  CGC  AGC  CGC  GCT        3123
Ser  Thr  Pro  Arg  Ala  Arg  Ala  Arg  Ala  Phe  Pro  Val  Arg  Ser  Arg  Ala
     940                            945                           950

CTG  CCC  CTC  CGT  CCC  CAG  GGT  GCA  GGC  GCG  CAC  CGC  CCA  ACC  CCC  ACC        3171
Leu  Pro  Leu  Arg  Pro  Gln  Gly  Ala  Gly  Ala  His  Arg  Pro  Thr  Pro  Thr
955                            960                           965                      970

TCC  CGG  TGT  ATG  CAG  TGG  TGATGCCTAA  AGGAATGTCA  CG                              3211
Ser  Arg  Cys  Met  Gln  Trp
                    975
```

( 2 ) INFORMATION FOR SEQ ID NO:22:

( i ) SEQUENCE CHARACTERISTICS:
        ( A ) LENGTH: 976 amino acids
        ( B ) TYPE: amino acid
        ( D ) TOPOLOGY: linear ( i i ) MOLECULE TYPE: protein ( x i ) SEQUENCE DESCRIPTION: SEQ ID NO:22:

```
Met  Ser  Thr  Met  Arg  Leu  Leu  Thr  Leu  Ala  Leu  Leu  Phe  Ser  Cys  Ser
1                   5                        10                       15

Val  Ala  Arg  Ala  Ala  Cys  Asp  Pro  Lys  Ile  Val  Asn  Ile  Gly  Ala  Val
               20                       25                       30
```

| | | | | | | | | | | | | | |
|---|---|---|---|---|---|---|---|---|---|---|---|---|---|
| Leu | Ser | Thr | Arg | Lys | His | Glu | Gln | Met | Phe | Arg | Glu | Ala | Val | Asn | Gln |
| | | 35 | | | | 40 | | | | | 45 | | | | |
| Ala | Asn | Lys | Arg | His | Gly | Ser | Trp | Lys | Ile | Gln | Leu | Asn | Ala | Thr | Ser |
| | 50 | | | | 55 | | | | | 60 | | | | | |
| Val | Thr | His | Lys | Pro | Asn | Ala | Ile | Gln | Met | Ala | Leu | Ser | Val | Cys | Glu |
| 65 | | | | | 70 | | | | 75 | | | | | | 80 |
| Asp | Leu | Ile | Ser | Ser | Gln | Val | Tyr | Ala | Ile | Leu | Val | Ser | His | Pro | Pro |
| | | | | 85 | | | | | 90 | | | | | 95 | |
| Thr | Pro | Asn | Asp | His | Phe | Thr | Pro | Thr | Pro | Val | Ser | Tyr | Thr | Ala | Gly |
| | | | 100 | | | | | 105 | | | | | 110 | | |
| Phe | Tyr | Arg | Ile | Pro | Val | Leu | Gly | Leu | Thr | Thr | Arg | Met | Ser | Ile | Tyr |
| | | 115 | | | | | 120 | | | | | 125 | | | |
| Ser | Asp | Lys | Ser | Ile | His | Leu | Ser | Phe | Leu | Arg | Thr | Val | Pro | Pro | Tyr |
| | 130 | | | | | 135 | | | | | 140 | | | | |
| Ser | His | Gln | Ser | Ser | Val | Trp | Phe | Glu | Met | Met | Arg | Val | Tyr | Ser | Trp |
| 145 | | | | | 150 | | | | | 155 | | | | | 160 |
| Asn | His | Ile | Ile | Leu | Leu | Val | Ser | Asp | Asp | His | Glu | Gly | Arg | Ala | Ala |
| | | | | 165 | | | | | 170 | | | | | 175 | |
| Gln | Lys | Arg | Leu | Glu | Thr | Leu | Leu | Glu | Arg | Glu | Ser | Lys | Ala | Glu | |
| | | | 180 | | | | | 185 | | | | | 190 | | |
| Lys | Val | Leu | Gln | Phe | Asp | Pro | Gly | Thr | Lys | Asn | Val | Thr | Ala | Leu | Leu |
| | | 195 | | | | | 200 | | | | | 205 | | | |
| Met | Glu | Ala | Lys | Glu | Leu | Glu | Ala | Arg | Val | Ile | Ile | Leu | Ser | Ala | Ser |
| 210 | | | | | 215 | | | | | 220 | | | | | |
| Glu | Asp | Asp | Ala | Ala | Thr | Val | Tyr | Arg | Ala | Ala | Ala | Met | Leu | Asn | Met |
| 225 | | | | | 230 | | | | | 235 | | | | | 240 |
| Thr | Gly | Ser | Gly | Tyr | Val | Trp | Leu | Val | Gly | Glu | Arg | Glu | Ile | Ser | Gly |
| | | | | 245 | | | | | 250 | | | | | 255 | |
| Asn | Ala | Leu | Arg | Tyr | Ala | Pro | Asp | Gly | Ile | Leu | Gly | Leu | Gln | Leu | Ile |
| | | | 260 | | | | | 265 | | | | | 270 | | |
| Asn | Gly | Lys | Asn | Glu | Ser | Ala | His | Ile | Ser | Asp | Ala | Val | Gly | Val | Val |
| | | 275 | | | | | 280 | | | | | 285 | | | |
| Ala | Gln | Ala | Val | His | Glu | Leu | Leu | Glu | Lys | Glu | Asn | Ile | Thr | Asp | Pro |
| | 290 | | | | | 295 | | | | | 300 | | | | |
| Pro | Arg | Gly | Cys | Val | Gly | Asn | Thr | Asn | Ile | Trp | Lys | Thr | Gly | Pro | Leu |
| 305 | | | | | 310 | | | | | 315 | | | | | 320 |
| Phe | Lys | Arg | Val | Leu | Met | Ser | Ser | Lys | Tyr | Ala | Asp | Gly | Val | Thr | Gly |
| | | | | 325 | | | | | 330 | | | | | 335 | |
| Arg | Val | Glu | Phe | Asn | Glu | Asp | Gly | Asp | Arg | Lys | Phe | Ala | Asn | Tyr | Ser |
| | | | 340 | | | | | 345 | | | | | 350 | | |
| Ile | Met | Asn | Leu | Gln | Asn | Arg | Lys | Leu | Val | Gln | Val | Gly | Ile | Tyr | Asn |
| | | 355 | | | | | 360 | | | | | 365 | | | |
| Gly | Thr | His | Val | Ile | Pro | Asn | Asp | Arg | Lys | Ile | Ile | Trp | Pro | Gly | Gly |
| | 370 | | | | | 375 | | | | | 380 | | | | |
| Glu | Thr | Glu | Lys | Pro | Arg | Gly | Tyr | Gln | Met | Ser | Thr | Arg | Leu | Lys | Ile |
| 385 | | | | | 390 | | | | | 395 | | | | | 400 |
| Val | Thr | Ile | His | Gln | Glu | Pro | Phe | Val | Tyr | Val | Lys | Pro | Thr | Leu | Ser |
| | | | | 405 | | | | | 410 | | | | | 415 | |
| Asp | Gly | Thr | Cys | Lys | Glu | Glu | Phe | Thr | Val | Asn | Gly | Asp | Pro | Val | Lys |
| | | | 420 | | | | | 425 | | | | | 430 | | |
| Lys | Val | Ile | Cys | Thr | Gly | Pro | Asn | Asp | Thr | Ser | Pro | Gly | Ser | Pro | Arg |
| | | 435 | | | | | 440 | | | | | 445 | | | |
| His | Thr | Val | Pro | Gln | Cys | Cys | Tyr | Gly | Phe | Cys | Ile | Asp | Leu | Leu | Ile |
| 450 | | | | | 455 | | | | | 460 | | | | | |

```
Lys  Leu  Ala  Arg  Thr  Met  Asn  Phe  Thr  Tyr  Glu  Val  His  Leu  Val  Ala
465                 470                 475                           480

Asp  Gly  Lys  Phe  Gly  Thr  Gln  Glu  Arg  Val  Asn  Asn  Ser  Asn  Lys  Lys
                    485                 490                      495

Glu  Trp  Asn  Gly  Met  Met  Gly  Glu  Leu  Leu  Ser  Gly  Gln  Ala  Asp  Met
               500                 505                      510

Ile  Val  Ala  Pro  Leu  Thr  Ile  Asn  Glu  Arg  Ala  Gln  Tyr  Ile  Glu
          515                 520                      525

Phe  Ser  Lys  Pro  Phe  Lys  Tyr  Gln  Gly  Leu  Thr  Ile  Leu  Val  Lys  Lys
     530                 535                      540

Glu  Ile  Pro  Arg  Ser  Thr  Leu  Asp  Ser  Phe  Met  Gln  Pro  Phe  Gln  Ser
545                 550                 555                           560

Thr  Leu  Trp  Leu  Leu  Val  Gly  Leu  Ser  Val  His  Val  Val  Ala  Val  Met
               565                 570                      575

Leu  Tyr  Leu  Leu  Asp  Arg  Phe  Ser  Pro  Phe  Gly  Arg  Phe  Lys  Val  Asn
               580                 585                      590

Ser  Glu  Glu  Glu  Glu  Asp  Ala  Leu  Thr  Leu  Ser  Ser  Ala  Met  Trp
          595                 600                 605

Phe  Ser  Trp  Gly  Val  Leu  Leu  Asn  Ser  Gly  Ile  Gly  Glu  Gly  Ala  Pro
     610                 615                 620

Arg  Ser  Phe  Ser  Ala  Arg  Ile  Leu  Gly  Met  Val  Trp  Ala  Gly  Phe  Ala
625                 630                 635                           640

Met  Ile  Ile  Val  Ala  Ser  Tyr  Thr  Ala  Asn  Leu  Ala  Ala  Phe  Leu  Val
               645                 650                      655

Leu  Asp  Arg  Pro  Glu  Glu  Arg  Ile  Thr  Gly  Ile  Asn  Asp  Pro  Arg  Leu
               660                 665                      670

Arg  Asn  Pro  Ser  Asp  Lys  Phe  Ile  Tyr  Ala  Thr  Val  Lys  Gln  Ser  Ser
          675                 680                      685

Val  Asp  Ile  Tyr  Phe  Arg  Arg  Gln  Val  Glu  Leu  Ser  Thr  Met  Tyr  Arg
          690                 695                      700

His  Met  Glu  Lys  His  Asn  Tyr  Glu  Ser  Ala  Ala  Glu  Ala  Ile  Gln  Ala
705                 710                 715                           720

Val  Arg  Asp  Asn  Lys  Leu  His  Ala  Phe  Ile  Trp  Asp  Ser  Ala  Val  Leu
               725                 730                      735

Glu  Phe  Glu  Ala  Ser  Gln  Lys  Cys  Asp  Leu  Val  Thr  Thr  Gly  Glu  Leu
               740                 745                      750

Phe  Phe  Arg  Ser  Gly  Phe  Gly  Ile  Gly  Met  Arg  Lys  Asp  Ser  Pro  Trp
          755                 760                      765

Lys  Gln  Asn  Val  Ser  Leu  Ser  Ile  Leu  Lys  Ser  His  Glu  Asn  Gly  Phe
     770                 775                      780

Met  Glu  Asp  Leu  Asp  Lys  Thr  Trp  Val  Arg  Tyr  Gln  Glu  Cys  Asp  Ser
785                 790                 795                           800

Arg  Ser  Asn  Ala  Pro  Ala  Thr  Leu  Thr  Phe  Glu  Asn  Met  Ala  Gly  Val
               805                 810                      815

Phe  Met  Leu  Val  Ala  Gly  Gly  Ile  Val  Ala  Gly  Ile  Phe  Leu  Ile  Phe
               820                 825                      830

Ile  Glu  Ile  Ala  Tyr  Lys  Arg  His  Lys  Asp  Ala  Arg  Arg  Lys  Gln  Met
               835                 840                      845

Gln  Leu  Ala  Phe  Ala  Ala  Val  Asn  Val  Trp  Arg  Lys  Asn  Leu  Gln  Asp
     850                 855                      860

Arg  Lys  Ser  Gly  Arg  Ala  Glu  Pro  Asp  Pro  Lys  Lys  Lys  Ala  Thr  Phe
865                 870                 875                           880

Arg  Ala  Ile  Thr  Ser  Thr  Leu  Ala  Ser  Ser  Phe  Lys  Arg  Arg  Arg  Ser
```

|  |  |  | 885 |  |  |  |  | 890 |  |  |  |  | 895 |  |  |
|---|---|---|---|---|---|---|---|---|---|---|---|---|---|---|---|
| Ser | Lys | Asp | Thr | Leu | Ala | Arg | Asp | Cys | Leu | Gln | Pro | Cys | Pro | Ala | Pro |
|  |  |  | 900 |  |  |  |  | 905 |  |  |  |  | 910 |  |  |
| Trp | Ala | Arg | Glu | Ser | Ala | Thr | Arg | Pro | Pro | Pro | Pro | Ser | Leu | Arg | Val |
|  |  | 915 |  |  |  |  | 920 |  |  |  |  | 925 |  |  |  |
| Arg | Asp | Arg | Pro | Ala | Thr | Leu | Tyr | Arg | Thr | Ser | Thr | Pro | Arg | Ala | Arg |
|  | 930 |  |  |  |  | 935 |  |  |  |  | 940 |  |  |  |  |
| Ala | Arg | Ala | Phe | Pro | Val | Arg | Ser | Arg | Ala | Leu | Pro | Leu | Arg | Pro | Gln |
| 945 |  |  |  |  | 950 |  |  |  |  | 955 |  |  |  |  | 960 |
| Gly | Ala | Gly | Ala | His | Arg | Pro | Thr | Pro | Thr | Ser | Arg | Cys | Met | Gln | Trp |
|  |  |  |  | 965 |  |  |  |  | 970 |  |  |  |  | 975 |  |

( 2 ) INFORMATION FOR SEQ ID NO:23:

( i ) SEQUENCE CHARACTERISTICS:
        ( A ) LENGTH: 4361 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..3141

( x i ) SEQUENCE DESCRIPTION: SEQ ID NO:23:

| CAAGCCGGGC | GTTCGGAGCT | GTGCCCGGCC | CCGCTTCAGC | ACCGCGGACA | GCGCCGGCCG | 60 |
|---|---|---|---|---|---|---|
| CGTGGGGCTG | AGCGCCGAGC | CCCCGCGCAC | GCTTCAGCCC | CCCTTCCCTC | GGCCGACGTC | 120 |
| CCGGGACCGC | CGCTCCGGGG | GAGACGTGGC | GTCCGCAGCC | CGCGGGGCCG | GGCGAGCGCA | 180 |
| GGACGGCCCG | GAAGCCCCGC | GGGGGATGCG | CCGAGGGCCC | CGCGTTCGCG | CCGCGCAGAG | 240 |
| CCAGGCCCGC | GGCCCGAGCC | C ATG AGC ACC ATG CGC CTG CTG ACG CTC GCC | | | | 291 |

Met Ser Thr Met Arg Leu Leu Thr Leu Ala
                             1             5                 10

| CTG | CTG | TTC | TCC | TGC | TCC | GTC | GCC | CGT | GCC | GCG | TGC | GAC | CCC | AAG | ATC | 339 |
|---|---|---|---|---|---|---|---|---|---|---|---|---|---|---|---|---|
| Leu | Leu | Phe | Ser | Cys | Ser | Val | Ala | Arg | Ala | Ala | Cys | Asp | Pro | Lys | Ile |  |
|  |  |  |  | 15 |  |  |  |  | 20 |  |  |  |  | 25 |  |  |
| GTC | AAC | ATT | GGC | GCG | GTG | CTG | AGC | ACG | CGG | AAG | CAC | GAG | CAG | ATG | TTC | 387 |
| Val | Asn | Ile | Gly | Ala | Val | Leu | Ser | Thr | Arg | Lys | His | Glu | Gln | Met | Phe |  |
|  |  |  | 30 |  |  |  |  | 35 |  |  |  |  | 40 |  |  |  |
| CGC | GAG | GCC | GTG | AAC | CAG | GCC | AAC | AAG | CGG | CAC | GGC | TCC | TGG | AAG | ATT | 435 |
| Arg | Glu | Ala | Val | Asn | Gln | Ala | Asn | Lys | Arg | His | Gly | Ser | Trp | Lys | Ile |  |
|  |  | 45 |  |  |  |  | 50 |  |  |  |  | 55 |  |  |  |  |
| CAG | CTC | AAT | GCC | ACC | TCC | GTC | ACG | CAC | AAG | CCC | AAC | GCC | ATC | CAG | ATG | 483 |
| Gln | Leu | Asn | Ala | Thr | Ser | Val | Thr | His | Lys | Pro | Asn | Ala | Ile | Gln | Met |  |
|  | 60 |  |  |  |  | 65 |  |  |  |  | 70 |  |  |  |  |  |
| GCT | CTG | TCG | GTG | TGC | GAG | GAC | CTC | ATC | TCC | AGC | CAG | GTC | TAC | GCC | ATC | 531 |
| Ala | Leu | Ser | Val | Cys | Glu | Asp | Leu | Ile | Ser | Ser | Gln | Val | Tyr | Ala | Ile |  |
| 75 |  |  |  |  | 80 |  |  |  |  | 85 |  |  |  |  | 90 |  |
| CTA | GTT | AGC | CAT | CCA | CCT | ACC | CCC | AAC | GAC | CAC | TTC | ACT | CCC | ACC | CCT | 579 |
| Leu | Val | Ser | His | Pro | Pro | Thr | Pro | Asn | Asp | His | Phe | Thr | Pro | Thr | Pro |  |
|  |  |  |  | 95 |  |  |  |  | 100 |  |  |  |  | 105 |  |  |
| GTC | TCC | TAC | ACA | GCC | GGC | TTC | TAC | CGC | ATA | CCC | GTG | CTG | GGG | CTG | ACC | 627 |
| Val | Ser | Tyr | Thr | Ala | Gly | Phe | Tyr | Arg | Ile | Pro | Val | Leu | Gly | Leu | Thr |  |
|  |  |  | 110 |  |  |  |  | 115 |  |  |  |  | 120 |  |  |  |
| ACC | CGC | ATG | TCC | ATC | TAC | TCG | GAC | AAG | AGC | ATC | CAC | CTG | AGC | TTC | CTG | 675 |
| Thr | Arg | Met | Ser | Ile | Tyr | Ser | Asp | Lys | Ser | Ile | His | Leu | Ser | Phe | Leu |  |
|  |  | 125 |  |  |  |  | 130 |  |  |  |  | 135 |  |  |  |  |
| CGC | ACC | GTG | CCG | CCC | TAC | TCC | CAC | CAG | TCC | AGC | GTG | TGG | TTT | GAG | ATG | 723 |
| Arg | Thr | Val | Pro | Pro | Tyr | Ser | His | Gln | Ser | Ser | Val | Trp | Phe | Glu | Met |  |

```
                   140                           145                              150
ATG  CGT  GTC  TAC  AGC  TGG  AAC  CAC  ATC  ATC  CTG  CTG  GTC  AGC  GAC  GAC     771
Met  Arg  Val  Tyr  Ser  Trp  Asn  His  Ile  Ile  Leu  Leu  Val  Ser  Asp  Asp
155                 160                      165                          170

CAC  GAG  GGC  CGG  GCG  GCT  CAG  AAA  CGC  CTG  GAG  ACG  CTG  CTG  GAG  GAG     819
His  Glu  Gly  Arg  Ala  Ala  Gln  Lys  Arg  Leu  Glu  Thr  Leu  Leu  Glu  Glu
               175                      180                          185

CGT  GAG  TCC  AAG  AGT  AAA  AAA  AGG  AAC  TAT  GAA  AAC  CTC  GAC  CAA  CTG     867
Arg  Glu  Ser  Lys  Ser  Lys  Lys  Arg  Asn  Tyr  Glu  Asn  Leu  Asp  Gln  Leu
               190                      195                     200

TCC  TAT  GAC  AAC  AAG  CGC  GGA  CCC  AAG  GCA  GAG  AAG  GTG  CTG  CAG  TTT     915
Ser  Tyr  Asp  Asn  Lys  Arg  Gly  Pro  Lys  Ala  Glu  Lys  Val  Leu  Gln  Phe
          205                      210                     215

GAC  CCA  GGG  ACC  AAG  AAC  GTG  ACG  GCC  CTG  CTG  ATG  GAG  GCG  AAA  GAG     963
Asp  Pro  Gly  Thr  Lys  Asn  Val  Thr  Ala  Leu  Leu  Met  Glu  Ala  Lys  Glu
220                      225                          230

CTG  GAG  GCC  CGG  GTC  ATC  ATC  CTT  TCT  GCC  AGC  GAG  GAC  GAT  GCT  GCC    1011
Leu  Glu  Ala  Arg  Val  Ile  Ile  Leu  Ser  Ala  Ser  Glu  Asp  Asp  Ala  Ala
235                      240                      245                     250

ACT  GTA  TAC  CGC  GCA  GCC  GCG  ATG  CTG  AAC  ATG  ACG  GGC  TCC  GGG  TAC    1059
Thr  Val  Tyr  Arg  Ala  Ala  Ala  Met  Leu  Asn  Met  Thr  Gly  Ser  Gly  Tyr
                    255                      260                     265

GTG  TGG  CTG  GTC  GGC  GAG  CGC  GAG  ATC  TCG  GGG  AAC  GCC  CTG  CGC  TAC    1107
Val  Trp  Leu  Val  Gly  Glu  Arg  Glu  Ile  Ser  Gly  Asn  Ala  Leu  Arg  Tyr
               270                      275                          280

GCC  CCA  GAC  GGC  ATC  CTC  GGG  CTG  CAG  CTC  ATC  AAC  GGC  AAG  AAC  GAG    1155
Ala  Pro  Asp  Gly  Ile  Leu  Gly  Leu  Gln  Leu  Ile  Asn  Gly  Lys  Asn  Glu
               285                      290                     295

TCG  GCC  CAC  ATC  AGC  GAC  GCC  GTG  GGC  GTG  GTG  GCC  CAG  GCC  GTG  CAC    1203
Ser  Ala  His  Ile  Ser  Asp  Ala  Val  Gly  Val  Val  Ala  Gln  Ala  Val  His
          300                      305                          310

GAG  CTC  CTC  GAG  AAG  GAG  AAC  ATC  ACC  GAC  CCG  CCG  CGG  GGC  TGC  GTG    1251
Glu  Leu  Leu  Glu  Lys  Glu  Asn  Ile  Thr  Asp  Pro  Pro  Arg  Gly  Cys  Val
315                      320                      325                     330

GGC  AAC  ACC  AAC  ATC  TGG  AAG  ACC  GGG  CCG  CTC  TTC  AAG  AGA  GTG  CTG    1299
Gly  Asn  Thr  Asn  Ile  Trp  Lys  Thr  Gly  Pro  Leu  Phe  Lys  Arg  Val  Leu
               335                      340                          345

ATG  TCT  TCC  AAG  TAT  GCG  GAT  GGG  GTG  ACT  GGT  CGC  GTG  GAG  TTC  AAT    1347
Met  Ser  Ser  Lys  Tyr  Ala  Asp  Gly  Val  Thr  Gly  Arg  Val  Glu  Phe  Asn
               350                      355                          360

GAG  GAT  GGG  GAC  CGG  AAG  TTC  GCC  AAC  TAC  AGC  ATC  ATG  AAC  CTG  CAG    1395
Glu  Asp  Gly  Asp  Arg  Lys  Phe  Ala  Asn  Tyr  Ser  Ile  Met  Asn  Leu  Gln
          365                      370                          375

AAC  CGC  AAG  CTG  GTG  CAA  GTG  GGC  ATC  TAC  AAT  GGC  ACC  CAC  GTC  ATC    1443
Asn  Arg  Lys  Leu  Val  Gln  Val  Gly  Ile  Tyr  Asn  Gly  Thr  His  Val  Ile
     380                      385                          390

CCT  AAT  GAC  AGG  AAG  ATC  ATC  TGG  CCA  GGC  GGA  GAG  ACA  GAG  AAG  CCT    1491
Pro  Asn  Asp  Arg  Lys  Ile  Ile  Trp  Pro  Gly  Gly  Glu  Thr  Glu  Lys  Pro
395                      400                      405                     410

CGA  GGG  TAC  CAG  ATG  TCC  ACC  AGA  CTG  AAG  ATT  GTG  ACG  ATC  CAC  CAG    1539
Arg  Gly  Tyr  Gln  Met  Ser  Thr  Arg  Leu  Lys  Ile  Val  Thr  Ile  His  Gln
                    415                      420                     425

GAG  CCC  TTC  GTG  TAC  GTC  AAG  CCC  ACG  CTG  AGT  GAT  GGG  ACA  TGC  AAG    1587
Glu  Pro  Phe  Val  Tyr  Val  Lys  Pro  Thr  Leu  Ser  Asp  Gly  Thr  Cys  Lys
               430                      435                          440

GAG  GAG  TTC  ACA  GTC  AAC  GGC  GAC  CCA  GTC  AAG  AAG  GTG  ATC  TGC  ACC    1635
Glu  Glu  Phe  Thr  Val  Asn  Gly  Asp  Pro  Val  Lys  Lys  Val  Ile  Cys  Thr
          445                      450                          455

GGG  CCC  AAC  GAC  ACG  TCG  CCG  GGC  AGC  CCC  CGC  CAC  ACG  GTG  CCT  CAG    1683
Gly  Pro  Asn  Asp  Thr  Ser  Pro  Gly  Ser  Pro  Arg  His  Thr  Val  Pro  Gln
```

|                         |       |
|-------------------------|-------|
| 460                     |       |
| TGT TGC TAC GGC TTT TGC ATC GAC CTG CTC ATC AAG CTG GCA CGG ACC | 1731 |
| Cys Cys Tyr Gly Phe Cys Ile Asp Leu Leu Ile Lys Leu Ala Arg Thr |      |
| 475             480             485             490            |      |
| ATG AAC TTC ACC TAC GAG GTG CAC CTG GTG GCA GAT GGC AAG TTC GGC | 1779 |
| Met Asn Phe Thr Tyr Glu Val His Leu Val Ala Asp Gly Lys Phe Gly |      |
|                 495             500             505            |      |
| ACA CAG GAG CGG GTG AAC AAC AGC AAC AAG AAG GAG TGG AAT GGG ATG | 1827 |
| Thr Gln Glu Arg Val Asn Asn Ser Asn Lys Lys Glu Trp Asn Gly Met |      |
|         510                     515             520            |      |
| ATG GGC GAG CTG CTC AGC GGG CAG GCA GAC ATG ATC GTG GCG CCG CTA | 1875 |
| Met Gly Glu Leu Leu Ser Gly Gln Ala Asp Met Ile Val Ala Pro Leu |      |
|         525             530             535                    |      |
| ACC ATA AAC AAC GAG CGC GCG CAG TAC ATC GAG TTT TCC AAG CCC TTC | 1923 |
| Thr Ile Asn Asn Glu Arg Ala Gln Tyr Ile Glu Phe Ser Lys Pro Phe |      |
| 540                     545                     550            |      |
| AAG TAC CAG GGC CTG ACT ATT CTG GTC AAG AAG GAG ATT CCC CGG AGC | 1971 |
| Lys Tyr Gln Gly Leu Thr Ile Leu Val Lys Lys Glu Ile Pro Arg Ser |      |
| 555                     560             565             570    |      |
| ACG CTG GAC TCG TTC ATG CAG CCG TTC CAG AGC ACA CTG TGG CTG CTG | 2019 |
| Thr Leu Asp Ser Phe Met Gln Pro Phe Gln Ser Thr Leu Trp Leu Leu |      |
|                 575             580                     585    |      |
| GTG GGG CTG TCG GTG CAC GTG GTG GCC GTG ATG CTG TAC CTG CTG GAC | 2067 |
| Val Gly Leu Ser Val His Val Val Ala Val Met Leu Tyr Leu Leu Asp |      |
|                 590             595             600            |      |
| CGC TTC AGC CCC TTC GGC CGG TTC AAG GTG AAC AGC GAG GAG GAG GAG | 2115 |
| Arg Phe Ser Pro Phe Gly Arg Phe Lys Val Asn Ser Glu Glu Glu Glu |      |
|             605             610             615                |      |
| GAG GAC GCA CTG ACC CTG TCC TCG GCC ATG TGG TTC TCC TGG GGC GTC | 2163 |
| Glu Asp Ala Leu Thr Leu Ser Ser Ala Met Trp Phe Ser Trp Gly Val |      |
|         620                     625             630            |      |
| CTG CTC AAC TCC GGC ATC GGG GAA GGC GCC CCC AGA AGC TTC TCA GCG | 2211 |
| Leu Leu Asn Ser Gly Ile Gly Glu Gly Ala Pro Arg Ser Phe Ser Ala |      |
| 635                     640             645             650    |      |
| CGC ATC CTG GGC ATG GTG TGG GCC GGC TTT GCC ATG ATC ATC GTG GCC | 2259 |
| Arg Ile Leu Gly Met Val Trp Ala Gly Phe Ala Met Ile Ile Val Ala |      |
|                 655             660             665            |      |
| TCC TAC ACC GCC AAC CTG GCG GCC TTC CTG GTG CTG GAC CGG CCG GAG | 2307 |
| Ser Tyr Thr Ala Asn Leu Ala Ala Phe Leu Val Leu Asp Arg Pro Glu |      |
|         670                     675             680            |      |
| GAG CGC ATC ACG GGC ATC AAC GAC CCT CGG CTG AGG AAC CCC TCG GAC | 2355 |
| Glu Arg Ile Thr Gly Ile Asn Asp Pro Arg Leu Arg Asn Pro Ser Asp |      |
|         685             690             695                    |      |
| AAG TTT ATC TAC GCC ACG GTG AAG CAG AGC TCC GTG GAT ATC TAC TTC | 2403 |
| Lys Phe Ile Tyr Ala Thr Val Lys Gln Ser Ser Val Asp Ile Tyr Phe |      |
| 700             705             710                            |      |
| CGG CGC CAG GTG GAG CTG AGC ACC ATG TAC CGG CAT ATG GAG AAG CAC | 2451 |
| Arg Arg Gln Val Glu Leu Ser Thr Met Tyr Arg His Met Glu Lys His |      |
| 715             720             725             730            |      |
| AAC TAC GAG AGT GCG GCG GAG GCC ATC CAG GCC GTG AGA GAC AAC AAG | 2499 |
| Asn Tyr Glu Ser Ala Ala Glu Ala Ile Gln Ala Val Arg Asp Asn Lys |      |
|             735             740                     745        |      |
| CTG CAT GCC TTC ATC TGG GAC TCG GCG GTG CTG GAG TTC GAG GCC TCG | 2547 |
| Leu His Ala Phe Ile Trp Asp Ser Ala Val Leu Glu Phe Glu Ala Ser |      |
|             750                     755             760        |      |
| CAG AAG TGC GAC CTG GTG ACG ACT GGA GAG CTG TTT TTC CGC TCG GGC | 2595 |
| Gln Lys Cys Asp Leu Val Thr Thr Gly Glu Leu Phe Phe Arg Ser Gly |      |
|         765             770                     775            |      |
| TTC GGC ATA GGC ATG CGC AAA GAC AGC CCC TGG AAG CAG AAC GTC TCC | 2643 |
| Phe Gly Ile Gly Met Arg Lys Asp Ser Pro Trp Lys Gln Asn Val Ser |      |

-continued

|     |     |     | 780 |     |     |     |     | 785 |     |     |     |     | 790 |     |     |      |
|-----|-----|-----|-----|-----|-----|-----|-----|-----|-----|-----|-----|-----|-----|-----|-----|------|
| CTG | TCC | ATC | CTC | AAG | TCC | CAC | GAG | AAT | GGC | TTC | ATG | GAA | GAC | CTG | GAC | 2691 |
| Leu | Ser | Ile | Leu | Lys | Ser | His | Glu | Asn | Gly | Phe | Met | Glu | Asp | Leu | Asp |      |
| 795 |     |     |     |     | 800 |     |     |     |     | 805 |     |     |     |     | 810 |      |

| AAG | ACG | TGG | GTT | CGG | TAT | CAG | GAA | TGT | GAC | TCG | CGC | AGC | AAC | GCC | CCT | 2739 |
|-----|-----|-----|-----|-----|-----|-----|-----|-----|-----|-----|-----|-----|-----|-----|-----|------|
| Lys | Thr | Trp | Val | Arg | Tyr | Gln | Glu | Cys | Asp | Ser | Arg | Ser | Asn | Ala | Pro |      |
|     |     |     |     | 815 |     |     |     |     | 820 |     |     |     |     | 825 |     |      |

| GCG | ACC | CTT | ACT | TTT | GAG | AAC | ATG | GCC | GGG | GTC | TTC | ATG | CTG | GTA | GCT | 2787 |
|-----|-----|-----|-----|-----|-----|-----|-----|-----|-----|-----|-----|-----|-----|-----|-----|------|
| Ala | Thr | Leu | Thr | Phe | Glu | Asn | Met | Ala | Gly | Val | Phe | Met | Leu | Val | Ala |      |
|     |     |     | 830 |     |     |     |     | 835 |     |     |     |     | 840 |     |     |      |

| GGG | GGC | ATC | GTG | GCC | GGG | ATC | TTC | CTG | ATT | TTC | ATC | GAG | ATT | GCC | TAC | 2835 |
|-----|-----|-----|-----|-----|-----|-----|-----|-----|-----|-----|-----|-----|-----|-----|-----|------|
| Gly | Gly | Ile | Val | Ala | Gly | Ile | Phe | Leu | Ile | Phe | Ile | Glu | Ile | Ala | Tyr |      |
|     |     | 845 |     |     |     |     | 850 |     |     |     |     | 855 |     |     |     |      |

| AAG | CGG | CAC | AAG | GAT | GCT | CGC | CGG | AAG | CAG | ATG | CAG | CTG | GCC | TTT | GCC | 2883 |
|-----|-----|-----|-----|-----|-----|-----|-----|-----|-----|-----|-----|-----|-----|-----|-----|------|
| Lys | Arg | His | Lys | Asp | Ala | Arg | Arg | Lys | Gln | Met | Gln | Leu | Ala | Phe | Ala |      |
|     | 860 |     |     |     |     | 865 |     |     |     |     | 870 |     |     |     |     |      |

| GCC | GTT | AAC | GTG | TGG | CGG | AAG | AAC | CTG | CAG | GAT | AGA | AAG | AGT | GGT | AGA | 2931 |
|-----|-----|-----|-----|-----|-----|-----|-----|-----|-----|-----|-----|-----|-----|-----|-----|------|
| Ala | Val | Asn | Val | Trp | Arg | Lys | Asn | Leu | Gln | Asp | Arg | Lys | Ser | Gly | Arg |      |
| 875 |     |     |     |     | 880 |     |     |     |     | 885 |     |     |     |     | 890 |      |

| GCA | GAG | CCT | GAC | CCT | AAA | AAG | AAA | GCC | ACA | TTT | AGG | GCT | ATC | ACC | TCC | 2979 |
|-----|-----|-----|-----|-----|-----|-----|-----|-----|-----|-----|-----|-----|-----|-----|-----|------|
| Ala | Glu | Pro | Asp | Pro | Lys | Lys | Lys | Ala | Thr | Phe | Arg | Ala | Ile | Thr | Ser |      |
|     |     |     |     | 895 |     |     |     |     | 900 |     |     |     |     | 905 |     |      |

| ACC | CTG | GCT | TCC | AGC | TTC | AAG | AGG | CGT | AGG | TCC | TCC | AAA | GAC | ACG | AGC | 3027 |
|-----|-----|-----|-----|-----|-----|-----|-----|-----|-----|-----|-----|-----|-----|-----|-----|------|
| Thr | Leu | Ala | Ser | Ser | Phe | Lys | Arg | Arg | Arg | Ser | Ser | Lys | Asp | Thr | Ser |      |
|     |     |     | 910 |     |     |     |     | 915 |     |     |     |     | 920 |     |     |      |

| ACC | GGG | GGT | GGA | CGC | GGT | GCT | TTG | CAA | AAC | CAA | AAA | GAC | ACA | GTG | CTG | 3075 |
|-----|-----|-----|-----|-----|-----|-----|-----|-----|-----|-----|-----|-----|-----|-----|-----|------|
| Thr | Gly | Gly | Gly | Arg | Gly | Ala | Leu | Gln | Asn | Gln | Lys | Asp | Thr | Val | Leu |      |
|     |     | 925 |     |     |     |     | 930 |     |     |     |     | 935 |     |     |     |      |

| CCG | CGA | CGC | GCT | ATT | GAG | AGG | GAG | GAG | GGC | CAG | CTG | CAG | CTG | TGT | TCC | 3123 |
|-----|-----|-----|-----|-----|-----|-----|-----|-----|-----|-----|-----|-----|-----|-----|-----|------|
| Pro | Arg | Arg | Ala | Ile | Glu | Arg | Glu | Glu | Gly | Gln | Leu | Gln | Leu | Cys | Ser |      |
|     | 940 |     |     |     |     | 945 |     |     |     |     | 950 |     |     |     |     |      |

| CGT | CAT | AGG | GAG | AGC | TGAGACTCCC | CGCCCGCCCT | CCTCTGCCCC | CTCCCCGCA | 3178 |
|-----|-----|-----|-----|-----|------------|------------|------------|-----------|------|
| Arg | His | Arg | Glu | Ser |            |            |            |           |      |
| 955 |     |     |     | 960 |            |            |            |           |      |

| GACAGACAGA | CAGACGGACG | GGACAGCGGC | CCGGCCCACG | CAGAGCCCCG | GAGCACCACG | 3238 |
|------------|------------|------------|------------|------------|------------|------|
| GGGTCGGGGG | AGGAGCACCC | CCAGCCTCCC | CCAGGCTGCG | CCTGCCCGCC | CGCCGGTTGG | 3298 |
| CCGGCTGGCC | GGTCCACCCC | GTCCCGGCCC | CGCGCGTGCC | CCCAGCGTGG | GGCTAACGGG | 3358 |
| CGCCTTGTCT | GTGTATTTCT | ATTTTGCAGC | AGTACCATCC | CACTGATATC | ACGGGCCCGC | 3418 |
| TCAACCTCTC | AGATCCCTCG | GTCAGCACCG | TGGTGTGAGG | CCCCCGGAGG | CGCCCACCTG | 3478 |
| CCCAGTTAGC | CCGGCCAAGG | ACACTGATGG | GTCCTGCTGC | TCGGGAAGGC | CTGAGGGAAG | 3538 |
| CCCACCCGCC | CCAGAGACTG | CCCACCCTGG | GCCTCCCGTC | CGTCCGCCCG | CCCACCCCGC | 3598 |
| TGCCTGGCGG | GCAGCCCCTG | CTGGACCAAG | GTGCGGACCG | GAGCGGCTGA | GGACGGGGCA | 3658 |
| GAGCTGAGTC | GGCTGGGCAG | GGCCGCAGGG | CGCTCCGGCA | GAGGCAGGCC | CCTGGGGTCT | 3718 |
| CTGAGCAGTG | GGGAGCGGGG | GCTAACTGCC | CCCAGGCGGA | GGGGCTTGGA | GCAGAGACGG | 3778 |
| CAGCCCCATC | CTTCCCGCAG | CACCAGCCTG | AGCCACAGTG | GGCCCATGG | CCCAGCTGG | 3838 |
| CTGGGTCGCC | CCTCCTCGGG | CGCCTGCGCT | CCTCTGCAGC | CTGAGCTCCA | CCCTCCCCTC | 3898 |
| TTCTTGCGGC | ACCGCCCACC | AAACACCCCG | TCTGCCCCTT | GACGCCACAC | GCCGGGGCTG | 3958 |
| GCGCTGCCCT | CCCCCACGGC | CGTCCCTGAC | TTCCCAGCTG | CAGCGCCTC | CCGCCGCCTC | 4018 |
| GGGCCGCCTC | CTCCAGAATC | GAGAGGGCTG | AGCCCCTCCT | CTCCTCGTCC | GGCCTGCAGC | 4078 |
| ACAGAAGGGG | GCCTCCCCGG | GGGTCCCCGG | ACGCTGGCTC | GGGACTGTCT | TCAACCCTGC | 4138 |
| CCTGCACCTT | GGGCACGGGA | GAGCGCCACC | CGCCCGCCCC | CGCCCTCGCT | CCGGGTGCGT | 4198 |

```
GACCGGCCCG CCACCTTGTA CAGAACCAGC ACTCCCAGGG CCCGAGCGCG TGCCTTCCCC    4258

GTGCGCAGCC GCGCTCTGCC CCTCCGTCCC CAGGGTGCAG GCGCGCACCG CCCAACCCCC    4318

ACCTCCCGGT GTATGCAGTG GTGATGCCTA AAGGAATGTC ACG                      4361
```

( 2 ) INFORMATION FOR SEQ ID NO:24:

( i ) SEQUENCE CHARACTERISTICS:
        ( A ) LENGTH: 959 amino acids
        ( B ) TYPE: amino acid
        ( D ) TOPOLOGY: linear ( i i ) MOLECULE TYPE: protein ( x i ) SEQUENCE DESCRIPTION: SEQ ID NO:24:

```
Met Ser Thr Met Arg Leu Leu Thr Leu Ala Leu Leu Phe Ser Cys Ser
  1               5                  10                  15
Val Ala Arg Ala Ala Cys Asp Pro Lys Ile Val Asn Ile Gly Ala Val
             20                  25                  30
Leu Ser Thr Arg Lys His Glu Gln Met Phe Arg Glu Ala Val Asn Gln
         35                  40                  45
Ala Asn Lys Arg His Gly Ser Trp Lys Ile Gln Leu Asn Ala Thr Ser
     50                  55                  60
Val Thr His Lys Pro Asn Ala Ile Gln Met Ala Leu Ser Val Cys Glu
 65                  70                  75                  80
Asp Leu Ile Ser Ser Gln Val Tyr Ala Ile Leu Val Ser His Pro Pro
                 85                  90                  95
Thr Pro Asn Asp His Phe Thr Pro Thr Pro Val Ser Tyr Thr Ala Gly
            100                 105                 110
Phe Tyr Arg Ile Pro Val Leu Gly Leu Thr Thr Arg Met Ser Ile Tyr
        115                 120                 125
Ser Asp Lys Ser Ile His Leu Ser Phe Leu Arg Thr Val Pro Pro Tyr
    130                 135                 140
Ser His Gln Ser Ser Val Trp Phe Glu Met Met Arg Val Tyr Ser Trp
145                 150                 155                 160
Asn His Ile Ile Leu Leu Val Ser Asp Asp His Glu Gly Arg Ala Ala
                165                 170                 175
Gln Lys Arg Leu Glu Thr Leu Leu Glu Glu Arg Glu Ser Lys Ser Lys
            180                 185                 190
Lys Arg Asn Tyr Glu Asn Leu Asp Gln Leu Ser Tyr Asp Asn Lys Arg
        195                 200                 205
Gly Pro Lys Ala Glu Lys Val Leu Gln Phe Asp Pro Gly Thr Lys Asn
    210                 215                 220
Val Thr Ala Leu Leu Met Glu Ala Lys Glu Leu Glu Ala Arg Val Ile
225                 230                 235                 240
Ile Leu Ser Ala Ser Glu Asp Asp Ala Ala Thr Val Tyr Arg Ala Ala
                245                 250                 255
Ala Met Leu Asn Met Thr Gly Ser Gly Tyr Val Trp Leu Val Gly Glu
            260                 265                 270
Arg Glu Ile Ser Gly Asn Ala Leu Arg Tyr Ala Pro Asp Gly Ile Leu
        275                 280                 285
Gly Leu Gln Leu Ile Asn Gly Lys Asn Glu Ser Ala His Ile Ser Asp
    290                 295                 300
Ala Val Gly Val Val Ala Gln Ala Val His Glu Leu Leu Glu Lys Glu
305                 310                 315                 320
Asn Ile Thr Asp Pro Pro Arg Gly Cys Val Gly Asn Thr Asn Ile Trp
                325                 330                 335
```

```
Lys Thr Gly Pro Leu Phe Lys Arg Val Leu Met Ser Ser Lys Tyr Ala
            340             345                 350

Asp Gly Val Thr Gly Arg Val Glu Phe Asn Glu Asp Gly Asp Arg Lys
            355             360                 365

Phe Ala Asn Tyr Ser Ile Met Asn Leu Gln Asn Arg Lys Leu Val Gln
            370             375                 380

Val Gly Ile Tyr Asn Gly Thr His Val Ile Pro Asn Asp Arg Lys Ile
385             390             395                             400

Ile Trp Pro Gly Gly Glu Thr Glu Lys Pro Arg Gly Tyr Gln Met Ser
            405             410                 415

Thr Arg Leu Lys Ile Val Thr Ile His Gln Glu Pro Phe Val Tyr Val
            420             425                 430

Lys Pro Thr Leu Ser Asp Gly Thr Cys Lys Glu Glu Phe Thr Val Asn
            435             440                 445

Gly Asp Pro Val Lys Lys Val Ile Cys Thr Gly Pro Asn Asp Thr Ser
            450             455                 460

Pro Gly Ser Pro Arg His Thr Val Pro Gln Cys Cys Tyr Gly Phe Cys
465             470             475                             480

Ile Asp Leu Leu Ile Lys Leu Ala Arg Thr Met Asn Phe Thr Tyr Glu
                485             490                 495

Val His Leu Val Ala Asp Gly Lys Phe Gly Thr Gln Glu Arg Val Asn
            500             505                 510

Asn Ser Asn Lys Lys Glu Trp Asn Gly Met Met Gly Glu Leu Leu Ser
            515             520                 525

Gly Gln Ala Asp Met Ile Val Ala Pro Leu Thr Ile Asn Asn Glu Arg
            530             535                 540

Ala Gln Tyr Ile Glu Phe Ser Lys Pro Phe Lys Tyr Gln Gly Leu Thr
545             550             555                             560

Ile Leu Val Lys Lys Glu Ile Pro Arg Ser Thr Leu Asp Ser Phe Met
                565             570                 575

Gln Pro Phe Gln Ser Thr Leu Trp Leu Leu Val Gly Leu Ser Val His
            580             585                 590

Val Val Ala Val Met Leu Tyr Leu Leu Asp Arg Phe Ser Pro Phe Gly
            595             600                 605

Arg Phe Lys Val Asn Ser Glu Glu Glu Glu Asp Ala Leu Thr Leu
610             615             620

Ser Ser Ala Met Trp Phe Ser Trp Gly Val Leu Leu Asn Ser Gly Ile
625             630             635                             640

Gly Glu Gly Ala Pro Arg Ser Phe Ser Ala Arg Ile Leu Gly Met Val
            645             650                 655

Trp Ala Gly Phe Ala Met Ile Ile Val Ala Ser Tyr Thr Ala Asn Leu
            660             665                 670

Ala Ala Phe Leu Val Leu Asp Arg Pro Glu Glu Arg Ile Thr Gly Ile
            675             680                 685

Asn Asp Pro Arg Leu Arg Asn Pro Ser Asp Lys Phe Ile Tyr Ala Thr
            690             695                 700

Val Lys Gln Ser Ser Val Asp Ile Tyr Phe Arg Arg Gln Val Glu Leu
705             710             715                             720

Ser Thr Met Tyr Arg His Met Glu Lys His Asn Tyr Glu Ser Ala Ala
            725             730                 735

Glu Ala Ile Gln Ala Val Arg Asp Asn Lys Leu His Ala Phe Ile Trp
            740             745                 750

Asp Ser Ala Val Leu Glu Phe Glu Ala Ser Gln Lys Cys Asp Leu Val
```

|     |     |     |     |     | 755 |     |     |     |     | 760 |     |     |     |     | 765 |
| --- | --- | --- | --- | --- | --- | --- | --- | --- | --- | --- | --- | --- | --- | --- | --- |
| Thr | Thr | Gly | Glu | Leu | Phe | Phe | Arg | Ser | Gly | Phe | Gly | Ile | Gly | Met | Arg |
|     | 770 |     |     |     |     | 775 |     |     |     |     | 780 |     |     |     |     |
| Lys | Asp | Ser | Pro | Trp | Lys | Gln | Asn | Val | Ser | Leu | Ser | Ile | Leu | Lys | Ser |
| 785 |     |     |     |     | 790 |     |     |     |     | 795 |     |     |     |     | 800 |
| His | Glu | Asn | Gly | Phe | Met | Glu | Asp | Leu | Asp | Lys | Thr | Trp | Val | Arg | Tyr |
|     |     |     |     | 805 |     |     |     |     | 810 |     |     |     |     | 815 |     |
| Gln | Glu | Cys | Asp | Ser | Arg | Ser | Asn | Ala | Pro | Ala | Thr | Leu | Thr | Phe | Glu |
|     |     |     | 820 |     |     |     |     | 825 |     |     |     |     | 830 |     |     |
| Asn | Met | Ala | Gly | Val | Phe | Met | Leu | Val | Ala | Gly | Gly | Ile | Val | Ala | Gly |
|     |     | 835 |     |     |     |     | 840 |     |     |     |     | 845 |     |     |     |
| Ile | Phe | Leu | Ile | Phe | Ile | Glu | Ile | Ala | Tyr | Lys | Arg | His | Lys | Asp | Ala |
|     | 850 |     |     |     |     | 855 |     |     |     |     | 860 |     |     |     |     |
| Arg | Arg | Lys | Gln | Met | Gln | Leu | Ala | Phe | Ala | Ala | Val | Asn | Val | Trp | Arg |
| 865 |     |     |     |     | 870 |     |     |     |     | 875 |     |     |     |     | 880 |
| Lys | Asn | Leu | Gln | Asp | Arg | Lys | Ser | Gly | Arg | Ala | Glu | Pro | Asp | Pro | Lys |
|     |     |     |     | 885 |     |     |     |     | 890 |     |     |     |     | 895 |     |
| Lys | Lys | Ala | Thr | Phe | Arg | Ala | Ile | Thr | Ser | Thr | Leu | Ala | Ser | Ser | Phe |
|     |     |     | 900 |     |     |     |     | 905 |     |     |     |     | 910 |     |     |
| Lys | Arg | Arg | Arg | Ser | Ser | Lys | Asp | Thr | Ser | Thr | Gly | Gly | Gly | Arg | Gly |
|     |     | 915 |     |     |     |     | 920 |     |     |     |     | 925 |     |     |     |
| Ala | Leu | Gln | Asn | Gln | Lys | Asp | Thr | Val | Leu | Pro | Arg | Arg | Ala | Ile | Glu |
|     | 930 |     |     |     |     | 935 |     |     |     |     | 940 |     |     |     |     |
| Arg | Glu | Glu | Gly | Gln | Leu | Gln | Leu | Cys | Ser | Arg | His | Arg | Glu | Ser |     |
| 945 |     |     |     |     | 950 |     |     |     |     | 955 |     |     |     |     |     |

( 2 ) INFORMATION FOR SEQ ID NO:25:

( i ) SEQUENCE CHARACTERISTICS:
        ( A ) LENGTH: 4157 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..2937

( x i ) SEQUENCE DESCRIPTION: SEQ ID NO:25:

| | | | | | |
| --- | --- | --- | --- | --- | --- |
| CAAGCCGGGC | GTTCGGAGCT | GTGCCCGGCC | CCGCTTCAGC | ACCGCGGACA | GCGCCGGCCG | 60 |
| CGTGGGGCTG | AGCGCCGAGC | CCCCGCGCAC | GCTTCAGCCC | CCCTTCCCTC | GGCCGACGTC | 120 |
| CCGGGACCGC | CGCTCCGGGG | GAGACGTGGC | GTCCGCAGCC | CGCGGGGCCG | GGCGAGCGCA | 180 |
| GGACGGCCCG | GAAGCCCCGC | GGGGGATGCG | CCGAGGGCCC | CGCGTTCGCG | CCGCGCAGAG | 240 |

```
CCAGGCCCGC  GGCCCGAGCC  C ATG AGC ACC ATG CGC CTG CTG ACG CTC GCC        291
                         Met Ser Thr Met Arg Leu Leu Thr Leu Ala
                           1               5                  10

CTG CTG TTC TCC TGC TCC GTC GCC CGT GCC GCG TGC GAC CCC AAG ATC          339
Leu Leu Phe Ser Cys Ser Val Ala Arg Ala Ala Cys Asp Pro Lys Ile
                15                  20                  25

GTC AAC ATT GGC GCG GTG CTG AGC ACG CGG AAG CAC GAG CAG ATG TTC          387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT          435
Arg Glu Ala Val Asn Gln Ala Asn Lys Arg His Gly Ser Trp Lys Ile
         45                  50                  55

CAG CTC AAT GCC ACC TCC GTC ACG CAC AAG CCC AAC GCC ATC CAG ATG          483
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     | Gln | Leu | Asn | Ala | Thr | Ser | Val | Thr | His | Lys | Pro | Asn | Ala | Ile | Gln | Met  |
|     |     | 60  |     |     |     |     | 65  |     |     |     |     | 70  |     |     |     |      |
| GCT | CTG | TCG | GTG | TGC | GAG | GAC | CTC | ATC | TCC | AGC | CAG | GTC | TAC | GCC | ATC | 531  |
| Ala | Leu | Ser | Val | Cys | Glu | Asp | Leu | Ile | Ser | Ser | Gln | Val | Tyr | Ala | Ile |      |
| 75  |     |     |     |     | 80  |     |     |     |     | 85  |     |     |     |     | 90  |      |
| CTA | GTT | AGC | CAT | CCA | CCT | ACC | CCC | AAC | GAC | CAC | TTC | ACT | CCC | ACC | CCT | 579  |
| Leu | Val | Ser | His | Pro | Pro | Thr | Pro | Asn | Asp | His | Phe | Thr | Pro | Thr | Pro |      |
|     |     |     |     | 95  |     |     |     |     | 100 |     |     |     |     | 105 |     |      |
| GTC | TCC | TAC | ACA | GCC | GGC | TTC | TAC | CGC | ATA | CCC | GTG | CTG | GGG | CTG | ACC | 627  |
| Val | Ser | Tyr | Thr | Ala | Gly | Phe | Tyr | Arg | Ile | Pro | Val | Leu | Gly | Leu | Thr |      |
|     |     |     | 110 |     |     |     |     | 115 |     |     |     |     | 120 |     |     |      |
| ACC | CGC | ATG | TCC | ATC | TAC | TCG | GAC | AAG | AGC | ATC | CAC | CTG | AGC | TTC | CTG | 675  |
| Thr | Arg | Met | Ser | Ile | Tyr | Ser | Asp | Lys | Ser | Ile | His | Leu | Ser | Phe | Leu |      |
|     |     | 125 |     |     |     |     | 130 |     |     |     |     | 135 |     |     |     |      |
| CGC | ACC | GTG | CCG | CCC | TAC | TCC | CAC | CAG | TCC | AGC | GTG | TGG | TTT | GAG | ATG | 723  |
| Arg | Thr | Val | Pro | Pro | Tyr | Ser | His | Gln | Ser | Ser | Val | Trp | Phe | Glu | Met |      |
|     | 140 |     |     |     |     | 145 |     |     |     |     | 150 |     |     |     |     |      |
| ATG | CGT | GTC | TAC | AGC | TGG | AAC | CAC | ATC | ATC | CTG | CTG | GTC | AGC | GAC | GAC | 771  |
| Met | Arg | Val | Tyr | Ser | Trp | Asn | His | Ile | Ile | Leu | Leu | Val | Ser | Asp | Asp |      |
| 155 |     |     |     |     | 160 |     |     |     |     | 165 |     |     |     |     | 170 |      |
| CAC | GAG | GGC | CGG | GCG | GCT | CAG | AAA | CGC | CTG | GAG | ACG | CTG | CTG | GAG | GAG | 819  |
| His | Glu | Gly | Arg | Ala | Ala | Gln | Lys | Arg | Leu | Glu | Thr | Leu | Leu | Glu | Glu |      |
|     |     |     |     | 175 |     |     |     |     | 180 |     |     |     |     | 185 |     |      |
| CGT | GAG | TCC | AAG | AGT | AAA | AAA | AGG | AAC | TAT | GAA | AAC | CTC | GAC | CAA | CTG | 867  |
| Arg | Glu | Ser | Lys | Ser | Lys | Lys | Arg | Asn | Tyr | Glu | Asn | Leu | Asp | Gln | Leu |      |
|     |     |     | 190 |     |     |     |     | 195 |     |     |     |     | 200 |     |     |      |
| TCC | TAT | GAC | AAC | AAG | CGC | GGA | CCC | AAG | GCA | GAG | AAG | GTG | CTG | CAG | TTT | 915  |
| Ser | Tyr | Asp | Asn | Lys | Arg | Gly | Pro | Lys | Ala | Glu | Lys | Val | Leu | Gln | Phe |      |
|     |     | 205 |     |     |     |     | 210 |     |     |     |     | 215 |     |     |     |      |
| GAC | CCA | GGG | ACC | AAG | AAC | GTG | ACG | GCC | CTG | CTG | ATG | GAG | GCG | AAA | GAG | 963  |
| Asp | Pro | Gly | Thr | Lys | Asn | Val | Thr | Ala | Leu | Leu | Met | Glu | Ala | Lys | Glu |      |
| 220 |     |     |     |     | 225 |     |     |     |     | 230 |     |     |     |     |     |      |
| CTG | GAG | GCC | CGG | GTC | ATC | ATC | CTT | TCT | GCC | AGC | GAG | GAC | GAT | GCT | GCC | 1011 |
| Leu | Glu | Ala | Arg | Val | Ile | Ile | Leu | Ser | Ala | Ser | Glu | Asp | Asp | Ala | Ala |      |
| 235 |     |     |     |     | 240 |     |     |     |     | 245 |     |     |     |     | 250 |      |
| ACT | GTA | TAC | CGC | GCA | GCC | GCG | ATG | CTG | AAC | ATG | ACG | GGC | AAC | ACC | AAC | 1059 |
| Thr | Val | Tyr | Arg | Ala | Ala | Ala | Met | Leu | Asn | Met | Thr | Gly | Asn | Thr | Asn |      |
|     |     |     |     | 255 |     |     |     |     | 260 |     |     |     |     | 265 |     |      |
| ATC | TGG | AAG | ACC | GGG | CCG | CTC | TTC | AAG | AGA | GTG | CTG | ATG | TCT | TCC | AAG | 1107 |
| Ile | Trp | Lys | Thr | Gly | Pro | Leu | Phe | Lys | Arg | Val | Leu | Met | Ser | Ser | Lys |      |
|     |     |     | 270 |     |     |     |     | 275 |     |     |     |     | 280 |     |     |      |
| TAT | GCG | GAT | GGG | GTG | ACT | GGT | CGC | GTG | GAG | TTC | AAT | GAG | GAT | GGG | GAC | 1155 |
| Tyr | Ala | Asp | Gly | Val | Thr | Gly | Arg | Val | Glu | Phe | Asn | Glu | Asp | Gly | Asp |      |
|     |     | 285 |     |     |     |     | 290 |     |     |     |     | 295 |     |     |     |      |
| CGG | AAG | TTC | GCC | AAC | TAC | AGC | ATC | ATG | AAC | CTG | CAG | AAC | CGC | AAG | CTG | 1203 |
| Arg | Lys | Phe | Ala | Asn | Tyr | Ser | Ile | Met | Asn | Leu | Gln | Asn | Arg | Lys | Leu |      |
|     | 300 |     |     |     |     | 305 |     |     |     |     | 310 |     |     |     |     |      |
| GTG | CAA | GTG | GGC | ATC | TAC | AAT | GGC | ACC | CAC | GTC | ATC | CCT | AAT | GAC | AGG | 1251 |
| Val | Gln | Val | Gly | Ile | Tyr | Asn | Gly | Thr | His | Val | Ile | Pro | Asn | Asp | Arg |      |
| 315 |     |     |     |     | 320 |     |     |     |     | 325 |     |     |     |     | 330 |      |
| AAG | ATC | ATC | TGG | CCA | GGC | GGA | GAG | ACA | GAG | AAG | CCT | CGA | GGG | TAC | CAG | 1299 |
| Lys | Ile | Ile | Trp | Pro | Gly | Gly | Glu | Thr | Glu | Lys | Pro | Arg | Gly | Tyr | Gln |      |
|     |     |     |     | 335 |     |     |     |     | 340 |     |     |     |     | 345 |     |      |
| ATG | TCC | ACC | AGA | CTG | AAG | ATT | GTG | ACG | ATC | CAC | CAG | GAG | CCC | TTC | GTG | 1347 |
| Met | Ser | Thr | Arg | Leu | Lys | Ile | Val | Thr | Ile | His | Gln | Glu | Pro | Phe | Val |      |
|     |     |     | 350 |     |     |     |     | 355 |     |     |     |     | 360 |     |     |      |
| TAC | GTC | AAG | CCC | ACG | CTG | AGT | GAT | GGG | ACA | TGC | AAG | GAG | GAG | TTC | ACA | 1395 |
| Tyr | Val | Lys | Pro | Thr | Leu | Ser | Asp | Gly | Thr | Cys | Lys | Glu | Glu | Phe | Thr |      |
|     |     | 365 |     |     |     |     | 370 |     |     |     |     | 375 |     |     |     |      |
| GTC | AAC | GGC | GAC | CCA | GTC | AAG | AAG | GTG | ATC | TGC | ACC | GGG | CCC | AAC | GAC | 1443 |

```
Val  Asn  Gly  Asp  Pro  Val  Lys  Lys  Val  Ile  Cys  Thr  Gly  Pro  Asn  Asp
     380                      385                      390

ACG  TCG  CCG  GGC  AGC  CCC  CGC  CAC  ACG  GTG  CCT  CAG  TGT  TGC  TAC  GGC    1491
Thr  Ser  Pro  Gly  Ser  Pro  Arg  His  Thr  Val  Pro  Gln  Cys  Cys  Tyr  Gly
395                      400                      405                      410

TTT  TGC  ATC  GAC  CTG  CTC  ATC  AAG  CTG  GCA  CGG  ACC  ATG  AAC  TTC  ACC    1539
Phe  Cys  Ile  Asp  Leu  Leu  Ile  Lys  Leu  Ala  Arg  Thr  Met  Asn  Phe  Thr
                    415                      420                      425

TAC  GAG  GTG  CAC  CTG  GTG  GCA  GAT  GGC  AAG  TTC  GGC  ACA  CAG  GAG  CGG    1587
Tyr  Glu  Val  His  Leu  Val  Ala  Asp  Gly  Lys  Phe  Gly  Thr  Gln  Glu  Arg
               430                      435                      440

GTG  AAC  AAC  AGC  AAC  AAG  AAG  GAG  TGG  AAT  GGG  ATG  ATG  GGC  GAG  CTG    1635
Val  Asn  Asn  Ser  Asn  Lys  Lys  Glu  Trp  Asn  Gly  Met  Met  Gly  Glu  Leu
          445                      450                      455

CTC  AGC  GGG  CAG  GCA  GAC  ATG  ATC  GTG  GCG  CCG  CTA  ACC  ATA  AAC  AAC    1683
Leu  Ser  Gly  Gln  Ala  Asp  Met  Ile  Val  Ala  Pro  Leu  Thr  Ile  Asn  Asn
     460                      465                      470

GAG  CGC  GCG  CAG  TAC  ATC  GAG  TTT  TCC  AAG  CCC  TTC  AAG  TAC  CAG  GGC    1731
Glu  Arg  Ala  Gln  Tyr  Ile  Glu  Phe  Ser  Lys  Pro  Phe  Lys  Tyr  Gln  Gly
475                      480                      485                      490

CTG  ACT  ATT  CTG  GTC  AAG  AAG  GAG  ATT  CCC  CGG  AGC  ACG  CTG  GAC  TCG    1779
Leu  Thr  Ile  Leu  Val  Lys  Lys  Glu  Ile  Pro  Arg  Ser  Thr  Leu  Asp  Ser
                    495                      500                      505

TTC  ATG  CAG  CCG  TTC  CAG  AGC  ACA  CTG  TGG  CTG  CTG  GTG  GGG  CTG  TCG    1827
Phe  Met  Gln  Pro  Phe  Gln  Ser  Thr  Leu  Trp  Leu  Leu  Val  Gly  Leu  Ser
               510                      515                      520

GTG  CAC  GTG  GTG  GCC  GTG  ATG  CTG  TAC  CTG  CTG  GAC  CGC  TTC  AGC  CCC    1875
Val  His  Val  Val  Ala  Val  Met  Leu  Tyr  Leu  Leu  Asp  Arg  Phe  Ser  Pro
          525                      530                      535

TTC  GGC  CGG  TTC  AAG  GTG  AAC  AGC  GAG  GAG  GAG  GAG  GAG  GAC  GCA  CTG    1923
Phe  Gly  Arg  Phe  Lys  Val  Asn  Ser  Glu  Glu  Glu  Glu  Glu  Asp  Ala  Leu
     540                      545                      550

ACC  CTG  TCC  TCG  GCC  ATG  TGG  TTC  TCC  TGG  GGC  GTC  CTG  CTC  AAC  TCC    1971
Thr  Leu  Ser  Ser  Ala  Met  Trp  Phe  Ser  Trp  Gly  Val  Leu  Leu  Asn  Ser
555                      560                      565                      570

GGC  ATC  GGG  GAA  GGC  GCC  CCC  AGA  AGC  TTC  TCA  GCG  CGC  ATC  CTG  GGC    2019
Gly  Ile  Gly  Glu  Gly  Ala  Pro  Arg  Ser  Phe  Ser  Ala  Arg  Ile  Leu  Gly
                    575                      580                      585

ATG  GTG  TGG  GCC  GGC  TTT  GCC  ATG  ATC  ATC  GTG  GCC  TCC  TAC  ACC  GCC    2067
Met  Val  Trp  Ala  Gly  Phe  Ala  Met  Ile  Ile  Val  Ala  Ser  Tyr  Thr  Ala
               590                      595                      600

AAC  CTG  GCG  GCC  TTC  CTG  GTG  CTG  GAC  CGG  CCG  GAG  GAG  CGC  ATC  ACG    2115
Asn  Leu  Ala  Ala  Phe  Leu  Val  Leu  Asp  Arg  Pro  Glu  Glu  Arg  Ile  Thr
          605                      610                      615

GGC  ATC  AAC  GAC  CCT  CGG  CTG  AGG  AAC  CCC  TCG  GAC  AAG  TTT  ATC  TAC    2163
Gly  Ile  Asn  Asp  Pro  Arg  Leu  Arg  Asn  Pro  Ser  Asp  Lys  Phe  Ile  Tyr
     620                      625                      630

GCC  ACG  GTG  AAG  CAG  AGC  TCC  GTG  GAT  ATC  TAC  TTC  CGG  CGC  CAG  GTG    2211
Ala  Thr  Val  Lys  Gln  Ser  Ser  Val  Asp  Ile  Tyr  Phe  Arg  Arg  Gln  Val
635                      640                      645                      650

GAG  CTG  AGC  ACC  ATG  TAC  CGG  CAT  ATG  GAG  AAG  CAC  AAC  TAC  GAG  AGT    2259
Glu  Leu  Ser  Thr  Met  Tyr  Arg  His  Met  Glu  Lys  His  Asn  Tyr  Glu  Ser
                    655                      660                      665

GCG  GCG  GAG  GCC  ATC  CAG  GCC  GTG  AGA  GAC  AAC  AAG  CTG  CAT  GCC  TTC    2307
Ala  Ala  Glu  Ala  Ile  Gln  Ala  Val  Arg  Asp  Asn  Lys  Leu  His  Ala  Phe
               670                      675                      680

ATC  TGG  GAC  TCG  GCG  GTG  CTG  GAG  TTC  GAG  GCC  TCG  CAG  AAG  TGC  GAC    2355
Ile  Trp  Asp  Ser  Ala  Val  Leu  Glu  Phe  Glu  Ala  Ser  Gln  Lys  Cys  Asp
          685                      690                      695

CTG  GTG  ACG  ACT  GGA  GAG  CTG  TTT  TTC  CGC  TCG  GGC  TTC  GGC  ATA  GGC    2403
```

-continued

| | | | | | | | | | | | | | | | |
|---|---|---|---|---|---|---|---|---|---|---|---|---|---|---|---|
| Leu | Val | Thr | Thr | Gly | Glu | Leu | Phe | Phe | Arg | Ser | Gly | Phe | Gly | Ile | Gly |
| | | | | 700 | | | 705 | | | | | 710 | | | |

| ATG | CGC | AAA | GAC | AGC | CCC | TGG | AAG | CAG | AAC | GTC | TCC | CTG | TCC | ATC | CTC | 2451 |
|---|---|---|---|---|---|---|---|---|---|---|---|---|---|---|---|---|
| Met | Arg | Lys | Asp | Ser | Pro | Trp | Lys | Gln | Asn | Val | Ser | Leu | Ser | Ile | Leu | |
| 715 | | | | | 720 | | | | 725 | | | | | | 730 | |

| AAG | TCC | CAC | GAG | AAT | GGC | TTC | ATG | GAA | GAC | CTG | GAC | AAG | ACG | TGG | GTT | 2499 |
|---|---|---|---|---|---|---|---|---|---|---|---|---|---|---|---|---|
| Lys | Ser | His | Glu | Asn | Gly | Phe | Met | Glu | Asp | Leu | Asp | Lys | Thr | Trp | Val | |
| | | | | 735 | | | | | 740 | | | | | 745 | | |

| CGG | TAT | CAG | GAA | TGT | GAC | TCG | CGC | AGC | AAC | GCC | CCT | GCG | ACC | CTT | ACT | 2547 |
|---|---|---|---|---|---|---|---|---|---|---|---|---|---|---|---|---|
| Arg | Tyr | Gln | Glu | Cys | Asp | Ser | Arg | Ser | Asn | Ala | Pro | Ala | Thr | Leu | Thr | |
| | | | 750 | | | | | 755 | | | | | 760 | | | |

| TTT | GAG | AAC | ATG | GCC | GGG | GTC | TTC | ATG | CTG | GTA | GCT | GGG | GGC | ATC | GTG | 2595 |
|---|---|---|---|---|---|---|---|---|---|---|---|---|---|---|---|---|
| Phe | Glu | Asn | Met | Ala | Gly | Val | Phe | Met | Leu | Val | Ala | Gly | Gly | Ile | Val | |
| | | | 765 | | | | | 770 | | | | | 775 | | | |

| GCC | GGG | ATC | TTC | CTG | ATT | TTC | ATC | GAG | ATT | GCC | TAC | AAG | CGG | CAC | AAG | 2643 |
|---|---|---|---|---|---|---|---|---|---|---|---|---|---|---|---|---|
| Ala | Gly | Ile | Phe | Leu | Ile | Phe | Ile | Glu | Ile | Ala | Tyr | Lys | Arg | His | Lys | |
| | 780 | | | | | 785 | | | | | 790 | | | | | |

| GAT | GCT | CGC | CGG | AAG | CAG | ATG | CAG | CTG | GCC | TTT | GCC | GCC | GTT | AAC | GTG | 2691 |
|---|---|---|---|---|---|---|---|---|---|---|---|---|---|---|---|---|
| Asp | Ala | Arg | Arg | Lys | Gln | Met | Gln | Leu | Ala | Phe | Ala | Ala | Val | Asn | Val | |
| 795 | | | | | 800 | | | | | 805 | | | | | 810 | |

| TGG | CGG | AAG | AAC | CTG | CAG | GAT | AGA | AAG | AGT | GGT | AGA | GCA | GAG | CCT | GAC | 2739 |
|---|---|---|---|---|---|---|---|---|---|---|---|---|---|---|---|---|
| Trp | Arg | Lys | Asn | Leu | Gln | Asp | Arg | Lys | Ser | Gly | Arg | Ala | Glu | Pro | Asp | |
| | | | | 815 | | | | | 820 | | | | | 825 | | |

| CCT | AAA | AAG | AAA | GCC | ACA | TTT | AGG | GCT | ATC | ACC | TCC | ACC | CTG | GCT | TCC | 2787 |
|---|---|---|---|---|---|---|---|---|---|---|---|---|---|---|---|---|
| Pro | Lys | Lys | Lys | Ala | Thr | Phe | Arg | Ala | Ile | Thr | Ser | Thr | Leu | Ala | Ser | |
| | | | 830 | | | | | 835 | | | | | 840 | | | |

| AGC | TTC | AAG | AGG | CGT | AGG | TCC | TCC | AAA | GAC | ACG | AGC | ACC | GGG | GGT | GGA | 2835 |
|---|---|---|---|---|---|---|---|---|---|---|---|---|---|---|---|---|
| Ser | Phe | Lys | Arg | Arg | Arg | Ser | Ser | Lys | Asp | Thr | Ser | Thr | Gly | Gly | Gly | |
| | | 845 | | | | | 850 | | | | | 855 | | | | |

| CGC | GGT | GCT | TTG | CAA | AAC | CAA | AAA | GAC | ACA | GTG | CTG | CCG | CGA | CGC | GCT | 2883 |
|---|---|---|---|---|---|---|---|---|---|---|---|---|---|---|---|---|
| Arg | Gly | Ala | Leu | Gln | Asn | Gln | Lys | Asp | Thr | Val | Leu | Pro | Arg | Arg | Ala | |
| | 860 | | | | | 865 | | | | | 870 | | | | | |

| ATT | GAG | AGG | GAG | GAG | GGC | CAG | CTG | CAG | CTG | TGT | TCC | CGT | CAT | AGG | GAG | 2931 |
|---|---|---|---|---|---|---|---|---|---|---|---|---|---|---|---|---|
| Ile | Glu | Arg | Glu | Glu | Gly | Gln | Leu | Gln | Leu | Cys | Ser | Arg | His | Arg | Glu | |
| 875 | | | | | 880 | | | | | 885 | | | | | 890 | |

| AGC | TGAGACTCCC | CGCCCGCCCT | CCTCTGCCCC | CTCCCCCGCA | GACAGACAGA | 2984 |
|---|---|---|---|---|---|---|
| Ser | | | | | | |

| CAGACGGACG | GGACAGCGGC | CCGGCCCACG | CAGAGCCCCG | GAGCACCACG | GGGTCGGGGG | 3044 |
|---|---|---|---|---|---|---|
| AGGAGCACCC | CCAGCCTCCC | CCAGGCTGCG | CCTGCCCGCC | CGCCGGTTGG | CCGGCTGGCC | 3104 |
| GGTCCACCCC | GTCCCGGCCC | CGCGCGTGCC | CCCAGCGTGG | GGCTAACGGG | CGCCTTGTCT | 3164 |
| GTGTATTTCT | ATTTTGCAGC | AGTACCATCC | CACTGATATC | ACGGGCCCGC | TCAACCTCTC | 3224 |
| AGATCCCTCG | GTCAGCACCG | TGGTGTGAGG | CCCCCGGAGG | CGCCCACCTG | CCCAGTTAGC | 3284 |
| CCGGCCAAGG | ACACTGATGG | GTCCTGCTGC | TCGGGAAGGC | CTGAGGGAAG | CCCACCCGCC | 3344 |
| CCAGAGACTG | CCCACCCTGG | GCCTCCCGTC | CGTCCGCCCG | CCCACCCCGC | TGCCTGGCGG | 3404 |
| GCAGCCCCTG | CTGGACCAAG | GTGCGGACCG | GAGCGGCTGA | GGACGGGGCA | GAGCTGAGTC | 3464 |
| GGCTGGGCAG | GGCCGCAGGG | CGCTCCGGCA | GAGGCAGGCC | CCTGGGTCT | CTGAGCAGTG | 3524 |
| GGGAGCGGGG | GCTAACTGCC | CCCAGGCGGA | GGGGCTTGGA | GCAGAGACGG | CAGCCCCATC | 3584 |
| CTTCCCGCAG | CACCAGCCTG | AGCCACAGTG | GGGCCCATGG | CCCCAGCTGG | CTGGGTCGCC | 3644 |
| CCTCCTCGGG | CGCCTGCGCT | CCTCTGCAGC | CTGAGCTCCA | CCCTCCCCTC | TTCTTGCGGC | 3704 |
| ACCGCCCACC | AAACACCCCG | TCTGCCCCTT | GACGCCACAC | GCCGGGGCTG | GCGCTGCCCT | 3764 |
| CCCCCACGGC | CGTCCCTGAC | TTCCCAGCTG | GCAGCGCCTC | CCGCCGCCTC | GGGCCGCCTC | 3824 |
| CTCCAGAATC | GAGAGGGCTG | AGCCCCTCCT | CTCCTCGTCC | GGCCTGCAGC | ACAGAAGGGG | 3884 |

```
GCCTCCCCGG GGGTCCCCGG ACGCTGGCTC GGGACTGTCT TCAACCCTGC CCTGCACCTT    3944

GGGCACGGGA GAGCGCCACC CGCCCGCCCC CGCCCTCGCT CCGGGTGCGT GACCGGCCCG    4004

CCACCTTGTA CAGAACCAGC ACTCCAGGG  CCCGAGCGCG TGCCTTCCCC GTGCGCAGCC    4064

GCGCTCTGCC CCTCCGTCCC CAGGGTGCAG GCGCGCACCG CCCAACCCCC ACCTCCCGGT    4124

GTATGCAGTG GTGATGCCTA AAGGAATGTC ACG                                 4157
```

( 2 ) INFORMATION FOR SEQ ID NO:26:

( i ) SEQUENCE CHARACTERISTICS:
        ( A ) LENGTH: 891 amino acids
        ( B ) TYPE: amino acid
        ( D ) TOPOLOGY: linear ( i i ) MOLECULE TYPE: protein ( x i ) SEQUENCE DESCRIPTION: SEQ ID NO:26:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
            20                  25                  30

Leu Ser Thr Arg Lys His Glu Gln Met Phe Arg Glu Ala Val Asn Gln
        35                  40                  45

Ala Asn Lys Arg His Gly Ser Trp Lys Ile Gln Leu Asn Ala Thr Ser
    50                  55                  60

Val Thr His Lys Pro Asn Ala Ile Gln Met Ala Leu Ser Val Cys Glu
65                  70                  75                   80

Asp Leu Ile Ser Ser Gln Val Tyr Ala Ile Leu Val Ser His Pro Pro
                85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp His Glu Gly Arg Ala Ala
                165                 170                 175

Gln Lys Arg Leu Glu Thr Leu Leu Glu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Ala Ala Thr Val Tyr Arg Ala Ala
                245                 250                 255

Ala Met Leu Asn Met Thr Gly Asn Thr Asn Ile Trp Lys Thr Gly Pro
            260                 265                 270

Leu Phe Lys Arg Val Leu Met Ser Ser Lys Tyr Ala Asp Gly Val Thr
        275                 280                 285

Gly Arg Val Glu Phe Asn Glu Asp Gly Asp Arg Lys Phe Ala Asn Tyr
    290                 295                 300

Ser Ile Met Asn Leu Gln Asn Arg Lys Leu Val Gln Val Gly Ile Tyr
```

-continued

```
305                    310                    315                    320
Asn  Gly  Thr  His  Val  Ile  Pro  Asn  Asp  Arg  Lys  Ile  Ile  Trp  Pro  Gly
                    325                    330                    335
Gly  Glu  Thr  Glu  Lys  Pro  Arg  Gly  Tyr  Gln  Met  Ser  Thr  Arg  Leu  Lys
                    340                    345                    350
Ile  Val  Thr  Ile  His  Gln  Glu  Pro  Phe  Val  Tyr  Val  Lys  Pro  Thr  Leu
                    355                    360                    365
Ser  Asp  Gly  Thr  Cys  Lys  Glu  Glu  Phe  Thr  Val  Asn  Gly  Asp  Pro  Val
          370                    375                    380
Lys  Lys  Val  Ile  Cys  Thr  Gly  Pro  Asn  Asp  Thr  Ser  Pro  Gly  Ser  Pro
385                    390                    395                         400
Arg  His  Thr  Val  Pro  Gln  Cys  Cys  Tyr  Gly  Phe  Cys  Ile  Asp  Leu  Leu
                    405                    410                    415
Ile  Lys  Leu  Ala  Arg  Thr  Met  Asn  Phe  Thr  Tyr  Glu  Val  His  Leu  Val
                    420                    425                    430
Ala  Asp  Gly  Lys  Phe  Gly  Thr  Gln  Glu  Arg  Val  Asn  Asn  Ser  Asn  Lys
               435                    440                    445
Lys  Glu  Trp  Asn  Gly  Met  Met  Gly  Glu  Leu  Leu  Ser  Gly  Gln  Ala  Asp
     450                    455                    460
Met  Ile  Val  Ala  Pro  Leu  Thr  Ile  Asn  Asn  Glu  Arg  Ala  Gln  Tyr  Ile
465                    470                    475                         480
Glu  Phe  Ser  Lys  Pro  Phe  Lys  Tyr  Gln  Gly  Leu  Thr  Ile  Leu  Val  Lys
                    485                    490                    495
Lys  Glu  Ile  Pro  Arg  Ser  Thr  Leu  Asp  Ser  Phe  Met  Gln  Pro  Phe  Gln
               500                    505                    510
Ser  Thr  Leu  Trp  Leu  Leu  Val  Gly  Leu  Ser  Val  His  Val  Val  Ala  Val
          515                    520                    525
Met  Leu  Tyr  Leu  Leu  Asp  Arg  Phe  Ser  Pro  Phe  Gly  Arg  Phe  Lys  Val
     530                    535                    540
Asn  Ser  Glu  Glu  Glu  Glu  Glu  Asp  Ala  Leu  Thr  Leu  Ser  Ser  Ala  Met
545                    550                    555                         560
Trp  Phe  Ser  Trp  Gly  Val  Leu  Leu  Asn  Ser  Gly  Ile  Gly  Glu  Gly  Ala
                    565                    570                    575
Pro  Arg  Ser  Phe  Ser  Ala  Arg  Ile  Leu  Gly  Met  Val  Trp  Ala  Gly  Phe
               580                    585                    590
Ala  Met  Ile  Ile  Val  Ala  Ser  Tyr  Thr  Ala  Asn  Leu  Ala  Ala  Phe  Leu
          595                    600                    605
Val  Leu  Asp  Arg  Pro  Glu  Glu  Arg  Ile  Thr  Gly  Ile  Asn  Asp  Pro  Arg
     610                    615                    620
Leu  Arg  Asn  Pro  Ser  Asp  Lys  Phe  Ile  Tyr  Ala  Thr  Val  Lys  Gln  Ser
625                    630                    635                         640
Ser  Val  Asp  Ile  Tyr  Phe  Arg  Arg  Gln  Val  Glu  Leu  Ser  Thr  Met  Tyr
                    645                    650                    655
Arg  His  Met  Glu  Lys  His  Asn  Tyr  Glu  Ser  Ala  Ala  Glu  Ala  Ile  Gln
               660                    665                    670
Ala  Val  Arg  Asp  Asn  Lys  Leu  His  Ala  Phe  Ile  Trp  Asp  Ser  Ala  Val
          675                    680                    685
Leu  Glu  Phe  Glu  Ala  Ser  Gln  Lys  Cys  Asp  Leu  Val  Thr  Thr  Gly  Glu
     690                    695                    700
Leu  Phe  Phe  Arg  Ser  Gly  Phe  Gly  Ile  Gly  Met  Arg  Lys  Asp  Ser  Pro
705                    710                    715                         720
Trp  Lys  Gln  Asn  Val  Ser  Leu  Ser  Ile  Leu  Lys  Ser  His  Glu  Asn  Gly
                    725                    730                    735
```

| Phe | Met | Glu | Asp | Leu | Asp | Lys | Thr | Trp | Val | Arg | Tyr | Gln | Glu | Cys | Asp |
|-----|-----|-----|-----|-----|-----|-----|-----|-----|-----|-----|-----|-----|-----|-----|-----|
|     |     |     | 740 |     |     |     | 745 |     |     |     |     |     | 750 |     |     |

| Ser | Arg | Ser | Asn | Ala | Pro | Ala | Thr | Leu | Thr | Phe | Glu | Asn | Met | Ala | Gly |
|-----|-----|-----|-----|-----|-----|-----|-----|-----|-----|-----|-----|-----|-----|-----|-----|
|     |     | 755 |     |     |     |     | 760 |     |     |     |     | 765 |     |     |     |

| Val | Phe | Met | Leu | Val | Ala | Gly | Gly | Ile | Val | Ala | Gly | Ile | Phe | Leu | Ile |
|-----|-----|-----|-----|-----|-----|-----|-----|-----|-----|-----|-----|-----|-----|-----|-----|
|     | 770 |     |     |     |     | 775 |     |     |     |     | 780 |     |     |     |     |

| Phe | Ile | Glu | Ile | Ala | Tyr | Lys | Arg | His | Lys | Asp | Ala | Arg | Arg | Lys | Gln |
|-----|-----|-----|-----|-----|-----|-----|-----|-----|-----|-----|-----|-----|-----|-----|-----|
| 785 |     |     |     |     | 790 |     |     |     |     | 795 |     |     |     |     | 800 |

| Met | Gln | Leu | Ala | Phe | Ala | Ala | Val | Asn | Val | Trp | Arg | Lys | Asn | Leu | Gln |
|-----|-----|-----|-----|-----|-----|-----|-----|-----|-----|-----|-----|-----|-----|-----|-----|
|     |     |     |     | 805 |     |     |     |     | 810 |     |     |     |     | 815 |     |

| Asp | Arg | Lys | Ser | Gly | Arg | Ala | Glu | Pro | Asp | Pro | Lys | Lys | Lys | Ala | Thr |
|-----|-----|-----|-----|-----|-----|-----|-----|-----|-----|-----|-----|-----|-----|-----|-----|
|     |     |     | 820 |     |     |     |     | 825 |     |     |     |     | 830 |     |     |

| Phe | Arg | Ala | Ile | Thr | Ser | Thr | Leu | Ala | Ser | Ser | Phe | Lys | Arg | Arg | Arg |
|-----|-----|-----|-----|-----|-----|-----|-----|-----|-----|-----|-----|-----|-----|-----|-----|
|     |     | 835 |     |     |     |     | 840 |     |     |     |     | 845 |     |     |     |

| Ser | Ser | Lys | Asp | Thr | Ser | Thr | Gly | Gly | Gly | Arg | Gly | Ala | Leu | Gln | Asn |
|-----|-----|-----|-----|-----|-----|-----|-----|-----|-----|-----|-----|-----|-----|-----|-----|
|     | 850 |     |     |     |     | 855 |     |     |     |     | 860 |     |     |     |     |

| Gln | Lys | Asp | Thr | Val | Leu | Pro | Arg | Arg | Ala | Ile | Glu | Arg | Glu | Glu | Gly |
|-----|-----|-----|-----|-----|-----|-----|-----|-----|-----|-----|-----|-----|-----|-----|-----|
| 865 |     |     |     |     | 870 |     |     |     |     | 875 |     |     |     |     | 880 |

| Gln | Leu | Gln | Leu | Cys | Ser | Arg | His | Arg | Glu | Ser |
|-----|-----|-----|-----|-----|-----|-----|-----|-----|-----|-----|
|     |     |     |     | 885 |     |     |     |     | 890 |     |

( 2 ) INFORMATION FOR SEQ ID NO:27:

( i ) SEQUENCE CHARACTERISTICS:
        ( A ) LENGTH: 3794 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..2889

( x i ) SEQUENCE DESCRIPTION: SEQ ID NO:27:

```
CAAGCCGGGC  GTTCGGAGCT  GTGCCCGGCC  CCGCTTCAGC  ACCGCGGACA  GCGCCGGCCG      60

CGTGGGGCTG  AGCGCCGAGC  CCCCGCGCAC  GCTTCAGCCC  CCCTTCCCTC  GGCCGACGTC     120

CCGGGACCGC  CGCTCCGGGG  GAGACGTGGC  GTCCGCAGCC  CGCGGGGCCG  GGCGAGCGCA     180

GGACGGCCCG  GAAGCCCCGC  GGGGGATGCG  CCGAGGGCCC  CGCGTTCGCG  CCGCGCAGAG     240

CCAGGCCCGC  GGCCCGAGCC  C ATG AGC ACC ATG CGC CTG CTG ACG CTC GCC         291
             Met Ser Thr Met Arg Leu Leu Thr Leu Ala
              1               5                  10

CTG CTG TTC TCC TGC TCC GTC GCC CGT GCC GCG TGC GAC CCC AAG ATC          339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC          387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT          435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG          483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC          531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT          579
```

-continued

| | | | | | | | | | | | | | | | |
|---|---|---|---|---|---|---|---|---|---|---|---|---|---|---|---|
| Leu | Val | Ser | His | Pro | Pro | Thr | Pro | Asn | Asp | His | Phe | Thr | Pro | Thr | Pro |
| | | | | 95 | | | | 100 | | | | | 105 | | |

| GTC | TCC | TAC | ACA | GCC | GGC | TTC | TAC | CGC | ATA | CCC | GTG | CTG | GGG | CTG | ACC | 627 |
|---|---|---|---|---|---|---|---|---|---|---|---|---|---|---|---|---|
| Val | Ser | Tyr | Thr | Ala | Gly | Phe | Tyr | Arg | Ile | Pro | Val | Leu | Gly | Leu | Thr | |
| | | 110 | | | | | 115 | | | | 120 | | | | | |

| ACC | CGC | ATG | TCC | ATC | TAC | TCG | GAC | AAG | AGC | ATC | CAC | CTG | AGC | TTC | CTG | 675 |
|---|---|---|---|---|---|---|---|---|---|---|---|---|---|---|---|---|
| Thr | Arg | Met | Ser | Ile | Tyr | Ser | Asp | Lys | Ser | Ile | His | Leu | Ser | Phe | Leu | |
| | | 125 | | | | | 130 | | | | 135 | | | | | |

| CGC | ACC | GTG | CCG | CCC | TAC | TCC | CAC | CAG | TCC | AGC | GTG | TGG | TTT | GAG | ATG | 723 |
|---|---|---|---|---|---|---|---|---|---|---|---|---|---|---|---|---|
| Arg | Thr | Val | Pro | Pro | Tyr | Ser | His | Gln | Ser | Ser | Val | Trp | Phe | Glu | Met | |
| | 140 | | | | | 145 | | | | 150 | | | | | | |

| ATG | CGT | GTC | TAC | AGC | TGG | AAC | CAC | ATC | ATC | CTG | CTG | GTC | AGC | GAC | GAC | 771 |
|---|---|---|---|---|---|---|---|---|---|---|---|---|---|---|---|---|
| Met | Arg | Val | Tyr | Ser | Trp | Asn | His | Ile | Ile | Leu | Leu | Val | Ser | Asp | Asp | |
| 155 | | | | | 160 | | | | 165 | | | | | 170 | | |

| CAC | GAG | GGC | CGG | GCG | GCT | CAG | AAA | CGC | CTG | GAG | ACG | CTG | CTG | GAG | GAG | 819 |
|---|---|---|---|---|---|---|---|---|---|---|---|---|---|---|---|---|
| His | Glu | Gly | Arg | Ala | Ala | Gln | Lys | Arg | Leu | Glu | Thr | Leu | Leu | Glu | Glu | |
| | | | | 175 | | | | | 180 | | | | | 185 | | |

| CGT | GAG | TCC | AAG | AGT | AAA | AAA | AGG | AAC | TAT | GAA | AAC | CTC | GAC | CAA | CTG | 867 |
|---|---|---|---|---|---|---|---|---|---|---|---|---|---|---|---|---|
| Arg | Glu | Ser | Lys | Ser | Lys | Lys | Arg | Asn | Tyr | Glu | Asn | Leu | Asp | Gln | Leu | |
| | | | 190 | | | | | 195 | | | | 200 | | | | |

| TCC | TAT | GAC | AAC | AAG | CGC | GGA | CCC | AAG | GCA | GAG | AAG | GTG | CTG | CAG | TTT | 915 |
|---|---|---|---|---|---|---|---|---|---|---|---|---|---|---|---|---|
| Ser | Tyr | Asp | Asn | Lys | Arg | Gly | Pro | Lys | Ala | Glu | Lys | Val | Leu | Gln | Phe | |
| | | 205 | | | | | 210 | | | | | 215 | | | | |

| GAC | CCA | GGG | ACC | AAG | AAC | GTG | ACG | GCC | CTG | CTG | ATG | GAG | GCG | AAA | GAG | 963 |
|---|---|---|---|---|---|---|---|---|---|---|---|---|---|---|---|---|
| Asp | Pro | Gly | Thr | Lys | Asn | Val | Thr | Ala | Leu | Leu | Met | Glu | Ala | Lys | Glu | |
| | 220 | | | | | 225 | | | | | 230 | | | | | |

| CTG | GAG | GCC | CGG | GTC | ATC | ATC | CTT | TCT | GCC | AGC | GAG | GAC | GAT | GCT | GCC | 1011 |
|---|---|---|---|---|---|---|---|---|---|---|---|---|---|---|---|---|
| Leu | Glu | Ala | Arg | Val | Ile | Ile | Leu | Ser | Ala | Ser | Glu | Asp | Asp | Ala | Ala | |
| 235 | | | | | 240 | | | | | 245 | | | | | 250 | |

| ACT | GTA | TAC | CGC | GCA | GCC | GCG | ATG | CTG | AAC | ATG | ACG | GGC | AAC | ACC | AAC | 1059 |
|---|---|---|---|---|---|---|---|---|---|---|---|---|---|---|---|---|
| Thr | Val | Tyr | Arg | Ala | Ala | Ala | Met | Leu | Asn | Met | Thr | Gly | Asn | Thr | Asn | |
| | | | | 255 | | | | | 260 | | | | | 265 | | |

| ATC | TGG | AAG | ACC | GGG | CCG | CTC | TTC | AAG | AGA | GTG | CTG | ATG | TCT | TCC | AAG | 1107 |
|---|---|---|---|---|---|---|---|---|---|---|---|---|---|---|---|---|
| Ile | Trp | Lys | Thr | Gly | Pro | Leu | Phe | Lys | Arg | Val | Leu | Met | Ser | Ser | Lys | |
| | | | 270 | | | | | 275 | | | | 280 | | | | |

| TAT | GCG | GAT | GGG | GTG | ACT | GGT | CGC | GTG | GAG | TTC | AAT | GAG | GAT | GGG | GAC | 1155 |
|---|---|---|---|---|---|---|---|---|---|---|---|---|---|---|---|---|
| Tyr | Ala | Asp | Gly | Val | Thr | Gly | Arg | Val | Glu | Phe | Asn | Glu | Asp | Gly | Asp | |
| | | 285 | | | | | 290 | | | | | 295 | | | | |

| CGG | AAG | TTC | GCC | AAC | TAC | AGC | ATC | ATG | AAC | CTG | CAG | AAC | CGC | AAG | CTG | 1203 |
|---|---|---|---|---|---|---|---|---|---|---|---|---|---|---|---|---|
| Arg | Lys | Phe | Ala | Asn | Tyr | Ser | Ile | Met | Asn | Leu | Gln | Asn | Arg | Lys | Leu | |
| | 300 | | | | | 305 | | | | | 310 | | | | | |

| GTG | CAA | GTG | GGC | ATC | TAC | AAT | GGC | ACC | CAC | GTC | ATC | CCT | AAT | GAC | AGG | 1251 |
|---|---|---|---|---|---|---|---|---|---|---|---|---|---|---|---|---|
| Val | Gln | Val | Gly | Ile | Tyr | Asn | Gly | Thr | His | Val | Ile | Pro | Asn | Asp | Arg | |
| 315 | | | | | 320 | | | | | 325 | | | | | 330 | |

| AAG | ATC | ATC | TGG | CCA | GGC | GGA | GAG | ACA | GAG | AAG | CCT | CGA | GGG | TAC | CAG | 1299 |
|---|---|---|---|---|---|---|---|---|---|---|---|---|---|---|---|---|
| Lys | Ile | Ile | Trp | Pro | Gly | Gly | Glu | Thr | Glu | Lys | Pro | Arg | Gly | Tyr | Gln | |
| | | | | 335 | | | | | 340 | | | | | 345 | | |

| ATG | TCC | ACC | AGA | CTG | AAG | ATT | GTG | ACG | ATC | CAC | CAG | GAG | CCC | TTC | GTG | 1347 |
|---|---|---|---|---|---|---|---|---|---|---|---|---|---|---|---|---|
| Met | Ser | Thr | Arg | Leu | Lys | Ile | Val | Thr | Ile | His | Gln | Glu | Pro | Phe | Val | |
| | | | 350 | | | | | 355 | | | | | 360 | | | |

| TAC | GTC | AAG | CCC | ACG | CTG | AGT | GAT | GGG | ACA | TGC | AAG | GAG | GAG | TTC | ACA | 1395 |
|---|---|---|---|---|---|---|---|---|---|---|---|---|---|---|---|---|
| Tyr | Val | Lys | Pro | Thr | Leu | Ser | Asp | Gly | Thr | Cys | Lys | Glu | Glu | Phe | Thr | |
| | | 365 | | | | | 370 | | | | | 375 | | | | |

| GTC | AAC | GGC | GAC | CCA | GTC | AAG | AAG | GTG | ATC | TGC | ACC | GGG | CCC | AAC | GAC | 1443 |
|---|---|---|---|---|---|---|---|---|---|---|---|---|---|---|---|---|
| Val | Asn | Gly | Asp | Pro | Val | Lys | Lys | Val | Ile | Cys | Thr | Gly | Pro | Asn | Asp | |
| | 380 | | | | | 385 | | | | | 390 | | | | | |

| ACG | TCG | CCG | GGC | AGC | CCC | CGC | CAC | ACG | GTG | CCT | CAG | TGT | TGC | TAC | GGC | 1491 |
|---|---|---|---|---|---|---|---|---|---|---|---|---|---|---|---|---|
| Thr | Ser | Pro | Gly | Ser | Pro | Arg | His | Thr | Val | Pro | Gln | Cys | Cys | Tyr | Gly | |
| 395 | | | | | 400 | | | | | 405 | | | | | 410 | |

| TTT | TGC | ATC | GAC | CTG | CTC | ATC | AAG | CTG | GCA | CGG | ACC | ATG | AAC | TTC | ACC | 1539 |

| Phe | Cys | Ile | Asp | Leu<br>415 | Leu | Ile | Lys | Leu<br>420 | Ala | Arg | Thr | Met | Asn<br>425 | Phe | Thr | |
|---|---|---|---|---|---|---|---|---|---|---|---|---|---|---|---|---|
| TAC<br>Tyr | GAG<br>Glu | GTG<br>Val | CAC<br>His<br>430 | CTG<br>Leu | GTG<br>Val | GCA<br>Ala | GAT<br>Asp | GGC<br>Gly<br>435 | AAG<br>Lys | TTC<br>Phe | GGC<br>Gly | ACA<br>Thr | CAG<br>Gln<br>440 | GAG<br>Glu | CGG<br>Arg | 1587 |
| GTG<br>Val | AAC<br>Asn | AAC<br>Asn<br>445 | AGC<br>Ser | AAC<br>Asn | AAG<br>Lys | AAG<br>Lys | GAG<br>Glu<br>450 | TGG<br>Trp | AAT<br>Asn | GGG<br>Gly | ATG<br>Met | ATG<br>Met<br>455 | GGC<br>Gly | GAG<br>Glu | CTG<br>Leu | 1635 |
| CTC<br>Leu | AGC<br>Ser<br>460 | GGG<br>Gly | CAG<br>Gln | GCA<br>Ala | GAC<br>Asp | ATG<br>Met<br>465 | ATC<br>Ile | GTG<br>Val | GCG<br>Ala | CCG<br>Pro | CTA<br>Leu<br>470 | ACC<br>Thr | ATA<br>Ile | AAC<br>Asn | AAC<br>Asn | 1683 |
| GAG<br>Glu<br>475 | CGC<br>Arg | GCG<br>Ala | CAG<br>Gln | TAC<br>Tyr | ATC<br>Ile<br>480 | GAG<br>Glu | TTT<br>Phe | TCC<br>Ser | AAG<br>Lys | CCC<br>Pro<br>485 | TTC<br>Phe | AAG<br>Lys | TAC<br>Tyr | CAG<br>Gln | GGC<br>Gly<br>490 | 1731 |
| CTG<br>Leu | ACT<br>Thr | ATT<br>Ile | CTG<br>Leu | GTC<br>Val<br>495 | AAG<br>Lys | AAG<br>Lys | GAG<br>Glu | ATT<br>Ile<br>500 | CCC<br>Pro | CGG<br>Arg | AGC<br>Ser | ACG<br>Thr | CTG<br>Leu<br>505 | GAC<br>Asp | TCG<br>Ser | 1779 |
| TTC<br>Phe | ATG<br>Met | CAG<br>Gln | CCG<br>Pro<br>510 | TTC<br>Phe | CAG<br>Gln | AGC<br>Ser | ACA<br>Thr | CTG<br>Leu<br>515 | TGG<br>Trp | CTG<br>Leu | CTG<br>Leu | GTG<br>Val | GGG<br>Gly<br>520 | CTG<br>Leu | TCG<br>Ser | 1827 |
| GTG<br>Val | CAC<br>His<br>525 | GTG<br>Val | GTG<br>Val | GCC<br>Ala | GTG<br>Val | ATG<br>Met<br>530 | CTG<br>Leu | TAC<br>Tyr | CTG<br>Leu | CTG<br>Leu | GAC<br>Asp<br>535 | CGC<br>Arg | TTC<br>Phe | AGC<br>Ser | CCC<br>Pro | 1875 |
| TTC<br>Phe | GGC<br>Gly<br>540 | CGG<br>Arg | TTC<br>Phe | AAG<br>Lys | GTG<br>Val | AAC<br>Asn<br>545 | AGC<br>Ser | GAG<br>Glu | GAG<br>Glu | GAG<br>Glu | GAG<br>Glu<br>550 | GAG<br>Glu | GAC<br>Asp | GCA<br>Ala | CTG<br>Leu | 1923 |
| ACC<br>Thr<br>555 | CTG<br>Leu | TCC<br>Ser | TCG<br>Ser | GCC<br>Ala | ATG<br>Met<br>560 | TGG<br>Trp | TTC<br>Phe | TCC<br>Ser | TGG<br>Trp | GGC<br>Gly<br>565 | GTC<br>Val | CTG<br>Leu | CTC<br>Leu | AAC<br>Asn | TCC<br>Ser<br>570 | 1971 |
| GGC<br>Gly | ATC<br>Ile | GGG<br>Gly | GAA<br>Glu | GGC<br>Gly<br>575 | GCC<br>Ala | CCC<br>Pro | AGA<br>Arg | AGC<br>Ser | TTC<br>Phe<br>580 | TCA<br>Ser | GCG<br>Ala | CGC<br>Arg | ATC<br>Ile | CTG<br>Leu<br>585 | GGC<br>Gly | 2019 |
| ATG<br>Met | GTG<br>Val | TGG<br>Trp<br>590 | GCC<br>Ala | GGC<br>Gly | TTT<br>Phe | GCC<br>Ala | ATG<br>Met<br>595 | ATC<br>Ile | ATC<br>Ile | GTG<br>Val | GCC<br>Ala | TCC<br>Ser<br>600 | TAC<br>Tyr | ACC<br>Thr | GCC<br>Ala | 2067 |
| AAC<br>Asn | CTG<br>Leu | GCG<br>Ala<br>605 | GCC<br>Ala | TTC<br>Phe | CTG<br>Leu | GTG<br>Val | CTG<br>Leu<br>610 | GAC<br>Asp | CGG<br>Arg | CCG<br>Pro | GAG<br>Glu | GAG<br>Glu<br>615 | CGC<br>Arg | ATC<br>Ile | ACG<br>Thr | 2115 |
| GGC<br>Gly | ATC<br>Ile<br>620 | AAC<br>Asn | GAC<br>Asp | CCT<br>Pro | CGG<br>Arg | CTG<br>Leu<br>625 | AGG<br>Arg | AAC<br>Asn | CCC<br>Pro | TCG<br>Ser | GAC<br>Asp<br>630 | AAG<br>Lys | TTT<br>Phe | ATC<br>Ile | TAC<br>Tyr | 2163 |
| GCC<br>Ala<br>635 | ACG<br>Thr | GTG<br>Val | AAG<br>Lys | CAG<br>Gln | AGC<br>Ser<br>640 | TCC<br>Ser | GTG<br>Val | GAT<br>Asp | ATC<br>Ile | TAC<br>Tyr<br>645 | TTC<br>Phe | CGG<br>Arg | CGC<br>Arg | CAG<br>Gln | GTG<br>Val<br>650 | 2211 |
| GAG<br>Glu | CTG<br>Leu | AGC<br>Ser | ACC<br>Thr | ATG<br>Met<br>655 | TAC<br>Tyr | CGG<br>Arg | CAT<br>His | ATG<br>Met | GAG<br>Glu<br>660 | AAG<br>Lys | CAC<br>His | AAC<br>Asn | TAC<br>Tyr | GAG<br>Glu<br>665 | AGT<br>Ser | 2259 |
| GCG<br>Ala | GCG<br>Ala | GAG<br>Glu<br>670 | GCC<br>Ala | ATC<br>Ile | CAG<br>Gln | GCC<br>Ala | GTG<br>Val<br>675 | AGA<br>Arg | GAC<br>Asp | AAC<br>Asn | AAG<br>Lys | CTG<br>Leu<br>680 | CAT<br>His | GCC<br>Ala | TTC<br>Phe | 2307 |
| ATC<br>Ile | TGG<br>Trp | GAC<br>Asp<br>685 | TCG<br>Ser | GCG<br>Ala | GTG<br>Val | CTG<br>Leu<br>690 | GAG<br>Glu | TTC<br>Phe | GAG<br>Glu | GCC<br>Ala | TCG<br>Ser<br>695 | CAG<br>Gln | AAG<br>Lys | TGC<br>Cys | GAC<br>Asp | 2355 |
| CTG<br>Leu | GTG<br>Val | ACG<br>Thr<br>700 | ACT<br>Thr | GGA<br>Gly | GAG<br>Glu | CTG<br>Leu<br>705 | TTT<br>Phe | TTC<br>Phe | CGC<br>Arg | TCG<br>Ser | GGC<br>Gly<br>710 | TTC<br>Phe | GGC<br>Gly | ATA<br>Ile | GGC<br>Gly | 2403 |
| ATG<br>Met | CGC<br>Arg<br>715 | AAA<br>Lys | GAC<br>Asp | AGC<br>Ser | CCC<br>Pro<br>720 | TGG<br>Trp | AAG<br>Lys | CAG<br>Gln | AAC<br>Asn | GTC<br>Val<br>725 | TCC<br>Ser | CTG<br>Leu | TCC<br>Ser | ATC<br>Ile | CTC<br>Leu<br>730 | 2451 |
| AAG | TCC | CAC | GAG | AAT | GGC | TTC | ATG | GAA | GAC | CTG | GAC | AAG | ACG | TGG | GTT | 2499 |

| | | | | | | | | | | | | | | |
|---|---|---|---|---|---|---|---|---|---|---|---|---|---|---|
| Lys | Ser | His | Glu | Asn<br>735 | Gly | Phe | Met | Glu<br>740 | Leu | Asp | Lys | Thr<br>745 | Trp | Val |

| | | | | | | | | | | | | | | | |
|---|---|---|---|---|---|---|---|---|---|---|---|---|---|---|---|
| CGG | TAT | CAG | GAA | TGT | GAC | TCG | CGC | AGC | AAC | GCC | CCT | GCG | ACC | CTT | ACT |
| Arg | Tyr | Gln<br>750 | Glu | Cys | Asp | Ser | Arg | Ser<br>755 | Asn | Ala | Pro | Ala<br>760 | Thr | Leu | Thr |

2547

| | | | | | | | | | | | | | | | |
|---|---|---|---|---|---|---|---|---|---|---|---|---|---|---|---|
| TTT | GAG | AAC | ATG | GCC | GGG | GTC | TTC | ATG | CTG | GTA | GCT | GGG | GGC | ATC | GTG |
| Phe | Glu | Asn<br>765 | Met | Ala | Gly | Val | Phe | Met<br>770 | Leu | Val | Ala | Gly<br>775 | Gly | Ile | Val |

2595

| | | | | | | | | | | | | | | | |
|---|---|---|---|---|---|---|---|---|---|---|---|---|---|---|---|
| GCC | GGG | ATC | TTC | CTG | ATT | TTC | ATC | GAG | ATT | GCC | TAC | AAG | CGG | CAC | AAG |
| Ala | Gly<br>780 | Ile | Phe | Leu | Ile | Phe<br>785 | Ile | Glu | Ile | Ala | Tyr<br>790 | Lys | Arg | His | Lys |

2643

| | | | | | | | | | | | | | | | |
|---|---|---|---|---|---|---|---|---|---|---|---|---|---|---|---|
| GAT | GCT | CGC | CGG | AAG | CAG | ATG | CAG | CTG | GCC | TTT | GCC | GCC | GTT | AAC | GTG |
| Asp<br>795 | Ala | Arg | Arg | Lys | Gln<br>800 | Met | Gln | Leu | Ala | Phe<br>805 | Ala | Ala | Val | Asn | Val<br>810 |

2691

| | | | | | | | | | | | | | | | |
|---|---|---|---|---|---|---|---|---|---|---|---|---|---|---|---|
| TGG | CGG | AAG | AAC | CTG | CAG | GAT | AGA | AAG | AGT | GGT | AGA | GCA | GAG | CCT | GAC |
| Trp | Arg | Lys | Asn | Leu<br>815 | Gln | Asp | Arg | Lys | Ser<br>820 | Gly | Arg | Ala | Glu | Pro<br>825 | Asp |

2739

| | | | | | | | | | | | | | | | |
|---|---|---|---|---|---|---|---|---|---|---|---|---|---|---|---|
| CCT | AAA | AAG | AAA | GCC | ACA | TTT | AGG | GCT | ATC | ACC | TCC | ACC | CTG | GCT | TCC |
| Pro | Lys | Lys | Lys<br>830 | Ala | Thr | Phe | Arg | Ala<br>835 | Ile | Thr | Ser | Thr<br>840 | Leu | Ala | Ser |

2787

| | | | | | | | | | | | | | | | |
|---|---|---|---|---|---|---|---|---|---|---|---|---|---|---|---|
| AGC | TTC | AAG | AGG | CGT | AGG | TCC | TCC | AAA | GAC | ACG | CAG | TAC | CAT | CCC | ACT |
| Ser | Phe | Lys<br>845 | Arg | Arg | Arg | Ser | Ser<br>850 | Lys | Asp | Thr | Gln | Tyr<br>855 | His | Pro | Thr |

2835

| | | | | | | | | | | | | | | | |
|---|---|---|---|---|---|---|---|---|---|---|---|---|---|---|---|
| GAT | ATC | ACG | GGC | CCG | CTC | AAC | CTC | TCA | GAT | CCC | TCG | GTC | AGC | ACC | GTG |
| Asp | Ile<br>860 | Thr | Gly | Pro | Leu | Asn<br>865 | Leu | Ser | Asp | Pro | Ser<br>870 | Val | Ser | Thr | Val |

2883

| | | | | | |
|---|---|---|---|---|---|
| GTG | TGAGGCCCCC | GGAGGCGCCC | ACCTGCCCAG | TTAGCCCGGC | CAAGGACACT |
| Val<br>875 | | | | | |

2936

| | | | | | |
|---|---|---|---|---|---|
| GATGGGTCCT | GCTGCTCGGG | AAGGCCTGAG | GGAAGCCCAC | CCGCCCCAGA | GACTGCCCAC | 2996 |
| CCTGGGCCTC | CCGTCCGTCC | GCCCGCCCAC | CCCGCTGCCT | GGCGGGCAGC | CCCTGCTGGA | 3056 |
| CCAAGGTGCG | GACCGGAGCG | GCTGAGGACG | GGCAGAGCT | GAGTCGGCTG | GCAGGGCCG | 3116 |
| CAGGGCGCTC | CGGCAGAGGC | AGGCCCCTGG | GGTCTCTGAG | CAGTGGGGAG | CGGGGGCTAA | 3176 |
| CTGCCCCCAG | GCGGAGGGGC | TTGGAGCAGA | GACGGCAGCC | CCATCCTTCC | CGCAGCACCA | 3236 |
| GCCTGAGCCA | CAGTGGGGCC | CATGGCCCCA | GCTGGCTGGG | TCGCCCCTCC | TCGGGCGCCT | 3296 |
| GCGCTCCTCT | GCAGCCTGAG | CTCCACCCTC | CCCTCTTCTT | GCGGCACCGC | CCACCAAACA | 3356 |
| CCCCGTCTGC | CCCTTGACGC | CACACGCCGG | GGCTGGCGCT | GCCCTCCCCC | ACGGCCGTCC | 3416 |
| CTGACTTCCC | AGCTGGCAGC | GCCTCCCGCC | GCCTCGGGCC | GCCTCCTCCA | GAATCGAGAG | 3476 |
| GGCTGAGCCC | CTCCTCTCCT | CGTCCGGCCT | GCAGCACAGA | AGGGGGCCTC | CCCGGGGGTC | 3536 |
| CCCGGACGCT | GGCTCGGGAC | TGTCTTCAAC | CCTGCCCTGC | ACCTTGGGCA | CGGGAGAGCG | 3596 |
| CCACCCGCCC | GCCCCCGCCC | TCGCTCCGGG | TGCGTGACCG | GCCCGCCACC | TTGTACAGAA | 3656 |
| CCAGCACTCC | CAGGGCCCGA | GCGCGTGCCT | TCCCCGTGCG | CAGCCGCGCT | CTGCCCCTCC | 3716 |
| GTCCCCAGGG | TGCAGGCGCG | CACCGCCCAA | CCCCCACCTC | CCGGTGTATG | CAGTGGTGAT | 3776 |
| GCCTAAAGGA | ATGTCACG | | | | | 3794 |

(2) INFORMATION FOR SEQ ID NO:28:

(i) SEQUENCE CHARACTERISTICS:
        (A) LENGTH: 875 amino acids
        (B) TYPE: amino acid
        (D) TOPOLOGY: linear (ii) MOLECULE TYPE: protein (xi) SEQUENCE DESCRIPTION: SEQ ID NO:28:

| | | | | | | | | | | | | | | |
|---|---|---|---|---|---|---|---|---|---|---|---|---|---|---|
| Met | Ser | Thr | Met | Arg | Leu | Leu | Thr | Leu | Ala | Leu | Leu | Phe | Ser | Cys | Ser |
| 1 | | | | 5 | | | | | 10 | | | | | 15 | |
| Val | Ala | Arg | Ala | Ala | Cys | Asp | Pro | Lys | Ile | Val | Asn | Ile | Gly | Ala | Val |
| | | | 20 | | | | 25 | | | | | 30 | | | |
| Leu | Ser | Thr | Arg | Lys | His | Glu | Gln | Met | Phe | Arg | Glu | Ala | Val | Asn | Gln |
| | | 35 | | | | | 40 | | | | | 45 | | | |
| Ala | Asn | Lys | Arg | His | Gly | Ser | Trp | Lys | Ile | Gln | Leu | Asn | Ala | Thr | Ser |
| | 50 | | | | | 55 | | | | | | 60 | | | |
| Val | Thr | His | Lys | Pro | Asn | Ala | Ile | Gln | Met | Ala | Leu | Ser | Val | Cys | Glu |
| 65 | | | | | 70 | | | | 75 | | | | | | 80 |
| Asp | Leu | Ile | Ser | Ser | Gln | Val | Tyr | Ala | Ile | Leu | Val | Ser | His | Pro | Pro |
| | | | | 85 | | | | | 90 | | | | | 95 | |
| Thr | Pro | Asn | Asp | His | Phe | Thr | Pro | Thr | Pro | Val | Ser | Tyr | Thr | Ala | Gly |
| | | | 100 | | | | | 105 | | | | | 110 | | |
| Phe | Tyr | Arg | Ile | Pro | Val | Leu | Gly | Leu | Thr | Thr | Arg | Met | Ser | Ile | Tyr |
| | | 115 | | | | | 120 | | | | | 125 | | | |
| Ser | Asp | Lys | Ser | Ile | His | Leu | Ser | Phe | Leu | Arg | Thr | Val | Pro | Pro | Tyr |
| | 130 | | | | | 135 | | | | | 140 | | | | |
| Ser | His | Gln | Ser | Ser | Val | Trp | Phe | Glu | Met | Met | Arg | Val | Tyr | Ser | Trp |
| 145 | | | | | 150 | | | | | 155 | | | | | 160 |
| Asn | His | Ile | Ile | Leu | Leu | Val | Ser | Asp | Asp | His | Glu | Gly | Arg | Ala | Ala |
| | | | | 165 | | | | | 170 | | | | | 175 | |
| Gln | Lys | Arg | Leu | Glu | Thr | Leu | Leu | Glu | Glu | Arg | Glu | Ser | Lys | Ser | Lys |
| | | | | 180 | | | | | 185 | | | | 190 | | |
| Lys | Arg | Asn | Tyr | Glu | Asn | Leu | Asp | Gln | Leu | Ser | Tyr | Asp | Asn | Lys | Arg |
| | | | 195 | | | | 200 | | | | | 205 | | | |
| Gly | Pro | Lys | Ala | Glu | Lys | Val | Leu | Gln | Phe | Asp | Pro | Gly | Thr | Lys | Asn |
| | 210 | | | | | 215 | | | | | 220 | | | | |
| Val | Thr | Ala | Leu | Leu | Met | Glu | Ala | Lys | Glu | Leu | Glu | Ala | Arg | Val | Ile |
| 225 | | | | | 230 | | | | | 235 | | | | | 240 |
| Ile | Leu | Ser | Ala | Ser | Glu | Asp | Asp | Ala | Ala | Thr | Val | Tyr | Arg | Ala | Ala |
| | | | | 245 | | | | | 250 | | | | | 255 | |
| Ala | Met | Leu | Asn | Met | Thr | Gly | Asn | Thr | Asn | Ile | Trp | Lys | Thr | Gly | Pro |
| | | | 260 | | | | | 265 | | | | | 270 | | |
| Leu | Phe | Lys | Arg | Val | Leu | Met | Ser | Ser | Lys | Tyr | Ala | Asp | Gly | Val | Thr |
| | | 275 | | | | | 280 | | | | | 285 | | | |
| Gly | Arg | Val | Glu | Phe | Asn | Glu | Asp | Gly | Asp | Arg | Lys | Phe | Ala | Asn | Tyr |
| | 290 | | | | | 295 | | | | | 300 | | | | |
| Ser | Ile | Met | Asn | Leu | Gln | Asn | Arg | Lys | Leu | Val | Gln | Val | Gly | Ile | Tyr |
| 305 | | | | | 310 | | | | | 315 | | | | | 320 |
| Asn | Gly | Thr | His | Val | Ile | Pro | Asn | Asp | Arg | Lys | Ile | Ile | Trp | Pro | Gly |
| | | | | 325 | | | | | 330 | | | | | 335 | |
| Gly | Glu | Thr | Glu | Lys | Pro | Arg | Gly | Tyr | Gln | Met | Ser | Thr | Arg | Leu | Lys |
| | | | 340 | | | | | 345 | | | | | 350 | | |
| Ile | Val | Thr | Ile | His | Gln | Glu | Pro | Phe | Val | Tyr | Val | Lys | Pro | Thr | Leu |
| | | 355 | | | | | 360 | | | | | 365 | | | |
| Ser | Asp | Gly | Thr | Cys | Lys | Glu | Glu | Phe | Thr | Val | Asn | Gly | Asp | Pro | Val |
| | 370 | | | | | 375 | | | | | 380 | | | | |
| Lys | Lys | Val | Ile | Cys | Thr | Gly | Pro | Asn | Asp | Thr | Ser | Pro | Gly | Ser | Pro |
| 385 | | | | | 390 | | | | | 395 | | | | | 400 |
| Arg | His | Thr | Val | Pro | Gln | Cys | Cys | Tyr | Gly | Phe | Cys | Ile | Asp | Leu | Leu |
| | | | | 405 | | | | | 410 | | | | | 415 | |
| Ile | Lys | Leu | Ala | Arg | Thr | Met | Asn | Phe | Thr | Tyr | Glu | Val | His | Leu | Val |

-continued

```
                        420                          425                          430
Ala  Asp  Gly  Lys  Phe  Gly  Thr  Gln  Glu  Arg  Val  Asn  Asn  Ser  Asn  Lys
               435                    440                    445

Lys  Glu  Trp  Asn  Gly  Met  Met  Gly  Glu  Leu  Leu  Ser  Gly  Gln  Ala  Asp
     450                    455                         460

Met  Ile  Val  Ala  Pro  Leu  Thr  Ile  Asn  Asn  Glu  Arg  Ala  Gln  Tyr  Ile
465                      470                    475                              480

Glu  Phe  Ser  Lys  Pro  Phe  Lys  Tyr  Gln  Gly  Leu  Thr  Ile  Leu  Val  Lys
                    485                         490                         495

Lys  Glu  Ile  Pro  Arg  Ser  Thr  Leu  Asp  Ser  Phe  Met  Gln  Pro  Phe  Gln
               500                    505                         510

Ser  Thr  Leu  Trp  Leu  Leu  Val  Gly  Leu  Ser  Val  His  Val  Ala  Val
               515                    520                    525

Met  Leu  Tyr  Leu  Leu  Asp  Arg  Phe  Ser  Pro  Phe  Gly  Arg  Phe  Lys  Val
     530                    535                         540

Asn  Ser  Glu  Glu  Glu  Glu  Asp  Ala  Leu  Thr  Leu  Ser  Ser  Ala  Met
545                         550                    555                         560

Trp  Phe  Ser  Trp  Gly  Val  Leu  Asn  Ser  Gly  Ile  Gly  Glu  Gly  Ala
                    565                    570                    575

Pro  Arg  Ser  Phe  Ser  Ala  Arg  Ile  Leu  Gly  Met  Val  Trp  Ala  Gly  Phe
               580                    585                    590

Ala  Met  Ile  Ile  Val  Ala  Ser  Tyr  Thr  Ala  Asn  Leu  Ala  Ala  Phe  Leu
          595                         600                    605

Val  Leu  Asp  Arg  Pro  Glu  Glu  Arg  Ile  Thr  Gly  Ile  Asn  Asp  Pro  Arg
     610                    615                    620

Leu  Arg  Asn  Pro  Ser  Asp  Lys  Phe  Ile  Tyr  Ala  Thr  Val  Lys  Gln  Ser
625                         630                    635                         640

Ser  Val  Asp  Ile  Tyr  Phe  Arg  Arg  Gln  Val  Glu  Leu  Ser  Thr  Met  Tyr
               645                    650                         655

Arg  His  Met  Glu  Lys  His  Asn  Tyr  Glu  Ser  Ala  Ala  Glu  Ala  Ile  Gln
               660                    665                    670

Ala  Val  Arg  Asp  Asn  Lys  Leu  His  Ala  Phe  Ile  Trp  Asp  Ser  Ala  Val
          675                    680                    685

Leu  Glu  Phe  Glu  Ala  Ser  Gln  Lys  Cys  Asp  Leu  Val  Thr  Thr  Gly  Glu
     690                    695                    700

Leu  Phe  Phe  Arg  Ser  Gly  Phe  Gly  Ile  Gly  Met  Arg  Lys  Asp  Ser  Pro
705                         710                    715                         720

Trp  Lys  Gln  Asn  Val  Ser  Leu  Ser  Ile  Leu  Lys  Ser  His  Glu  Asn  Gly
                    725                    730                         735

Phe  Met  Glu  Asp  Leu  Asp  Lys  Thr  Trp  Val  Arg  Tyr  Gln  Glu  Cys  Asp
               740                    745                         750

Ser  Arg  Ser  Asn  Ala  Pro  Ala  Thr  Leu  Thr  Phe  Glu  Asn  Met  Ala  Gly
          755                    760                         765

Val  Phe  Met  Leu  Val  Ala  Gly  Gly  Ile  Val  Ala  Gly  Ile  Phe  Leu  Ile
     770                    775                    780

Phe  Ile  Glu  Ile  Ala  Tyr  Lys  Arg  His  Lys  Asp  Ala  Arg  Arg  Lys  Gln
785                    790                    795                              800

Met  Gln  Leu  Ala  Phe  Ala  Ala  Val  Asn  Val  Trp  Arg  Lys  Asn  Leu  Gln
                    805                    810                         815

Asp  Arg  Lys  Ser  Gly  Arg  Ala  Glu  Pro  Asp  Pro  Lys  Lys  Lys  Ala  Thr
               820                    825                    830

Phe  Arg  Ala  Ile  Thr  Ser  Thr  Leu  Ala  Ser  Ser  Phe  Lys  Arg  Arg  Arg
          835                    840                    845
```

```
Ser  Ser  Lys  Asp  Thr  Gln  Tyr  His  Pro  Thr  Asp  Ile  Thr  Gly  Pro  Leu
     850                      855                      860

Asn  Leu  Ser  Asp  Pro  Ser  Val  Ser  Thr  Val  Val
865                      870                      875
```

( 2 ) INFORMATION FOR SEQ ID NO:29:

( i ) SEQUENCE CHARACTERISTICS:
        ( A ) LENGTH: 4094 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..2874

( x i ) SEQUENCE DESCRIPTION: SEQ ID NO:29:

```
CAAGCCGGGC  GTTCGGAGCT  GTGCCCGGCC  CCGCTTCAGC  ACCGCGGACA  GCGCCGGCCG         60

CGTGGGGCTG  AGCGCCGAGC  CCCCGCGCAC  GCTTCAGCCC  CCCTTCCCTC  GGCCGACGTC        120

CCGGGACCGC  CGCTCCGGGG  GAGACGTGGC  GTCCGCAGCC  CGCGGGGCCG  GGCGAGCGCA        180

GGACGGCCCG  GAAGCCCCGC  GGGGGATGCG  CCGAGGGCCC  CGCGTTCGCG  CCGCGCAGAG        240

CCAGGCCCGC  GGCCCGAGCC C  ATG  AGC  ACC  ATG  CGC  CTG  CTG  ACG  CTC  GCC   291
                          Met  Ser  Thr  Met  Arg  Leu  Leu  Thr  Leu  Ala
                           1             5                          10

CTG  CTG  TTC  TCC  TGC  TCC  GTC  GCC  CGT  GCC  GCG  TGC  GAC  CCC  AAG  ATC   339
Leu  Leu  Phe  Ser  Cys  Ser  Val  Ala  Arg  Ala  Ala  Cys  Asp  Pro  Lys  Ile
                    15                       20                       25

GTC  AAC  ATT  GGC  GCG  GTG  CTG  AGC  ACG  CGG  AAG  CAC  GAG  CAG  ATG  TTC   387
Val  Asn  Ile  Gly  Ala  Val  Leu  Ser  Thr  Arg  Lys  His  Glu  Gln  Met  Phe
               30                       35                       40

CGC  GAG  GCC  GTG  AAC  CAG  GCC  AAC  AAG  CGG  CAC  GGC  TCC  TGG  AAG  ATT   435
Arg  Glu  Ala  Val  Asn  Gln  Ala  Asn  Lys  Arg  His  Gly  Ser  Trp  Lys  Ile
               45                       50                       55

CAG  CTC  AAT  GCC  ACC  TCC  GTC  ACG  CAC  AAG  CCC  AAC  GCC  ATC  CAG  ATG   483
Gln  Leu  Asn  Ala  Thr  Ser  Val  Thr  His  Lys  Pro  Asn  Ala  Ile  Gln  Met
 60                       65                       70

GCT  CTG  TCG  GTG  TGC  GAG  GAC  CTC  ATC  TCC  AGC  CAG  GTC  TAC  GCC  ATC   531
Ala  Leu  Ser  Val  Cys  Glu  Asp  Leu  Ile  Ser  Ser  Gln  Val  Tyr  Ala  Ile
 75                       80                       85                       90

CTA  GTT  AGC  CAT  CCA  CCT  ACC  CCC  AAC  GAC  CAC  TTC  ACT  CCC  ACC  CCT   579
Leu  Val  Ser  His  Pro  Pro  Thr  Pro  Asn  Asp  His  Phe  Thr  Pro  Thr  Pro
                    95                      100                      105

GTC  TCC  TAC  ACA  GCC  GGC  TTC  TAC  CGC  ATA  CCC  GTG  CTG  GGG  CTG  ACC   627
Val  Ser  Tyr  Thr  Ala  Gly  Phe  Tyr  Arg  Ile  Pro  Val  Leu  Gly  Leu  Thr
              110                      115                      120

ACC  CGC  ATG  TCC  ATC  TAC  TCG  GAC  AAG  AGC  ATC  CAC  CTG  AGC  TTC  CTG   675
Thr  Arg  Met  Ser  Ile  Tyr  Ser  Asp  Lys  Ser  Ile  His  Leu  Ser  Phe  Leu
              125                      130                      135

CGC  ACC  GTG  CCG  CCC  TAC  TCC  CAC  CAG  TCC  AGC  GTG  TGG  TTT  GAG  ATG   723
Arg  Thr  Val  Pro  Pro  Tyr  Ser  His  Gln  Ser  Ser  Val  Trp  Phe  Glu  Met
     140                      145                      150

ATG  CGT  GTC  TAC  AGC  TGG  AAC  CAC  ATC  ATC  CTG  CTG  GTC  AGC  GAC  GAC   771
Met  Arg  Val  Tyr  Ser  Trp  Asn  His  Ile  Ile  Leu  Leu  Val  Ser  Asp  Asp
155                      160                      165                      170

CAC  GAG  GGC  CGG  GCG  GCT  CAG  AAA  CGC  CTG  GAG  ACG  CTG  CTG  GAG  GAG   819
His  Glu  Gly  Arg  Ala  Ala  Gln  Lys  Arg  Leu  Glu  Thr  Leu  Leu  Glu  Glu
                    175                      180                      185

CGT  GAG  TCC  AAG  GCA  GAG  AAG  GTG  CTG  CAG  TTT  GAC  CCA  GGG  ACC  AAG   867
```

-continued

```
            Arg  Glu  Ser  Lys  Ala  Glu  Lys  Val  Leu  Gln  Phe  Asp  Pro  Gly  Thr  Lys
                           190                 195                           200

AAC  GTG  ACG  GCC  CTG  CTG  ATG  GAG  GCG  AAA  GAG  CTG  GAG  GCC  CGG  GTC          915
Asn  Val  Thr  Ala  Leu  Leu  Met  Glu  Ala  Lys  Glu  Leu  Glu  Ala  Arg  Val
          205                      210                      215

ATC  ATC  CTT  TCT  GCC  AGC  GAG  GAC  GAT  GCT  GCC  ACT  GTA  TAC  CGC  GCA          963
Ile  Ile  Leu  Ser  Ala  Ser  Glu  Asp  Asp  Ala  Ala  Thr  Val  Tyr  Arg  Ala
          220                      225                      230

GCC  GCG  ATG  CTG  AAC  ATG  ACG  GGC  AAC  ACC  AAC  ATC  TGG  AAG  ACC  GGG         1011
Ala  Ala  Met  Leu  Asn  Met  Thr  Gly  Asn  Thr  Asn  Ile  Trp  Lys  Thr  Gly
235                      240                      245                      250

CCG  CTC  TTC  AAG  AGA  GTG  CTG  ATG  TCT  TCC  AAG  TAT  GCG  GAT  GGG  GTG         1059
Pro  Leu  Phe  Lys  Arg  Val  Leu  Met  Ser  Ser  Lys  Tyr  Ala  Asp  Gly  Val
                    255                      260                      265

ACT  GGT  CGC  GTG  GAG  TTC  AAT  GAG  GAT  GGG  GAC  CGG  AAG  TTC  GCC  AAC         1107
Thr  Gly  Arg  Val  Glu  Phe  Asn  Glu  Asp  Gly  Asp  Arg  Lys  Phe  Ala  Asn
               270                      275                      280

TAC  AGC  ATC  ATG  AAC  CTG  CAG  AAC  CGC  AAG  CTG  GTG  CAA  GTG  GGC  ATC         1155
Tyr  Ser  Ile  Met  Asn  Leu  Gln  Asn  Arg  Lys  Leu  Val  Gln  Val  Gly  Ile
          285                      290                      295

TAC  AAT  GGC  ACC  CAC  GTC  ATC  CCT  AAT  GAC  AGG  AAG  ATC  ATC  TGG  CCA         1203
Tyr  Asn  Gly  Thr  His  Val  Ile  Pro  Asn  Asp  Arg  Lys  Ile  Ile  Trp  Pro
     300                      305                      310

GGC  GGA  GAG  ACA  GAG  AAG  CCT  CGA  GGG  TAC  CAG  ATG  TCC  ACC  AGA  CTG         1251
Gly  Gly  Glu  Thr  Glu  Lys  Pro  Arg  Gly  Tyr  Gln  Met  Ser  Thr  Arg  Leu
315                      320                      325                      330

AAG  ATT  GTG  ACG  ATC  CAC  CAG  GAG  CCC  TTC  GTG  TAC  GTC  AAG  CCC  ACG         1299
Lys  Ile  Val  Thr  Ile  His  Gln  Glu  Pro  Phe  Val  Tyr  Val  Lys  Pro  Thr
                    335                      340                      345

CTG  AGT  GAT  GGG  ACA  TGC  AAG  GAG  GAG  TTC  ACA  GTC  AAC  GGC  GAC  CCA         1347
Leu  Ser  Asp  Gly  Thr  Cys  Lys  Glu  Glu  Phe  Thr  Val  Asn  Gly  Asp  Pro
               350                      355                      360

GTC  AAG  AAG  GTG  ATC  TGC  ACC  GGG  CCC  AAC  GAC  ACG  TCG  CCG  GGC  AGC         1395
Val  Lys  Lys  Val  Ile  Cys  Thr  Gly  Pro  Asn  Asp  Thr  Ser  Pro  Gly  Ser
          365                      370                      375

CCC  CGC  CAC  ACG  GTG  CCT  CAG  TGT  TGC  TAC  GGC  TTT  TGC  ATC  GAC  CTG         1443
Pro  Arg  His  Thr  Val  Pro  Gln  Cys  Cys  Tyr  Gly  Phe  Cys  Ile  Asp  Leu
     380                      385                      390

CTC  ATC  AAG  CTG  GCA  CGG  ACC  ATG  AAC  TTC  ACC  TAC  GAG  GTG  CAC  CTG         1491
Leu  Ile  Lys  Leu  Ala  Arg  Thr  Met  Asn  Phe  Thr  Tyr  Glu  Val  His  Leu
395                      400                      405                      410

GTG  GCA  GAT  GGC  AAG  TTC  GGC  ACA  CAG  GAG  CGG  GTG  AAC  AAC  AGC  AAC         1539
Val  Ala  Asp  Gly  Lys  Phe  Gly  Thr  Gln  Glu  Arg  Val  Asn  Asn  Ser  Asn
                    415                      420                      425

AAG  AAG  GAG  TGG  AAT  GGG  ATG  ATG  GGC  GAG  CTG  CTC  AGC  GGG  CAG  GCA         1587
Lys  Lys  Glu  Trp  Asn  Gly  Met  Met  Gly  Glu  Leu  Leu  Ser  Gly  Gln  Ala
               430                      435                      440

GAC  ATG  ATC  GTG  GCG  CCG  CTA  ACC  ATA  AAC  AAC  GAG  CGC  GCG  CAG  TAC         1635
Asp  Met  Ile  Val  Ala  Pro  Leu  Thr  Ile  Asn  Asn  Glu  Arg  Ala  Gln  Tyr
          445                      450                      455

ATC  GAG  TTT  TCC  AAG  CCC  TTC  AAG  TAC  CAG  GGC  CTG  ACT  ATT  CTG  GTC         1683
Ile  Glu  Phe  Ser  Lys  Pro  Phe  Lys  Tyr  Gln  Gly  Leu  Thr  Ile  Leu  Val
     460                      465                      470

AAG  AAG  GAG  ATT  CCC  CGG  AGC  ACG  CTG  GAC  TCG  TTC  ATG  CAG  CCG  TTC         1731
Lys  Lys  Glu  Ile  Pro  Arg  Ser  Thr  Leu  Asp  Ser  Phe  Met  Gln  Pro  Phe
475                      480                      485                      490

CAG  AGC  ACA  CTG  TGG  CTG  CTG  GTG  GGG  CTG  TCG  GTG  CAC  GTG  GTG  GCC         1779
Gln  Ser  Thr  Leu  Trp  Leu  Leu  Val  Gly  Leu  Ser  Val  His  Val  Val  Ala
                    495                      500                      505

GTG  ATG  CTG  TAC  CTG  CTG  GAC  CGC  TTC  AGC  CCC  TTC  GGC  CGG  TTC  AAG         1827
```

| | | | | | | | | | | | | | | | | |
|---|---|---|---|---|---|---|---|---|---|---|---|---|---|---|---|---|
| Val | Met | Leu | Tyr 510 | Leu | Leu | Asp | Arg | Phe 515 | Ser | Pro | Phe | Gly | Arg 520 | Phe | Lys | |
| GTG | AAC | AGC | GAG | GAG | GAG | GAG | GAG | GAC | GCA | CTG | ACC | CTG | TCC | TCG | GCC | 1875 |
| Val | Asn | Ser 525 | Glu | Glu | Glu | Glu | Glu 530 | Asp | Ala | Leu | Thr | Leu 535 | Ser | Ser | Ala | |
| ATG | TGG | TTC | TCC | TGG | GGC | GTC | CTG | CTC | AAC | TCC | GGC | ATC | GGG | GAA | GGC | 1923 |
| Met | Trp 540 | Phe | Ser | Trp | Gly | Val | Leu 545 | Leu | Asn | Ser | Gly | Ile 550 | Gly | Glu | Gly | |
| GCC | CCC | AGA | AGC | TTC | TCA | GCG | CGC | ATC | CTG | GGC | ATG | GTG | TGG | GCC | GGC | 1971 |
| Ala 555 | Pro | Arg | Ser | Phe | Ser 560 | Ala | Arg | Ile | Leu | Gly 565 | Met | Val | Trp | Ala | Gly 570 | |
| TTT | GCC | ATG | ATC | ATC | GTG | GCC | TCC | TAC | ACC | GCC | AAC | CTG | GCG | GCC | TTC | 2019 |
| Phe | Ala | Met | Ile | Ile 575 | Val | Ala | Ser | Tyr | Thr 580 | Ala | Asn | Leu | Ala | Ala 585 | Phe | |
| CTG | GTG | CTG | GAC | CGG | CCG | GAG | GAG | CGC | ATC | ACG | GGC | ATC | AAC | GAC | CCT | 2067 |
| Leu | Val | Leu | Asp | Arg 590 | Pro | Glu | Glu | Arg | Ile 595 | Thr | Gly | Ile | Asn | Asp 600 | Pro | |
| CGG | CTG | AGG | AAC | CCC | TCG | GAC | AAG | TTT | ATC | TAC | GCC | ACG | GTG | AAG | CAG | 2115 |
| Arg | Leu | Arg | Asn | Pro | Ser | Asp | Lys | Phe | Ile | Tyr | Ala | Thr | Val | Lys | Gln | |
| | | 605 | | | | 610 | | | | | 615 | | | | | |
| AGC | TCC | GTG | GAT | ATC | TAC | TTC | CGG | CGC | CAG | GTG | GAG | CTG | AGC | ACC | ATG | 2163 |
| Ser | Ser | Val | Asp | Ile | Tyr | Phe | Arg | Arg | Gln | Val | Glu | Leu | Ser | Thr | Met | |
| | 620 | | | | | 625 | | | | | 630 | | | | | |
| TAC | CGG | CAT | ATG | GAG | AAG | CAC | AAC | TAC | GAG | AGT | GCG | GCG | GAG | GCC | ATC | 2211 |
| Tyr 635 | Arg | His | Met | Glu | Lys 640 | His | Asn | Tyr | Glu | Ser 645 | Ala | Ala | Glu | Ala | Ile 650 | |
| CAG | GCC | GTG | AGA | GAC | AAC | AAG | CTG | CAT | GCC | TTC | ATC | TGG | GAC | TCG | GCG | 2259 |
| Gln | Ala | Val | Arg | Asp | Asn | Lys | Leu | His | Ala | Phe | Ile | Trp | Asp | Ser | Ala | |
| | | | | 655 | | | | 660 | | | | | 665 | | | |
| GTG | CTG | GAG | TTC | GAG | GCC | TCG | CAG | AAG | TGC | GAC | CTG | GTG | ACG | ACT | GGA | 2307 |
| Val | Leu | Glu | Phe 670 | Glu | Ala | Ser | Gln | Lys 675 | Cys | Asp | Leu | Val | Thr 680 | Thr | Gly | |
| GAG | CTG | TTT | TTC | CGC | TCG | GGC | TTC | GGC | ATA | GGC | ATG | CGC | AAA | GAC | AGC | 2355 |
| Glu | Leu | Phe 685 | Phe | Arg | Ser | Gly | Phe | Gly | Ile 690 | Gly | Met | Arg | Lys 695 | Asp | Ser | |
| CCC | TGG | AAG | CAG | AAC | GTC | TCC | CTG | TCC | ATC | CTC | AAG | TCC | CAC | GAG | AAT | 2403 |
| Pro | Trp | Lys | Gln | Asn | Val | Ser | Leu | Ser | Ile | Leu | Lys | Ser | His | Glu | Asn | |
| | 700 | | | | | 705 | | | | | 710 | | | | | |
| GGC | TTC | ATG | GAA | GAC | CTG | GAC | AAG | ACG | TGG | GTT | CGG | TAT | CAG | GAA | TGT | 2451 |
| Gly 715 | Phe | Met | Glu | Asp | Leu 720 | Asp | Lys | Thr | Trp | Val 725 | Arg | Tyr | Gln | Glu | Cys 730 | |
| GAC | TCG | CGC | AGC | AAC | GCC | CCT | GCG | ACC | CTT | ACT | TTT | GAG | AAC | ATG | GCC | 2499 |
| Asp | Ser | Arg | Ser | Asn 735 | Ala | Pro | Ala | Thr | Leu 740 | Thr | Phe | Glu | Asn | Met 745 | Ala | |
| GGG | GTC | TTC | ATG | CTG | GTA | GCT | GGG | GGC | ATC | GTG | GCC | GGG | ATC | TTC | CTG | 2547 |
| Gly | Val | Phe | Met 750 | Leu | Val | Ala | Gly | Gly | Ile 755 | Val | Ala | Gly | Ile 760 | Phe | Leu | |
| ATT | TTC | ATC | GAG | ATT | GCC | TAC | AAG | CGG | CAC | AAG | GAT | GCT | CGC | CGG | AAG | 2595 |
| Ile | Phe | Ile 765 | Glu | Ile | Ala | Tyr | Lys 770 | Arg | His | Lys | Asp | Ala 775 | Arg | Arg | Lys | |
| CAG | ATG | CAG | CTG | GCC | TTT | GCC | GCC | GTT | AAC | GTG | TGG | CGG | AAG | AAC | CTG | 2643 |
| Gln | Met 780 | Gln | Leu | Ala | Phe | Ala 785 | Ala | Val | Asn | Val | Trp 790 | Arg | Lys | Asn | Leu | |
| CAG | GAT | AGA | AAG | AGT | GGT | AGA | GCA | GAG | CCT | GAC | CCT | AAA | AAG | AAA | GCC | 2691 |
| Gln 795 | Asp | Arg | Lys | Ser | Gly 800 | Arg | Ala | Glu | Pro | Asp 805 | Pro | Lys | Lys | Lys | Ala 810 | |
| ACA | TTT | AGG | GCT | ATC | ACC | TCC | ACC | CTG | GCT | TCC | AGC | TTC | AAG | AGG | CGT | 2739 |
| Thr | Phe | Arg | Ala | Ile 815 | Thr | Ser | Thr | Leu | Ala 820 | Ser | Ser | Phe | Lys | Arg 825 | Arg | |
| AGG | TCC | TCC | AAA | GAC | ACG | AGC | ACC | GGG | GGT | GGA | CGC | GGT | GCT | TTG | CAA | 2787 |

|  |  |  |  |  |  |  |  |  |  |  |  |  |  |  |  |
|--|--|--|--|--|--|--|--|--|--|--|--|--|--|--|--|
| Arg | Ser | Ser | Lys<br>830 | Asp | Thr | Ser | Thr | Gly<br>835 | Gly | Gly | Arg | Gly | Ala<br>840 | Leu | Gln |

| AAC | CAA | AAA | GAC | ACA | GTG | CTG | CCG | CGA | CGC | GCT | ATT | GAG | AGG | GAG | GAG | 2835 |
|--|--|--|--|--|--|--|--|--|--|--|--|--|--|--|--|--|
| Asn | Gln<br> | Lys<br>845 | Asp | Thr | Val | Leu | Pro<br>850 | Arg | Arg | Ala | Ile | Glu<br>855 | Arg | Glu | Glu | |

| GGC | CAG | CTG | CAG | CTG | TGT | TCC | CGT | CAT | AGG | GAG | AGC | TGAGACTCCC | 2881 |
|--|--|--|--|--|--|--|--|--|--|--|--|--|--|
| Gly | Gln<br> | Leu<br>860 | Gln | Leu | Cys | Ser<br>865 | Arg | His | Arg | Glu | Ser<br>870 | | |

| | | | | | |
|--|--|--|--|--|--|
| CGCCCGCCCT | CCTCTGCCCC | CTCCCCCGCA | GACAGACAGA | CAGACGGACG | GGACAGCGGC | 2941 |
| CCGGCCCACG | CAGAGCCCCG | GAGCACCACG | GGGTCGGGGG | AGGAGCACCC | CCAGCCTCCC | 3001 |
| CCAGGCTGCG | CCTGCCCGCC | CGCCGGTTGG | CCGGCTGGCC | GGTCCACCCC | GTCCCGGCCC | 3061 |
| CGCGCGTGCC | CCCAGCGTGG | GGCTAACGGG | CGCCTTGTCT | GTGTATTTCT | ATTTTGCAGC | 3121 |
| AGTACCATCC | CACTGATATC | ACGGGCCCGC | TCAACCTCTC | AGATCCCTCG | GTCAGCACCG | 3181 |
| TGGTGTGAGG | CCCCCGGAGG | CGCCCACCTG | CCCAGTTAGC | CCGGCCAAGG | ACACTGATGG | 3241 |
| GTCCTGCTGC | TCGGGAAGGC | CTGAGGGAAG | CCCACCCGCC | CCAGAGACTG | CCCACCCTGG | 3301 |
| GCCTCCCGTC | CGTCCGCCCG | CCCACCCCGC | TGCCTGGCGG | GCAGCCCCTG | CTGGACCAAG | 3361 |
| GTGCGGACCG | GAGCGGCTGA | GGACGGGGCA | GAGCTGAGTC | GGCTGGGCAG | GGCCGCAGGG | 3421 |
| CGCTCCGGCA | GAGGCAGGCC | CCTGGGGTCT | CTGAGCAGTG | GGGAGCGGGG | GCTAACTGCC | 3481 |
| CCCAGGCGGA | GGGGCTTGGA | GCAGAGACGG | CAGCCCCATC | CTTCCCGCAG | CACCAGCCTG | 3541 |
| AGCCACAGTG | GGGCCCATGG | CCCCAGCTGG | CTGGGTCGCC | CCTCCTCGGG | CGCCTGCGCT | 3601 |
| CCTCTGCAGC | CTGAGCTCCA | CCCTCCCCTC | TTCTTGCGGC | ACCGCCCACC | AAACACCCCG | 3661 |
| TCTGCCCCTT | GACGCCACAC | GCCGGGGCTG | GCGCTGCCCT | CCCCCACGGC | CGTCCCTGAC | 3721 |
| TTCCCAGCTG | GCAGCGCCTC | CCGCCGCCTC | GGGCCGCCTC | CTCCAGAATC | GAGAGGGCTG | 3781 |
| AGCCCCTCCT | CTCCTCGTCC | GGCCTGCAGC | ACAGAAGGGG | GCCTCCCCGG | GGGTCCCCGG | 3841 |
| ACGCTGGCTC | GGGACTGTCT | TCAACCCTGC | CCTGCACCTT | GGGCACGGGA | GAGCGCCACC | 3901 |
| CGCCCGCCCC | CGCCCTCGCT | CCGGGTGCGT | GACCGGCCCG | CCACCTTGTA | CAGAACCAGC | 3961 |
| ACTCCCAGGG | CCCGAGCGCG | TGCCTTCCCC | GTGCGCAGCC | GCGCTCTGCC | CCTCCGTCCC | 4021 |
| CAGGGTGCAG | GCGCGCACCG | CCCAACCCCC | ACCTCCCGGT | GTATGCAGTG | GTGATGCCTA | 4081 |
| AAGGAATGTC | ACG | | | | | 4094 |

( 2 ) INFORMATION FOR SEQ ID NO:30:

( i ) SEQUENCE CHARACTERISTICS:
        ( A ) LENGTH: 870 amino acids
        ( B ) TYPE: amino acid
        ( D ) TOPOLOGY: linear ( i i ) MOLECULE TYPE: protein ( x i ) SEQUENCE DESCRIPTION: SEQ ID NO:30:

| Met<br>1 | Ser | Thr | Met | Arg<br>5 | Leu | Leu | Thr | Leu | Ala<br>10 | Leu | Leu | Phe | Ser | Cys<br>15 | Ser |
|--|--|--|--|--|--|--|--|--|--|--|--|--|--|--|--|
| Val | Ala | Arg | Ala<br>20 | Ala | Cys | Asp | Pro | Lys<br>25 | Ile | Val | Asn | Ile | Gly<br>30 | Ala | Val |
| Leu | Ser | Thr<br>35 | Arg | Lys | His | Glu | Gln<br>40 | Met | Phe | Arg | Glu | Ala<br>45 | Val | Asn | Gln |
| Ala | Asn<br>50 | Lys | Arg | His | Gly | Ser<br>55 | Trp | Lys | Ile | Gln | Leu<br>60 | Asn | Ala | Thr | Ser |
| Val<br>65 | Thr | His | Lys | Pro | Asn<br>70 | Ala | Ile | Gln | Met | Ala<br>75 | Leu | Ser | Val | Cys | Glu<br>80 |

-continued

```
Asp Leu Ile Ser Ser Gln Val Tyr Ala Ile Leu Val Ser His Pro Pro
                85                  90                  95
Thr Pro Asn Asp His Phe Thr Pro Thr Pro Val Ser Tyr Thr Ala Gly
            100             105                 110
Phe Tyr Arg Ile Pro Val Leu Gly Leu Thr Thr Arg Met Ser Ile Tyr
        115                 120                 125
Ser Asp Lys Ser Ile His Leu Ser Phe Leu Arg Thr Val Pro Pro Tyr
    130             135                 140
Ser His Gln Ser Ser Val Trp Phe Glu Met Met Arg Val Tyr Ser Trp
145             150                 155                     160
Asn His Ile Ile Leu Leu Val Ser Asp His Glu Gly Arg Ala Ala
                165             170                 175
Gln Lys Arg Leu Glu Thr Leu Leu Glu Glu Arg Glu Ser Lys Ala Glu
            180                 185                 190
Lys Val Leu Gln Phe Asp Pro Gly Thr Lys Asn Val Thr Ala Leu Leu
        195                 200                 205
Met Glu Ala Lys Glu Leu Glu Ala Arg Val Ile Ile Leu Ser Ala Ser
    210                 215                 220
Glu Asp Asp Ala Ala Thr Val Tyr Arg Ala Ala Ala Met Leu Asn Met
225                 230                 235                 240
Thr Gly Asn Thr Asn Ile Trp Lys Thr Gly Pro Leu Phe Lys Arg Val
                245                 250                 255
Leu Met Ser Ser Lys Tyr Ala Asp Gly Val Thr Gly Arg Val Glu Phe
            260                 265                 270
Asn Glu Asp Gly Asp Arg Lys Phe Ala Asn Tyr Ser Ile Met Asn Leu
        275                 280                 285
Gln Asn Arg Lys Leu Val Gln Val Gly Ile Tyr Asn Gly Thr His Val
    290                 295                 300
Ile Pro Asn Asp Arg Lys Ile Ile Trp Pro Gly Gly Glu Thr Glu Lys
305                 310                 315                 320
Pro Arg Gly Tyr Gln Met Ser Thr Arg Leu Lys Ile Val Thr Ile His
                325                 330                 335
Gln Glu Pro Phe Val Tyr Val Lys Pro Thr Leu Ser Asp Gly Thr Cys
            340                 345                 350
Lys Glu Glu Phe Thr Val Asn Gly Asp Pro Val Lys Lys Val Ile Cys
        355                 360                 365
Thr Gly Pro Asn Asp Thr Ser Pro Gly Ser Pro Arg His Thr Val Pro
    370                 375                 380
Gln Cys Cys Tyr Gly Phe Cys Ile Asp Leu Leu Ile Lys Leu Ala Arg
385                 390                 395                 400
Thr Met Asn Phe Thr Tyr Glu Val His Leu Val Ala Asp Gly Lys Phe
                405                 410                 415
Gly Thr Gln Glu Arg Val Asn Asn Ser Asn Lys Lys Glu Trp Asn Gly
            420                 425                 430
Met Met Gly Glu Leu Leu Ser Gly Gln Ala Asp Met Ile Val Ala Pro
        435                 440                 445
Leu Thr Ile Asn Asn Glu Arg Ala Gln Tyr Ile Glu Phe Ser Lys Pro
    450                 455                 460
Phe Lys Tyr Gln Gly Leu Thr Ile Leu Val Lys Lys Glu Ile Pro Arg
465                 470                 475                 480
Ser Thr Leu Asp Ser Phe Met Gln Pro Phe Gln Ser Thr Leu Trp Leu
                485                 490                 495
Leu Val Gly Leu Ser Val His Val Val Ala Val Met Leu Tyr Leu Leu
            500                 505                 510
```

Asp Arg Phe Ser Pro Phe Gly Arg Phe Lys Val Asn Ser Glu Glu Glu
        515             520                 525

Glu Glu Asp Ala Leu Thr Leu Ser Ser Ala Met Trp Phe Ser Trp Gly
    530             535                 540

Val Leu Leu Asn Ser Gly Ile Gly Gly Ala Pro Arg Ser Phe Ser
545             550                 555                 560

Ala Arg Ile Leu Gly Met Val Trp Ala Gly Phe Ala Met Ile Ile Val
            565                 570                     575

Ala Ser Tyr Thr Ala Asn Leu Ala Ala Phe Leu Val Leu Asp Arg Pro
        580                 585                 590

Glu Glu Arg Ile Thr Gly Ile Asn Asp Pro Arg Leu Arg Asn Pro Ser
        595             600                 605

Asp Lys Phe Ile Tyr Ala Thr Val Lys Gln Ser Ser Val Asp Ile Tyr
    610             615                 620

Phe Arg Arg Gln Val Glu Leu Ser Thr Met Tyr Arg His Met Glu Lys
625             630                 635                 640

His Asn Tyr Glu Ser Ala Ala Glu Ala Ile Gln Ala Val Arg Asp Asn
                645             650                 655

Lys Leu His Ala Phe Ile Trp Asp Ser Ala Val Leu Glu Phe Glu Ala
            660             665                 670

Ser Gln Lys Cys Asp Leu Val Thr Thr Gly Glu Leu Phe Phe Arg Ser
        675             680                 685

Gly Phe Gly Ile Gly Met Arg Lys Asp Ser Pro Trp Lys Gln Asn Val
    690             695                 700

Ser Leu Ser Ile Leu Lys Ser His Glu Asn Gly Phe Met Glu Asp Leu
705             710             715                     720

Asp Lys Thr Trp Val Arg Tyr Gln Glu Cys Asp Ser Arg Ser Asn Ala
            725                 730                 735

Pro Ala Thr Leu Thr Phe Glu Asn Met Ala Gly Val Phe Met Leu Val
            740             745                 750

Ala Gly Gly Ile Val Ala Gly Ile Phe Leu Ile Phe Ile Glu Ile Ala
        755                 760             765

Tyr Lys Arg His Lys Asp Ala Arg Arg Lys Gln Met Gln Leu Ala Phe
    770             775                 780

Ala Ala Val Asn Val Trp Arg Lys Asn Leu Gln Asp Arg Lys Ser Gly
785                 790                 795                 800

Arg Ala Glu Pro Asp Pro Lys Lys Lys Ala Thr Phe Arg Ala Ile Thr
            805             810                 815

Ser Thr Leu Ala Ser Ser Phe Lys Arg Arg Ser Ser Lys Asp Thr
            820             825                 830

Ser Thr Gly Gly Gly Arg Gly Ala Leu Gln Asn Gln Lys Asp Thr Val
        835             840                 845

Leu Pro Arg Arg Ala Ile Glu Arg Glu Glu Gly Gln Leu Gln Leu Cys
    850             855                 860

Ser Arg His Arg Glu Ser
865             870

( 2 ) INFORMATION FOR SEQ ID NO:31:

( i ) SEQUENCE CHARACTERISTICS:
        ( A ) LENGTH: 3731 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
    ( A ) NAME/KEY: CDS
    ( B ) LOCATION: 262..2826

( x i ) SEQUENCE DESCRIPTION: SEQ ID NO:31:

```
CAAGCCGGGC  GTTCGGAGCT  GTGCCCGGCC  CCGCTTCAGC  ACCGCGGACA  GCGCCGGCCG       60

CGTGGGGCTG  AGCGCCGAGC  CCCCGCGCAC  GCTTCAGCCC  CCCTTCCCTC  GGCCGACGTC      120

CCGGGACCGC  CGCTCCGGGG  GAGACGTGGC  GTCCGCAGCC  CGCGGGGCCG  GGCGAGCGCA      180

GGACGGCCCG  GAAGCCCCGC  GGGGGATGCG  CCGAGGGCCC  CGCGTTCGCG  CCGCGCAGAG      240

CCAGGCCCGC  GGCCCGAGCC  C ATG AGC ACC ATG CGC CTG CTG ACG CTC GCC          291
              Met Ser Thr Met Arg Leu Leu Thr Leu Ala
               1               5                  10

CTG CTG TTC TCC TGC TCC GTC GCC CGT GCC GCG TGC GAC CCC AAG ATC            339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC            387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT            435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG            483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC            531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT            579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC            627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG            675
Thr Arg Met Ser Ile Tyr Ser Asp Lys Ser Ile His Leu Ser Phe Leu
         125                 130                 135

CGC ACC GTG CCG CCC TAC TCC CAC CAG TCC AGC GTG TGG TTT GAG ATG            723
Arg Thr Val Pro Pro Tyr Ser His Gln Ser Ser Val Trp Phe Glu Met
     140                 145                 150

ATG CGT GTC TAC AGC TGG AAC CAC ATC ATC CTG CTG GTC AGC GAC GAC            771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG            819
His Glu Gly Arg Ala Ala Gln Lys Arg Leu Glu Thr Leu Leu Glu Glu
                 175                 180                 185

CGT GAG TCC AAG GCA GAG AAG GTG CTG CAG TTT GAC CCA GGG ACC AAG            867
Arg Glu Ser Lys Ala Glu Lys Val Leu Gln Phe Asp Pro Gly Thr Lys
             190                 195                 200

AAC GTG ACG GCC CTG CTG ATG GAG GCG AAA GAG CTG GAG GCC CGG GTC            915
Asn Val Thr Ala Leu Leu Met Glu Ala Lys Glu Leu Glu Ala Arg Val
         205                 210                 215

ATC ATC CTT TCT GCC AGC GAG GAC GAT GCT GCC ACT GTA TAC CGC GCA            963
Ile Ile Leu Ser Ala Ser Glu Asp Asp Ala Ala Thr Val Tyr Arg Ala
     220                 225                 230

GCC GCG ATG CTG AAC ATG ACG GGC AAC ACC AAC ATC TGG AAG ACC GGG           1011
Ala Ala Met Leu Asn Met Thr Gly Asn Thr Asn Ile Trp Lys Thr Gly
235                 240                 245                 250

CCG CTC TTC AAG AGA GTG CTG ATG TCT TCC AAG TAT GCG GAT GGG GTG           1059
```

|  |  |  |  |  |  |  |  |  |  |  |  |  |  |  |  |
|---|---|---|---|---|---|---|---|---|---|---|---|---|---|---|---|
| Pro | Leu | Phe | Lys | Arg 255 | Val | Leu | Met | Ser 260 | Ser | Lys | Tyr | Ala | Asp 265 | Gly | Val |

| ACT | GGT | CGC | GTG | GAG | TTC | AAT | GAG | GAT | GGG | GAC | CGG | AAG | TTC | GCC | AAC | 1107 |
|---|---|---|---|---|---|---|---|---|---|---|---|---|---|---|---|---|
| Thr | Gly | Arg | Val 270 | Glu | Phe | Asn | Glu 275 | Asp | Gly | Asp | Arg | Lys 280 | Phe | Ala | Asn | |

| TAC | AGC | ATC | ATG | AAC | CTG | CAG | AAC | CGC | AAG | CTG | GTG | CAA | GTG | GGC | ATC | 1155 |
|---|---|---|---|---|---|---|---|---|---|---|---|---|---|---|---|---|
| Tyr | Ser | Ile 285 | Met | Asn | Leu | Gln | Asn 290 | Arg | Lys | Leu | Val | Gln 295 | Val | Gly | Ile | |

| TAC | AAT | GGC | ACC | CAC | GTC | ATC | CCT | AAT | GAC | AGG | AAG | ATC | ATC | TGG | CCA | 1203 |
|---|---|---|---|---|---|---|---|---|---|---|---|---|---|---|---|---|
| Tyr | Asn | Gly 300 | Thr | His | Val | Ile | Pro 305 | Asn | Asp | Arg | Lys | Ile 310 | Ile | Trp | Pro | |

| GGC | GGA | GAG | ACA | GAG | AAG | CCT | CGA | GGG | TAC | CAG | ATG | TCC | ACC | AGA | CTG | 1251 |
|---|---|---|---|---|---|---|---|---|---|---|---|---|---|---|---|---|
| Gly 315 | Gly | Glu | Thr | Glu | Lys 320 | Pro | Arg | Gly | Tyr | Gln 325 | Met | Ser | Thr | Arg | Leu 330 | |

| AAG | ATT | GTG | ACG | ATC | CAC | CAG | GAG | CCC | TTC | GTG | TAC | GTC | AAG | CCC | ACG | 1299 |
|---|---|---|---|---|---|---|---|---|---|---|---|---|---|---|---|---|
| Lys | Ile | Val | Thr | Ile 335 | His | Gln | Glu | Pro | Phe 340 | Val | Tyr | Val | Lys | Pro 345 | Thr | |

| CTG | AGT | GAT | GGG | ACA | TGC | AAG | GAG | GAG | TTC | ACA | GTC | AAC | GGC | GAC | CCA | 1347 |
|---|---|---|---|---|---|---|---|---|---|---|---|---|---|---|---|---|
| Leu | Ser | Asp | Gly 350 | Thr | Cys | Lys | Glu | Glu 355 | Phe | Thr | Val | Asn | Gly 360 | Asp | Pro | |

| GTC | AAG | AAG | GTG | ATC | TGC | ACC | GGG | CCC | AAC | GAC | ACG | TCG | CCG | GGC | AGC | 1395 |
|---|---|---|---|---|---|---|---|---|---|---|---|---|---|---|---|---|
| Val | Lys | Lys 365 | Val | Ile | Cys | Thr | Gly 370 | Pro | Asn | Asp | Thr | Ser 375 | Pro | Gly | Ser | |

| CCC | CGC | CAC | ACG | GTG | CCT | CAG | TGT | TGC | TAC | GGC | TTT | TGC | ATC | GAC | CTG | 1443 |
|---|---|---|---|---|---|---|---|---|---|---|---|---|---|---|---|---|
| Pro | Arg 380 | His | Thr | Val | Pro | Gln 385 | Cys | Cys | Tyr | Gly | Phe 390 | Cys | Ile | Asp | Leu | |

| CTC | ATC | AAG | CTG | GCA | CGG | ACC | ATG | AAC | TTC | ACC | TAC | GAG | GTG | CAC | CTG | 1491 |
|---|---|---|---|---|---|---|---|---|---|---|---|---|---|---|---|---|
| Leu 395 | Ile | Lys | Leu | Ala | Arg 400 | Thr | Met | Asn | Phe | Thr 405 | Tyr | Glu | Val | His | Leu 410 | |

| GTG | GCA | GAT | GGC | AAG | TTC | GGC | ACA | CAG | GAG | CGG | GTG | AAC | AAC | AGC | AAC | 1539 |
|---|---|---|---|---|---|---|---|---|---|---|---|---|---|---|---|---|
| Val | Ala | Asp | Gly | Lys 415 | Phe | Gly | Thr | Gln | Glu 420 | Arg | Val | Asn | Asn | Ser 425 | Asn | |

| AAG | AAG | GAG | TGG | AAT | GGG | ATG | ATG | GGC | GAG | CTG | CTC | AGC | GGG | CAG | GCA | 1587 |
|---|---|---|---|---|---|---|---|---|---|---|---|---|---|---|---|---|
| Lys | Lys | Glu | Trp 430 | Asn | Gly | Met | Met | Gly 435 | Glu | Leu | Leu | Ser | Gly 440 | Gln | Ala | |

| GAC | ATG | ATC | GTG | GCG | CCG | CTA | ACC | ATA | AAC | AAC | GAG | CGC | GCG | CAG | TAC | 1635 |
|---|---|---|---|---|---|---|---|---|---|---|---|---|---|---|---|---|
| Asp | Met | Ile 445 | Val | Ala | Pro | Leu | Thr 450 | Ile | Asn | Asn | Glu | Arg 455 | Ala | Gln | Tyr | |

| ATC | GAG | TTT | TCC | AAG | CCC | TTC | AAG | TAC | CAG | GGC | CTG | ACT | ATT | CTG | GTC | 1683 |
|---|---|---|---|---|---|---|---|---|---|---|---|---|---|---|---|---|
| Ile | Glu 460 | Phe | Ser | Lys | Pro | Phe 465 | Lys | Tyr | Gln | Gly | Leu 470 | Thr | Ile | Leu | Val | |

| AAG | AAG | GAG | ATT | CCC | CGG | AGC | ACG | CTG | GAC | TCG | TTC | ATG | CAG | CCG | TTC | 1731 |
|---|---|---|---|---|---|---|---|---|---|---|---|---|---|---|---|---|
| Lys 475 | Lys | Glu | Ile | Pro | Arg 480 | Ser | Thr | Leu | Asp | Ser 485 | Phe | Met | Gln | Pro | Phe 490 | |

| CAG | AGC | ACA | CTG | TGG | CTG | CTG | GTG | GGG | CTG | TCG | GTG | CAC | GTG | GTG | GCC | 1779 |
|---|---|---|---|---|---|---|---|---|---|---|---|---|---|---|---|---|
| Gln | Ser | Thr | Leu | Trp 495 | Leu | Leu | Val | Gly | Leu 500 | Ser | Val | His | Val | Val 505 | Ala | |

| GTG | ATG | CTG | TAC | CTG | CTG | GAC | CGC | TTC | AGC | CCC | TTC | GGC | CGG | TTC | AAG | 1827 |
|---|---|---|---|---|---|---|---|---|---|---|---|---|---|---|---|---|
| Val | Met | Leu | Tyr 510 | Leu | Leu | Asp | Arg | Phe 515 | Ser | Pro | Phe | Gly | Arg 520 | Phe | Lys | |

| GTG | AAC | AGC | GAG | GAG | GAG | GAG | GAG | GAC | GCA | CTG | ACC | CTG | TCC | TCG | GCC | 1875 |
|---|---|---|---|---|---|---|---|---|---|---|---|---|---|---|---|---|
| Val | Asn | Ser 525 | Glu | Glu | Glu | Glu | Glu 530 | Asp | Ala | Leu | Thr | Leu 535 | Ser | Ser | Ala | |

| ATG | TGG | TTC | TCC | TGG | GGC | GTC | CTG | CTC | AAC | TCC | GGC | ATC | GGG | GAA | GGC | 1923 |
|---|---|---|---|---|---|---|---|---|---|---|---|---|---|---|---|---|
| Met | Trp | Phe | Ser 540 | Trp | Gly | Val | Leu | Leu 545 | Asn | Ser | Gly | Ile | Gly 550 | Glu | Gly | |

| GCC | CCC | AGA | AGC | TTC | TCA | GCG | CGC | ATC | CTG | GGC | ATG | GTG | TGG | GCC | GGC | 1971 |
|---|---|---|---|---|---|---|---|---|---|---|---|---|---|---|---|---|
| Ala Pro 555 | Arg | Ser | Phe | Ser 560 | Ala | Arg | Ile | Leu | Gly 565 | Met | Val | Trp | Ala | Gly 570 | | |

| TTT | GCC | ATG | ATC | ATC | GTG | GCC | TCC | TAC | ACC | GCC | AAC | CTG | GCG | GCC | TTC | 2019 |

|     |     |     |     |     |     |     |     |     |     |     |     |     |     |     |     |
| --- | --- | --- | --- | --- | --- | --- | --- | --- | --- | --- | --- | --- | --- | --- | --- |
| Phe | Ala | Met | Ile | Ile | Val | Ala | Ser | Tyr | Thr | Ala | Asn | Leu | Ala | Ala | Phe |
|     |     |     |     | 575 |     |     |     | 580 |     |     |     |     | 585 |     |     |

| CTG | GTG | CTG | GAC | CGG | CCG | GAG | GAG | CGC | ATC | ACG | GGC | ATC | AAC | GAC | CCT | 2067 |
| --- | --- | --- | --- | --- | --- | --- | --- | --- | --- | --- | --- | --- | --- | --- | --- | --- |
| Leu | Val | Leu | Asp | Arg | Pro | Glu | Glu | Arg | Ile | Thr | Gly | Ile | Asn | Asp | Pro |     |
|     |     |     |     | 590 |     |     |     | 595 |     |     |     |     | 600 |     |     |     |

| CGG | CTG | AGG | AAC | CCC | TCG | GAC | AAG | TTT | ATC | TAC | GCC | ACG | GTG | AAG | CAG | 2115 |
| Arg | Leu | Arg | Asn | Pro | Ser | Asp | Lys | Phe | Ile | Tyr | Ala | Thr | Val | Lys | Gln |     |
|     |     | 605 |     |     |     |     | 610 |     |     |     |     | 615 |     |     |     |     |

| AGC | TCC | GTG | GAT | ATC | TAC | TTC | CGG | CGC | CAG | GTG | GAG | CTG | AGC | ACC | ATG | 2163 |
| Ser | Ser | Val | Asp | Ile | Tyr | Phe | Arg | Arg | Gln | Val | Glu | Leu | Ser | Thr | Met |     |
|     | 620 |     |     |     |     | 625 |     |     |     |     | 630 |     |     |     |     |     |

| TAC | CGG | CAT | ATG | GAG | AAG | CAC | AAC | TAC | GAG | AGT | GCG | GCG | GAG | GCC | ATC | 2211 |
| Tyr | Arg | His | Met | Glu | Lys | His | Asn | Tyr | Glu | Ser | Ala | Ala | Glu | Ala | Ile |     |
| 635 |     |     |     |     | 640 |     |     |     |     | 645 |     |     |     |     | 650 |     |

| CAG | GCC | GTG | AGA | GAC | AAC | AAG | CTG | CAT | GCC | TTC | ATC | TGG | GAC | TCG | GCG | 2259 |
| Gln | Ala | Val | Arg | Asp | Asn | Lys | Leu | His | Ala | Phe | Ile | Trp | Asp | Ser | Ala |     |
|     |     |     |     | 655 |     |     |     | 660 |     |     |     |     | 665 |     |     |     |

| GTG | CTG | GAG | TTC | GAG | GCC | TCG | CAG | AAG | TGC | GAC | CTG | GTG | ACG | ACT | GGA | 2307 |
| Val | Leu | Glu | Phe | Glu | Ala | Ser | Gln | Lys | Cys | Asp | Leu | Val | Thr | Thr | Gly |     |
|     |     |     | 670 |     |     |     |     | 675 |     |     |     |     | 680 |     |     |     |

| GAG | CTG | TTT | TTC | CGC | TCG | GGC | TTC | GGC | ATA | GGC | ATG | CGC | AAA | GAC | AGC | 2355 |
| Glu | Leu | Phe | Phe | Arg | Ser | Gly | Phe | Gly | Ile | Gly | Met | Arg | Lys | Asp | Ser |     |
|     |     | 685 |     |     |     |     | 690 |     |     |     |     | 695 |     |     |     |     |

| CCC | TGG | AAG | CAG | AAC | GTC | TCC | CTG | TCC | ATC | CTC | AAG | TCC | CAC | GAG | AAT | 2403 |
| Pro | Trp | Lys | Gln | Asn | Val | Ser | Leu | Ser | Ile | Leu | Lys | Ser | His | Glu | Asn |     |
|     | 700 |     |     |     |     | 705 |     |     |     |     | 710 |     |     |     |     |     |

| GGC | TTC | ATG | GAA | GAC | CTG | GAC | AAG | ACG | TGG | GTT | CGG | TAT | CAG | GAA | TGT | 2451 |
| Gly | Phe | Met | Glu | Asp | Leu | Asp | Lys | Thr | Trp | Val | Arg | Tyr | Gln | Glu | Cys |     |
| 715 |     |     |     |     | 720 |     |     |     |     | 725 |     |     |     |     | 730 |     |

| GAC | TCG | CGC | AGC | AAC | GCC | CCT | GCG | ACC | CTT | ACT | TTT | GAG | AAC | ATG | GCC | 2499 |
| Asp | Ser | Arg | Ser | Asn | Ala | Pro | Ala | Thr | Leu | Thr | Phe | Glu | Asn | Met | Ala |     |
|     |     |     |     | 735 |     |     |     | 740 |     |     |     |     | 745 |     |     |     |

| GGG | GTC | TTC | ATG | CTG | GTA | GCT | GGG | GGC | ATC | GTG | GCC | GGG | ATC | TTC | CTG | 2547 |
| Gly | Val | Phe | Met | Leu | Val | Ala | Gly | Gly | Ile | Val | Ala | Gly | Ile | Phe | Leu |     |
|     |     |     | 750 |     |     |     |     | 755 |     |     |     |     | 760 |     |     |     |

| ATT | TTC | ATC | GAG | ATT | GCC | TAC | AAG | CGG | CAC | AAG | GAT | GCT | CGC | CGG | AAG | 2595 |
| Ile | Phe | Ile | Glu | Ile | Ala | Tyr | Lys | Arg | His | Lys | Asp | Ala | Arg | Arg | Lys |     |
|     |     | 765 |     |     |     |     | 770 |     |     |     |     | 775 |     |     |     |     |

| CAG | ATG | CAG | CTG | GCC | TTT | GCC | GCC | GTT | AAC | GTG | TGG | CGG | AAG | AAC | CTG | 2643 |
| Gln | Met | Gln | Leu | Ala | Phe | Ala | Ala | Val | Asn | Val | Trp | Arg | Lys | Asn | Leu |     |
|     | 780 |     |     |     |     | 785 |     |     |     |     | 790 |     |     |     |     |     |

| CAG | GAT | AGA | AAG | AGT | GGT | AGA | GCA | GAG | CCT | GAC | CCT | AAA | AAG | AAA | GCC | 2691 |
| Gln | Asp | Arg | Lys | Ser | Gly | Arg | Ala | Glu | Pro | Asp | Pro | Lys | Lys | Lys | Ala |     |
| 795 |     |     |     | 800 |     |     |     | 805 |     |     |     |     |     | 810 |     |     |

| ACA | TTT | AGG | GCT | ATC | ACC | TCC | ACC | CTG | GCT | TCC | AGC | TTC | AAG | AGG | CGT | 2739 |
| Thr | Phe | Arg | Ala | Ile | Thr | Ser | Thr | Leu | Ala | Ser | Ser | Phe | Lys | Arg | Arg |     |
|     |     |     |     | 815 |     |     |     | 820 |     |     |     |     | 825 |     |     |     |

| AGG | TCC | TCC | AAA | GAC | ACG | CAG | TAC | CAT | CCC | ACT | GAT | ATC | ACG | GGC | CCG | 2787 |
| Arg | Ser | Ser | Lys | Asp | Thr | Gln | Tyr | His | Pro | Thr | Asp | Ile | Thr | Gly | Pro |     |
|     |     |     | 830 |     |     |     |     | 835 |     |     |     |     | 840 |     |     |     |

| CTC | AAC | CTC | TCA | GAT | CCC | TCG | GTC | AGC | ACC | GTG | GTG | TGAGGCCCCC |     |     |     | 2833 |
| Leu | Asn | Leu | Ser | Asp | Pro | Ser | Val | Ser | Thr | Val | Val |     |     |     |     |     |
|     |     | 845 |     |     |     |     | 850 |     |     |     |     | 855 |     |     |     |     |

| GGAGGCGCCC | ACCTGCCCAG | TTAGCCCGGC | CAAGGACACT | GATGGGTCCT | GCTGCTCGGG | 2893 |
| --- | --- | --- | --- | --- | --- | --- |
| AAGGCCTGAG | GGAAGCCCAC | CCGCCCCAGA | GACTGCCCAC | CCTGGGCCTC | CCGTCCGTCC | 2953 |
| GCCCGCCCAC | CCCGCTGCCT | GGCGGGCAGC | CCCTGCTGGA | CCAAGGTGCG | GACCGGAGCG | 3013 |
| GCTGAGGACG | GGGCAGAGCT | GAGTCGGCTG | GGCAGGGCCG | CAGGGCGCTC | CGGCAGAGGC | 3073 |
| AGGCCCCTGG | GGTCTCTGAG | CAGTGGGGAG | CGGGGGCTAA | CTGCCCCCAG | GCGGAGGGGC | 3133 |

```
TTGGAGCAGA  GACGGCAGCC  CCATCCTTCC  CGCAGCACCA  GCCTGAGCCA  CAGTGGGGCC    3193
CATGGCCCCA  GCTGGCTGGG  TCGCCCCTCC  TCGGGCGCCT  GCGCTCCTCT  GCAGCCTGAG    3253
CTCCACCCTC  CCCTCTTCTT  GCGGCACCGC  CCACCAAACA  CCCCGTCTGC  CCCTTGACGC    3313
CACACGCCGG  GGCTGGCGCT  GCCCTCCCCC  ACGGCCGTCC  CTGACTTCCC  AGCTGGCAGC    3373
GCCTCCCGCC  GCCTCGGGCC  GCCTCCTCCA  GAATCGAGAG  GGCTGAGCCC  CTCCTCTCCT    3433
CGTCCGGCCT  GCAGCACAGA  AGGGGGCCTC  CCCGGGGGTC  CCCGGACGCT  GGCTCGGGAC    3493
TGTCTTCAAC  CCTGCCCTGC  ACCTTGGGCA  CGGGAGAGCG  CCACCCGCCC  GCCCCCGCCC    3553
TCGCTCCGGG  TGCGTGACCG  GCCCGCCACC  TTGTACAGAA  CCAGCACTCC  CAGGGCCCGA    3613
GCGCGTGCCT  TCCCCGTGCG  CAGCCGCGCT  CTGCCCCTCC  GTCCCAGGG   TGCAGGCGCG    3673
CACCGCCCAA  CCCCCACCTC  CCGGTGTATG  CAGTGGTGAT  GCCTAAAGGA  ATGTCACG     3731
```

(2) INFORMATION FOR SEQ ID NO:32:

(i) SEQUENCE CHARACTERISTICS:
      (A) LENGTH: 854 amino acids
      (B) TYPE: amino acid
      (D) TOPOLOGY: linear (ii) MOLECULE TYPE: protein (xi) SEQUENCE DESCRIPTION: SEQ ID NO:32:

```
Met Ser Thr Met Arg Leu Leu Thr Leu Ala Leu Leu Phe Ser Cys Ser
 1               5                  10                  15

Val Ala Arg Ala Ala Cys Asp Pro Lys Ile Val Asn Ile Gly Ala Val
             20                  25                  30

Leu Ser Thr Arg Lys His Glu Gln Met Phe Arg Glu Ala Val Asn Gln
         35                  40                  45

Ala Asn Lys Arg His Gly Ser Trp Lys Ile Gln Leu Asn Ala Thr Ser
     50                  55                  60

Val Thr His Lys Pro Asn Ala Ile Gln Met Ala Leu Ser Val Cys Glu
 65                  70                  75                  80

Asp Leu Ile Ser Ser Gln Val Tyr Ala Ile Leu Val Ser His Pro Pro
                 85                  90                  95

Thr Pro Asn Asp His Phe Thr Pro Thr Pro Val Ser Tyr Thr Ala Gly
            100                 105                 110

Phe Tyr Arg Ile Pro Val Leu Gly Leu Thr Thr Arg Met Ser Ile Tyr
        115                 120                 125

Ser Asp Lys Ser Ile His Leu Ser Phe Leu Arg Thr Val Pro Pro Tyr
    130                 135                 140

Ser His Gln Ser Ser Val Trp Phe Glu Met Met Arg Val Tyr Ser Trp
145                 150                 155                 160

Asn His Ile Ile Leu Leu Val Ser Asp Asp His Glu Gly Arg Ala Ala
                165                 170                 175

Gln Lys Arg Leu Glu Thr Leu Leu Glu Glu Arg Glu Ser Lys Ala Glu
            180                 185                 190

Lys Val Leu Gln Phe Asp Pro Gly Thr Lys Asn Val Thr Ala Leu Leu
        195                 200                 205

Met Glu Ala Lys Glu Leu Glu Ala Arg Val Ile Ile Leu Ser Ala Ser
    210                 215                 220

Glu Asp Asp Ala Ala Thr Val Tyr Arg Ala Ala Met Leu Asn Met
225                 230                 235                 240

Thr Gly Asn Thr Asn Ile Trp Lys Thr Gly Pro Leu Phe Lys Arg Val
                245                 250                 255
```

```
Leu  Met  Ser  Ser  Lys  Tyr  Ala  Asp  Gly  Val  Thr  Gly  Arg  Val  Glu  Phe
               260                 265                      270

Asn  Glu  Asp  Gly  Asp  Arg  Lys  Phe  Ala  Asn  Tyr  Ser  Ile  Met  Asn  Leu
          275                 280                      285

Gln  Asn  Arg  Lys  Leu  Val  Gln  Val  Gly  Ile  Tyr  Asn  Gly  Thr  His  Val
     290                 295                      300

Ile  Pro  Asn  Asp  Arg  Lys  Ile  Ile  Trp  Pro  Gly  Gly  Glu  Thr  Glu  Lys
305                      310                 315                           320

Pro  Arg  Gly  Tyr  Gln  Met  Ser  Thr  Arg  Leu  Lys  Ile  Val  Thr  Ile  His
                    325                 330                           335

Gln  Glu  Pro  Phe  Val  Tyr  Val  Lys  Pro  Thr  Leu  Ser  Asp  Gly  Thr  Cys
               340                 345                      350

Lys  Glu  Glu  Phe  Thr  Val  Asn  Gly  Asp  Pro  Val  Lys  Lys  Val  Ile  Cys
               355                 360                      365

Thr  Gly  Pro  Asn  Asp  Thr  Ser  Pro  Gly  Ser  Pro  Arg  His  Thr  Val  Pro
     370                      375                      380

Gln  Cys  Cys  Tyr  Gly  Phe  Cys  Ile  Asp  Leu  Leu  Ile  Lys  Leu  Ala  Arg
385                      390                 395                           400

Thr  Met  Asn  Phe  Thr  Tyr  Glu  Val  His  Leu  Val  Ala  Asp  Gly  Lys  Phe
               405                 410                      415

Gly  Thr  Gln  Glu  Arg  Val  Asn  Asn  Ser  Asn  Lys  Lys  Glu  Trp  Asn  Gly
               420                 425                      430

Met  Met  Gly  Glu  Leu  Leu  Ser  Gly  Gln  Ala  Asp  Met  Ile  Val  Ala  Pro
               435                 440                      445

Leu  Thr  Ile  Asn  Asn  Glu  Arg  Ala  Gln  Tyr  Ile  Glu  Phe  Ser  Lys  Pro
     450                      455                 460

Phe  Lys  Tyr  Gln  Gly  Leu  Thr  Ile  Leu  Val  Lys  Lys  Glu  Ile  Pro  Arg
465                      470                 475                           480

Ser  Thr  Leu  Asp  Ser  Phe  Met  Gln  Pro  Phe  Gln  Ser  Thr  Leu  Trp  Leu
                    485                 490                      495

Leu  Val  Gly  Leu  Ser  Val  His  Val  Val  Ala  Val  Met  Leu  Tyr  Leu  Leu
               500                 505                      510

Asp  Arg  Phe  Ser  Pro  Phe  Gly  Arg  Phe  Lys  Val  Asn  Ser  Glu  Glu  Glu
          515                 520                      525

Glu  Glu  Asp  Ala  Leu  Thr  Leu  Ser  Ser  Ala  Met  Trp  Phe  Ser  Trp  Gly
     530                 535                      540

Val  Leu  Leu  Asn  Ser  Gly  Ile  Gly  Glu  Gly  Ala  Pro  Arg  Ser  Phe  Ser
545                      550                 555                           560

Ala  Arg  Ile  Leu  Gly  Met  Val  Trp  Ala  Gly  Phe  Ala  Met  Ile  Ile  Val
               565                 570                      575

Ala  Ser  Tyr  Thr  Ala  Asn  Leu  Ala  Ala  Phe  Leu  Val  Leu  Asp  Arg  Pro
               580                 585                      590

Glu  Glu  Arg  Ile  Thr  Gly  Ile  Asn  Asp  Pro  Arg  Leu  Arg  Asn  Pro  Ser
          595                 600                      605

Asp  Lys  Phe  Ile  Tyr  Ala  Thr  Val  Lys  Gln  Ser  Ser  Val  Asp  Ile  Tyr
     610                 615                      620

Phe  Arg  Arg  Gln  Val  Glu  Leu  Ser  Thr  Met  Tyr  Arg  His  Met  Glu  Lys
625                      630                 635                           640

His  Asn  Tyr  Glu  Ser  Ala  Ala  Glu  Ala  Ile  Gln  Ala  Val  Arg  Asp  Asn
               645                 650                      655

Lys  Leu  His  Ala  Phe  Ile  Trp  Asp  Ser  Ala  Val  Leu  Glu  Phe  Glu  Ala
               660                 665                      670

Ser  Gln  Lys  Cys  Asp  Leu  Val  Thr  Thr  Gly  Glu  Leu  Phe  Phe  Arg  Ser
```

|     |     |     |     |     | 675 |     |     |     |     | 680 |     |     |     |     | 685 |     |     |     |
| --- | --- | --- | --- | --- | --- | --- | --- | --- | --- | --- | --- | --- | --- | --- | --- | --- | --- | --- |
| Gly | Phe<br>690 | Gly | Ile | Gly | Met | Arg<br>695 | Lys | Asp | Ser | Pro | Trp<br>700 | Lys | Gln | Asn | Val |
| Ser<br>705 | Leu | Ser | Ile | Leu | Lys<br>710 | Ser | His | Glu | Asn | Gly<br>715 | Phe | Met | Glu | Asp | Leu<br>720 |
| Asp | Lys | Thr | Trp | Val<br>725 | Arg | Tyr | Gln | Glu | Cys<br>730 | Asp | Ser | Arg | Ser | Asn<br>735 | Ala |
| Pro | Ala | Thr | Leu<br>740 | Thr | Phe | Glu | Asn | Met<br>745 | Ala | Gly | Val | Phe | Met<br>750 | Leu | Val |
| Ala | Gly | Gly<br>755 | Ile | Val | Ala | Gly | Ile<br>760 | Phe | Leu | Ile | Phe | Ile<br>765 | Glu | Ile | Ala |
| Tyr | Lys<br>770 | Arg | His | Lys | Asp | Ala<br>775 | Arg | Arg | Lys | Gln | Met<br>780 | Gln | Leu | Ala | Phe |
| Ala<br>785 | Ala | Val | Asn | Val | Trp<br>790 | Arg | Lys | Asn | Leu | Gln<br>795 | Asp | Arg | Lys | Ser | Gly<br>800 |
| Arg | Ala | Glu | Pro | Asp<br>805 | Pro | Lys | Lys | Lys | Ala<br>810 | Thr | Phe | Arg | Ala | Ile<br>815 | Thr |
| Ser | Thr | Leu | Ala<br>820 | Ser | Ser | Phe | Lys | Arg<br>825 | Arg | Arg | Ser | Ser | Lys<br>830 | Asp | Thr |
| Gln | Tyr | His<br>835 | Pro | Thr | Asp | Ile | Thr<br>840 | Gly | Pro | Leu | Asn | Leu<br>845 | Ser | Asp | Pro |
| Ser | Val<br>850 | Ser | Thr | Val | Val |

( 2 ) INFORMATION FOR SEQ ID NO:33:

( i ) SEQUENCE CHARACTERISTICS:
        ( A ) LENGTH: 3007 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 262..2988

( x i ) SEQUENCE DESCRIPTION: SEQ ID NO:33:

```
CAAGCCGGGC  GTTCGGAGCT  GTGCCCGGCC  CCGCTTCAGC  ACCGCGGACA  GCGCCGGCCG        60

CGTGGGGCTG  AGCGCCGAGC  CCCCGCGCAC  GCTTCAGCCC  CCCTTCCCTC  GGCCGACGTC       120

CCGGGACCGC  CGCTCCGGGG  GAGACGTGGC  GTCCGCAGCC  CGCGGGGCCG  GGCGAGCGCA       180

GGACGGCCCG  GAAGCCCCGC  GGGGGATGCG  CCGAGGGCCC  CGCGTTCGCG  CCGCGCAGAG       240

CCAGGCCCGC  GGCCCGAGCC  C  ATG  AGC  ACC  ATG  CGC  CTG  CTG  ACG  CTC  GCC   291
              Met  Ser  Thr  Met  Arg  Leu  Leu  Thr  Leu  Ala
               1                 5                           10

CTG  CTG  TTC  TCC  TGC  TCC  GTC  GCC  CGT  GCC  GCG  TGC  GAC  CCC  AAG  ATC   339
Leu  Leu  Phe  Ser  Cys  Ser  Val  Ala  Arg  Ala  Ala  Cys  Asp  Pro  Lys  Ile
                    15                     20                          25

GTC  AAC  ATT  GGC  GCG  GTG  CTG  AGC  ACG  CGG  AAG  CAC  GAG  CAG  ATG  TTC   387
Val  Asn  Ile  Gly  Ala  Val  Leu  Ser  Thr  Arg  Lys  His  Glu  Gln  Met  Phe
               30                      35                          40

CGC  GAG  GCC  GTG  AAC  CAG  GCC  AAC  AAG  CGG  CAC  GGC  TCC  TGG  AAG  ATT   435
Arg  Glu  Ala  Val  Asn  Gln  Ala  Asn  Lys  Arg  His  Gly  Ser  Trp  Lys  Ile
           45                      50                          55

CAG  CTC  AAT  GCC  ACC  TCC  GTC  ACG  CAC  AAG  CCC  AAC  GCC  ATC  CAG  ATG   483
Gln  Leu  Asn  Ala  Thr  Ser  Val  Thr  His  Lys  Pro  Asn  Ala  Ile  Gln  Met
       60                      65                          70
```

| | | | | | | | | | | | | | | | | |
|---|---|---|---|---|---|---|---|---|---|---|---|---|---|---|---|---|
| GCT | CTG | TCG | GTG | TGC | GAG | GAC | CTC | ATC | TCC | AGC | CAG | GTC | TAC | GCC | ATC | 531 |
| Ala | Leu | Ser | Val | Cys | Glu | Asp | Leu | Ile | Ser | Ser | Gln | Val | Tyr | Ala | Ile | |
| 75 | | | | 80 | | | | | 85 | | | | | | 90 | |
| CTA | GTT | AGC | CAT | CCA | CCT | ACC | CCC | AAC | GAC | CAC | TTC | ACT | CCC | ACC | CCT | 579 |
| Leu | Val | Ser | His | Pro | Pro | Thr | Pro | Asn | Asp | His | Phe | Thr | Pro | Thr | Pro | |
| | | | | 95 | | | | | 100 | | | | | 105 | | |
| GTC | TCC | TAC | ACA | GCC | GGC | TTC | TAC | CGC | ATA | CCC | GTG | CTG | GGG | CTG | ACC | 627 |
| Val | Ser | Tyr | Thr | Ala | Gly | Phe | Tyr | Arg | Ile | Pro | Val | Leu | Gly | Leu | Thr | |
| | | | 110 | | | | | 115 | | | | | 120 | | | |
| ACC | CGC | ATG | TCC | ATC | TAC | TCG | GAC | AAG | AGC | ATC | CAC | CTG | AGC | TTC | CTG | 675 |
| Thr | Arg | Met | Ser | Ile | Tyr | Ser | Asp | Lys | Ser | Ile | His | Leu | Ser | Phe | Leu | |
| | | 125 | | | | | 130 | | | | | 135 | | | | |
| CGC | ACC | GTG | CCG | CCC | TAC | TCC | CAC | CAG | TCC | AGC | GTG | TGG | TTT | GAG | ATG | 723 |
| Arg | Thr | Val | Pro | Pro | Tyr | Ser | His | Gln | Ser | Ser | Val | Trp | Phe | Glu | Met | |
| | 140 | | | | | 145 | | | | | 150 | | | | | |
| ATG | CGT | GTC | TAC | AGC | TGG | AAC | CAC | ATC | ATC | CTG | CTG | GTC | AGC | GAC | GAC | 771 |
| Met | Arg | Val | Tyr | Ser | Trp | Asn | His | Ile | Ile | Leu | Leu | Val | Ser | Asp | Asp | |
| 155 | | | | | 160 | | | | | 165 | | | | | 170 | |
| CAC | GAG | GGC | CGG | GCG | GCT | CAG | AAA | CGC | CTG | GAG | ACG | CTG | CTG | GAG | GAG | 819 |
| His | Glu | Gly | Arg | Ala | Ala | Gln | Lys | Arg | Leu | Glu | Thr | Leu | Leu | Glu | Glu | |
| | | | | 175 | | | | | 180 | | | | | 185 | | |
| CGT | GAG | TCC | AAG | GCA | GAG | AAG | GTG | CTG | CAG | TTT | GAC | CCA | GGG | ACC | AAG | 867 |
| Arg | Glu | Ser | Lys | Ala | Glu | Lys | Val | Leu | Gln | Phe | Asp | Pro | Gly | Thr | Lys | |
| | | | 190 | | | | | 195 | | | | | 200 | | | |
| AAC | GTG | ACG | GCC | CTG | CTG | ATG | GAG | GCG | AAA | GAG | CTG | GAG | GCC | CGG | GTC | 915 |
| Asn | Val | Thr | Ala | Leu | Leu | Met | Glu | Ala | Lys | Glu | Leu | Glu | Ala | Arg | Val | |
| | | 205 | | | | | 210 | | | | | 215 | | | | |
| ATC | ATC | CTT | TCT | GCC | AGC | GAG | GAC | GAT | GCT | GCC | ACT | GTA | TAC | CGC | GCA | 963 |
| Ile | Ile | Leu | Ser | Ala | Ser | Glu | Asp | Asp | Ala | Ala | Thr | Val | Tyr | Arg | Ala | |
| | | 220 | | | | | 225 | | | | | 230 | | | | |
| GCC | GCG | ATG | CTG | AAC | ATG | ACG | GGC | AAC | ACC | AAC | ATC | TGG | AAG | ACC | GGG | 1011 |
| Ala | Ala | Met | Leu | Asn | Met | Thr | Gly | Asn | Thr | Asn | Ile | Trp | Lys | Thr | Gly | |
| 235 | | | | | 240 | | | | | 245 | | | | | 250 | |
| CCG | CTC | TTC | AAG | AGA | GTG | CTG | ATG | TCT | TCC | AAG | TAT | GCG | GAT | GGG | GTG | 1059 |
| Pro | Leu | Phe | Lys | Arg | Val | Leu | Met | Ser | Ser | Lys | Tyr | Ala | Asp | Gly | Val | |
| | | | | 255 | | | | | 260 | | | | | 265 | | |
| ACT | GGT | CGC | GTG | GAG | TTC | AAT | GAG | GAT | GGG | GAC | CGG | AAG | TTC | GCC | AAC | 1107 |
| Thr | Gly | Arg | Val | Glu | Phe | Asn | Glu | Asp | Gly | Asp | Arg | Lys | Phe | Ala | Asn | |
| | | | 270 | | | | | 275 | | | | | 280 | | | |
| TAC | AGC | ATC | ATG | AAC | CTG | CAG | AAC | CGC | AAG | CTG | GTG | CAA | GTG | GGC | ATC | 1155 |
| Tyr | Ser | Ile | Met | Asn | Leu | Gln | Asn | Arg | Lys | Leu | Val | Gln | Val | Gly | Ile | |
| | | 285 | | | | | 290 | | | | | 295 | | | | |
| TAC | AAT | GGC | ACC | CAC | GTC | ATC | CCT | AAT | GAC | AGG | AAG | ATC | ATC | TGG | CCA | 1203 |
| Tyr | Asn | Gly | Thr | His | Val | Ile | Pro | Asn | Asp | Arg | Lys | Ile | Ile | Trp | Pro | |
| | | 300 | | | | | 305 | | | | | 310 | | | | |
| GGC | GGA | GAG | ACA | GAG | AAG | CCT | CGA | GGG | TAC | CAG | ATG | TCC | ACC | AGA | CTG | 1251 |
| Gly | Gly | Glu | Thr | Glu | Lys | Pro | Arg | Gly | Tyr | Gln | Met | Ser | Thr | Arg | Leu | |
| 315 | | | | | 320 | | | | | | 325 | | | | 330 | |
| AAG | ATT | GTG | ACG | ATC | CAC | CAG | GAG | CCC | TTC | GTG | TAC | GTC | AAG | CCC | ACG | 1299 |
| Lys | Ile | Val | Thr | Ile | His | Gln | Glu | Pro | Phe | Val | Tyr | Val | Lys | Pro | Thr | |
| | | | | 335 | | | | | 340 | | | | | 345 | | |
| CTG | AGT | GAT | GGG | ACA | TGC | AAG | GAG | GAG | TTC | ACA | GTC | AAC | GGC | GAC | CCA | 1347 |
| Leu | Ser | Asp | Gly | Thr | Cys | Lys | Glu | Glu | Phe | Thr | Val | Asn | Gly | Asp | Pro | |
| | | | 350 | | | | | 355 | | | | | 360 | | | |
| GTC | AAG | AAG | GTG | ATC | TGC | ACC | GGG | CCC | AAC | GAC | ACG | TCG | CCG | GGC | AGC | 1395 |
| Val | Lys | Lys | Val | Ile | Cys | Thr | Gly | Pro | Asn | Asp | Thr | Ser | Pro | Gly | Ser | |
| | | 365 | | | | | 370 | | | | | 375 | | | | |
| CCC | CGC | CAC | ACG | GTG | CCT | CAG | TGT | TGC | TAC | GGC | TTT | TGC | ATC | GAC | CTG | 1443 |
| Pro | Arg | His | Thr | Val | Pro | Gln | Cys | Cys | Tyr | Gly | Phe | Cys | Ile | Asp | Leu | |
| | 380 | | | | | 385 | | | | | 390 | | | | | |

| | | | | | | | | | | | | | | | | |
|---|---|---|---|---|---|---|---|---|---|---|---|---|---|---|---|---|
| CTC | ATC | AAG | CTG | GCA | CGG | ACC | ATG | AAC | TTC | ACC | TAC | GAG | GTG | CAC | CTG | 1491 |
| Leu | Ile | Lys | Leu | Ala | Arg | Thr | Met | Asn | Phe | Thr | Tyr | Glu | Val | His | Leu | |
| 395 | | | | 400 | | | | | 405 | | | | | | 410 | |
| GTG | GCA | GAT | GGC | AAG | TTC | GGC | ACA | CAG | GAG | CGG | GTG | AAC | AAC | AGC | AAC | 1539 |
| Val | Ala | Asp | Gly | Lys | Phe | Gly | Thr | Gln | Glu | Arg | Val | Asn | Asn | Ser | Asn | |
| | | | | 415 | | | | 420 | | | | | | 425 | | |
| AAG | AAG | GAG | TGG | AAT | GGG | ATG | ATG | GGC | GAG | CTG | CTC | AGC | GGG | CAG | GCA | 1587 |
| Lys | Lys | Glu | Trp | Asn | Gly | Met | Met | Gly | Glu | Leu | Leu | Ser | Gly | Gln | Ala | |
| | | | 430 | | | | | 435 | | | | | 440 | | | |
| GAC | ATG | ATC | GTG | GCG | CCG | CTA | ACC | ATA | AAC | AAC | GAG | CGC | GCG | CAG | TAC | 1635 |
| Asp | Met | Ile | Val | Ala | Pro | Leu | Thr | Ile | Asn | Asn | Glu | Arg | Ala | Gln | Tyr | |
| | | 445 | | | | | 450 | | | | | 455 | | | | |
| ATC | GAG | TTT | TCC | AAG | CCC | TTC | AAG | TAC | CAG | GGC | CTG | ACT | ATT | CTG | GTC | 1683 |
| Ile | Glu | Phe | Ser | Lys | Pro | Phe | Lys | Tyr | Gln | Gly | Leu | Thr | Ile | Leu | Val | |
| 460 | | | | | 465 | | | | | 470 | | | | | | |
| AAG | AAG | GAG | ATT | CCC | CGG | AGC | ACG | CTG | GAC | TCG | TTC | ATG | CAG | CCG | TTC | 1731 |
| Lys | Lys | Glu | Ile | Pro | Arg | Ser | Thr | Leu | Asp | Ser | Phe | Met | Gln | Pro | Phe | |
| 475 | | | | | 480 | | | | 485 | | | | | | 490 | |
| CAG | AGC | ACA | CTG | TGG | CTG | CTG | GTG | GGG | CTG | TCG | GTG | CAC | GTG | GTG | GCC | 1779 |
| Gln | Ser | Thr | Leu | Trp | Leu | Leu | Val | Gly | Leu | Ser | Val | His | Val | Val | Ala | |
| | | | | 495 | | | | | 500 | | | | | 505 | | |
| GTG | ATG | CTG | TAC | CTG | CTG | GAC | CGC | TTC | AGC | CCC | TTC | GGC | CGG | TTC | AAG | 1827 |
| Val | Met | Leu | Tyr | Leu | Leu | Asp | Arg | Phe | Ser | Pro | Phe | Gly | Arg | Phe | Lys | |
| | | | 510 | | | | | 515 | | | | | 520 | | | |
| GTG | AAC | AGC | GAG | GAG | GAG | GAG | GAG | GAC | GCA | CTG | ACC | CTG | TCC | TCG | GCC | 1875 |
| Val | Asn | Ser | Glu | Glu | Glu | Glu | Glu | Asp | Ala | Leu | Thr | Leu | Ser | Ser | Ala | |
| | | 525 | | | | | 530 | | | | | 535 | | | | |
| ATG | TGG | TTC | TCC | TGG | GGC | GTC | CTG | CTC | AAC | TCC | GGC | ATC | GGG | GAA | GGC | 1923 |
| Met | Trp | Phe | Ser | Trp | Gly | Val | Leu | Leu | Asn | Ser | Gly | Ile | Gly | Glu | Gly | |
| | 540 | | | | | 545 | | | | | 550 | | | | | |
| GCC | CCC | AGA | AGC | TTC | TCA | GCG | CGC | ATC | CTG | GGC | ATG | GTG | TGG | GCC | GGC | 1971 |
| Ala | Pro | Arg | Ser | Phe | Ser | Ala | Arg | Ile | Leu | Gly | Met | Val | Trp | Ala | Gly | |
| 555 | | | | | 560 | | | | | 565 | | | | | 570 | |
| TTT | GCC | ATG | ATC | ATC | GTG | GCC | TCC | TAC | ACC | GCC | AAC | CTG | GCG | GCC | TTC | 2019 |
| Phe | Ala | Met | Ile | Ile | Val | Ala | Ser | Tyr | Thr | Ala | Asn | Leu | Ala | Ala | Phe | |
| | | | | 575 | | | | | 580 | | | | | 585 | | |
| CTG | GTG | CTG | GAC | CGG | CCG | GAG | GAG | CGC | ATC | ACG | GGC | ATC | AAC | GAC | CCT | 2067 |
| Leu | Val | Leu | Asp | Arg | Pro | Glu | Glu | Arg | Ile | Thr | Gly | Ile | Asn | Asp | Pro | |
| | | | 590 | | | | | 595 | | | | | 600 | | | |
| CGG | CTG | AGG | AAC | CCC | TCG | GAC | AAG | TTT | ATC | TAC | GCC | ACG | GTG | AAG | CAG | 2115 |
| Arg | Leu | Arg | Asn | Pro | Ser | Asp | Lys | Phe | Ile | Tyr | Ala | Thr | Val | Lys | Gln | |
| | | 605 | | | | | 610 | | | | | 615 | | | | |
| AGC | TCC | GTG | GAT | ATC | TAC | TTC | CGG | CGC | CAG | GTG | GAG | CTG | AGC | ACC | ATG | 2163 |
| Ser | Ser | Val | Asp | Ile | Tyr | Phe | Arg | Arg | Gln | Val | Glu | Leu | Ser | Thr | Met | |
| | | 620 | | | | | 625 | | | | | 630 | | | | |
| TAC | CGG | CAT | ATG | GAG | AAG | CAC | AAC | TAC | GAG | AGT | GCG | GCG | GAG | GCC | ATC | 2211 |
| Tyr | Arg | His | Met | Glu | Lys | His | Asn | Tyr | Glu | Ser | Ala | Ala | Glu | Ala | Ile | |
| 635 | | | | | 640 | | | | | 645 | | | | | 650 | |
| CAG | GCC | GTG | AGA | GAC | AAC | AAG | CTG | CAT | GCC | TTC | ATC | TGG | GAC | TCG | GCG | 2259 |
| Gln | Ala | Val | Arg | Asp | Asn | Lys | Leu | His | Ala | Phe | Ile | Trp | Asp | Ser | Ala | |
| | | | | 655 | | | | | 660 | | | | | 665 | | |
| GTG | CTG | GAG | TTC | GAG | GCC | TCG | CAG | AAG | TGC | GAC | CTG | GTG | ACG | ACT | GGA | 2307 |
| Val | Leu | Glu | Phe | Glu | Ala | Ser | Gln | Lys | Cys | Asp | Leu | Val | Thr | Thr | Gly | |
| | | | 670 | | | | | 675 | | | | | 680 | | | |
| GAG | CTG | TTT | TTC | CGC | TCG | GGC | TTC | GGC | ATA | GGC | ATG | CGC | AAA | GAC | AGC | 2355 |
| Glu | Leu | Phe | Phe | Arg | Ser | Gly | Phe | Gly | Ile | Gly | Met | Arg | Lys | Asp | Ser | |
| | | 685 | | | | | 690 | | | | | 695 | | | | |
| CCC | TGG | AAG | CAG | AAC | GTC | TCC | CTG | TCC | ATC | CTC | AAG | TCC | CAC | GAG | AAT | 2403 |
| Pro | Trp | Lys | Gln | Asn | Val | Ser | Leu | Ser | Ile | Leu | Lys | Ser | His | Glu | Asn | |
| | 700 | | | | | 705 | | | | | 710 | | | | | |

| | | | | | | | | | | | | | | | | |
|---|---|---|---|---|---|---|---|---|---|---|---|---|---|---|---|---|
| GGC | TTC | ATG | GAA | GAC | CTG | GAC | AAG | ACG | TGG | GTT | CGG | TAT | CAG | GAA | TGT | 2451 |
| Gly | Phe | Met | Glu | Asp | Leu | Asp | Lys | Thr | Trp | Val | Arg | Tyr | Gln | Glu | Cys | |
| 715 | | | | 720 | | | | | 725 | | | | | | 730 | |
| GAC | TCG | CGC | AGC | AAC | GCC | CCT | GCG | ACC | CTT | ACT | TTT | GAG | AAC | ATG | GCC | 2499 |
| Asp | Ser | Arg | Ser | Asn | Ala | Pro | Ala | Thr | Leu | Thr | Phe | Glu | Asn | Met | Ala | |
| | | | | 735 | | | | 740 | | | | | | 745 | | |
| GGG | GTC | TTC | ATG | CTG | GTA | GCT | GGG | GGC | ATC | GTG | GCC | GGG | ATC | TTC | CTG | 2547 |
| Gly | Val | Phe | Met | Leu | Val | Ala | Gly | Gly | Ile | Val | Ala | Gly | Ile | Phe | Leu | |
| | | | 750 | | | | | 755 | | | | | 760 | | | |
| ATT | TTC | ATC | GAG | ATT | GCC | TAC | AAG | CGG | CAC | AAG | GAT | GCT | CGC | CGG | AAG | 2595 |
| Ile | Phe | Ile | Glu | Ile | Ala | Tyr | Lys | Arg | His | Lys | Asp | Ala | Arg | Arg | Lys | |
| | | 765 | | | | | 770 | | | | | 775 | | | | |
| CAG | ATG | CAG | CTG | GCC | TTT | GCC | GCC | GTT | AAC | GTG | TGG | CGG | AAG | AAC | CTG | 2643 |
| Gln | Met | Gln | Leu | Ala | Phe | Ala | Ala | Val | Asn | Val | Trp | Arg | Lys | Asn | Leu | |
| | 780 | | | | | 785 | | | | | 790 | | | | | |
| CAG | GAT | AGA | AAG | AGT | GGT | AGA | GCA | GAG | CCT | GAC | CCT | AAA | AAG | AAA | GCC | 2691 |
| Gln | Asp | Arg | Lys | Ser | Gly | Arg | Ala | Glu | Pro | Asp | Pro | Lys | Lys | Lys | Ala | |
| 795 | | | | | 800 | | | | | 805 | | | | | 810 | |
| ACA | TTT | AGG | GCT | ATC | ACC | TCC | ACC | CTG | GCT | TCC | AGC | TTC | AAG | AGG | CGT | 2739 |
| Thr | Phe | Arg | Ala | Ile | Thr | Ser | Thr | Leu | Ala | Ser | Ser | Phe | Lys | Arg | Arg | |
| | | | | 815 | | | | | 820 | | | | | 825 | | |
| AGG | TCC | TCC | AAA | GAC | ACG | CTG | GCT | CGG | GAC | TGT | CTT | CAA | CCC | TGC | CCT | 2787 |
| Arg | Ser | Ser | Lys | Asp | Thr | Leu | Ala | Arg | Asp | Cys | Leu | Gln | Pro | Cys | Pro | |
| | | | 830 | | | | | 835 | | | | | 840 | | | |
| GCA | CCT | TGG | GCA | CGG | GAG | AGC | GCC | ACC | CGC | CCG | CCG | CCC | TCG | CTC | | 2835 |
| Ala | Pro | Trp | Ala | Arg | Glu | Ser | Ala | Thr | Arg | Pro | Pro | Pro | Ser | Leu | | |
| | | 845 | | | | | 850 | | | | | 855 | | | | |
| CGG | GTG | CGT | GAC | CGG | CCC | GCC | ACC | TTG | TAC | AGA | ACC | AGC | ACT | CCC | AGG | 2883 |
| Arg | Val | Arg | Asp | Arg | Pro | Ala | Thr | Leu | Tyr | Arg | Thr | Ser | Thr | Pro | Arg | |
| | | | 860 | | | | 865 | | | | | 870 | | | | |
| GCC | CGA | GCG | CGT | GCC | TTC | CCC | GTG | CGC | AGC | CGC | GCT | CTG | CCC | CTC | CGT | 2931 |
| Ala | Arg | Ala | Arg | Ala | Phe | Pro | Val | Arg | Ser | Arg | Ala | Leu | Pro | Leu | Arg | |
| 875 | | | | | 880 | | | | | 885 | | | | | 890 | |
| CCC | CAG | GGT | GCA | GGC | GCG | CAC | CGC | CCA | ACC | CCC | ACC | TCC | CGG | TGT | ATG | 2979 |
| Pro | Gln | Gly | Ala | Gly | Ala | His | Arg | Pro | Thr | Pro | Thr | Ser | Arg | Cys | Met | |
| | | | | 895 | | | | | 900 | | | | | 905 | | |
| CAG | TGG | TGATGCCTAA | | AGGAATGTCA | | CG | | | | | | | | | | 3007 |
| Gln | Trp | | | | | | | | | | | | | | | |

( 2 ) INFORMATION FOR SEQ ID NO:34:

( i ) SEQUENCE CHARACTERISTICS:
        ( A ) LENGTH: 908 amino acids
        ( B ) TYPE: amino acid
        ( D ) TOPOLOGY: linear ( i i ) MOLECULE TYPE: protein ( x i ) SEQUENCE DESCRIPTION: SEQ ID NO:34:

| | | | | | | | | | | | | | | |
|---|---|---|---|---|---|---|---|---|---|---|---|---|---|---|
| Met | Ser | Thr | Met | Arg | Leu | Leu | Thr | Leu | Ala | Leu | Leu | Phe | Ser | Cys | Ser |
| 1 | | | | 5 | | | | | 10 | | | | | 15 | |
| Val | Ala | Arg | Ala | Ala | Cys | Asp | Pro | Lys | Ile | Val | Asn | Ile | Gly | Ala | Val |
| | | | 20 | | | | | 25 | | | | | 30 | | |
| Leu | Ser | Thr | Arg | Lys | His | Glu | Gln | Met | Phe | Arg | Glu | Ala | Val | Asn | Gln |
| | | | 35 | | | | 40 | | | | | 45 | | | |
| Ala | Asn | Lys | Arg | His | Gly | Ser | Trp | Lys | Ile | Gln | Leu | Asn | Ala | Thr | Ser |
| | | 50 | | | | | 55 | | | | | 60 | | | |
| Val | Thr | His | Lys | Pro | Asn | Ala | Ile | Gln | Met | Ala | Leu | Ser | Val | Cys | Glu |
| 65 | | | | | 70 | | | | | 75 | | | | | 80 |
| Asp | Leu | Ile | Ser | Ser | Gln | Val | Tyr | Ala | Ile | Leu | Val | Ser | His | Pro | Pro |
| | | | | 85 | | | | | 90 | | | | | 95 | |

-continued

```
Thr  Pro  Asn  Asp  His  Phe  Thr  Pro  Thr  Pro  Val  Ser  Tyr  Thr  Ala  Gly
               100                      105                      110

Phe  Tyr  Arg  Ile  Pro  Val  Leu  Gly  Leu  Thr  Thr  Arg  Met  Ser  Ile  Tyr
               115                      120                      125

Ser  Asp  Lys  Ser  Ile  His  Leu  Ser  Phe  Leu  Arg  Thr  Val  Pro  Pro  Tyr
               130                      135                      140

Ser  His  Gln  Ser  Ser  Val  Trp  Phe  Glu  Met  Met  Arg  Val  Tyr  Ser  Trp
145                      150                      155                           160

Asn  His  Ile  Ile  Leu  Leu  Val  Ser  Asp  His  Glu  Gly  Arg  Ala  Ala
                    165                      170                      175

Gln  Lys  Arg  Leu  Glu  Thr  Leu  Leu  Glu  Arg  Glu  Ser  Lys  Ala  Glu
               180                      185                      190

Lys  Val  Leu  Gln  Phe  Asp  Pro  Gly  Thr  Lys  Asn  Val  Thr  Ala  Leu  Leu
               195                      200                      205

Met  Glu  Ala  Lys  Glu  Leu  Glu  Ala  Arg  Val  Ile  Ile  Leu  Ser  Ala  Ser
     210                      215                      220

Glu  Asp  Asp  Ala  Ala  Thr  Val  Tyr  Arg  Ala  Ala  Ala  Met  Leu  Asn  Met
225                      230                      235                           240

Thr  Gly  Asn  Thr  Asn  Ile  Trp  Lys  Thr  Gly  Pro  Leu  Phe  Lys  Arg  Val
                    245                      250                      255

Leu  Met  Ser  Ser  Lys  Tyr  Ala  Asp  Gly  Val  Thr  Gly  Arg  Val  Glu  Phe
               260                      265                      270

Asn  Glu  Asp  Gly  Asp  Arg  Lys  Phe  Ala  Asn  Tyr  Ser  Ile  Met  Asn  Leu
          275                      280                      285

Gln  Asn  Arg  Lys  Leu  Val  Gln  Val  Gly  Ile  Tyr  Asn  Gly  Thr  His  Val
     290                      295                      300

Ile  Pro  Asn  Asp  Arg  Lys  Ile  Ile  Trp  Pro  Gly  Gly  Glu  Thr  Glu  Lys
305                      310                      315                           320

Pro  Arg  Gly  Tyr  Gln  Met  Ser  Thr  Arg  Leu  Lys  Ile  Val  Thr  Ile  His
               325                      330                      335

Gln  Glu  Pro  Phe  Val  Tyr  Val  Lys  Pro  Thr  Leu  Ser  Asp  Gly  Thr  Cys
               340                      345                      350

Lys  Glu  Glu  Phe  Thr  Val  Asn  Gly  Asp  Pro  Val  Lys  Lys  Val  Ile  Cys
          355                      360                      365

Thr  Gly  Pro  Asn  Asp  Thr  Ser  Pro  Gly  Ser  Pro  Arg  His  Thr  Val  Pro
     370                      375                      380

Gln  Cys  Cys  Tyr  Gly  Phe  Cys  Ile  Asp  Leu  Leu  Ile  Lys  Leu  Ala  Arg
385                      390                      395                           400

Thr  Met  Asn  Phe  Thr  Tyr  Glu  Val  His  Leu  Val  Ala  Asp  Gly  Lys  Phe
               405                      410                      415

Gly  Thr  Gln  Glu  Arg  Val  Asn  Asn  Ser  Asn  Lys  Lys  Glu  Trp  Asn  Gly
               420                      425                      430

Met  Met  Gly  Glu  Leu  Leu  Ser  Gly  Gln  Ala  Asp  Met  Ile  Val  Ala  Pro
          435                      440                      445

Leu  Thr  Ile  Asn  Asn  Glu  Arg  Ala  Gln  Tyr  Ile  Glu  Phe  Ser  Lys  Pro
     450                      455                      460

Phe  Lys  Tyr  Gln  Gly  Leu  Thr  Ile  Leu  Val  Lys  Lys  Glu  Ile  Pro  Arg
465                      470                      475                           480

Ser  Thr  Leu  Asp  Ser  Phe  Met  Gln  Pro  Phe  Gln  Ser  Thr  Leu  Trp  Leu
               485                      490                      495

Leu  Val  Gly  Leu  Ser  Val  His  Val  Val  Ala  Val  Met  Leu  Tyr  Leu  Leu
               500                      505                      510

Asp  Arg  Phe  Ser  Pro  Phe  Gly  Arg  Phe  Lys  Val  Asn  Ser  Glu  Glu  Glu
```

|     |     |     |     | 515 |     |     |     |     | 520 |     |     |     |     | 525 |     |
| --- | --- | --- | --- | --- | --- | --- | --- | --- | --- | --- | --- | --- | --- | --- | --- |
| Glu | Glu | Asp | Ala | Leu | Thr | Leu | Ser | Ser | Ala | Met | Trp | Phe | Ser | Trp | Gly |
|     | 530 |     |     |     | 535 |     |     |     |     | 540 |     |     |     |     |     |
| Val | Leu | Leu | Asn | Ser | Gly | Ile | Glu | Gly | Ala | Pro | Arg | Ser | Phe | Ser |     |
| 545 |     |     |     | 550 |     |     |     |     | 555 |     |     |     |     | 560 |     |
| Ala | Arg | Ile | Leu | Gly | Met | Val | Trp | Ala | Gly | Phe | Ala | Met | Ile | Ile | Val |
|     |     |     |     | 565 |     |     |     |     | 570 |     |     |     |     | 575 |     |
| Ala | Ser | Tyr | Thr | Ala | Asn | Leu | Ala | Ala | Phe | Leu | Val | Leu | Asp | Arg | Pro |
|     |     |     | 580 |     |     |     |     | 585 |     |     |     |     | 590 |     |     |
| Glu | Glu | Arg | Ile | Thr | Gly | Ile | Asn | Asp | Pro | Arg | Leu | Arg | Asn | Pro | Ser |
|     |     | 595 |     |     |     |     | 600 |     |     |     |     | 605 |     |     |     |
| Asp | Lys | Phe | Ile | Tyr | Ala | Thr | Val | Lys | Gln | Ser | Ser | Val | Asp | Ile | Tyr |
|     | 610 |     |     |     |     | 615 |     |     |     |     | 620 |     |     |     |     |
| Phe | Arg | Arg | Gln | Val | Glu | Leu | Ser | Thr | Met | Tyr | Arg | His | Met | Glu | Lys |
| 625 |     |     |     |     | 630 |     |     |     |     | 635 |     |     |     |     | 640 |
| His | Asn | Tyr | Glu | Ser | Ala | Ala | Glu | Ala | Ile | Gln | Ala | Val | Arg | Asp | Asn |
|     |     |     |     | 645 |     |     |     |     | 650 |     |     |     |     | 655 |     |
| Lys | Leu | His | Ala | Phe | Ile | Trp | Asp | Ser | Ala | Val | Leu | Glu | Phe | Glu | Ala |
|     |     |     | 660 |     |     |     |     | 665 |     |     |     |     | 670 |     |     |
| Ser | Gln | Lys | Cys | Asp | Leu | Val | Thr | Thr | Gly | Glu | Leu | Phe | Phe | Arg | Ser |
|     |     | 675 |     |     |     |     | 680 |     |     |     |     | 685 |     |     |     |
| Gly | Phe | Gly | Ile | Gly | Met | Arg | Lys | Asp | Ser | Pro | Trp | Lys | Gln | Asn | Val |
|     | 690 |     |     |     |     | 695 |     |     |     |     | 700 |     |     |     |     |
| Ser | Leu | Ser | Ile | Leu | Lys | Ser | His | Glu | Asn | Gly | Phe | Met | Glu | Asp | Leu |
| 705 |     |     |     |     | 710 |     |     |     |     | 715 |     |     |     |     | 720 |
| Asp | Lys | Thr | Trp | Val | Arg | Tyr | Gln | Glu | Cys | Asp | Ser | Arg | Ser | Asn | Ala |
|     |     |     |     | 725 |     |     |     |     | 730 |     |     |     |     | 735 |     |
| Pro | Ala | Thr | Leu | Thr | Phe | Glu | Asn | Met | Ala | Gly | Val | Phe | Met | Leu | Val |
|     |     |     | 740 |     |     |     |     | 745 |     |     |     |     | 750 |     |     |
| Ala | Gly | Gly | Ile | Val | Ala | Gly | Ile | Phe | Leu | Ile | Phe | Ile | Glu | Ile | Ala |
|     |     | 755 |     |     |     |     | 760 |     |     |     |     | 765 |     |     |     |
| Tyr | Lys | Arg | His | Lys | Asp | Ala | Arg | Arg | Lys | Gln | Met | Gln | Leu | Ala | Phe |
|     | 770 |     |     |     |     | 775 |     |     |     |     | 780 |     |     |     |     |
| Ala | Ala | Val | Asn | Val | Trp | Arg | Lys | Asn | Leu | Gln | Asp | Arg | Lys | Ser | Gly |
| 785 |     |     |     |     | 790 |     |     |     |     | 795 |     |     |     |     | 800 |
| Arg | Ala | Glu | Pro | Asp | Pro | Lys | Lys | Lys | Ala | Thr | Phe | Arg | Ala | Ile | Thr |
|     |     |     |     | 805 |     |     |     |     | 810 |     |     |     |     | 815 |     |
| Ser | Thr | Leu | Ala | Ser | Ser | Phe | Lys | Arg | Arg | Ser | Ser | Lys | Asp | Thr |     |
|     |     |     | 820 |     |     |     |     | 825 |     |     |     |     | 830 |     |     |
| Leu | Ala | Arg | Asp | Cys | Leu | Gln | Pro | Cys | Pro | Ala | Pro | Trp | Ala | Arg | Glu |
|     |     | 835 |     |     |     |     | 840 |     |     |     |     | 845 |     |     |     |
| Ser | Ala | Thr | Arg | Pro | Pro | Pro | Ser | Leu | Arg | Val | Arg | Asp | Arg | Pro |     |
|     | 850 |     |     |     |     | 855 |     |     |     |     | 860 |     |     |     |     |
| Ala | Thr | Leu | Tyr | Arg | Thr | Ser | Thr | Pro | Arg | Ala | Arg | Ala | Arg | Ala | Phe |
| 865 |     |     |     |     | 870 |     |     |     |     | 875 |     |     |     |     | 880 |
| Pro | Val | Arg | Ser | Arg | Ala | Leu | Pro | Leu | Arg | Pro | Gln | Gly | Ala | Gly | Ala |
|     |     |     |     | 885 |     |     |     |     | 890 |     |     |     |     | 895 |     |
| His | Arg | Pro | Thr | Pro | Thr | Ser | Arg | Cys | Met | Gln | Trp |     |     |     |     |
|     |     |     | 900 |     |     |     |     | 905 |     |     |     |     |     |     |     |

( 2 ) INFORMATION FOR SEQ ID NO:35:

( i ) SEQUENCE CHARACTERISTICS:
        ( A ) LENGTH: 3998 base pairs
        ( B ) TYPE: nucleic acid (C) STRANDEDNESS: both
(D) TOPOLOGY: both (ii) MOLECULE TYPE: cDNA (ix) FEATURE:
 (A) NAME/KEY: CDS
 (B) LOCATION: 262..3093

(xi) SEQUENCE DESCRIPTION: SEQ ID NO:35:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                       Met Ser Thr Met Arg Leu Leu Thr Leu Ala
                        1               5                    10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
            15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
        45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
    60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
            110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
        125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
    140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
            190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
        205                 210                 215

GAC CCA GGG ACC AAG AAC GTG ACG GCC CTG CTG ATG GAG GCG AAA GAG      963
Asp Pro Gly Thr Lys Asn Val Thr Ala Leu Leu Met Glu Ala Lys Glu
    220                 225                 230

CTG GAG GCC CGG GTC ATC ATC CTT TCT GCC AGC GAG GAC GAT GCT GCC     1011
```

```
Leu Glu Ala Arg Val Ile Ile Leu Ser Ala Ser Glu Asp Asp Ala Ala
235                 240                 245                 250

ACT GTA TAC CGC GCA GCC GCG ATG CTG AAC ATG ACG GGC TCC GGG TAC      1059
Thr Val Tyr Arg Ala Ala Ala Met Leu Asn Met Thr Gly Ser Gly Tyr
                    255                 260                 265

GTG TGG CTG GTC GGC GAG CGC GAG ATC TCG GGG AAC GCC CTG CGC TAC      1107
Val Trp Leu Val Gly Glu Arg Glu Ile Ser Gly Asn Ala Leu Arg Tyr
                270                 275                 280

GCC CCA GAC GGC ATC CTC GGG CTG CAG CTC ATC AAC GGC AAG AAC GAG      1155
Ala Pro Asp Gly Ile Leu Gly Leu Gln Leu Ile Asn Gly Lys Asn Glu
            285                 290                 295

TCG GCC CAC ATC AGC GAC GCC GTG GGC GTG GTG GCC CAG GCC GTG CAC      1203
Ser Ala His Ile Ser Asp Ala Val Gly Val Val Ala Gln Ala Val His
        300                 305                 310

GAG CTC CTC GAG AAG GAG AAC ATC ACC GAC CCG CCG CGG GGC TGC GTG      1251
Glu Leu Leu Glu Lys Glu Asn Ile Thr Asp Pro Pro Arg Gly Cys Val
315                 320                 325                 330

GGC AAC ACC AAC ATC TGG AAG ACC GGG CCG CTC TTC AAG AGA GTG CTG      1299
Gly Asn Thr Asn Ile Trp Lys Thr Gly Pro Leu Phe Lys Arg Val Leu
                335                 340                 345

ATG TCT TCC AAG TAT GCG GAT GGG GTG ACT GGT CGC GTG GAG TTC AAT      1347
Met Ser Ser Lys Tyr Ala Asp Gly Val Thr Gly Arg Val Glu Phe Asn
            350                 355                 360

GAG GAT GGG GAC CGG AAG TTC GCC AAC TAC AGC ATC ATG AAC CTG CAG      1395
Glu Asp Gly Asp Arg Lys Phe Ala Asn Tyr Ser Ile Met Asn Leu Gln
        365                 370                 375

AAC CGC AAG CTG GTG CAA GTG GGC ATC TAC AAT GGC ACC CAC GTC ATC      1443
Asn Arg Lys Leu Val Gln Val Gly Ile Tyr Asn Gly Thr His Val Ile
    380                 385                 390

CCT AAT GAC AGG AAG ATC ATC TGG CCA GGC GGA GAG ACA GAG AAG CCT      1491
Pro Asn Asp Arg Lys Ile Ile Trp Pro Gly Gly Glu Thr Glu Lys Pro
395                 400                 405                 410

CGA GGG TAC CAG ATG TCC ACC AGA CTG AAG ATT GTG ACG ATC CAC CAG      1539
Arg Gly Tyr Gln Met Ser Thr Arg Leu Lys Ile Val Thr Ile His Gln
                415                 420                 425

GAG CCC TTC GTG TAC GTC AAG CCC ACG CTG AGT GAT GGG ACA TGC AAG      1587
Glu Pro Phe Val Tyr Val Lys Pro Thr Leu Ser Asp Gly Thr Cys Lys
            430                 435                 440

GAG GAG TTC ACA GTC AAC GGC GAC CCA GTC AAG AAG GTG ATC TGC ACC      1635
Glu Glu Phe Thr Val Asn Gly Asp Pro Val Lys Lys Val Ile Cys Thr
        445                 450                 455

GGG CCC AAC GAC ACG TCG CCG GGC AGC CCC CGC CAC ACG GTG CCT CAG      1683
Gly Pro Asn Asp Thr Ser Pro Gly Ser Pro Arg His Thr Val Pro Gln
    460                 465                 470

TGT TGC TAC GGC TTT TGC ATC GAC CTG CTC ATC AAG CTG GCA CGG ACC      1731
Cys Cys Tyr Gly Phe Cys Ile Asp Leu Leu Ile Lys Leu Ala Arg Thr
475                 480                 485                 490

ATG AAC TTC ACC TAC GAG GTG CAC CTG GTG GCA GAT GGC AAG TTC GGC      1779
Met Asn Phe Thr Tyr Glu Val His Leu Val Ala Asp Gly Lys Phe Gly
                495                 500                 505

ACA CAG GAG CGG GTG AAC AAC AGC AAC AAG AAG GAG TGG AAT GGG ATG      1827
Thr Gln Glu Arg Val Asn Asn Ser Asn Lys Lys Glu Trp Asn Gly Met
            510                 515                 520

ATG GGC GAG CTG CTC AGC GGG CAG GCA GAC ATG ATC GTG GCG CCG CTA      1875
Met Gly Glu Leu Leu Ser Gly Gln Ala Asp Met Ile Val Ala Pro Leu
        525                 530                 535

ACC ATA AAC AAC GAG CGC GCG CAG TAC ATC GAG TTT TCC AAG CCC TTC      1923
Thr Ile Asn Asn Glu Arg Ala Gln Tyr Ile Glu Phe Ser Lys Pro Phe
    540                 545                 550

AAG TAC CAG GGC CTG ACT ATT CTG GTC AAG AAG GAG ATT CCC CGG AGC      1971
```

|     |     |     |     |     |     |     |     |     |     |     |     |     |     |     |      |
| --- | --- | --- | --- | --- | --- | --- | --- | --- | --- | --- | --- | --- | --- | --- | ---- |
| Lys | Tyr | Gln | Gly | Leu | Thr | Ile | Leu | Val | Lys | Lys | Glu | Ile | Pro | Arg | Ser  |
| 555 |     |     |     | 560 |     |     |     |     | 565 |     |     |     |     |     | 570  |

| ACG | CTG | GAC | TCG | TTC | ATG | CAG | CCG | TTC | CAG | AGC | ACA | CTG | TGG | CTG | CTG | 2019 |
| --- | --- | --- | --- | --- | --- | --- | --- | --- | --- | --- | --- | --- | --- | --- | --- | ---- |
| Thr | Leu | Asp | Ser | Phe | Met | Gln | Pro | Phe | Gln | Ser | Thr | Leu | Trp | Leu | Leu |      |
|     |     |     |     | 575 |     |     |     |     | 580 |     |     |     |     | 585 |     |      |

| GTG | GGG | CTG | TCG | GTG | CAC | GTG | GTG | GCC | GTG | ATG | CTG | TAC | CTG | CTG | GAC | 2067 |
| Val | Gly | Leu | Ser | Val | His | Val | Val | Ala | Val | Met | Leu | Tyr | Leu | Leu | Asp |      |
|     |     |     |     | 590 |     |     |     | 595 |     |     |     |     |     | 600 |     |      |

| CGC | TTC | AGC | CCC | TTC | GGC | CGG | TTC | AAG | GTG | AAC | AGC | GAG | GAG | GAG | GAG | 2115 |
| Arg | Phe | Ser | Pro | Phe | Gly | Arg | Phe | Lys | Val | Asn | Ser | Glu | Glu | Glu | Glu |      |
|     |     | 605 |     |     |     |     | 610 |     |     |     |     | 615 |     |     |     |      |

| GAG | GAC | GCA | CTG | ACC | CTG | TCC | TCG | GCC | ATG | TGG | TTC | TCC | TGG | GGC | GTC | 2163 |
| Glu | Asp | Ala | Leu | Thr | Leu | Ser | Ser | Ala | Met | Trp | Phe | Ser | Trp | Gly | Val |      |
|     | 620 |     |     |     |     | 625 |     |     |     |     | 630 |     |     |     |     |      |

| CTG | CTC | AAC | TCC | GGC | ATC | GGG | GAA | GGC | GCC | CCC | AGA | AGC | TTC | TCA | GCG | 2211 |
| Leu | Leu | Asn | Ser | Gly | Ile | Gly | Glu | Gly | Ala | Pro | Arg | Ser | Phe | Ser | Ala |      |
| 635 |     |     |     |     | 640 |     |     |     |     | 645 |     |     |     |     | 650 |      |

| CGC | ATC | CTG | GGC | ATG | GTG | TGG | GCC | GGC | TTT | GCC | ATG | ATC | ATC | GTG | GCC | 2259 |
| Arg | Ile | Leu | Gly | Met | Val | Trp | Ala | Gly | Phe | Ala | Met | Ile | Ile | Val | Ala |      |
|     |     |     |     | 655 |     |     |     |     | 660 |     |     |     |     | 665 |     |      |

| TCC | TAC | ACC | GCC | AAC | CTG | GCG | GCC | TTC | CTG | GTG | CTG | GAC | CGG | CCG | GAG | 2307 |
| Ser | Tyr | Thr | Ala | Asn | Leu | Ala | Ala | Phe | Leu | Val | Leu | Asp | Arg | Pro | Glu |      |
|     |     |     | 670 |     |     |     |     | 675 |     |     |     |     | 680 |     |     |      |

| GAG | CGC | ATC | ACG | GGC | ATC | AAC | GAC | CCT | CGG | CTG | AGG | AAC | CCC | TCG | GAC | 2355 |
| Glu | Arg | Ile | Thr | Gly | Ile | Asn | Asp | Pro | Arg | Leu | Arg | Asn | Pro | Ser | Asp |      |
|     |     | 685 |     |     |     |     | 690 |     |     |     |     | 695 |     |     |     |      |

| AAG | TTT | ATC | TAC | GCC | ACG | GTG | AAG | CAG | AGC | TCC | GTG | GAT | ATC | TAC | TTC | 2403 |
| Lys | Phe | Ile | Tyr | Ala | Thr | Val | Lys | Gln | Ser | Ser | Val | Asp | Ile | Tyr | Phe |      |
|     | 700 |     |     |     |     | 705 |     |     |     |     | 710 |     |     |     |     |      |

| CGG | CGC | CAG | GTG | GAG | CTG | AGC | ACC | ATG | TAC | CGG | CAT | ATG | GAG | AAG | CAC | 2451 |
| Arg | Arg | Gln | Val | Glu | Leu | Ser | Thr | Met | Tyr | Arg | His | Met | Glu | Lys | His |      |
| 715 |     |     |     |     | 720 |     |     |     |     | 725 |     |     |     |     | 730 |      |

| AAC | TAC | GAG | AGT | GCG | GCG | GAG | GCC | ATC | CAG | GCC | GTG | AGA | GAC | AAC | AAG | 2499 |
| Asn | Tyr | Glu | Ser | Ala | Ala | Glu | Ala | Ile | Gln | Ala | Val | Arg | Asp | Asn | Lys |      |
|     |     |     |     | 735 |     |     |     |     | 740 |     |     |     |     | 745 |     |      |

| CTG | CAT | GCC | TTC | ATC | TGG | GAC | TCG | GCG | GTG | CTG | GAG | TTC | GAG | GCC | TCG | 2547 |
| Leu | His | Ala | Phe | Ile | Trp | Asp | Ser | Ala | Val | Leu | Glu | Phe | Glu | Ala | Ser |      |
|     |     |     | 750 |     |     |     |     | 755 |     |     |     |     | 760 |     |     |      |

| CAG | AAG | TGC | GAC | CTG | GTG | ACG | ACT | GGA | GAG | CTG | TTT | TTC | CGC | TCG | GGC | 2595 |
| Gln | Lys | Cys | Asp | Leu | Val | Thr | Thr | Gly | Glu | Leu | Phe | Phe | Arg | Ser | Gly |      |
|     |     | 765 |     |     |     |     | 770 |     |     |     |     | 775 |     |     |     |      |

| TTC | GGC | ATA | GGC | ATG | CGC | AAA | GAC | AGC | CCC | TGG | AAG | CAG | AAC | GTC | TCC | 2643 |
| Phe | Gly | Ile | Gly | Met | Arg | Lys | Asp | Ser | Pro | Trp | Lys | Gln | Asn | Val | Ser |      |
| 780 |     |     |     |     | 785 |     |     |     |     | 790 |     |     |     |     |     |      |

| CTG | TCC | ATC | CTC | AAG | TCC | CAC | GAG | AAT | GGC | TTC | ATG | GAA | GAC | CTG | GAC | 2691 |
| Leu | Ser | Ile | Leu | Lys | Ser | His | Glu | Asn | Gly | Phe | Met | Glu | Asp | Leu | Asp |      |
| 795 |     |     |     |     | 800 |     |     |     |     | 805 |     |     |     |     | 810 |      |

| AAG | ACG | TGG | GTT | CGG | TAT | CAG | GAA | TGT | GAC | TCG | CGC | AGC | AAC | GCC | CCT | 2739 |
| Lys | Thr | Trp | Val | Arg | Tyr | Gln | Glu | Cys | Asp | Ser | Arg | Ser | Asn | Ala | Pro |      |
|     |     |     |     | 815 |     |     |     |     | 820 |     |     |     |     | 825 |     |      |

| GCG | ACC | CTT | ACT | TTT | GAG | AAC | ATG | GCC | GGG | GTC | TTC | ATG | CTG | GTA | GCT | 2787 |
| Ala | Thr | Leu | Thr | Phe | Glu | Asn | Met | Ala | Gly | Val | Phe | Met | Leu | Val | Ala |      |
|     |     |     | 830 |     |     |     |     | 835 |     |     |     |     | 840 |     |     |      |

| GGG | GGC | ATC | GTG | GCC | GGG | ATC | TTC | CTG | ATT | TTC | ATC | GAG | ATT | GCC | TAC | 2835 |
| Gly | Gly | Ile | Val | Ala | Gly | Ile | Phe | Leu | Ile | Phe | Ile | Glu | Ile | Ala | Tyr |      |
|     |     | 845 |     |     |     |     | 850 |     |     |     |     | 855 |     |     |     |      |

| AAG | CGG | CAC | AAG | GAT | GCT | CGC | CGG | AAG | CAG | ATG | CAG | CTG | GCC | TTT | GCC | 2883 |
| Lys | Arg | His | Lys | Asp | Ala | Arg | Arg | Lys | Gln | Met | Gln | Leu | Ala | Phe | Ala |      |
|     | 860 |     |     |     |     | 865 |     |     |     |     | 870 |     |     |     |     |      |

| GCC | GTT | AAC | GTG | TGG | CGG | AAG | AAC | CTG | CAG | GAT | AGA | AAG | AGT | GGT | AGA | 2931 |

| | | | | | | | | | | | | | | | |
|---|---|---|---|---|---|---|---|---|---|---|---|---|---|---|---|
| Ala | Val | Asn | Val | Trp | Arg | Lys | Asn | Leu | Gln | Asp | Arg | Lys | Ser | Gly | Arg |
| 875 | | | | 880 | | | | | 885 | | | | | 890 | |

| GCA | GAG | CCT | GAC | CCT | AAA | AAG | AAA | GCC | ACA | TTT | AGG | GCT | ATC | ACC | TCC | 2979 |
|---|---|---|---|---|---|---|---|---|---|---|---|---|---|---|---|---|
| Ala | Glu | Pro | Asp | Pro | Lys | Lys | Lys | Ala | Thr | Phe | Arg | Ala | Ile | Thr | Ser | |
| | | | | 895 | | | | | 900 | | | | | 905 | | |

| ACC | CTG | GCT | TCC | AGC | TTC | AAG | AGG | CGT | AGG | TCC | TCC | AAA | GAC | ACG | CAG | 3027 |
|---|---|---|---|---|---|---|---|---|---|---|---|---|---|---|---|---|
| Thr | Leu | Ala | Ser | Ser | Phe | Lys | Arg | Arg | Arg | Ser | Ser | Lys | Asp | Thr | Gln | |
| | | | | 910 | | | | | 915 | | | | | 920 | | |

| TAC | CAT | CCC | ACT | GAT | ATC | ACG | GGC | CCG | CTC | AAC | CTC | TCA | GAT | CCC | TCG | 3075 |
|---|---|---|---|---|---|---|---|---|---|---|---|---|---|---|---|---|
| Tyr | His | Pro | Thr | Asp | Ile | Thr | Gly | Pro | Leu | Asn | Leu | Ser | Asp | Pro | Ser | |
| | | 925 | | | | | 930 | | | | | 935 | | | | |

| GTC | AGC | ACC | GTG | GTG | TGAGGCCCCC | GGAGGCGCCC | ACCTGCCCAG | TTAGCCCGGC | 3130 |
|---|---|---|---|---|---|---|---|---|---|
| Val | Ser | Thr | Val | Val | | | | | |
| | | 940 | | | | | | | |

| CAAGGACACT | GATGGGTCCT | GCTGCTCGGG | AAGGCCTGAG | GGAAGCCCAC | CCGCCCCAGA | 3190 |
|---|---|---|---|---|---|---|
| GACTGCCCAC | CCTGGGCCTC | CCGTCCGTCC | GCCCGCCCAC | CCCGCTGCCT | GGCGGGCAGC | 3250 |
| CCCTGCTGGA | CCAAGGTGCG | GACCGGAGCG | GCTGAGGACG | GGGCAGAGCT | GAGTCGGCTG | 3310 |
| GGCAGGGCCG | CAGGGCGCTC | CGGCAGAGGC | AGGCCCCTGG | GGTCTCTGAG | CAGTGGGGAG | 3370 |
| CGGGGGCTAA | CTGCCCCCAG | GCGGAGGGGC | TTGGAGCAGA | GACGGCAGCC | CCATCCTTCC | 3430 |
| CGCAGCACCA | GCCTGAGCCA | CAGTGGGGCC | CATGGCCCCA | GCTGGCTGGG | TCGCCCCTCC | 3490 |
| TCGGGCGCCT | GCGCTCCTCT | GCAGCCTGAG | CTCCACCCTC | CCCTCTTCTT | GCGGCACCGC | 3550 |
| CCACCAAACA | CCCCGTCTGC | CCCTTGACGC | CACACGCCGG | GGCTGGCGCT | GCCCTCCCCC | 3610 |
| ACGGCCGTCC | CTGACTTCCC | AGCTGGCAGC | GCCTCCCGCC | GCCTCGGGCC | GCCTCCTCCA | 3670 |
| GAATCGAGAG | GGCTGAGCCC | CTCCTCTCCT | CGTCCGGCCT | GCAGCACAGA | AGGGGGCCTC | 3730 |
| CCCGGGGGTC | CCCGGACGCT | GGCTCGGGAC | TGTCTTCAAC | CCTGCCCTGC | ACCTTGGGCA | 3790 |
| CGGGAGAGCG | CCACCCGCCC | GCCCCCGCCC | TCGCTCCGGG | TGCGTGACCG | GCCCGCCACC | 3850 |
| TTGTACAGAA | CCAGCACTCC | CAGGGCCCGA | GCGCGTGCCT | TCCCCGTGCG | CAGCCGCGCT | 3910 |
| CTGCCCCTCC | GTCCCCAGGG | TGCAGGCGCG | CACCGCCCAA | CCCCCACCTC | CCGGTGTATG | 3970 |
| CAGTGGTGAT | GCCTAAAGGA | ATGTCACG | | | | 3998 |

( 2 ) INFORMATION FOR SEQ ID NO:36:

( i ) SEQUENCE CHARACTERISTICS:
        ( A ) LENGTH: 943 amino acids
        ( B ) TYPE: amino acid
        ( D ) TOPOLOGY: linear ( i i ) MOLECULE TYPE: protein ( x i ) SEQUENCE DESCRIPTION: SEQ ID NO:36:

| Met | Ser | Thr | Met | Arg | Leu | Leu | Thr | Leu | Ala | Leu | Leu | Phe | Ser | Cys | Ser |
|---|---|---|---|---|---|---|---|---|---|---|---|---|---|---|---|
| 1 | | | | 5 | | | | | 10 | | | | | 15 | |

| Val | Ala | Arg | Ala | Ala | Cys | Asp | Pro | Lys | Ile | Val | Asn | Ile | Gly | Ala | Val |
|---|---|---|---|---|---|---|---|---|---|---|---|---|---|---|---|
| | | | 20 | | | | | 25 | | | | | 30 | | |

| Leu | Ser | Thr | Arg | Lys | His | Glu | Gln | Met | Phe | Arg | Glu | Ala | Val | Asn | Gln |
|---|---|---|---|---|---|---|---|---|---|---|---|---|---|---|---|
| | | 35 | | | | | 40 | | | | | 45 | | | |

| Ala | Asn | Lys | Arg | His | Gly | Ser | Trp | Lys | Ile | Gln | Leu | Asn | Ala | Thr | Ser |
|---|---|---|---|---|---|---|---|---|---|---|---|---|---|---|---|
| | 50 | | | | | 55 | | | | | 60 | | | | |

| Val | Thr | His | Lys | Pro | Asn | Ala | Ile | Gln | Met | Ala | Leu | Ser | Val | Cys | Glu |
|---|---|---|---|---|---|---|---|---|---|---|---|---|---|---|---|
| 65 | | | | | 70 | | | | | 75 | | | | | 80 |

| Asp | Leu | Ile | Ser | Ser | Gln | Val | Tyr | Ala | Ile | Leu | Val | Ser | His | Pro | Pro |
|---|---|---|---|---|---|---|---|---|---|---|---|---|---|---|---|
| | | | | 85 | | | | | 90 | | | | | 95 | |

| Thr | Pro | Asn | Asp | His | Phe | Thr | Pro | Thr | Pro | Val | Ser | Tyr | Thr | Ala | Gly |
|---|---|---|---|---|---|---|---|---|---|---|---|---|---|---|---|

-continued

```
                        100                            105                           110
Phe  Tyr  Arg  Ile  Pro  Val  Leu  Gly  Leu  Thr  Thr  Arg  Met  Ser  Ile  Tyr
               115                      120                      125

Ser  Asp  Lys  Ser  Ile  His  Leu  Ser  Phe  Leu  Arg  Thr  Val  Pro  Pro  Tyr
     130                      135                     140

Ser  His  Gln  Ser  Ser  Val  Trp  Phe  Glu  Met  Met  Arg  Val  Tyr  Ser  Trp
145                           150                     155                     160

Asn  His  Ile  Ile  Leu  Leu  Val  Ser  Asp  His  Glu  Gly  Arg  Ala  Ala
                         165                 170                      175

Gln  Lys  Arg  Leu  Glu  Thr  Leu  Leu  Glu  Glu  Arg  Glu  Ser  Lys  Ser  Lys
               180                      185                      190

Lys  Arg  Asn  Tyr  Glu  Asn  Leu  Asp  Gln  Leu  Ser  Tyr  Asp  Asn  Lys  Arg
          195                      200                      205

Gly  Pro  Lys  Ala  Glu  Lys  Val  Leu  Gln  Phe  Asp  Pro  Gly  Thr  Lys  Asn
     210                      215                      220

Val  Thr  Ala  Leu  Leu  Met  Glu  Ala  Lys  Glu  Leu  Glu  Ala  Arg  Val  Ile
225                      230                      235                      240

Ile  Leu  Ser  Ala  Ser  Glu  Asp  Ala  Ala  Thr  Val  Tyr  Arg  Ala  Ala
                    245                      250                      255

Ala  Met  Leu  Asn  Met  Thr  Gly  Ser  Gly  Tyr  Val  Trp  Leu  Val  Gly  Glu
               260                      265                      270

Arg  Glu  Ile  Ser  Gly  Asn  Ala  Leu  Arg  Tyr  Ala  Pro  Asp  Gly  Ile  Leu
               275                      280                      285

Gly  Leu  Gln  Leu  Ile  Asn  Gly  Lys  Asn  Glu  Ser  Ala  His  Ile  Ser  Asp
     290                      295                      300

Ala  Val  Gly  Val  Val  Ala  Gln  Ala  Val  His  Glu  Leu  Leu  Glu  Lys  Glu
305                      310                      315                      320

Asn  Ile  Thr  Asp  Pro  Pro  Arg  Gly  Cys  Val  Gly  Asn  Thr  Asn  Ile  Trp
                    325                      330                      335

Lys  Thr  Gly  Pro  Leu  Phe  Lys  Arg  Val  Leu  Met  Ser  Ser  Lys  Tyr  Ala
               340                      345                      350

Asp  Gly  Val  Thr  Gly  Arg  Val  Glu  Phe  Asn  Glu  Asp  Gly  Asp  Arg  Lys
          355                      360                      365

Phe  Ala  Asn  Tyr  Ser  Ile  Met  Asn  Leu  Gln  Asn  Arg  Lys  Leu  Val  Gln
370                      375                      380

Val  Gly  Ile  Tyr  Asn  Gly  Thr  His  Val  Ile  Pro  Asn  Asp  Arg  Lys  Ile
385                      390                      395                      400

Ile  Trp  Pro  Gly  Gly  Glu  Thr  Glu  Lys  Pro  Arg  Gly  Tyr  Gln  Met  Ser
                    405                      410                      415

Thr  Arg  Leu  Lys  Ile  Val  Thr  Ile  His  Gln  Glu  Pro  Phe  Val  Tyr  Val
               420                      425                      430

Lys  Pro  Thr  Leu  Ser  Asp  Gly  Thr  Cys  Lys  Glu  Glu  Phe  Thr  Val  Asn
          435                      440                      445

Gly  Asp  Pro  Val  Lys  Lys  Val  Ile  Cys  Thr  Gly  Pro  Asn  Asp  Thr  Ser
     450                      455                      460

Pro  Gly  Ser  Pro  Arg  His  Thr  Val  Pro  Gln  Cys  Cys  Tyr  Gly  Phe  Cys
465                      470                      475                      480

Ile  Asp  Leu  Leu  Ile  Lys  Leu  Ala  Arg  Thr  Met  Asn  Phe  Thr  Tyr  Glu
                    485                      490                      495

Val  His  Leu  Val  Ala  Asp  Gly  Lys  Phe  Gly  Thr  Gln  Glu  Arg  Val  Asn
               500                      505                      510

Asn  Ser  Asn  Lys  Lys  Glu  Trp  Asn  Gly  Met  Met  Gly  Glu  Leu  Leu  Ser
          515                      520                      525
```

| | | | | | | | | | | | | | | |
|---|---|---|---|---|---|---|---|---|---|---|---|---|---|---|
| Gly | Gln | Ala | Asp | Met | Ile | Val | Ala | Pro | Leu | Thr | Ile | Asn | Asn | Glu | Arg |
| | 530 | | | | 535 | | | | | 540 | | | | | |
| Ala | Gln | Tyr | Ile | Glu | Phe | Ser | Lys | Pro | Phe | Lys | Tyr | Gln | Gly | Leu | Thr |
| 545 | | | | | 550 | | | | | 555 | | | | | 560 |
| Ile | Leu | Val | Lys | Lys | Glu | Ile | Pro | Arg | Ser | Thr | Leu | Asp | Ser | Phe | Met |
| | | | | 565 | | | | | 570 | | | | | 575 | |
| Gln | Pro | Phe | Gln | Ser | Thr | Leu | Trp | Leu | Leu | Val | Gly | Leu | Ser | Val | His |
| | | | 580 | | | | | 585 | | | | | 590 | | |
| Val | Val | Ala | Val | Met | Leu | Tyr | Leu | Leu | Asp | Arg | Phe | Ser | Pro | Phe | Gly |
| | | 595 | | | | | 600 | | | | | 605 | | | |
| Arg | Phe | Lys | Val | Asn | Ser | Glu | Glu | Glu | Glu | Asp | Ala | Leu | Thr | Leu |
| | 610 | | | | | 615 | | | | | 620 | | | | |
| Ser | Ser | Ala | Met | Trp | Phe | Ser | Trp | Gly | Val | Leu | Leu | Asn | Ser | Gly | Ile |
| 625 | | | | | 630 | | | | | 635 | | | | | 640 |
| Gly | Glu | Gly | Ala | Pro | Arg | Ser | Phe | Ser | Ala | Arg | Ile | Leu | Gly | Met | Val |
| | | | | 645 | | | | | 650 | | | | | 655 | |
| Trp | Ala | Gly | Phe | Ala | Met | Ile | Ile | Val | Ala | Ser | Tyr | Thr | Ala | Asn | Leu |
| | | | 660 | | | | | 665 | | | | | 670 | | |
| Ala | Ala | Phe | Leu | Val | Leu | Asp | Arg | Pro | Glu | Glu | Arg | Ile | Thr | Gly | Ile |
| | | 675 | | | | | 680 | | | | | 685 | | | |
| Asn | Asp | Pro | Arg | Leu | Arg | Asn | Pro | Ser | Asp | Lys | Phe | Ile | Tyr | Ala | Thr |
| | 690 | | | | | 695 | | | | | 700 | | | | |
| Val | Lys | Gln | Ser | Ser | Val | Asp | Ile | Tyr | Phe | Arg | Arg | Gln | Val | Glu | Leu |
| 705 | | | | | 710 | | | | | 715 | | | | | 720 |
| Ser | Thr | Met | Tyr | Arg | His | Met | Glu | Lys | His | Asn | Tyr | Glu | Ser | Ala | Ala |
| | | | | 725 | | | | | 730 | | | | | 735 | |
| Glu | Ala | Ile | Gln | Ala | Val | Arg | Asp | Asn | Lys | Leu | His | Ala | Phe | Ile | Trp |
| | | | 740 | | | | | 745 | | | | | 750 | | |
| Asp | Ser | Ala | Val | Leu | Glu | Phe | Glu | Ala | Ser | Gln | Lys | Cys | Asp | Leu | Val |
| | | 755 | | | | | 760 | | | | | 765 | | | |
| Thr | Thr | Gly | Glu | Leu | Phe | Phe | Arg | Ser | Gly | Phe | Gly | Ile | Gly | Met | Arg |
| | 770 | | | | | 775 | | | | | 780 | | | | |
| Lys | Asp | Ser | Pro | Trp | Lys | Gln | Asn | Val | Ser | Leu | Ser | Ile | Leu | Lys | Ser |
| 785 | | | | | 790 | | | | | 795 | | | | | 800 |
| His | Glu | Asn | Gly | Phe | Met | Glu | Asp | Leu | Asp | Lys | Thr | Trp | Val | Arg | Tyr |
| | | | | 805 | | | | | 810 | | | | | 815 | |
| Gln | Glu | Cys | Asp | Ser | Arg | Ser | Asn | Ala | Pro | Ala | Thr | Leu | Thr | Phe | Glu |
| | | | 820 | | | | | 825 | | | | | 830 | | |
| Asn | Met | Ala | Gly | Val | Phe | Met | Leu | Val | Ala | Gly | Gly | Ile | Val | Ala | Gly |
| | | 835 | | | | | 840 | | | | | 845 | | | |
| Ile | Phe | Leu | Ile | Phe | Ile | Glu | Ile | Ala | Tyr | Lys | Arg | His | Lys | Asp | Ala |
| | 850 | | | | | 855 | | | | | 860 | | | | |
| Arg | Arg | Lys | Gln | Met | Gln | Leu | Ala | Phe | Ala | Ala | Val | Asn | Val | Trp | Arg |
| 865 | | | | | 870 | | | | | 875 | | | | | 880 |
| Lys | Asn | Leu | Gln | Asp | Arg | Lys | Ser | Gly | Arg | Ala | Glu | Pro | Asp | Pro | Lys |
| | | | | 885 | | | | | 890 | | | | | 895 | |
| Lys | Lys | Ala | Thr | Phe | Arg | Ala | Ile | Thr | Ser | Thr | Leu | Ala | Ser | Ser | Phe |
| | | | 900 | | | | | 905 | | | | | 910 | | |
| Lys | Arg | Arg | Arg | Ser | Ser | Lys | Asp | Thr | Gln | Tyr | His | Pro | Thr | Asp | Ile |
| | | 915 | | | | | 920 | | | | | 925 | | | |
| Thr | Gly | Pro | Leu | Asn | Leu | Ser | Asp | Pro | Ser | Val | Ser | Thr | Val | Val |
| | 930 | | | | | 935 | | | | | 940 | | | | |

( 2 ) INFORMATION FOR SEQ ID NO:37:

( i ) SEQUENCE CHARACTERISTICS:
    ( A ) LENGTH: 3274 base pairs
    ( B ) TYPE: nucleic acid
    ( C ) STRANDEDNESS: both
    ( D ) TOPOLOGY: both ( i i ) MOLECULE TYPE: cDNA ( i x ) FEATURE:
    ( A ) NAME/KEY: CDS
    ( B ) LOCATION: 262..3255

( x i ) SEQUENCE DESCRIPTION: SEQ ID NO:37:

```
CAAGCCGGGC GTTCGGAGCT GTGCCCGGCC CCGCTTCAGC ACCGCGGACA GCGCCGGCCG      60

CGTGGGGCTG AGCGCCGAGC CCCCGCGCAC GCTTCAGCCC CCCTTCCCTC GGCCGACGTC     120

CCGGGACCGC CGCTCCGGGG GAGACGTGGC GTCCGCAGCC CGCGGGGCCG GGCGAGCGCA     180

GGACGGCCCG GAAGCCCCGC GGGGGATGCG CCGAGGGCCC CGCGTTCGCG CCGCGCAGAG     240

CCAGGCCCGC GGCCCGAGCC C ATG AGC ACC ATG CGC CTG CTG ACG CTC GCC      291
                       Met Ser Thr Met Arg Leu Leu Thr Leu Ala
                        1               5                    10

CTG CTG TTC TCC TGC TCC GTC GCC CGT GCC GCG TGC GAC CCC AAG ATC      339
Leu Leu Phe Ser Cys Ser Val Ala Arg Ala Ala Cys Asp Pro Lys Ile
             15                  20                  25

GTC AAC ATT GGC GCG GTG CTG AGC ACG CGG AAG CAC GAG CAG ATG TTC      387
Val Asn Ile Gly Ala Val Leu Ser Thr Arg Lys His Glu Gln Met Phe
         30                  35                  40

CGC GAG GCC GTG AAC CAG GCC AAC AAG CGG CAC GGC TCC TGG AAG ATT      435
Arg Glu Ala Val Asn Gln Ala Asn Lys Arg His Gly Ser Trp Lys Ile
     45                  50                  55

CAG CTC AAT GCC ACC TCC GTC ACG CAC AAG CCC AAC GCC ATC CAG ATG      483
Gln Leu Asn Ala Thr Ser Val Thr His Lys Pro Asn Ala Ile Gln Met
 60                  65                  70

GCT CTG TCG GTG TGC GAG GAC CTC ATC TCC AGC CAG GTC TAC GCC ATC      531
Ala Leu Ser Val Cys Glu Asp Leu Ile Ser Ser Gln Val Tyr Ala Ile
 75                  80                  85                  90

CTA GTT AGC CAT CCA CCT ACC CCC AAC GAC CAC TTC ACT CCC ACC CCT      579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC      627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG      675
Thr Arg Met Ser Ile Tyr Ser Asp Lys Ser Ile His Leu Ser Phe Leu
         125                 130                 135

CGC ACC GTG CCG CCC TAC TCC CAC CAG TCC AGC GTG TGG TTT GAG ATG      723
Arg Thr Val Pro Pro Tyr Ser His Gln Ser Ser Val Trp Phe Glu Met
     140                 145                 150

ATG CGT GTC TAC AGC TGG AAC CAC ATC ATC CTG CTG GTC AGC GAC GAC      771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG      819
His Glu Gly Arg Ala Ala Gln Lys Arg Leu Glu Thr Leu Leu Glu Glu
                 175                 180                 185

CGT GAG TCC AAG AGT AAA AAA AGG AAC TAT GAA AAC CTC GAC CAA CTG      867
Arg Glu Ser Lys Ser Lys Lys Arg Asn Tyr Glu Asn Leu Asp Gln Leu
             190                 195                 200

TCC TAT GAC AAC AAG CGC GGA CCC AAG GCA GAG AAG GTG CTG CAG TTT      915
Ser Tyr Asp Asn Lys Arg Gly Pro Lys Ala Glu Lys Val Leu Gln Phe
         205                 210                 215

GAC CCA GGG ACC AAG AAC GTG ACG GCC CTG CTG ATG GAG GCG AAA GAG      963
```

| | | | | | | | | | | | | | | | |
|---|---|---|---|---|---|---|---|---|---|---|---|---|---|---|---|
| Asp | Pro<br>220 | Gly | Thr | Lys | Asn | Val<br>225 | Thr | Ala | Leu | Leu | Met<br>230 | Glu | Ala | Lys | Glu |

| CTG | GAG | GCC | CGG | GTC | ATC | ATC | CTT | TCT | GCC | AGC | GAG | GAC | GAT | GCT | GCC | 1011 |
|---|---|---|---|---|---|---|---|---|---|---|---|---|---|---|---|---|
| Leu<br>235 | Glu | Ala | Arg | Val<br>240 | Ile | Ile | Leu | Ser | Ala<br>245 | Ser | Glu | Asp | Asp | Ala | Ala<br>250 | |

| ACT | GTA | TAC | CGC | GCA | GCC | GCG | ATG | CTG | AAC | ATG | ACG | GGC | TCC | GGG | TAC | 1059 |
|---|---|---|---|---|---|---|---|---|---|---|---|---|---|---|---|---|
| Thr | Val | Tyr | Arg | Ala<br>255 | Ala | Ala | Met | Leu | Asn<br>260 | Met | Thr | Gly | Ser | Gly<br>265 | Tyr | |

| GTG | TGG | CTG | GTC | GGC | GAG | CGC | GAG | ATC | TCG | GGG | AAC | GCC | CTG | CGC | TAC | 1107 |
|---|---|---|---|---|---|---|---|---|---|---|---|---|---|---|---|---|
| Val | Trp | Leu | Val<br>270 | Gly | Glu | Arg | Glu | Ile<br>275 | Ser | Gly | Asn | Ala | Leu<br>280 | Arg | Tyr | |

| GCC | CCA | GAC | GGC | ATC | CTC | GGG | CTG | CAG | CTC | ATC | AAC | GGC | AAG | AAC | GAG | 1155 |
|---|---|---|---|---|---|---|---|---|---|---|---|---|---|---|---|---|
| Ala | Pro | Asp<br>285 | Gly | Ile | Leu | Gly | Leu<br>290 | Gln | Leu | Ile | Asn | Gly<br>295 | Lys | Asn | Glu | |

| TCG | GCC | CAC | ATC | AGC | GAC | GCC | GTG | GGC | GTG | GTG | GCC | CAG | GCC | GTG | CAC | 1203 |
|---|---|---|---|---|---|---|---|---|---|---|---|---|---|---|---|---|
| Ser | Ala<br>300 | His | Ile | Ser | Asp | Ala<br>305 | Val | Gly | Val | Val | Ala<br>310 | Gln | Ala | Val | His | |

| GAG | CTC | CTC | GAG | AAG | GAG | AAC | ATC | ACC | GAC | CCG | CCG | CGG | GGC | TGC | GTG | 1251 |
|---|---|---|---|---|---|---|---|---|---|---|---|---|---|---|---|---|
| Glu<br>315 | Leu | Leu | Glu | Lys | Glu<br>320 | Asn | Ile | Thr | Asp | Pro<br>325 | Pro | Arg | Gly | Cys | Val<br>330 | |

| GGC | AAC | ACC | AAC | ATC | TGG | AAG | ACC | GGG | CCG | CTC | TTC | AAG | AGA | GTG | CTG | 1299 |
|---|---|---|---|---|---|---|---|---|---|---|---|---|---|---|---|---|
| Gly | Asn | Thr | Asn | Ile<br>335 | Trp | Lys | Thr | Gly | Pro<br>340 | Leu | Phe | Lys | Arg | Val<br>345 | Leu | |

| ATG | TCT | TCC | AAG | TAT | GCG | GAT | GGG | GTG | ACT | GGT | CGC | GTG | GAG | TTC | AAT | 1347 |
|---|---|---|---|---|---|---|---|---|---|---|---|---|---|---|---|---|
| Met | Ser | Ser | Lys<br>350 | Tyr | Ala | Asp | Gly | Val<br>355 | Thr | Gly | Arg | Val | Glu<br>360 | Phe | Asn | |

| GAG | GAT | GGG | GAC | CGG | AAG | TTC | GCC | AAC | TAC | AGC | ATC | ATG | AAC | CTG | CAG | 1395 |
|---|---|---|---|---|---|---|---|---|---|---|---|---|---|---|---|---|
| Glu | Asp | Gly<br>365 | Asp | Arg | Lys | Phe | Ala<br>370 | Asn | Tyr | Ser | Ile | Met<br>375 | Asn | Leu | Gln | |

| AAC | CGC | AAG | CTG | GTG | CAA | GTG | GGC | ATC | TAC | AAT | GGC | ACC | CAC | GTC | ATC | 1443 |
|---|---|---|---|---|---|---|---|---|---|---|---|---|---|---|---|---|
| Asn | Arg | Lys<br>380 | Leu | Val | Gln | Val | Gly<br>385 | Ile | Tyr | Asn | Gly | Thr<br>390 | His | Val | Ile | |

| CCT | AAT | GAC | AGG | AAG | ATC | ATC | TGG | CCA | GGC | GGA | GAG | ACA | GAG | AAG | CCT | 1491 |
|---|---|---|---|---|---|---|---|---|---|---|---|---|---|---|---|---|
| Pro<br>395 | Asn | Asp | Arg | Lys | Ile<br>400 | Ile | Trp | Pro | Gly | Gly<br>405 | Glu | Thr | Glu | Lys | Pro<br>410 | |

| CGA | GGG | TAC | CAG | ATG | TCC | ACC | AGA | CTG | AAG | ATT | GTG | ACG | ATC | CAC | CAG | 1539 |
|---|---|---|---|---|---|---|---|---|---|---|---|---|---|---|---|---|
| Arg | Gly | Tyr | Gln | Met<br>415 | Ser | Thr | Arg | Leu | Lys<br>420 | Ile | Val | Thr | Ile | His<br>425 | Gln | |

| GAG | CCC | TTC | GTG | TAC | GTC | AAG | CCC | ACG | CTG | AGT | GAT | GGG | ACA | TGC | AAG | 1587 |
|---|---|---|---|---|---|---|---|---|---|---|---|---|---|---|---|---|
| Glu | Pro | Phe | Val<br>430 | Tyr | Val | Lys | Pro | Thr<br>435 | Leu | Ser | Asp | Gly | Thr<br>440 | Cys | Lys | |

| GAG | GAG | TTC | ACA | GTC | AAC | GGC | GAC | CCA | GTC | AAG | AAG | GTG | ATC | TGC | ACC | 1635 |
|---|---|---|---|---|---|---|---|---|---|---|---|---|---|---|---|---|
| Glu | Glu | Phe<br>445 | Thr | Val | Asn | Gly | Asp<br>450 | Pro | Val | Lys | Lys | Val<br>455 | Ile | Cys | Thr | |

| GGG | CCC | AAC | GAC | ACG | TCG | CCG | GGC | AGC | CCC | CGC | CAC | ACG | GTG | CCT | CAG | 1683 |
|---|---|---|---|---|---|---|---|---|---|---|---|---|---|---|---|---|
| Gly | Pro | Asn | Asp<br>460 | Thr | Ser | Pro | Gly | Ser<br>465 | Pro | Arg | His | Thr<br>470 | Val | Pro | Gln | |

| TGT | TGC | TAC | GGC | TTT | TGC | ATC | GAC | CTG | CTC | ATC | AAG | CTG | GCA | CGG | ACC | 1731 |
|---|---|---|---|---|---|---|---|---|---|---|---|---|---|---|---|---|
| Cys<br>475 | Cys | Tyr | Gly | Phe | Cys<br>480 | Ile | Asp | Leu | Leu | Ile<br>485 | Lys | Leu | Ala | Arg | Thr<br>490 | |

| ATG | AAC | TTC | ACC | TAC | GAG | GTG | CAC | CTG | GTG | GCA | GAT | GGC | AAG | TTC | GGC | 1779 |
|---|---|---|---|---|---|---|---|---|---|---|---|---|---|---|---|---|
| Met | Asn | Phe | Thr | Tyr<br>495 | Glu | Val | His | Leu | Val<br>500 | Ala | Asp | Gly | Lys | Phe<br>505 | Gly | |

| ACA | CAG | GAG | CGG | GTG | AAC | AAC | AGC | AAC | AAG | AAG | GAG | TGG | AAT | GGG | ATG | 1827 |
|---|---|---|---|---|---|---|---|---|---|---|---|---|---|---|---|---|
| Thr | Gln | Glu | Arg<br>510 | Val | Asn | Asn | Ser | Asn<br>515 | Lys | Lys | Glu | Trp | Asn<br>520 | Gly | Met | |

| ATG | GGC | GAG | CTG | CTC | AGC | GGG | CAG | GCA | GAC | ATG | ATC | GTG | GCG | CCG | CTA | 1875 |
|---|---|---|---|---|---|---|---|---|---|---|---|---|---|---|---|---|
| Met | Gly | Glu<br>525 | Leu | Leu | Ser | Gly | Gln<br>530 | Ala | Asp | Met | Ile | Val<br>535 | Ala | Pro | Leu | |

| ACC | ATA | AAC | AAC | GAG | CGC | GCG | CAG | TAC | ATC | GAG | TTT | TCC | AAG | CCC | TTC | 1923 |
|---|---|---|---|---|---|---|---|---|---|---|---|---|---|---|---|---|

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Thr | Ile | Asn | Asn | Glu | Arg | Ala | Gln | Tyr | Ile | Glu | Phe | Ser | Lys | Pro | Phe |      |
|     | 540 |     |     |     | 545 |     |     |     |     | 550 |     |     |     |     |     |      |
| AAG | TAC | CAG | GGC | CTG | ACT | ATT | CTG | GTC | AAG | AAG | GAG | ATT | CCC | CGG | AGC | 1971 |
| Lys | Tyr | Gln | Gly | Leu | Thr | Ile | Leu | Val | Lys | Lys | Glu | Ile | Pro | Arg | Ser |      |
| 555 |     |     |     | 560 |     |     |     |     | 565 |     |     |     |     |     | 570 |      |
| ACG | CTG | GAC | TCG | TTC | ATG | CAG | CCG | TTC | CAG | AGC | ACA | CTG | TGG | CTG | CTG | 2019 |
| Thr | Leu | Asp | Ser | Phe | Met | Gln | Pro | Phe | Gln | Ser | Thr | Leu | Trp | Leu | Leu |      |
|     |     |     |     | 575 |     |     |     |     | 580 |     |     |     |     | 585 |     |      |
| GTG | GGG | CTG | TCG | GTG | CAC | GTG | GTG | GCC | GTG | ATG | CTG | TAC | CTG | CTG | GAC | 2067 |
| Val | Gly | Leu | Ser | Val | His | Val | Val | Ala | Val | Met | Leu | Tyr | Leu | Leu | Asp |      |
|     |     |     | 590 |     |     |     |     | 595 |     |     |     |     | 600 |     |     |      |
| CGC | TTC | AGC | CCC | TTC | GGC | CGG | TTC | AAG | GTG | AAC | AGC | GAG | GAG | GAG | GAG | 2115 |
| Arg | Phe | Ser | Pro | Phe | Gly | Arg | Phe | Lys | Val | Asn | Ser | Glu | Glu | Glu | Glu |      |
|     |     | 605 |     |     |     |     | 610 |     |     |     |     | 615 |     |     |     |      |
| GAG | GAC | GCA | CTG | ACC | CTG | TCC | TCG | GCC | ATG | TGG | TTC | TCC | TGG | GGC | GTC | 2163 |
| Glu | Asp | Ala | Leu | Thr | Leu | Ser | Ser | Ala | Met | Trp | Phe | Ser | Trp | Gly | Val |      |
|     | 620 |     |     |     |     | 625 |     |     |     |     | 630 |     |     |     |     |      |
| CTG | CTC | AAC | TCC | GGC | ATC | GGG | GAA | GGC | GCC | CCC | AGA | AGC | TTC | TCA | GCG | 2211 |
| Leu | Leu | Asn | Ser | Gly | Ile | Gly | Glu | Gly | Ala | Pro | Arg | Ser | Phe | Ser | Ala |      |
| 635 |     |     |     |     | 640 |     |     |     |     | 645 |     |     |     |     | 650 |      |
| CGC | ATC | CTG | GGC | ATG | GTG | TGG | GCC | GGC | TTT | GCC | ATG | ATC | ATC | GTG | GCC | 2259 |
| Arg | Ile | Leu | Gly | Met | Val | Trp | Ala | Gly | Phe | Ala | Met | Ile | Ile | Val | Ala |      |
|     |     |     |     | 655 |     |     |     |     | 660 |     |     |     |     | 665 |     |      |
| TCC | TAC | ACC | GCC | AAC | CTG | GCG | GCC | TTC | CTG | GTG | CTG | GAC | CGG | CCG | GAG | 2307 |
| Ser | Tyr | Thr | Ala | Asn | Leu | Ala | Ala | Phe | Leu | Val | Leu | Asp | Arg | Pro | Glu |      |
|     |     |     | 670 |     |     |     |     | 675 |     |     |     |     | 680 |     |     |      |
| GAG | CGC | ATC | ACG | GGC | ATC | AAC | GAC | CCT | CGG | CTG | AGG | AAC | CCC | TCG | GAC | 2355 |
| Glu | Arg | Ile | Thr | Gly | Ile | Asn | Asp | Pro | Arg | Leu | Arg | Asn | Pro | Ser | Asp |      |
|     |     | 685 |     |     |     |     | 690 |     |     |     |     | 695 |     |     |     |      |
| AAG | TTT | ATC | TAC | GCC | ACG | GTG | AAG | CAG | AGC | TCC | GTG | GAT | ATC | TAC | TTC | 2403 |
| Lys | Phe | Ile | Tyr | Ala | Thr | Val | Lys | Gln | Ser | Ser | Val | Asp | Ile | Tyr | Phe |      |
|     | 700 |     |     |     |     | 705 |     |     |     |     | 710 |     |     |     |     |      |
| CGG | CGC | CAG | GTG | GAG | CTG | AGC | ACC | ATG | TAC | CGG | CAT | ATG | GAG | AAG | CAC | 2451 |
| Arg | Arg | Gln | Val | Glu | Leu | Ser | Thr | Met | Tyr | Arg | His | Met | Glu | Lys | His |      |
| 715 |     |     |     |     | 720 |     |     |     |     | 725 |     |     |     |     | 730 |      |
| AAC | TAC | GAG | AGT | GCG | GCG | GAG | GCC | ATC | CAG | GCC | GTG | AGA | GAC | AAC | AAG | 2499 |
| Asn | Tyr | Glu | Ser | Ala | Ala | Glu | Ala | Ile | Gln | Ala | Val | Arg | Asp | Asn | Lys |      |
|     |     |     |     | 735 |     |     |     |     | 740 |     |     |     |     | 745 |     |      |
| CTG | CAT | GCC | TTC | ATC | TGG | GAC | TCG | GCG | GTG | CTG | GAG | TTC | GAG | GCC | TCG | 2547 |
| Leu | His | Ala | Phe | Ile | Trp | Asp | Ser | Ala | Val | Leu | Glu | Phe | Glu | Ala | Ser |      |
|     |     |     | 750 |     |     |     |     | 755 |     |     |     |     | 760 |     |     |      |
| CAG | AAG | TGC | GAC | CTG | GTG | ACG | ACT | GGA | GAG | CTG | TTT | TTC | CGC | TCG | GGC | 2595 |
| Gln | Lys | Cys | Asp | Leu | Val | Thr | Thr | Gly | Glu | Leu | Phe | Phe | Arg | Ser | Gly |      |
|     |     | 765 |     |     |     |     | 770 |     |     |     |     | 775 |     |     |     |      |
| TTC | GGC | ATA | GGC | ATG | CGC | AAA | GAC | AGC | CCC | TGG | AAG | CAG | AAC | GTC | TCC | 2643 |
| Phe | Gly | Ile | Gly | Met | Arg | Lys | Asp | Ser | Pro | Trp | Lys | Gln | Asn | Val | Ser |      |
|     | 780 |     |     |     |     | 785 |     |     |     |     | 790 |     |     |     |     |      |
| CTG | TCC | ATC | CTC | AAG | TCC | CAC | GAG | AAT | GGC | TTC | ATG | GAA | GAC | CTG | GAC | 2691 |
| Leu | Ser | Ile | Leu | Lys | Ser | His | Glu | Asn | Gly | Phe | Met | Glu | Asp | Leu | Asp |      |
| 795 |     |     |     |     | 800 |     |     |     |     | 805 |     |     |     |     | 810 |      |
| AAG | ACG | TGG | GTT | CGG | TAT | CAG | GAA | TGT | GAC | TCG | CGC | AGC | AAC | GCC | CCT | 2739 |
| Lys | Thr | Trp | Val | Arg | Tyr | Gln | Glu | Cys | Asp | Ser | Arg | Ser | Asn | Ala | Pro |      |
|     |     |     |     | 815 |     |     |     |     | 820 |     |     |     |     | 825 |     |      |
| GCG | ACC | CTT | ACT | TTT | GAG | AAC | ATG | GCC | GGG | GTC | TTC | ATG | CTG | GTA | GCT | 2787 |
| Ala | Thr | Leu | Thr | Phe | Glu | Asn | Met | Ala | Gly | Val | Phe | Met | Leu | Val | Ala |      |
|     |     |     | 830 |     |     |     |     | 835 |     |     |     |     | 840 |     |     |      |
| GGG | GGC | ATC | GTG | GCC | GGG | ATC | TTC | CTG | ATT | TTC | ATC | GAG | ATT | GCC | TAC | 2835 |
| Gly | Gly | Ile | Val | Ala | Gly | Ile | Phe | Leu | Ile | Phe | Ile | Glu | Ile | Ala | Tyr |      |
|     |     | 845 |     |     |     |     | 850 |     |     |     |     | 855 |     |     |     |      |
| AAG | CGG | CAC | AAG | GAT | GCT | CGC | CGG | AAG | CAG | ATG | CAG | CTG | GCC | TTT | GCC | 2883 |

| | | | | | | | | | | | | | | | |
|---|---|---|---|---|---|---|---|---|---|---|---|---|---|---|---|
| Lys | Arg | His | Lys | Asp | Ala | Arg | Arg | Lys | Gln | Met | Gln | Leu | Ala | Phe | Ala |
| | | 860 | | | | 865 | | | | 870 | | | | | |

| GCC | GTT | AAC | GTG | TGG | CGG | AAG | AAC | CTG | CAG | GAT | AGA | AAG | AGT | GGT | AGA | 2931 |
|---|---|---|---|---|---|---|---|---|---|---|---|---|---|---|---|---|
| Ala | Val | Asn | Val | Trp | Arg | Lys | Asn | Leu | Gln | Asp | Arg | Lys | Ser | Gly | Arg | |
| 875 | | | | 880 | | | | 885 | | | | | | 890 | | |

| GCA | GAG | CCT | GAC | CCT | AAA | AAG | AAA | GCC | ACA | TTT | AGG | GCT | ATC | ACC | TCC | 2979 |
|---|---|---|---|---|---|---|---|---|---|---|---|---|---|---|---|---|
| Ala | Glu | Pro | Asp | Pro | Lys | Lys | Lys | Ala | Thr | Phe | Arg | Ala | Ile | Thr | Ser | |
| | | | | 895 | | | | | 900 | | | | | 905 | | |

| ACC | CTG | GCT | TCC | AGC | TTC | AAG | AGG | CGT | AGG | TCC | TCC | AAA | GAC | ACG | CTG | 3027 |
|---|---|---|---|---|---|---|---|---|---|---|---|---|---|---|---|---|
| Thr | Leu | Ala | Ser | Ser | Phe | Lys | Arg | Arg | Arg | Ser | Ser | Lys | Asp | Thr | Leu | |
| | | | | 910 | | | | 915 | | | | | 920 | | | |

| GCT | CGG | GAC | TGT | CTT | CAA | CCC | TGC | CCT | GCA | CCT | TGG | GCA | CGG | GAG | AGC | 3075 |
|---|---|---|---|---|---|---|---|---|---|---|---|---|---|---|---|---|
| Ala | Arg | Asp | Cys | Leu | Gln | Pro | Cys | Pro | Ala | Pro | Trp | Ala | Arg | Glu | Ser | |
| | | 925 | | | | | 930 | | | | | 935 | | | | |

| GCC | ACC | CGC | CCG | CCC | CCG | CCC | TCG | CTC | CGG | GTG | CGT | GAC | CGG | CCC | GCC | 3123 |
|---|---|---|---|---|---|---|---|---|---|---|---|---|---|---|---|---|
| Ala | Thr | Arg | Pro | Pro | Pro | Pro | Ser | Leu | Arg | Val | Arg | Asp | Arg | Pro | Ala | |
| | 940 | | | | | 945 | | | | | 950 | | | | | |

| ACC | TTG | TAC | AGA | ACC | AGC | ACT | CCC | AGG | GCC | CGA | GCG | CGT | GCC | TTC | CCC | 3171 |
|---|---|---|---|---|---|---|---|---|---|---|---|---|---|---|---|---|
| Thr | Leu | Tyr | Arg | Thr | Ser | Thr | Pro | Arg | Ala | Arg | Ala | Arg | Ala | Phe | Pro | |
| 955 | | | | | 960 | | | | | 965 | | | | | 970 | |

| GTG | CGC | AGC | CGC | GCT | CTG | CCC | CTC | CGT | CCC | CAG | GGT | GCA | GGC | GCG | CAC | 3219 |
|---|---|---|---|---|---|---|---|---|---|---|---|---|---|---|---|---|
| Val | Arg | Ser | Arg | Ala | Leu | Pro | Leu | Arg | Pro | Gln | Gly | Ala | Gly | Ala | His | |
| | | | | 975 | | | | | 980 | | | | | 985 | | |

| CGC | CCA | ACC | CCC | ACC | TCC | CGG | TGT | ATG | CAG | TGG | TGATGCCTAA | | AGGAATGTCA | | | 3272 |
|---|---|---|---|---|---|---|---|---|---|---|---|---|---|---|---|---|
| Arg | Pro | Thr | Pro | Thr | Ser | Arg | Cys | Met | Gln | Trp | | | | | | |
| | | | 990 | | | | | 995 | | | | | | | | |

| CG | | | | | | | | | | | | | | | | 3274 |

(2) INFORMATION FOR SEQ ID NO:38:

(i) SEQUENCE CHARACTERISTICS:
        (A) LENGTH: 997 amino acids
        (B) TYPE: amino acid
        (D) TOPOLOGY: linear (ii) MOLECULE TYPE: protein (xi) SEQUENCE DESCRIPTION: SEQ ID NO:38:

| Met | Ser | Thr | Met | Arg | Leu | Leu | Thr | Leu | Ala | Leu | Leu | Phe | Ser | Cys | Ser |
|---|---|---|---|---|---|---|---|---|---|---|---|---|---|---|---|
| 1 | | | | 5 | | | | | 10 | | | | | 15 | |

| Val | Ala | Arg | Ala | Ala | Cys | Asp | Pro | Lys | Ile | Val | Asn | Ile | Gly | Ala | Val |
|---|---|---|---|---|---|---|---|---|---|---|---|---|---|---|---|
| | | | 20 | | | | | 25 | | | | | 30 | | |

| Leu | Ser | Thr | Arg | Lys | His | Glu | Gln | Met | Phe | Arg | Glu | Ala | Val | Asn | Gln |
|---|---|---|---|---|---|---|---|---|---|---|---|---|---|---|---|
| | | | 35 | | | | | 40 | | | | | 45 | | |

| Ala | Asn | Lys | Arg | His | Gly | Ser | Trp | Lys | Ile | Gln | Leu | Asn | Ala | Thr | Ser |
|---|---|---|---|---|---|---|---|---|---|---|---|---|---|---|---|
| | | 50 | | | | | 55 | | | | | 60 | | | |

| Val | Thr | His | Lys | Pro | Asn | Ala | Ile | Gln | Met | Ala | Leu | Ser | Val | Cys | Glu |
|---|---|---|---|---|---|---|---|---|---|---|---|---|---|---|---|
| 65 | | | | | 70 | | | | | 75 | | | | | 80 |

| Asp | Leu | Ile | Ser | Ser | Gln | Val | Tyr | Ala | Ile | Leu | Val | Ser | His | Pro | Pro |
|---|---|---|---|---|---|---|---|---|---|---|---|---|---|---|---|
| | | | | 85 | | | | | 90 | | | | | 95 | |

| Thr | Pro | Asn | Asp | His | Phe | Thr | Pro | Thr | Pro | Val | Ser | Tyr | Thr | Ala | Gly |
|---|---|---|---|---|---|---|---|---|---|---|---|---|---|---|---|
| | | | | 100 | | | | | 105 | | | | | 110 | |

| Phe | Tyr | Arg | Ile | Pro | Val | Leu | Gly | Leu | Thr | Thr | Arg | Met | Ser | Ile | Tyr |
|---|---|---|---|---|---|---|---|---|---|---|---|---|---|---|---|
| | | | 115 | | | | | 120 | | | | | 125 | | |

| Ser | Asp | Lys | Ser | Ile | His | Leu | Ser | Phe | Leu | Arg | Thr | Val | Pro | Pro | Tyr |
|---|---|---|---|---|---|---|---|---|---|---|---|---|---|---|---|
| | | 130 | | | | | 135 | | | | | 140 | | | |

| Ser | His | Gln | Ser | Ser | Val | Trp | Phe | Glu | Met | Met | Arg | Val | Tyr | Ser | Trp |
|---|---|---|---|---|---|---|---|---|---|---|---|---|---|---|---|
| 145 | | | | | 150 | | | | | 155 | | | | | 160 |

| Asn | His | Ile | Ile | Leu | Leu | Val | Ser | Asp | Asp | His | Glu | Gly | Arg | Ala | Ala |
|---|---|---|---|---|---|---|---|---|---|---|---|---|---|---|---|

-continued

|     |     |     |     | 165 |     |     |     |     | 170 |     |     |     |     | 175 |     |
| --- | --- | --- | --- | --- | --- | --- | --- | --- | --- | --- | --- | --- | --- | --- | --- |

Gln Lys Arg Leu Glu Thr Leu Leu Glu Arg Glu Ser Lys Ser Lys
            180                 185                 190

Lys Arg Asn Tyr Glu Asn Leu Asp Gln Leu Ser Tyr Asp Asn Lys Arg
        195                 200                 205

Gly Pro Lys Ala Glu Lys Val Leu Gln Phe Asp Pro Gly Thr Lys Asn
    210                 215                 220

Val Thr Ala Leu Leu Met Glu Ala Lys Glu Leu Glu Ala Arg Val Ile
225                 230                 235                 240

Ile Leu Ser Ala Ser Glu Asp Ala Ala Thr Val Tyr Arg Ala Ala
                245                 250                 255

Ala Met Leu Asn Met Thr Gly Ser Gly Tyr Val Trp Leu Val Gly Glu
            260                 265                 270

Arg Glu Ile Ser Gly Asn Ala Leu Arg Tyr Ala Pro Asp Gly Ile Leu
        275                 280                 285

Gly Leu Gln Leu Ile Asn Gly Lys Asn Glu Ser Ala His Ile Ser Asp
    290                 295                 300

Ala Val Gly Val Val Ala Gln Ala Val His Glu Leu Leu Glu Lys Glu
305                 310                 315                 320

Asn Ile Thr Asp Pro Pro Arg Gly Cys Val Gly Asn Thr Asn Ile Trp
                325                 330                 335

Lys Thr Gly Pro Leu Phe Lys Arg Val Leu Met Ser Ser Lys Tyr Ala
            340                 345                 350

Asp Gly Val Thr Gly Arg Val Glu Phe Asn Glu Asp Gly Asp Arg Lys
        355                 360                 365

Phe Ala Asn Tyr Ser Ile Met Asn Leu Gln Asn Arg Lys Leu Val Gln
    370                 375                 380

Val Gly Ile Tyr Asn Gly Thr His Val Ile Pro Asn Asp Arg Lys Ile
385                 390                 395                 400

Ile Trp Pro Gly Gly Glu Thr Glu Lys Pro Arg Gly Tyr Gln Met Ser
                405                 410                 415

Thr Arg Leu Lys Ile Val Thr Ile His Gln Glu Pro Phe Val Tyr Val
            420                 425                 430

Lys Pro Thr Leu Ser Asp Gly Thr Cys Lys Glu Glu Phe Thr Val Asn
        435                 440                 445

Gly Asp Pro Val Lys Lys Val Ile Cys Thr Gly Pro Asn Asp Thr Ser
450                 455                 460

Pro Gly Ser Pro Arg His Thr Val Pro Gln Cys Cys Tyr Gly Phe Cys
465                 470                 475                 480

Ile Asp Leu Leu Ile Lys Leu Ala Arg Thr Met Asn Phe Thr Tyr Glu
                485                 490                 495

Val His Leu Val Ala Asp Gly Lys Phe Gly Thr Gln Glu Arg Val Asn
            500                 505                 510

Asn Ser Asn Lys Lys Glu Trp Asn Gly Met Met Gly Glu Leu Leu Ser
        515                 520                 525

Gly Gln Ala Asp Met Ile Val Ala Pro Leu Thr Ile Asn Asn Glu Arg
    530                 535                 540

Ala Gln Tyr Ile Glu Phe Ser Lys Pro Phe Lys Tyr Gln Gly Leu Thr
545                 550                 555                 560

Ile Leu Val Lys Lys Glu Ile Pro Arg Ser Thr Leu Asp Ser Phe Met
                565                 570                 575

Gln Pro Phe Gln Ser Thr Leu Trp Leu Leu Val Gly Leu Ser Val His
            580                 585                 590

| | | | | | | | | | | | | | | |
|---|---|---|---|---|---|---|---|---|---|---|---|---|---|---|
|Val|Val|Ala|Val|Met|Leu|Tyr|Leu|Leu|Asp|Arg|Phe|Ser|Pro|Phe|Gly|
| | |595| | | |600| | | | |605| | | |
|Arg|Phe|Lys|Val|Asn|Ser|Glu|Glu|Glu|Glu|Asp|Ala|Leu|Thr|Leu|
| |610| | | | |615| | | |620| | | | |
|Ser|Ser|Ala|Met|Trp|Phe|Ser|Trp|Gly|Val|Leu|Leu|Asn|Ser|Gly|Ile|
|625| | | | |630| | | | |635| | | | |640|
|Gly|Glu|Gly|Ala|Pro|Arg|Ser|Phe|Ser|Ala|Arg|Ile|Leu|Gly|Met|Val|
| | | | |645| | | |650| | | | |655| |
|Trp|Ala|Gly|Phe|Ala|Met|Ile|Ile|Val|Ala|Ser|Tyr|Thr|Ala|Asn|Leu|
| | | |660| | | |665| | | | |670| | |
|Ala|Ala|Phe|Leu|Val|Leu|Asp|Arg|Pro|Glu|Glu|Arg|Ile|Thr|Gly|Ile|
| | |675| | | |680| | | | |685| | | |
|Asn|Asp|Pro|Arg|Leu|Arg|Asn|Pro|Ser|Asp|Lys|Phe|Ile|Tyr|Ala|Thr|
| |690| | | | |695| | | |700| | | | |
|Val|Lys|Gln|Ser|Ser|Val|Asp|Ile|Tyr|Phe|Arg|Arg|Gln|Val|Glu|Leu|
|705| | | | |710| | | |715| | | | |720| |
|Ser|Thr|Met|Tyr|Arg|His|Met|Glu|Lys|His|Asn|Tyr|Glu|Ser|Ala|Ala|
| | | | |725| | | |730| | | | |735| |
|Glu|Ala|Ile|Gln|Ala|Val|Arg|Asp|Asn|Lys|Leu|His|Ala|Phe|Ile|Trp|
| | | |740| | | |745| | | | |750| | |
|Asp|Ser|Ala|Val|Leu|Glu|Phe|Glu|Ala|Ser|Gln|Lys|Cys|Asp|Leu|Val|
| | |755| | | |760| | | | |765| | | |
|Thr|Thr|Gly|Glu|Leu|Phe|Phe|Arg|Ser|Gly|Phe|Gly|Ile|Gly|Met|Arg|
| |770| | | | |775| | | |780| | | | |
|Lys|Asp|Ser|Pro|Trp|Lys|Gln|Asn|Val|Ser|Leu|Ser|Ile|Leu|Lys|Ser|
|785| | | | |790| | | |795| | | | |800|
|His|Glu|Asn|Gly|Phe|Met|Glu|Asp|Leu|Asp|Lys|Thr|Trp|Val|Arg|Tyr|
| | | |805| | | |810| | | | |815| | |
|Gln|Glu|Cys|Asp|Ser|Arg|Ser|Asn|Ala|Pro|Ala|Thr|Leu|Thr|Phe|Glu|
| | |820| | | |825| | | | |830| | | |
|Asn|Met|Ala|Gly|Val|Phe|Met|Leu|Val|Ala|Gly|Gly|Ile|Val|Ala|Gly|
| |835| | | | |840| | | |845| | | | |
|Ile|Phe|Leu|Ile|Phe|Ile|Glu|Ile|Ala|Tyr|Lys|Arg|His|Lys|Asp|Ala|
|850| | | | |855| | | |860| | | | | |
|Arg|Arg|Lys|Gln|Met|Gln|Leu|Ala|Phe|Ala|Ala|Val|Asn|Val|Trp|Arg|
|865| | | |870| | | |875| | | | | |880|
|Lys|Asn|Leu|Gln|Asp|Arg|Lys|Ser|Gly|Arg|Ala|Glu|Pro|Asp|Pro|Lys|
| | | |885| | | |890| | | | |895| | |
|Lys|Lys|Ala|Thr|Phe|Arg|Ala|Ile|Thr|Ser|Thr|Leu|Ala|Ser|Ser|Phe|
| | |900| | | |905| | | |910| | | | |
|Lys|Arg|Arg|Arg|Ser|Ser|Lys|Asp|Thr|Leu|Ala|Arg|Asp|Cys|Leu|Gln|
| |915| | | | |920| | | |925| | | | |
|Pro|Cys|Pro|Ala|Pro|Trp|Ala|Arg|Glu|Ser|Ala|Thr|Arg|Pro|Pro|Pro|
|930| | | | |935| | | |940| | | | | |
|Pro|Ser|Leu|Arg|Val|Arg|Asp|Arg|Pro|Ala|Thr|Leu|Tyr|Arg|Thr|Ser|
|945| | | |950| | | |955| | | | |960| |
|Thr|Pro|Arg|Ala|Arg|Ala|Arg|Ala|Phe|Pro|Val|Arg|Ser|Arg|Ala|Leu|
| | | |965| | | |970| | | | |975| | |
|Pro|Leu|Arg|Pro|Gln|Gly|Ala|Gly|Ala|His|Arg|Pro|Thr|Pro|Thr|Ser|
| | |980| | | |985| | | |990| | | | |
|Arg|Cys|Met|Gln|Trp|
| | |995| | |

( 2 ) INFORMATION FOR SEQ ID NO:39:

(i) SEQUENCE CHARACTERISTICS:
   (A) LENGTH: 3070 base pairs
   (B) TYPE: nucleic acid
   (C) STRANDEDNESS: both
   (D) TOPOLOGY: both (ii) MOLECULE TYPE: cDNA (ix) FEATURE:
   (A) NAME/KEY: CDS
   (B) LOCATION: 262..3051

(xi) SEQUENCE DESCRIPTION: SEQ ID NO:39:

```
CAAGCCGGGC GTTCGGAGCT GTGCCCGGCC CCGCTTCAGC ACCGCGGACA GCGCCGGCCG        60

CGTGGGGCTG AGCGCCGAGC CCCCGCGCAC GCTTCAGCCC CCCTTCCCTC GGCCGACGTC       120

CCGGGACCGC CGCTCCGGGG GAGACGTGGC GTCCGCAGCC CGCGGGGCCG GGCGAGCGCA       180

GGACGGCCCG GAAGCCCCGC GGGGGATGCG CCGAGGGCCC CGCGTTCGCG CCGCGCAGAG       240

CCAGGCCCGC GGCCCGAGCC C ATG AGC ACC ATG CGC CTG CTG ACG CTC GCC         291
                         Met Ser Thr Met Arg Leu Leu Thr Leu Ala
                           1               5                  10

CTG CTG TTC TCC TGC TCC GTC GCC CGT GCC GCG TGC GAC CCC AAG ATC         339
Leu Leu Phe Ser Cys Ser Val Ala Arg Ala Ala Cys Asp Pro Lys Ile
              15                  20                  25

GTC AAC ATT GGC GCG GTG CTG AGC ACG CGG AAG CAC GAG CAG ATG TTC         387
Val Asn Ile Gly Ala Val Leu Ser Thr Arg Lys His Glu Gln Met Phe
             30                  35                  40

CGC GAG GCC GTG AAC CAG GCC AAC AAG CGG CAC GGC TCC TGG AAG ATT         435
Arg Glu Ala Val Asn Gln Ala Asn Lys Arg His Gly Ser Trp Lys Ile
            45                  50                  55

CAG CTC AAT GCC ACC TCC GTC ACG CAC AAG CCC AAC GCC ATC CAG ATG         483
Gln Leu Asn Ala Thr Ser Val Thr His Lys Pro Asn Ala Ile Gln Met
        60                  65                  70

GCT CTG TCG GTG TGC GAG GAC CTC ATC TCC AGC CAG GTC TAC GCC ATC         531
Ala Leu Ser Val Cys Glu Asp Leu Ile Ser Ser Gln Val Tyr Ala Ile
75                  80                  85                  90

CTA GTT AGC CAT CCA CCT ACC CCC AAC GAC CAC TTC ACT CCC ACC CCT         579
Leu Val Ser His Pro Pro Thr Pro Asn Asp His Phe Thr Pro Thr Pro
                 95                 100                 105

GTC TCC TAC ACA GCC GGC TTC TAC CGC ATA CCC GTG CTG GGG CTG ACC         627
Val Ser Tyr Thr Ala Gly Phe Tyr Arg Ile Pro Val Leu Gly Leu Thr
             110                 115                 120

ACC CGC ATG TCC ATC TAC TCG GAC AAG AGC ATC CAC CTG AGC TTC CTG         675
Thr Arg Met Ser Ile Tyr Ser Asp Lys Ser Ile His Leu Ser Phe Leu
            125                 130                 135

CGC ACC GTG CCG CCC TAC TCC CAC CAG TCC AGC GTG TGG TTT GAG ATG         723
Arg Thr Val Pro Pro Tyr Ser His Gln Ser Ser Val Trp Phe Glu Met
        140                 145                 150

ATG CGT GTC TAC AGC TGG AAC CAC ATC ATC CTG CTG GTC AGC GAC GAC         771
Met Arg Val Tyr Ser Trp Asn His Ile Ile Leu Leu Val Ser Asp Asp
155                 160                 165                 170

CAC GAG GGC CGG GCG GCT CAG AAA CGC CTG GAG ACG CTG CTG GAG GAG         819
His Glu Gly Arg Ala Ala Gln Lys Arg Leu Glu Thr Leu Leu Glu Glu
                 175                 180                 185

CGT GAG TCC AAG AGT AAA AAA AGG AAC TAT GAA AAC CTC GAC CAA CTG         867
Arg Glu Ser Lys Ser Lys Lys Arg Asn Tyr Glu Asn Leu Asp Gln Leu
             190                 195                 200

TCC TAT GAC AAC AAG CGC GGA CCC AAG GCA GAG AAG GTG CTG CAG TTT         915
Ser Tyr Asp Asn Lys Arg Gly Pro Lys Ala Glu Lys Val Leu Gln Phe
            205                 210                 215

GAC CCA GGG ACC AAG AAC GTG ACG GCC CTG CTG ATG GAG GCG AAA GAG         963
```

```
                Asp  Pro  Gly  Thr  Lys  Asn  Val  Thr  Ala  Leu  Leu  Met  Glu  Ala  Lys  Glu
                     220                 225                      230

CTG  GAG  GCC  CGG  GTC  ATC  ATC  CTT  TCT  GCC  AGC  GAG  GAC  GAT  GCT  GCC                  1011
Leu  Glu  Ala  Arg  Val  Ile  Ile  Leu  Ser  Ala  Ser  Glu  Asp  Asp  Ala  Ala
235                 240                 245                           250

ACT  GTA  TAC  CGC  GCA  GCC  GCG  ATG  CTG  AAC  ATG  ACG  GGC  AAC  ACC  AAC                  1059
Thr  Val  Tyr  Arg  Ala  Ala  Ala  Met  Leu  Asn  Met  Thr  Gly  Asn  Thr  Asn
                    255                 260                           265

ATC  TGG  AAG  ACC  GGG  CCG  CTC  TTC  AAG  AGA  GTG  CTG  ATG  TCT  TCC  AAG                  1107
Ile  Trp  Lys  Thr  Gly  Pro  Leu  Phe  Lys  Arg  Val  Leu  Met  Ser  Ser  Lys
               270                 275                      280

TAT  GCG  GAT  GGG  GTG  ACT  GGT  CGC  GTG  GAG  TTC  AAT  GAG  GAT  GGG  GAC                  1155
Tyr  Ala  Asp  Gly  Val  Thr  Gly  Arg  Val  Glu  Phe  Asn  Glu  Asp  Gly  Asp
          285                 290                 295

CGG  AAG  TTC  GCC  AAC  TAC  AGC  ATC  ATG  AAC  CTG  CAG  AAC  CGC  AAG  CTG                  1203
Arg  Lys  Phe  Ala  Asn  Tyr  Ser  Ile  Met  Asn  Leu  Gln  Asn  Arg  Lys  Leu
     300                 305                      310

GTG  CAA  GTG  GGC  ATC  TAC  AAT  GGC  ACC  CAC  GTC  ATC  CCT  AAT  GAC  AGG                  1251
Val  Gln  Val  Gly  Ile  Tyr  Asn  Gly  Thr  His  Val  Ile  Pro  Asn  Asp  Arg
315                 320                 325                           330

AAG  ATC  ATC  TGG  CCA  GGC  GGA  GAG  ACA  GAG  AAG  CCT  CGA  GGG  TAC  CAG                  1299
Lys  Ile  Ile  Trp  Pro  Gly  Gly  Glu  Thr  Glu  Lys  Pro  Arg  Gly  Tyr  Gln
               335                 340                      345

ATG  TCC  ACC  AGA  CTG  AAG  ATT  GTG  ACG  ATC  CAC  CAG  GAG  CCC  TTC  GTG                  1347
Met  Ser  Thr  Arg  Leu  Lys  Ile  Val  Thr  Ile  His  Gln  Glu  Pro  Phe  Val
          350                 355                 360

TAC  GTC  AAG  CCC  ACG  CTG  AGT  GAT  GGG  ACA  TGC  AAG  GAG  GAG  TTC  ACA                  1395
Tyr  Val  Lys  Pro  Thr  Leu  Ser  Asp  Gly  Thr  Cys  Lys  Glu  Glu  Phe  Thr
     365                 370                      375

GTC  AAC  GGC  GAC  CCA  GTC  AAG  AAG  GTG  ATC  TGC  ACC  GGG  CCC  AAC  GAC                  1443
Val  Asn  Gly  Asp  Pro  Val  Lys  Lys  Val  Ile  Cys  Thr  Gly  Pro  Asn  Asp
380                 385                 390

ACG  TCG  CCG  GGC  AGC  CCC  CGC  CAC  ACG  GTG  CCT  CAG  TGT  TGC  TAC  GGC                  1491
Thr  Ser  Pro  Gly  Ser  Pro  Arg  His  Thr  Val  Pro  Gln  Cys  Cys  Tyr  Gly
395                 400                 405                           410

TTT  TGC  ATC  GAC  CTG  CTC  ATC  AAG  CTG  GCA  CGG  ACC  ATG  AAC  TTC  ACC                  1539
Phe  Cys  Ile  Asp  Leu  Leu  Ile  Lys  Leu  Ala  Arg  Thr  Met  Asn  Phe  Thr
               415                 420                      425

TAC  GAG  GTG  CAC  CTG  GTG  GCA  GAT  GGC  AAG  TTC  GGC  ACA  CAG  GAG  CGG                  1587
Tyr  Glu  Val  His  Leu  Val  Ala  Asp  Gly  Lys  Phe  Gly  Thr  Gln  Glu  Arg
          430                 435                 440

GTG  AAC  AAC  AGC  AAC  AAG  AAG  GAG  TGG  AAT  GGG  ATG  ATG  GGC  GAG  CTG                  1635
Val  Asn  Asn  Ser  Asn  Lys  Lys  Glu  Trp  Asn  Gly  Met  Met  Gly  Glu  Leu
     445                 450                      455

CTC  AGC  GGG  CAG  GCA  GAC  ATG  ATC  GTG  GCG  CCG  CTA  ACC  ATA  AAC  AAC                  1683
Leu  Ser  Gly  Gln  Ala  Asp  Met  Ile  Val  Ala  Pro  Leu  Thr  Ile  Asn  Asn
460                 465                 470

GAG  CGC  GCG  CAG  TAC  ATC  GAG  TTT  TCC  AAG  CCC  TTC  AAG  TAC  CAG  GGC                  1731
Glu  Arg  Ala  Gln  Tyr  Ile  Glu  Phe  Ser  Lys  Pro  Phe  Lys  Tyr  Gln  Gly
475                 480                 485                           490

CTG  ACT  ATT  CTG  GTC  AAG  AAG  GAG  ATT  CCC  CGG  AGC  ACG  CTG  GAC  TCG                  1779
Leu  Thr  Ile  Leu  Val  Lys  Lys  Glu  Ile  Pro  Arg  Ser  Thr  Leu  Asp  Ser
               495                 500                      505

TTC  ATG  CAG  CCG  TTC  CAG  AGC  ACA  CTG  TGG  CTG  CTG  GTG  GGG  CTG  TCG                  1827
Phe  Met  Gln  Pro  Phe  Gln  Ser  Thr  Leu  Trp  Leu  Leu  Val  Gly  Leu  Ser
          510                 515                 520

GTG  CAC  GTG  GTG  GCC  GTG  ATG  CTG  TAC  CTG  CTG  GAC  CGC  TTC  AGC  CCC                  1875
Val  His  Val  Val  Ala  Val  Met  Leu  Tyr  Leu  Leu  Asp  Arg  Phe  Ser  Pro
     525                 530                      535

TTC  GGC  CGG  TTC  AAG  GTG  AAC  AGC  GAG  GAG  GAG  GAG  GAG  GAC  GCA  CTG                  1923
```

|     |     |     |     |     |     |     |     |     |     |     |     |     |     |     |     |
|---|---|---|---|---|---|---|---|---|---|---|---|---|---|---|---|
| Phe | Gly | Arg | Phe | Lys | Val | Asn | Ser | Glu | Glu | Glu | Glu | Asp | Ala | Leu | |
| | 540 | | | | 545 | | | | | 550 | | | | | |

| ACC | CTG | TCC | TCG | GCC | ATG | TGG | TTC | TCC | TGG | GGC | GTC | CTG | CTC | AAC | TCC | 1971 |
|---|---|---|---|---|---|---|---|---|---|---|---|---|---|---|---|---|
| Thr | Leu | Ser | Ser | Ala | Met | Trp | Phe | Ser | Trp | Gly | Val | Leu | Leu | Asn | Ser | |
| 555 | | | | | 560 | | | | | 565 | | | | | 570 | |

| GGC | ATC | GGG | GAA | GGC | GCC | CCC | AGA | AGC | TTC | TCA | GCG | CGC | ATC | CTG | GGC | 2019 |
| Gly | Ile | Gly | Glu | Gly | Ala | Pro | Arg | Ser | Phe | Ser | Ala | Arg | Ile | Leu | Gly | |
| | | | | 575 | | | | | 580 | | | | | 585 | | |

| ATG | GTG | TGG | GCC | GGC | TTT | GCC | ATG | ATC | ATC | GTG | GCC | TCC | TAC | ACC | GCC | 2067 |
| Met | Val | Trp | Ala | Gly | Phe | Ala | Met | Ile | Ile | Val | Ala | Ser | Tyr | Thr | Ala | |
| | | | 590 | | | | | 595 | | | | | 600 | | | |

| AAC | CTG | GCG | GCC | TTC | CTG | GTG | CTG | GAC | CGG | CCG | GAG | GAG | CGC | ATC | ACG | 2115 |
| Asn | Leu | Ala | Ala | Phe | Leu | Val | Leu | Asp | Arg | Pro | Glu | Glu | Arg | Ile | Thr | |
| | | 605 | | | | 610 | | | | | 615 | | | | | |

| GGC | ATC | AAC | GAC | CCT | CGG | CTG | AGG | AAC | CCC | TCG | GAC | AAG | TTT | ATC | TAC | 2163 |
| Gly | Ile | Asn | Asp | Pro | Arg | Leu | Arg | Asn | Pro | Ser | Asp | Lys | Phe | Ile | Tyr | |
| | 620 | | | | 625 | | | | | 630 | | | | | | |

| GCC | ACG | GTG | AAG | CAG | AGC | TCC | GTG | GAT | ATC | TAC | TTC | CGG | CGC | CAG | GTG | 2211 |
| Ala | Thr | Val | Lys | Gln | Ser | Ser | Val | Asp | Ile | Tyr | Phe | Arg | Arg | Gln | Val | |
| 635 | | | | | 640 | | | | | 645 | | | | | 650 | |

| GAG | CTG | AGC | ACC | ATG | TAC | CGG | CAT | ATG | GAG | AAG | CAC | AAC | TAC | GAG | AGT | 2259 |
| Glu | Leu | Ser | Thr | Met | Tyr | Arg | His | Met | Glu | Lys | His | Asn | Tyr | Glu | Ser | |
| | | | | 655 | | | | | 660 | | | | | 665 | | |

| GCG | GCG | GAG | GCC | ATC | CAG | GCC | GTG | AGA | GAC | AAC | AAG | CTG | CAT | GCC | TTC | 2307 |
| Ala | Ala | Glu | Ala | Ile | Gln | Ala | Val | Arg | Asp | Asn | Lys | Leu | His | Ala | Phe | |
| | | | 670 | | | | | 675 | | | | | 680 | | | |

| ATC | TGG | GAC | TCG | GCG | GTG | CTG | GAG | TTC | GAG | GCC | TCG | CAG | AAG | TGC | GAC | 2355 |
| Ile | Trp | Asp | Ser | Ala | Val | Leu | Glu | Phe | Glu | Ala | Ser | Gln | Lys | Cys | Asp | |
| | | 685 | | | | 690 | | | | | 695 | | | | | |

| CTG | GTG | ACG | ACT | GGA | GAG | CTG | TTT | TTC | CGC | TCG | GGC | TTC | GGC | ATA | GGC | 2403 |
| Leu | Val | Thr | Thr | Gly | Glu | Leu | Phe | Phe | Arg | Ser | Gly | Phe | Gly | Ile | Gly | |
| | 700 | | | | 705 | | | | | 710 | | | | | | |

| ATG | CGC | AAA | GAC | AGC | CCC | TGG | AAG | CAG | AAC | GTC | TCC | CTG | TCC | ATC | CTC | 2451 |
| Met | Arg | Lys | Asp | Ser | Pro | Trp | Lys | Gln | Asn | Val | Ser | Leu | Ser | Ile | Leu | |
| 715 | | | | | 720 | | | | | 725 | | | | | 730 | |

| AAG | TCC | CAC | GAG | AAT | GGC | TTC | ATG | GAA | GAC | CTG | GAC | AAG | ACG | TGG | GTT | 2499 |
| Lys | Ser | His | Glu | Asn | Gly | Phe | Met | Glu | Asp | Leu | Asp | Lys | Thr | Trp | Val | |
| | | | | 735 | | | | | 740 | | | | | 745 | | |

| CGG | TAT | CAG | GAA | TGT | GAC | TCG | CGC | AGC | AAC | GCC | CCT | GCG | ACC | CTT | ACT | 2547 |
| Arg | Tyr | Gln | Glu | Cys | Asp | Ser | Arg | Ser | Asn | Ala | Pro | Ala | Thr | Leu | Thr | |
| | | | 750 | | | | | 755 | | | | | 760 | | | |

| TTT | GAG | AAC | ATG | GCC | GGG | GTC | TTC | ATG | CTG | GTA | GCT | GGG | GGC | ATC | GTG | 2595 |
| Phe | Glu | Asn | Met | Ala | Gly | Val | Phe | Met | Leu | Val | Ala | Gly | Gly | Ile | Val | |
| | | 765 | | | | | 770 | | | | | 775 | | | | |

| GCC | GGG | ATC | TTC | CTG | ATT | TTC | ATC | GAG | ATT | GCC | TAC | AAG | CGG | CAC | AAG | 2643 |
| Ala | Gly | Ile | Phe | Leu | Ile | Phe | Ile | Glu | Ile | Ala | Tyr | Lys | Arg | His | Lys | |
| | 780 | | | | 785 | | | | | 790 | | | | | | |

| GAT | GCT | CGC | CGG | AAG | CAG | ATG | CAG | CTG | GCC | TTT | GCC | GCC | GTT | AAC | GTG | 2691 |
| Asp | Ala | Arg | Arg | Lys | Gln | Met | Gln | Leu | Ala | Phe | Ala | Ala | Val | Asn | Val | |
| 795 | | | | | 800 | | | | | 805 | | | | | 810 | |

| TGG | CGG | AAG | AAC | CTG | CAG | GAT | AGA | AAG | AGT | GGT | AGA | GCA | GAG | CCT | GAC | 2739 |
| Trp | Arg | Lys | Asn | Leu | Gln | Asp | Arg | Lys | Ser | Gly | Arg | Ala | Glu | Pro | Asp | |
| | | | | 815 | | | | | 820 | | | | | 825 | | |

| CCT | AAA | AAG | AAA | GCC | ACA | TTT | AGG | GCT | ATC | ACC | TCC | ACC | CTG | GCT | TCC | 2787 |
| Pro | Lys | Lys | Lys | Ala | Thr | Phe | Arg | Ala | Ile | Thr | Ser | Thr | Leu | Ala | Ser | |
| | | | 830 | | | | | 835 | | | | | 840 | | | |

| AGC | TTC | AAG | AGG | CGT | AGG | TCC | TCC | AAA | GAC | ACG | CTG | GCT | CGG | GAC | TGT | 2835 |
| Ser | Phe | Lys | Arg | Arg | Arg | Ser | Ser | Lys | Asp | Thr | Leu | Ala | Arg | Asp | Cys | |
| | | 845 | | | | | 850 | | | | | 855 | | | | |

| CTT | CAA | CCC | TGC | CCT | GCA | CCT | TGG | GCA | CGG | GAG | AGC | GCC | ACC | CGC | CCG | 2883 |

| Leu | Gln | Pro | Cys | Pro | Ala | Pro | Trp | Ala | Arg | Glu | Ser | Ala | Thr | Arg | Pro | |
|---|---|---|---|---|---|---|---|---|---|---|---|---|---|---|---|---|
| | 860 | | | | 865 | | | | | 870 | | | | | | |

| CCC | CCG | CCC | TCG | CTC | CGG | GTG | CGT | GAC | CGG | CCC | GCC | ACC | TTG | TAC | AGA | 2931 |
|---|---|---|---|---|---|---|---|---|---|---|---|---|---|---|---|---|
| Pro | Pro | Pro | Ser | Leu | Arg | Val | Arg | Asp | Arg | Pro | Ala | Thr | Leu | Tyr | Arg | |
| 875 | | | | | 880 | | | | | 885 | | | | | 890 | |

| ACC | AGC | ACT | CCC | AGG | GCC | CGA | GCG | CGT | GCC | TTC | CCC | GTG | CGC | AGC | CGC | 2979 |
|---|---|---|---|---|---|---|---|---|---|---|---|---|---|---|---|---|
| Thr | Ser | Thr | Pro | Arg | Ala | Arg | Ala | Arg | Ala | Phe | Pro | Val | Arg | Ser | Arg | |
| | | | | 895 | | | | | 900 | | | | | 905 | | |

| GCT | CTG | CCC | CTC | CGT | CCC | CAG | GGT | GCA | GGC | GCG | CAC | CGC | CCA | ACC | CCC | 3027 |
|---|---|---|---|---|---|---|---|---|---|---|---|---|---|---|---|---|
| Ala | Leu | Pro | Leu | Arg | Pro | Gln | Gly | Ala | Gly | Ala | His | Arg | Pro | Thr | Pro | |
| | | | 910 | | | | | 915 | | | | | 920 | | | |

| ACC | TCC | CGG | TGT | ATG | CAG | TGG | TGATGCCTAA | AGGAATGTCA | CG | | | | | | | 3070 |
|---|---|---|---|---|---|---|---|---|---|---|---|---|---|---|---|---|
| Thr | Ser | Arg | Cys | Met | Gln | Trp | | | | | | | | | | |
| | | 925 | | | | 930 | | | | | | | | | | |

( 2 ) INFORMATION FOR SEQ ID NO:40:

( i ) SEQUENCE CHARACTERISTICS:
        ( A ) LENGTH: 929 amino acids
        ( B ) TYPE: amino acid
        ( D ) TOPOLOGY: linear ( i i ) MOLECULE TYPE: protein ( x i ) SEQUENCE DESCRIPTION: SEQ ID NO:40:

| Met | Ser | Thr | Met | Arg | Leu | Leu | Thr | Leu | Ala | Leu | Leu | Phe | Ser | Cys | Ser |
|---|---|---|---|---|---|---|---|---|---|---|---|---|---|---|---|
| 1 | | | | 5 | | | | | 10 | | | | | 15 | |

| Val | Ala | Arg | Ala | Ala | Cys | Asp | Pro | Lys | Ile | Val | Asn | Ile | Gly | Ala | Val |
|---|---|---|---|---|---|---|---|---|---|---|---|---|---|---|---|
| | | | | 20 | | | | 25 | | | | | 30 | | |

| Leu | Ser | Thr | Arg | Lys | His | Glu | Gln | Met | Phe | Arg | Glu | Ala | Val | Asn | Gln |
|---|---|---|---|---|---|---|---|---|---|---|---|---|---|---|---|
| | | | 35 | | | | 40 | | | | | 45 | | | |

| Ala | Asn | Lys | Arg | His | Gly | Ser | Trp | Lys | Ile | Gln | Leu | Asn | Ala | Thr | Ser |
|---|---|---|---|---|---|---|---|---|---|---|---|---|---|---|---|
| | 50 | | | | | 55 | | | | | 60 | | | | |

| Val | Thr | His | Lys | Pro | Asn | Ala | Ile | Gln | Met | Ala | Leu | Ser | Val | Cys | Glu |
|---|---|---|---|---|---|---|---|---|---|---|---|---|---|---|---|
| 65 | | | | | 70 | | | | 75 | | | | | | 80 |

| Asp | Leu | Ile | Ser | Ser | Gln | Val | Tyr | Ala | Ile | Leu | Val | Ser | His | Pro | Pro |
|---|---|---|---|---|---|---|---|---|---|---|---|---|---|---|---|
| | | | | 85 | | | | | 90 | | | | | 95 | |

| Thr | Pro | Asn | Asp | His | Phe | Thr | Pro | Thr | Pro | Val | Ser | Tyr | Thr | Ala | Gly |
|---|---|---|---|---|---|---|---|---|---|---|---|---|---|---|---|
| | | | 100 | | | | | 105 | | | | | 110 | | |

| Phe | Tyr | Arg | Ile | Pro | Val | Leu | Gly | Leu | Thr | Thr | Arg | Met | Ser | Ile | Tyr |
|---|---|---|---|---|---|---|---|---|---|---|---|---|---|---|---|
| | | 115 | | | | | 120 | | | | | 125 | | | |

| Ser | Asp | Lys | Ser | Ile | His | Leu | Ser | Phe | Leu | Arg | Thr | Val | Pro | Pro | Tyr |
|---|---|---|---|---|---|---|---|---|---|---|---|---|---|---|---|
| | | 130 | | | | | 135 | | | | | 140 | | | |

| Ser | His | Gln | Ser | Ser | Val | Trp | Phe | Glu | Met | Met | Arg | Val | Tyr | Ser | Trp |
|---|---|---|---|---|---|---|---|---|---|---|---|---|---|---|---|
| 145 | | | | | 150 | | | | | 155 | | | | | 160 |

| Asn | His | Ile | Ile | Leu | Leu | Val | Ser | Asp | Asp | His | Glu | Gly | Arg | Ala | Ala |
|---|---|---|---|---|---|---|---|---|---|---|---|---|---|---|---|
| | | | | 165 | | | | | 170 | | | | | 175 | |

| Gln | Lys | Arg | Leu | Glu | Thr | Leu | Leu | Glu | Glu | Arg | Glu | Ser | Lys | Ser | Lys |
|---|---|---|---|---|---|---|---|---|---|---|---|---|---|---|---|
| | | | 180 | | | | | 185 | | | | | 190 | | |

| Lys | Arg | Asn | Tyr | Glu | Asn | Leu | Asp | Gln | Leu | Ser | Tyr | Asp | Asn | Lys | Arg |
|---|---|---|---|---|---|---|---|---|---|---|---|---|---|---|---|
| | | 195 | | | | | 200 | | | | | 205 | | | |

| Gly | Pro | Lys | Ala | Glu | Lys | Val | Leu | Gln | Phe | Asp | Pro | Gly | Thr | Lys | Asn |
|---|---|---|---|---|---|---|---|---|---|---|---|---|---|---|---|
| | 210 | | | | | 215 | | | | | 220 | | | | |

| Val | Thr | Ala | Leu | Leu | Met | Glu | Ala | Lys | Glu | Leu | Glu | Ala | Arg | Val | Ile |
|---|---|---|---|---|---|---|---|---|---|---|---|---|---|---|---|
| 225 | | | | | 230 | | | | | 235 | | | | | 240 |

| Ile | Leu | Ser | Ala | Ser | Glu | Asp | Asp | Ala | Ala | Thr | Val | Tyr | Arg | Ala | Ala |
|---|---|---|---|---|---|---|---|---|---|---|---|---|---|---|---|
| | | | | 245 | | | | | 250 | | | | | 255 | |

| Ala | Met | Leu | Asn | Met | Thr | Gly | Asn | Thr | Asn | Ile | Trp | Lys | Thr | Gly | Pro |
|---|---|---|---|---|---|---|---|---|---|---|---|---|---|---|---|

-continued

|   |   |   |   |   | 260 |   |   |   |   | 265 |   |   |   |   | 270 |   |
|---|---|---|---|---|---|---|---|---|---|---|---|---|---|---|---|---|

Leu Phe Lys Arg Val Leu Met Ser Ser Lys Tyr Ala Asp Gly Val Thr
            275                 280                 285

Gly Arg Val Glu Phe Asn Glu Asp Gly Asp Arg Lys Phe Ala Asn Tyr
    290                 295                 300

Ser Ile Met Asn Leu Gln Asn Arg Lys Leu Val Gln Val Gly Ile Tyr
305                 310                 315                 320

Asn Gly Thr His Val Ile Pro Asn Asp Arg Lys Ile Ile Trp Pro Gly
                325                 330                 335

Gly Glu Thr Glu Lys Pro Arg Gly Tyr Gln Met Ser Thr Arg Leu Lys
            340                 345                 350

Ile Val Thr Ile His Gln Glu Pro Phe Val Tyr Val Lys Pro Thr Leu
            355                 360                 365

Ser Asp Gly Thr Cys Lys Glu Phe Thr Val Asn Gly Asp Pro Val
    370                 375                 380

Lys Lys Val Ile Cys Thr Gly Pro Asn Asp Thr Ser Pro Gly Ser Pro
385                 390                 395                 400

Arg His Thr Val Pro Gln Cys Cys Tyr Gly Phe Cys Ile Asp Leu Leu
                405                 410                 415

Ile Lys Leu Ala Arg Thr Met Asn Phe Thr Tyr Glu Val His Leu Val
            420                 425                 430

Ala Asp Gly Lys Phe Gly Thr Gln Glu Arg Val Asn Asn Ser Asn Lys
            435                 440                 445

Lys Glu Trp Asn Gly Met Met Gly Glu Leu Leu Ser Gly Gln Ala Asp
        450                 455                 460

Met Ile Val Ala Pro Leu Thr Ile Asn Asn Glu Arg Ala Gln Tyr Ile
465                 470                 475                 480

Glu Phe Ser Lys Pro Phe Lys Tyr Gln Gly Leu Thr Ile Leu Val Lys
                485                 490                 495

Lys Glu Ile Pro Arg Ser Thr Leu Asp Ser Phe Met Gln Pro Phe Gln
            500                 505                 510

Ser Thr Leu Trp Leu Leu Val Gly Leu Ser Val His Val Val Ala Val
        515                 520                 525

Met Leu Tyr Leu Leu Asp Arg Phe Ser Pro Phe Gly Arg Phe Lys Val
    530                 535                 540

Asn Ser Glu Glu Glu Glu Glu Asp Ala Leu Thr Leu Ser Ser Ala Met
545                 550                 555                 560

Trp Phe Ser Trp Gly Val Leu Leu Asn Ser Gly Ile Gly Glu Gly Ala
                565                 570                 575

Pro Arg Ser Phe Ser Ala Arg Ile Leu Gly Met Val Trp Ala Gly Phe
            580                 585                 590

Ala Met Ile Ile Val Ala Ser Tyr Thr Ala Asn Leu Ala Ala Phe Leu
        595                 600                 605

Val Leu Asp Arg Pro Glu Glu Arg Ile Thr Gly Ile Asn Asp Pro Arg
    610                 615                 620

Leu Arg Asn Pro Ser Asp Lys Phe Ile Tyr Ala Thr Val Lys Gln Ser
625                 630                 635                 640

Ser Val Asp Ile Tyr Phe Arg Arg Gln Val Glu Leu Ser Thr Met Tyr
                645                 650                 655

Arg His Met Glu Lys His Asn Tyr Glu Ser Ala Ala Glu Ala Ile Gln
            660                 665                 670

Ala Val Arg Asp Asn Lys Leu His Ala Phe Ile Trp Asp Ser Ala Val
        675                 680                 685

| Leu | Glu | Phe | Glu | Ala | Ser | Gln | Lys | Cys | Asp | Leu | Val | Thr | Thr | Gly | Glu |
|---|---|---|---|---|---|---|---|---|---|---|---|---|---|---|---|
| 690 | | | | | 695 | | | | | 700 | | | | | |

| Leu | Phe | Phe | Arg | Ser | Gly | Phe | Gly | Ile | Gly | Met | Arg | Lys | Asp | Ser | Pro |
|---|---|---|---|---|---|---|---|---|---|---|---|---|---|---|---|
| 705 | | | | | 710 | | | | 715 | | | | | | 720 |

| Trp | Lys | Gln | Asn | Val | Ser | Leu | Ser | Ile | Leu | Lys | Ser | His | Glu | Asn | Gly |
|---|---|---|---|---|---|---|---|---|---|---|---|---|---|---|---|
| | | | | 725 | | | | | 730 | | | | | 735 | |

| Phe | Met | Glu | Asp | Leu | Asp | Lys | Thr | Trp | Val | Arg | Tyr | Gln | Glu | Cys | Asp |
|---|---|---|---|---|---|---|---|---|---|---|---|---|---|---|---|
| | | | 740 | | | | 745 | | | | | 750 | | | |

| Ser | Arg | Ser | Asn | Ala | Pro | Ala | Thr | Leu | Thr | Phe | Glu | Asn | Met | Ala | Gly |
|---|---|---|---|---|---|---|---|---|---|---|---|---|---|---|---|
| | | 755 | | | | | 760 | | | | | 765 | | | |

| Val | Phe | Met | Leu | Val | Ala | Gly | Gly | Ile | Val | Ala | Gly | Ile | Phe | Leu | Ile |
|---|---|---|---|---|---|---|---|---|---|---|---|---|---|---|---|
| | 770 | | | | | 775 | | | | | 780 | | | | |

| Phe | Ile | Glu | Ile | Ala | Tyr | Lys | Arg | His | Lys | Asp | Ala | Arg | Arg | Lys | Gln |
|---|---|---|---|---|---|---|---|---|---|---|---|---|---|---|---|
| 785 | | | | | 790 | | | | | 795 | | | | | 800 |

| Met | Gln | Leu | Ala | Phe | Ala | Ala | Val | Asn | Val | Trp | Arg | Lys | Asn | Leu | Gln |
|---|---|---|---|---|---|---|---|---|---|---|---|---|---|---|---|
| | | | | 805 | | | | | 810 | | | | | 815 | |

| Asp | Arg | Lys | Ser | Gly | Arg | Ala | Glu | Pro | Asp | Pro | Lys | Lys | Lys | Ala | Thr |
|---|---|---|---|---|---|---|---|---|---|---|---|---|---|---|---|
| | | | 820 | | | | | 825 | | | | | 830 | | |

| Phe | Arg | Ala | Ile | Thr | Ser | Thr | Leu | Ala | Ser | Ser | Phe | Lys | Arg | Arg | Arg |
|---|---|---|---|---|---|---|---|---|---|---|---|---|---|---|---|
| | | 835 | | | | | 840 | | | | | 845 | | | |

| Ser | Ser | Lys | Asp | Thr | Leu | Ala | Arg | Asp | Cys | Leu | Gln | Pro | Cys | Pro | Ala |
|---|---|---|---|---|---|---|---|---|---|---|---|---|---|---|---|
| 850 | | | | | 855 | | | | | 860 | | | | | |

| Pro | Trp | Ala | Arg | Glu | Ser | Ala | Thr | Arg | Pro | Pro | Pro | Pro | Ser | Leu | Arg |
|---|---|---|---|---|---|---|---|---|---|---|---|---|---|---|---|
| 865 | | | | | 870 | | | | | 875 | | | | | 880 |

| Val | Arg | Asp | Arg | Pro | Ala | Thr | Leu | Tyr | Arg | Thr | Ser | Thr | Pro | Arg | Ala |
|---|---|---|---|---|---|---|---|---|---|---|---|---|---|---|---|
| | | | | 885 | | | | | 890 | | | | | 895 | |

| Arg | Ala | Arg | Ala | Phe | Pro | Val | Arg | Ser | Arg | Ala | Leu | Pro | Leu | Arg | Pro |
|---|---|---|---|---|---|---|---|---|---|---|---|---|---|---|---|
| | | | 900 | | | | | 905 | | | | | 910 | | |

| Gln | Gly | Ala | Gly | Ala | His | Arg | Pro | Thr | Pro | Thr | Ser | Arg | Cys | Met | Gln |
|---|---|---|---|---|---|---|---|---|---|---|---|---|---|---|---|
| | | | 915 | | | | | 920 | | | | | 925 | | |

Trp (2) INFORMATION FOR SEQ ID NO:41:

(i) SEQUENCE CHARACTERISTICS:
        (A) LENGTH: 2326 base pairs
        (B) TYPE: nucleic acid
        (C) STRANDEDNESS: both
        (D) TOPOLOGY: both (ii) MOLECULE TYPE: cDNA (ix) FEATURE:
        (A) NAME/KEY: CDS
        (B) LOCATION: 3..2324

(xi) SEQUENCE DESCRIPTION: SEQ ID NO:41:

| CC | GGC | CAC | GTG | TGG | CTG | GTG | CCC | AAC | CTG | GCG | CTG | GGC | AGC | ACC | GAT | 47 |
|---|---|---|---|---|---|---|---|---|---|---|---|---|---|---|---|---|
| | Gly | His | Val | Trp | Leu | Val | Pro | Asn | Leu | Ala | Leu | Gly | Ser | Thr | Asp | |
| | 1 | | | | 5 | | | | | 10 | | | | | 15 | |

| GCG | CCC | CCC | GCC | ACC | TTC | CCC | GTG | GGC | CTC | ATC | AGC | GTC | GTC | ACC | GAG | 95 |
|---|---|---|---|---|---|---|---|---|---|---|---|---|---|---|---|---|
| Ala | Pro | Pro | Ala | Thr | Phe | Pro | Val | Gly | Leu | Ile | Ser | Val | Val | Thr | Glu | |
| | | | | 20 | | | | | 25 | | | | | 30 | | |

| AGC | TGG | CGC | CTC | AGC | CTG | CGC | CAG | AAG | GTG | CGC | GAC | GGC | GTG | GCC | ATT | 143 |
|---|---|---|---|---|---|---|---|---|---|---|---|---|---|---|---|---|
| Ser | Trp | Arg | Leu | Ser | Leu | Arg | Gln | Lys | Val | Arg | Asp | Gly | Val | Ala | Ile | |
| | | | 35 | | | | | 40 | | | | | 45 | | | |

| CTG | GCC | CTG | GGC | GCC | CAC | AGC | TAC | TGG | CGC | CAG | CAT | GGA | ACC | CTG | CCA | 191 |
|---|---|---|---|---|---|---|---|---|---|---|---|---|---|---|---|---|
| Leu | Ala | Leu | Gly | Ala | His | Ser | Tyr | Trp | Arg | Gln | His | Gly | Thr | Leu | Pro | |
| | | | 50 | | | | | 55 | | | | | 60 | | | |

| | | | | | | | | | | | | | | | | |
|---|---|---|---|---|---|---|---|---|---|---|---|---|---|---|---|---|
| GCC | CCG | GCC | GGG | GAC | TGC | CGT | GTT | CAC | CCT | GGG | CCC | GTC | AGC | CCT | GCC | 239 |
| Ala | Pro | Ala | Gly | Asp | Cys | Arg | Val | His | Pro | Gly | Pro | Val | Ser | Pro | Ala | |
| | 65 | | | | 70 | | | | 75 | | | | | | | |
| CGG | GAG | GCC | TTC | TAC | AGG | CAC | CTA | CTG | AAT | GTC | ACC | TGG | GAG | GGC | CGA | 287 |
| Arg | Glu | Ala | Phe | Tyr | Arg | His | Leu | Leu | Asn | Val | Thr | Trp | Glu | Gly | Arg | |
| 80 | | | | | 85 | | | | | 90 | | | | | 95 | |
| GAC | TTC | TCC | TTC | AGC | CCT | GGT | GGG | TAC | CTG | GTC | CAG | CCC | ACC | ATG | GTG | 335 |
| Asp | Phe | Ser | Phe | Ser | Pro | Gly | Gly | Tyr | Leu | Val | Gln | Pro | Thr | Met | Val | |
| | | | | 100 | | | | | 105 | | | | | 110 | | |
| GTG | ATC | GCC | CTC | AAC | CGG | CAC | CGC | CTC | TGG | GAG | ATG | GTG | GGG | CGC | TGG | 383 |
| Val | Ile | Ala | Leu | Asn | Arg | His | Arg | Leu | Trp | Glu | Met | Val | Gly | Arg | Trp | |
| | | | | 115 | | | | | 120 | | | | | 125 | | |
| GAG | CAT | GGC | GTC | CTA | TAC | ATG | AAG | TAC | CCC | GTG | TGG | CCT | CGC | TAC | AGT | 431 |
| Glu | His | Gly | Val | Leu | Tyr | Met | Lys | Tyr | Pro | Val | Trp | Pro | Arg | Tyr | Ser | |
| | | 130 | | | | | 135 | | | | | 140 | | | | |
| GCC | TCT | CTG | CAG | CCT | GTG | GTG | GAC | AGT | CGG | CAC | CTG | ACG | GTG | GCC | ACG | 479 |
| Ala | Ser | Leu | Gln | Pro | Val | Val | Asp | Ser | Arg | His | Leu | Thr | Val | Ala | Thr | |
| | 145 | | | | | 150 | | | | | 155 | | | | | |
| CTG | GAA | GAG | CGG | CCC | TTT | GTC | ATC | GTG | GAG | AGC | CCT | GAC | CCT | GGC | ACA | 527 |
| Leu | Glu | Glu | Arg | Pro | Phe | Val | Ile | Val | Glu | Ser | Pro | Asp | Pro | Gly | Thr | |
| 160 | | | | | 165 | | | | | 170 | | | | | 175 | |
| GGA | GGC | TGT | GTC | CCC | AAC | ACC | GTG | CCC | TGC | CGC | AGG | CAG | AGC | AAC | CAC | 575 |
| Gly | Gly | Cys | Val | Pro | Asn | Thr | Val | Pro | Cys | Arg | Arg | Gln | Ser | Asn | His | |
| | | | | 180 | | | | | 185 | | | | | 190 | | |
| ACC | TTC | AGC | AGC | GGG | GAC | GTG | GCC | CCC | TAC | ACC | AAG | CTC | TGC | TGT | AAG | 623 |
| Thr | Phe | Ser | Ser | Gly | Asp | Val | Ala | Pro | Tyr | Thr | Lys | Leu | Cys | Cys | Lys | |
| | | | 195 | | | | | 200 | | | | | 205 | | | |
| GGA | TTC | TGC | ATC | GAC | ATC | CTC | AAG | AAG | CTG | GCC | AGA | GTG | GTC | AAA | TTC | 671 |
| Gly | Phe | Cys | Ile | Asp | Ile | Leu | Lys | Lys | Leu | Ala | Arg | Val | Val | Lys | Phe | |
| | | 210 | | | | | 215 | | | | | 220 | | | | |
| TCC | TAC | GAC | CTG | TAC | CTG | GTG | ACC | AAC | GGC | AAG | CAT | GGC | AAG | CGG | GTG | 719 |
| Ser | Tyr | Asp | Leu | Tyr | Leu | Val | Thr | Asn | Gly | Lys | His | Gly | Lys | Arg | Val | |
| | 225 | | | | | 230 | | | | | 235 | | | | | |
| CGC | GGC | GTA | TGG | AAC | GGC | ATG | ATT | GGG | GAG | GTG | TAC | TAC | AAG | CGG | GCA | 767 |
| Arg | Gly | Val | Trp | Asn | Gly | Met | Ile | Gly | Glu | Val | Tyr | Tyr | Lys | Arg | Ala | |
| 240 | | | | | 245 | | | | | 250 | | | | | 255 | |
| GAC | ATG | GCC | ATC | GGC | TCC | CTC | ACC | ATC | AAT | GAG | GAA | CGC | TCC | GAG | ATC | 815 |
| Asp | Met | Ala | Ile | Gly | Ser | Leu | Thr | Ile | Asn | Glu | Glu | Arg | Ser | Glu | Ile | |
| | | | | 260 | | | | | 265 | | | | | 270 | | |
| GTA | GAC | TTC | TCT | GTA | CCC | TTT | GTG | GAG | ACG | GGC | ATC | AGT | GTG | ATG | GTG | 863 |
| Val | Asp | Phe | Ser | Val | Pro | Phe | Val | Glu | Thr | Gly | Ile | Ser | Val | Met | Val | |
| | | | 275 | | | | | 280 | | | | | 285 | | | |
| GCT | CGC | AGC | AAT | GGC | ACC | GTC | TCC | CCC | TCG | GCC | TTC | TTG | GAG | CCA | TAT | 911 |
| Ala | Arg | Ser | Asn | Gly | Thr | Val | Ser | Pro | Ser | Ala | Phe | Leu | Glu | Pro | Tyr | |
| | | 290 | | | | | 295 | | | | | 300 | | | | |
| AGC | CCT | GCA | GTG | TGG | GTG | ATG | ATG | TTT | GTC | ATG | TGC | CTC | ACT | GTG | GTG | 959 |
| Ser | Pro | Ala | Val | Trp | Val | Met | Met | Phe | Val | Met | Cys | Leu | Thr | Val | Val | |
| | 305 | | | | | 310 | | | | | 315 | | | | | |
| GCC | ATC | ACC | GTC | TTC | ATG | TTC | GAG | TAC | TTC | AGC | CCT | GTC | AGC | TAC | AAC | 1007 |
| Ala | Ile | Thr | Val | Phe | Met | Phe | Glu | Tyr | Phe | Ser | Pro | Val | Ser | Tyr | Asn | |
| 320 | | | | | 325 | | | | | 330 | | | | | 335 | |
| CAG | AAC | CTC | ACC | AGA | GGC | AAG | AAG | TCC | GGG | GGC | CCA | GCT | TTC | ACT | ATC | 1055 |
| Gln | Asn | Leu | Thr | Arg | Gly | Lys | Lys | Ser | Gly | Gly | Pro | Ala | Phe | Thr | Ile | |
| | | | | 340 | | | | | 345 | | | | | 350 | | |
| GGC | AAG | TCC | GTG | TGG | CTG | CTG | TGG | GCG | CTG | GTC | TTC | AAC | AAC | TCA | GTG | 1103 |
| Gly | Lys | Ser | Val | Trp | Leu | Leu | Trp | Ala | Leu | Val | Phe | Asn | Asn | Ser | Val | |
| | | | 355 | | | | | 360 | | | | | 365 | | | |
| CCC | ATC | GAG | AAC | CCG | CGG | GGC | ACC | ACC | AGC | AAG | ATC | ATG | GTT | CTG | GTC | 1151 |
| Pro | Ile | Glu | Asn | Pro | Arg | Gly | Thr | Thr | Ser | Lys | Ile | Met | Val | Leu | Val | |
| | | 370 | | | | | 375 | | | | | 380 | | | | |

```
TGG GCC TTC TTT GCT GTC ATC TTC CTC GCC AGA TAC ACG GCC AAC CTG       1199
Trp Ala Phe Phe Ala Val Ile Phe Leu Ala Arg Tyr Thr Ala Asn Leu
    385             390                 395

GCC GCC TTC ATG ATC CAA GAG CAA TAC ATC GAC ACT GTG TCG GGC CTC       1247
Ala Ala Phe Met Ile Gln Glu Gln Tyr Ile Asp Thr Val Ser Gly Leu
400             405                 410                         415

AGT GAC AAG AAG TTT CAG CGG CCT CAA GAT CAG TAC CCA CCT TTC CGC       1295
Ser Asp Lys Lys Phe Gln Arg Pro Gln Asp Gln Tyr Pro Pro Phe Arg
                    420                 425                 430

TTC GGC ACG GTG CCC AAC GGC AGC ACG GAG CGG AAC ATC CGC AGT AAC       1343
Phe Gly Thr Val Pro Asn Gly Ser Thr Glu Arg Asn Ile Arg Ser Asn
            435                 440                 445

TAC CGT GAC ATG CAC ACC CAC ATG GTC AAG TTC AAC CAG CGC TCG GTG       1391
Tyr Arg Asp Met His Thr His Met Val Lys Phe Asn Gln Arg Ser Val
            450             455                 460

GAG GAC GCG CTC ACC AGC CTC AAG ATG GGC AAG GAC GAG GGC TGC AAG       1439
Glu Asp Ala Leu Thr Ser Leu Lys Met Gly Lys Asp Glu Gly Cys Lys
    465                 470                 475

CTG GTC ACC ATT GGG TCT GGC AAG GTC TTT GCT ACC ACT GGC TAC GGC       1487
Leu Val Thr Ile Gly Ser Gly Lys Val Phe Ala Thr Thr Gly Tyr Gly
480             485                 490                         495

ATC GCC ATG CAG AAG GAC TCC CAC TGG AAG CGG GCC ATA GAC CTG GCG       1535
Ile Ala Met Gln Lys Asp Ser His Trp Lys Arg Ala Ile Asp Leu Ala
                    500                 505                 510

CTC TTG CAG TTC CTG GGG GAC GGA GAG ACA CAG AAA CTG GAG ACA GTG       1583
Leu Leu Gln Phe Leu Gly Asp Gly Glu Thr Gln Lys Leu Glu Thr Val
            515                 520                 525

TGG CTC TCA GGG ATC TGC CAG AAT GAG AAG AAC GAG GTG ATG AGC AGC       1631
Trp Leu Ser Gly Ile Cys Gln Asn Glu Lys Asn Glu Val Met Ser Ser
            530                 535                 540

AAG CTG GAC ATC GAC AAC ATG GGA GGC GTC TTC TAC ATG CTG CTG GTG       1679
Lys Leu Asp Ile Asp Asn Met Gly Gly Val Phe Tyr Met Leu Leu Val
    545                 550                 555

GCC ATG GGG CTG GCC CTG CTG GTC TTC GCC TGG GAG CAC CTG GTC TAC       1727
Ala Met Gly Leu Ala Leu Leu Val Phe Ala Trp Glu His Leu Val Tyr
560             565                 570                         575

TGG AAG CTG CGC CAC TCG GTG CCC AAC TCA TCC CAG CTG GAC TTC CTG       1775
Trp Lys Leu Arg His Ser Val Pro Asn Ser Ser Gln Leu Asp Phe Leu
                580                 585                 590

CTG GCT TTC AGC AGG GGC ATC TAC AGC TGC TTC AGC GGG GTG CAG AGC       1823
Leu Ala Phe Ser Arg Gly Ile Tyr Ser Cys Phe Ser Gly Val Gln Ser
            595                 600                 605

CTC GCC AGC CCA CCG CGG CAG GCC AGC CCG GAC CTC ACG GCC AGC TCG       1871
Leu Ala Ser Pro Pro Arg Gln Ala Ser Pro Asp Leu Thr Ala Ser Ser
            610                 615                 620

GCC CAG GCC AGC GTG CTC AAG ATT CTG CAG GCA GCC CGC GAC ATG GTG       1919
Ala Gln Ala Ser Val Leu Lys Ile Leu Gln Ala Ala Arg Asp Met Val
    625                 630                 635

ACC ACG GCG GGC GTA AGC AAC TCC CTG GAC CGC GCC ACT CGC ACC ATC       1967
Thr Thr Ala Gly Val Ser Asn Ser Leu Asp Arg Ala Thr Arg Thr Ile
640             645                 650                 655

GAG AAT TGG GGT GGC GGC CGC CGT GCG CCC CCA CCG TCC CCC TGC CCG       2015
Glu Asn Trp Gly Gly Gly Arg Arg Ala Pro Pro Pro Ser Pro Cys Pro
                    660                 665                 670

ACC CCG CGG TCT GGC CCC AGC CCA TGC CTG CCC ACC CCC GAC CCG CCC       2063
Thr Pro Arg Ser Gly Pro Ser Pro Cys Leu Pro Thr Pro Asp Pro Pro
            675                 680                 685

CCA GAG CCG AGC CCC ACG GGC TGG GGA CCG CCA GAC GGG GGT CGC GCG       2111
Pro Glu Pro Ser Pro Thr Gly Trp Gly Pro Pro Asp Gly Gly Arg Ala
    690                 695                 700
```

| | | | | | | | | | | | | | | | | |
|---|---|---|---|---|---|---|---|---|---|---|---|---|---|---|---|---|
| GCG | CTT | GTG | CGC | AGG | GCT | CCG | CAG | CCC | CCG | GGC | CGC | CCC | CCG | ACG | CCG | 2159 |
| Ala | Leu | Val | Arg | Arg | Ala | Pro | Gln | Pro | Pro | Gly | Arg | Pro | Pro | Thr | Pro | |
| | 705 | | | | | 710 | | | | | 715 | | | | | |
| GGG | CCG | CCC | CTG | TCC | GAC | GTC | TCC | CGA | GTG | TCG | CGC | CGC | CCA | GCC | TGG | 2207 |
| Gly | Pro | Pro | Leu | Ser | Asp | Val | Ser | Arg | Val | Ser | Arg | Arg | Pro | Ala | Trp | |
| 720 | | | | | 725 | | | | | 730 | | | | | 735 | |
| GAG | GCG | CGG | TGG | CCG | GTG | CGG | ACC | GGG | CAC | TGC | GGG | AGG | CAC | CTC | TCG | 2255 |
| Glu | Ala | Arg | Trp | Pro | Val | Arg | Thr | Gly | His | Cys | Gly | Arg | His | Leu | Ser | |
| | | | | 740 | | | | | 745 | | | | | 750 | | |
| GCC | TCC | GAG | CGG | CCC | CTG | TCG | CCC | GCG | CGC | TGT | CAC | TAC | AGC | TCC | TTT | 2303 |
| Ala | Ser | Glu | Arg | Pro | Leu | Ser | Pro | Ala | Arg | Cys | His | Tyr | Ser | Ser | Phe | |
| | | | 755 | | | | | 760 | | | | | 765 | | | |
| CCT | CGA | GCC | GAC | CGA | TCC | GGC | CG | | | | | | | | | 2326 |
| Pro | Arg | Ala | Asp | Arg | Ser | Gly | | | | | | | | | | |
| | | 770 | | | | | | | | | | | | | | |

( 2 ) INFORMATION FOR SEQ ID NO:42:

( i ) SEQUENCE CHARACTERISTICS:
        ( A ) LENGTH: 774 amino acids
        ( B ) TYPE: amino acid
        ( D ) TOPOLOGY: linear ( i i ) MOLECULE TYPE: protein ( x i ) SEQUENCE DESCRIPTION: SEQ ID NO:42:

| | | | | | | | | | | | | | | |
|---|---|---|---|---|---|---|---|---|---|---|---|---|---|---|
| Gly | His | Val | Trp | Leu | Val | Pro | Asn | Leu | Ala | Leu | Gly | Ser | Thr | Asp | Ala |
| 1 | | | | 5 | | | | | 10 | | | | | 15 | |
| Pro | Pro | Ala | Thr | Phe | Pro | Val | Gly | Leu | Ile | Ser | Val | Val | Thr | Glu | Ser |
| | | | 20 | | | | | 25 | | | | | 30 | | |
| Trp | Arg | Leu | Ser | Leu | Arg | Gln | Lys | Val | Arg | Asp | Gly | Val | Ala | Ile | Leu |
| | | 35 | | | | | 40 | | | | | 45 | | | |
| Ala | Leu | Gly | Ala | His | Ser | Tyr | Trp | Arg | Gln | His | Gly | Thr | Leu | Pro | Ala |
| | 50 | | | | | 55 | | | | | 60 | | | | |
| Pro | Ala | Gly | Asp | Cys | Arg | Val | His | Pro | Gly | Pro | Val | Ser | Pro | Ala | Arg |
| 65 | | | | | 70 | | | | | 75 | | | | | 80 |
| Glu | Ala | Phe | Tyr | Arg | His | Leu | Leu | Asn | Val | Thr | Trp | Glu | Gly | Arg | Asp |
| | | | | 85 | | | | | 90 | | | | | 95 | |
| Phe | Ser | Phe | Ser | Pro | Gly | Gly | Tyr | Leu | Val | Gln | Pro | Thr | Met | Val | Val |
| | | | | 100 | | | | | 105 | | | | | 110 | |
| Ile | Ala | Leu | Asn | Arg | His | Arg | Leu | Trp | Glu | Met | Val | Gly | Arg | Trp | Glu |
| | | | 115 | | | | | 120 | | | | | 125 | | |
| His | Gly | Val | Leu | Tyr | Met | Lys | Tyr | Pro | Val | Trp | Pro | Arg | Tyr | Ser | Ala |
| | | 130 | | | | | 135 | | | | | 140 | | | |
| Ser | Leu | Gln | Pro | Val | Val | Asp | Ser | Arg | His | Leu | Thr | Val | Ala | Thr | Leu |
| 145 | | | | | 150 | | | | | 155 | | | | | 160 |
| Glu | Glu | Arg | Pro | Phe | Val | Ile | Val | Glu | Ser | Pro | Asp | Pro | Gly | Thr | Gly |
| | | | | 165 | | | | | 170 | | | | | 175 | |
| Gly | Cys | Val | Pro | Asn | Thr | Val | Pro | Cys | Arg | Arg | Gln | Ser | Asn | His | Thr |
| | | | 180 | | | | | 185 | | | | | 190 | | |
| Phe | Ser | Ser | Gly | Asp | Val | Ala | Pro | Tyr | Thr | Lys | Leu | Cys | Cys | Lys | Gly |
| | | | 195 | | | | | 200 | | | | | 205 | | |
| Phe | Cys | Ile | Asp | Ile | Leu | Lys | Lys | Leu | Ala | Arg | Val | Val | Lys | Phe | Ser |
| | | 210 | | | | | 215 | | | | | 220 | | | |
| Tyr | Asp | Leu | Tyr | Leu | Val | Thr | Asn | Gly | Lys | His | Gly | Lys | Arg | Val | Arg |
| 225 | | | | | 230 | | | | | 235 | | | | | 240 |
| Gly | Val | Trp | Asn | Gly | Met | Ile | Gly | Glu | Val | Tyr | Tyr | Lys | Arg | Ala | Asp |
| | | | | 245 | | | | | 250 | | | | | 255 | |

```
Met Ala Ile Gly Ser Leu Thr Ile Asn Glu Glu Arg Ser Glu Ile Val
                260                 265                 270
Asp Phe Ser Val Pro Phe Val Glu Thr Gly Ile Ser Val Met Val Ala
            275                 280                 285
Arg Ser Asn Gly Thr Val Ser Pro Ser Ala Phe Glu Pro Tyr Ser
    290                 295                 300
Pro Ala Val Trp Val Met Met Phe Val Met Cys Leu Thr Val Val Ala
305             310                 315                 320
Ile Thr Val Phe Met Phe Glu Tyr Phe Ser Pro Val Ser Tyr Asn Gln
                325                 330                 335
Asn Leu Thr Arg Gly Lys Lys Ser Gly Pro Ala Phe Thr Ile Gly
            340                 345                 350
Lys Ser Val Trp Leu Leu Trp Ala Leu Val Phe Asn Asn Ser Val Pro
            355                 360                 365
Ile Glu Asn Pro Arg Gly Thr Thr Ser Lys Ile Met Val Leu Val Trp
    370                 375                 380
Ala Phe Phe Ala Val Ile Phe Leu Ala Arg Tyr Thr Ala Asn Leu Ala
385                 390                 395                 400
Ala Phe Met Ile Gln Glu Gln Tyr Ile Asp Thr Val Ser Gly Leu Ser
                405                 410                 415
Asp Lys Lys Phe Gln Arg Pro Gln Asp Gln Tyr Pro Pro Phe Arg Phe
            420                 425                 430
Gly Thr Val Pro Asn Gly Ser Thr Glu Arg Asn Ile Arg Ser Asn Tyr
        435                 440                 445
Arg Asp Met His Thr His Met Val Lys Phe Asn Gln Arg Ser Val Glu
    450                 455                 460
Asp Ala Leu Thr Ser Leu Lys Met Gly Lys Asp Glu Gly Cys Lys Leu
465                 470                 475                 480
Val Thr Ile Gly Ser Gly Lys Val Phe Ala Thr Thr Gly Tyr Gly Ile
                485                 490                 495
Ala Met Gln Lys Asp Ser His Trp Lys Arg Ala Ile Asp Leu Ala Leu
            500                 505                 510
Leu Gln Phe Leu Gly Asp Gly Glu Thr Gln Lys Leu Glu Thr Val Trp
        515                 520                 525
Leu Ser Gly Ile Cys Gln Asn Glu Lys Asn Glu Val Met Ser Ser Lys
    530                 535                 540
Leu Asp Ile Asp Asn Met Gly Gly Val Phe Tyr Met Leu Leu Val Ala
545                 550                 555                 560
Met Gly Leu Ala Leu Leu Val Phe Ala Trp Glu His Leu Val Tyr Trp
                565                 570                 575
Lys Leu Arg His Ser Val Pro Asn Ser Ser Gln Leu Asp Phe Leu Leu
            580                 585                 590
Ala Phe Ser Arg Gly Ile Tyr Ser Cys Phe Ser Gly Val Gln Ser Leu
        595                 600                 605
Ala Ser Pro Pro Arg Gln Ala Ser Pro Asp Leu Thr Ala Ser Ser Ala
    610                 615                 620
Gln Ala Ser Val Leu Lys Ile Leu Gln Ala Ala Arg Asp Met Val Thr
625                 630                 635                 640
Thr Ala Gly Val Ser Asn Ser Leu Asp Arg Ala Thr Arg Thr Ile Glu
                645                 650                 655
Asn Trp Gly Gly Gly Arg Arg Ala Pro Pro Pro Ser Pro Cys Pro Thr
            660                 665                 670
Pro Arg Ser Gly Pro Ser Pro Cys Leu Pro Thr Pro Asp Pro Pro Pro
        675                 680                 685
```

```
Glu  Pro  Ser  Pro  Thr  Gly  Trp  Gly  Pro  Pro  Asp  Gly  Gly  Arg  Ala  Ala
     690                 695                 700

Leu  Val  Arg  Arg  Ala  Pro  Gln  Pro  Pro  Gly  Arg  Pro  Pro  Thr  Pro  Gly
705                      710                 715                           720

Pro  Pro  Leu  Ser  Asp  Val  Ser  Arg  Val  Ser  Arg  Arg  Pro  Ala  Trp  Glu
               725                      730                      735

Ala  Arg  Trp  Pro  Val  Arg  Thr  Gly  His  Cys  Gly  Arg  His  Leu  Ser  Ala
          740                      745                      750

Ser  Glu  Arg  Pro  Leu  Ser  Pro  Ala  Arg  Cys  His  Tyr  Ser  Ser  Phe  Pro
          755                      760                 765

Arg  Ala  Asp  Arg  Ser  Gly
770
```

(2) INFORMATION FOR SEQ ID NO:43:

(i) SEQUENCE CHARACTERISTICS:
        (A) LENGTH: 3698 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 3...3698

(xi) SEQUENCE DESCRIPTION: SEQ ID NO:43:

```
TG  GAG  ATC  CAG  CCG  CTC  ACA  GTT  GGG  GTC  AAC  ACC  ACC  AAC  CCC  AGC      47
    Glu  Ile  Gln  Pro  Leu  Thr  Val  Gly  Val  Asn  Thr  Thr  Asn  Pro  Ser
    1                   5                        10                      15

AGC  CTC  CTC  ACC  CAG  ATC  TGC  GGC  CTC  CTG  GGT  GCT  GCC  CAC  GTC  CAC     95
Ser  Leu  Leu  Thr  Gln  Ile  Cys  Gly  Leu  Leu  Gly  Ala  Ala  His  Val  His
                20                      25                      30

GGC  ATT  GTC  TTT  GAG  GAC  AAC  GTG  GAC  ACC  GAG  GCG  GTG  GCC  CAG  ATC    143
Gly  Ile  Val  Phe  Glu  Asp  Asn  Val  Asp  Thr  Glu  Ala  Val  Ala  Gln  Ile
                35                      40                      45

CTT  GAC  TTC  ATC  TCC  TCC  CAG  ACC  CAT  GTG  CCC  ATC  CTC  AGC  ATC  AGC    191
Leu  Asp  Phe  Ile  Ser  Ser  Gln  Thr  His  Val  Pro  Ile  Leu  Ser  Ile  Ser
          50                      55                      60

GGA  GGC  TCT  GCT  GTG  GTC  CTC  ACC  CCC  AAG  GAG  CCG  GGC  TCC  GCC  TTC    239
Gly  Gly  Ser  Ala  Val  Val  Leu  Thr  Pro  Lys  Glu  Pro  Gly  Ser  Ala  Phe
65                       70                      75

CTG  CAG  CTG  GGC  GTG  TCC  CTG  GAG  CAG  CAG  CTG  CAG  GTG  CTG  TTC  AAG    287
Leu  Gln  Leu  Gly  Val  Ser  Leu  Glu  Gln  Gln  Leu  Gln  Val  Leu  Phe  Lys
80                       85                      90                      95

GTG  CTG  GAA  GAG  TAC  GAC  TGG  AGC  GCC  TTC  GCC  GTC  ATC  ACC  AGC  CTG    335
Val  Leu  Glu  Glu  Tyr  Asp  Trp  Ser  Ala  Phe  Ala  Val  Ile  Thr  Ser  Leu
               100                     105                     110

CAC  CCG  GGC  CAC  GCG  CTC  TTC  CTG  GAG  GGC  GTG  CGC  GCC  GTC  GCC  GAC    383
His  Pro  Gly  His  Ala  Leu  Phe  Leu  Glu  Gly  Val  Arg  Ala  Val  Ala  Asp
               115                     120                     125

GCC  AGC  CAC  GTG  AGT  TGG  CGG  CTG  CTG  GAC  GTG  GTC  ACG  CTG  GAA  CTG    431
Ala  Ser  His  Val  Ser  Trp  Arg  Leu  Leu  Asp  Val  Val  Thr  Leu  Glu  Leu
               130                     135                     140

GAC  CCG  GGA  GGG  CCG  CGC  GCG  CGC  ACG  CAG  CGC  CTG  CTG  CGC  CAG  CTC    479
Asp  Pro  Gly  Gly  Pro  Arg  Ala  Arg  Thr  Gln  Arg  Leu  Leu  Arg  Gln  Leu
145                      150                     155

GAC  GCG  CCC  GTG  TTT  GTG  GCC  TAC  TGC  TCG  CGC  GAG  GAG  GCC  GAG  GTG    527
Asp  Ala  Pro  Val  Phe  Val  Ala  Tyr  Cys  Ser  Arg  Glu  Glu  Ala  Glu  Val
160                      165                     170                     175
```

| | | | | | | | | | | | | | | | | |
|---|---|---|---|---|---|---|---|---|---|---|---|---|---|---|---|---|
| CTC | TTC | GCC | GAG | GCG | GCG | CAG | GCC | GGT | CTG | GTG | GGG | CCC | GGC | CAC | GTG | 575 |
| Leu | Phe | Ala | Glu | Ala 180 | Ala | Gln | Ala | Gly | Leu 185 | Val | Gly | Pro | Gly | His 190 | Val | |
| TGG | CTG | GTG | CCC | AAC | CTG | GCG | CTG | GGC | AGC | ACC | GAT | GCG | CCC | CCC | GCC | 623 |
| Trp | Leu | Val | Pro 195 | Asn | Leu | Ala | Leu | Gly | Ser 200 | Thr | Asp | Ala | Pro 205 | Pro | Ala | |
| ACC | TTC | CCC | GTG | GGC | CTC | ATC | AGC | GTC | GTC | ACC | GAG | AGC | TGG | CGC | CTC | 671 |
| Thr | Phe | Pro 210 | Val | Gly | Leu | Ile | Ser 215 | Val | Val | Thr | Glu | Ser 220 | Trp | Arg | Leu | |
| AGC | CTG | CGC | CAG | AAG | GTG | CGC | GAC | GGC | GTG | GCC | ATT | CTG | GCC | CTG | GGC | 719 |
| Ser | Leu 225 | Arg | Gln | Lys | Val | Arg 230 | Asp | Gly | Val | Ala | Ile 235 | Leu | Ala | Leu | Gly | |
| GCC | CAC | AGC | TAC | TGG | CGC | CAG | CAT | GGA | ACC | CAG | AAG | GGG | GTG | TGC | CAG | 767 |
| Ala 240 | His | Ser | Tyr | Trp | Arg 245 | Gln | His | Gly | Thr | Gln 250 | Lys | Gly | Val | Cys | Gln 255 | |
| CCC | CGG | CCG | GGG | ACT | GCC | GTG | TTC | ACC | CTG | GGC | CCG | TCA | GCC | CTG | CCC | 815 |
| Pro | Arg | Pro | Gly | Thr 260 | Ala | Val | Phe | Thr | Leu 265 | Gly | Pro | Ser | Ala | Leu 270 | Pro | |
| GGG | AGG | CCT | TCT | ACA | GGC | ACC | TAC | TGA | ATG | TCA | CCT | GGG | AGG | GCC | GAG | 863 |
| Gly | Arg | Pro | Ser 275 | Thr | Gly | Thr | Tyr | * 280 | Met | Ser | Pro | Gly | Arg 285 | Ala | Glu | |
| ACT | TCT | CCT | TCA | GCC | CTG | GTG | GGT | ACC | TGG | TCC | AGC | CCA | CCA | TGG | TGG | 911 |
| Thr | Ser | Pro | Ser 290 | Ala | Leu | Val | Gly | Thr 295 | Trp | Ser | Ser | Pro | Pro 300 | Trp | Trp | |
| TGA | TCG | CCC | TCA | ACC | GGC | ACC | GCC | TCT | GGG | AGA | TGG | TGG | GGC | GCT | GGG | 959 |
| * | Ser | Pro 305 | Ser | Thr | Gly | Thr | Ala 310 | Ser | Gly | Arg | Trp | Trp 315 | Gly | Ala | Gly | |
| AGC | ATG | GCG | TCC | TAT | ACA | TGA | AGT | ACC | CCG | TGT | GGC | CTC | GCT | ACA | GTG | 1007 |
| Ser | Met | Ala 320 | Ser | Tyr | Thr | * 325 | Ser | Thr | Pro | Cys 330 | Gly | Leu | Ala | Thr | Val 335 | |
| CCT | CTC | TGC | AGC | CTG | TGG | TGG | ACA | GTC | GGC | ACC | TGA | CGG | TGG | CCA | CGC | 1055 |
| Pro | Leu | Cys | Ser | Leu 340 | Trp | Trp | Thr | Val | Gly 345 | Thr | * | Arg | Trp | Pro 350 | Arg | |
| TGG | AAG | AGC | GGC | CCT | TTG | TCA | TCG | TGG | AGA | GCC | CTG | ACC | CTG | GCA | CAG | 1103 |
| Trp | Lys | Ser | Gly 355 | Pro | Leu | Ser | Ser | Trp 360 | Arg | Ala | Leu | Thr | Leu 365 | Ala | Gln | |
| GAG | GCT | GTG | TCC | CCA | ACA | CCG | TGC | CCT | GCC | GCA | GGC | AGA | GCA | ACC | ACA | 1151 |
| Glu | Ala | Val 370 | Ser | Pro | Thr | Pro | Cys 375 | Pro | Ala | Ala | Gly | Arg 380 | Ala | Thr | Thr | |
| CCT | TCA | GCA | GCG | GGG | ACG | TGG | CCC | CCT | ACA | CCA | AGC | TCT | GCT | GTA | AGG | 1199 |
| Pro | Ser 385 | Ala | Ala | Gly | Thr | Trp 390 | Pro | Pro | Thr | Pro | Ser 395 | Ser | Ala | Val | Arg | |
| GAT | TCT | GCA | TCG | ACA | TCC | TCA | AGA | AGC | TGG | CCA | GAG | TGG | TCA | AAT | TCT | 1247 |
| Asp 400 | Ser | Ala | Ser | Thr | Ser 405 | Ser | Arg | Ser | Trp | Pro 410 | Glu | Trp | Ser | Asn | Ser 415 | |
| CCT | ACG | ACC | TGT | ACC | TGG | TGA | CCA | ACG | GCA | AGC | ATG | GCA | AGC | GGG | TGC | 1295 |
| Pro | Thr | Thr | Cys | Thr 420 | Trp | * | Pro | Thr | Ala 425 | Ser | Met | Ala | Ser | Gly 430 | Cys | |
| GCG | GCG | TAT | GGA | ACG | GCA | TGA | TTG | GGG | AGG | TGT | ACT | ACA | AGC | GGG | CAG | 1343 |
| Ala | Ala | Tyr | Gly 435 | Thr | Ala | * | Leu | Gly 440 | Arg | Cys | Thr | Thr | Ser 445 | Gly | Gln | |
| ACA | TGG | CCA | TCG | GCT | CCC | TCA | CCA | TCA | ATG | AGG | AAC | GCT | CCG | AGA | TCG | 1391 |
| Thr | Trp | Pro 450 | Ser | Ala | Pro | Ser 455 | Pro | Ser | Met | Arg | Asn 460 | Ala | Pro | Arg | Ser | |
| TAG | ACT | TCT | CTG | TAC | CCT | TTG | TGG | AGA | CGG | GCA | TCA | GTG | TGA | TGG | TGG | 1439 |
| * | Thr | Ser | Leu 465 | Tyr | Pro | Leu | Trp | Arg 470 | Arg | Ala | Ser | Val 475 | * | Trp | Trp | |
| CTC | GCA | GCA | ATG | GCA | CCG | TCT | CCC | CCT | CGG | CCT | TCT | TGG | AGC | CAT | ATA | 1487 |
| Leu 480 | Ala | Ala | Met | Ala | Pro 485 | Ser | Pro | Pro | Arg | Pro 490 | Ser | Trp | Ser | His | Ile 495 | |

| | | | | | | | | | | | | | | | | |
|---|---|---|---|---|---|---|---|---|---|---|---|---|---|---|---|---|
| GCC | CTG | CAG | TGT | GGG | TGA | TGA | TGT | TTG | TCA | TGT | GCC | TCA | CTG | TGG | TGG | 1535 |
| Ala | Leu | Gln | Cys | Gly 500 | * | * | Cys | Leu | Ser 505 | Cys | Ala | Ser | Leu | Trp 510 | Trp | |
| CCA | TCA | CCG | TCT | TCA | TGT | TCG | AGT | ACT | TCA | GCC | CTG | TCA | GCT | ACA | ACC | 1583 |
| Pro | Ser | Pro | Ser 515 | Ser | Cys | Ser | Ser | Thr 520 | Ser | Ala | Leu | Ser | Ala 525 | Thr | Thr | |
| AGA | ACC | TCA | CCA | GAG | GCA | AGA | CTT | TCA | CTA | TCG | GCA | AGT | CCG | TGT | GGC | 1631 |
| Arg | Thr | Ser 530 | Pro | Glu | Ala | Arg | Leu | Ser 535 | Leu | Ser | Ala | Ser | Pro 540 | Cys | Gly | |
| TGC | TGT | GGG | CGC | TGG | TCT | TCA | ACA | ACT | CAG | TGC | CCA | TCG | AGA | ACC | CGC | 1679 |
| Cys | Cys 545 | Gly | Arg | Trp | Ser | Ser 550 | Thr | Thr | Gln | Cys | Pro 555 | Ser | Arg | Thr | Arg | |
| GGG | GCA | CCA | CCA | GCA | AGA | TCA | TGG | TTC | TGG | TCT | GGG | CCT | TCT | TTG | CTG | 1727 |
| Gly 560 | Ala | Pro | Pro | Ala | Arg 565 | Ser | Trp | Phe | Trp | Ser 570 | Gly | Pro | Ser | Leu | Leu 575 | |
| TCA | TCT | TCC | TCG | CCA | GAT | ACA | CGG | CCA | ACC | TGG | CCG | CCT | TCA | TGA | TCC | 1775 |
| Ser | Ser | Ser | Ser | Pro 580 | Asp | Thr | Arg | Pro | Thr 585 | Trp | Pro | Pro | Ser | * 590 | Ser | |
| AAG | AGC | AAT | ACA | TCG | ACA | CTG | TGT | CGG | GCC | TCA | GTG | ACA | AGA | AGT | TTC | 1823 |
| Lys | Ser | Asn | Thr 595 | Ser | Thr | Leu | Cys | Arg | Ala 600 | Ser | Val | Thr | Arg 605 | Ser | Phe | |
| AGC | GGC | CTC | AAG | ATC | AGT | ACC | CAC | CTT | TCC | GCT | TCG | GCA | CGG | TGC | CCA | 1871 |
| Ser | Gly | Leu 610 | Lys | Ile | Ser | Thr | His 615 | Leu | Ser | Ala | Ser | Ala 620 | Arg | Cys | Pro | |
| ACG | GCA | GCA | CGG | AGC | GGA | ACA | TCC | GCA | GTA | ACT | ACC | GTG | ACA | TGC | ACA | 1919 |
| Thr | Ala 625 | Ala | Arg | Ser | Gly | Thr 630 | Ser | Ala | Val | Thr | Thr 635 | Val | Thr | Cys | Thr | |
| CCC | ACA | TGG | TCA | AGT | TCA | ACC | AGC | GCT | CGG | TGG | AGG | ACG | CGC | TCA | CCA | 1967 |
| Pro 640 | Thr | Trp | Ser | Ser | Ser 645 | Thr | Ser | Ala | Arg | Trp 650 | Arg | Thr | Arg | Ser | Pro 655 | |
| GCC | TCA | AGA | TGG | GGA | AGC | TGG | ATG | CCT | TCA | TCT | ATG | ATG | CTG | CTG | TCC | 2015 |
| Ala | Ser | Arg | Trp | Gly 660 | Ser | Trp | Met | Pro | Ser 665 | Ser | Met | Met | Leu | Leu 670 | Ser | |
| TCA | ACT | ACA | TGG | CAG | GCA | AGG | ACG | AGG | GCT | GCA | AGC | TGG | TCA | CCA | TTG | 2063 |
| Ser | Thr | Thr | Trp 675 | Gln | Ala | Arg | Thr | Arg 680 | Ala | Ala | Ser | Trp | Ser 685 | Pro | Leu | |
| GGT | CTG | GCA | AGG | TCT | TTG | CTA | CCA | CTG | GCT | ACG | GCA | TCG | CCA | TGC | AGA | 2111 |
| Gly | Leu | Ala 690 | Arg | Ser | Leu | Leu | Pro 695 | Leu | Ala | Thr | Ala | Ser 700 | Pro | Cys | Arg | |
| AGG | ACT | CCC | ACT | GGA | AGC | GGG | CCA | TAG | ACC | TGG | CGC | TCT | TGC | AGT | TCC | 2159 |
| Arg | Thr 705 | Pro | Thr | Gly | Ser | Gly 710 | Pro | * | Thr | Trp | Arg 715 | Ser | Cys | Ser | Ser | |
| TGG | GGG | ACG | GAG | AGA | CAC | AGA | AAC | TGG | AGA | CAG | TGT | GGC | TCT | CAG | GGA | 2207 |
| Trp | Gly | Thr | Glu | Arg 725 | His | Arg | Asn | Trp | Arg 730 | Gln | Cys | Gly | Ser | Gln 735 | Gly | |
| Trp 720 | | | | | | | | | | | | | | | | |
| TCT | GCC | AGA | ATG | AGA | AGA | ACG | AGG | TGA | TGA | GCA | GCA | AGC | TGG | ACA | TCG | 2255 |
| Ser | Ala | Arg | Met | Arg 740 | Arg | Thr | Arg | * | * 745 | Ala | Ala | Ser | Trp | Thr 750 | Ser | |
| ACA | ACA | TGG | GAG | GCG | TCT | TCT | ACA | TGC | TGC | TGG | TGG | CCA | TGG | GGC | TGG | 2303 |
| Thr | Thr | Trp | Glu 755 | Ala | Ser | Ser | Thr | Cys 760 | Cys | Trp | Trp | Pro | Trp 765 | Gly | Trp | |
| CCC | TGC | TGG | TCT | TCG | CCT | GGG | AGC | ACC | TGG | TCT | ACT | GGA | AGC | TGC | GCC | 2351 |
| Pro | Cys | Trp 770 | Ser | Ser | Pro | Gly | Ser 775 | Thr | Trp | Ser | Thr | Gly 780 | Ser | Cys | Ala | |
| ACT | CGG | TGC | CCA | ACT | CAT | CCC | AGC | TGG | ACT | TCC | TGC | TGG | CTT | TCA | GCA | 2399 |
| Thr | Arg | Cys 785 | Pro | Thr | His | Pro | Ser 790 | Trp | Thr | Ser | Cys | Trp 795 | Leu | Ser | Ala | |
| GGG | GCA | TCT | ACA | GCT | GCT | TCA | GCG | GGG | TGC | AGA | GCC | TCG | CCA | GCC | CAC | 2447 |
| Gly | Ala | Ser | Thr 800 | Ala | Ala 805 | Ser | Ala | Gly | Cys | Arg 810 | Ala | Ser | Pro | Ala | His 815 | |

```
CGC GGC AGG CCA GCC CGG ACC TCA CGG CCA GCT CGG CCC AGG CCA GCG    2495
Arg Gly Arg Pro Ala Arg Thr Ser Arg Pro Ala Arg Pro Arg Pro Ala
                820             825                 830

TGC TCA AGA TTC TGC AGG CAG CCC GCG ACA TGG TGA CCA CGG CGG GCG    2543
Cys Ser Arg Phe Cys Arg Gln Pro Ala Thr Trp  *  Pro Arg Arg Ala
                835             840                 845

TAA GCA ACT CCC TGG ACC GCG CCA CTC GCA CCA TCG AGA ATT GGG GTG    2591
 *  Ala Thr Pro Trp Thr Ala Pro Leu Ala Pro Ser Arg Ile Gly Val
                850             855                 860

GCG GCC GCC GTG CGC CCC CAC CGT CCC CCT GCC CGA CCC CGC GGT CTG    2639
Ala Ala Ala Val Arg Pro His Arg Pro Pro Ala Arg Pro Arg Gly Leu
                865             870                 875

GCC CCA GCC CAT GCC TGC CCA CCC CCG ACC CGC CCC CAG AGC CGA GCC    2687
Ala Pro Ala His Ala Cys Pro Pro Pro Thr Arg Pro Gln Ser Arg Ala
880                 885             890                     895

CCA CGG GCT GGG GAC CGC CAG ACG GGG GTC GCG CGG CGC TTG TGC GCA    2735
Pro Arg Ala Gly Asp Arg Gln Thr Gly Val Ala Arg Arg Leu Cys Ala
                900             905                 910

GGG CTC CGC AGC CCC CGG GCC GCC CCC CGA CGC CGG GGC CGC CCC TGT    2783
Gly Leu Arg Ser Pro Arg Ala Ala Pro Arg Arg Arg Gly Arg Pro Cys
                915             920                 925

CCG ACG TCT CCC GAG TGT CGC GCC GCC CAG CCT GGG AGG CGC GGT GGC    2831
Pro Thr Ser Pro Glu Cys Arg Ala Ala Gln Pro Gly Arg Arg Gly Gly
                930             935                 940

CGG TGC GGA CCG GGC ACT GCG GGA GGC ACC TCT CGG CCT CCG AGC GGC    2879
Arg Cys Gly Pro Gly Thr Ala Gly Gly Thr Ser Arg Pro Pro Ser Gly
945                 950             955

CCC TGT CGC CCG CGC GCT GTC ACT ACA GCT CCT TTC CTC GAG CCG ACC    2927
Pro Cys Arg Pro Arg Ala Val Thr Thr Ala Pro Phe Leu Glu Pro Thr
960                 965             970                 975

GAT CCG GCC GCC CCT TCC TCC CGC TCT TCC CGG AGC CCC CGG AGC TGG    2975
Asp Pro Ala Ala Pro Ser Ser Arg Ser Ser Arg Ser Pro Arg Ser Trp
                980             985                 990

AGG ACC TGC CGC TGC TCG GTC CGG AGC AGC TGG CCC GGC GGG AGG CCC    3023
Arg Thr Cys Arg Cys Ser Val Arg Ser Ser Trp Pro Gly Gly Arg Pro
                995             1000                1005

TGC TGA ACG CGG CCT GGG CCC GGG GCT CGC GCC CGA GTC ACG CTT CCC    3071
Cys  *  Thr Arg Pro Gly Pro Gly Ala Arg Ala Arg Val Thr Leu Pro
        1010                1015                1020

TGC CCA GCT CCG TGG CCG AGG CCT TCG CTC GGC CCA GCT CGC TGC CCG    3119
Cys Pro Ala Pro Trp Pro Arg Pro Ser Leu Gly Pro Ala Arg Cys Pro
        1025                1030                1035

CTG GGT GCA CCG GCC CCG CCT GCG CCC GCC CCG ACG GCC ACT CGG CCT    3167
Leu Gly Ala Pro Ala Pro Pro Ala Pro Ala Pro Thr Ala Thr Arg Pro
1040                1045                1050                1055

GCA GGC GCT TGG CGC AGG CGC AGT CGA TGT GCT TGC CGA TCT ACC GGG    3215
Ala Gly Ala Trp Arg Arg Arg Ser Arg Cys Ala Cys Arg Ser Thr Gly
                1060                1065                1070

AGG CCT GCC AGG AGG GCG AGC AGG CAG GGC CCC GCC TGG CAG CAC A     3263
Arg Pro Ala Arg Arg Ala Ser Arg Gln Gly Pro Pro Gly Ser Thr
                1075                1080                1085

GAC AGC ACG TCT GCC TGC ACG CCC ACG CCC ACC TGC CAT TGT GCT GGG    3311
Asp Ser Thr Ser Ala Cys Thr Pro Thr Pro Thr Cys His Cys Ala Gly
                1090                1095                1100

GGG CTG TCT GTC CTC ACC TTC CAC CCT GTG ACA GCC ACG GCT CCT GGC    3359
Gly Leu Ser Val Leu Thr Phe His Pro Val Thr Ala Thr Ala Pro Gly
                1105                1110                1115

TCT CCG GCG CCT GGG GGC CTC TGG GGC ACA GCG GCA GGA CTC TGG GGC    3407
Ser Pro Ala Pro Gly Gly Leu Trp Gly Thr Ala Ala Gly Leu Trp Gly
1120                1125                1130                1135
```

```
TGG  GCA  CAG  GCT  ACA  GAG  ACA  GTG  GGG  GAC  TGG  ACG  AGA  TCA  GCA  GTG          3455
Trp  Ala  Gln  Ala  Thr  Glu  Thr  Val  Gly  Asp  Trp  Thr  Arg  Ser  Ala  Val
               1140                    1145                    1150

TAG  CCC  GTG  GGA  CGC  AAG  GCT  TCC  CGG  GAC  CCT  GCA  CCT  GGA  GAC  GGA          3503
 *   Pro  Val  Gly  Arg  Lys  Ala  Ser  Arg  Asp  Pro  Ala  Pro  Gly  Asp  Gly
               1155                    1160                    1165

TCT  CCA  GTC  TGG  AGT  CAG  AAG  TGT  GAG  TTA  TCA  GCC  ACT  CAG  GCT  CCG          3551
Ser  Pro  Val  Trp  Ser  Gln  Lys  Cys  Glu  Leu  Ser  Ala  Thr  Gln  Ala  Pro
          1170                    1175                    1180

AGC  CAG  CTG  GAT  TCT  CTG  CCT  GCC  ACT  GTC  AGG  GTT  AAG  CGG  CAG  GCA          3599
Ser  Gln  Leu  Asp  Ser  Leu  Pro  Ala  Thr  Val  Arg  Val  Lys  Arg  Gln  Ala
     1185                    1190                    1195

GGA  TTG  GCC  CTT  CTC  TGG  CTT  CTA  CCA  TGA  AAT  CCT  GGC  CAT  GGC  ACC          3647
Gly  Leu  Ala  Leu  Leu  Trp  Leu  Leu  Pro   *   Asn  Pro  Gly  His  Gly  Thr
1200                1205                    1210                    1215

CCA  GTG  ACA  GAT  GAT  GTC  TTC  CAT  GGT  CAT  CAG  TGA  CCT  CAG  CTA  GCC          3695
Pro  Val  Thr  Asp  Asp  Val  Phe  His  Gly  His  Gln   *   Pro  Gln  Leu  Ala
                    1220                    1225                    1230

TCA                                                                                       3698
Ser
```

( 2 ) INFORMATION FOR SEQ ID NO:44:

( i ) SEQUENCE CHARACTERISTICS:
        ( A ) LENGTH: 3243 base pairs
        ( B ) TYPE: nucleic acid
        ( C ) STRANDEDNESS: unknown
        ( D ) TOPOLOGY: unknown ( i i ) MOLECULE TYPE: cDNA ( i x ) FEATURE:
        ( A ) NAME/KEY: Coding Sequence
        ( B ) LOCATION: 1...3243

( x i ) SEQUENCE DESCRIPTION: SEQ ID NO:44:

```
GTG  GCC  TAC  TGC  TCG  CGC  GAG  GAG  GCC  GAG  GTG  CTC  TTC  GCC  GAG  GCG            48
Val  Ala  Tyr  Cys  Ser  Arg  Glu  Glu  Ala  Glu  Val  Leu  Phe  Ala  Glu  Ala
 1              5                   10                  15

GCG  CAG  GCC  GGT  CTG  GTG  GGG  CCC  GGC  CAC  GTG  TGG  CTG  GTG  CCC  AAC            96
Ala  Gln  Ala  Gly  Leu  Val  Gly  Pro  Gly  His  Val  Trp  Leu  Val  Pro  Asn
          20                    25                      30

CTG  GCG  CTG  GGC  AGC  ACC  GAT  GCG  CCC  CCC  GCC  ACC  TTC  CCC  GTG  GGC           144
Leu  Ala  Leu  Gly  Ser  Thr  Asp  Ala  Pro  Pro  Ala  Thr  Phe  Pro  Val  Gly
               35                  40                  45

CTC  ATC  AGC  GTC  GTC  ACC  GAG  AGC  TGG  CGC  CTC  AGC  CTG  CGC  CAG  AAG           192
Leu  Ile  Ser  Val  Val  Thr  Glu  Ser  Trp  Arg  Leu  Ser  Leu  Arg  Gln  Lys
          50                  55                   60

GTG  CGC  GAC  GGC  GTG  GCC  ATT  CTG  GCC  CTG  GGC  GCC  CAC  AGC  TAC  TGG           240
Val  Arg  Asp  Gly  Val  Ala  Ile  Leu  Ala  Leu  Gly  Ala  His  Ser  Tyr  Trp
 65                 70                  75                      80

CGC  CAG  CAT  GGA  ACC  CAG  AAG  GGG  GTG  TGC  CAG  CCC  CGG  CCG  GGG  ACT           288
Arg  Gln  His  Gly  Thr  Gln  Lys  Gly  Val  Cys  Gln  Pro  Arg  Pro  Gly  Thr
                    85                  90                      95

GCC  GTG  TTC  ACC  CTG  GGC  CCG  TCA  GCC  CTG  CCC  GGG  AGG  CCT  TCT  ACA           336
Ala  Val  Phe  Thr  Leu  Gly  Pro  Ser  Ala  Leu  Pro  Gly  Arg  Pro  Ser  Thr
               100                 105                 110

GGC  ACC  TAC  TGA  ATG  TCA  CCT  GGG  AGG  GCC  GAG  ACT  TCT  CCT  TCA  GCC           384
Gly  Thr  Tyr   *   Met  Ser  Pro  Gly  Arg  Ala  Glu  Thr  Ser  Pro  Ser  Ala
               115                 120                 125

CTG  GTG  GGT  ACC  TGG  TCC  AGC  CCA  CCA  TGG  TGG  TGA  TCG  CCC  TCA  ACC           432
Leu  Val  Gly  Thr  Trp  Ser  Ser  Pro  Pro  Trp  Trp   *   Ser  Pro  Ser  Thr
     130                 135                     140
```

| | | | | | | | | | | | | | | | | |
|---|---|---|---|---|---|---|---|---|---|---|---|---|---|---|---|---|
| GGC | ACC | GCC | TCT | GGG | AGA | TGG | TGG | GGC | GCT | GGG | AGC | ATG | GCG | TCC | TAT | 480 |
| Gly | Thr | Ala | Ser | Gly | Arg | Trp | Trp | Gly | Ala | Gly | Ser | Met | Ala | Ser | Tyr | |
| 145 | | | | 150 | | | | | 155 | | | | | 160 | | |
| ACA | TGA | AGT | ACC | CCG | TGT | GGC | CTC | GCT | ACA | GTG | CCT | CTC | TGC | AGC | CTG | 528 |
| Thr | * | Ser | Thr | Pro | Cys | Gly | Leu | Ala | Thr | Val | Pro | Leu | Cys | Ser | Leu | |
| | | | | 165 | | | | | 170 | | | | | 175 | | |
| TGG | TGG | ACA | GTC | GGC | ACC | TGA | CGG | TGG | CCA | CGC | TGG | AAG | AGC | GGC | CCT | 576 |
| Trp | Trp | Thr | Val | Gly | Thr | * | Arg | Trp | Pro | Arg | Trp | Lys | Ser | Gly | Pro | |
| | | | 180 | | | | | 185 | | | | | 190 | | | |
| TTG | TCA | TCG | TGG | AGA | GCC | CTG | ACC | CTG | GCA | CAG | GAG | GCT | GTG | TCC | CCA | 624 |
| Leu | Ser | Ser | Trp | Arg | Ala | Leu | Thr | Leu | Ala | Gln | Glu | Ala | Val | Ser | Pro | |
| | | 195 | | | | | 200 | | | | | 205 | | | | |
| ACA | CCG | TGC | CCT | GCC | GCA | GGC | AGA | GCA | ACC | ACA | CCT | TCA | GCA | GCG | GGG | 672 |
| Thr | Pro | Cys | Pro | Ala | Ala | Gly | Arg | Ala | Thr | Thr | Pro | Ser | Ala | Ala | Gly | |
| 210 | | | | | 215 | | | | | 220 | | | | | | |
| ACG | TGG | CCC | CCT | ACA | CCA | AGC | TCT | GCT | GTA | AGG | GAT | TCT | GCA | TCG | ACA | 720 |
| Thr | Trp | Pro | Pro | Thr | Pro | Ser | Ser | Ala | Val | Arg | Asp | Ser | Ala | Ser | Thr | |
| 225 | | | | | 230 | | | | | 235 | | | | | 240 | |
| TCC | TCA | AGA | AGC | TGG | CCA | GAG | TGG | TCA | AAT | TCT | CCT | ACG | ACC | TGT | ACC | 768 |
| Ser | Ser | Arg | Ser | Trp | Pro | Glu | Trp | Ser | Asn | Ser | Pro | Thr | Thr | Cys | Thr | |
| | | | | 245 | | | | | 250 | | | | | 255 | | |
| TGG | TGA | CCA | ACG | GCA | AGC | ATG | GCA | AGC | GGG | TGC | GCG | GCG | TAT | GGA | ACG | 816 |
| Trp | * | Pro | Thr | Ala | Ser | Met | Ala | Ser | Gly | Cys | Ala | Ala | Tyr | Gly | Thr | |
| | | 260 | | | | | 265 | | | | | 270 | | | | |
| GCA | TGA | TTG | GGG | AGG | TGT | ACT | ACA | AGC | GGG | CAG | ACA | TGG | CCA | TCG | GCT | 864 |
| Ala | * | Leu | Gly | Arg | Cys | Thr | Thr | Ser | Gly | Gln | Thr | Trp | Pro | Ser | Ala | |
| | | 275 | | | | | 280 | | | | | 285 | | | | |
| CCC | TCA | CCA | TCA | ATG | AGG | AAC | GCT | CCG | AGA | TCG | TAG | ACT | TCT | CTG | TAC | 912 |
| Pro | Ser | Pro | Ser | Met | Arg | Asn | Ala | Pro | Arg | Ser | * | Thr | Ser | Leu | Tyr | |
| 290 | | | | | 295 | | | | | 300 | | | | | | |
| CCT | TTG | TGG | AGA | CGG | GCA | TCA | GTG | TGA | TGG | TGG | CTC | GCA | GCA | ATG | GCA | 960 |
| Pro | Leu | Trp | Arg | Arg | Ala | Ser | Val | * | Trp | Trp | Leu | Ala | Ala | Met | Ala | |
| 305 | | | | 310 | | | | | 315 | | | | | 320 | | |
| CCG | TCT | CCC | CCT | CGG | CCT | TCT | TGG | AGC | CAT | ATA | GCC | CTG | CAG | TGT | GGG | 1008 |
| Pro | Ser | Pro | Pro | Arg | Pro | Ser | Trp | Ser | His | Ile | Ala | Leu | Gln | Cys | Gly | |
| | | | | 325 | | | | | 330 | | | | | 335 | | |
| TGA | TGA | TGT | TTG | TCA | TGT | GCC | TCA | CTG | TGG | TGG | CCA | TCA | CCG | TCT | TCA | 1056 |
| * | * | Cys | Leu | Ser | Cys | Ala | Ser | Leu | Trp | Trp | Pro | Ser | Pro | Ser | Ser | |
| | | | 340 | | | | | 345 | | | | | 350 | | | |
| TGT | TCG | AGT | ACT | TCA | GCC | CTG | TCA | GCT | ACA | ACC | AGA | ACC | TCA | CCA | GAG | 1104 |
| Cys | Ser | Ser | Thr | Ser | Ala | Leu | Ser | Ala | Thr | Thr | Arg | Thr | Ser | Pro | Glu | |
| | | 355 | | | | | 360 | | | | | 365 | | | | |
| GCA | AGA | AGT | CCG | GGG | GCC | CAG | CTT | TCA | CTA | TCG | GCA | AGT | CCG | TGT | GGC | 1152 |
| Ala | Arg | Ser | Pro | Gly | Ala | Gln | Leu | Ser | Leu | Ser | Ala | Ser | Pro | Cys | Gly | |
| | 370 | | | | | 375 | | | | | 380 | | | | | |
| TGC | TGT | GGG | CGC | TGG | TCT | TCA | ACA | ACT | CAG | TGC | CCA | TCG | AGA | ACC | CGC | 1200 |
| Cys | Cys | Gly | Arg | Trp | Ser | Ser | Thr | Thr | Gln | Cys | Pro | Ser | Arg | Thr | Arg | |
| 385 | | | | | 390 | | | | | 395 | | | | | 400 | |
| GGG | GCA | CCA | CCA | GCA | AGA | TCA | TGG | TTC | TGG | TCT | GGG | CCT | TCT | TTG | CTG | 1248 |
| Gly | Ala | Pro | Pro | Ala | Arg | Ser | Trp | Phe | Trp | Ser | Gly | Pro | Ser | Leu | Leu | |
| | | | | 405 | | | | | 410 | | | | | 415 | | |
| TCA | TCT | TCC | TCG | CCA | GAT | ACA | CGG | CCA | ACC | TGG | CCG | CCT | TCA | TGA | TCC | 1296 |
| Ser | Ser | Ser | Ser | Pro | Asp | Thr | Arg | Pro | Thr | Trp | Pro | Pro | Ser | * | Ser | |
| | | | | 420 | | | | | 425 | | | | | 430 | | |
| AAG | AGC | AAT | ACA | TCG | ACA | CTG | TGT | CGG | GCC | TCA | GTG | ACA | AGA | AGT | TTC | 1344 |
| Lys | Ser | Asn | Thr | Ser | Thr | Leu | Cys | Arg | Ala | Ser | Val | Thr | Arg | Ser | Phe | |
| | | 435 | | | | | 440 | | | | | 445 | | | | |
| AGC | GGC | CTC | AAG | ATC | AGT | ACC | CAC | CTT | TCC | GCT | TCG | GCA | CGG | TGC | CCA | 1392 |
| Ser | Gly | Leu | Lys | Ile | Ser | Thr | His | Leu | Ser | Ala | Ser | Ala | Arg | Cys | Pro | |
| 450 | | | | | 455 | | | | | 460 | | | | | | |

| | | | | | | | | | | | | | | | | |
|---|---|---|---|---|---|---|---|---|---|---|---|---|---|---|---|---|
| ACG | GCA | GCA | CGG | AGC | GGA | ACA | TCC | GCA | GTA | ACT | ACC | GTG | ACA | TGC | ACA | 1440 |
| Thr | Ala | Ala | Arg | Ser | Gly | Thr | Ser | Ala | Val | Thr | Thr | Val | Thr | Cys | Thr | |
| 465 | | | | 470 | | | | | 475 | | | | | | 480 | |
| CCC | ACA | TGG | TCA | AGT | TCA | ACC | AGC | GCT | CGG | TGG | AGG | ACG | CGC | TCA | CCA | 1488 |
| Pro | Thr | Trp | Ser | Ser | Ser | Thr | Ser | Ala | Arg | Trp | Arg | Thr | Arg | Ser | Pro | |
| | | | | 485 | | | | | 490 | | | | | 495 | | |
| GCC | TCA | AGA | TGG | GCT | CTG | AGG | CTC | AGC | CTG | TCC | CCA | GGA | AGC | TGG | ATG | 1536 |
| Ala | Ser | Arg | Trp | Ala | Leu | Arg | Leu | Ser | Leu | Ser | Pro | Gly | Ser | Trp | Met | |
| | | | 500 | | | | | 505 | | | | | 510 | | | |
| CCT | TCA | TCT | ATG | ATG | CTG | CTG | TCC | TCA | ACT | ACA | TGG | CAG | GCA | AGG | ACG | 1584 |
| Pro | Ser | Ser | Met | Met | Leu | Leu | Ser | Ser | Thr | Thr | Trp | Gln | Ala | Arg | Thr | |
| | | | 515 | | | | 520 | | | | | 525 | | | | |
| AGG | GCT | GCA | AGC | TGG | TCA | CCA | TTG | GGT | CTG | GCA | AGG | TCT | TTG | CTA | CCA | 1632 |
| Arg | Ala | Ala | Ser | Trp | Ser | Pro | Leu | Gly | Leu | Ala | Arg | Ser | Leu | Leu | Pro | |
| | 530 | | | | | 535 | | | | | 540 | | | | | |
| CTG | GCT | ACG | GCA | TCG | CCA | TGC | AGA | AGG | ACT | CCC | ACT | GGA | AGC | GGG | CCA | 1680 |
| Leu | Ala | Thr | Ala | Ser | Pro | Cys | Arg | Arg | Thr | Pro | Thr | Gly | Ser | Gly | Pro | |
| 545 | | | | | 550 | | | | | 555 | | | | | 560 | |
| TAG | ACC | TGG | CGC | TCT | TGC | AGT | TCC | TGG | GGG | ACG | GAG | AGA | CAC | AGA | AAC | 1728 |
| * | Thr | Trp | Arg | Ser | Cys | Ser | Ser | Trp | Gly | Thr | Glu | Arg | His | Arg | Asn | |
| | | | | 565 | | | | | 570 | | | | | 575 | | |
| TGG | AGA | CAG | TGT | GGC | TCT | CAG | GGA | TCT | GCC | AGA | ATG | AGA | AGA | ACG | AGG | 1776 |
| Trp | Arg | Gln | Cys | Gly | Ser | Gln | Gly | Ser | Ala | Arg | Met | Arg | Arg | Thr | Arg | |
| | | | 580 | | | | | 585 | | | | | 590 | | | |
| TGA | TGA | GCA | GCA | AGC | TGG | ACA | TCG | ACA | ACA | TGG | GAG | GCG | TCT | TCT | ACA | 1824 |
| * | * | Ala | Ala | Ser | Trp | Thr | Ser | Thr | Thr | Trp | Glu | Ala | Ser | Ser | Thr | |
| | | 595 | | | | | 600 | | | | | 605 | | | | |
| TGC | TGC | TGG | TGG | CCA | TGG | GGC | TGG | CCC | TGC | TGG | TCT | TCG | CCT | GGG | AGC | 1872 |
| Cys | Cys | Trp | Trp | Pro | Trp | Gly | Trp | Pro | Cys | Trp | Ser | Ser | Pro | Gly | Ser | |
| 610 | | | | | 615 | | | | | 620 | | | | | | |
| ACC | TGG | TCT | ACT | GGA | AGC | TGC | GCC | ACT | CGG | TGC | CCA | ACT | CAT | CCC | AGC | 1920 |
| Thr | Trp | Ser | Thr | Gly | Ser | Cys | Ala | Thr | Arg | Cys | Pro | Thr | His | Pro | Ser | |
| 625 | | | | | 630 | | | | | 635 | | | | | 640 | |
| TGG | ACT | TCC | TGC | TGG | CTT | TCA | GCA | GGG | GCA | TCT | ACA | GCT | GCT | TCA | GCG | 1968 |
| Trp | Thr | Ser | Cys | Trp | Leu | Ser | Ala | Gly | Ala | Ser | Thr | Ala | Ala | Ser | Ala | |
| | | | | 645 | | | | | 650 | | | | | 655 | | |
| GGG | TGC | AGA | GCC | TCG | CCA | GCC | CAC | CGC | GGC | AGG | CCA | GCC | CGG | ACC | TCA | 2016 |
| Gly | Cys | Arg | Ala | Ser | Pro | Ala | His | Arg | Gly | Arg | Pro | Ala | Arg | Thr | Ser | |
| | | | 660 | | | | | 665 | | | | | 670 | | | |
| CGG | CCA | GCT | CGG | CCC | AGG | CCA | GCG | TGC | TCA | AGA | TTC | TGC | AGG | CAG | CCC | 2064 |
| Arg | Pro | Ala | Arg | Pro | Arg | Pro | Ala | Cys | Ser | Arg | Phe | Cys | Arg | Gln | Pro | |
| | | | 675 | | | | | 680 | | | | | 685 | | | |
| GCG | ACA | TGG | TGA | CCA | CGG | CGG | GCG | TAA | GCA | ACT | CCC | TGG | ACC | GCG | CCA | 2112 |
| Ala | Thr | Trp | * | Pro | Arg | Arg | Ala | * | Ala | Thr | Pro | Trp | Thr | Ala | Pro | |
| 690 | | | | | | 695 | | | | | | 700 | | | | |
| CTC | GCA | CCA | TCG | AGA | ATT | GGG | GTG | GCG | GCC | GCC | GTG | CGC | CCC | CAC | CGT | 2160 |
| Leu | Ala | Pro | Ser | Arg | Ile | Gly | Val | Ala | Ala | Ala | Val | Arg | Pro | His | Arg | |
| 705 | | | | | 710 | | | | | 715 | | | | | 720 | |
| CCC | CCT | GCC | CGA | CCC | CGC | GGT | CTG | GCC | CCA | GCC | CAT | GCC | TGC | CCA | CCC | 2208 |
| Pro | Pro | Ala | Arg | Pro | Arg | Gly | Leu | Ala | Pro | Ala | His | Ala | Cys | Pro | Pro | |
| | | | | 725 | | | | | 730 | | | | | 735 | | |
| CCG | ACC | CGC | CCC | CAG | AGC | CGA | GCC | CCA | CGG | GCT | GGG | GAC | CGC | AGA | ACG | 2256 |
| Pro | Thr | Arg | Pro | Gln | Ser | Arg | Ala | Pro | Arg | Ala | Gly | Asp | Arg | Gln | Thr | |
| | | | 740 | | | | | 745 | | | | | 750 | | | |
| GGG | GTC | GCG | CGG | CGC | TTG | TGC | GCA | GGG | CTC | CGC | AGC | CCC | CGG | GCC | GCC | 2304 |
| Gly | Val | Ala | Arg | Arg | Leu | Cys | Ala | Gly | Leu | Arg | Ser | Pro | Arg | Ala | Ala | |
| | | | 755 | | | | | 760 | | | | | 765 | | | |
| CCC | CGA | CGC | CGG | GGC | CGC | CCC | TGT | CCG | ACG | TCT | CCC | GAG | TGT | CGC | GCC | 2352 |
| Pro | Arg | Arg | Arg | Gly | Arg | Pro | Cys | Pro | Thr | Ser | Pro | Glu | Cys | Arg | Ala | |

-continued

```
            770                           775                         780
GCC  CAG  CCT  GGG  AGG  CGC  GGT  GGC  CGG  TGC  GGA  CCG  GGC  ACT  GCG  GGA      2400
Ala  Gln  Pro  Gly  Arg  Arg  Gly  Gly  Arg  Cys  Gly  Pro  Gly  Thr  Ala  Gly
785                 790                      795                           800

GGC  ACC  TCT  CGG  CCT  CCG  AGC  GGC  CCC  TGT  CGC  CCG  CGC  GCT  GTC  ACT      2448
Gly  Thr  Ser  Arg  Pro  Pro  Ser  Gly  Pro  Cys  Arg  Pro  Arg  Ala  Val  Thr
                    805                      810                      815

ACA  GCT  CCT  TTC  CTC  GAG  CCG  ACC  GAT  CCG  GCC  GCC  CCT  TCC  TCC  CGC      2496
Thr  Ala  Pro  Phe  Leu  Glu  Pro  Thr  Asp  Pro  Ala  Ala  Pro  Ser  Ser  Arg
               820                      825                     830

TCT  TCC  CGG  AGC  CCC  CGG  AGC  TGG  AGG  ACC  TGC  CGC  TGC  TCG  GTC  CGG      2544
Ser  Ser  Arg  Ser  Pro  Arg  Ser  Trp  Arg  Thr  Cys  Arg  Cys  Ser  Val  Arg
          835                            840                     845

AGC  AGC  TGG  CCC  GGC  GGG  AGG  CCC  TGC  TGA  ACG  CGG  CCT  GGG  CCC  GGG      2592
Ser  Ser  Trp  Pro  Gly  Gly  Arg  Pro  Cys   *   Thr  Arg  Pro  Gly  Pro  Gly
850                           855                      860

GCT  CGC  GCC  CGA  GTC  ACG  CTT  CCC  TGC  CCA  GCT  CCG  TGG  CCG  AGG  CCT      2640
Ala  Arg  Ala  Arg  Val  Thr  Leu  Pro  Cys  Pro  Ala  Pro  Trp  Pro  Arg  Pro
865                      870                     875                      880

TCG  CTC  GGC  CCA  GCT  CGC  TGC  CCG  CTG  GGT  GCA  CCG  GCC  CCG  CCT  GCG      2688
Ser  Leu  Gly  Pro  Ala  Arg  Cys  Pro  Leu  Gly  Ala  Pro  Ala  Pro  Pro  Ala
                         885                     890                      895

CCC  GCC  CCG  ACG  GCC  ACT  CGG  CCT  GCA  GGC  GCT  TGG  CGC  AGG  CGC  AGT      2736
Pro  Ala  Pro  Thr  Ala  Thr  Arg  Pro  Ala  Gly  Ala  Trp  Arg  Arg  Arg  Ser
                    900                      905                      910

CGA  TGT  GCT  TGC  CGA  TCT  ACC  GGG  AGG  CCT  GCC  AGG  AGG  GCG  AGC  AGG      2784
Arg  Cys  Ala  Cys  Arg  Ser  Thr  Gly  Arg  Pro  Ala  Arg  Arg  Ala  Ser  Arg
               915                           920                     925

CAG  GGG  CCC  CCG  CCT  GGC  AGC  ACA  GAC  AGC  ACG  TCT  GCC  TGC  ACG  CCC      2832
Gln  Gly  Pro  Pro  Pro  Gly  Ser  Thr  Asp  Ser  Thr  Ser  Ala  Cys  Thr  Pro
930                           935                     940

ACG  CCC  ACC  TGC  CAT  TGT  GCT  GGG  GGG  CTG  TCT  GTC  CTC  ACC  TTC  CAC      2880
Thr  Pro  Thr  Cys  His  Cys  Ala  Gly  Gly  Leu  Ser  Val  Leu  Thr  Phe  His
945                           950                     955                      960

CCT  GTG  ACA  GCC  ACG  GCT  CCT  GGC  TCT  CCG  GCG  CCT  GGG  GGC  CTC  TGG      2928
Pro  Val  Thr  Ala  Thr  Ala  Pro  Gly  Ser  Pro  Ala  Pro  Gly  Gly  Leu  Trp
                    965                      970                      975

GGC  ACA  GCG  GCA  GGA  CTC  TGG  GGC  TGG  GCA  CAG  GCT  ACA  GAG  ACA  GTG      2976
Gly  Thr  Ala  Ala  Gly  Leu  Trp  Gly  Trp  Ala  Gln  Ala  Thr  Glu  Thr  Val
               980                           985                     990

GGG  GAC  TGG  ACG  AGA  TCA  GCA  GTG  TAG  CCC  GTG  GGA  CGC  AAG  GCT  TCC      3024
Gly  Asp  Trp  Thr  Arg  Ser  Ala  Val   *   Pro  Val  Gly  Arg  Lys  Ala  Ser
          995                           1000                    1005

CGG  GAC  CCT  GCA  CCT  GGA  GAC  GGA  TCT  CCA  GTC  TGG  AGT  CAG  AAG  TGT      3072
Arg  Asp  Pro  Ala  Pro  Gly  Asp  Gly  Ser  Pro  Val  Trp  Ser  Gln  Lys  Cys
1010                          1015                    1020

GAG  TTA  TCA  GCC  ACT  CAG  GCT  CCG  AGC  CAG  CTG  GAT  TCT  CTG  CCT  GCC      3120
Glu  Leu  Ser  Ala  Thr  Gln  Ala  Pro  Ser  Gln  Leu  Asp  Ser  Leu  Pro  Ala
1025                          1030                    1035                    1040

ACT  GTC  AGG  GTT  AAG  CGG  CAG  GCA  GGA  TTG  GCC  CTT  CTC  TGG  CTT  CTA      3168
Thr  Val  Arg  Val  Lys  Arg  Gln  Ala  Gly  Leu  Ala  Leu  Leu  Trp  Leu  Leu
                    1045                     1050                     1055

CCA  TGA  AAT  CCT  GGC  CAT  GGC  ACC  CCA  GTG  ACA  GAT  GAT  GTC  TTC  CAT      3216
Pro   *   Asn  Pro  Gly  His  Gly  Thr  Pro  Val  Thr  Asp  Asp  Val  Phe  His
               1060                          1065                    1070

GGT  CAT  CAG  TGA  CCT  CAG  CTA  GCC  TCA                                         3243
Gly  His  Gln   *   Pro  Gln  Leu  Ala  Ser
               1075                    1080
```

( 2 ) INFORMATION FOR SEQ ID NO:45:

(i) SEQUENCE CHARACTERISTICS:
  (A) LENGTH: 4092 base pairs
  (B) TYPE: nucleic acid
  (C) STRANDEDNESS: both
  (D) TOPOLOGY: both (ii) MOLECULE TYPE: cDNA (ix) FEATURE:
  (A) NAME/KEY: CDS
  (B) LOCATION: 189..3923

(xi) SEQUENCE DESCRIPTION: SEQ ID NO:45:

```
CCCTTAATAA GATTTGCNAC GTACACTCGA GCCATCGCGA GTGTCCTTGA GCCGCGGGTG        60

ACGGTGGCTC TCGCTGCTCG CGCCCCCTCC TCCCGCGGGG GGAGCCTGAT GCCACGTTCC       120

CTATGAATTA TTTATCGCCG GCCTAAAAAT ACCCCGAACT TCACAGCCCG AGTGACCCTC       180

CGGTGGAC ATG GGT GGG GCC CTG GGG CCG GCC CTG TTG CTC ACC TCG CTC       230
         Met Gly Gly Ala Leu Gly Pro Ala Leu Leu Leu Thr Ser Leu
          1           5                          10

TTC GGT GCC TGG GCA GGG CTG GGT CCG GGG CAG GGC GAG CAG GGC ATG        278
Phe Gly Ala Trp Ala Gly Leu Gly Pro Gly Gln Gly Glu Gln Gly Met
 15              20                  25                      30

ACG GTG GCC GTG GTG TTT AGC AGC TCA GGG CCG CCC CAG GCC CAG TTC        326
Thr Val Ala Val Val Phe Ser Ser Ser Gly Pro Pro Gln Ala Gln Phe
                    35                  40                  45

CGT GTC CGC CTC ACC CCC CAG AGC TTC CTG GAC CTA CCC CTG GAG ATC        374
Arg Val Arg Leu Thr Pro Gln Ser Phe Leu Asp Leu Pro Leu Glu Ile
                50                  55                  60

CAG CCG CTC ACA GTT GGG GTC AAC ACC ACC AAC CCC AGC AGC CTC CTC        422
Gln Pro Leu Thr Val Gly Val Asn Thr Thr Asn Pro Ser Ser Leu Leu
             65                  70                  75

ACC CAG ATC TGC GGC CTC CTG GGT GCT GCC CAC GTC CAC GGC ATT GTC        470
Thr Gln Ile Cys Gly Leu Leu Gly Ala Ala His Val His Gly Ile Val
         80                  85                  90

TTT GAG GAC AAC GTG GAC ACC GAG GCG GTG GCC CAG ATC CTT GAC TTC        518
Phe Glu Asp Asn Val Asp Thr Glu Ala Val Ala Gln Ile Leu Asp Phe
 95                 100                 105                 110

ATC TCC TCC CAG ACC CAT GTG CCC ATC CTC AGC ATC AGC GGA GGC TCT        566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG        614
Ala Val Val Leu Thr Pro Lys Glu Pro Gly Ser Ala Phe Leu Gln Leu
                130                 135                 140

GGC GTG TCC CTG GAG CAG CAG CTG CAG GTG CTG TTC AAG GTG CTG GAA        662
Gly Val Ser Leu Glu Gln Gln Leu Gln Val Leu Phe Lys Val Leu Glu
            145                 150                 155

GAG TAC GAC TGG AGC GCC TTC GCC GTC ATC ACC AGC CTG CAC CCG GGC        710
Glu Tyr Asp Trp Ser Ala Phe Ala Val Ile Thr Ser Leu His Pro Gly
        160                 165                 170

CAC GCG CTC TTC CTG GAG GGC GTG CGC GCC GTC GCC GAC GCC AGC CAC        758
His Ala Leu Phe Leu Glu Gly Val Arg Ala Val Ala Asp Ala Ser His
175             180                 185                 190

GTG AGT TGG CGG CTG CTG GAC GTG GTC ACG CTG GAA CTG GAC CCG GGA        806
Val Ser Trp Arg Leu Leu Asp Val Val Thr Leu Glu Leu Asp Pro Gly
            195                 200                 205

GGG CCG CGC GCG CGC ACG CAG CGC CTG CTG CGC CAG CTC GAC GCG CCC        854
Gly Pro Arg Ala Arg Thr Gln Arg Leu Leu Arg Gln Leu Asp Ala Pro
        210                 215                 220

GTG TTT GTG GCC TAC TGC TCG CGC GAG GAG GCC GAG GTG CTC TTC GCC        902
Val Phe Val Ala Tyr Cys Ser Arg Glu Glu Ala Glu Val Leu Phe Ala
            225                 230                 235
```

```
GAG  GCG  GCG  CAG  GCC  GGT  CTG  GTG  GGG  CCC  GGC  CAC  GTG  TGG  CTG  GTG        950
Glu  Ala  Ala  Gln  Ala  Gly  Leu  Val  Gly  Pro  Gly  His  Val  Trp  Leu  Val
240                      245                     250

CCC  AAC  CTG  GCG  CTG  GGC  AGC  ACC  GAT  GCG  CCC  CCC  GCC  ACC  TTC  CCC        998
Pro  Asn  Leu  Ala  Leu  Gly  Ser  Thr  Asp  Ala  Pro  Pro  Ala  Thr  Phe  Pro
255                      260                     265                     270

GTG  GGC  CTC  ATC  AGC  GTC  GTC  ACC  GAG  AGC  TGG  CGC  CTC  AGC  CTG  CGC       1046
Val  Gly  Leu  Ile  Ser  Val  Val  Thr  Glu  Ser  Trp  Arg  Leu  Ser  Leu  Arg
                    275                     280                     285

CAG  AAG  GTG  CGC  GAC  GGC  GTG  GCC  ATT  CTG  GCC  CTG  GGC  GCC  CAC  AGC       1094
Gln  Lys  Val  Arg  Asp  Gly  Val  Ala  Ile  Leu  Ala  Leu  Gly  Ala  His  Ser
               290                     295                     300

TAC  TGG  CGC  CAG  CAT  GGA  ACC  CTG  CCA  GCC  CCG  GCC  GGG  GAC  TGC  CGT       1142
Tyr  Trp  Arg  Gln  His  Gly  Thr  Leu  Pro  Ala  Pro  Ala  Gly  Asp  Cys  Arg
          305                     310                     315

GTT  CAC  CCT  GGG  CCC  GTC  AGC  CCT  GCC  CGG  GAG  GCC  TTC  TAC  AGG  CAC       1190
Val  His  Pro  Gly  Pro  Val  Ser  Pro  Ala  Arg  Glu  Ala  Phe  Tyr  Arg  His
320                     325                     330

CTA  CTG  AAT  GTC  ACC  TGG  GAG  GGC  CGA  GAC  TTC  TCC  TTC  AGC  CCT  GGT       1238
Leu  Leu  Asn  Val  Thr  Trp  Glu  Gly  Arg  Asp  Phe  Ser  Phe  Ser  Pro  Gly
335                     340                     345                     350

GGG  TAC  CTG  GTC  CAG  CCC  ACC  ATG  GTG  GTG  ATC  GCC  CTC  AAC  CGG  CAC       1286
Gly  Tyr  Leu  Val  Gln  Pro  Thr  Met  Val  Val  Ile  Ala  Leu  Asn  Arg  His
                    355                     360                     365

CGC  CTC  TGG  GAG  ATG  GTG  GGG  CGC  TGG  GAG  CAT  GGC  GTC  CTA  TAC  ATG       1334
Arg  Leu  Trp  Glu  Met  Val  Gly  Arg  Trp  Glu  His  Gly  Val  Leu  Tyr  Met
               370                     375                     380

AAG  TAC  CCC  GTG  TGG  CCT  CGC  TAC  AGT  GCC  TCT  CTG  CAG  CCT  GTG  GTG       1382
Lys  Tyr  Pro  Val  Trp  Pro  Arg  Tyr  Ser  Ala  Ser  Leu  Gln  Pro  Val  Val
          385                     390                     395

GAC  AGT  CGG  CAC  CTG  ACG  GTG  GCC  ACG  CTG  GAA  GAG  CGG  CCC  TTT  GTC       1430
Asp  Ser  Arg  His  Leu  Thr  Val  Ala  Thr  Leu  Glu  Glu  Arg  Pro  Phe  Val
400                     405                     410

ATC  GTG  GAG  AGC  CCT  GAC  CCT  GGC  ACA  GGA  GGC  TGT  GTC  CCC  AAC  ACC       1478
Ile  Val  Glu  Ser  Pro  Asp  Pro  Gly  Thr  Gly  Gly  Cys  Val  Pro  Asn  Thr
415                     420                     425                     430

GTG  CCC  TGC  CGC  AGG  CAG  AGC  AAC  CAC  ACC  TTC  AGC  AGC  GGG  GAC  GTG       1526
Val  Pro  Cys  Arg  Arg  Gln  Ser  Asn  His  Thr  Phe  Ser  Ser  Gly  Asp  Val
                    435                     440                     445

GCC  CCC  TAC  ACC  AAG  CTC  TGC  TGT  AAG  GGA  TTC  TGC  ATC  GAC  ATC  CTC       1574
Ala  Pro  Tyr  Thr  Lys  Leu  Cys  Cys  Lys  Gly  Phe  Cys  Ile  Asp  Ile  Leu
               450                     455                     460

AAG  AAG  CTG  GCC  AGA  GTG  GTC  AAA  TTC  TCC  TAC  GAC  CTG  TAC  CTG  GTG       1622
Lys  Lys  Leu  Ala  Arg  Val  Val  Lys  Phe  Ser  Tyr  Asp  Leu  Tyr  Leu  Val
          465                     470                     475

ACC  AAC  GGC  AAG  CAT  GGC  AAG  CGG  GTG  CGC  GGC  GTA  TGG  AAC  GGC  ATG       1670
Thr  Asn  Gly  Lys  His  Gly  Lys  Arg  Val  Arg  Gly  Val  Trp  Asn  Gly  Met
480                     485                     490

ATT  GGG  GAG  GTG  TAC  TAC  AAG  CGG  GCA  GAC  ATG  GCC  ATC  GGC  TCC  CTC       1718
Ile  Gly  Glu  Val  Tyr  Tyr  Lys  Arg  Ala  Asp  Met  Ala  Ile  Gly  Ser  Leu
495                     500                     505                     510

ACC  ATC  AAT  GAG  GAA  CGC  TCC  GAG  ATC  GTA  GAC  TTC  TCT  GTA  CCC  TTT       1766
Thr  Ile  Asn  Glu  Glu  Arg  Ser  Glu  Ile  Val  Asp  Phe  Ser  Val  Pro  Phe
                    515                     520                     525

GTG  GAG  ACG  GGC  ATC  AGT  GTG  ATG  GTG  GCT  CGC  AGC  AAT  GGC  ACC  GTC       1814
Val  Glu  Thr  Gly  Ile  Ser  Val  Met  Val  Ala  Arg  Ser  Asn  Gly  Thr  Val
               530                     535                     540

TCC  CCC  TCG  GCC  TTC  TTG  GAG  CCA  TAT  AGC  CCT  GCA  GTG  TGG  GTG  ATG       1862
Ser  Pro  Ser  Ala  Phe  Leu  Glu  Pro  Tyr  Ser  Pro  Ala  Val  Trp  Val  Met
          545                     550                     555
```

| | | | | | | | | | | | | | | | | |
|---|---|---|---|---|---|---|---|---|---|---|---|---|---|---|---|---|
| ATG | TTT | GTC | ATG | TGC | CTC | ACT | GTG | GTG | GCC | ATC | ACC | GTC | TTC | ATG | TTC | 1910 |
| Met | Phe | Val | Met | Cys | Leu | Thr | Val | Val | Ala | Ile | Thr | Val | Phe | Met | Phe | |
| | 560 | | | | 565 | | | | | 570 | | | | | | |
| GAG | TAC | TTC | AGC | CCT | GTC | AGC | TAC | AAC | CAG | AAC | CTC | ACC | AGA | GGC | AAG | 1958 |
| Glu | Tyr | Phe | Ser | Pro | Val | Ser | Tyr | Asn | Gln | Asn | Leu | Thr | Arg | Gly | Lys | |
| 575 | | | | | 580 | | | | | 585 | | | | | 590 | |
| AAG | TCC | GGG | GGC | CCA | GCT | TTC | ACT | ATC | GGC | AAG | TCC | GTG | TGG | CTG | CTG | 2006 |
| Lys | Ser | Gly | Gly | Pro | Ala | Phe | Thr | Ile | Gly | Lys | Ser | Val | Trp | Leu | Leu | |
| | | | | 595 | | | | | 600 | | | | | 605 | | |
| TGG | GCG | CTG | GTC | TTC | AAC | AAC | TCA | GTG | CCC | ATC | GAG | AAC | CCG | CGG | GGC | 2054 |
| Trp | Ala | Leu | Val | Phe | Asn | Asn | Ser | Val | Pro | Ile | Glu | Asn | Pro | Arg | Gly | |
| | | | 610 | | | | | 615 | | | | | 620 | | | |
| ACC | ACC | AGC | AAG | ATC | ATG | GTT | CTG | GTC | TGG | GCC | TTC | TTT | GCT | GTC | ATC | 2102 |
| Thr | Thr | Ser | Lys | Ile | Met | Val | Leu | Val | Trp | Ala | Phe | Phe | Ala | Val | Ile | |
| | | 625 | | | | | 630 | | | | | 635 | | | | |
| TTC | CTC | GCC | AGA | TAC | ACG | GCC | AAC | CTG | GCC | GCC | TTC | ATG | ATC | CAA | GAG | 2150 |
| Phe | Leu | Ala | Arg | Tyr | Thr | Ala | Asn | Leu | Ala | Ala | Phe | Met | Ile | Gln | Glu | |
| 640 | | | | | 645 | | | | | 650 | | | | | | |
| CAA | TAC | ATC | GAC | ACT | GTG | TCG | GGC | CTC | AGT | GAC | AAG | AAG | TTT | CAG | CGG | 2198 |
| Gln | Tyr | Ile | Asp | Thr | Val | Ser | Gly | Leu | Ser | Asp | Lys | Lys | Phe | Gln | Arg | |
| 655 | | | | | 660 | | | | | 665 | | | | | 670 | |
| CCT | CAA | GAT | CAG | TAC | CCA | CCT | TTC | CGC | TTC | GGC | ACG | GTG | CCC | AAC | GGC | 2246 |
| Pro | Gln | Asp | Gln | Tyr | Pro | Pro | Phe | Arg | Phe | Gly | Thr | Val | Pro | Asn | Gly | |
| | | | | 675 | | | | | 680 | | | | | 685 | | |
| AGC | ACG | GAG | CGG | AAC | ATC | CGC | AGT | AAC | TAC | CGT | GAC | ATG | CAC | ACC | CAC | 2294 |
| Ser | Thr | Glu | Arg | Asn | Ile | Arg | Ser | Asn | Tyr | Arg | Asp | Met | His | Thr | His | |
| | | | 690 | | | | | 695 | | | | | 700 | | | |
| ATG | GTC | AAG | TTC | AAC | CAG | CGC | TCG | GTG | GAG | GAC | GCG | CTC | ACC | AGC | CTC | 2342 |
| Met | Val | Lys | Phe | Asn | Gln | Arg | Ser | Val | Glu | Asp | Ala | Leu | Thr | Ser | Leu | |
| | | 705 | | | | | 710 | | | | | 715 | | | | |
| AAG | ATG | GGC | TCT | GAG | GCT | CAG | CCT | GTC | CCC | AGG | AAG | CTG | GAT | GCC | TTC | 2390 |
| Lys | Met | Gly | Ser | Glu | Ala | Gln | Pro | Val | Pro | Arg | Lys | Leu | Asp | Ala | Phe | |
| | 720 | | | | | 725 | | | | | 730 | | | | | |
| ATC | TAT | GAT | GCT | GCT | GTC | CTC | AAC | TAC | ATG | GCA | GGC | AAG | GAC | GAG | GGC | 2438 |
| Ile | Tyr | Asp | Ala | Ala | Val | Leu | Asn | Tyr | Met | Ala | Gly | Lys | Asp | Glu | Gly | |
| 735 | | | | | 740 | | | | | 745 | | | | | 750 | |
| TGC | AAG | CTG | GTC | ACC | ATT | GGG | TCT | GGC | AAG | GTC | TTT | GCT | ACC | ACT | GGC | 2486 |
| Cys | Lys | Leu | Val | Thr | Ile | Gly | Ser | Gly | Lys | Val | Phe | Ala | Thr | Thr | Gly | |
| | | | | 755 | | | | | 760 | | | | | 765 | | |
| TAC | GGC | ATC | GCC | ATG | CAG | AAG | GAC | TCC | CAC | TGG | AAG | CGG | GCC | ATA | GAC | 2534 |
| Tyr | Gly | Ile | Ala | Met | Gln | Lys | Asp | Ser | His | Trp | Lys | Arg | Ala | Ile | Asp | |
| | | | 770 | | | | | 775 | | | | | 780 | | | |
| CTG | GCG | CTC | TTG | CAG | TTC | CTG | GGG | GAC | GGA | GAG | ACA | CAG | AAA | CTG | GAG | 2582 |
| Leu | Ala | Leu | Leu | Gln | Phe | Leu | Gly | Asp | Gly | Glu | Thr | Gln | Lys | Leu | Glu | |
| | | 785 | | | | | 790 | | | | | 795 | | | | |
| ACA | GTG | TGG | CTC | TCA | GGG | ATC | TGC | CAG | AAT | GAG | AAG | AAC | GAG | GTG | ATG | 2630 |
| Thr | Val | Trp | Leu | Ser | Gly | Ile | Cys | Gln | Asn | Glu | Lys | Asn | Glu | Val | Met | |
| | 800 | | | | | 805 | | | | | 810 | | | | | |
| AGC | AGC | AAG | CTG | GAC | ATC | GAC | AAC | ATG | GGA | GGC | GTC | TTC | TAC | ATG | CTG | 2678 |
| Ser | Ser | Lys | Leu | Asp | Ile | Asp | Asn | Met | Gly | Gly | Val | Phe | Tyr | Met | Leu | |
| 815 | | | | | 820 | | | | | 825 | | | | | 830 | |
| CTG | GTG | GCC | ATG | GGG | CTG | GCC | CTG | CTG | GTC | TTC | GCC | TGG | GAG | CAC | CTG | 2726 |
| Leu | Val | Ala | Met | Gly | Leu | Ala | Leu | Leu | Val | Phe | Ala | Trp | Glu | His | Leu | |
| | | | | 835 | | | | | 840 | | | | | 845 | | |
| GTC | TAC | TGG | AAG | CTG | CGC | CAC | TCG | GTG | CCC | AAC | TCA | TCC | CAG | CTG | GAC | 2774 |
| Val | Tyr | Trp | Lys | Leu | Arg | His | Ser | Val | Pro | Asn | Ser | Ser | Gln | Leu | Asp | |
| | | | 850 | | | | | 855 | | | | | 860 | | | |
| TTC | CTG | CTG | GCT | TTC | AGC | AGG | GGC | ATC | TAC | AGC | TGC | TTC | AGC | GGG | GTG | 2822 |
| Phe | Leu | Leu | Ala | Phe | Ser | Arg | Gly | Ile | Tyr | Ser | Cys | Phe | Ser | Gly | Val | |
| | | 865 | | | | | 870 | | | | | 875 | | | | |

```
CAG  AGC  CTC  GCC  AGC  CCA  CCG  CGG  CAG  GCC  AGC  CCG  GAC  CTC  ACG  GCC    2870
Gln  Ser  Leu  Ala  Ser  Pro  Pro  Arg  Gln  Ala  Ser  Pro  Asp  Leu  Thr  Ala
     880                 885                      890

AGC  TCG  GCC  CAG  GCC  AGC  GTG  CTC  AAG  ATT  CTG  CAG  GCA  GCC  CGC  GAC    2918
Ser  Ser  Ala  Gln  Ala  Ser  Val  Leu  Lys  Ile  Leu  Gln  Ala  Ala  Arg  Asp
895                      900                      905                      910

ATG  GTG  ACC  ACG  GCG  GGC  GTA  AGC  AAC  TCC  CTG  GAC  CGC  GCC  ACT  CGC    2966
Met  Val  Thr  Thr  Ala  Gly  Val  Ser  Asn  Ser  Leu  Asp  Arg  Ala  Thr  Arg
                    915                      920                      925

ACC  ATC  GAG  AAT  TGG  GGT  GGC  GGC  CGC  CGT  GCG  CCC  CCA  CCG  TCC  CCC    3014
Thr  Ile  Glu  Asn  Trp  Gly  Gly  Gly  Arg  Arg  Ala  Pro  Pro  Pro  Ser  Pro
               930                      935                      940

TGC  CCG  ACC  CCG  CGG  TCT  GGC  CCC  AGC  CCA  TGC  CTG  CCC  ACC  CCC  GAC    3062
Cys  Pro  Thr  Pro  Arg  Ser  Gly  Pro  Ser  Pro  Cys  Leu  Pro  Thr  Pro  Asp
          945                      950                      955

CCG  CCC  CCA  GAG  CCG  AGC  CCC  ACG  GGC  TGG  GGA  CCG  CCA  GAC  GGG  GGT    3110
Pro  Pro  Pro  Glu  Pro  Ser  Pro  Thr  Gly  Trp  Gly  Pro  Pro  Asp  Gly  Gly
960                      965                      970

CGC  GCG  GCG  CTT  GTG  CGC  AGG  GCT  CCG  CAG  CCC  CGG  CGC  CCC  CCG         3158
Arg  Ala  Ala  Leu  Val  Arg  Arg  Ala  Pro  Gln  Pro  Pro  Gly  Arg  Pro  Pro
975                      980                      985                      990

ACG  CCG  GGG  CCG  CCC  CTG  TCC  GAC  GTC  TCC  CGA  GTG  TCG  CGC  CGC  CCA    3206
Thr  Pro  Gly  Pro  Pro  Leu  Ser  Asp  Val  Ser  Arg  Val  Ser  Arg  Arg  Pro
                    995                      1000                     1005

GCC  TGG  GAG  GCG  CGG  TGG  CCG  GTG  CGG  ACC  GGG  CAC  TGC  GGG  AGG  CAC    3254
Ala  Trp  Glu  Ala  Arg  Trp  Pro  Val  Arg  Thr  Gly  His  Cys  Gly  Arg  His
               1010                     1015                     1020

CTC  TCG  GCC  TCC  GAG  CGG  CCC  CTG  TCG  CCC  GCG  CGC  TGT  CAC  TAC  AGC    3302
Leu  Ser  Ala  Ser  Glu  Arg  Pro  Leu  Ser  Pro  Ala  Arg  Cys  His  Tyr  Ser
          1025                     1030                     1035

TCC  TTT  CCT  CGA  GCC  GAC  CGA  TCC  GGC  CGC  CCC  TTC  CTC  CCG  CTC  TTC    3350
Ser  Phe  Pro  Arg  Ala  Asp  Arg  Ser  Gly  Arg  Pro  Phe  Leu  Pro  Leu  Phe
     1040                     1045                     1050

CCG  GAG  CCC  CCG  GAG  CTG  GAG  GAC  CTG  CCG  CTG  CTC  GGT  CCG  GAG  CAG    3398
Pro  Glu  Pro  Pro  Glu  Leu  Glu  Asp  Leu  Pro  Leu  Leu  Gly  Pro  Glu  Gln
1055                     1060                     1065                     1070

CTG  GCC  CGG  CGG  GAG  GCC  CTG  CTG  AAC  GCG  GCC  TGG  GCC  CGG  GGC  TCG    3446
Leu  Ala  Arg  Arg  Glu  Ala  Leu  Leu  Asn  Ala  Ala  Trp  Ala  Arg  Gly  Ser
               1075                     1080                     1085

CGC  CCG  AGT  CAC  GCT  TCC  CTG  CCC  AGC  TCC  GTG  GCC  GAG  GCC  TTC  GCT    3494
Arg  Pro  Ser  His  Ala  Ser  Leu  Pro  Ser  Ser  Val  Ala  Glu  Ala  Phe  Ala
          1090                     1095                     1100

CGG  CCC  AGC  TCG  CTG  CCC  GCT  GGG  TGC  ACC  GGC  CCC  GCC  TGC  GCC  CGC    3542
Arg  Pro  Ser  Ser  Leu  Pro  Ala  Gly  Cys  Thr  Gly  Pro  Ala  Cys  Ala  Arg
     1105                     1110                     1115

CCC  GAC  GGC  CAC  TCG  GCC  TGC  AGG  CGC  TTG  GCG  CAG  GCG  CAG  TCG  ATG    3590
Pro  Asp  Gly  His  Ser  Ala  Cys  Arg  Arg  Leu  Ala  Gln  Ala  Gln  Ser  Met
1120                     1125                     1130

TGC  TTG  CCG  ATC  TAC  CGG  GAG  GCC  TGC  CAG  GAG  GGC  GAG  CAG  GCA  GGG    3638
Cys  Leu  Pro  Ile  Tyr  Arg  Glu  Ala  Cys  Gln  Glu  Gly  Glu  Gln  Ala  Gly
1135                     1140                     1145                     1150

GCC  CCC  GCC  TGG  CAG  CAC  AGA  CAG  CAC  GTC  TGC  CTG  CAC  GCC  CAC  GCC    3686
Ala  Pro  Ala  Trp  Gln  His  Arg  Gln  His  Val  Cys  Leu  His  Ala  His  Ala
               1155                     1160                     1165

CAC  CTG  CCA  TTG  TGC  TGG  GGG  GCT  GTC  TGT  CCT  CAC  CTT  CCA  CCC  TGT    3734
His  Leu  Pro  Leu  Cys  Trp  Gly  Ala  Val  Cys  Pro  His  Leu  Pro  Pro  Cys
          1170                     1175                     1180

GAC  AGC  CAC  GGC  TCC  TGG  CTC  TCC  GGC  GCC  TGG  GGG  CCT  CTG  GGG  CAC    3782
Asp  Ser  His  Gly  Ser  Trp  Leu  Ser  Gly  Ala  Trp  Gly  Pro  Leu  Gly  His
     1185                     1190                     1195
```

```
AGC GGC AGG ACT CTG GGG CTG GGC ACA GGC TAC AGA GAC AGT GGG GGA          3830
Ser Gly Arg Thr Leu Gly Leu Gly Thr Gly Tyr Arg Asp Ser Gly Gly
    1200            1205                1210

CTG GAC GAG ATC AGC AGT GTA GCC CGT GGG ACG CAA GGC TTC CCG GGA          3878
Leu Asp Glu Ile Ser Ser Val Ala Arg Gly Thr Gln Gly Phe Pro Gly
1215                1220                1225                1230

CCC TGC ACC TGG AGA CGG ATC TCC AGT CTG GAG TCA GAA GTG TGAGTTATCA      3930
Pro Cys Thr Trp Arg Arg Ile Ser Ser Leu Glu Ser Glu Val
                1235                1240                124

GCCACTCAGG CTCCGAGCCA GCTGGATTCT CTGCCTGCCA CTGTCAGGGT TAAGCGGCAG       3990

GCAGGATTGG CCCTTCTCTG GCTTCTACCA TGAAATCCTG GCCATGGCAC CCCAGTGACA       4050

GATGATGTCT TCCATGGTCA TCAGTGACCT CAGCTAGCCT CA                           4092
```

(2) INFORMATION FOR SEQ ID NO:46:

(i) SEQUENCE CHARACTERISTICS:
        (A) LENGTH: 1244 amino acids
        (B) TYPE: amino acid
        (D) TOPOLOGY: linear (ii) MOLECULE TYPE: protein (xi) SEQUENCE DESCRIPTION: SEQ ID NO:46:

```
Met Gly Gly Ala Leu Gly Pro Ala Leu Leu Leu Thr Ser Leu Phe Gly
1               5                   10                  15

Ala Trp Ala Gly Leu Gly Pro Gly Gln Gly Glu Gln Gly Met Thr Val
            20                  25                  30

Ala Val Val Phe Ser Ser Ser Gly Pro Pro Gln Ala Gln Phe Arg Val
                35                  40                  45

Arg Leu Thr Pro Gln Ser Phe Leu Asp Leu Pro Leu Glu Ile Gln Pro
        50                  55                  60

Leu Thr Val Gly Val Asn Thr Thr Asn Pro Ser Ser Leu Leu Thr Gln
65                  70                  75                  80

Ile Cys Gly Leu Leu Gly Ala Ala His Val His Gly Ile Val Phe Glu
                    85                  90                  95

Asp Asn Val Asp Thr Glu Ala Val Ala Gln Ile Leu Asp Phe Ile Ser
                100                 105                 110

Ser Gln Thr His Val Pro Ile Leu Ser Ile Ser Gly Gly Ser Ala Val
        115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
        195                 200                 205

Arg Ala Arg Thr Gln Arg Leu Leu Arg Gln Leu Asp Ala Pro Val Phe
    210                 215                 220

Val Ala Tyr Cys Ser Arg Glu Glu Ala Glu Val Leu Phe Ala Glu Ala
225                 230                 235                 240

Ala Gln Ala Gly Leu Val Gly Pro Gly His Val Trp Leu Val Pro Asn
                245                 250                 255

Leu Ala Leu Gly Ser Thr Asp Ala Pro Pro Ala Thr Phe Pro Val Gly
```

-continued

```
                        260                             265                             270
Leu  Ile  Ser  Val  Val  Thr  Glu  Ser  Trp  Arg  Leu  Ser  Leu  Arg  Gln  Lys
          275                      280                      285

Val  Arg  Asp  Gly  Val  Ala  Ile  Leu  Ala  Leu  Gly  Ala  His  Ser  Tyr  Trp
     290                      295                      300

Arg  Gln  His  Gly  Thr  Leu  Pro  Ala  Pro  Ala  Gly  Asp  Cys  Arg  Val  His
305                           310                      315                      320

Pro  Gly  Pro  Val  Ser  Pro  Ala  Arg  Glu  Ala  Phe  Tyr  Arg  His  Leu  Leu
                         325                      330                      335

Asn  Val  Thr  Trp  Glu  Gly  Arg  Asp  Phe  Ser  Phe  Ser  Pro  Gly  Gly  Tyr
               340                      345                           350

Leu  Val  Gln  Pro  Thr  Met  Val  Val  Ile  Ala  Leu  Asn  Arg  His  Arg  Leu
               355                      360                      365

Trp  Glu  Met  Val  Gly  Arg  Trp  Glu  His  Gly  Val  Leu  Tyr  Met  Lys  Tyr
          370                      375                      380

Pro  Val  Trp  Pro  Arg  Tyr  Ser  Ala  Ser  Leu  Gln  Pro  Val  Val  Asp  Ser
385                           390                      395                      400

Arg  His  Leu  Thr  Val  Ala  Thr  Leu  Glu  Glu  Arg  Pro  Phe  Val  Ile  Val
                    405                      410                           415

Glu  Ser  Pro  Asp  Pro  Gly  Thr  Gly  Gly  Cys  Val  Pro  Asn  Thr  Val  Pro
               420                      425                      430

Cys  Arg  Arg  Gln  Ser  Asn  His  Thr  Phe  Ser  Ser  Gly  Asp  Val  Ala  Pro
               435                      440                      445

Tyr  Thr  Lys  Leu  Cys  Cys  Lys  Gly  Phe  Cys  Ile  Asp  Ile  Leu  Lys  Lys
          450                      455                      460

Leu  Ala  Arg  Val  Val  Lys  Phe  Ser  Tyr  Asp  Leu  Tyr  Leu  Val  Thr  Asn
465                           470                      475                      480

Gly  Lys  His  Gly  Lys  Arg  Val  Arg  Gly  Val  Trp  Asn  Gly  Met  Ile  Gly
                    485                      490                           495

Glu  Val  Tyr  Tyr  Lys  Arg  Ala  Asp  Met  Ala  Ile  Gly  Ser  Leu  Thr  Ile
               500                      505                      510

Asn  Glu  Glu  Arg  Ser  Glu  Ile  Val  Asp  Phe  Ser  Val  Pro  Phe  Val  Glu
          515                      520                      525

Thr  Gly  Ile  Ser  Val  Met  Val  Ala  Arg  Ser  Asn  Gly  Thr  Val  Ser  Pro
          530                      535                      540

Ser  Ala  Phe  Leu  Glu  Pro  Tyr  Ser  Pro  Ala  Val  Trp  Val  Met  Met  Phe
545                      550                      555                           560

Val  Met  Cys  Leu  Thr  Val  Val  Ala  Ile  Thr  Val  Phe  Met  Phe  Glu  Tyr
                    565                      570                           575

Phe  Ser  Pro  Val  Ser  Tyr  Asn  Gln  Asn  Leu  Thr  Arg  Gly  Lys  Lys  Ser
               580                      585                      590

Gly  Gly  Pro  Ala  Phe  Thr  Ile  Gly  Lys  Ser  Val  Trp  Leu  Leu  Trp  Ala
          595                      600                      605

Leu  Val  Phe  Asn  Asn  Ser  Val  Pro  Ile  Glu  Asn  Pro  Arg  Gly  Thr  Thr
610                           615                      620

Ser  Lys  Ile  Met  Val  Leu  Val  Trp  Ala  Phe  Phe  Ala  Val  Ile  Phe  Leu
625                      630                      635                           640

Ala  Arg  Tyr  Thr  Ala  Asn  Leu  Ala  Ala  Phe  Met  Ile  Gln  Glu  Gln  Tyr
                    645                      650                      655

Ile  Asp  Thr  Val  Ser  Gly  Leu  Ser  Asp  Lys  Lys  Phe  Gln  Arg  Pro  Gln
               660                      665                      670

Asp  Gln  Tyr  Pro  Pro  Phe  Arg  Phe  Gly  Thr  Val  Pro  Asn  Gly  Ser  Thr
          675                      680                      685
```

| | | | | | | | | | | | | | |
|---|---|---|---|---|---|---|---|---|---|---|---|---|---|
| Glu | Arg | Asn | Ile | Arg | Ser | Asn | Tyr | Arg | Asp | Met | His | Thr | His | Met | Val |
| | 690 | | | | 695 | | | | 700 | | | | | | |
| Lys | Phe | Asn | Gln | Arg | Ser | Val | Glu | Asp | Ala | Leu | Thr | Ser | Leu | Lys | Met |
| 705 | | | | | 710 | | | | 715 | | | | | | 720 |
| Gly | Ser | Glu | Ala | Gln | Pro | Val | Pro | Arg | Lys | Leu | Asp | Ala | Phe | Ile | Tyr |
| | | | | 725 | | | | | 730 | | | | | 735 | |
| Asp | Ala | Ala | Val | Leu | Asn | Tyr | Met | Ala | Gly | Lys | Asp | Glu | Gly | Cys | Lys |
| | | | 740 | | | | | 745 | | | | | 750 | | |
| Leu | Val | Thr | Ile | Gly | Ser | Gly | Lys | Val | Phe | Ala | Thr | Thr | Gly | Tyr | Gly |
| | | 755 | | | | | 760 | | | | 765 | | | | |
| Ile | Ala | Met | Gln | Lys | Asp | Ser | His | Trp | Lys | Arg | Ala | Ile | Asp | Leu | Ala |
| | 770 | | | | | 775 | | | | | 780 | | | | |
| Leu | Leu | Gln | Phe | Leu | Gly | Asp | Gly | Glu | Thr | Gln | Lys | Leu | Glu | Thr | Val |
| 785 | | | | | 790 | | | | 795 | | | | | | 800 |
| Trp | Leu | Ser | Gly | Ile | Cys | Gln | Asn | Glu | Lys | Asn | Glu | Val | Met | Ser | Ser |
| | | | | 805 | | | | | 810 | | | | | 815 | |
| Lys | Leu | Asp | Ile | Asp | Asn | Met | Gly | Gly | Val | Phe | Tyr | Met | Leu | Leu | Val |
| | | | 820 | | | | | 825 | | | | | 830 | | |
| Ala | Met | Gly | Leu | Ala | Leu | Leu | Val | Phe | Ala | Trp | Glu | His | Leu | Val | Tyr |
| | | 835 | | | | | 840 | | | | | 845 | | | |
| Trp | Lys | Leu | Arg | His | Ser | Val | Pro | Asn | Ser | Ser | Gln | Leu | Asp | Phe | Leu |
| | 850 | | | | | 855 | | | | | 860 | | | | |
| Leu | Ala | Phe | Ser | Arg | Gly | Ile | Tyr | Ser | Cys | Phe | Ser | Gly | Val | Gln | Ser |
| 865 | | | | | 870 | | | | | 875 | | | | | 880 |
| Leu | Ala | Ser | Pro | Pro | Arg | Gln | Ala | Ser | Pro | Asp | Leu | Thr | Ala | Ser | Ser |
| | | | | 885 | | | | | 890 | | | | | 895 | |
| Ala | Gln | Ala | Ser | Val | Leu | Lys | Ile | Leu | Gln | Ala | Ala | Arg | Asp | Met | Val |
| | | | 900 | | | | | 905 | | | | | 910 | | |
| Thr | Thr | Ala | Gly | Val | Ser | Asn | Ser | Leu | Asp | Arg | Ala | Thr | Arg | Thr | Ile |
| | | 915 | | | | | 920 | | | | | 925 | | | |
| Glu | Asn | Trp | Gly | Gly | Gly | Arg | Arg | Ala | Pro | Pro | Pro | Ser | Pro | Cys | Pro |
| | 930 | | | | | 935 | | | | | 940 | | | | |
| Thr | Pro | Arg | Ser | Gly | Pro | Ser | Pro | Cys | Leu | Pro | Thr | Pro | Asp | Pro | Pro |
| 945 | | | | | 950 | | | | | 955 | | | | | 960 |
| Pro | Glu | Pro | Ser | Pro | Thr | Gly | Trp | Gly | Pro | Pro | Asp | Gly | Gly | Arg | Ala |
| | | | | 965 | | | | | 970 | | | | | 975 | |
| Ala | Leu | Val | Arg | Arg | Ala | Pro | Gln | Pro | Gly | Arg | Pro | Pro | Thr | Pro | |
| | | | 980 | | | | | 985 | | | | | 990 | | |
| Gly | Pro | Pro | Leu | Ser | Asp | Val | Ser | Arg | Val | Ser | Arg | Arg | Pro | Ala | Trp |
| | | 995 | | | | | 1000 | | | | | 1005 | | | |
| Glu | Ala | Arg | Trp | Pro | Val | Arg | Thr | Gly | His | Cys | Gly | Arg | His | Leu | Ser |
| | 1010 | | | | | 1015 | | | | | 1020 | | | | |
| Ala | Ser | Glu | Arg | Pro | Leu | Ser | Pro | Ala | Arg | Cys | His | Tyr | Ser | Ser | Phe |
| 1025 | | | | | 1030 | | | | | 1035 | | | | | 1040 |
| Pro | Arg | Ala | Asp | Arg | Ser | Gly | Arg | Pro | Phe | Leu | Pro | Leu | Phe | Pro | Glu |
| | | | | 1045 | | | | | 1050 | | | | | 1055 | |
| Pro | Pro | Glu | Leu | Glu | Asp | Leu | Pro | Leu | Leu | Gly | Pro | Glu | Gln | Leu | Ala |
| | | | | 1060 | | | | | 1065 | | | | | 1070 | |
| Arg | Arg | Glu | Ala | Leu | Leu | Asn | Ala | Ala | Trp | Ala | Arg | Gly | Ser | Arg | Pro |
| | | | 1075 | | | | | 1080 | | | | | 1085 | | |
| Ser | His | Ala | Ser | Leu | Pro | Ser | Ser | Val | Ala | Glu | Ala | Phe | Ala | Arg | Pro |
| | | 1090 | | | | | 1095 | | | | | 1100 | | | |
| Ser | Ser | Leu | Pro | Ala | Gly | Cys | Thr | Gly | Pro | Ala | Cys | Ala | Arg | Pro | Asp |
| 1105 | | | | | 1110 | | | | | 1115 | | | | | 1120 |

```
Gly  His  Ser  Ala  Cys  Arg  Arg  Leu  Ala  Gln  Ala  Gln  Ser  Met  Cys  Leu
               1125                    1130                    1135

Pro  Ile  Tyr  Arg  Glu  Ala  Cys  Gln  Glu  Gly  Glu  Gln  Ala  Gly  Ala  Pro
               1140                    1145                    1150

Ala  Trp  Gln  His  Arg  Gln  His  Val  Cys  Leu  His  Ala  His  Ala  His  Leu
               1155                    1160                    1165

Pro  Leu  Cys  Trp  Gly  Ala  Val  Cys  Pro  His  Leu  Pro  Pro  Cys  Asp  Ser
          1170                    1175                    1180

His  Gly  Ser  Trp  Leu  Ser  Gly  Ala  Trp  Gly  Pro  Leu  Gly  His  Ser  Gly
1185                         1190                    1195                    1200

Arg  Thr  Leu  Gly  Leu  Gly  Thr  Gly  Tyr  Arg  Asp  Ser  Gly  Gly  Leu  Asp
               1205                    1210                    1215

Glu  Ile  Ser  Ser  Val  Ala  Arg  Gly  Thr  Gln  Gly  Phe  Pro  Gly  Pro  Cys
               1220                    1225                    1230

Thr  Trp  Arg  Arg  Ile  Ser  Ser  Leu  Glu  Ser  Glu  Val
               1235                    1240
```

( 2 ) INFORMATION FOR SEQ ID NO:47:

( i ) SEQUENCE CHARACTERISTICS:
        ( A ) LENGTH: 4053 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 189..3884

( x i ) SEQUENCE DESCRIPTION: SEQ ID NO:47:

```
CCCTTAATAA  GATTTGCNAC  GTACACTCGA  GCCATCGCGA  GTGTCCTTGA  GCCGCGGGTG      60

ACGGTGGCTC  TCGCTGCTCG  CGCCCCCTCC  TCCCGCGGGG  GGAGCCTGAT  GCCACGTTCC     120

CTATGAATTA  TTTATCGCCG  GCCTAAAAAT  ACCCCGAACT  TCACAGCCCG  AGTGACCCTC     180

CGGTGGAC  ATG  GGT  GGG  GCC  CTG  GGG  CCG  GCC  CTG  TTG  CTC  ACC  TCG  CTC      230
          Met  Gly  Gly  Ala  Leu  Gly  Pro  Ala  Leu  Leu  Leu  Thr  Ser  Leu
           1              5                          10

TTC  GGT  GCC  TGG  GCA  GGG  CTG  GGT  CCG  GGG  CAG  GGC  GAG  CAG  GGC  ATG      278
Phe  Gly  Ala  Trp  Ala  Gly  Leu  Gly  Pro  Gly  Gln  Gly  Glu  Gln  Gly  Met
15                   20                        25                        30

ACG  GTG  GCC  GTG  GTG  TTT  AGC  AGC  TCA  GGG  CCG  CCC  CAG  GCC  CAG  TTC      326
Thr  Val  Ala  Val  Val  Phe  Ser  Ser  Ser  Gly  Pro  Pro  Gln  Ala  Gln  Phe
                    35                        40                        45

CGT  GTC  CGC  CTC  ACC  CCC  CAG  AGC  TTC  CTG  GAC  CTA  CCC  CTG  GAG  ATC      374
Arg  Val  Arg  Leu  Thr  Pro  Gln  Ser  Phe  Leu  Asp  Leu  Pro  Leu  Glu  Ile
               50                        55                        60

CAG  CCG  CTC  ACA  GTT  GGG  GTC  AAC  ACC  ACC  AAC  CCC  AGC  AGC  CTC  CTC      422
Gln  Pro  Leu  Thr  Val  Gly  Val  Asn  Thr  Thr  Asn  Pro  Ser  Ser  Leu  Leu
               65                        70                        75

ACC  CAG  ATC  TGC  GGC  CTC  CTG  GGT  GCT  GCC  CAC  GTC  CAC  GGC  ATT  GTC      470
Thr  Gln  Ile  Cys  Gly  Leu  Leu  Gly  Ala  Ala  His  Val  His  Gly  Ile  Val
          80                        85                        90

TTT  GAG  GAC  AAC  GTG  GAC  ACC  GAG  GCG  GTG  GCC  CAG  ATC  CTT  GAC  TTC      518
Phe  Glu  Asp  Asn  Val  Asp  Thr  Glu  Ala  Val  Ala  Gln  Ile  Leu  Asp  Phe
95                        100                       105                       110

ATC  TCC  TCC  CAG  ACC  CAT  GTG  CCC  ATC  CTC  AGC  ATC  AGC  GGA  GGC  TCT      566
Ile  Ser  Ser  Gln  Thr  His  Val  Pro  Ile  Leu  Ser  Ile  Ser  Gly  Gly  Ser
                    115                       120                       125
```

| | | | | | | | | | | | | | | | | |
|---|---|---|---|---|---|---|---|---|---|---|---|---|---|---|---|---|
| GCT | GTG | GTC | CTC | ACC | CCC | AAG | GAG | CCG | GGC | TCC | GCC | TTC | CTG | CAG | CTG | 614 |
| Ala | Val | Val | Leu | Thr | Pro | Lys | Glu | Pro | Gly | Ser | Ala | Phe | Leu | Gln | Leu | |
| | | | 130 | | | | 135 | | | | | | 140 | | | |
| GGC | GTG | TCC | CTG | GAG | CAG | CAG | CTG | CAG | GTG | CTG | TTC | AAG | GTG | CTG | GAA | 662 |
| Gly | Val | Ser | Leu | Glu | Gln | Gln | Leu | Gln | Val | Leu | Phe | Lys | Val | Leu | Glu | |
| | | 145 | | | | | 150 | | | | | 155 | | | | |
| GAG | TAC | GAC | TGG | AGC | GCC | TTC | GCC | GTC | ATC | ACC | AGC | CTG | CAC | CCG | GGC | 710 |
| Glu | Tyr | Asp | Trp | Ser | Ala | Phe | Ala | Val | Ile | Thr | Ser | Leu | His | Pro | Gly | |
| | 160 | | | | | 165 | | | | | 170 | | | | | |
| CAC | GCG | CTC | TTC | CTG | GAG | GGC | GTG | CGC | GCC | GTC | GCC | GAC | GCC | AGC | CAC | 758 |
| His | Ala | Leu | Phe | Leu | Glu | Gly | Val | Arg | Ala | Val | Ala | Asp | Ala | Ser | His | |
| 175 | | | | | 180 | | | | 185 | | | | | | 190 | |
| GTG | AGT | TGG | CGG | CTG | CTG | GAC | GTG | GTC | ACG | CTG | GAA | CTG | GAC | CCG | GGA | 806 |
| Val | Ser | Trp | Arg | Leu | Leu | Asp | Val | Val | Thr | Leu | Glu | Leu | Asp | Pro | Gly | |
| | | | | 195 | | | | | 200 | | | | | 205 | | |
| GGG | CCG | CGC | GCG | CGC | ACG | CAG | CGC | CTG | CTG | CGC | CAG | CTC | GAC | GCG | CCC | 854 |
| Gly | Pro | Arg | Ala | Arg | Thr | Gln | Arg | Leu | Leu | Arg | Gln | Leu | Asp | Ala | Pro | |
| | | | 210 | | | | 215 | | | | | | 220 | | | |
| GTG | TTT | GTG | GCC | TAC | TGC | TCG | CGC | GAG | GAG | GCC | GAG | GTG | CTC | TTC | GCC | 902 |
| Val | Phe | Val | Ala | Tyr | Cys | Ser | Arg | Glu | Glu | Ala | Glu | Val | Leu | Phe | Ala | |
| | | 225 | | | | | 230 | | | | | 235 | | | | |
| GAG | GCG | GCG | CAG | GCC | GGT | CTG | GTG | GGG | CCC | GGC | CAC | GTG | TGG | CTG | GTG | 950 |
| Glu | Ala | Ala | Gln | Ala | Gly | Leu | Val | Gly | Pro | Gly | His | Val | Trp | Leu | Val | |
| | 240 | | | | | 245 | | | | | 250 | | | | | |
| CCC | AAC | CTG | GCG | CTG | GGC | AGC | ACC | GAT | GCG | CCC | CCC | GCC | ACC | TTC | CCC | 998 |
| Pro | Asn | Leu | Ala | Leu | Gly | Ser | Thr | Asp | Ala | Pro | Pro | Ala | Thr | Phe | Pro | |
| 255 | | | | | 260 | | | | 265 | | | | | | 270 | |
| GTG | GGC | CTC | ATC | AGC | GTC | GTC | ACC | GAG | AGC | TGG | CGC | CTC | AGC | CTG | CGC | 1046 |
| Val | Gly | Leu | Ile | Ser | Val | Val | Thr | Glu | Ser | Trp | Arg | Leu | Ser | Leu | Arg | |
| | | | | 275 | | | | | 280 | | | | | 285 | | |
| CAG | AAG | GTG | CGC | GAC | GGC | GTG | GCC | ATT | CTG | GCC | CTG | GGC | GCC | CAC | AGC | 1094 |
| Gln | Lys | Val | Arg | Asp | Gly | Val | Ala | Ile | Leu | Ala | Leu | Gly | Ala | His | Ser | |
| | | | 290 | | | | | 295 | | | | | 300 | | | |
| TAC | TGG | CGC | CAG | CAT | GGA | ACC | CTG | CCA | GCC | CCG | GCC | GGG | GAC | TGC | CGT | 1142 |
| Tyr | Trp | Arg | Gln | His | Gly | Thr | Leu | Pro | Ala | Pro | Ala | Gly | Asp | Cys | Arg | |
| | | 305 | | | | | 310 | | | | | 315 | | | | |
| GTT | CAC | CCT | GGG | CCC | GTC | AGC | CCT | GCC | CGG | GAG | GCC | TTC | TAC | AGG | CAC | 1190 |
| Val | His | Pro | Gly | Pro | Val | Ser | Pro | Ala | Arg | Glu | Ala | Phe | Tyr | Arg | His | |
| | 320 | | | | | 325 | | | | | 330 | | | | | |
| CTA | CTG | AAT | GTC | ACC | TGG | GAG | GGC | CGA | GAC | TTC | TCC | TTC | AGC | CCT | GGT | 1238 |
| Leu | Leu | Asn | Val | Thr | Trp | Glu | Gly | Arg | Asp | Phe | Ser | Phe | Ser | Pro | Gly | |
| 335 | | | | | 340 | | | | 345 | | | | | | 350 | |
| GGG | TAC | CTG | GTC | CAG | CCC | ACC | ATG | GTG | GTG | ATC | GCC | CTC | AAC | CGG | CAC | 1286 |
| Gly | Tyr | Leu | Val | Gln | Pro | Thr | Met | Val | Val | Ile | Ala | Leu | Asn | Arg | His | |
| | | | | 355 | | | | | 360 | | | | | 365 | | |
| CGC | CTC | TGG | GAG | ATG | GTG | GGG | CGC | TGG | GAG | CAT | GGC | GTC | CTA | TAC | ATG | 1334 |
| Arg | Leu | Trp | Glu | Met | Val | Gly | Arg | Trp | Glu | His | Gly | Val | Leu | Tyr | Met | |
| | | | 370 | | | | | 375 | | | | | 380 | | | |
| AAG | TAC | CCC | GTG | TGG | CCT | CGC | TAC | AGT | GCC | TCT | CTG | CAG | CCT | GTG | GTG | 1382 |
| Lys | Tyr | Pro | Val | Trp | Pro | Arg | Tyr | Ser | Ala | Ser | Leu | Gln | Pro | Val | Val | |
| | | 385 | | | | | 390 | | | | | 395 | | | | |
| GAC | AGT | CGG | CAC | CTG | ACG | GTG | GCC | ACG | CTG | GAA | GAG | CGG | CCC | TTT | GTC | 1430 |
| Asp | Ser | Arg | His | Leu | Thr | Val | Ala | Thr | Leu | Glu | Glu | Arg | Pro | Phe | Val | |
| | 400 | | | | | 405 | | | | | 410 | | | | | |
| ATC | GTG | GAG | AGC | CCT | GAC | CCT | GGC | ACA | GGA | GGC | TGT | GTC | CCC | AAC | ACC | 1478 |
| Ile | Val | Glu | Ser | Pro | Asp | Pro | Gly | Thr | Gly | Gly | Cys | Val | Pro | Asn | Thr | |
| 415 | | | | | 420 | | | | 425 | | | | | | 430 | |
| GTG | CCC | TGC | CGC | AGG | CAG | AGC | AAC | CAC | ACC | TTC | AGC | AGC | GGG | GAC | GTG | 1526 |
| Val | Pro | Cys | Arg | Arg | Gln | Ser | Asn | His | Thr | Phe | Ser | Ser | Gly | Asp | Val | |
| | | | 435 | | | | | 440 | | | | | 445 | | | |

| | | | | | | | | | | | | | | | | |
|---|---|---|---|---|---|---|---|---|---|---|---|---|---|---|---|---|
| GCC | CCC | TAC | ACC | AAG | CTC | TGC | TGT | AAG | GGA | TTC | TGC | ATC | GAC | ATC | CTC | 1574 |
| Ala | Pro | Tyr | Thr 450 | Lys | Leu | Cys | Cys | Lys 455 | Gly | Phe | Cys | Ile | Asp 460 | Ile | Leu | |
| AAG | AAG | CTG | GCC | AGA | GTG | GTC | AAA | TTC | TCC | TAC | GAC | CTG | TAC | CTG | GTG | 1622 |
| Lys | Lys | Leu | Ala 465 | Arg | Val | Val | Lys 470 | Phe | Ser | Tyr | Asp 475 | Leu | Tyr | Leu | Val | |
| ACC | AAC | GGC | AAG | CAT | GGC | AAG | CGG | GTG | CGC | GGC | GTA | TGG | AAC | GGC | ATG | 1670 |
| Thr | Asn | Gly 480 | Lys | His | Gly | Lys 485 | Arg | Val | Arg | Gly | Val 490 | Trp | Asn | Gly | Met | |
| ATT | GGG | GAG | GTG | TAC | TAC | AAG | CGG | GCA | GAC | ATG | GCC | ATC | GGC | TCC | CTC | 1718 |
| Ile 495 | Gly | Glu | Val | Tyr | Tyr 500 | Lys | Arg | Ala | Asp | Met 505 | Ala | Ile | Gly | Ser | Leu 510 | |
| ACC | ATC | AAT | GAG | GAA | CGC | TCC | GAG | ATC | GTA | GAC | TTC | TCT | GTA | CCC | TTT | 1766 |
| Thr | Ile | Asn | Glu | Glu 515 | Arg | Ser | Glu | Ile | Val 520 | Asp | Phe | Ser | Val | Pro 525 | Phe | |
| GTG | GAG | ACG | GGC | ATC | AGT | GTG | ATG | GTG | GCT | CGC | AGC | AAT | GGC | ACC | GTC | 1814 |
| Val | Glu | Thr | Gly 530 | Ile | Ser | Val | Met | Val 535 | Ala | Arg | Ser | Asn | Gly 540 | Thr | Val | |
| TCC | CCC | TCG | GCC | TTC | TTG | GAG | CCA | TAT | AGC | CCT | GCA | GTG | TGG | GTG | ATG | 1862 |
| Ser | Pro | Ser 545 | Ala | Phe | Leu | Glu | Pro 550 | Tyr | Ser | Pro | Ala | Val 555 | Trp | Val | Met | |
| ATG | TTT | GTC | ATG | TGC | CTC | ACT | GTG | GTG | GCC | ATC | ACC | GTC | TTC | ATG | TTC | 1910 |
| Met | Phe 560 | Val | Met | Cys | Leu | Thr 565 | Val | Val | Ala | Ile | Thr 570 | Val | Phe | Met | Phe | |
| GAG | TAC | TTC | AGC | CCT | GTC | AGC | TAC | AAC | CAG | AAC | CTC | ACC | AGA | GGC | AAG | 1958 |
| Glu 575 | Tyr | Phe | Ser | Pro | Val 580 | Ser | Tyr | Asn | Gln | Asn 585 | Leu | Thr | Arg | Gly | Lys 590 | |
| ACT | TTC | ACT | ATC | GGC | AAG | TCC | GTG | TGG | CTG | CTG | TGG | GCG | CTG | GTC | TTC | 2006 |
| Thr | Phe | Thr | Ile | Gly 595 | Lys | Ser | Val | Trp | Leu 600 | Leu | Trp | Ala | Leu | Val 605 | Phe | |
| AAC | AAC | TCA | GTG | CCC | ATC | GAG | AAC | CCG | CGG | GGC | ACC | ACC | AGC | AAG | ATC | 2054 |
| Asn | Asn | Ser | Val 610 | Pro | Ile | Glu | Asn | Pro 615 | Arg | Gly | Thr | Thr | Ser 620 | Lys | Ile | |
| ATG | GTT | CTG | GTC | TGG | GCC | TTC | TTT | GCT | GTC | ATC | TTC | CTC | GCC | AGA | TAC | 2102 |
| Met | Val | Leu | Val 625 | Trp | Ala | Phe | Phe | Ala 630 | Val | Ile | Phe | Leu | Ala 635 | Arg | Tyr | |
| ACG | GCC | AAC | CTG | GCC | GCC | TTC | ATG | ATC | CAA | GAG | CAA | TAC | ATC | GAC | ACT | 2150 |
| Thr | Ala | Asn 640 | Leu | Ala | Ala | Phe | Met 645 | Ile | Gln | Glu | Gln | Tyr 650 | Ile | Asp | Thr | |
| GTG | TCG | GGC | CTC | AGT | GAC | AAG | AAG | TTT | CAG | CGG | CCT | CAA | GAT | CAG | TAC | 2198 |
| Val | Ser 655 | Gly | Leu | Ser | Asp | Lys 660 | Lys | Phe | Gln | Arg | Pro 665 | Gln | Asp | Gln | Tyr 670 | |
| CCA | CCT | TTC | CGC | TTC | GGC | ACG | GTG | CCC | AAC | GGC | AGC | ACG | GAG | CGG | AAC | 2246 |
| Pro | Pro | Phe | Arg | Phe 675 | Gly | Thr | Val | Pro | Asn 680 | Gly | Ser | Thr | Glu | Arg 685 | Asn | |
| ATC | CGC | AGT | AAC | TAC | CGT | GAC | ATG | CAC | ACC | CAC | ATG | GTC | AAG | TTC | AAC | 2294 |
| Ile | Arg | Ser | Asn 690 | Tyr | Arg | Asp | Met | His 695 | Thr | His | Met | Val | Lys 700 | Phe | Asn | |
| CAG | CGC | TCG | GTG | GAG | GAC | GCG | CTC | ACC | AGC | CTC | AAG | ATG | GGG | AAG | CTG | 2342 |
| Gln | Arg | Ser 705 | Val | Glu | Asp | Ala | Leu 710 | Thr | Ser | Leu | Lys | Met 715 | Gly | Lys | Leu | |
| GAT | GCC | TTC | ATC | TAT | GAT | GCT | GCT | GTC | CTC | AAC | TAC | ATG | GCA | GGC | AAG | 2390 |
| Asp | Ala | Phe | Ile | Tyr 720 | Asp | Ala | Ala | Val | Leu 725 | Asn | Tyr | Met | Ala | Gly 730 | Lys | |
| GAC | GAG | GGC | TGC | AAG | CTG | GTC | ACC | ATT | GGG | TCT | GGC | AAG | GTC | TTT | GCT | 2438 |
| Asp | Glu | Gly | Cys 735 | Lys | Leu | Val | Thr | Ile 740 | Gly | Ser | Gly | Lys | Val 745 | Phe | Ala | 750 |
| ACC | ACT | GGC | TAC | GGC | ATC | GCC | ATG | CAG | AAG | GAC | TCC | CAC | TGG | AAG | CGG | 2486 |
| Thr | Thr | Gly | Tyr | Gly 755 | Ile | Ala | Met | Gln | Lys 760 | Asp | Ser | His | Trp | Lys 765 | Arg | |

| | | | | | | | | | | | | | | | | |
|---|---|---|---|---|---|---|---|---|---|---|---|---|---|---|---|---|
| GCC | ATA | GAC | CTG | GCG | CTC | TTG | CAG | TTC | CTG | GGG | GAC | GGA | GAG | ACA | CAG | 2534 |
| Ala | Ile | Asp | Leu | Ala | Leu | Leu | Gln | Phe | Leu | Gly | Asp | Gly | Glu | Thr | Gln | |
| | 770 | | | | | | 775 | | | | | 780 | | | | |
| AAA | CTG | GAG | ACA | GTG | TGG | CTC | TCA | GGG | ATC | TGC | CAG | AAT | GAG | AAG | AAC | 2582 |
| Lys | Leu | Glu | Thr | Val | Trp | Leu | Ser | Gly | Ile | Cys | Gln | Asn | Glu | Lys | Asn | |
| | | 785 | | | | | 790 | | | | | 795 | | | | |
| GAG | GTG | ATG | AGC | AGC | AAG | CTG | GAC | ATC | GAC | AAC | ATG | GGA | GGC | GTC | TTC | 2630 |
| Glu | Val | Met | Ser | Ser | Lys | Leu | Asp | Ile | Asp | Asn | Met | Gly | Gly | Val | Phe | |
| 800 | | | | | | 805 | | | | | 810 | | | | | |
| TAC | ATG | CTG | CTG | GTG | GCC | ATG | GGG | CTG | GCC | CTG | CTG | GTC | TTC | GCC | TGG | 2678 |
| Tyr | Met | Leu | Leu | Val | Ala | Met | Gly | Leu | Ala | Leu | Leu | Val | Phe | Ala | Trp | |
| 815 | | | | | 820 | | | | | 825 | | | | | 830 | |
| GAG | CAC | CTG | GTC | TAC | TGG | AAG | CTG | CGC | CAC | TCG | GTG | CCC | AAC | TCA | TCC | 2726 |
| Glu | His | Leu | Val | Tyr | Trp | Lys | Leu | Arg | His | Ser | Val | Pro | Asn | Ser | Ser | |
| | | | | 835 | | | | | 840 | | | | | 845 | | |
| CAG | CTG | GAC | TTC | CTG | CTG | GCT | TTC | AGC | AGG | GGC | ATC | TAC | AGC | TGC | TTC | 2774 |
| Gln | Leu | Asp | Phe | Leu | Leu | Ala | Phe | Ser | Arg | Gly | Ile | Tyr | Ser | Cys | Phe | |
| | | | 850 | | | | | 855 | | | | | 860 | | | |
| AGC | GGG | GTG | CAG | AGC | CTC | GCC | AGC | CCA | CCG | CGG | CAG | GCC | AGC | CCG | GAC | 2822 |
| Ser | Gly | Val | Gln | Ser | Leu | Ala | Ser | Pro | Pro | Arg | Gln | Ala | Ser | Pro | Asp | |
| | | 865 | | | | | 870 | | | | | 875 | | | | |
| CTC | ACG | GCC | AGC | TCG | GCC | CAG | GCC | AGC | GTG | CTC | AAG | ATT | CTG | CAG | GCA | 2870 |
| Leu | Thr | Ala | Ser | Ser | Ala | Gln | Ala | Ser | Val | Leu | Lys | Ile | Leu | Gln | Ala | |
| | 880 | | | | | 885 | | | | | 890 | | | | | |
| GCC | CGC | GAC | ATG | GTG | ACC | ACG | GCG | GGC | GTA | AGC | AAC | TCC | CTG | GAC | CGC | 2918 |
| Ala | Arg | Asp | Met | Val | Thr | Thr | Ala | Gly | Val | Ser | Asn | Ser | Leu | Asp | Arg | |
| 895 | | | | | 900 | | | | | 905 | | | | | 910 | |
| GCC | ACT | CGC | ACC | ATC | GAG | AAT | TGG | GGT | GGC | GGC | CGT | GCG | CCC | CCA | | 2966 |
| Ala | Thr | Arg | Thr | Ile | Glu | Asn | Trp | Gly | Gly | Gly | Arg | Arg | Ala | Pro | Pro | |
| | | | | 915 | | | | | 920 | | | | | 925 | | |
| CCG | TCC | CCC | TGC | CCG | ACC | CCG | CGG | TCT | GGC | CCC | AGC | CCA | TGC | CTG | CCC | 3014 |
| Pro | Ser | Pro | Cys | Pro | Thr | Pro | Arg | Ser | Gly | Pro | Ser | Pro | Cys | Leu | Pro | |
| | | | 930 | | | | | 935 | | | | | 940 | | | |
| ACC | CCC | GAC | CCG | CCC | CCA | GAG | CCG | AGC | CCC | ACG | GGC | TGG | GGA | CCG | CCA | 3062 |
| Thr | Pro | Asp | Pro | Pro | Pro | Glu | Pro | Ser | Pro | Thr | Gly | Trp | Gly | Pro | Pro | |
| | | | 945 | | | | | 950 | | | | | 955 | | | |
| GAC | GGG | GGT | CGC | GCG | GCG | CTT | GTG | CGC | AGG | GCT | CCG | CAG | CCC | CCG | GGC | 3110 |
| Asp | Gly | Gly | Arg | Ala | Ala | Leu | Val | Arg | Arg | Ala | Pro | Gln | Pro | Pro | Gly | |
| | 960 | | | | | 965 | | | | | 970 | | | | | |
| CGC | CCC | CCG | ACG | CCG | GGG | CCG | CCC | CTG | TCC | GAC | GTC | TCC | CGA | GTG | TCG | 3158 |
| Arg | Pro | Pro | Thr | Pro | Gly | Pro | Pro | Leu | Ser | Asp | Val | Ser | Arg | Val | Ser | |
| 975 | | | | | 980 | | | | | 985 | | | | | 990 | |
| CGC | CGC | CCA | GCC | TGG | GAG | GCG | CGG | TGG | CCG | GTG | CGG | ACC | GGG | CAC | TGC | 3206 |
| Arg | Arg | Pro | Ala | Trp | Glu | Ala | Arg | Trp | Pro | Val | Arg | Thr | Gly | His | Cys | |
| | | | | 995 | | | | | 1000 | | | | | 1005 | | |
| GGG | AGG | CAC | CTC | TCG | GCC | TCC | GAG | CGG | CCC | CTG | TCG | CCC | GCG | CGC | TGT | 3254 |
| Gly | Arg | His | Leu | Ser | Ala | Ser | Glu | Arg | Pro | Leu | Ser | Pro | Ala | Arg | Cys | |
| | | | 1010 | | | | | 1015 | | | | | 1020 | | | |
| CAC | TAC | AGC | TCC | TTT | CCT | CGA | GCC | GAC | CGA | TCC | GGC | CGC | CCC | TTC | CTC | 3302 |
| His | Tyr | Ser | Ser | Phe | Pro | Arg | Ala | Asp | Arg | Ser | Gly | Arg | Pro | Phe | Leu | |
| | | 1025 | | | | | 1030 | | | | | 1035 | | | | |
| CCG | CTC | TTC | CCG | GAG | CCC | CCG | GAG | CTG | GAG | GAC | CTG | CCG | CTG | CTC | GGT | 3350 |
| Pro | Leu | Phe | Pro | Glu | Pro | Pro | Glu | Leu | Glu | Asp | Leu | Pro | Leu | Leu | Gly | |
| | 1040 | | | | | 1045 | | | | | 1050 | | | | | |
| CCG | GAG | CAG | CTG | GCC | CGG | CGG | GAG | GCC | CTG | CTG | AAC | GCG | GCC | TGG | GCC | 3398 |
| Pro | Glu | Gln | Leu | Ala | Arg | Arg | Glu | Ala | Leu | Leu | Asn | Ala | Ala | Trp | Ala | |
| 1055 | | | | | 1060 | | | | | 1065 | | | | | 1070 | |
| CGG | GGC | TCG | CGC | CCG | AGT | CAC | GCT | TCC | CTG | CCC | AGC | TCC | GTG | GCC | GAG | 3446 |
| Arg | Gly | Ser | Arg | Pro | Ser | His | Ala | Ser | Leu | Pro | Ser | Ser | Val | Ala | Glu | |
| | | | | 1075 | | | | | 1080 | | | | | 1085 | | |

| | | | | | | | | | | | | | | | | |
|---|---|---|---|---|---|---|---|---|---|---|---|---|---|---|---|---|
| GCC | TTC | GCT | CGG | CCC | AGC | TCG | CTG | CCC | GCT | GGG | TGC | ACC | GGC | CCC | GCC | 3494 |
| Ala | Phe | Ala | Arg 1090 | Pro | Ser | Ser | Leu | Pro 1095 | Ala | Gly | Cys | Thr | Gly 1100 | Pro | Ala | |
| TGC | GCC | CGC | CCC | GAC | GGC | CAC | TCG | GCC | TGC | AGG | CGC | TTG | GCG | CAG | GCG | 3542 |
| Cys | Ala | Arg 1105 | Pro | Asp | Gly | His | Ser 1110 | Ala | Cys | Arg | Arg | Leu 1115 | Ala | Gln | Ala | |
| CAG | TCG | ATG | TGC | TTG | CCG | ATC | TAC | CGG | GAG | GCC | TGC | CAG | GAG | GGC | GAG | 3590 |
| Gln | Ser | Met 1120 | Cys | Leu | Pro | Ile | Tyr 1125 | Arg | Glu | Ala | Cys | Gln 1130 | Glu | Gly | Glu | |
| CAG | GCA | GGG | GCC | CCC | GCC | TGG | CAG | CAC | AGA | CAG | CAC | GTC | TGC | CTG | CAC | 3638 |
| Gln | Ala | Gly 1135 | Ala | Pro | Ala | Trp 1140 | Gln | His | Arg | Gln | His 1145 | Val | Cys | Leu | His 1150 | |
| GCC | CAC | GCC | CAC | CTG | CCA | TTG | TGC | TGG | GGG | GCT | GTC | TGT | CCT | CAC | CTT | 3686 |
| Ala | His | Ala | His | Leu 1155 | Pro | Leu | Cys | Trp | Gly 1160 | Ala | Val | Cys | Pro | His 1165 | Leu | |
| CCA | CCC | TGT | GAC | AGC | CAC | GGC | TCC | TGG | CTC | TCC | GGC | GCC | TGG | GGG | CCT | 3734 |
| Pro | Pro | Cys | Asp 1170 | Ser | His | Gly | Ser | Trp 1175 | Leu | Ser | Gly | Ala | Trp 1180 | Gly | Pro | |
| CTG | GGG | CAC | AGC | GGC | AGG | ACT | CTG | GGG | CTG | GGC | ACA | GGC | TAC | AGA | GAC | 3782 |
| Leu | Gly | His | Ser 1185 | Gly | Arg | Thr | Leu | Gly 1190 | Leu | Gly | Thr | Gly | Tyr 1195 | Arg | Asp | |
| AGT | GGG | GGA | CTG | GAC | GAG | ATC | AGC | AGT | GTA | GCC | CGT | GGG | ACG | CAA | GGC | 3830 |
| Ser | Gly | Gly 1200 | Leu | Asp | Glu | Ile | Ser 1205 | Ser | Val | Ala | Arg | Gly 1210 | Thr | Gln | Gly | |
| TTC | CCG | GGA | CCC | TGC | ACC | TGG | AGA | CGG | ATC | TCC | AGT | CTG | GAG | TCA | GAA | 3878 |
| Phe | Pro 1215 | Gly | Pro | Cys | Thr | Trp 1220 | Arg | Arg | Ile | Ser | Ser 1225 | Leu | Glu | Ser | Glu 1230 | |
| GTG | | | | | | | | | | | | | | | | |
| Val | | | | | | | | | | | | | | | | |

| | |
|---|---|
| GTG TGAGTTATCA GCCACTCAGG CTCCGAGCCA GCTGGATTCT CTGCCTGCCA | 3931 |
| CTGTCAGGGT TAAGCGGCAG GCAGGATTGG CCCTTCTCTG GCTTCTACCA TGAAATCCTG | 3991 |
| GCCATGGCAC CCCAGTGACA GATGATGTCT TCCATGGTCA TCAGTGACCT CAGCTAGCCT | 4051 |
| CA | 4053 |

( 2 ) INFORMATION FOR SEQ ID NO:48:

( i ) SEQUENCE CHARACTERISTICS:
        ( A ) LENGTH: 1231 amino acids
        ( B ) TYPE: amino acid
        ( D ) TOPOLOGY: linear ( i i ) MOLECULE TYPE: protein ( x i ) SEQUENCE DESCRIPTION: SEQ ID NO:48:

| | | | | | | | | | | | | | | |
|---|---|---|---|---|---|---|---|---|---|---|---|---|---|---|
| Met 1 | Gly | Gly | Ala | Leu 5 | Gly | Pro | Ala | Leu | Leu 10 | Thr | Ser | Leu | Phe | Gly 15 |
| Ala | Trp | Ala | Gly 20 | Leu | Gly | Pro | Gly | Gln 25 | Gly | Glu | Gln | Gly | Met 30 | Thr | Val |
| Ala | Val | Val 35 | Phe | Ser | Ser | Ser | Gly 40 | Pro | Pro | Gln | Ala | Gln 45 | Phe | Arg | Val |
| Arg | Leu 50 | Thr | Pro | Gln | Ser | Phe 55 | Leu | Asp | Leu | Pro | Leu 60 | Glu | Ile | Gln | Pro |
| Leu 65 | Thr | Val | Gly | Val | Asn 70 | Thr | Thr | Asn | Pro | Ser 75 | Ser | Leu | Leu | Thr | Gln 80 |
| Ile | Cys | Gly | Leu | Leu 85 | Gly | Ala | Ala | His | Val 90 | His | Gly | Ile | Val | Phe 95 | Glu |
| Asp | Asn | Val | Asp 100 | Thr | Glu | Ala | Val | Ala 105 | Gln | Ile | Leu | Asp | Phe 110 | Ile | Ser |
| Ser | Gln | Thr 115 | His | Val | Pro | Ile | Leu 120 | Ser | Ile | Ser | Gly | Gly 125 | Ser | Ala | Val |

-continued

```
Val Leu Thr Pro Lys Glu Pro Gly Ser Ala Phe Leu Gln Leu Gly Val
    130             135                 140
Ser Leu Glu Gln Gln Leu Gln Val Leu Phe Lys Val Leu Glu Glu Tyr
145             150                 155                         160
Asp Trp Ser Ala Phe Ala Val Ile Thr Ser Leu His Pro Gly His Ala
                165                 170                 175
Leu Phe Leu Glu Gly Val Arg Ala Val Ala Asp Ala Ser His Val Ser
            180                 185                 190
Trp Arg Leu Leu Asp Val Val Thr Leu Glu Leu Asp Pro Gly Gly Pro
        195                 200                 205
Arg Ala Arg Thr Gln Arg Leu Leu Arg Gln Leu Asp Ala Pro Val Phe
    210                 215                 220
Val Ala Tyr Cys Ser Arg Glu Glu Ala Glu Val Leu Phe Ala Glu Ala
225                 230                 235                     240
Ala Gln Ala Gly Leu Val Gly Pro Gly His Val Trp Leu Val Pro Asn
                245                 250                 255
Leu Ala Leu Gly Ser Thr Asp Ala Pro Pro Ala Thr Phe Pro Val Gly
            260                 265                 270
Leu Ile Ser Val Val Thr Glu Ser Trp Arg Leu Ser Leu Arg Gln Lys
            275                 280                 285
Val Arg Asp Gly Val Ala Ile Leu Ala Leu Gly Ala His Ser Tyr Trp
    290                 295                 300
Arg Gln His Gly Thr Leu Pro Ala Pro Ala Gly Asp Cys Arg Val His
305                 310                 315                     320
Pro Gly Pro Val Ser Pro Ala Arg Glu Ala Phe Tyr Arg His Leu Leu
                325                 330                 335
Asn Val Thr Trp Glu Gly Arg Asp Phe Ser Phe Ser Pro Gly Gly Tyr
            340                 345                 350
Leu Val Gln Pro Thr Met Val Val Ile Ala Leu Asn Arg His Arg Leu
            355                 360                 365
Trp Glu Met Val Gly Arg Trp Glu His Gly Val Leu Tyr Met Lys Tyr
    370                 375                 380
Pro Val Trp Pro Arg Tyr Ser Ala Ser Leu Gln Pro Val Val Asp Ser
385                 390                 395                     400
Arg His Leu Thr Val Ala Thr Leu Glu Glu Arg Pro Phe Val Ile Val
                405                 410                 415
Glu Ser Pro Asp Pro Gly Thr Gly Gly Cys Val Pro Asn Thr Val Pro
            420                 425                 430
Cys Arg Arg Gln Ser Asn His Thr Phe Ser Ser Gly Asp Val Ala Pro
            435                 440                 445
Tyr Thr Lys Leu Cys Cys Lys Gly Phe Cys Ile Asp Ile Leu Lys Lys
    450                 455                 460
Leu Ala Arg Val Val Lys Phe Ser Tyr Asp Leu Tyr Leu Val Thr Asn
465                 470                 475                     480
Gly Lys His Gly Lys Arg Val Arg Gly Val Trp Asn Gly Met Ile Gly
                485                 490                 495
Glu Val Tyr Tyr Lys Arg Ala Asp Met Ala Ile Gly Ser Leu Thr Ile
            500                 505                 510
Asn Glu Glu Arg Ser Glu Ile Val Asp Phe Ser Val Pro Phe Val Glu
            515                 520                 525
Thr Gly Ile Ser Val Met Val Ala Arg Ser Asn Gly Thr Val Ser Pro
    530                 535                 540
Ser Ala Phe Leu Glu Pro Tyr Ser Pro Ala Val Trp Val Met Met Phe
```

-continued

```
545                     550                     555                     560
Val  Met  Cys  Leu  Thr  Val  Val  Ala  Ile  Thr  Val  Phe  Met  Phe  Glu  Tyr
               565                     570                     575
Phe  Ser  Pro  Val  Ser  Tyr  Asn  Gln  Asn  Leu  Thr  Arg  Gly  Lys  Thr  Phe
               580                     585                     590
Thr  Ile  Gly  Lys  Ser  Val  Trp  Leu  Leu  Trp  Ala  Leu  Val  Phe  Asn  Asn
               595                     600                     605
Ser  Val  Pro  Ile  Glu  Asn  Pro  Arg  Gly  Thr  Thr  Ser  Lys  Ile  Met  Val
          610                     615                     620
Leu  Val  Trp  Ala  Phe  Phe  Ala  Val  Ile  Phe  Leu  Ala  Arg  Tyr  Thr  Ala
625                     630                     635                     640
Asn  Leu  Ala  Ala  Phe  Met  Ile  Gln  Glu  Gln  Tyr  Ile  Asp  Thr  Val  Ser
               645                     650                     655
Gly  Leu  Ser  Asp  Lys  Lys  Phe  Gln  Arg  Pro  Gln  Asp  Gln  Tyr  Pro  Pro
               660                     665                     670
Phe  Arg  Phe  Gly  Thr  Val  Pro  Asn  Gly  Ser  Thr  Glu  Arg  Asn  Ile  Arg
          675                     680                     685
Ser  Asn  Tyr  Arg  Asp  Met  His  Thr  His  Met  Val  Lys  Phe  Asn  Gln  Arg
          690                     695                     700
Ser  Val  Glu  Asp  Ala  Leu  Thr  Ser  Leu  Lys  Met  Gly  Lys  Leu  Asp  Ala
705                     710                     715                     720
Phe  Ile  Tyr  Asp  Ala  Ala  Val  Leu  Asn  Tyr  Met  Ala  Gly  Lys  Asp  Glu
               725                     730                     735
Gly  Cys  Lys  Leu  Val  Thr  Ile  Gly  Ser  Gly  Lys  Val  Phe  Ala  Thr  Thr
               740                     745                     750
Gly  Tyr  Gly  Ile  Ala  Met  Gln  Lys  Asp  Ser  His  Trp  Lys  Arg  Ala  Ile
          755                     760                     765
Asp  Leu  Ala  Leu  Leu  Gln  Phe  Leu  Gly  Asp  Gly  Glu  Thr  Gln  Lys  Leu
770                     775                     780
Glu  Thr  Val  Trp  Leu  Ser  Gly  Ile  Cys  Gln  Asn  Glu  Lys  Asn  Glu  Val
785                     790                     795                     800
Met  Ser  Ser  Lys  Leu  Asp  Ile  Asp  Asn  Met  Gly  Gly  Val  Phe  Tyr  Met
               805                     810                     815
Leu  Leu  Val  Ala  Met  Gly  Leu  Ala  Leu  Leu  Val  Phe  Ala  Trp  Glu  His
               820                     825                     830
Leu  Val  Tyr  Trp  Lys  Leu  Arg  His  Ser  Val  Pro  Asn  Ser  Ser  Gln  Leu
               835                     840                     845
Asp  Phe  Leu  Leu  Ala  Phe  Ser  Arg  Gly  Ile  Tyr  Ser  Cys  Phe  Ser  Gly
          850                     855                     860
Val  Gln  Ser  Leu  Ala  Ser  Pro  Pro  Arg  Gln  Ala  Ser  Pro  Asp  Leu  Thr
865                     870                     875                     880
Ala  Ser  Ser  Ala  Gln  Ala  Ser  Val  Leu  Lys  Ile  Leu  Gln  Ala  Ala  Arg
               885                     890                     895
Asp  Met  Val  Thr  Thr  Ala  Gly  Val  Ser  Asn  Ser  Leu  Asp  Arg  Ala  Thr
               900                     905                     910
Arg  Thr  Ile  Glu  Asn  Trp  Gly  Gly  Arg  Arg  Ala  Pro  Pro  Pro  Ser
          915                     920                     925
Pro  Cys  Pro  Thr  Pro  Arg  Ser  Gly  Pro  Ser  Pro  Cys  Leu  Pro  Thr  Pro
     930                     935                     940
Asp  Pro  Pro  Pro  Glu  Pro  Ser  Pro  Thr  Gly  Trp  Gly  Pro  Pro  Asp  Gly
945                     950                     955                     960
Gly  Arg  Ala  Ala  Leu  Val  Arg  Arg  Ala  Pro  Gln  Pro  Pro  Gly  Arg  Pro
               965                     970                     975
```

| | | | | | | | | | | | | | | | |
|---|---|---|---|---|---|---|---|---|---|---|---|---|---|---|---|
| Pro | Thr | Pro | Gly 980 | Pro | Pro | Leu | Ser | Asp 985 | Val | Ser | Arg | Val | Ser 990 | Arg | Arg |
| Pro | Ala | Trp 995 | Glu | Ala | Arg | Trp | Pro 1000 | Val | Arg | Thr | Gly | His 1005 | Cys | Gly | Arg |
| His | Leu 1010 | Ser | Ala | Ser | Glu | Arg 1015 | Pro | Leu | Ser | Pro | Ala 1020 | Arg | Cys | His | Tyr |
| Ser 1025 | Ser | Phe | Pro | Arg 1030 | Ala | Asp | Arg | Ser | Gly 1035 | Arg | Pro | Phe | Leu | Pro 1040 | Leu |
| Phe | Pro | Glu | Pro | Pro 1045 | Glu | Leu | Glu | Asp | Leu 1050 | Pro | Leu | Leu | Gly 1055 | Pro | Glu |
| Gln | Leu | Ala | Arg 1060 | Arg | Glu | Ala | Leu | Leu 1065 | Asn | Ala | Ala | Trp | Ala 1070 | Arg | Gly |
| Ser | Arg | Pro 1075 | Ser | His | Ala | Ser | Leu 1080 | Pro | Ser | Ser | Val | Ala 1085 | Glu | Ala | Phe |
| Ala | Arg | Pro 1090 | Ser | Ser | Leu | Pro | Ala 1095 | Gly | Cys | Thr | Gly | Pro 1100 | Ala | Cys | Ala |
| Arg | Pro | Asp | Gly | His 1110 | Ser | Ala | Cys | Arg | Arg 1115 | Leu | Ala | Gln | Ala | Gln 1120 | Ser |
| Met | Cys | Leu | Pro | Ile 1125 | Tyr | Arg | Glu | Ala | Cys 1130 | Gln | Glu | Gly | Glu | Gln 1135 | Ala |
| Gly | Ala | Pro | Ala 1140 | Trp | Gln | His | Arg | Gln 1145 | His | Val | Cys | Leu | His 1150 | Ala | His |
| Ala | His | Leu 1155 | Pro | Leu | Cys | Trp | Gly 1160 | Ala | Val | Cys | Pro | His 1165 | Leu | Pro | Pro |
| Cys | Asp | Ser 1170 | His | Gly | Ser | Trp | Leu 1175 | Ser | Gly | Ala | Trp | Gly 1180 | Pro | Leu | Gly |
| His 1185 | Ser | Gly | Arg | Thr | Leu 1190 | Gly | Leu | Gly | Thr | Gly 1195 | Tyr | Arg | Asp | Ser | Gly 1200 |
| Gly | Leu | Asp | Glu | Ile 1205 | Ser | Ser | Val | Ala | Arg 1210 | Gly | Thr | Gln | Gly | Phe 1215 | Pro |
| Gly | Pro | Cys | Thr 1220 | Trp | Arg | Arg | Ile | Ser 1225 | Ser | Leu | Glu | Ser | Glu 1230 | Val | |

( 2 ) INFORMATION FOR SEQ ID NO:49:

( i ) SEQUENCE CHARACTERISTICS:
        ( A ) LENGTH: 4017 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 189..3848

( x i ) SEQUENCE DESCRIPTION: SEQ ID NO:49:

```
CCCTTAATAA GATTTGCNAC GTACACTCGA GCCATCGCGA GTGTCCTTGA GCCGCGGGTG        60

ACGGTGGCTC TCGCTGCTCG CGCCCCCTCC TCCCGCGGGG GGAGCCTGAT GCCACGTTCC       120

CTATGAATTA TTTATCGCCG GCCTAAAAAT ACCCCGAACT TCACAGCCCG AGTGACCCTC       180

CGGTGGAC ATG GGT GGG GCC CTG GGG CCG GCC CTG TTG CTC ACC TCG CTC       230
         Met Gly Gly Ala Leu Gly Pro Ala Leu Leu Leu Thr Ser Leu
          1               5                  10

TTC GGT GCC TGG GCA GGG CTG GGT CCG GGG CAG GGC GAG CAG GGC ATG       278
Phe Gly Ala Trp Ala Gly Leu Gly Pro Gly Gln Gly Glu Gln Gly Met
 15              20                  25                  30

ACG GTG GCC GTG GTG TTT AGC AGC TCA GGG CCG CCC CAG GCC CAG TTC       326
```

```
              Thr  Val  Ala  Val  Val  Phe  Ser  Ser  Ser  Gly  Pro  Pro  Gln  Ala  Gln  Phe
                              35                  40                            45

CGT  GTC  CGC  CTC  ACC  CCC  CAG  AGC  TTC  CTG  GAC  CTA  CCC  CTG  GAG  ATC    374
              Arg  Val  Arg  Leu  Thr  Pro  Gln  Ser  Phe  Leu  Asp  Leu  Pro  Leu  Glu  Ile
                              50                  55                            60

CAG  CCG  CTC  ACA  GTT  GGG  GTC  AAC  ACC  ACC  AAC  CCC  AGC  AGC  CTC  CTC    422
              Gln  Pro  Leu  Thr  Val  Gly  Val  Asn  Thr  Thr  Asn  Pro  Ser  Ser  Leu  Leu
                              65                  70                            75

ACC  CAG  ATC  TGC  GGC  CTC  CTG  GGT  GCT  GCC  CAC  GTC  CAC  GGC  ATT  GTC    470
              Thr  Gln  Ile  Cys  Gly  Leu  Leu  Gly  Ala  Ala  His  Val  His  Gly  Ile  Val
                   80                       85                       90

TTT  GAG  GAC  AAC  GTG  GAC  ACC  GAG  GCG  GTG  GCC  CAG  ATC  CTT  GAC  TTC    518
              Phe  Glu  Asp  Asn  Val  Asp  Thr  Glu  Ala  Val  Ala  Gln  Ile  Leu  Asp  Phe
              95                  100                      105                           110

ATC  TCC  TCC  CAG  ACC  CAT  GTG  CCC  ATC  CTC  AGC  ATC  AGC  GGA  GGC  TCT    566
              Ile  Ser  Ser  Gln  Thr  His  Val  Pro  Ile  Leu  Ser  Ile  Ser  Gly  Gly  Ser
                                  115                      120                           125

GCT  GTG  GTC  CTC  ACC  CCC  AAG  GAG  CCG  GGC  TCC  GCC  TTC  CTG  CAG  CTG    614
              Ala  Val  Val  Leu  Thr  Pro  Lys  Glu  Pro  Gly  Ser  Ala  Phe  Leu  Gln  Leu
                             130                       135                      140

GGC  GTG  TCC  CTG  GAG  CAG  CAG  CTG  CAG  GTG  CTG  TTC  AAG  GTG  CTG  GAA    662
              Gly  Val  Ser  Leu  Glu  Gln  Gln  Leu  Gln  Val  Leu  Phe  Lys  Val  Leu  Glu
                             145                       150                      155

GAG  TAC  GAC  TGG  AGC  GCC  TTC  GCC  GTC  ATC  ACC  AGC  CTG  CAC  CCG  GGC    710
              Glu  Tyr  Asp  Trp  Ser  Ala  Phe  Ala  Val  Ile  Thr  Ser  Leu  His  Pro  Gly
                   160                      165                      170

CAC  GCG  CTC  TTC  CTG  GAG  GGC  GTG  CGC  GCC  GTC  GCC  GAC  GCC  AGC  CAC    758
              His  Ala  Leu  Phe  Leu  Glu  Gly  Val  Arg  Ala  Val  Ala  Asp  Ala  Ser  His
              175                      180                      185                      190

GTG  AGT  TGG  CGG  CTG  CTG  GAC  GTG  GTC  ACG  CTG  GAA  CTG  GAC  CCG  GGA    806
              Val  Ser  Trp  Arg  Leu  Leu  Asp  Val  Val  Thr  Leu  Glu  Leu  Asp  Pro  Gly
                                  195                      200                           205

GGG  CCG  CGC  GCG  CGC  ACG  CAG  CGC  CTG  CTG  CGC  CAG  CTC  GAC  GCG  CCC    854
              Gly  Pro  Arg  Ala  Arg  Thr  Gln  Arg  Leu  Leu  Arg  Gln  Leu  Asp  Ala  Pro
                             210                       215                      220

GTG  TTT  GTG  GCC  TAC  TGC  TCG  CGC  GAG  GAG  GCC  GAG  GTG  CTC  TTC  GCC    902
              Val  Phe  Val  Ala  Tyr  Cys  Ser  Arg  Glu  Glu  Ala  Glu  Val  Leu  Phe  Ala
                        225                      230                           235

GAG  GCG  GCG  CAG  GCC  GGT  CTG  GTG  GGG  CCC  GGC  CAC  GTG  TGG  CTG  GTG    950
              Glu  Ala  Ala  Gln  Ala  Gly  Leu  Val  Gly  Pro  Gly  His  Val  Trp  Leu  Val
                   240                      245                      250

CCC  AAC  CTG  GCG  CTG  GGC  AGC  ACC  GAT  GCG  CCC  CCC  GCC  ACC  TTC  CCC    998
              Pro  Asn  Leu  Ala  Leu  Gly  Ser  Thr  Asp  Ala  Pro  Pro  Ala  Thr  Phe  Pro
              255                      260                      265                      270

GTG  GGC  CTC  ATC  AGC  GTC  GTC  ACC  GAG  AGC  TGG  CGC  CTC  AGC  CTG  CGC   1046
              Val  Gly  Leu  Ile  Ser  Val  Val  Thr  Glu  Ser  Trp  Arg  Leu  Ser  Leu  Arg
                                  275                      280                           285

CAG  AAG  GTG  CGC  GAC  GGC  GTG  GCC  ATT  CTG  GCC  CTG  GGC  GCC  CAC  AGC   1094
              Gln  Lys  Val  Arg  Asp  Gly  Val  Ala  Ile  Leu  Ala  Leu  Gly  Ala  His  Ser
                             290                       295                      300

TAC  TGG  CGC  CAG  CAT  GGA  ACC  CTG  CCA  GCC  CCG  GCC  GGG  GAC  TGC  CGT   1142
              Tyr  Trp  Arg  Gln  His  Gly  Thr  Leu  Pro  Ala  Pro  Ala  Gly  Asp  Cys  Arg
                        305                      310                           315

GTT  CAC  CCT  GGG  CCC  GTC  AGC  CCT  GCC  CGG  GAG  GCC  TTC  TAC  AGG  CAC   1190
              Val  His  Pro  Gly  Pro  Val  Ser  Pro  Ala  Arg  Glu  Ala  Phe  Tyr  Arg  His
                   320                      325                           330

CTA  CTG  AAT  GTC  ACC  TGG  GAG  GGC  CGA  GAC  TTC  TCC  TTC  AGC  CCT  GGT   1238
              Leu  Leu  Asn  Val  Thr  Trp  Glu  Gly  Arg  Asp  Phe  Ser  Phe  Ser  Pro  Gly
              335                      340                      345                      350

GGG  TAC  CTG  GTC  CAG  CCC  ACC  ATG  GTG  GTG  ATC  GCC  CTC  AAC  CGG  CAC   1286
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| Gly | Tyr | Leu | Val | Gln | Pro | Thr | Met | Val | Val | Ile | Ala | Leu | Asn | Arg | His |      |
|     |     |     |     | 355 |     |     | 360 |     |     |     |     |     |     | 365 |     |      |
| CGC | CTC | TGG | GAG | ATG | GTG | GGG | CGC | TGG | GAG | CAT | GGC | GTC | CTA | TAC | ATG | 1334 |
| Arg | Leu | Trp | Glu | Met | Val | Gly | Arg | Trp | Glu | His | Gly | Val | Leu | Tyr | Met |      |
|     |     | 370 |     |     |     |     | 375 |     |     |     |     |     | 380 |     |     |      |
| AAG | TAC | CCC | GTG | TGG | CCT | CGC | TAC | AGT | GCC | TCT | CTG | CAG | CCT | GTG | GTG | 1382 |
| Lys | Tyr | Pro | Val | Trp | Pro | Arg | Tyr | Ser | Ala | Ser | Leu | Gln | Pro | Val | Val |      |
|     |     | 385 |     |     |     |     | 390 |     |     |     |     | 395 |     |     |     |      |
| GAC | AGT | CGG | CAC | CTG | ACG | GTG | GCC | ACG | CTG | GAA | GAG | CGG | CCC | TTT | GTC | 1430 |
| Asp | Ser | Arg | His | Leu | Thr | Val | Ala | Thr | Leu | Glu | Glu | Arg | Pro | Phe | Val |      |
|     | 400 |     |     |     |     | 405 |     |     |     |     |     | 410 |     |     |     |      |
| ATC | GTG | GAG | AGC | CCT | GAC | CCT | GGC | ACA | GGA | GGC | TGT | GTC | CCC | AAC | ACC | 1478 |
| Ile | Val | Glu | Ser | Pro | Asp | Pro | Gly | Thr | Gly | Gly | Cys | Val | Pro | Asn | Thr |      |
| 415 |     |     |     |     | 420 |     |     |     |     | 425 |     |     |     |     | 430 |      |
| GTG | CCC | TGC | CGC | AGG | CAG | AGC | AAC | CAC | ACC | TTC | AGC | AGC | GGG | GAC | GTG | 1526 |
| Val | Pro | Cys | Arg | Arg | Gln | Ser | Asn | His | Thr | Phe | Ser | Ser | Gly | Asp | Val |      |
|     |     |     |     | 435 |     |     |     |     | 440 |     |     |     |     | 445 |     |      |
| GCC | CCC | TAC | ACC | AAG | CTC | TGC | TGT | AAG | GGA | TTC | TGC | ATC | GAC | ATC | CTC | 1574 |
| Ala | Pro | Tyr | Thr | Lys | Leu | Cys | Cys | Lys | Gly | Phe | Cys | Ile | Asp | Ile | Leu |      |
|     |     |     | 450 |     |     |     |     | 455 |     |     |     |     | 460 |     |     |      |
| AAG | AAG | CTG | GCC | AGA | GTG | GTC | AAA | TTC | TCC | TAC | GAC | CTG | TAC | CTG | GTG | 1622 |
| Lys | Lys | Leu | Ala | Arg | Val | Val | Lys | Phe | Ser | Tyr | Asp | Leu | Tyr | Leu | Val |      |
|     | 465 |     |     |     |     |     | 470 |     |     |     |     | 475 |     |     |     |      |
| ACC | AAC | GGC | AAG | CAT | GGC | AAG | CGG | GTG | CGC | GGC | GTA | TGG | AAC | GGC | ATG | 1670 |
| Thr | Asn | Gly | Lys | His | Gly | Lys | Arg | Val | Arg | Gly | Val | Trp | Asn | Gly | Met |      |
|     | 480 |     |     |     |     | 485 |     |     |     |     | 490 |     |     |     |     |      |
| ATT | GGG | GAG | GTG | TAC | TAC | AAG | CGG | GCA | GAC | ATG | GCC | ATC | GGC | TCC | CTC | 1718 |
| Ile | Gly | Glu | Val | Tyr | Tyr | Lys | Arg | Ala | Asp | Met | Ala | Ile | Gly | Ser | Leu |      |
| 495 |     |     |     |     | 500 |     |     |     |     | 505 |     |     |     |     | 510 |      |
| ACC | ATC | AAT | GAG | GAA | CGC | TCC | GAG | ATC | GTA | GAC | TTC | TCT | GTA | CCC | TTT | 1766 |
| Thr | Ile | Asn | Glu | Glu | Arg | Ser | Glu | Ile | Val | Asp | Phe | Ser | Val | Pro | Phe |      |
|     |     |     |     | 515 |     |     |     |     | 520 |     |     |     |     | 525 |     |      |
| GTG | GAG | ACG | GGC | ATC | AGT | GTG | ATG | GTG | GCT | CGC | AGC | AAT | GGC | ACC | GTC | 1814 |
| Val | Glu | Thr | Gly | Ile | Ser | Val | Met | Val | Ala | Arg | Ser | Asn | Gly | Thr | Val |      |
|     |     |     | 530 |     |     |     |     | 535 |     |     |     |     | 540 |     |     |      |
| TCC | CCC | TCG | GCC | TTC | TTG | GAG | CCA | TAT | AGC | CCT | GCA | GTG | TGG | GTG | ATG | 1862 |
| Ser | Pro | Ser | Ala | Phe | Leu | Glu | Pro | Tyr | Ser | Pro | Ala | Val | Trp | Val | Met |      |
|     |     | 545 |     |     |     |     | 550 |     |     |     |     | 555 |     |     |     |      |
| ATG | TTT | GTC | ATG | TGC | CTC | ACT | GTG | GTG | GCC | ATC | ACC | GTC | TTC | ATG | TTC | 1910 |
| Met | Phe | Val | Met | Cys | Leu | Thr | Val | Val | Ala | Ile | Thr | Val | Phe | Met | Phe |      |
|     | 560 |     |     |     |     | 565 |     |     |     |     | 570 |     |     |     |     |      |
| GAG | TAC | TTC | AGC | CCT | GTC | AGC | TAC | AAC | CAG | AAC | CTC | ACC | AGA | GGC | AAG | 1958 |
| Glu | Tyr | Phe | Ser | Pro | Val | Ser | Tyr | Asn | Gln | Asn | Leu | Thr | Arg | Gly | Lys |      |
| 575 |     |     |     |     | 580 |     |     |     |     | 585 |     |     |     |     | 590 |      |
| AAG | TCC | GGG | GGC | CCA | GCT | TTC | ACT | ATC | GGC | AAG | TCC | GTG | TGG | CTG | CTG | 2006 |
| Lys | Ser | Gly | Gly | Pro | Ala | Phe | Thr | Ile | Gly | Lys | Ser | Val | Trp | Leu | Leu |      |
|     |     |     |     | 595 |     |     |     |     | 600 |     |     |     |     | 605 |     |      |
| TGG | GCG | CTG | GTC | TTC | AAC | AAC | TCA | GTG | CCC | ATC | GAG | AAC | CCG | CGG | GGC | 2054 |
| Trp | Ala | Leu | Val | Phe | Asn | Asn | Ser | Val | Pro | Ile | Glu | Asn | Pro | Arg | Gly |      |
|     |     |     | 610 |     |     |     |     | 615 |     |     |     |     | 620 |     |     |      |
| ACC | ACC | AGC | AAG | ATC | ATG | GTT | CTG | GTC | TGG | GCC | TTC | TTT | GCT | GTC | ATC | 2102 |
| Thr | Thr | Ser | Lys | Ile | Met | Val | Leu | Val | Trp | Ala | Phe | Phe | Ala | Val | Ile |      |
|     |     | 625 |     |     |     |     | 630 |     |     |     |     | 635 |     |     |     |      |
| TTC | CTC | GCC | AGA | TAC | ACG | GCC | AAC | CTG | GCC | GCC | TTC | ATG | ATC | CAA | GAG | 2150 |
| Phe | Leu | Ala | Arg | Tyr | Thr | Ala | Asn | Leu | Ala | Ala | Phe | Met | Ile | Gln | Glu |      |
|     | 640 |     |     |     |     | 645 |     |     |     |     | 650 |     |     |     |     |      |
| CAA | TAC | ATC | GAC | ACT | GTG | TCG | GGC | CTC | AGT | GAC | AAG | AAG | TTT | CAG | CGG | 2198 |
| Gln | Tyr | Ile | Asp | Thr | Val | Ser | Gly | Leu | Ser | Asp | Lys | Lys | Phe | Gln | Arg |      |
| 655 |     |     |     |     | 660 |     |     |     |     | 665 |     |     |     |     | 670 |      |
| CCT | CAA | GAT | CAG | TAC | CCA | CCT | TTC | CGC | TTC | GGC | ACG | GTG | CCC | AAC | GGC | 2246 |

| | | | | | | | | | | | | | | | |
|---|---|---|---|---|---|---|---|---|---|---|---|---|---|---|---|
| Pro | Gln | Asp | Gln | Tyr<br>675 | Pro | Pro | Phe | Arg | Phe<br>680 | Gly | Thr | Val | Pro | Asn<br>685 | Gly |
| AGC | ACG | GAG | CGG | AAC | ATC | CGC | AGT | AAC | TAC | CGT | GAC | ATG | CAC | ACC | CAC | 2294
| Ser | Thr | Glu | Arg<br>690 | Asn | Ile | Arg | Ser | Asn<br>695 | Tyr | Arg | Asp | Met | His<br>700 | Thr | His |
| ATG | GTC | AAG | TTC | AAC | CAG | CGC | TCG | GTG | GAG | GAC | GCG | CTC | ACC | AGC | CTC | 2342
| Met | Val | Lys<br>705 | Phe | Asn | Gln | Arg | Ser<br>710 | Val | Glu | Asp | Ala | Leu<br>715 | Thr | Ser | Leu |
| AAG | ATG | GGC | AAG | GAC | GAG | GGC | TGC | AAG | CTG | GTC | ACC | ATT | GGG | TCT | GGC | 2390
| Lys | Met<br>720 | Gly | Lys | Asp | Glu<br>725 | Gly | Cys | Lys | Leu | Val<br>730 | Thr | Ile | Gly | Ser | Gly |
| AAG | GTC | TTT | GCT | ACC | ACT | GGC | TAC | GGC | ATC | GCC | ATG | CAG | AAG | GAC | TCC | 2438
| Lys | Val | Phe<br>735 | Ala | Thr | Thr<br>740 | Gly | Tyr | Gly | Ile | Ala<br>745 | Met | Gln | Lys | Asp | Ser<br>750 |
| CAC | TGG | AAG | CGG | GCC | ATA | GAC | CTG | GCG | CTC | TTG | CAG | TTC | CTG | GGG | GAC | 2486
| His | Trp | Lys | Arg | Ala<br>755 | Ile | Asp | Leu | Ala | Leu<br>760 | Leu | Gln | Phe | Leu | Gly<br>765 | Asp |
| GGA | GAG | ACA | CAG | AAA | CTG | GAG | ACA | GTG | TGG | CTC | TCA | GGG | ATC | TGC | CAG | 2534
| Gly | Glu | Thr | Gln<br>770 | Lys | Leu | Glu | Thr | Val<br>775 | Trp | Leu | Ser | Gly | Ile<br>780 | Cys | Gln |
| AAT | GAG | AAG | AAC | GAG | GTG | ATG | AGC | AGC | AAG | CTG | GAC | ATC | GAC | AAC | ATG | 2582
| Asn | Glu | Lys<br>785 | Asn | Glu | Val | Met | Ser<br>790 | Ser | Lys | Leu | Asp | Ile<br>795 | Asp | Asn | Met |
| GGA | GGC | GTC | TTC | TAC | ATG | CTG | CTG | GTG | GCC | ATG | GGG | CTG | GCC | CTG | CTG | 2630
| Gly | Gly<br>800 | Val | Phe | Tyr | Met | Leu<br>805 | Leu | Val | Ala | Met | Gly<br>810 | Leu | Ala | Leu | Leu |
| GTC | TTC | GCC | TGG | GAG | CAC | CTG | GTC | TAC | TGG | AAG | CTG | CGC | CAC | TCG | GTG | 2678
| Val<br>815 | Phe | Ala | Trp | Glu | His<br>820 | Leu | Val | Tyr | Trp | Lys<br>825 | Leu | Arg | His | Ser | Val<br>830 |
| CCC | AAC | TCA | TCC | CAG | CTG | GAC | TTC | CTG | CTG | GCT | TTC | AGC | AGG | GGC | ATC | 2726
| Pro | Asn | Ser | Ser | Gln<br>835 | Leu | Asp | Phe | Leu | Leu<br>840 | Ala | Phe | Ser | Arg | Gly<br>845 | Ile |
| TAC | AGC | TGC | TTC | AGC | GGG | GTG | CAG | AGC | CTC | GCC | AGC | CCA | CCG | CGG | CAG | 2774
| Tyr | Ser | Cys | Phe<br>850 | Ser | Gly | Val | Gln | Ser<br>855 | Leu | Ala | Ser | Pro | Pro<br>860 | Arg | Gln |
| GCC | AGC | CCG | GAC | CTC | ACG | GCC | AGC | TCG | GCC | CAG | GCC | AGC | GTG | CTC | AAG | 2822
| Ala | Ser | Pro<br>865 | Asp | Leu | Thr | Ala | Ser<br>870 | Ser | Ala | Gln | Ala | Ser<br>875 | Val | Leu | Lys |
| ATT | CTG | CAG | GCA | GCC | CGC | GAC | ATG | GTG | ACC | ACG | GCG | GGC | GTA | AGC | AAC | 2870
| Ile | Leu | Gln | Ala<br>880 | Ala | Arg | Asp | Met | Val<br>885 | Thr | Thr | Ala | Gly | Val<br>890 | Ser | Asn |
| TCC | CTG | GAC | CGC | GCC | ACT | CGC | ACC | ATC | GAG | AAT | TGG | GGT | GGC | GGC | CGC | 2918
| Ser | Leu | Asp | Arg<br>895 | Ala | Thr | Arg<br>900 | Thr | Ile | Glu | Asn | Trp<br>905 | Gly | Gly | Gly | Arg<br>910 |
| CGT | GCG | CCC | CCA | CCG | TCC | CCC | TGC | CCG | ACC | CCG | CGG | TCT | GGC | CCC | AGC | 2966
| Arg | Ala | Pro | Pro | Pro<br>915 | Ser | Pro | Cys | Pro | Thr<br>920 | Pro | Arg | Ser | Gly | Pro<br>925 | Ser |
| CCA | TGC | CTG | CCC | ACC | CCC | GAC | CCG | CCC | GAG | CCG | AGC | CCC | ACG | GGC | | 3014
| Pro | Cys | Leu | Pro<br>930 | Thr | Pro | Asp | Pro | Pro<br>935 | Glu | Pro | Ser | Pro | Thr<br>940 | Gly | |
| TGG | GGA | CCG | CCA | GAC | GGG | GGT | CGC | GCG | GCG | CTT | GTG | CGC | AGG | GCT | CCG | 3062
| Trp | Gly | Pro | Pro<br>945 | Asp | Gly | Gly | Arg | Ala<br>950 | Ala | Leu | Val | Arg | Arg<br>955 | Ala | Pro |
| CAG | CCC | CCG | GGC | CGC | CCC | CCG | ACG | CCG | GGG | CCG | CCC | CTG | TCC | GAC | GTC | 3110
| Gln | Pro | Pro<br>960 | Gly | Arg | Pro | Pro<br>965 | Thr | Pro | Gly | Pro | Pro<br>970 | Leu | Ser | Asp | Val |
| TCC | CGA | GTG | TCG | CGC | CGC | CCA | GCC | TGG | GAG | GCG | CGG | TGG | CCG | GTG | CGG | 3158
| Ser | Arg | Val<br>975 | Ser | Arg | Arg<br>980 | Pro | Ala | Trp | Glu | Ala<br>985 | Arg | Trp | Pro | Val | Arg<br>990 |
| ACC | GGG | CAC | TGC | GGG | AGG | CAC | CTC | TCG | GCC | TCC | GAG | CGG | CCC | CTG | TCG | 3206

```
Thr  Gly  His  Cys  Gly  Arg  His  Leu  Ser  Ala  Ser  Glu  Arg  Pro  Leu  Ser
          995                      1000                    1005

CCC  GCG  CGC  TGT  CAC  TAC  AGC  TCC  TTT  CCT  CGA  GCC  GAC  CGA  TCC  GGC         3254
Pro  Ala  Arg  Cys  His  Tyr  Ser  Ser  Phe  Pro  Arg  Ala  Asp  Arg  Ser  Gly
          1010                      1015                    1020

CGC  CCC  TTC  CTC  CCG  CTC  TTC  CCG  GAG  CCC  CCG  GAG  CTG  GAG  GAC  CTG         3302
Arg  Pro  Phe  Leu  Pro  Leu  Phe  Pro  Glu  Pro  Pro  Glu  Leu  Glu  Asp  Leu
          1025                      1030                    1035

CCG  CTG  CTC  GGT  CCG  GAG  CAG  CTG  GCC  CGG  CGG  GAG  GCC  CTG  CTG  AAC         3350
Pro  Leu  Leu  Gly  Pro  Glu  Gln  Leu  Ala  Arg  Arg  Glu  Ala  Leu  Leu  Asn
          1040                      1045                    1050

GCG  GCC  TGG  GCC  CGG  GGC  TCG  CGC  CCG  AGT  CAC  GCT  TCC  CTG  CCC  AGC         3398
Ala  Ala  Trp  Ala  Arg  Gly  Ser  Arg  Pro  Ser  His  Ala  Ser  Leu  Pro  Ser
1055           1060                     1065                    1070

TCC  GTG  GCC  GAG  GCC  TTC  GCT  CGG  CCC  AGC  TCG  CTG  CCC  GCT  GGG  TGC         3446
Ser  Val  Ala  Glu  Ala  Phe  Ala  Arg  Pro  Ser  Ser  Leu  Pro  Ala  Gly  Cys
          1075                      1080                    1085

ACC  GGC  CCC  GCC  TGC  GCC  CGC  CCC  GAC  GGC  CAC  TCG  GCC  TGC  AGG  CGC         3494
Thr  Gly  Pro  Ala  Cys  Ala  Arg  Pro  Asp  Gly  His  Ser  Ala  Cys  Arg  Arg
          1090                      1095                    1100

TTG  GCG  CAG  GCG  CAG  TCG  ATG  TGC  TTG  CCG  ATC  TAC  CGG  GAG  GCC  TGC         3542
Leu  Ala  Gln  Ala  Gln  Ser  Met  Cys  Leu  Pro  Ile  Tyr  Arg  Glu  Ala  Cys
          1105                      1110                    1115

CAG  GAG  GGC  GAG  CAG  GCA  GGG  GCC  CCC  GCC  TGG  CAG  CAC  AGA  CAG  CAC         3590
Gln  Glu  Gly  Glu  Gln  Ala  Gly  Ala  Pro  Ala  Trp  Gln  His  Arg  Gln  His
          1120                      1125                    1130

GTC  TGC  CTG  CAC  GCC  CAC  GCC  CAC  CTG  CCA  TTG  TGC  TGG  GGG  GCT  GTC         3638
Val  Cys  Leu  His  Ala  His  Ala  His  Leu  Pro  Leu  Cys  Trp  Gly  Ala  Val
1135           1140                     1145                    1150

TGT  CCT  CAC  CTT  CCA  CCC  TGT  GAC  AGC  CAC  GGC  TCC  TGG  CTC  TCC  GGC         3686
Cys  Pro  His  Leu  Pro  Pro  Cys  Asp  Ser  His  Gly  Ser  Trp  Leu  Ser  Gly
          1155                      1160                    1165

GCC  TGG  GGG  CCT  CTG  GGG  CAC  AGC  GGC  AGG  ACT  CTG  GGG  CTG  GGC  ACA         3734
Ala  Trp  Gly  Pro  Leu  Gly  His  Ser  Gly  Arg  Thr  Leu  Gly  Leu  Gly  Thr
          1170                      1175                    1180

GGC  TAC  AGA  GAC  AGT  GGG  GGA  CTG  GAC  GAG  ATC  AGC  AGT  GTA  GCC  CGT         3782
Gly  Tyr  Arg  Asp  Ser  Gly  Gly  Leu  Asp  Glu  Ile  Ser  Ser  Val  Ala  Arg
          1185                      1190                    1195

GGG  ACG  CAA  GGC  TTC  CCG  GGA  CCC  TGC  ACC  TGG  AGA  CGG  ATC  TCC  AGT         3830
Gly  Thr  Gln  Gly  Phe  Pro  Gly  Pro  Cys  Thr  Trp  Arg  Arg  Ile  Ser  Ser
          1200                      1205                    1210

CTG  GAG  TCA  GAA  GTG  TGAGTTATCA  GCCACTCAGG  CTCCGAGCCA  GCTGGATTCT              3885
Leu  Glu  Ser  Glu  Val
1215                     122

CTGCCTGCCA  CTGTCAGGGT  TAAGCGGCAG  GCAGGATTGG  CCCTTCTCTG  GCTTCTACCA              3945

TGAAATCCTG  GCCATGGCAC  CCCAGTGACA  GATGATGTCT  TCCATGGTCA  TCAGTGACCT              4005

CAGCTAGCCT  CA                                                                       4017
```

( 2 ) INFORMATION FOR SEQ ID NO:50:

( i ) SEQUENCE CHARACTERISTICS:
        ( A ) LENGTH: 1219 amino acids
        ( B ) TYPE: amino acid
        ( D ) TOPOLOGY: linear ( i i ) MOLECULE TYPE: protein ( x i ) SEQUENCE DESCRIPTION: SEQ ID NO:50:

```
Met  Gly  Gly  Ala  Leu  Gly  Pro  Ala  Leu  Leu  Leu  Thr  Ser  Leu  Phe  Gly
  1            5                      10                      15
```

| | | | | | | | | | | | | | | |
|---|---|---|---|---|---|---|---|---|---|---|---|---|---|---|
| Ala | Trp | Ala | Gly 20 | Leu | Gly | Pro | Gly 25 | Gln | Gly | Glu | Gln 30 | Gly | Met | Thr Val |
| Ala | Val | Val 35 | Phe | Ser | Ser | Ser | Gly 40 | Pro | Pro | Gln | Ala 45 | Gln | Phe | Arg Val |
| Arg | Leu 50 | Thr | Pro | Gln | Ser | Phe 55 | Leu | Asp | Leu | Pro | Leu 60 | Glu | Ile | Gln Pro |
| Leu 65 | Thr | Val | Gly | Val | Asn 70 | Thr | Thr | Asn | Pro | Ser 75 | Ser | Leu | Leu | Thr Gln 80 |
| Ile | Cys | Gly | Leu | Leu 85 | Gly | Ala | Ala | His | Val 90 | His | Gly | Ile | Val | Phe 95 Glu |
| Asp | Asn | Val | Asp 100 | Thr | Glu | Ala | Val | Ala 105 | Gln | Ile | Leu | Asp | Phe 110 | Ile Ser |
| Ser | Gln | Thr 115 | His | Val | Pro | Ile | Leu 120 | Ser | Ile | Ser | Gly | Gly 125 | Ser | Ala Val |
| Val | Leu 130 | Thr | Pro | Lys | Glu | Pro 135 | Gly | Ser | Ala | Phe | Leu 140 | Gln | Leu | Gly Val |
| Ser 145 | Leu | Glu | Gln | Gln | Leu 150 | Gln | Val | Leu | Phe | Lys 155 | Val | Leu | Glu | Glu Tyr 160 |
| Asp | Trp | Ser | Ala | Phe 165 | Ala | Val | Ile | Thr | Ser 170 | Leu | His | Pro | Gly | His 175 Ala |
| Leu | Phe | Leu | Glu 180 | Gly | Val | Arg | Ala | Val 185 | Ala | Asp | Ala | Ser | His 190 | Val Ser |
| Trp | Arg 195 | Leu | Leu | Asp | Val | Val 200 | Thr | Leu | Glu | Leu | Asp 205 | Pro | Gly | Gly Pro |
| Arg | Ala 210 | Arg | Thr | Gln | Arg | Leu 215 | Leu | Arg | Gln | Leu | Asp 220 | Ala | Pro | Val Phe |
| Val 225 | Ala | Tyr | Cys | Ser | Arg 230 | Glu | Glu | Ala | Glu | Val 235 | Leu | Phe | Ala | Glu Ala 240 |
| Ala | Gln | Ala | Gly | Leu 245 | Val | Gly | Pro | Gly | His 250 | Val | Trp | Leu | Val | Pro 255 Asn |
| Leu | Ala | Leu | Gly 260 | Ser | Thr | Asp | Ala | Pro 265 | Pro | Ala | Thr | Phe | Pro 270 | Val Gly |
| Leu | Ile | Ser 275 | Val | Val | Thr | Glu | Ser 280 | Trp | Arg | Leu | Ser | Leu 285 | Arg | Gln Lys |
| Val | Arg 290 | Asp | Gly | Val | Ala | Ile 295 | Leu | Ala | Leu | Gly | Ala 300 | His | Ser | Tyr Trp |
| Arg 305 | Gln | His | Gly | Thr | Leu 310 | Pro | Ala | Pro | Ala | Gly 315 | Asp | Cys | Arg | Val His 320 |
| Pro | Gly | Pro | Val | Ser 325 | Pro | Ala | Arg | Glu | Ala 330 | Phe | Tyr | Arg | His | Leu 335 Leu |
| Asn | Val | Thr | Trp 340 | Glu | Gly | Arg | Asp | Phe 345 | Ser | Phe | Ser | Pro | Gly 350 | Gly Tyr |
| Leu | Val | Gln 355 | Pro | Thr | Met | Val | Val 360 | Ile | Ala | Leu | Asn | Arg 365 | His | Arg Leu |
| Trp | Glu 370 | Met | Val | Gly | Arg | Trp 375 | Glu | His | Gly | Val | Leu 380 | Tyr | Met | Lys Tyr |
| Pro 385 | Val | Trp | Pro | Arg | Tyr 390 | Ser | Ala | Ser | Leu | Gln 395 | Pro | Val | Val | Asp Ser 400 |
| Arg | His | Leu | Thr | Val 405 | Ala | Thr | Leu | Glu | Glu 410 | Arg | Pro | Phe | Val | Ile 415 Val |
| Glu | Ser | Pro | Asp 420 | Pro | Gly | Thr | Gly | Gly 425 | Cys | Val | Pro | Asn | Thr 430 | Val Pro |
| Cys | Arg | Arg 435 | Gln | Ser | Asn | His | Thr 440 | Phe | Ser | Ser | Gly | Asp 445 | Val | Ala Pro |

```
Tyr Thr Lys Leu Cys Cys Lys Gly Phe Cys Ile Asp Ile Leu Lys Lys
    450             455             460

Leu Ala Arg Val Val Lys Phe Ser Tyr Asp Leu Tyr Leu Val Thr Asn
465             470             475             480

Gly Lys His Gly Lys Arg Val Arg Gly Val Trp Asn Gly Met Ile Gly
                485             490             495

Glu Val Tyr Tyr Lys Arg Ala Asp Met Ala Ile Gly Ser Leu Thr Ile
            500             505             510

Asn Glu Glu Arg Ser Glu Ile Val Asp Phe Ser Val Pro Phe Val Glu
        515             520             525

Thr Gly Ile Ser Val Met Val Ala Arg Ser Asn Gly Thr Val Ser Pro
    530             535             540

Ser Ala Phe Leu Glu Pro Tyr Ser Pro Ala Val Trp Val Met Met Phe
545             550             555             560

Val Met Cys Leu Thr Val Val Ala Ile Thr Val Phe Met Phe Glu Tyr
                565             570             575

Phe Ser Pro Val Ser Tyr Asn Gln Asn Leu Thr Arg Gly Lys Lys Ser
            580             585             590

Gly Gly Pro Ala Phe Thr Ile Gly Lys Ser Val Trp Leu Leu Trp Ala
        595             600             605

Leu Val Phe Asn Asn Ser Val Pro Ile Glu Asn Pro Arg Gly Thr Thr
    610             615             620

Ser Lys Ile Met Val Leu Val Trp Ala Phe Phe Ala Val Ile Phe Leu
625             630             635             640

Ala Arg Tyr Thr Ala Asn Leu Ala Ala Phe Met Ile Gln Glu Gln Tyr
                645             650             655

Ile Asp Thr Val Ser Gly Leu Ser Asp Lys Lys Phe Gln Arg Pro Gln
            660             665             670

Asp Gln Tyr Pro Pro Phe Arg Phe Gly Thr Val Pro Asn Gly Ser Thr
        675             680             685

Glu Arg Asn Ile Arg Ser Asn Tyr Arg Asp Met His Thr His Met Val
    690             695             700

Lys Phe Asn Gln Arg Ser Val Glu Asp Ala Leu Thr Ser Leu Lys Met
705             710             715             720

Gly Lys Asp Glu Gly Cys Lys Leu Val Thr Ile Gly Ser Gly Lys Val
                725             730             735

Phe Ala Thr Thr Gly Tyr Gly Ile Ala Met Gln Lys Asp Ser His Trp
            740             745             750

Lys Arg Ala Ile Asp Leu Ala Leu Leu Gln Phe Leu Gly Asp Gly Glu
        755             760             765

Thr Gln Lys Leu Glu Thr Val Trp Leu Ser Gly Ile Cys Gln Asn Glu
    770             775             780

Lys Asn Glu Val Met Ser Ser Lys Leu Asp Ile Asp Asn Met Gly Gly
785             790             795             800

Val Phe Tyr Met Leu Leu Val Ala Met Gly Leu Ala Leu Leu Val Phe
                805             810             815

Ala Trp Glu His Leu Val Tyr Trp Lys Leu Arg His Ser Val Pro Asn
            820             825             830

Ser Ser Gln Leu Asp Phe Leu Leu Ala Phe Ser Arg Gly Ile Tyr Ser
        835             840             845

Cys Phe Ser Gly Val Gln Ser Leu Ala Ser Pro Pro Arg Gln Ala Ser
850             855             860

Pro Asp Leu Thr Ala Ser Ser Ala Gln Ala Ser Val Leu Lys Ile Leu
```

|  865 | | | | | 870 | | | | | 875 | | | | | 880 |
| --- | --- | --- | --- | --- | --- | --- | --- | --- | --- | --- | --- | --- | --- | --- | --- |

Gln Ala Ala Arg Asp Met Val Thr Thr Ala Gly Val Ser Asn Ser Leu
                885                     890                     895

Asp Arg Ala Thr Arg Thr Ile Glu Asn Trp Gly Gly Gly Arg Arg Ala
                900                     905                     910

Pro Pro Pro Ser Pro Cys Pro Thr Pro Arg Ser Gly Pro Ser Pro Cys
                915                     920                     925

Leu Pro Thr Pro Asp Pro Pro Pro Glu Pro Ser Pro Thr Gly Trp Gly
            930                 935                 940

Pro Pro Asp Gly Gly Arg Ala Ala Leu Val Arg Arg Ala Pro Gln Pro
945                     950                     955                     960

Pro Gly Arg Pro Pro Thr Pro Gly Pro Pro Leu Ser Asp Val Ser Arg
                965                     970                     975

Val Ser Arg Arg Pro Ala Trp Glu Ala Arg Trp Pro Val Arg Thr Gly
            980                 985                 990

His Cys Gly Arg His Leu Ser Ala Ser Glu Arg Pro Leu Ser Pro Ala
            995                 1000                1005

Arg Cys His Tyr Ser Ser Phe Pro Arg Ala Asp Arg Ser Gly Arg Pro
            1010                1015                1020

Phe Leu Pro Leu Phe Pro Glu Pro Pro Glu Leu Glu Asp Leu Pro Leu
1025                    1030                    1035                    1040

Leu Gly Pro Glu Gln Leu Ala Arg Arg Glu Ala Leu Leu Asn Ala Ala
                1045                    1050                    1055

Trp Ala Arg Gly Ser Arg Pro Ser His Ala Ser Leu Pro Ser Ser Val
                1060                    1065                    1070

Ala Glu Ala Phe Ala Arg Pro Ser Ser Leu Pro Ala Gly Cys Thr Gly
            1075                    1080                    1085

Pro Ala Cys Ala Arg Pro Asp Gly His Ser Ala Cys Arg Arg Leu Ala
            1090                    1095                    1100

Gln Ala Gln Ser Met Cys Leu Pro Ile Tyr Arg Glu Ala Cys Gln Glu
1105                    1110                    1115                    1120

Gly Glu Gln Ala Gly Ala Pro Ala Trp Gln His Arg Gln His Val Cys
                1125                    1130                    1135

Leu His Ala His Ala His Leu Pro Leu Cys Trp Gly Ala Val Cys Pro
                1140                    1145                    1150

His Leu Pro Pro Cys Asp Ser His Gly Ser Trp Leu Ser Gly Ala Trp
            1155                    1160                    1165

Gly Pro Leu Gly His Ser Gly Arg Thr Leu Gly Leu Gly Thr Gly Tyr
            1170                    1175                    1180

Arg Asp Ser Gly Gly Leu Asp Glu Ile Ser Ser Val Ala Arg Gly Thr
1185                    1190                    1195                    1200

Gln Gly Phe Pro Gly Pro Cys Thr Trp Arg Arg Ile Ser Ser Leu Glu
            1205                    1210                    1215

Ser Glu Val ( 2 ) INFORMATION FOR SEQ ID NO:51:

( i ) SEQUENCE CHARACTERISTICS:
        ( A ) LENGTH: 4077 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS (B) LOCATION: 189..3908

(xi) SEQUENCE DESCRIPTION: SEQ ID NO:51:

| | | | | | |
|---|---|---|---|---|---|
| CCCTTAATAA GATTTGCNAC GTACACTCGA GCCATCGCGA GTGTCCTTGA GCCGCGGGTG | | | | | 60 |
| ACGGTGGCTC TCGCTGCTCG CGCCCCCTCC TCCCGCGGGG GGAGCCTGAT GCCACGTTCC | | | | | 120 |
| CTATGAATTA TTTATCGCCG GCCTAAAAAT ACCCCGAACT TCACAGCCCG AGTGACCCTC | | | | | 180 |

```
CGGTGGAC ATG GGT GGG GCC CTG GGG CCG GCC CTG TTG CTC ACC TCG CTC     230
         Met Gly Gly Ala Leu Gly Pro Ala Leu Leu Leu Thr Ser Leu
         1               5                   10

TTC GGT GCC TGG GCA GGG CTG GGT CCG GGG CAG GGC GAG CAG GGC ATG     278
Phe Gly Ala Trp Ala Gly Leu Gly Pro Gly Gln Gly Glu Gln Gly Met
15              20                  25                  30

ACG GTG GCC GTG GTG TTT AGC AGC TCA GGG CCG CCC CAG GCC CAG TTC     326
Thr Val Ala Val Val Phe Ser Ser Ser Gly Pro Pro Gln Ala Gln Phe
                35                  40                  45

CGT GTC CGC CTC ACC CCC CAG AGC TTC CTG GAC CTA CCC CTG GAG ATC     374
Arg Val Arg Leu Thr Pro Gln Ser Phe Leu Asp Leu Pro Leu Glu Ile
                50                  55                  60

CAG CCG CTC ACA GTT GGG GTC AAC ACC ACC AAC CCC AGC AGC CTC CTC     422
Gln Pro Leu Thr Val Gly Val Asn Thr Thr Asn Pro Ser Ser Leu Leu
        65                  70                  75

ACC CAG ATC TGC GGC CTC CTG GGT GCT GCC CAC GTC CAC GGC ATT GTC     470
Thr Gln Ile Cys Gly Leu Leu Gly Ala Ala His Val His Gly Ile Val
        80                  85                  90

TTT GAG GAC AAC GTG GAC ACC GAG GCG GTG GCC CAG ATC CTT GAC TTC     518
Phe Glu Asp Asn Val Asp Thr Glu Ala Val Ala Gln Ile Leu Asp Phe
95                  100                 105                 110

ATC TCC TCC CAG ACC CAT GTG CCC ATC CTC AGC ATC AGC GGA GGC TCT     566
Ile Ser Ser Gln Thr His Val Pro Ile Leu Ser Ile Ser Gly Gly Ser
                115                 120                 125

GCT GTG GTC CTC ACC CCC AAG GAG CCG GGC TCC GCC TTC CTG CAG CTG     614
Ala Val Val Leu Thr Pro Lys Glu Pro Gly Ser Ala Phe Leu Gln Leu
                130                 135                 140

GGC GTG TCC CTG GAG CAG CAG CTG CAG GTG CTG TTC AAG GTG CTG GAA     662
Gly Val Ser Leu Glu Gln Gln Leu Gln Val Leu Phe Lys Val Leu Glu
        145                 150                 155

GAG TAC GAC TGG AGC GCC TTC GCC GTC ATC ACC AGC CTG CAC CCG GGC     710
Glu Tyr Asp Trp Ser Ala Phe Ala Val Ile Thr Ser Leu His Pro Gly
160                 165                 170

CAC GCG CTC TTC CTG GAG GGC GTG CGC GCC GTC GCC GAC GCC AGC CAC     758
His Ala Leu Phe Leu Glu Gly Val Arg Ala Val Ala Asp Ala Ser His
175                 180                 185                 190

GTG AGT TGG CGG CTG CTG GAC GTG GTC ACG CTG GAA CTG GAC CCG GGA     806
Val Ser Trp Arg Leu Leu Asp Val Val Thr Leu Glu Leu Asp Pro Gly
                195                 200                 205

GGG CCG CGC GCG CGC ACG CAG CGC CTG CTG CGC CAG CTC GAC GCG CCC     854
Gly Pro Arg Ala Arg Thr Gln Arg Leu Leu Arg Gln Leu Asp Ala Pro
                210                 215                 220

GTG TTT GTG GCC TAC TGC TCG CGC GAG GAG GCC GAG GTG CTC TTC GCC     902
Val Phe Val Ala Tyr Cys Ser Arg Glu Glu Ala Glu Val Leu Phe Ala
                225                 230                 235

GAG GCG GCG CAG GCC GGT CTG GTG GGG CCC GGC CAC GTG TGG CTG GTG     950
Glu Ala Ala Gln Ala Gly Leu Val Gly Pro Gly His Val Trp Leu Val
240                 245                 250

CCC AAC CTG GCG CTG GGC AGC ACC GAT GCG CCC CCC GCC ACC TTC CCC     998
Pro Asn Leu Ala Leu Gly Ser Thr Asp Ala Pro Pro Ala Thr Phe Pro
255                 260                 265                 270

GTG GGC CTC ATC AGC GTC GTC ACC GAG AGC TGG CGC CTC AGC CTG CGC    1046
Val Gly Leu Ile Ser Val Val Thr Glu Ser Trp Arg Leu Ser Leu Arg
```

-continued

|  |  | 275 |  |  |  |  | 280 |  |  |  |  | 285 |  |  |  |  |
|---|---|---|---|---|---|---|---|---|---|---|---|---|---|---|---|---|
| CAG | AAG | GTG | CGC | GAC | GGC | GTG | GCC | ATT | CTG | GCC | CTG | GGC | GCC | CAC | AGC | 1094 |
| Gln | Lys | Val | Arg<br>290 | Asp | Gly | Val | Ala<br>295 | Ile | Leu | Ala | Leu | Gly<br>300 | Ala | His | Ser | |
| TAC | TGG | CGC | CAG | CAT | GGA | ACC | CTG | CCA | GCC | CCG | GCC | GGG | GAC | TGC | CGT | 1142 |
| Tyr | Trp | Arg<br>305 | Gln | His | Gly | Thr | Leu<br>310 | Pro | Ala | Pro | Ala | Gly<br>315 | Asp | Cys | Arg | |
| GTT | CAC | CCT | GGG | CCC | GTC | AGC | CCT | GCC | CGG | GAG | GCC | TTC | TAC | AGG | CAC | 1190 |
| Val | His<br>320 | Pro | Gly | Pro | Val | Ser<br>325 | Pro | Ala | Arg | Glu | Ala<br>330 | Phe | Tyr | Arg | His | |
| CTA | CTG | AAT | GTC | ACC | TGG | GAG | GGC | CGA | GAC | TTC | TCC | TTC | AGC | CCT | GGT | 1238 |
| Leu<br>335 | Leu | Asn | Val | Thr | Trp<br>340 | Glu | Gly | Arg | Asp | Phe<br>345 | Ser | Phe | Ser | Pro | Gly<br>350 | |
| GGG | TAC | CTG | GTC | CAG | CCC | ACC | ATG | GTG | GTG | ATC | GCC | CTC | AAC | CGG | CAC | 1286 |
| Gly | Tyr | Leu | Val | Gln<br>355 | Pro | Thr | Met | Val | Val<br>360 | Ile | Ala | Leu | Asn | Arg<br>365 | His | |
| CGC | CTC | TGG | GAG | ATG | GTG | GGG | CGC | TGG | GAG | CAT | GGC | GTC | CTA | TAC | ATG | 1334 |
| Arg | Leu | Trp<br>370 | Glu | Met | Val | Gly | Arg<br>375 | Trp | Glu | His | Gly | Val<br>380 | Leu | Tyr | Met | |
| AAG | TAC | CCC | GTG | TGG | CCT | CGC | TAC | AGT | GCC | TCT | CTG | CAG | CCT | GTG | GTG | 1382 |
| Lys | Tyr | Pro<br>385 | Val | Trp | Pro | Arg | Tyr<br>390 | Ser | Ala | Ser | Leu | Gln<br>395 | Pro | Val | Val | |
| GAC | AGT | CGG | CAC | CTG | ACG | GTG | GCC | ACG | CTG | GAA | GAG | CGG | CCC | TTT | GTC | 1430 |
| Asp | Ser | Arg<br>400 | His | Leu | Thr | Val | Ala<br>405 | Thr | Leu | Glu | Glu | Arg<br>410 | Pro | Phe | Val | |
| ATC | GTG | GAG | AGC | CCT | GAC | CCT | GGC | ACA | GGA | GGC | TGT | GTC | CCC | AAC | ACC | 1478 |
| Ile<br>415 | Val | Glu | Ser | Pro | Asp<br>420 | Pro | Gly | Thr | Gly | Gly<br>425 | Cys | Val | Pro | Asn | Thr<br>430 | |
| GTG | CCC | TGC | CGC | AGG | CAG | AGC | AAC | CAC | ACC | TTC | AGC | AGC | GGG | GAC | GTG | 1526 |
| Val | Pro | Cys | Arg | Arg<br>435 | Gln | Ser | Asn | His | Thr<br>440 | Phe | Ser | Ser | Gly | Asp<br>445 | Val | |
| GCC | CCC | TAC | ACC | AAG | CTC | TGC | TGT | AAG | GGA | TTC | TGC | ATC | GAC | ATC | CTC | 1574 |
| Ala | Pro | Tyr | Thr<br>450 | Lys | Leu | Cys | Cys | Lys<br>455 | Gly | Phe | Cys | Ile | Asp<br>460 | Ile | Leu | |
| AAG | AAG | CTG | GCC | AGA | GTG | GTC | AAA | TTC | TCC | TAC | GAC | CTG | TAC | CTG | GTG | 1622 |
| Lys | Lys | Leu<br>465 | Ala | Arg | Val | Val | Lys<br>470 | Phe | Ser | Tyr | Asp | Leu<br>475 | Tyr | Leu | Val | |
| ACC | AAC | GGC | AAG | CAT | GGC | AAG | CGG | GTG | CGC | GGC | GTA | TGG | AAC | GGC | ATG | 1670 |
| Thr | Asn | Gly<br>480 | Lys | His | Gly | Lys | Arg<br>485 | Val | Arg | Gly | Val | Trp<br>490 | Asn | Gly | Met | |
| ATT | GGG | GAG | GTG | TAC | TAC | AAG | CGG | GCA | GAC | ATG | GCC | ATC | GGC | TCC | CTC | 1718 |
| Ile<br>495 | Gly | Glu | Val | Tyr | Tyr<br>500 | Lys | Arg | Ala | Asp | Met<br>505 | Ala | Ile | Gly | Ser | Leu<br>510 | |
| ACC | ATC | AAT | GAG | GAA | CGC | TCC | GAG | ATC | GTA | GAC | TTC | TCT | GTA | CCC | TTT | 1766 |
| Thr | Ile | Asn | Glu | Glu<br>515 | Arg | Ser | Glu | Ile | Val<br>520 | Asp | Phe | Ser | Val | Pro<br>525 | Phe | |
| GTG | GAG | ACG | GGC | ATC | AGT | GTG | ATG | GTG | GCT | CGC | AGC | AAT | GGC | ACC | GTC | 1814 |
| Val | Glu | Thr | Gly<br>530 | Ile | Ser | Val | Met | Val<br>535 | Ala | Arg | Ser | Asn | Gly<br>540 | Thr | Val | |
| TCC | CCC | TCG | GCC | TTC | TTG | GAG | CCA | TAT | AGC | CCT | GCA | GTG | TGG | GTG | ATG | 1862 |
| Ser | Pro | Ser<br>545 | Ala | Phe | Leu | Glu | Pro<br>550 | Tyr | Ser | Pro | Ala | Val<br>555 | Trp | Val | Met | |
| ATG | TTT | GTC | ATG | TGC | CTC | ACT | GTG | GTG | GCC | ATC | ACC | GTC | TTC | ATG | TTC | 1910 |
| Met | Phe<br>560 | Val | Met | Cys | Leu | Thr<br>565 | Val | Val | Ala | Ile | Thr<br>570 | Val | Phe | Met | Phe | |
| GAG | TAC | TTC | AGC | CCT | GTC | AGC | TAC | AAC | CAG | AAC | CTC | ACC | AGA | GGC | AAG | 1958 |
| Glu | Tyr | Phe | Ser | Pro<br>575 | Val | Ser | Tyr | Asn<br>580 | Gln | Asn | Leu | Thr<br>585 | Arg | Gly | Lys<br>590 | |
| ACT | TTC | ACT | ATC | GGC | AAG | TCC | GTG | TGG | CTG | CTG | TGG | GCG | CTG | GTC | TTC | 2006 |
| Thr | Phe | Thr | Ile | Gly | Lys | Ser | Val | Trp | Leu | Leu | Trp | Ala | Leu | Val | Phe | |

-continued

```
                            595                         600                         605
AAC  AAC  TCA  GTG  CCC  ATC  GAG  AAC  CCG  CGG  GGC  ACC  ACC  AGC  AAG  ATC        2054
Asn  Asn  Ser  Val  Pro  Ile  Glu  Asn  Pro  Arg  Gly  Thr  Thr  Ser  Lys  Ile
               610                 615                           620

ATG  GTT  CTG  GTC  TGG  GCC  TTC  TTT  GCT  GTC  ATC  TTC  CTC  GCC  AGA  TAC        2102
Met  Val  Leu  Val  Trp  Ala  Phe  Phe  Ala  Val  Ile  Phe  Leu  Ala  Arg  Tyr
          625                      630                      635

ACG  GCC  AAC  CTG  GCC  GCC  TTC  ATG  ATC  CAA  GAG  CAA  TAC  ATC  GAC  ACT        2150
Thr  Ala  Asn  Leu  Ala  Ala  Phe  Met  Ile  Gln  Glu  Gln  Tyr  Ile  Asp  Thr
     640                           645                      650

GTG  TCG  GGC  CTC  AGT  GAC  AAG  AAG  TTT  CAG  CGG  CCT  CAA  GAT  CAG  TAC        2198
Val  Ser  Gly  Leu  Ser  Asp  Lys  Lys  Phe  Gln  Arg  Pro  Gln  Asp  Gln  Tyr
655                           660                      665                      670

CCA  CCT  TTC  CGC  TTC  GGC  ACG  GTG  CCC  AAC  GGC  AGC  ACG  GAG  CGG  AAC        2246
Pro  Pro  Phe  Arg  Phe  Gly  Thr  Val  Pro  Asn  Gly  Ser  Thr  Glu  Arg  Asn
                    675                      680                      685

ATC  CGC  AGT  AAC  TAC  CGT  GAC  ATG  CAC  ACC  CAC  ATG  GTC  AAG  TTC  AAC        2294
Ile  Arg  Ser  Asn  Tyr  Arg  Asp  Met  His  Thr  His  Met  Val  Lys  Phe  Asn
               690                      695                      700

CAG  CGC  TCG  GTG  GAG  GAC  GCG  CTC  ACC  AGC  CTC  AAG  ATG  GGC  TCT  GAG        2342
Gln  Arg  Ser  Val  Glu  Asp  Ala  Leu  Thr  Ser  Leu  Lys  Met  Gly  Ser  Glu
          705                           710                      715

GCT  CAG  CCT  GTC  CCC  AGG  AAG  CTG  GAT  GCC  TTC  ATC  TAT  GAT  GCT  GCT        2390
Ala  Gln  Pro  Val  Pro  Arg  Lys  Leu  Asp  Ala  Phe  Ile  Tyr  Asp  Ala  Ala
     720                      725                           730

GTC  CTC  AAC  TAC  ATG  GCA  GGC  AAG  GAC  GAG  GGC  TGC  AAG  CTG  GTC  ACC        2438
Val  Leu  Asn  Tyr  Met  Ala  Gly  Lys  Asp  Glu  Gly  Cys  Lys  Leu  Val  Thr
735                           740                      745                      750

ATT  GGG  TCT  GGC  AAG  GTC  TTT  GCT  ACC  ACT  GGC  TAC  GGC  ATC  GCC  ATG        2486
Ile  Gly  Ser  Gly  Lys  Val  Phe  Ala  Thr  Thr  Gly  Tyr  Gly  Ile  Ala  Met
                    755                      760                      765

CAG  AAG  GAC  TCC  CAC  TGG  AAG  CGG  GCC  ATA  GAC  CTG  GCG  CTC  TTG  CAG        2534
Gln  Lys  Asp  Ser  His  Trp  Lys  Arg  Ala  Ile  Asp  Leu  Ala  Leu  Leu  Gln
               770                      775                      780

TTC  CTG  GGG  GAC  GGA  GAG  ACA  CAG  AAA  CTG  GAG  ACA  GTG  TGG  CTC  TCA        2582
Phe  Leu  Gly  Asp  Gly  Glu  Thr  Gln  Lys  Leu  Glu  Thr  Val  Trp  Leu  Ser
          785                           790                      795

GGG  ATC  TGC  CAG  AAT  GAG  AAG  AAC  GAG  GTG  ATG  AGC  AGC  AAG  CTG  GAC        2630
Gly  Ile  Cys  Gln  Asn  Glu  Lys  Asn  Glu  Val  Met  Ser  Ser  Lys  Leu  Asp
800                           805                      810

ATC  GAC  AAC  ATG  GGA  GGC  GTC  TTC  TAC  ATG  CTG  CTG  GTG  GCC  ATG  GGG        2678
Ile  Asp  Asn  Met  Gly  Gly  Val  Phe  Tyr  Met  Leu  Leu  Val  Ala  Met  Gly
815                      820                      825                      830

CTG  GCC  CTG  CTG  GTC  TTC  GCC  TGG  GAG  CAC  CTG  GTC  TAC  TGG  AAG  CTG        2726
Leu  Ala  Leu  Leu  Val  Phe  Ala  Trp  Glu  His  Leu  Val  Tyr  Trp  Lys  Leu
                    835                      840                      845

CGC  CAC  TCG  GTG  CCC  AAC  TCA  TCC  CAG  CTG  GAC  TTC  CTG  CTG  GCT  TTC        2774
Arg  His  Ser  Val  Pro  Asn  Ser  Ser  Gln  Leu  Asp  Phe  Leu  Leu  Ala  Phe
               850                      855                      860

AGC  AGG  GGC  ATC  TAC  AGC  TGC  TTC  AGC  GGG  GTG  CAG  AGC  CTC  GCC  AGC        2822
Ser  Arg  Gly  Ile  Tyr  Ser  Cys  Phe  Ser  Gly  Val  Gln  Ser  Leu  Ala  Ser
          865                           870                      875

CCA  CCG  CGG  CAG  GCC  AGC  CCG  GAC  CTC  ACG  GCC  AGC  TCG  GCC  CAG  GCC        2870
Pro  Pro  Arg  Gln  Ala  Ser  Pro  Asp  Leu  Thr  Ala  Ser  Ser  Ala  Gln  Ala
880                      885                      890

AGC  GTG  CTC  AAG  ATT  CTG  CAG  GCA  GCC  CGC  GAC  ATG  GTG  ACC  ACG  GCG        2918
Ser  Val  Leu  Lys  Ile  Leu  Gln  Ala  Ala  Arg  Asp  Met  Val  Thr  Thr  Ala
895                      900                      905                      910

GGC  GTA  AGC  AAC  TCC  CTG  GAC  CGC  GCC  ACT  CGC  ACC  ATC  GAG  AAT  TGG        2966
Gly  Val  Ser  Asn  Ser  Leu  Asp  Arg  Ala  Thr  Arg  Thr  Ile  Glu  Asn  Trp
```

-continued

|  |  |  |  |  |  |  |  |  |  |  |  |  |  |  |  |
|---|---|---|---|---|---|---|---|---|---|---|---|---|---|---|---|
| | | | | 915 | | | | | 920 | | | | | 925 | |

```
              915                           920                           925
GGT  GGC  GGC  CGC  CGT  GCG  CCC  CCA  CCG  TCC  CCC  TGC  CCG  ACC  CCG  CGG         3014
Gly  Gly  Gly  Arg  Arg  Ala  Pro  Pro  Pro  Ser  Pro  Cys  Pro  Thr  Pro  Arg
              930                           935                           940

TCT  GGC  CCC  AGC  CCA  TGC  CTG  CCC  ACC  CCC  GAC  CCG  CCC  CCA  GAG  CCG         3062
Ser  Gly  Pro  Ser  Pro  Cys  Leu  Pro  Thr  Pro  Asp  Pro  Pro  Pro  Glu  Pro
              945                           950                           955

AGC  CCC  ACG  GGC  TGG  GGA  CCG  CCA  GAC  GGG  GGT  CGC  GCG  GCG  CTT  GTG         3110
Ser  Pro  Thr  Gly  Trp  Gly  Pro  Pro  Asp  Gly  Gly  Arg  Ala  Ala  Leu  Val
              960                           965                           970

CGC  AGG  GCT  CCG  CAG  CCC  CCG  GGC  CGC  CCC  CCG  ACG  CCG  GGG  CCG  CCC         3158
Arg  Arg  Ala  Pro  Gln  Pro  Pro  Gly  Arg  Pro  Pro  Thr  Pro  Gly  Pro  Pro
975                           980                           985                 990

CTG  TCC  GAC  GTC  TCC  CGA  GTG  TCG  CGC  CGC  CCA  GCC  TGG  GAG  GCG  CGG         3206
Leu  Ser  Asp  Val  Ser  Arg  Val  Ser  Arg  Arg  Pro  Ala  Trp  Glu  Ala  Arg
              995                           1000                          1005

TGG  CCG  GTG  CGG  ACC  GGG  CAC  TGC  GGG  AGG  CAC  CTC  TCG  GCC  TCC  GAG         3254
Trp  Pro  Val  Arg  Thr  Gly  His  Cys  Gly  Arg  His  Leu  Ser  Ala  Ser  Glu
              1010                          1015                          1020

CGG  CCC  CTG  TCG  CCC  GCG  CGC  TGT  CAC  TAC  AGC  TCC  TTT  CCT  CGA  GCC         3302
Arg  Pro  Leu  Ser  Pro  Ala  Arg  Cys  His  Tyr  Ser  Ser  Phe  Pro  Arg  Ala
              1025                          1030                          1035

GAC  CGA  TCC  GGC  CGC  CCC  TTC  CTC  CCG  CTC  TTC  CCG  GAG  CCC  CCG  GAG         3350
Asp  Arg  Ser  Gly  Arg  Pro  Phe  Leu  Pro  Leu  Phe  Pro  Glu  Pro  Pro  Glu
              1040                          1045                          1050

CTG  GAG  GAC  CTG  CCG  CTG  CTC  GGT  CCG  GAG  CAG  CTG  GCC  CGG  CGG  GAG         3398
Leu  Glu  Asp  Leu  Pro  Leu  Leu  Gly  Pro  Glu  Gln  Leu  Ala  Arg  Arg  Glu
1055                          1060                          1065                1070

GCC  CTG  CTG  AAC  GCG  GCC  TGG  GCC  CGG  GGC  TCG  CGC  CCG  AGT  CAC  GCT         3446
Ala  Leu  Leu  Asn  Ala  Ala  Trp  Ala  Arg  Gly  Ser  Arg  Pro  Ser  His  Ala
              1075                          1080                          1085

TCC  CTG  CCC  AGC  TCC  GTG  GCC  GAG  GCC  TTC  GCT  CGG  CCC  AGC  TCG  CTG         3494
Ser  Leu  Pro  Ser  Ser  Val  Ala  Glu  Ala  Phe  Ala  Arg  Pro  Ser  Ser  Leu
              1090                          1095                          1100

CCC  GCT  GGG  TGC  ACC  GGC  CCC  GCC  TGC  GCC  CGC  CCC  GAC  GGC  CAC  TCG         3542
Pro  Ala  Gly  Cys  Thr  Gly  Pro  Ala  Cys  Ala  Arg  Pro  Asp  Gly  His  Ser
              1105                          1110                          1115

GCC  TGC  AGG  CGC  TTG  GCG  CAG  GCG  CAG  TCG  ATG  TGC  TTG  CCG  ATC  TAC         3590
Ala  Cys  Arg  Arg  Leu  Ala  Gln  Ala  Gln  Ser  Met  Cys  Leu  Pro  Ile  Tyr
1120                          1125                          1130

CGG  GAG  GCC  TGC  CAG  GAG  GGC  GAG  CAG  GCA  GGG  GCC  CCC  GCC  TGG  CAG         3638
Arg  Glu  Ala  Cys  Gln  Glu  Gly  Glu  Gln  Ala  Gly  Ala  Pro  Ala  Trp  Gln
1135                          1140                          1145                1150

CAC  AGA  CAG  CAC  GTC  TGC  CTG  CAC  GCC  CAC  GCC  CAC  CTG  CCA  TTG  TGC         3686
His  Arg  Gln  His  Val  Cys  Leu  His  Ala  His  Ala  His  Leu  Pro  Leu  Cys
              1155                          1160                          1165

TGG  GGG  GCT  GTC  TGT  CCT  CAC  CTT  CCA  CCC  TGT  GAC  AGC  CAC  GGC  TCC         3734
Trp  Gly  Ala  Val  Cys  Pro  His  Leu  Pro  Pro  Cys  Asp  Ser  His  Gly  Ser
              1170                          1175                          1180

TGG  CTC  TCC  GGC  GCC  TGG  GGG  CCT  CTG  GGG  CAC  AGC  GGC  AGG  ACT  CTG         3782
Trp  Leu  Ser  Gly  Ala  Trp  Gly  Pro  Leu  Gly  His  Ser  Gly  Arg  Thr  Leu
              1185                          1190                          1195

GGG  CTG  GGC  ACA  GGC  TAC  AGA  GAC  AGT  GGG  GGA  CTG  GAC  GAG  ATC  AGC         3830
Gly  Leu  Gly  Thr  Gly  Tyr  Arg  Asp  Ser  Gly  Gly  Leu  Asp  Glu  Ile  Ser
              1200                          1205                          1210

AGT  GTA  GCC  CGT  GGG  ACG  CAA  GGC  TTC  CCG  GGA  CCC  TGC  ACC  TGG  AGA         3878
Ser  Val  Ala  Arg  Gly  Thr  Gln  Gly  Phe  Pro  Gly  Pro  Cys  Thr  Trp  Arg
1215                          1220                          1225                1230

CGG  ATC  TCC  AGT  CTG  GAG  TCA  GAA  GTG  TGAGTTATCA  GCCACTCAGG                    3925
Arg  Ile  Ser  Ser  Leu  Glu  Ser  Glu  Val
```

```
                    1235                      124
CTCCGAGCCA  GCTGGATTCT  CTGCCTGCCA  CTGTCAGGGT  TAAGCGGCAG  GCAGGATTGG    3985

CCCTTCTCTG  GCTTCTACCA  TGAAATCCTG  GCCATGGCAC  CCCAGTGACA  GATGATGTCT    4045

TCCATGGTCA  TCAGTGACCT  CAGCTAGCCT  CA                                    4077
```

( 2 ) INFORMATION FOR SEQ ID NO:52:

( i ) SEQUENCE CHARACTERISTICS:
        ( A ) LENGTH: 1239 amino acids
        ( B ) TYPE: amino acid
        ( D ) TOPOLOGY: linear ( i i ) MOLECULE TYPE: protein ( x i ) SEQUENCE DESCRIPTION: SEQ ID NO:52:

```
Met  Gly  Gly  Ala  Leu  Gly  Pro  Ala  Leu  Leu  Leu  Thr  Ser  Leu  Phe  Gly
 1                    5                        10                       15

Ala  Trp  Ala  Gly  Leu  Gly  Pro  Gly  Gln  Gly  Glu  Gln  Gly  Met  Thr  Val
               20                       25                       30

Ala  Val  Val  Phe  Ser  Ser  Ser  Gly  Pro  Pro  Gln  Ala  Gln  Phe  Arg  Val
          35                        40                       45

Arg  Leu  Thr  Pro  Gln  Ser  Phe  Leu  Asp  Leu  Pro  Leu  Glu  Ile  Gln  Pro
     50                        55                       60

Leu  Thr  Val  Gly  Val  Asn  Thr  Thr  Asn  Pro  Ser  Ser  Leu  Leu  Thr  Gln
65                       70                       75                       80

Ile  Cys  Gly  Leu  Leu  Gly  Ala  Ala  His  Val  His  Gly  Ile  Val  Phe  Glu
                    85                       90                       95

Asp  Asn  Val  Asp  Thr  Glu  Ala  Val  Ala  Gln  Ile  Leu  Asp  Phe  Ile  Ser
               100                      105                      110

Ser  Gln  Thr  His  Val  Pro  Ile  Leu  Ser  Ile  Ser  Gly  Gly  Ser  Ala  Val
          115                      120                      125

Val  Leu  Thr  Pro  Lys  Glu  Pro  Gly  Ser  Ala  Phe  Leu  Gln  Leu  Gly  Val
     130                      135                      140

Ser  Leu  Glu  Gln  Gln  Leu  Gln  Val  Leu  Phe  Lys  Val  Leu  Glu  Glu  Tyr
145                      150                      155                      160

Asp  Trp  Ser  Ala  Phe  Ala  Val  Ile  Thr  Ser  Leu  His  Pro  Gly  His  Ala
                    165                      170                      175

Leu  Phe  Leu  Glu  Gly  Val  Arg  Ala  Val  Ala  Asp  Ala  Ser  His  Val  Ser
               180                      185                      190

Trp  Arg  Leu  Leu  Asp  Val  Val  Thr  Leu  Glu  Leu  Asp  Pro  Gly  Gly  Pro
          195                      200                      205

Arg  Ala  Arg  Thr  Gln  Arg  Leu  Leu  Arg  Gln  Leu  Asp  Ala  Pro  Val  Phe
     210                      215                      220

Val  Ala  Tyr  Cys  Ser  Arg  Glu  Glu  Ala  Glu  Val  Leu  Phe  Ala  Glu  Ala
225                      230                      235                      240

Ala  Gln  Ala  Gly  Leu  Val  Gly  Pro  Gly  His  Val  Trp  Leu  Val  Pro  Asn
                    245                      250                      255

Leu  Ala  Leu  Gly  Ser  Thr  Asp  Ala  Pro  Pro  Ala  Thr  Phe  Pro  Val  Gly
               260                      265                      270

Leu  Ile  Ser  Val  Val  Thr  Glu  Ser  Trp  Arg  Leu  Ser  Leu  Arg  Gln  Lys
          275                      280                      285

Val  Arg  Asp  Gly  Val  Ala  Ile  Leu  Ala  Leu  Gly  Ala  His  Ser  Tyr  Trp
     290                      295                      300

Arg  Gln  His  Gly  Thr  Leu  Pro  Ala  Pro  Ala  Gly  Asp  Cys  Arg  Val  His
305                      310                      315                      320
```

-continued

| | | | | | | | | | | | | | | |
|---|---|---|---|---|---|---|---|---|---|---|---|---|---|---|
| Pro | Gly | Pro | Val | Ser 325 | Pro | Ala | Arg | Glu 330 | Ala | Phe | Tyr | Arg | His 335 | Leu | Leu |
| Asn | Val | Thr | Trp 340 | Glu | Gly | Arg | Asp 345 | Phe | Ser | Phe | Ser | Pro 350 | Gly | Gly | Tyr |
| Leu | Val | Gln 355 | Pro | Thr | Met | Val 360 | Ile | Ala | Leu | Asn | Arg 365 | His | Arg | Leu |
| Trp | Glu 370 | Met | Val | Gly | Arg | Trp 375 | Glu | His | Gly | Val | Leu 380 | Tyr | Met | Lys | Tyr |
| Pro 385 | Val | Trp | Pro | Arg | Tyr 390 | Ser | Ala | Ser | Leu | Gln 395 | Pro | Val | Val | Asp | Ser 400 |
| Arg | His | Leu | Thr | Val 405 | Ala | Thr | Leu | Glu | Glu 410 | Arg | Pro | Phe | Val | Ile 415 | Val |
| Glu | Ser | Pro | Asp 420 | Pro | Gly | Thr | Gly | Gly 425 | Cys | Val | Pro | Asn | Thr 430 | Val | Pro |
| Cys | Arg | Arg 435 | Gln | Ser | Asn | His | Thr 440 | Phe | Ser | Ser | Gly | Asp 445 | Val | Ala | Pro |
| Tyr | Thr 450 | Lys | Leu | Cys | Cys | Lys 455 | Gly | Phe | Cys | Ile | Asp 460 | Ile | Leu | Lys | Lys |
| Leu 465 | Ala | Arg | Val | Val | Lys 470 | Phe | Ser | Tyr | Asp | Leu 475 | Tyr | Leu | Val | Thr | Asn 480 |
| Gly | Lys | His | Gly | Lys 485 | Arg | Val | Arg | Gly | Val 490 | Trp | Asn | Gly | Met | Ile 495 | Gly |
| Glu | Val | Tyr | Tyr 500 | Lys | Arg | Ala | Asp | Met 505 | Ala | Ile | Gly | Ser | Leu 510 | Thr | Ile |
| Asn | Glu | Glu 515 | Arg | Ser | Glu | Ile | Val 520 | Asp | Phe | Ser | Val | Pro 525 | Phe | Val | Glu |
| Thr | Gly 530 | Ile | Ser | Val | Met | Val 535 | Ala | Arg | Ser | Asn | Gly 540 | Thr | Val | Ser | Pro |
| Ser 545 | Ala | Phe | Leu | Glu | Pro 550 | Tyr | Ser | Pro | Ala | Val 555 | Trp | Val | Met | Met | Phe 560 |
| Val | Met | Cys | Leu | Thr 565 | Val | Val | Ala | Ile | Thr 570 | Val | Phe | Met | Phe | Glu 575 | Tyr |
| Phe | Ser | Pro | Val 580 | Ser | Tyr | Asn | Gln | Asn 585 | Leu | Thr | Arg | Gly | Lys 590 | Thr | Phe |
| Thr | Ile | Gly 595 | Lys | Ser | Val | Trp | Leu 600 | Leu | Trp | Ala | Leu | Val 605 | Phe | Asn | Asn |
| Ser | Val 610 | Pro | Ile | Glu | Asn | Pro 615 | Arg | Gly | Thr | Thr | Ser 620 | Lys | Ile | Met | Val |
| Leu 625 | Val | Trp | Ala | Phe | Phe 630 | Ala | Val | Ile | Phe | Leu 635 | Ala | Arg | Tyr | Thr | Ala 640 |
| Asn | Leu | Ala | Ala | Phe 645 | Met | Ile | Gln | Glu | Gln 650 | Tyr | Ile | Asp | Thr | Val 655 | Ser |
| Gly | Leu | Ser | Asp 660 | Lys | Lys | Phe | Gln | Arg 665 | Pro | Gln | Asp | Gln | Tyr 670 | Pro | Pro |
| Phe | Arg | Phe 675 | Gly | Thr | Val | Pro | Asn 680 | Gly | Ser | Thr | Glu | Arg 685 | Asn | Ile | Arg |
| Ser | Asn 690 | Tyr | Arg | Asp | Met | His 695 | Thr | His | Met | Val | Lys 700 | Phe | Asn | Gln | Arg |
| Ser 705 | Val | Glu | Asp | Ala | Leu 710 | Thr | Ser | Leu | Lys | Met 715 | Gly | Ser | Glu | Ala | Gln 720 |
| Pro | Val | Pro | Arg | Lys 725 | Leu | Asp | Ala | Phe | Ile 730 | Tyr | Asp | Ala | Ala | Val 735 | Leu |
| Asn | Tyr | Met | Ala 740 | Gly | Lys | Asp | Glu | Gly 745 | Cys | Lys | Leu | Val | Thr 750 | Ile | Gly |

-continued

```
Ser Gly Lys Val Phe Ala Thr Thr Gly Tyr Gly Ile Ala Met Gln Lys
        755                 760                 765
Asp Ser His Trp Lys Arg Ala Ile Asp Leu Ala Leu Leu Gln Phe Leu
        770                 775                 780
Gly Asp Gly Glu Thr Gln Lys Leu Glu Thr Val Trp Leu Ser Gly Ile
785                 790                 795                 800
Cys Gln Asn Glu Lys Asn Glu Val Met Ser Ser Lys Leu Asp Ile Asp
                805                 810                 815
Asn Met Gly Gly Val Phe Tyr Met Leu Leu Val Ala Met Gly Leu Ala
                820                 825                 830
Leu Leu Val Phe Ala Trp Glu His Leu Val Tyr Trp Lys Leu Arg His
            835                 840                 845
Ser Val Pro Asn Ser Ser Gln Leu Asp Phe Leu Leu Ala Phe Ser Arg
    850                 855                 860
Gly Ile Tyr Ser Cys Phe Ser Gly Val Gln Ser Leu Ala Ser Pro Pro
865                 870                 875                 880
Arg Gln Ala Ser Pro Asp Leu Thr Ala Ser Ala Gln Ala Ser Val
                885                 890                 895
Leu Lys Ile Leu Gln Ala Ala Arg Asp Met Val Thr Thr Ala Gly Val
                900                 905                 910
Ser Asn Ser Leu Asp Arg Ala Thr Arg Ile Glu Asn Trp Gly Gly
            915                 920                 925
Gly Arg Arg Ala Pro Pro Pro Ser Pro Cys Pro Thr Pro Arg Ser Gly
930                 935                 940
Pro Ser Pro Cys Leu Pro Thr Pro Asp Pro Pro Glu Pro Ser Pro
945                 950                 955                 960
Thr Gly Trp Gly Pro Pro Asp Gly Gly Arg Ala Ala Leu Val Arg Arg
                965                 970                 975
Ala Pro Gln Pro Pro Gly Arg Pro Thr Pro Gly Pro Pro Leu Ser
                980                 985                 990
Asp Val Ser Arg Val Ser Arg Arg Pro Ala Trp Glu Ala Arg Trp Pro
            995                 1000                1005
Val Arg Thr Gly His Cys Gly Arg His Leu Ser Ala Ser Glu Arg Pro
    1010                1015                1020
Leu Ser Pro Ala Arg Cys His Tyr Ser Ser Phe Pro Arg Ala Asp Arg
1025                1030                1035                1040
Ser Gly Arg Pro Phe Leu Pro Leu Phe Pro Glu Pro Pro Glu Leu Glu
                1045                1050                1055
Asp Leu Pro Leu Leu Gly Pro Glu Gln Leu Ala Arg Arg Glu Ala Leu
                1060                1065                1070
Leu Asn Ala Ala Trp Ala Arg Gly Ser Arg Pro Ser His Ala Ser Leu
            1075                1080                1085
Pro Ser Ser Val Ala Glu Ala Phe Ala Arg Pro Ser Ser Leu Pro Ala
    1090                1095                1100
Gly Cys Thr Gly Pro Ala Cys Ala Arg Pro Asp Gly His Ser Ala Cys
1105                1110                1115                1120
Arg Arg Leu Ala Gln Ala Gln Ser Met Cys Leu Pro Ile Tyr Arg Glu
                1125                1130                1135
Ala Cys Gln Glu Gly Glu Gln Ala Gly Ala Pro Ala Trp Gln His Arg
                1140                1145                1150
Gln His Val Cys Leu His Ala His Ala His Leu Pro Leu Cys Trp Gly
            1155                1160                1165
Ala Val Cys Pro His Leu Pro Pro Cys Asp Ser His Gly Ser Trp Leu
```

|  |  |  | 1170 |  |  |  |  | 1175 |  |  |  |  | 1180 |  |  |
|---|---|---|---|---|---|---|---|---|---|---|---|---|---|---|---|
| Ser | Gly | Ala | Trp | Gly | Pro | Leu | Gly | His | Ser | Gly | Arg | Thr | Leu | Gly | Leu |
| 1185 |  |  |  |  | 1190 |  |  |  |  | 1195 |  |  |  |  | 1200 |
| Gly | Thr | Gly | Tyr | Arg | Asp | Ser | Gly | Gly | Leu | Asp | Glu | Ile | Ser | Ser | Val |
|  |  |  |  | 1205 |  |  |  |  | 1210 |  |  |  |  | 1215 |  |
| Ala | Arg | Gly | Thr | Gln | Gly | Phe | Pro | Gly | Pro | Cys | Thr | Trp | Arg | Arg | Ile |
|  |  |  |  | 1220 |  |  |  |  | 1225 |  |  |  |  | 1230 |  |
| Ser | Ser | Leu | Glu | Ser | Glu | Val |  |  |  |  |  |  |  |  |  |
|  |  |  |  | 1235 |  |  |  |  |  |  |  |  |  |  |  |

( 2 ) INFORMATION FOR SEQ ID NO:53:

( i ) SEQUENCE CHARACTERISTICS:
        ( A ) LENGTH: 4002 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 189..3833

( x i ) SEQUENCE DESCRIPTION: SEQ ID NO:53:

```
CCCTTAATAA  GATTTGCNAC  GTACACTCGA  GCCATCGCGA  GTGTCCTTGA  GCCGCGGGTG      60

ACGGTGGCTC  TCGCTGCTCG  CGCCCCCTCC  TCCCGCGGGG  GGAGCCTGAT  GCCACGTTCC     120

CTATGAATTA  TTTATCGCCG  GCCTAAAAAT  ACCCCGAACT  TCACAGCCCG  AGTGACCCTC     180
```

| CGGTGGAC | ATG | GGT | GGG | GCC | CTG | GGG | CCG | GCC | CTG | TTG | CTC | ACC | TCG | CTC | 230 |
|---|---|---|---|---|---|---|---|---|---|---|---|---|---|---|---|
|  | Met | Gly | Gly | Ala | Leu | Gly | Pro | Ala | Leu | Leu | Leu | Thr | Ser | Leu |  |
|  | 1 |  |  |  | 5 |  |  |  |  | 10 |  |  |  |  |  |
| TTC | GGT | GCC | TGG | GCA | GGG | CTG | GGT | CCG | GGG | CAG | GGC | GAG | CAG | GGC | ATG | 278 |
| Phe | Gly | Ala | Trp | Ala | Gly | Leu | Gly | Pro | Gly | Gln | Gly | Glu | Gln | Gly | Met |  |
| 15 |  |  |  |  | 20 |  |  |  |  | 25 |  |  |  |  | 30 |  |
| ACG | GTG | GCC | GTG | GTG | TTT | AGC | AGC | TCA | GGG | CCG | CCC | CAG | GCC | CAG | TTC | 326 |
| Thr | Val | Ala | Val | Val | Phe | Ser | Ser | Ser | Gly | Pro | Pro | Gln | Ala | Gln | Phe |  |
|  |  |  |  | 35 |  |  |  |  | 40 |  |  |  |  | 45 |  |  |
| CGT | GTC | CGC | CTC | ACC | CCC | CAG | AGC | TTC | CTG | GAC | CTA | CCC | CTG | GAG | ATC | 374 |
| Arg | Val | Arg | Leu | Thr | Pro | Gln | Ser | Phe | Leu | Asp | Leu | Pro | Leu | Glu | Ile |  |
|  |  |  |  | 50 |  |  |  |  | 55 |  |  |  |  | 60 |  |  |
| CAG | CCG | CTC | ACA | GTT | GGG | GTC | AAC | ACC | ACC | AAC | CCC | AGC | AGC | CTC | CTC | 422 |
| Gln | Pro | Leu | Thr | Val | Gly | Val | Asn | Thr | Thr | Asn | Pro | Ser | Ser | Leu | Leu |  |
|  |  |  |  | 65 |  |  |  |  | 70 |  |  |  |  | 75 |  |  |
| ACC | CAG | ATC | TGC | GGC | CTC | CTG | GGT | GCT | GCC | CAC | GTC | CAC | GGC | ATT | GTC | 470 |
| Thr | Gln | Ile | Cys | Gly | Leu | Leu | Gly | Ala | Ala | His | Val | His | Gly | Ile | Val |  |
|  |  |  | 80 |  |  |  |  | 85 |  |  |  |  | 90 |  |  |  |
| TTT | GAG | GAC | AAC | GTG | GAC | ACC | GAG | GCG | GTG | GCC | CAG | ATC | CTT | GAC | TTC | 518 |
| Phe | Glu | Asp | Asn | Val | Asp | Thr | Glu | Ala | Val | Ala | Gln | Ile | Leu | Asp | Phe |  |
| 95 |  |  |  |  | 100 |  |  |  |  | 105 |  |  |  |  | 110 |  |
| ATC | TCC | TCC | CAG | ACC | CAT | GTG | CCC | ATC | CTC | AGC | ATC | AGC | GGA | GGC | TCT | 566 |
| Ile | Ser | Ser | Gln | Thr | His | Val | Pro | Ile | Leu | Ser | Ile | Ser | Gly | Gly | Ser |  |
|  |  |  |  | 115 |  |  |  |  | 120 |  |  |  |  | 125 |  |  |
| GCT | GTG | GTC | CTC | ACC | CCC | AAG | GAG | CCG | GGC | TCC | GCC | TTC | CTG | CAG | CTG | 614 |
| Ala | Val | Val | Leu | Thr | Pro | Lys | Glu | Pro | Gly | Ser | Ala | Phe | Leu | Gln | Leu |  |
|  |  |  |  | 130 |  |  |  |  | 135 |  |  |  |  | 140 |  |  |
| GGC | GTG | TCC | CTG | GAG | CAG | CAG | CTG | CAG | GTG | CTG | TTC | AAG | GTG | CTG | GAA | 662 |
| Gly | Val | Ser | Leu | Glu | Gln | Gln | Leu | Gln | Val | Leu | Phe | Lys | Val | Leu | Glu |  |
|  |  |  |  | 145 |  |  |  |  | 150 |  |  |  |  | 155 |  |  |
| GAG | TAC | GAC | TGG | AGC | GCC | TTC | GCC | GTC | ATC | ACC | AGC | CTG | CAC | CCG | GGC | 710 |
| Glu | Tyr | Asp | Trp | Ser | Ala | Phe | Ala | Val | Ile | Thr | Ser | Leu | His | Pro | Gly |  |
|  |  |  |  | 160 |  |  |  |  | 165 |  |  |  |  | 170 |  |  |

```
CAC  GCG  CTC  TTC  CTG  GAG  GGC  GTG  CGC  GCC  GTC  GCC  GAC  GCC  AGC  CAC     758
His  Ala  Leu  Phe  Leu  Glu  Gly  Val  Arg  Ala  Val  Ala  Asp  Ala  Ser  His
175                      180                     185                      190

GTG  AGT  TGG  CGG  CTG  CTG  GAC  GTG  GTC  ACG  CTG  GAA  CTG  GAC  CCG  GGA     806
Val  Ser  Trp  Arg  Leu  Leu  Asp  Val  Val  Thr  Leu  Glu  Leu  Asp  Pro  Gly
                    195                     200                      205

GGG  CCG  CGC  GCG  CGC  ACG  CAG  CGC  CTG  CTG  CGC  CAG  CTC  GAC  GCG  CCC     854
Gly  Pro  Arg  Ala  Arg  Thr  Gln  Arg  Leu  Leu  Arg  Gln  Leu  Asp  Ala  Pro
               210                     215                      220

GTG  TTT  GTG  GCC  TAC  TGC  TCG  CGC  GAG  GAG  GCC  GAG  GTG  CTC  TTC  GCC     902
Val  Phe  Val  Ala  Tyr  Cys  Ser  Arg  Glu  Glu  Ala  Glu  Val  Leu  Phe  Ala
               225                     230                      235

GAG  GCG  GCG  CAG  GCC  GGT  CTG  GTG  GGG  CCC  GGC  CAC  GTG  TGG  CTG  GTG     950
Glu  Ala  Ala  Gln  Ala  Gly  Leu  Val  Gly  Pro  Gly  His  Val  Trp  Leu  Val
240                      245                     250

CCC  AAC  CTG  GCG  CTG  GGC  AGC  ACC  GAT  GCG  CCC  CCC  GCC  ACC  TTC  CCC     998
Pro  Asn  Leu  Ala  Leu  Gly  Ser  Thr  Asp  Ala  Pro  Pro  Ala  Thr  Phe  Pro
255                      260                     265                      270

GTG  GGC  CTC  ATC  AGC  GTC  GTC  ACC  GAG  AGC  TGG  CGC  CTC  AGC  CTG  CGC    1046
Val  Gly  Leu  Ile  Ser  Val  Val  Thr  Glu  Ser  Trp  Arg  Leu  Ser  Leu  Arg
                    275                     280                      285

CAG  AAG  GTG  CGC  GAC  GGC  GTG  GCC  ATT  CTG  GCC  CTG  GGC  GCC  CAC  AGC    1094
Gln  Lys  Val  Arg  Asp  Gly  Val  Ala  Ile  Leu  Ala  Leu  Gly  Ala  His  Ser
               290                     295                      300

TAC  TGG  CGC  CAG  CAT  GGA  ACC  CTG  CCA  GCC  CCG  GCC  GGG  GAC  TGC  CGT    1142
Tyr  Trp  Arg  Gln  His  Gly  Thr  Leu  Pro  Ala  Pro  Ala  Gly  Asp  Cys  Arg
               305                     310                      315

GTT  CAC  CCT  GGG  CCC  GTC  AGC  CCT  GCC  CGG  GAG  GCC  TTC  TAC  AGG  CAC    1190
Val  His  Pro  Gly  Pro  Val  Ser  Pro  Ala  Arg  Glu  Ala  Phe  Tyr  Arg  His
     320                     325                     330

CTA  CTG  AAT  GTC  ACC  TGG  GAG  GGC  CGA  GAC  TTC  TCC  TTC  AGC  CCT  GGT    1238
Leu  Leu  Asn  Val  Thr  Trp  Glu  Gly  Arg  Asp  Phe  Ser  Phe  Ser  Pro  Gly
335                      340                     345                      350

GGG  TAC  CTG  GTC  CAG  CCC  ACC  ATG  GTG  GTG  ATC  GCC  CTC  AAC  CGG  CAC    1286
Gly  Tyr  Leu  Val  Gln  Pro  Thr  Met  Val  Val  Ile  Ala  Leu  Asn  Arg  His
                    355                     360                      365

CGC  CTC  TGG  GAG  ATG  GTG  GGG  CGC  TGG  GAG  CAT  GGC  GTC  CTA  TAC  ATG    1334
Arg  Leu  Trp  Glu  Met  Val  Gly  Arg  Trp  Glu  His  Gly  Val  Leu  Tyr  Met
               370                     375                      380

AAG  TAC  CCC  GTG  TGG  CCT  CGC  TAC  AGT  GCC  TCT  CTG  CAG  CCT  GTG  GTG    1382
Lys  Tyr  Pro  Val  Trp  Pro  Arg  Tyr  Ser  Ala  Ser  Leu  Gln  Pro  Val  Val
               385                     390                      395

GAC  AGT  CGG  CAC  CTG  ACG  GTG  GCC  ACG  CTG  GAA  GAG  CGG  CCC  TTT  GTC    1430
Asp  Ser  Arg  His  Leu  Thr  Val  Ala  Thr  Leu  Glu  Glu  Arg  Pro  Phe  Val
     400                     405                     410

ATC  GTG  GAG  AGC  CCT  GAC  CCT  GGC  ACA  GGA  GGC  TGT  GTC  CCC  AAC  ACC    1478
Ile  Val  Glu  Ser  Pro  Asp  Pro  Gly  Thr  Gly  Gly  Cys  Val  Pro  Asn  Thr
415                      420                     425                      430

GTG  CCC  TGC  CGC  AGG  CAG  AGC  AAC  CAC  ACC  TTC  AGC  AGC  GGG  GAC  GTG    1526
Val  Pro  Cys  Arg  Arg  Gln  Ser  Asn  His  Thr  Phe  Ser  Ser  Gly  Asp  Val
               435                     440                      445

GCC  CCC  TAC  ACC  AAG  CTC  TGC  TGT  AAG  GGA  TTC  TGC  ATC  GAC  ATC  CTC    1574
Ala  Pro  Tyr  Thr  Lys  Leu  Cys  Cys  Lys  Gly  Phe  Cys  Ile  Asp  Ile  Leu
               450                     455                      460

AAG  AAG  CTG  GCC  AGA  GTG  GTC  AAA  TTC  TCC  TAC  GAC  CTG  TAC  CTG  GTG    1622
Lys  Lys  Leu  Ala  Arg  Val  Val  Lys  Phe  Ser  Tyr  Asp  Leu  Tyr  Leu  Val
          465                     470                     475

ACC  AAC  GGC  AAG  CAT  GGC  AAG  CGG  GTG  CGC  GGC  GTA  TGG  AAC  GGC  ATG    1670
Thr  Asn  Gly  Lys  His  Gly  Lys  Arg  Val  Arg  Gly  Val  Trp  Asn  Gly  Met
480                      485                     490
```

-continued

| | | | | | | | | | | | | | | | | |
|---|---|---|---|---|---|---|---|---|---|---|---|---|---|---|---|---|
| ATT | GGG | GAG | GTG | TAC | TAC | AAG | CGG | GCA | GAC | ATG | GCC | ATC | GGC | TCC | CTC | 1718 |
| Ile | Gly | Glu | Val | Tyr | Tyr | Lys | Arg | Ala | Asp | Met | Ala | Ile | Gly | Ser | Leu | |
| 495 | | | | | 500 | | | | | 505 | | | | | 510 | |
| ACC | ATC | AAT | GAG | GAA | CGC | TCC | GAG | ATC | GTA | GAC | TTC | TCT | GTA | CCC | TTT | 1766 |
| Thr | Ile | Asn | Glu | Glu | Arg | Ser | Glu | Ile | Val | Asp | Phe | Ser | Val | Pro | Phe | |
| | | | | 515 | | | | | 520 | | | | | 525 | | |
| GTG | GAG | ACG | GGC | ATC | AGT | GTG | ATG | GTG | GCT | CGC | AGC | AAT | GGC | ACC | GTC | 1814 |
| Val | Glu | Thr | Gly | Ile | Ser | Val | Met | Val | Ala | Arg | Ser | Asn | Gly | Thr | Val | |
| | | | 530 | | | | | 535 | | | | | 540 | | | |
| TCC | CCC | TCG | GCC | TTC | TTG | GAG | CCA | TAT | AGC | CCT | GCA | GTG | TGG | GTG | ATG | 1862 |
| Ser | Pro | Ser | Ala | Phe | Leu | Glu | Pro | Tyr | Ser | Pro | Ala | Val | Trp | Val | Met | |
| | | 545 | | | | | 550 | | | | | 555 | | | | |
| ATG | TTT | GTC | ATG | TGC | CTC | ACT | GTG | GTG | GCC | ATC | ACC | GTC | TTC | ATG | TTC | 1910 |
| Met | Phe | Val | Met | Cys | Leu | Thr | Val | Val | Ala | Ile | Thr | Val | Phe | Met | Phe | |
| 560 | | | | | 565 | | | | | 570 | | | | | | |
| GAG | TAC | TTC | AGC | CCT | GTC | AGC | TAC | AAC | CAG | AAC | CTC | ACC | AGA | GGC | AAG | 1958 |
| Glu | Tyr | Phe | Ser | Pro | Val | Ser | Tyr | Asn | Gln | Asn | Leu | Thr | Arg | Gly | Lys | |
| 575 | | | | | 580 | | | | | 585 | | | | | 590 | |
| ACT | TTC | ACT | ATC | GGC | AAG | TCC | GTG | TGG | CTG | CTG | TGG | GCG | CTG | GTC | TTC | 2006 |
| Thr | Phe | Thr | Ile | Gly | Lys | Ser | Val | Trp | Leu | Leu | Trp | Ala | Leu | Val | Phe | |
| | | | | 595 | | | | | 600 | | | | | 605 | | |
| AAC | AAC | TCA | GTG | CCC | ATC | GAG | AAC | CCG | CGG | GGC | ACC | ACC | AGC | AAG | ATC | 2054 |
| Asn | Asn | Ser | Val | Pro | Ile | Glu | Asn | Pro | Arg | Gly | Thr | Thr | Ser | Lys | Ile | |
| | | | 610 | | | | | 615 | | | | | 620 | | | |
| ATG | GTT | CTG | GTC | TGG | GCC | TTC | TTT | GCT | GTC | ATC | TTC | CTC | GCC | AGA | TAC | 2102 |
| Met | Val | Leu | Val | Trp | Ala | Phe | Phe | Ala | Val | Ile | Phe | Leu | Ala | Arg | Tyr | |
| | | 625 | | | | | 630 | | | | | 635 | | | | |
| ACG | GCC | AAC | CTG | GCC | GCC | TTC | ATG | ATC | CAA | GAG | CAA | TAC | ATC | GAC | ACT | 2150 |
| Thr | Ala | Asn | Leu | Ala | Ala | Phe | Met | Ile | Gln | Glu | Gln | Tyr | Ile | Asp | Thr | |
| 640 | | | | | 645 | | | | | 650 | | | | | | |
| GTG | TCG | GGC | CTC | AGT | GAC | AAG | AAG | TTT | CAG | CGG | CCT | CAA | GAT | CAG | TAC | 2198 |
| Val | Ser | Gly | Leu | Ser | Asp | Lys | Lys | Phe | Gln | Arg | Pro | Gln | Asp | Gln | Tyr | |
| 655 | | | | | 660 | | | | | 665 | | | | | 670 | |
| CCA | CCT | TTC | CGC | TTC | GGC | ACG | GTG | CCC | AAC | GGC | AGC | ACG | GAG | CGG | AAC | 2246 |
| Pro | Pro | Phe | Arg | Phe | Gly | Thr | Val | Pro | Asn | Gly | Ser | Thr | Glu | Arg | Asn | |
| | | | | 675 | | | | | 680 | | | | | 685 | | |
| ATC | CGC | AGT | AAC | TAC | CGT | GAC | ATG | CAC | ACC | CAC | ATG | GTC | AAG | TTC | AAC | 2294 |
| Ile | Arg | Ser | Asn | Tyr | Arg | Asp | Met | His | Thr | His | Met | Val | Lys | Phe | Asn | |
| | | | | 690 | | | | | 695 | | | | | 700 | | |
| CAG | CGC | TCG | GTG | GAG | GAC | GCG | CTC | ACC | AGC | CTC | AAG | ATG | GGC | AAG | GAC | 2342 |
| Gln | Arg | Ser | Val | Glu | Asp | Ala | Leu | Thr | Ser | Leu | Lys | Met | Gly | Lys | Asp | |
| | | 705 | | | | | 710 | | | | | 715 | | | | |
| GAG | GGC | TGC | AAG | CTG | GTC | ACC | ATT | GGG | TCT | GGC | AAG | GTC | TTT | GCT | ACC | 2390 |
| Glu | Gly | Cys | Lys | Leu | Val | Thr | Ile | Gly | Ser | Gly | Lys | Val | Phe | Ala | Thr | |
| | 720 | | | | | 725 | | | | | 730 | | | | | |
| ACT | GGC | TAC | GGC | ATC | GCC | ATG | CAG | AAG | GAC | TCC | CAC | TGG | AAG | CGG | GCC | 2438 |
| Thr | Gly | Tyr | Gly | Ile | Ala | Met | Gln | Lys | Asp | Ser | His | Trp | Lys | Arg | Ala | |
| 735 | | | | | 740 | | | | | 745 | | | | | 750 | |
| ATA | GAC | CTG | GCG | CTC | TTG | CAG | TTC | CTG | GGG | GAC | GGA | GAG | ACA | CAG | AAA | 2486 |
| Ile | Asp | Leu | Ala | Leu | Leu | Gln | Phe | Leu | Gly | Asp | Gly | Glu | Thr | Gln | Lys | |
| | | | | 755 | | | | | 760 | | | | | 765 | | |
| CTG | GAG | ACA | GTG | TGG | CTC | TCA | GGG | ATC | TGC | CAG | AAT | GAG | AAG | AAC | GAG | 2534 |
| Leu | Glu | Thr | Val | Trp | Leu | Ser | Gly | Ile | Cys | Gln | Asn | Glu | Lys | Asn | Glu | |
| | | | 770 | | | | | 775 | | | | | 780 | | | |
| GTG | ATG | AGC | AGC | AAG | CTG | GAC | ATC | GAC | AAC | ATG | GGA | GGC | GTC | TTC | TAC | 2582 |
| Val | Met | Ser | Ser | Lys | Leu | Asp | Ile | Asp | Asn | Met | Gly | Gly | Val | Phe | Tyr | |
| | | 785 | | | | | 790 | | | | | 795 | | | | |
| ATG | CTG | CTG | GTG | GCC | ATG | GGG | CTG | GCC | CTG | CTG | GTC | TTC | GCC | TGG | GAG | 2630 |
| Met | Leu | Leu | Val | Ala | Met | Gly | Leu | Ala | Leu | Leu | Val | Phe | Ala | Trp | Glu | |
| 800 | | | | | 805 | | | | | 810 | | | | | | |

| | | | | | | | | | | | | | | | | |
|---|---|---|---|---|---|---|---|---|---|---|---|---|---|---|---|---|
| CAC | CTG | GTC | TAC | TGG | AAG | CTG | CGC | CAC | TCG | GTG | CCC | AAC | TCA | TCC | CAG | 2678 |
| His | Leu | Val | Tyr | Trp | Lys | Leu | Arg | His | Ser | Val | Pro | Asn | Ser | Ser | Gln | |
| 815 | | | | | 820 | | | | | 825 | | | | | 830 | |
| CTG | GAC | TTC | CTG | CTG | GCT | TTC | AGC | AGG | GGC | ATC | TAC | AGC | TGC | TTC | AGC | 2726 |
| Leu | Asp | Phe | Leu | Leu | Ala | Phe | Ser | Arg | Gly | Ile | Tyr | Ser | Cys | Phe | Ser | |
| | | | | 835 | | | | | 840 | | | | | 845 | | |
| GGG | GTG | CAG | AGC | CTC | GCC | AGC | CCA | CCG | CGG | CAG | GCC | AGC | CCG | GAC | CTC | 2774 |
| Gly | Val | Gln | Ser | Leu | Ala | Ser | Pro | Pro | Arg | Gln | Ala | Ser | Pro | Asp | Leu | |
| | | | 850 | | | | | 855 | | | | | 860 | | | |
| ACG | GCC | AGC | TCG | GCC | CAG | GCC | AGC | GTG | CTC | AAG | ATT | CTG | CAG | GCA | GCC | 2822 |
| Thr | Ala | Ser | Ser | Ala | Gln | Ala | Ser | Val | Leu | Lys | Ile | Leu | Gln | Ala | Ala | |
| | | 865 | | | | | 870 | | | | | 875 | | | | |
| CGC | GAC | ATG | GTG | ACC | ACG | GCG | GGC | GTA | AGC | AAC | TCC | CTG | GAC | CGC | GCC | 2870 |
| Arg | Asp | Met | Val | Thr | Thr | Ala | Gly | Val | Ser | Asn | Ser | Leu | Asp | Arg | Ala | |
| | | 880 | | | | | 885 | | | | | 890 | | | | |
| ACT | CGC | ACC | ATC | GAG | AAT | TGG | GGT | GGC | GGC | CGT | GCG | CCC | CCA | CCG | | 2918 |
| Thr | Arg | Thr | Ile | Glu | Asn | Trp | Gly | Gly | Gly | Arg | Arg | Ala | Pro | Pro | Pro | |
| 895 | | | | | 900 | | | | | 905 | | | | | 910 | |
| TCC | CCC | TGC | CCG | ACC | CCG | CGG | TCT | GGC | CCC | AGC | CCA | TGC | CTG | CCC | ACC | 2966 |
| Ser | Pro | Cys | Pro | Thr | Pro | Arg | Ser | Gly | Pro | Ser | Pro | Cys | Leu | Pro | Thr | |
| | | | | 915 | | | | | 920 | | | | | 925 | | |
| CCC | GAC | CCG | CCC | CCA | GAG | CCG | AGC | CCC | ACG | GGC | TGG | GGA | CCG | CCA | GAC | 3014 |
| Pro | Asp | Pro | Pro | Pro | Glu | Pro | Ser | Pro | Thr | Gly | Trp | Gly | Pro | Pro | Asp | |
| | | | 930 | | | | | 935 | | | | | 940 | | | |
| GGG | GGT | CGC | GCG | GCG | CTT | GTG | CGC | AGG | GCT | CCG | CAG | CCC | CCG | GGC | CGC | 3062 |
| Gly | Gly | Arg | Ala | Ala | Leu | Val | Arg | Arg | Ala | Pro | Gln | Pro | Pro | Gly | Arg | |
| | | 945 | | | | | 950 | | | | | 955 | | | | |
| CCC | CCG | ACG | CCG | GGG | CCG | CCC | CTG | TCC | GAC | GTC | TCC | CGA | GTG | TCG | CGC | 3110 |
| Pro | Pro | Thr | Pro | Gly | Pro | Pro | Leu | Ser | Asp | Val | Ser | Arg | Val | Ser | Arg | |
| | | 960 | | | | | 965 | | | | | 970 | | | | |
| CGC | CCA | GCC | TGG | GAG | GCG | CGG | TGG | CCG | GTG | CGG | ACC | GGG | CAC | TGC | GGG | 3158 |
| Arg | Pro | Ala | Trp | Glu | Ala | Arg | Trp | Pro | Val | Arg | Thr | Gly | His | Cys | Gly | |
| 975 | | | | | 980 | | | | | 985 | | | | | 990 | |
| AGG | CAC | CTC | TCG | GCC | TCC | GAG | CGG | CCC | CTG | TCG | CCC | GCG | CGC | TGT | CAC | 3206 |
| Arg | His | Leu | Ser | Ala | Ser | Glu | Arg | Pro | Leu | Ser | Pro | Ala | Arg | Cys | His | |
| | | | | 995 | | | | | 1000 | | | | | 1005 | | |
| TAC | AGC | TCC | TTT | CCT | CGA | GCC | GAC | CGA | TCC | GGC | CGC | CCC | TTC | CTC | CCG | 3254 |
| Tyr | Ser | Ser | Phe | Pro | Arg | Ala | Asp | Arg | Ser | Gly | Arg | Pro | Phe | Leu | Pro | |
| | | | 1010 | | | | | 1015 | | | | | 1020 | | | |
| CTC | TTC | CCG | GAG | CCC | CCG | GAG | CTG | GAG | GAC | CTG | CCG | CTG | CTC | GGT | CCG | 3302 |
| Leu | Phe | Pro | Glu | Pro | Pro | Glu | Leu | Glu | Asp | Leu | Pro | Leu | Leu | Gly | Pro | |
| | | 1025 | | | | | 1030 | | | | | 1035 | | | | |
| GAG | CAG | CTG | GCC | CGG | CGG | GAG | GCC | CTG | CTG | AAC | GCG | GCC | TGG | GCC | CGG | 3350 |
| Glu | Gln | Leu | Ala | Arg | Arg | Glu | Ala | Leu | Leu | Asn | Ala | Ala | Trp | Ala | Arg | |
| | | 1040 | | | | | 1045 | | | | | 1050 | | | | |
| GGC | TCG | CGC | CCG | AGT | CAC | GCT | TCC | CTG | CCC | AGC | TCC | GTG | GCC | GAG | GCC | 3398 |
| Gly | Ser | Arg | Pro | Ser | His | Ala | Ser | Leu | Pro | Ser | Ser | Val | Ala | Glu | Ala | |
| 1055 | | | | | 1060 | | | | | 1065 | | | | | 1070 | |
| TTC | GCT | CGG | CCC | AGC | TCG | CTG | CCC | GCT | GGG | TGC | ACC | GGC | CCC | GCC | TGC | 3446 |
| Phe | Ala | Arg | Pro | Ser | Ser | Leu | Pro | Ala | Gly | Cys | Thr | Gly | Pro | Ala | Cys | |
| | | | | 1075 | | | | | 1080 | | | | | 1085 | | |
| GCC | CGC | CCC | GAC | GGC | CAC | TCG | GCC | TGC | AGG | CGC | TTG | GCG | CAG | GCG | CAG | 3494 |
| Ala | Arg | Pro | Asp | Gly | His | Ser | Ala | Cys | Arg | Arg | Leu | Ala | Gln | Ala | Gln | |
| | | | 1090 | | | | | 1095 | | | | | 1100 | | | |
| TCG | ATG | TGC | TTG | CCG | ATC | TAC | CGG | GAG | GCC | TGC | CAG | GAG | GGC | GAG | CAG | 3542 |
| Ser | Met | Cys | Leu | Pro | Ile | Tyr | Arg | Glu | Ala | Cys | Gln | Glu | Gly | Glu | Gln | |
| | | | 1105 | | | | | 1110 | | | | | 1115 | | | |
| GCA | GGG | GCC | CCC | GCC | TGG | CAG | CAC | AGA | CAG | CAC | GTC | TGC | CTG | CAC | GCC | 3590 |
| Ala | Gly | Ala | Pro | Ala | Trp | Gln | His | Arg | Gln | His | Val | Cys | Leu | His | Ala | |
| | | 1120 | | | | | 1125 | | | | | 1130 | | | | |

| | | | | | | | | | | | | | | | | |
|---|---|---|---|---|---|---|---|---|---|---|---|---|---|---|---|---|
| CAC | GCC | CAC | CTG | CCA | TTG | TGC | TGG | GGG | GCT | GTC | TGT | CCT | CAC | CTT | CCA | 3638 |
| His | Ala | His | Leu | Pro | Leu | Cys | Trp | Gly | Ala | Val | Cys | Pro | His | Leu | Pro | |
| 1135 | | | | 1140 | | | | | 1145 | | | | | | 1150 | |
| CCC | TGT | GAC | AGC | CAC | GGC | TCC | TGG | CTC | TCC | GGC | GCC | TGG | GGG | CCT | CTG | 3686 |
| Pro | Cys | Asp | Ser | His | Gly | Ser | Trp | Leu | Ser | Gly | Ala | Trp | Gly | Pro | Leu | |
| | | | | 1155 | | | | | 1160 | | | | | 1165 | | |
| GGG | CAC | AGC | GGC | AGG | ACT | CTG | GGG | CTG | GGC | ACA | GGC | TAC | AGA | GAC | AGT | 3734 |
| Gly | His | Ser | Gly | Arg | Thr | Leu | Gly | Leu | Gly | Thr | Gly | Tyr | Arg | Asp | Ser | |
| | | | 1170 | | | | | 1175 | | | | | 1180 | | | |
| GGG | GGA | CTG | GAC | GAG | ATC | AGC | AGT | GTA | GCC | CGT | GGG | ACG | CAA | GGC | TTC | 3782 |
| Gly | Gly | Leu | Asp | Glu | Ile | Ser | Ser | Val | Ala | Arg | Gly | Thr | Gln | Gly | Phe | |
| | | | 1185 | | | | | 1190 | | | | | 1195 | | | |
| CCG | GGA | CCC | TGC | ACC | TGG | AGA | CGG | ATC | TCC | AGT | CTG | GAG | TCA | GAA | GTG | 3830 |
| Pro | Gly | Pro | Cys | Thr | Trp | Arg | Arg | Ile | Ser | Ser | Leu | Glu | Ser | Glu | Val | |
| | | 1200 | | | | | 1205 | | | | | 1210 | | | | |

TGAGTTATCA GCCACTCAGG CTCCGAGCCA GCTGGATTCT CTGCCTGCCA CTGTCAGGGT  3890

TAAGCGGCAG GCAGGATTGG CCCTTCTCTG GCTTCTACCA TGAAATCCTG GCCATGGCAC  3950

CCCAGTGACA GATGATGTCT TCCATGGTCA TCAGTGACCT CAGCTAGCCT CA  4002

(2) INFORMATION FOR SEQ ID NO:54:

(i) SEQUENCE CHARACTERISTICS:
    (A) LENGTH: 1214 amino acids
    (B) TYPE: amino acid
    (D) TOPOLOGY: linear (ii) MOLECULE TYPE: protein (xi) SEQUENCE DESCRIPTION: SEQ ID NO:54:

Met Gly Gly Ala Leu Gly Pro Ala Leu Leu Leu Thr Ser Leu Phe Gly
 1               5                  10                  15

Ala Trp Ala Gly Leu Gly Pro Gly Gln Gly Glu Gln Gly Met Thr Val
                20                  25                  30

Ala Val Val Phe Ser Ser Ser Gly Pro Pro Gln Ala Gln Phe Arg Val
            35                  40                  45

Arg Leu Thr Pro Gln Ser Phe Leu Asp Leu Pro Leu Glu Ile Gln Pro
    50                  55                  60

Leu Thr Val Gly Val Asn Thr Thr Asn Pro Ser Ser Leu Leu Thr Gln
65                  70                  75                  80

Ile Cys Gly Leu Leu Gly Ala Ala His Val His Gly Ile Val Phe Glu
                85                  90                  95

Asp Asn Val Asp Thr Glu Ala Val Ala Gln Ile Leu Asp Phe Ile Ser
               100                 105                 110

Ser Gln Thr His Val Pro Ile Leu Ser Ile Ser Gly Gly Ser Ala Val
            115                 120                 125

Val Leu Thr Pro Lys Glu Pro Gly Ser Ala Phe Leu Gln Leu Gly Val
    130                 135                 140

Ser Leu Glu Gln Gln Leu Gln Val Leu Phe Lys Val Leu Glu Glu Tyr
145                 150                 155                 160

Asp Trp Ser Ala Phe Ala Val Ile Thr Ser Leu His Pro Gly His Ala
                165                 170                 175

Leu Phe Leu Glu Gly Val Arg Ala Val Ala Asp Ala Ser His Val Ser
            180                 185                 190

Trp Arg Leu Leu Asp Val Val Thr Leu Glu Leu Asp Pro Gly Gly Pro
    195                 200                 205

Arg Ala Arg Thr Gln Arg Leu Leu Arg Gln Leu Asp Ala Pro Val Phe
210                 215                 220

```
Val Ala Tyr Cys Ser Arg Glu Glu Ala Glu Val Leu Phe Ala Glu Ala
225             230                 235                 240

Ala Gln Ala Gly Leu Val Gly Pro Gly His Val Trp Leu Val Pro Asn
            245             250                 255

Leu Ala Leu Gly Ser Thr Asp Ala Pro Pro Ala Thr Phe Pro Val Gly
            260             265                 270

Leu Ile Ser Val Val Thr Glu Ser Trp Arg Leu Ser Leu Arg Gln Lys
        275             280                 285

Val Arg Asp Gly Val Ala Ile Leu Ala Leu Gly Ala His Ser Tyr Trp
    290             295             300

Arg Gln His Gly Thr Leu Pro Ala Pro Ala Gly Asp Cys Arg Val His
305             310             315                 320

Pro Gly Pro Val Ser Pro Ala Arg Glu Ala Phe Tyr Arg His Leu Leu
                325             330                 335

Asn Val Thr Trp Glu Gly Arg Asp Phe Ser Phe Ser Pro Gly Gly Tyr
            340             345             350

Leu Val Gln Pro Thr Met Val Val Ile Ala Leu Asn Arg His Arg Leu
        355             360             365

Trp Glu Met Val Gly Arg Trp Glu His Gly Val Leu Tyr Met Lys Tyr
    370             375             380

Pro Val Trp Pro Arg Tyr Ser Ala Ser Leu Gln Pro Val Val Asp Ser
385             390             395                 400

Arg His Leu Thr Val Ala Thr Leu Glu Glu Arg Pro Phe Val Ile Val
            405             410             415

Glu Ser Pro Asp Pro Gly Thr Gly Gly Cys Val Pro Asn Thr Val Pro
            420             425             430

Cys Arg Arg Gln Ser Asn His Thr Phe Ser Ser Gly Asp Val Ala Pro
        435             440             445

Tyr Thr Lys Leu Cys Cys Lys Gly Phe Cys Ile Asp Ile Leu Lys Lys
        450             455             460

Leu Ala Arg Val Val Lys Phe Ser Tyr Asp Leu Tyr Leu Val Thr Asn
465             470             475             480

Gly Lys His Gly Lys Arg Val Arg Gly Val Trp Asn Gly Met Ile Gly
            485             490             495

Glu Val Tyr Tyr Lys Arg Ala Asp Met Ala Ile Gly Ser Leu Thr Ile
        500             505             510

Asn Glu Glu Arg Ser Glu Ile Val Asp Phe Ser Val Pro Phe Val Glu
        515             520             525

Thr Gly Ile Ser Val Met Val Ala Arg Ser Asn Gly Thr Val Ser Pro
    530             535             540

Ser Ala Phe Leu Glu Pro Tyr Ser Pro Ala Val Trp Val Met Met Phe
545             550             555             560

Val Met Cys Leu Thr Val Val Ala Ile Thr Val Phe Met Phe Glu Tyr
            565             570             575

Phe Ser Pro Val Ser Tyr Asn Gln Asn Leu Thr Arg Gly Lys Thr Phe
            580             585             590

Thr Ile Gly Lys Ser Val Trp Leu Leu Trp Ala Leu Val Phe Asn Asn
        595             600             605

Ser Val Pro Ile Glu Asn Pro Arg Gly Thr Thr Ser Lys Ile Met Val
    610             615             620

Leu Val Trp Ala Phe Phe Ala Val Ile Phe Leu Ala Arg Tyr Thr Ala
625             630             635             640

Asn Leu Ala Ala Phe Met Ile Gln Glu Gln Tyr Ile Asp Thr Val Ser
```

-continued

|     |     |     | 645 |     |     |     |     | 650 |     |     |     |     | 655 |     |
| --- | --- | --- | --- | --- | --- | --- | --- | --- | --- | --- | --- | --- | --- | --- |

Gly Leu Ser Asp Lys Lys Phe Gln Arg Pro Gln Asp Gln Pro Pro
            660                 665             670

Phe Arg Phe Gly Thr Val Pro Asn Gly Ser Thr Glu Arg Asn Ile Arg
        675                 680             685

Ser Asn Tyr Arg Asp Met His Thr His Met Val Lys Phe Asn Gln Arg
    690             695             700

Ser Val Glu Asp Ala Leu Thr Ser Leu Lys Met Gly Lys Asp Glu Gly
705             710             715             720

Cys Lys Leu Val Thr Ile Gly Ser Gly Lys Val Phe Ala Thr Thr Gly
            725             730             735

Tyr Gly Ile Ala Met Gln Lys Asp Ser His Trp Lys Arg Ala Ile Asp
            740             745             750

Leu Ala Leu Leu Gln Phe Leu Gly Asp Gly Glu Thr Gln Lys Leu Glu
            755             760             765

Thr Val Trp Leu Ser Gly Ile Cys Gln Asn Glu Lys Asn Glu Val Met
        770             775             780

Ser Ser Lys Leu Asp Ile Asp Asn Met Gly Gly Val Phe Tyr Met Leu
785             790             795             800

Leu Val Ala Met Gly Leu Ala Leu Leu Val Phe Ala Trp Glu His Leu
            805             810             815

Val Tyr Trp Lys Leu Arg His Ser Val Pro Asn Ser Ser Gln Leu Asp
            820             825             830

Phe Leu Leu Ala Phe Ser Arg Gly Ile Tyr Ser Cys Phe Ser Gly Val
            835             840             845

Gln Ser Leu Ala Ser Pro Pro Arg Gln Ala Ser Pro Asp Leu Thr Ala
    850             855             860

Ser Ser Ala Gln Ala Ser Val Leu Lys Ile Leu Gln Ala Ala Arg Asp
865             870             875             880

Met Val Thr Thr Ala Gly Val Ser Asn Ser Leu Asp Arg Ala Thr Arg
            885             890             895

Thr Ile Glu Asn Trp Gly Gly Gly Arg Arg Ala Pro Pro Pro Ser Pro
            900             905             910

Cys Pro Thr Pro Arg Ser Gly Pro Ser Pro Cys Leu Pro Thr Pro Asp
            915             920             925

Pro Pro Pro Glu Pro Ser Pro Thr Gly Trp Gly Pro Pro Asp Gly Gly
930             935             940

Arg Ala Ala Leu Val Arg Arg Ala Pro Gln Pro Gly Arg Pro Pro
945             950             955             960

Thr Pro Gly Pro Pro Leu Ser Asp Val Ser Arg Val Ser Arg Arg Pro
            965             970             975

Ala Trp Glu Ala Arg Trp Pro Val Arg Thr Gly His Cys Gly Arg His
            980             985             990

Leu Ser Ala Ser Glu Arg Pro Leu Ser Pro Ala Arg Cys His Tyr Ser
            995             1000            1005

Ser Phe Pro Arg Ala Asp Arg Ser Gly Arg Pro Phe Leu Pro Leu Phe
        1010            1015            1020

Pro Glu Pro Pro Glu Leu Glu Asp Leu Pro Leu Leu Gly Pro Glu Gln
1025            1030            1035            1040

Leu Ala Arg Arg Glu Ala Leu Leu Asn Ala Ala Trp Ala Arg Gly Ser
            1045            1050            1055

Arg Pro Ser His Ala Ser Leu Pro Ser Ser Val Ala Glu Ala Phe Ala
            1060            1065            1070

| | | | | | | | | | | | | | | |
|---|---|---|---|---|---|---|---|---|---|---|---|---|---|---|
| Arg | Pro | Ser | Ser | Leu | Pro | Ala | Gly | Cys | Thr | Gly | Pro | Ala | Cys | Ala | Arg |
| | | 1075 | | | | 1080 | | | | | 1085 | | | | |
| Pro | Asp | Gly | His | Ser | Ala | Cys | Arg | Arg | Leu | Ala | Gln | Ala | Gln | Ser | Met |
| | | 1090 | | | | 1095 | | | | 1100 | | | | | |
| Cys | Leu | Pro | Ile | Tyr | Arg | Glu | Ala | Cys | Gln | Glu | Gly | Glu | Gln | Ala | Gly |
| 1105 | | | | | 1110 | | | | 1115 | | | | | | 1120 |
| Ala | Pro | Ala | Trp | Gln | His | Arg | Gln | His | Val | Cys | Leu | His | Ala | His | Ala |
| | | | | 1125 | | | | | 1130 | | | | | 1135 | |
| His | Leu | Pro | Leu | Cys | Trp | Gly | Ala | Val | Cys | Pro | His | Leu | Pro | Pro | Cys |
| | | | | 1140 | | | | 1145 | | | | | 1150 | | |
| Asp | Ser | His | Gly | Ser | Trp | Leu | Ser | Gly | Ala | Trp | Gly | Pro | Leu | Gly | His |
| | | | 1155 | | | | 1160 | | | | | 1165 | | | |
| Ser | Gly | Arg | Thr | Leu | Gly | Leu | Gly | Thr | Gly | Tyr | Arg | Asp | Ser | Gly | Gly |
| | | 1170 | | | | 1175 | | | | | 1180 | | | | |
| Leu | Asp | Glu | Ile | Ser | Ser | Val | Ala | Arg | Gly | Thr | Gln | Gly | Phe | Pro | Gly |
| 1185 | | | | | 1190 | | | | 1195 | | | | | | 1200 |
| Pro | Cys | Thr | Trp | Arg | Arg | Ile | Ser | Ser | Leu | Glu | Ser | Glu | Val | | |
| | | | | 1205 | | | | | 1210 | | | | | | |

( 2 ) INFORMATION FOR SEQ ID NO:55:

( i ) SEQUENCE CHARACTERISTICS:
        ( A ) LENGTH: 5538 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 210..4664

( x i ) SEQUENCE DESCRIPTION: SEQ ID NO:55:

```
TTGAATTTGC ATCTCTTCAA GACACAAGAT TAAAACAAAA TTTACGCTAA ATTGGATTTT        60

AAATTATCTT CCGTTCATTT ATCCTTCGTC TTTCTTATGT GGATATGCAA GCGAGAAGAA       120

GGGACTGGAC ATTCCCAACA TGCTCACTCC CTTAATCTGT CCGTCTAGAG GTTTGGCTTC       180

TACAAACCAA GGGAGTCGAC GAGTTGAAG ATG AAG CCC AGA GCG GAG TGC TGT        233
                                Met Lys Pro Arg Ala Glu Cys Cys
                                 1               5

TCT CCC AAG TTC TGG TTG GTG TTG GCC GTC CTG GCC GTG TCA GGC AGC        281
Ser Pro Lys Phe Trp Leu Val Leu Ala Val Leu Ala Val Ser Gly Ser
         10              15              20

AGA GCT CGT TCT CAG AAG AGC CCC CCC AGC ATT GGC ATT GCT GTC ATC        329
Arg Ala Arg Ser Gln Lys Ser Pro Pro Ser Ile Gly Ile Ala Val Ile
 25              30              35              40

CTC GTG GGC ACT TCC GAC GAG GTG GCC ATC AAG GAT GCC CAC GAG AAA        377
Leu Val Gly Thr Ser Asp Glu Val Ala Ile Lys Asp Ala His Glu Lys
                 45              50              55

GAT GAT TTC CAC CAT CTC TCC GTG GTA CCC CGG GTG GAA CTG GTA GCC        425
Asp Asp Phe His His Leu Ser Val Val Pro Arg Val Glu Leu Val Ala
                 60              65              70

ATG AAT GAG ACC GAC CCA AAG AGC ATC ATC ACC CGC ATC TGT GAT CTC        473
Met Asn Glu Thr Asp Pro Lys Ser Ile Ile Thr Arg Ile Cys Asp Leu
         75              80              85

ATG TCT GAC CGG AAG ATC CAG GGG GTG GTG TTT GCT GAT GAC ACA GAC        521
Met Ser Asp Arg Lys Ile Gln Gly Val Val Phe Ala Asp Asp Thr Asp
 90              95             100

CAG GAA GCC ATC GCC CAG ATC CTC GAT TTC ATT TCA GCA CAG ACT CTC        569
Gln Glu Ala Ile Ala Gln Ile Leu Asp Phe Ile Ser Ala Gln Thr Leu
```

```
           105                           110                           115                           120
ACC   CCG   ATC   CTG   GGC   ATC   CAC   GGG   GGC   TCC   TCT   ATG   ATA   ATG   GCA   GAT         617
Thr   Pro   Ile   Leu   Gly   Ile   His   Gly   Gly   Ser   Ser   Met   Ile   Met   Ala   Asp
                        125               130                           135

AAG   GAT   GAA   TCC   TCC   ATG   TTC   TTC   CAG   TTT   GGC   CCA   TCA   ATT   GAA   CAG         665
Lys   Asp   Glu   Ser   Ser   Met   Phe   Phe   Gln   Phe   Gly   Pro   Ser   Ile   Glu   Gln
                  140                           145                     150

CAA   GCT   TCC   GTA   ATG   CTC   AAC   ATC   ATG   GAA   GAA   TAT   GAC   TGG   TAC   ATC         713
Gln   Ala   Ser   Val   Met   Leu   Asn   Ile   Met   Glu   Glu   Tyr   Asp   Trp   Tyr   Ile
            155                           160                           165

TTT   TCT   ATC   GTC   ACC   ACC   TAT   TTC   CCT   GGC   TAC   CAG   GAC   TTT   GTA   AAC         761
Phe   Ser   Ile   Val   Thr   Thr   Tyr   Phe   Pro   Gly   Tyr   Gln   Asp   Phe   Val   Asn
      170                           175                           180

AAG   ATC   CGC   AGC   ACC   ATT   GAG   AAT   AGC   TTT   GTG   GGC   TGG   GAG   CTA   GAG         809
Lys   Ile   Arg   Ser   Thr   Ile   Glu   Asn   Ser   Phe   Val   Gly   Trp   Glu   Leu   Glu
185                           190                           195                           200

GAG   GTC   CTC   CTA   CTG   GAC   ATG   TCC   CTG   GAC   GAT   GGA   GAT   TCT   AAG   ATC         857
Glu   Val   Leu   Leu   Leu   Asp   Met   Ser   Leu   Asp   Asp   Gly   Asp   Ser   Lys   Ile
                        205                           210                           215

CAG   AAT   CAG   CTC   AAG   AAA   CTT   CAA   AGC   CCC   ATC   ATT   CTT   CTT   TAC   TGT         905
Gln   Asn   Gln   Leu   Lys   Lys   Leu   Gln   Ser   Pro   Ile   Ile   Leu   Leu   Tyr   Cys
                  220                           225                           230

ACC   AAG   GAA   GAA   GCC   ACC   TAC   ATC   TTT   GAA   GTG   GCC   AAC   TCA   GTA   GGG         953
Thr   Lys   Glu   Glu   Ala   Thr   Tyr   Ile   Phe   Glu   Val   Ala   Asn   Ser   Val   Gly
            235                           240                           245

CTG   ACT   GGC   TAT   GGC   TAC   ACG   TGG   ATC   GTG   CCC   AGT   CTG   GTG   GCA   GGG        1001
Leu   Thr   Gly   Tyr   Gly   Tyr   Thr   Trp   Ile   Val   Pro   Ser   Leu   Val   Ala   Gly
      250                           255                           260

GAT   ACA   GAC   ACA   GTG   CCT   GCG   GAG   TTC   CCC   ACT   GGG   CTC   ATC   TCT   GTA        1049
Asp   Thr   Asp   Thr   Val   Pro   Ala   Glu   Phe   Pro   Thr   Gly   Leu   Ile   Ser   Val
265                           270                           275                           280

TCA   TAT   GAT   GAA   TGG   GAC   TAT   GGC   CTC   CCC   CCC   AGA   GTG   AGA   GAT   GGA        1097
Ser   Tyr   Asp   Glu   Trp   Asp   Tyr   Gly   Leu   Pro   Pro   Arg   Val   Arg   Asp   Gly
                        285                           290                           295

ATT   GCC   ATA   ATC   ACC   ACT   GCT   GCT   TCT   GAC   ATG   CTG   TCT   GAG   CAC   AGC        1145
Ile   Ala   Ile   Ile   Thr   Thr   Ala   Ala   Ser   Asp   Met   Leu   Ser   Glu   His   Ser
                  300                           305                           310

TTC   ATC   CCT   GAG   CCC   AAA   AGC   AGT   TGT   TAC   AAC   ACC   CAC   GAG   AAG   AGA        1193
Phe   Ile   Pro   Glu   Pro   Lys   Ser   Ser   Cys   Tyr   Asn   Thr   His   Glu   Lys   Arg
            315                           320                           325

ATC   TAC   CAG   TCC   AAT   ATG   CTA   AAT   AGG   TAT   CTG   ATC   AAT   GTC   ACT   TTT        1241
Ile   Tyr   Gln   Ser   Asn   Met   Leu   Asn   Arg   Tyr   Leu   Ile   Asn   Val   Thr   Phe
      330                           335                           340

GAG   GGG   AGG   AAT   TTG   TCC   TTC   AGT   GAA   GAT   GGC   TAC   CAG   ATG   CAC   CCG        1289
Glu   Gly   Arg   Asn   Leu   Ser   Phe   Ser   Glu   Asp   Gly   Tyr   Gln   Met   His   Pro
345                           350                           355                           360

AAA   CTG   GTG   ATA   ATT   CTT   CTG   AAC   AAG   GAG   AGG   AAG   TGG   GAA   AGG   GTG        1337
Lys   Leu   Val   Ile   Ile   Leu   Leu   Asn   Lys   Glu   Arg   Lys   Trp   Glu   Arg   Val
                        365                           370                           375

GGG   AAG   TGG   AAA   GAC   AAG   TCC   CTG   CAG   ATG   AAG   TAC   TAT   GTG   TGG   CCC        1385
Gly   Lys   Trp   Lys   Asp   Lys   Ser   Leu   Gln   Met   Lys   Tyr   Tyr   Val   Trp   Pro
                  380                           385                           390

CGA   ATG   TGT   CCA   GAG   ACT   GAA   GAG   CAG   GAG   GAT   GAC   CAT   CTG   AGC   ATT        1433
Arg   Met   Cys   Pro   Glu   Thr   Glu   Glu   Gln   Glu   Asp   Asp   His   Leu   Ser   Ile
            395                           400                           405

GTG   ACC   CTG   GAG   GAG   GCA   CCA   TTT   GTC   ATT   GTG   GAA   AGT   GTG   GAC   CCT        1481
Val   Thr   Leu   Glu   Glu   Ala   Pro   Phe   Val   Ile   Val   Glu   Ser   Val   Asp   Pro
      410                           415                           420

CTG   AGT   GGA   ACC   TGC   ATG   AGG   AAC   ACA   GTC   CCC   TGC   CAA   AAA   CGC   ATA        1529
Leu   Ser   Gly   Thr   Cys   Met   Arg   Asn   Thr   Val   Pro   Cys   Gln   Lys   Arg   Ile
```

```
425                         430                         435                         440
GTC ACT GAG AAT AAA ACA GAC GAG GAG CCG GGT TAC ATC AAA AAA TGC      1577
Val Thr Glu Asn Lys Thr Asp Glu Glu Pro Gly Tyr Ile Lys Lys Cys
                445                         450                         455

TGC AAG GGG TTC TGT ATT GAC ATC CTT AAG AAA ATT TCT AAA TCT GTG      1625
Cys Lys Gly Phe Cys Ile Asp Ile Leu Lys Lys Ile Ser Lys Ser Val
            460                         465                         470

AAG TTC ACC TAT GAC CTT TAC CTG GTT ACC AAT GGC AAG CAT GGG AAG      1673
Lys Phe Thr Tyr Asp Leu Tyr Leu Val Thr Asn Gly Lys His Gly Lys
        475                         480                         485

AAA ATC AAT GGA ACC TGG AAT GGT ATG ATT GGA GAG GTG GTC ATG AAG      1721
Lys Ile Asn Gly Thr Trp Asn Gly Met Ile Gly Glu Val Val Met Lys
        490                         495                         500

AGG GCC TAC ATG GCA GTG GGC TCA CTC ACC ATC AAT GAG GAA CGA TCG      1769
Arg Ala Tyr Met Ala Val Gly Ser Leu Thr Ile Asn Glu Glu Arg Ser
505                         510                         515                         520

GAG GTG GTC GAC TTC TCT GTG CCC TTC ATA GAG ACA GGC ATC AGT GTC      1817
Glu Val Val Asp Phe Ser Val Pro Phe Ile Glu Thr Gly Ile Ser Val
                525                         530                         535

ATG GTG TCA CGC AGC AAT GGG ACT GTC TCA CCT TCT GCC TTC TTA GAG      1865
Met Val Ser Arg Ser Asn Gly Thr Val Ser Pro Ser Ala Phe Leu Glu
            540                         545                         550

CCA TTC AGC GCT GAC GTA TGG GTG ATG ATG TTT GTG ATG CTG CTC ATC      1913
Pro Phe Ser Ala Asp Val Trp Val Met Met Phe Val Met Leu Leu Ile
        555                         560                         565

GTC TCA GCC GTG GCT GTC TTT GTC TTT GAG TAC TTC AGC CCT GTG GGT      1961
Val Ser Ala Val Ala Val Phe Val Phe Glu Tyr Phe Ser Pro Val Gly
        570                         575                         580

TAT AAC AGG TGC CTC GCT GAT GGC AGA GAG CCT GGT GGA CCC TCT TTC      2009
Tyr Asn Arg Cys Leu Ala Asp Gly Arg Glu Pro Gly Gly Pro Ser Phe
585                         590                         595                         600

ACC ATC GGC AAA GCT ATT TGG TTG CTC TGG GGT CTG GTG TTT AAC AAC      2057
Thr Ile Gly Lys Ala Ile Trp Leu Leu Trp Gly Leu Val Phe Asn Asn
                605                         610                         615

TCC GTA CCT GTG CAG AAC CCA AAG GGG ACC ACC TCC AAG ATC ATG GTG      2105
Ser Val Pro Val Gln Asn Pro Lys Gly Thr Thr Ser Lys Ile Met Val
            620                         625                         630

TCA GTG TGG GCC TTC TTT GCT GTC ATC TTC CTG GCC AGC TAC ACT GCC      2153
Ser Val Trp Ala Phe Phe Ala Val Ile Phe Leu Ala Ser Tyr Thr Ala
            635                         640                         645

AAC TTA GCT GCC TTC ATG ATC CAA GAG GAA TAT GTG GAC CAG GTT TCT      2201
Asn Leu Ala Ala Phe Met Ile Gln Glu Glu Tyr Val Asp Gln Val Ser
        650                         655                         660

GGC CTG AGC GAC AAA AAG TTC CAG AGA CCT AAT GAC TTC TCA CCC CCT      2249
Gly Leu Ser Asp Lys Lys Phe Gln Arg Pro Asn Asp Phe Ser Pro Pro
665                         670                         675                         680

TTC CGC TTT GGG ACC GTG CCC AAC GGC AGC ACA GAG AGA AAT ATT CGC      2297
Phe Arg Phe Gly Thr Val Pro Asn Gly Ser Thr Glu Arg Asn Ile Arg
                685                         690                         695

AAT AAC TAT GCA GAA ATG CAT GCC TAC ATG GGA AAG TTC AAC CAG AGG      2345
Asn Asn Tyr Ala Glu Met His Ala Tyr Met Gly Lys Phe Asn Gln Arg
                700                         705                         710

GGT GTA GAT GAT GCA TTG CTC TCC CTG AAA ACA GGG AAA CTG GAT GCC      2393
Gly Val Asp Asp Ala Leu Leu Ser Leu Lys Thr Gly Lys Leu Asp Ala
            715                         720                         725

TTC ATC TAT GAT GCA GCA GTG CTG AAC TAT ATG GCA GGC AGA GAT GAA      2441
Phe Ile Tyr Asp Ala Ala Val Leu Asn Tyr Met Ala Gly Arg Asp Glu
        730                         735                         740

GGC TGC AAG CTG GTG ACC ATT GGC AGT GGG AAG GTC TTT GCT TCC ACT      2489
Gly Cys Lys Leu Val Thr Ile Gly Ser Gly Lys Val Phe Ala Ser Thr
```

```
745                        750                        755                        760
GGC TAT GGC ATT GCC ATC CAA AAA GAT TCT GGG TGG AAG CGC CAG GTG      2537
Gly Tyr Gly Ile Ala Ile Gln Lys Asp Ser Gly Trp Lys Arg Gln Val
                765                     770                     775

GAC CTT GCT ATC CTG CAG CTC TTT GGA GAT GGG GAG ATG GAA GAA CTG      2585
Asp Leu Ala Ile Leu Gln Leu Phe Gly Asp Gly Glu Met Glu Glu Leu
                780                     785                     790

GAA GCT CTC TGG CTC ACT GGC ATT TGT CAC AAT GAG AAG AAT GAG GTC      2633
Glu Ala Leu Trp Leu Thr Gly Ile Cys His Asn Glu Lys Asn Glu Val
            795                     800                     805

ATG AGC AGC CAG CTG GAC ATT GAC AAC ATG GCA GGG GTC TTC TAC ATG      2681
Met Ser Ser Gln Leu Asp Ile Asp Asn Met Ala Gly Val Phe Tyr Met
        810                     815                     820

TTG GGG GCG GCC ATG GCT CTC AGC CTC ATC ACC TTC ATC TGC GAA CAC      2729
Leu Gly Ala Ala Met Ala Leu Ser Leu Ile Thr Phe Ile Cys Glu His
825                     830                     835                     840

CTT TTC TAT TGG CAG TTC CGA CAT TGC TTT ATG GGT GTC TGT TCT GGC      2777
Leu Phe Tyr Trp Gln Phe Arg His Cys Phe Met Gly Val Cys Ser Gly
                845                     850                     855

AAG CCT GGC ATG GTC TTC TCC ATC AGC AGA GGT ATC TAC AGC TGC ATC      2825
Lys Pro Gly Met Val Phe Ser Ile Ser Arg Gly Ile Tyr Ser Cys Ile
                860                     865                     870

CAT GGG GTG GCG ATC GAG GAG CGC CAG TCT GTA ATG AAC TCC CCC ACC      2873
His Gly Val Ala Ile Glu Glu Arg Gln Ser Val Met Asn Ser Pro Thr
            875                     880                     885

GCA ACC ATG AAC AAC ACA CAC TCC AAC ATC CTG CGC CTG CTG CGC ACG      2921
Ala Thr Met Asn Asn Thr His Ser Asn Ile Leu Arg Leu Leu Arg Thr
        890                     895                     900

GCC AAG AAC ATG GCT AAC CTG TCT GGT GTG AAT GGC TCA CCG CAG AGC      2969
Ala Lys Asn Met Ala Asn Leu Ser Gly Val Asn Gly Ser Pro Gln Ser
905                     910                     915                     920

GCC CTG GAC TTC ATC CGA CGG GAG TCA TCC GTC TAT GAC ATC TCA GAG      3017
Ala Leu Asp Phe Ile Arg Arg Glu Ser Ser Val Tyr Asp Ile Ser Glu
                925                     930                     935

CAC CGC CGC AGC TTC ACG CAT TCT GAC TGC AAA TCC TAC AAC AAC CCG      3065
His Arg Arg Ser Phe Thr His Ser Asp Cys Lys Ser Tyr Asn Asn Pro
                940                     945                     950

CCC TGT GAG GAG AAC CTC TTC AGT GAC TAC ATC AGT GAG GTA GAG AGA      3113
Pro Cys Glu Glu Asn Leu Phe Ser Asp Tyr Ile Ser Glu Val Glu Arg
            955                     960                     965

ACG TTC GGG AAC CTG CAG CTG AAG GAC AGC AAC GTG TAC CAA GAT CAC      3161
Thr Phe Gly Asn Leu Gln Leu Lys Asp Ser Asn Val Tyr Gln Asp His
        970                     975                     980

TAC CAC CAT CAC CAC CGG CCC CAT AGT ATT GGC AGT GCC AGC TCC ATC      3209
Tyr His His His His Arg Pro His Ser Ile Gly Ser Ala Ser Ser Ile
985                     990                     995                     1000

GAT GGG CTC TAC GAC TGT GAC AAC CCA CCC TTC ACC ACC AGT CC AGG      3257
Asp Gly Leu Tyr Asp Cys Asp Asn Pro Pro Phe Thr Thr Gln Ser Arg
                1005                    1010                    1015

TCC ATC AGC AAG AAG CCC CTG GAC ATC GGC CTC CCC TCC TCC AAG CAC      3305
Ser Ile Ser Lys Lys Pro Leu Asp Ile Gly Leu Pro Ser Ser Lys His
                1020                    1025                    1030

AGC CAG CTC AGT GAC CTG TAC GGC AAA TTC TCC TTC AAG AGC GAC CGC      3353
Ser Gln Leu Ser Asp Leu Tyr Gly Lys Phe Ser Phe Lys Ser Asp Arg
            1035                    1040                    1045

TAC AGT GGC CAC GAC GAC TTG ATC CGC TCC GAT GTC TCT GAC ATC TCA      3401
Tyr Ser Gly His Asp Asp Leu Ile Arg Ser Asp Val Ser Asp Ile Ser
        1050                    1055                    1060

ACC CAC ACC GTC ACC TAT GGG AAC ATC GAG GGC AAT GCC GCC AAG AGG      3449
Thr His Thr Val Thr Tyr Gly Asn Ile Glu Gly Asn Ala Ala Lys Arg
```

```
1065                    1070                     1075                      1080

CGT  AAG  CAG  CAA  TAT  AAG  GAC  AGC  CTG  AAG  AAG  CGG  CCT  GCC  TCG  GCC       3497
Arg  Lys  Gln  Gln  Tyr  Lys  Asp  Ser  Leu  Lys  Lys  Arg  Pro  Ala  Ser  Ala
                    1085                     1090                      1095

AAG  TCC  CGC  AGG  GAG  TTT  GAC  GAG  ATC  GAG  CTG  GCC  TAC  CGT  CGC  CGA       3545
Lys  Ser  Arg  Arg  Glu  Phe  Asp  Glu  Ile  Glu  Leu  Ala  Tyr  Arg  Arg  Arg
          1100                     1105                      1110

CCG  CCC  CGC  TCC  CCT  GAC  CAC  AAG  CGC  TAC  TTC  AGG  GAC  AAG  GAA  GGG       3593
Pro  Pro  Arg  Ser  Pro  Asp  His  Lys  Arg  Tyr  Phe  Arg  Asp  Lys  Glu  Gly
               1115                     1120                      1125

CTA  CGG  GAC  TTC  TAC  CTG  GAC  CAG  TTC  CGA  ACA  AAG  GAG  AAC  TCA  CCC       3641
Leu  Arg  Asp  Phe  Tyr  Leu  Asp  Gln  Phe  Arg  Thr  Lys  Glu  Asn  Ser  Pro
     1130                     1135                      1140

CAC  TGG  GAG  CAC  GTA  GAC  CTG  ACC  GAC  ATC  TAC  AAG  GAG  CGG  AGT  GAT       3689
His  Trp  Glu  His  Val  Asp  Leu  Thr  Asp  Ile  Tyr  Lys  Glu  Arg  Ser  Asp
1145                     1150                     1155                      1160

GAC  TTT  AAG  CGC  GAC  TCC  ATC  AGC  GGA  GGA  GGG  CCC  TGT  ACC  AAC  AGG       3737
Asp  Phe  Lys  Arg  Asp  Ser  Ile  Ser  Gly  Gly  Gly  Pro  Cys  Thr  Asn  Arg
                              1165                     1170                      1175

TCT  CAC  ATC  AAG  CAC  GGG  ACG  GGC  GAC  AAA  CAC  GGC  GTG  GTC  AGC  GGG       3785
Ser  His  Ile  Lys  His  Gly  Thr  Gly  Asp  Lys  His  Gly  Val  Val  Ser  Gly
               1180                     1185                      1190

GTA  CCT  GCA  CCT  TGG  GAG  AAG  AAC  CTG  ACC  AAC  GTG  GAG  TGG  GAG  GAC       3833
Val  Pro  Ala  Pro  Trp  Glu  Lys  Asn  Leu  Thr  Asn  Val  Glu  Trp  Glu  Asp
                         1195                     1200                      1205

CGG  TCC  GGG  GGC  AAC  TTC  TGC  CGC  AGC  TGT  CCC  TCC  AAG  CTG  CAC  AAC       3881
Arg  Ser  Gly  Gly  Asn  Phe  Cys  Arg  Ser  Cys  Pro  Ser  Lys  Leu  His  Asn
          1210                     1215                      1220

TAC  TCC  ACG  ACG  GTG  ACG  GGT  CAG  AAC  TCG  GGC  AGG  CAG  GCG  TGC  ATC       3929
Tyr  Ser  Thr  Thr  Val  Thr  Gly  Gln  Asn  Ser  Gly  Arg  Gln  Ala  Cys  Ile
1225                     1230                     1235                      1240

CGG  TGT  GAG  GCT  TGC  AAG  AAA  GCA  GGC  AAC  CTG  TAT  GAC  ATC  AGT  GAG       3977
Arg  Cys  Glu  Ala  Cys  Lys  Lys  Ala  Gly  Asn  Leu  Tyr  Asp  Ile  Ser  Glu
                    1245                     1250                      1255

GAC  AAC  TCC  CTG  CAG  GAA  CTG  GAC  CAG  CCG  GCT  GCC  CCA  GTG  GCG  GTG       4025
Asp  Asn  Ser  Leu  Gln  Glu  Leu  Asp  Gln  Pro  Ala  Ala  Pro  Val  Ala  Val
               1260                     1265                      1270

ACG  TCA  AAC  GCC  TCC  ACC  ACT  AAG  TAC  CCT  CAG  AGC  CCG  ACT  AAT  TCC       4073
Thr  Ser  Asn  Ala  Ser  Thr  Thr  Lys  Tyr  Pro  Gln  Ser  Pro  Thr  Asn  Ser
          1275                     1280                      1285

AAG  GCC  CAG  AAG  AAG  AAC  CGG  AAC  AAA  CTG  CGC  CGG  CAG  CAC  TCC  TAC       4121
Lys  Ala  Gln  Lys  Lys  Asn  Arg  Asn  Lys  Leu  Arg  Arg  Gln  His  Ser  Tyr
     1290                     1295                      1300

GAC  ACC  TTC  GTG  GAC  CTG  CAG  AAG  GAA  GAA  GCC  GCC  CTG  GCC  CCG  CGC       4169
Asp  Thr  Phe  Val  Asp  Leu  Gln  Lys  Glu  Glu  Ala  Ala  Leu  Ala  Pro  Arg
1305                     1310                     1315                      1320

AGC  GTA  AGC  CTG  AAA  GAC  AAG  GGC  CGA  TTC  ATG  GAT  GGG  AGC  CCC  TAC       4217
Ser  Val  Ser  Leu  Lys  Asp  Lys  Gly  Arg  Phe  Met  Asp  Gly  Ser  Pro  Tyr
                    1325                     1330                      1335

GCC  CAC  ATG  TTT  GAG  ATG  TCA  GCT  GGC  GAG  AGC  ACC  TTT  GCC  AAC  AAC       4265
Ala  His  Met  Phe  Glu  Met  Ser  Ala  Gly  Glu  Ser  Thr  Phe  Ala  Asn  Asn
               1340                     1345                      1350

AAG  TCC  TCA  GTG  CCC  ACT  GCC  GGA  CAT  CAC  CAC  CAC  AAC  AAC  CCC  GGC       4313
Lys  Ser  Ser  Val  Pro  Thr  Ala  Gly  His  His  His  His  Asn  Asn  Pro  Gly
          1355                     1360                      1365

GGC  GGG  TAC  ATG  CTC  AGC  AAG  TCG  CTC  TAC  CCT  GAC  CGG  GTC  ACG  CAA       4361
Gly  Gly  Tyr  Met  Leu  Ser  Lys  Ser  Leu  Tyr  Pro  Asp  Arg  Val  Thr  Gln
     1370                     1375                      1380

AAC  CCT  TTC  ATC  CCC  ACT  TTT  GGG  GAC  GAC  CAG  TGC  TTG  CTC  CAT  GGC       4409
Asn  Pro  Phe  Ile  Pro  Thr  Phe  Gly  Asp  Asp  Gln  Cys  Leu  Leu  His  Gly
```

-continued

```
1385                    1390                    1395                    1400
AGC  AAA  TCC  TAC  TTC  TTC  AGG  CAG  CCC  ACG  GTG  GCG  GGG  GCG  TCG  AAA     4457
Ser  Lys  Ser  Tyr  Phe  Phe  Arg  Gln  Pro  Thr  Val  Ala  Gly  Ala  Ser  Lys
                    1405                    1410                         1415

GCC  AGG  CCG  GAC  TTC  CGG  GCC  CTT  GTC  ACC  AAC  AAG  CCG  GTG  GTC  TCG     4505
Ala  Arg  Pro  Asp  Phe  Arg  Ala  Leu  Val  Thr  Asn  Lys  Pro  Val  Val  Ser
               1420                    1425                    1430

GCC  CTT  CAT  GGG  GCC  GTG  CCA  GCC  CGT  TTC  CAG  AAG  GAC  ATC  TGT  ATA     4553
Ala  Leu  His  Gly  Ala  Val  Pro  Ala  Arg  Phe  Gln  Lys  Asp  Ile  Cys  Ile
          1435                    1440                    1445

GGG  AAC  CAG  TCC  AAC  CCC  TGT  GTG  CCT  AAC  AAC  ACA  AAC  CCC  AGG  GCT     4601
Gly  Asn  Gln  Ser  Asn  Pro  Cys  Val  Pro  Asn  Asn  Thr  Asn  Pro  Arg  Ala
     1450                    1455                    1460

TTC  AAT  GGC  TCC  AGC  AAT  GGG  CAT  GTT  TAT  GAG  AAA  CTT  TCT  AGT  ATT     4649
Phe  Asn  Gly  Ser  Ser  Asn  Gly  His  Val  Tyr  Glu  Lys  Leu  Ser  Ser  Ile
1465                    1470                    1475                    1480

GAG  TCT  GAT  GTC  TGAGTGAGGG  AACAGAGAGG  TTAAGGTGGG  TACGGGAGGG                 4701
Glu  Ser  Asp  Val
                    148

TAAGGCTGTG  GGTCGCGTGA  TGCGCATGTC  ACGGAGGGTG  ACGGGGGTGA  ACTTGGTTCC             4761

CATTTGCTCC  TTTCTTGTTT  TAATTTATTT  ATGGGATCCT  GGAGTTCTGG  TTCCTACTGG             4821

GGGCAACCCT  GGTGACCAGC  ACCATCTCTC  CTCCTTTTCA  CAGTTCTCTC  CTTCTTCCCC             4881

CCGCTGTCAG  CCATTCCTGT  TCCCATGAGA  TGATGCCATG  GGCCCTCTCA  GCAGGGGAGG             4941

GTAGAGCGGA  GAAAGGAAGG  GCTGCATGCG  GGCTTCCTCC  TGGTGTGGAA  GAGCTCCTTG             5001

ATATCCTCTT  TGAGTGAAGC  TGGGAGAACC  AAAAAGAGGC  TATGTGAGCA  CAAAGGTAGC             5061

TTTTCCCAAA  CTGATCTTTT  CATTTAGGTG  AGGAAGCAAA  AGCATCTATG  TGAGACCATT             5121

TAGCACACTG  CTTGTGAAAG  GAAAGAGGCT  CTGGCTAAAT  TCATGCTGCT  TAGATGACAT             5181

CTGTCTAGGA  ATCATGTGCC  AAGCAGAGGT  TGGGAGGCCA  TTTGTGTTTA  TATATAAGCC             5241

CAAAAATGCT  TGCTTCAACC  CCATGAGACT  CGATAGTGGT  GGTGAACAGA  ACCCAAGGTC             5301

ATTGGTGGCA  GAGTGGATTC  TTGAACAAAC  TGGAAAGTAC  GTTATGATAG  TGTCCCCCGG             5361

TGCCTTGGGG  ACAAGAGCAG  GTGGATTGTG  CGTGCATGTG  TGTTCATGCA  CACTTGCACC             5421

CATGTGTAGT  CAGGTGCCTC  AAGAGAAGGC  AACCTTGACT  CTTTCGTTGA  ATTTGCATCT             5481

CTTCAAGACA  CAAGATTAAA  ACAAAATTTA  CGCTAAATTG  GATTTTAAAT  TATCTTC                5538
```

( 2 ) INFORMATION FOR SEQ ID NO:56:

( i ) SEQUENCE CHARACTERISTICS:
        ( A ) LENGTH: 1484 amino acids
        ( B ) TYPE: amino acid
        ( D ) TOPOLOGY: linear ( i i ) MOLECULE TYPE: protein ( x i ) SEQUENCE DESCRIPTION: SEQ ID NO:56:

```
Met  Lys  Pro  Arg  Ala  Glu  Cys  Cys  Ser  Pro  Lys  Phe  Trp  Leu  Val  Leu
 1                    5                   10                         15

Ala  Val  Leu  Ala  Val  Ser  Gly  Ser  Arg  Ala  Arg  Ser  Gln  Lys  Ser  Pro
               20                    25                    30

Pro  Ser  Ile  Gly  Ile  Ala  Val  Ile  Leu  Val  Gly  Thr  Ser  Asp  Glu  Val
          35                    40                    45

Ala  Ile  Lys  Asp  Ala  His  Glu  Lys  Asp  Asp  Phe  His  His  Leu  Ser  Val
     50                    55                    60

Val  Pro  Arg  Val  Glu  Leu  Val  Ala  Met  Asn  Glu  Thr  Asp  Pro  Lys  Ser
65                    70                    75                         80
```

| | | | | | | | | | | | | | | |
|---|---|---|---|---|---|---|---|---|---|---|---|---|---|---|
|Ile|Ile|Thr|Arg|Ile 85|Cys|Asp|Leu|Met|Ser 90|Asp|Arg|Lys|Ile|Gln 95|Gly|
|Val|Val|Phe|Ala 100|Asp|Asp|Thr|Asp|Gln 105|Glu|Ala|Ile|Ala|Gln 110|Ile|Leu|
|Asp|Phe|Ile|Ser 115|Ala|Gln|Thr|Leu|Thr 120|Pro|Ile|Leu|Gly 125|Ile|His|Gly|
|Gly|Ser 130|Ser|Met|Ile|Met|Ala 135|Asp|Lys|Asp|Glu|Ser 140|Ser|Met|Phe|Phe|
|Gln 145|Phe|Gly|Pro|Ser|Ile 150|Gln|Gln|Ala|Ser|Val 155|Met|Leu|Asn|Ile 160|
|Met|Glu|Glu|Tyr|Asp 165|Trp|Tyr|Ile|Phe|Ser 170|Ile|Val|Thr|Thr|Tyr 175|Phe|
|Pro|Gly|Tyr|Gln 180|Asp|Phe|Val|Asn|Lys 185|Ile|Arg|Ser|Thr|Ile 190|Glu|Asn|
|Ser|Phe|Val 195|Gly|Trp|Glu|Leu|Glu 200|Glu|Val|Leu|Leu|Leu 205|Asp|Met|Ser|
|Leu|Asp|Asp 210|Gly|Asp|Ser|Lys|Ile 215|Gln|Asn|Gln|Leu|Lys 220|Lys|Leu|Gln|
|Ser 225|Pro|Ile|Ile|Leu|Leu 230|Tyr|Cys|Thr|Lys|Glu 235|Glu|Ala|Thr|Tyr|Ile 240|
|Phe|Glu|Val|Ala|Asn 245|Ser|Val|Gly|Leu|Thr 250|Gly|Tyr|Gly|Tyr|Thr 255|Trp|
|Ile|Val|Pro|Ser 260|Leu|Val|Ala|Gly|Asp 265|Thr|Asp|Thr|Val|Pro 270|Ala|Glu|
|Phe|Pro|Thr 275|Gly|Leu|Ile|Ser|Val 280|Ser|Tyr|Asp|Glu|Trp 285|Asp|Tyr|Gly|
|Leu|Pro 290|Pro|Arg|Val|Arg|Asp 295|Gly|Ile|Ala|Ile|Ile 300|Thr|Thr|Ala|Ala|
|Ser 305|Asp|Met|Leu|Ser|Glu 310|His|Ser|Phe|Ile|Pro 315|Glu|Pro|Lys|Ser|Ser 320|
|Cys|Tyr|Asn|Thr|His 325|Glu|Lys|Arg|Ile|Tyr 330|Gln|Ser|Asn|Met|Leu 335|Asn|
|Arg|Tyr|Leu|Ile 340|Asn|Val|Thr|Phe|Glu 345|Gly|Arg|Asn|Leu|Ser 350|Phe|Ser|
|Glu|Asp|Gly 355|Tyr|Gln|Met|His|Pro 360|Lys|Leu|Val|Ile|Ile 365|Leu|Leu|Asn|
|Lys|Glu 370|Arg|Lys|Trp|Glu|Arg 375|Val|Gly|Lys|Trp|Lys 380|Asp|Lys|Ser|Leu|
|Gln 385|Met|Lys|Tyr|Tyr|Val 390|Trp|Pro|Arg|Met|Cys 395|Pro|Glu|Thr|Glu|Glu 400|
|Gln|Glu|Asp|Asp|His 405|Leu|Ser|Ile|Val|Thr 410|Leu|Glu|Glu|Ala|Pro 415|Phe|
|Val|Ile|Val|Glu 420|Ser|Val|Asp|Pro|Leu 425|Ser|Gly|Thr|Cys|Met 430|Arg|Asn|
|Thr|Val|Pro|Cys 435|Gln|Lys|Arg|Ile|Val 440|Thr|Glu|Asn|Lys|Thr 445|Asp|Glu|
|Glu|Pro|Gly 450|Tyr|Ile|Lys|Lys|Cys 455|Cys|Lys|Gly|Phe|Cys 460|Ile|Asp|Ile|
|Leu|Lys 465|Lys|Ile|Ser|Lys|Ser 470|Val|Lys|Phe|Thr|Tyr 475|Asp|Leu|Tyr|Leu 480|
|Val|Thr|Asn|Gly|Lys 485|His|Gly|Lys|Lys|Ile 490|Asn|Gly|Thr|Trp|Asn 495|Gly|
|Met|Ile|Gly|Glu|Val|Val|Met|Lys|Arg|Ala|Tyr|Met|Ala|Val|Gly|Ser|

-continued

|     |     |     | 500 |     |     |     | 505 |     |     |     | 510 |     |     |     |
|-----|-----|-----|-----|-----|-----|-----|-----|-----|-----|-----|-----|-----|-----|-----|
| Leu | Thr | Ile | Asn | Glu | Glu | Arg | Ser | Glu | Val | Val | Asp | Phe | Ser | Val | Pro |
|     |     | 515 |     |     |     |     | 520 |     |     |     |     | 525 |     |     |
| Phe | Ile | Glu | Thr | Gly | Ile | Ser | Val | Met | Val | Ser | Arg | Ser | Asn | Gly | Thr |
|     |     | 530 |     |     |     | 535 |     |     |     |     | 540 |     |     |     |
| Val | Ser | Pro | Ser | Ala | Phe | Leu | Glu | Pro | Phe | Ser | Ala | Asp | Val | Trp | Val |
| 545 |     |     |     |     | 550 |     |     |     | 555 |     |     |     |     |     | 560 |
| Met | Met | Phe | Val | Met | Leu | Leu | Ile | Val | Ser | Ala | Val | Ala | Val | Phe | Val |
|     |     |     |     | 565 |     |     |     |     | 570 |     |     |     |     | 575 |     |
| Phe | Glu | Tyr | Phe | Ser | Pro | Val | Gly | Tyr | Asn | Arg | Cys | Leu | Ala | Asp | Gly |
|     |     |     | 580 |     |     |     |     | 585 |     |     |     |     | 590 |     |     |
| Arg | Glu | Pro | Gly | Gly | Pro | Ser | Phe | Thr | Ile | Gly | Lys | Ala | Ile | Trp | Leu |
|     |     | 595 |     |     |     |     | 600 |     |     |     |     | 605 |     |     |     |
| Leu | Trp | Gly | Leu | Val | Phe | Asn | Asn | Ser | Val | Pro | Val | Gln | Asn | Pro | Lys |
|     |     | 610 |     |     |     |     | 615 |     |     |     | 620 |     |     |     |     |
| Gly | Thr | Thr | Ser | Lys | Ile | Met | Val | Ser | Val | Trp | Ala | Phe | Phe | Ala | Val |
| 625 |     |     |     |     |     | 630 |     |     |     |     | 635 |     |     |     | 640 |
| Ile | Phe | Leu | Ala | Ser | Tyr | Thr | Ala | Asn | Leu | Ala | Ala | Phe | Met | Ile | Gln |
|     |     |     |     | 645 |     |     |     |     | 650 |     |     |     |     | 655 |     |
| Glu | Glu | Tyr | Val | Asp | Gln | Val | Ser | Gly | Leu | Ser | Asp | Lys | Lys | Phe | Gln |
|     |     |     | 660 |     |     |     |     | 665 |     |     |     |     | 670 |     |     |
| Arg | Pro | Asn | Asp | Phe | Ser | Pro | Pro | Phe | Arg | Phe | Gly | Thr | Val | Pro | Asn |
|     |     | 675 |     |     |     |     | 680 |     |     |     |     | 685 |     |     |     |
| Gly | Ser | Thr | Glu | Arg | Asn | Ile | Arg | Asn | Asn | Tyr | Ala | Glu | Met | His | Ala |
|     |     | 690 |     |     |     |     | 695 |     |     |     |     | 700 |     |     |     |
| Tyr | Met | Gly | Lys | Phe | Asn | Gln | Arg | Gly | Val | Asp | Asp | Ala | Leu | Leu | Ser |
| 705 |     |     |     |     | 710 |     |     |     |     | 715 |     |     |     |     | 720 |
| Leu | Lys | Thr | Gly | Lys | Leu | Asp | Ala | Phe | Ile | Tyr | Asp | Ala | Ala | Val | Leu |
|     |     |     |     | 725 |     |     |     |     | 730 |     |     |     |     | 735 |     |
| Asn | Tyr | Met | Ala | Gly | Arg | Asp | Glu | Gly | Cys | Lys | Leu | Val | Thr | Ile | Gly |
|     |     |     | 740 |     |     |     |     | 745 |     |     |     |     | 750 |     |     |
| Ser | Gly | Lys | Val | Phe | Ala | Ser | Thr | Gly | Tyr | Gly | Ile | Ala | Ile | Gln | Lys |
|     |     | 755 |     |     |     |     | 760 |     |     |     |     | 765 |     |     |     |
| Asp | Ser | Gly | Trp | Lys | Arg | Gln | Val | Asp | Leu | Ala | Ile | Leu | Gln | Leu | Phe |
|     |     | 770 |     |     |     |     | 775 |     |     |     | 780 |     |     |     |     |
| Gly | Asp | Gly | Glu | Met | Glu | Glu | Leu | Glu | Ala | Leu | Trp | Leu | Thr | Gly | Ile |
| 785 |     |     |     |     | 790 |     |     |     |     | 795 |     |     |     |     | 800 |
| Cys | His | Asn | Glu | Lys | Asn | Glu | Val | Met | Ser | Ser | Gln | Leu | Asp | Ile | Asp |
|     |     |     |     | 805 |     |     |     |     | 810 |     |     |     |     | 815 |     |
| Asn | Met | Ala | Gly | Val | Phe | Tyr | Met | Leu | Gly | Ala | Ala | Met | Ala | Leu | Ser |
|     |     |     | 820 |     |     |     |     | 825 |     |     |     |     | 830 |     |     |
| Leu | Ile | Thr | Phe | Ile | Cys | Glu | His | Leu | Phe | Tyr | Trp | Gln | Phe | Arg | His |
|     |     | 835 |     |     |     |     | 840 |     |     |     |     | 845 |     |     |     |
| Cys | Phe | Met | Gly | Val | Cys | Ser | Gly | Lys | Pro | Gly | Met | Val | Phe | Ser | Ile |
|     | 850 |     |     |     |     | 855 |     |     |     |     | 860 |     |     |     |     |
| Ser | Arg | Gly | Ile | Tyr | Ser | Cys | Ile | His | Gly | Val | Ala | Ile | Glu | Glu | Arg |
| 865 |     |     |     |     | 870 |     |     |     |     | 875 |     |     |     |     | 880 |
| Gln | Ser | Val | Met | Asn | Ser | Pro | Thr | Ala | Thr | Met | Asn | Asn | Thr | His | Ser |
|     |     |     |     | 885 |     |     |     |     | 890 |     |     |     |     | 895 |     |
| Asn | Ile | Leu | Arg | Leu | Leu | Arg | Thr | Ala | Lys | Asn | Met | Ala | Asn | Leu | Ser |
|     |     |     | 900 |     |     |     |     | 905 |     |     |     |     | 910 |     |     |
| Gly | Val | Asn | Gly | Ser | Pro | Gln | Ser | Ala | Leu | Asp | Phe | Ile | Arg | Arg | Glu |
|     |     | 915 |     |     |     |     | 920 |     |     |     |     | 925 |     |     |     |

```
Ser  Ser  Val  Tyr  Asp  Ile  Ser  Glu  His  Arg  Arg  Ser  Phe  Thr  His  Ser
     930                 935                 940
Asp  Cys  Lys  Ser  Tyr  Asn  Asn  Pro  Pro  Cys  Glu  Glu  Asn  Leu  Phe  Ser
945                      950                 955                           960
Asp  Tyr  Ile  Ser  Glu  Val  Glu  Arg  Thr  Phe  Gly  Asn  Leu  Gln  Leu  Lys
                    965                      970                      975
Asp  Ser  Asn  Val  Tyr  Gln  Asp  His  Tyr  His  His  His  Arg  Pro  His
               980                 985                           990
Ser  Ile  Gly  Ser  Ala  Ser  Ser  Ile  Asp  Gly  Leu  Tyr  Asp  Cys  Asp  Asn
          995                      1000                      1005
Pro  Pro  Phe  Thr  Thr  Gln  Ser  Arg  Ser  Ile  Ser  Lys  Lys  Pro  Leu  Asp
     1010                 1015                      1020
Ile  Gly  Leu  Pro  Ser  Ser  Lys  His  Ser  Gln  Leu  Ser  Asp  Leu  Tyr  Gly
1025                 1030                      1035                           1040
Lys  Phe  Ser  Phe  Lys  Ser  Asp  Arg  Tyr  Ser  Gly  His  Asp  Asp  Leu  Ile
               1045                      1050                      1055
Arg  Ser  Asp  Val  Ser  Asp  Ile  Ser  Thr  His  Thr  Val  Thr  Tyr  Gly  Asn
          1060                      1065                      1070
Ile  Glu  Gly  Asn  Ala  Ala  Lys  Arg  Arg  Lys  Gln  Gln  Tyr  Lys  Asp  Ser
     1075                      1080                      1085
Leu  Lys  Lys  Arg  Pro  Ala  Ser  Ala  Lys  Ser  Arg  Arg  Glu  Phe  Asp  Glu
     1090                      1095                      1100
Ile  Glu  Leu  Ala  Tyr  Arg  Arg  Arg  Pro  Pro  Arg  Ser  Pro  Asp  His  Lys
1105                      1110                      1115                      1120
Arg  Tyr  Phe  Arg  Asp  Lys  Glu  Gly  Leu  Arg  Asp  Phe  Tyr  Leu  Asp  Gln
                    1125                      1130                      1135
Phe  Arg  Thr  Lys  Glu  Asn  Ser  Pro  His  Trp  Glu  His  Val  Asp  Leu  Thr
               1140                      1145                      1150
Asp  Ile  Tyr  Lys  Glu  Arg  Ser  Asp  Asp  Phe  Lys  Arg  Asp  Ser  Ile  Ser
               1155                      1160                      1165
Gly  Gly  Gly  Pro  Cys  Thr  Asn  Arg  Ser  His  Ile  Lys  His  Gly  Thr  Gly
          1170                      1175                      1180
Asp  Lys  His  Gly  Val  Val  Ser  Gly  Val  Pro  Ala  Pro  Trp  Glu  Lys  Asn
1185                      1190                      1195                      1200
Leu  Thr  Asn  Val  Glu  Trp  Glu  Asp  Arg  Ser  Gly  Gly  Asn  Phe  Cys  Arg
                    1205                      1210                      1215
Ser  Cys  Pro  Ser  Lys  Leu  His  Asn  Tyr  Ser  Thr  Thr  Val  Thr  Gly  Gln
                    1220                      1225                      1230
Asn  Ser  Gly  Arg  Gln  Ala  Cys  Ile  Arg  Cys  Glu  Ala  Cys  Lys  Lys  Ala
          1235                      1240                      1245
Gly  Asn  Leu  Tyr  Asp  Ile  Ser  Glu  Asp  Asn  Ser  Leu  Gln  Glu  Leu  Asp
     1250                      1255                      1260
Gln  Pro  Ala  Ala  Pro  Val  Ala  Val  Thr  Ser  Asn  Ala  Ser  Thr  Thr  Lys
1265                      1270                      1275                      1280
Tyr  Pro  Gln  Ser  Pro  Thr  Asn  Ser  Lys  Ala  Gln  Lys  Lys  Asn  Arg  Asn
                    1285                      1290                      1295
Lys  Leu  Arg  Arg  Gln  His  Ser  Tyr  Asp  Thr  Phe  Val  Asp  Leu  Gln  Lys
               1300                      1305                      1310
Glu  Glu  Ala  Ala  Leu  Ala  Pro  Arg  Ser  Val  Ser  Leu  Lys  Asp  Lys  Gly
               1315                      1320                      1325
Arg  Phe  Met  Asp  Gly  Ser  Pro  Tyr  Ala  His  Met  Phe  Glu  Met  Ser  Ala
               1330                      1335                      1340
Gly  Glu  Ser  Thr  Phe  Ala  Asn  Asn  Lys  Ser  Ser  Val  Pro  Thr  Ala  Gly
1345                      1350                      1355                      1360
```

| | | | | | | | | | | | | | | |
|---|---|---|---|---|---|---|---|---|---|---|---|---|---|---|
| His | His | His | His | Asn | Asn | Pro | Gly | Gly | Gly | Tyr | Met | Leu | Ser | Lys | Ser |
| | | | | 1365 | | | | 1370 | | | | | | 1375 | |
| Leu | Tyr | Pro | Asp | Arg | Val | Thr | Gln | Asn | Pro | Phe | Ile | Pro | Thr | Phe | Gly |
| | | | 1380 | | | | | 1385 | | | | | 1390 | | |
| Asp | Asp | Gln | Cys | Leu | Leu | His | Gly | Ser | Lys | Ser | Tyr | Phe | Phe | Arg | Gln |
| | | | 1395 | | | | 1400 | | | | | 1405 | | | |
| Pro | Thr | Val | Ala | Gly | Ala | Ser | Lys | Ala | Arg | Pro | Asp | Phe | Arg | Ala | Leu |
| | | | 1410 | | | 1415 | | | | | 1420 | | | | |
| Val | Thr | Asn | Lys | Pro | Val | Val | Ser | Ala | Leu | His | Gly | Ala | Val | Pro | Ala |
| 1425 | | | | | 1430 | | | | | 1435 | | | | | 1440 |
| Arg | Phe | Gln | Lys | Asp | Ile | Cys | Ile | Gly | Asn | Gln | Ser | Asn | Pro | Cys | Val |
| | | | | 1445 | | | | 1450 | | | | | 1455 | | |
| Pro | Asn | Asn | Thr | Asn | Pro | Arg | Ala | Phe | Asn | Gly | Ser | Ser | Asn | Gly | His |
| | | | | 1460 | | | | 1465 | | | | | 1470 | | |
| Val | Tyr | Glu | Lys | Leu | Ser | Ser | Ile | Glu | Ser | Asp | Val | | | | |
| | | | 1475 | | | | | 1480 | | | | | | | |

( 2 ) INFORMATION FOR SEQ ID NO:57:

( i ) SEQUENCE CHARACTERISTICS:
        ( A ) LENGTH: 4695 base pairs
        ( B ) TYPE: nucleic acid
        ( C ) STRANDEDNESS: both
        ( D ) TOPOLOGY: both ( i i ) MOLECULE TYPE: cDNA ( i x ) FEATURE:
        ( A ) NAME/KEY: CDS
        ( B ) LOCATION: 485..4495

( x i ) SEQUENCE DESCRIPTION: SEQ ID NO:57:

```
CGAGAACACA  GCGAGTGTGT  GAGTCCCTCC  CGCTCCAGCT  CCTCCAAGCC  GCGGCCGCCG      60

CCGCCACCCT  CGCCCGCAGC  CTCCCGCAGC  CTCCCTCGGC  CACCGGTGTC  TGGTGGGGGT     120

GTTGCCTGGG  TAGGTCGGCC  CGGCCCCCAG  GGGTCTCTCG  AGCGTCTGCC  ATCTGCCCGA     180

GAAACATGTG  TGGCCACGTC  CTCGCCTAGT  CCAGGTGGCC  GCAACCTTGG  GGGAGAGACA     240

GGGCAGGACA  GGACCAAGGT  AAGAGGTAAG  GAGGAGACGG  CGCCAGGGAC  AGACAGGAGG     300

TCCCGGCTTG  CCGTTGTGCG  CACCACCACT  GCCGCCGCCC  CGGGGCCTGC  CCCCGACATC     360

GGCTCTCTGA  GCCCTCCTCG  GAATCTTGGG  GTCGCTGGAC  GCCGGGTTCC  GGTCCTGGCC     420

CCCCCGCCAT  CCCCCCAACA  GAACAGGGTC  ATGAAAAGAG  GCCGCCCGGC  GGGGCCCGCA     480
```

| | | | | | | | | | | | | | | | | |
|---|---|---|---|---|---|---|---|---|---|---|---|---|---|---|---|---|
| GGCG | ATG | CGC | GGC | GCC | GGT | GGC | CCC | CGC | GGC | CCT | CGG | GGC | CCC | GCT | AAG | 529 |
| | Met | Arg | Gly | Ala | Gly | Gly | Pro | Arg | Gly | Pro | Arg | Gly | Pro | Ala | Lys | |
| | 1 | | | | 5 | | | | | 10 | | | | | 15 | |
| ATG | CTG | CTG | CTG | CTG | GCG | CTG | GCC | TGC | GCC | AGC | CCG | TTC | CCG | GAG | GAG | 577 |
| Met | Leu | Leu | Leu | Leu | Ala | Leu | Ala | Cys | Ala | Ser | Pro | Phe | Pro | Glu | Glu | |
| | | | | 20 | | | | | 25 | | | | | 30 | | |
| GCG | CCG | GGG | CCG | GGC | GGG | GCC | GGT | GGG | CCC | GGC | GGC | GGC | CTC | GGC | GGG | 625 |
| Ala | Pro | Gly | Pro | Gly | Gly | Ala | Gly | Gly | Pro | Gly | Gly | Gly | Leu | Gly | Gly | |
| | | | 35 | | | | | 40 | | | | | 45 | | | |
| GCG | CGG | CCG | CTC | AAC | GTG | GCG | CTC | GTG | TTC | TCG | GGG | CCC | GCG | TAC | GCG | 673 |
| Ala | Arg | Pro | Leu | Asn | Val | Ala | Leu | Val | Phe | Ser | Gly | Pro | Ala | Tyr | Ala | |
| | | 50 | | | | | 55 | | | | | 60 | | | | |
| GCC | GAG | GCG | GCA | CGC | CTG | GGC | CCG | GCC | GTG | GCG | GCG | GCG | GTG | CGC | AGC | 721 |
| Ala | Glu | Ala | Ala | Arg | Leu | Gly | Pro | Ala | Val | Ala | Ala | Ala | Val | Arg | Ser | |
| | 65 | | | | | 70 | | | | | 75 | | | | | |
| CCG | GGC | CTA | GAC | GTG | CGG | CCC | GTG | GCG | CTG | GTG | CTC | AAC | GGC | TCG | GAC | 769 |
| Pro | Gly | Leu | Asp | Val | Arg | Pro | Val | Ala | Leu | Val | Leu | Asn | Gly | Ser | Asp | |

|     |     |     |     |     |     |     |     |     |     |     |     |     |     |     |     |
|-----|-----|-----|-----|-----|-----|-----|-----|-----|-----|-----|-----|-----|-----|-----|-----|
| 80  |     |     |     |     | 85  |     |     |     |     | 90  |     |     |     |     | 95  |

| CCG | CGC | AGC | CTC | GTG | CTG | CAG | CTC | TGC | GAC | CTG | CTG | TCG | GGG | TTG | CGC | 817 |
| Pro | Arg | Ser | Leu | Val | Leu | Gln | Leu | Cys | Asp | Leu | Leu | Ser | Gly | Leu | Arg | |
|     |     |     |     | 100 |     |     |     | 105 |     |     |     |     |     | 110 |     |     |

| GTG | CAC | GGC | GTG | GTC | TTC | GAA | GAC | GAC | TCG | CGC | GCG | CCC | GCC | GTC | GCG | 865 |
| Val | His | Gly | Val | Val | Phe | Glu | Asp | Asp | Ser | Arg | Ala | Pro | Ala | Val | Ala | |
|     |     |     |     | 115 |     |     |     | 120 |     |     |     |     |     | 125 |     |     |

| CCC | ATC | CTC | GAC | TTC | CTG | TCG | GCG | CAG | ACC | TCG | CTC | CCC | ATC | GTG | TCC | 913 |
| Pro | Ile | Leu | Asp | Phe | Leu | Ser | Ala | Gln | Thr | Ser | Leu | Pro | Ile | Val | Ser | |
|     |     |     | 130 |     |     |     | 135 |     |     |     |     | 140 |     |     |     |     |

| GAG | CAC | GGC | GGC | GCC | GCG | CTC | GTG | CTC | ACG | CCC | AAG | GAG | AAG | GGC | TCC | 961 |
| Glu | His | Gly | Gly | Ala | Ala | Leu | Val | Leu | Thr | Pro | Lys | Glu | Lys | Gly | Ser | |
|     |     | 145 |     |     |     | 150 |     |     |     |     | 155 |     |     |     |     |     |

| ACC | TTC | CTC | CAC | CTG | GGC | TCT | TCC | CCC | GAG | CAA | CAG | CTT | CAG | GTC | ATC | 1009 |
| Thr | Phe | Leu | His | Leu | Gly | Ser | Ser | Pro | Glu | Gln | Gln | Leu | Gln | Val | Ile | |
| 160 |     |     |     |     | 165 |     |     |     |     | 170 |     |     |     |     | 175 |     |

| TTT | GAG | GTG | CTG | GAG | GAG | TAT | GAC | TGG | ACG | TCC | TTT | GTA | GCC | GTG | ACC | 1057 |
| Phe | Glu | Val | Leu | Glu | Glu | Tyr | Asp | Trp | Thr | Ser | Phe | Val | Ala | Val | Thr | |
|     |     |     |     | 180 |     |     |     |     | 185 |     |     |     |     | 190 |     |     |

| ACT | CGT | GCC | CCT | GGC | CAC | CGG | GCC | TTC | CTG | TCC | TAC | ATT | GAG | GTG | CTG | 1105 |
| Thr | Arg | Ala | Pro | Gly | His | Arg | Ala | Phe | Leu | Ser | Tyr | Ile | Glu | Val | Leu | |
|     |     |     | 195 |     |     |     | 200 |     |     |     |     | 205 |     |     |     |     |

| ACT | GAC | GGC | AGT | CTG | GTG | GGC | TGG | GAG | CAC | CGC | GGA | GCG | CTG | ACG | CTG | 1153 |
| Thr | Asp | Gly | Ser | Leu | Val | Gly | Trp | Glu | His | Arg | Gly | Ala | Leu | Thr | Leu | |
|     |     | 210 |     |     |     | 215 |     |     |     |     | 220 |     |     |     |     |     |

| GAC | CCT | GGG | GCG | GGC | GAG | GCC | GTG | CTC | AGT | GCC | CAG | CTC | CGC | AGT | GTC | 1201 |
| Asp | Pro | Gly | Ala | Gly | Glu | Ala | Val | Leu | Ser | Ala | Gln | Leu | Arg | Ser | Val | |
|     | 225 |     |     |     |     | 230 |     |     |     |     | 235 |     |     |     |     |     |

| AGC | GCG | CAG | ATC | CGC | CTG | CTC | TTC | TGC | GCC | CGA | GAG | GAG | GCC | GAG | CCC | 1249 |
| Ser | Ala | Gln | Ile | Arg | Leu | Leu | Phe | Cys | Ala | Arg | Glu | Glu | Ala | Glu | Pro | |
| 240 |     |     |     |     | 245 |     |     |     |     | 250 |     |     |     |     | 255 |     |

| GTG | TTC | CGC | GCA | GCT | GAG | GAG | GCT | GGC | CTC | ACT | GGA | TCT | GGC | TAC | GTC | 1297 |
| Val | Phe | Arg | Ala | Ala | Glu | Glu | Ala | Gly | Leu | Thr | Gly | Ser | Gly | Tyr | Val | |
|     |     |     |     | 260 |     |     |     |     | 265 |     |     |     |     | 270 |     |     |

| TGG | TTC | ATG | GTG | GGG | CCC | CAG | CTG | GCT | GGA | GGC | GGG | GGC | TCT | GGG | GCC | 1345 |
| Trp | Phe | Met | Val | Gly | Pro | Gln | Leu | Ala | Gly | Gly | Gly | Gly | Ser | Gly | Ala | |
|     |     |     | 275 |     |     |     |     | 280 |     |     |     |     | 285 |     |     |     |

| CCT | GGT | GAG | CCC | CCT | CTT | CTG | CCA | GGA | GGC | GCC | CCC | CTG | CCT | GCC | GGG | 1393 |
| Pro | Gly | Glu | Pro | Pro | Leu | Leu | Pro | Gly | Gly | Ala | Pro | Leu | Pro | Ala | Gly | |
|     |     | 290 |     |     |     |     | 295 |     |     |     |     | 300 |     |     |     |     |

| CTG | TTT | GCA | GTG | CGC | TCG | GCT | GGC | TGG | CGG | GAT | GAC | CTG | GCT | CGG | CGA | 1441 |
| Leu | Phe | Ala | Val | Arg | Ser | Ala | Gly | Trp | Arg | Asp | Asp | Leu | Ala | Arg | Arg | |
|     |     | 305 |     |     |     |     | 310 |     |     |     |     | 315 |     |     |     |     |

| GTG | GCA | GCT | GGC | GTG | GCC | GTA | GTG | GCC | AGA | GGT | GCC | CAG | GCC | CTG | CTG | 1489 |
| Val | Ala | Ala | Gly | Val | Ala | Val | Val | Ala | Arg | Gly | Ala | Gln | Ala | Leu | Leu | |
| 320 |     |     |     |     | 325 |     |     |     |     | 330 |     |     |     |     | 335 |     |

| CGT | GAT | TAT | GGT | TTC | CTT | CCT | GAG | CTC | GGC | CAC | GAC | TGT | CGC | GCC | CAG | 1537 |
| Arg | Asp | Tyr | Gly | Phe | Leu | Pro | Glu | Leu | Gly | His | Asp | Cys | Arg | Ala | Gln | |
|     |     |     |     | 340 |     |     |     |     | 345 |     |     |     |     | 350 |     |     |

| AAC | CGC | ACC | CAC | CGC | GGG | GAG | AGT | CTG | CAT | AGG | TAC | TTC | ATG | AAC | ATC | 1585 |
| Asn | Arg | Thr | His | Arg | Gly | Glu | Ser | Leu | His | Arg | Tyr | Phe | Met | Asn | Ile | |
|     |     |     | 355 |     |     |     |     | 360 |     |     |     |     | 365 |     |     |     |

| ACG | TGG | GAT | AAC | CGG | GAT | TAC | TCC | TTC | AAT | GAG | GAC | GGC | TTC | CTA | GTG | 1633 |
| Thr | Trp | Asp | Asn | Arg | Asp | Tyr | Ser | Phe | Asn | Glu | Asp | Gly | Phe | Leu | Val | |
|     |     | 370 |     |     |     |     | 375 |     |     |     |     | 380 |     |     |     |     |

| AAC | CCC | TCC | CTG | GTG | GTC | ATC | TCC | CTC | ACC | AGA | GAC | AGG | ACG | TGG | GAG | 1681 |
| Asn | Pro | Ser | Leu | Val | Val | Ile | Ser | Leu | Thr | Arg | Asp | Arg | Thr | Trp | Glu | |
|     | 385 |     |     |     |     | 390 |     |     |     |     | 395 |     |     |     |     |     |

| GTG | GTG | GGC | AGC | TGG | GAG | CAG | CAG | ACG | CTC | CGC | CTC | AAG | TAC | CCG | CTG | 1729 |
| Val | Val | Gly | Ser | Trp | Glu | Gln | Gln | Thr | Leu | Arg | Leu | Lys | Tyr | Pro | Leu | |

-continued

| 400 | | | | | 405 | | | | | 410 | | | | | 415 | | | |
|---|---|---|---|---|---|---|---|---|---|---|---|---|---|---|---|---|---|---|

```
TGG  TCC  CGC  TAT  GGT  CGC  TTC  CTG  CAG  CCA  GTG  GAC  GAC  ACG  CAG  CAC       1777
Trp  Ser  Arg  Tyr  Gly  Arg  Phe  Leu  Gln  Pro  Val  Asp  Asp  Thr  Gln  His
               420                    425                         430

CTC  GCG  GTG  GCC  ACG  CTG  GAG  GAA  AGG  CCG  TTT  GTC  ATC  GTG  GAG  CCT       1825
Leu  Ala  Val  Ala  Thr  Leu  Glu  Glu  Arg  Pro  Phe  Val  Ile  Val  Glu  Pro
               435                    440                         445

GCA  GAC  CCT  ATC  AGC  GGC  ACC  TGC  ATC  CGA  GAC  TCC  GTC  CCC  TGC  CGG       1873
Ala  Asp  Pro  Ile  Ser  Gly  Thr  Cys  Ile  Arg  Asp  Ser  Val  Pro  Cys  Arg
               450                    455                         460

AGC  CAG  CTC  AAC  CGA  ACC  CAC  AGC  CCT  CCA  CCG  GAT  GCC  CCC  CGC  CCG       1921
Ser  Gln  Leu  Asn  Arg  Thr  His  Ser  Pro  Pro  Pro  Asp  Ala  Pro  Arg  Pro
          465                    470                         475

GAA  AAG  CGC  TGC  TGC  AAG  GGT  TTC  TGC  ATC  GAC  ATT  CTG  AAG  CGG  CTG       1969
Glu  Lys  Arg  Cys  Cys  Lys  Gly  Phe  Cys  Ile  Asp  Ile  Leu  Lys  Arg  Leu
480                         485                    490                         495

GCG  CAT  ACC  ATC  GGC  TTC  AGC  TAC  GAC  CTC  TAC  CTG  GTC  ACC  AAT  GGC       2017
Ala  His  Thr  Ile  Gly  Phe  Ser  Tyr  Asp  Leu  Tyr  Leu  Val  Thr  Asn  Gly
                         500                    505                         510

AAG  CAC  GGA  AAG  AAG  ATC  GAT  GGC  GTC  TGG  AAC  GGC  ATG  ATC  GGG  GAG       2065
Lys  His  Gly  Lys  Lys  Ile  Asp  Gly  Val  Trp  Asn  Gly  Met  Ile  Gly  Glu
               515                    520                         525

GTG  TTC  TAC  CAG  CGC  GCA  GAC  ATG  GCC  ATC  GGC  TCC  CTC  ACC  ATC  AAC       2113
Val  Phe  Tyr  Gln  Arg  Ala  Asp  Met  Ala  Ile  Gly  Ser  Leu  Thr  Ile  Asn
               530                    535                         540

GAG  GAG  CGC  TCC  GAG  ATC  GTG  GAC  TTC  TCC  GTC  CCC  TTC  GTG  GAG  ACC       2161
Glu  Glu  Arg  Ser  Glu  Ile  Val  Asp  Phe  Ser  Val  Pro  Phe  Val  Glu  Thr
545                         550                    555

GGC  ATC  AGC  GTC  ATG  GTG  GCG  CGC  AGC  AAT  GGC  ACG  GTG  TCC  CCC  TCG       2209
Gly  Ile  Ser  Val  Met  Val  Ala  Arg  Ser  Asn  Gly  Thr  Val  Ser  Pro  Ser
560                         565                    570                         575

GCC  TTC  CTC  GAG  CCC  TAC  AGC  CCC  GCC  GTG  TGG  GTG  ATG  ATG  TTC  GTC       2257
Ala  Phe  Leu  Glu  Pro  Tyr  Ser  Pro  Ala  Val  Trp  Val  Met  Met  Phe  Val
                         580                    585                         590

ATG  TGC  CTC  ACT  GTG  GTC  GCC  GTC  ACT  GTT  TTC  ATC  TTC  GAG  TAC  CTC       2305
Met  Cys  Leu  Thr  Val  Val  Ala  Val  Thr  Val  Phe  Ile  Phe  Glu  Tyr  Leu
               595                    600                         605

AGT  CCT  GTT  GGT  TAC  AAC  CGC  AGC  CTG  GCC  ACG  GGC  AAG  CGC  CCT  GGC       2353
Ser  Pro  Val  Gly  Tyr  Asn  Arg  Ser  Leu  Ala  Thr  Gly  Lys  Arg  Pro  Gly
               610                    615                         620

GGT  TCA  ACC  TTC  ACC  ATT  GGG  AAA  TCC  ATC  TGG  CTG  CTC  TGG  GCC  CTG       2401
Gly  Ser  Thr  Phe  Thr  Ile  Gly  Lys  Ser  Ile  Trp  Leu  Leu  Trp  Ala  Leu
          625                    630                         635

GTG  TTC  AAT  AAT  TCG  GTG  CCC  GTG  GAG  AAC  CCC  CGG  GGA  ACC  ACC  AGC       2449
Val  Phe  Asn  Asn  Ser  Val  Pro  Val  Glu  Asn  Pro  Arg  Gly  Thr  Thr  Ser
640                         645                    650                         655

AAA  ATC  ATG  GTG  CTG  GTG  TGG  GCC  TTC  TTC  GCC  GTC  ATC  TTC  CTC  GCC       2497
Lys  Ile  Met  Val  Leu  Val  Trp  Ala  Phe  Phe  Ala  Val  Ile  Phe  Leu  Ala
               660                    665                         670

AGC  TAC  ACA  GCC  AAC  CTG  GCC  GCC  TTC  ATG  ATC  CAG  GAG  GAG  TAC  GTG       2545
Ser  Tyr  Thr  Ala  Asn  Leu  Ala  Ala  Phe  Met  Ile  Gln  Glu  Glu  Tyr  Val
               675                    680                         685

GAT  ACT  GTG  TCT  GGG  CTC  AGT  GAC  CGC  AAG  TTC  CAG  AGG  CCC  CAG  GAG       2593
Asp  Thr  Val  Ser  Gly  Leu  Ser  Asp  Arg  Lys  Phe  Gln  Arg  Pro  Gln  Glu
               690                    695                         700

CAG  TAC  CCG  CCC  CTG  AAG  TTT  GGG  ACC  GTG  CCC  AAC  GGC  TCC  ACG  GAG       2641
Gln  Tyr  Pro  Pro  Leu  Lys  Phe  Gly  Thr  Val  Pro  Asn  Gly  Ser  Thr  Glu
          705                    710                         715

AAG  AAC  ATC  CGC  AGC  AAC  TAT  CCC  GAC  ATG  CAC  AGC  TAC  ATG  GTG  CGC       2689
Lys  Asn  Ile  Arg  Ser  Asn  Tyr  Pro  Asp  Met  His  Ser  Tyr  Met  Val  Arg
```

```
   720                        725                        730                        735

TAC  AAC  CAG  CCC  CGC  GTA  GAG  GAA  GCG  CTC  ACT  CAG  CTC  AAG  GCA  GGG     2737
Tyr  Asn  Gln  Pro  Arg  Val  Glu  Glu  Ala  Leu  Thr  Gln  Leu  Lys  Ala  Gly
               740                        745                        750

AAG  CTG  GAC  GCC  TTC  ATC  TAC  GAT  GCT  GCA  GTG  CTC  AAT  TAC  ATG  GCC     2785
Lys  Leu  Asp  Ala  Phe  Ile  Tyr  Asp  Ala  Ala  Val  Leu  Asn  Tyr  Met  Ala
               755                        760                        765

CGC  AAG  GAC  GAG  GGC  TGC  AAG  CTT  GTC  ACC  ATC  GGC  TCC  GGC  AAG  GTC     2833
Arg  Lys  Asp  Glu  Gly  Cys  Lys  Leu  Val  Thr  Ile  Gly  Ser  Gly  Lys  Val
               770                        775                        780

TTC  GCC  ACG  ACA  GGC  TAT  GGC  ATC  GCC  CTG  CAC  AAG  GGC  TCC  CGC  TGG     2881
Phe  Ala  Thr  Thr  Gly  Tyr  Gly  Ile  Ala  Leu  His  Lys  Gly  Ser  Arg  Trp
          785                        790                        795

AAG  CGG  CCC  ATC  GAC  CTG  GCG  TTG  CTG  CAG  TTC  CTG  GGG  GAT  GAT  GAG     2929
Lys  Arg  Pro  Ile  Asp  Leu  Ala  Leu  Leu  Gln  Phe  Leu  Gly  Asp  Asp  Glu
800                        805                        810                        815

ATC  GAG  ATG  CTG  GAG  CGG  CTG  TGG  CTC  TCT  GGG  ATC  TGC  CAC  AAT  GAC     2977
Ile  Glu  Met  Leu  Glu  Arg  Leu  Trp  Leu  Ser  Gly  Ile  Cys  His  Asn  Asp
                    820                        825                        830

AAA  ATC  GAG  GTG  ATG  AGC  AGC  AAG  CTG  GAC  ATC  GAC  AAC  ATG  GCG  GGC     3025
Lys  Ile  Glu  Val  Met  Ser  Ser  Lys  Leu  Asp  Ile  Asp  Asn  Met  Ala  Gly
                    835                        840                        845

GTC  TTC  TAC  ATG  CTC  CTG  GTG  GCC  ATG  GGC  CTG  TCC  CTG  CTG  GTC  TTC     3073
Val  Phe  Tyr  Met  Leu  Leu  Val  Ala  Met  Gly  Leu  Ser  Leu  Leu  Val  Phe
               850                        855                        860

GCC  TGG  GAG  CAC  CTG  GTG  TAC  TGG  CGC  CTG  CGG  CAC  TGC  CTG  GGG  CCC     3121
Ala  Trp  Glu  His  Leu  Val  Tyr  Trp  Arg  Leu  Arg  His  Cys  Leu  Gly  Pro
          865                        870                        875

ACC  CAC  CGC  ATG  GAC  TTC  CTG  CTG  GCC  TTC  TCC  AGG  GGC  ATG  TAC  AGC     3169
Thr  His  Arg  Met  Asp  Phe  Leu  Leu  Ala  Phe  Ser  Arg  Gly  Met  Tyr  Ser
880                        885                        890                        895

TGC  TGC  AGC  GCT  GAG  GCC  GCC  CCA  CCG  CCC  GCC  AAG  CCC  CCG  CCG  CCG     3217
Cys  Cys  Ser  Ala  Glu  Ala  Ala  Pro  Pro  Pro  Ala  Lys  Pro  Pro  Pro  Pro
                    900                        905                        910

CCA  CAG  CCC  CTG  CCC  AGC  CCC  GCG  TAC  CCC  GCG  CCG  GGG  CCG  GCT  CCC     3265
Pro  Gln  Pro  Leu  Pro  Ser  Pro  Ala  Tyr  Pro  Ala  Pro  Gly  Pro  Ala  Pro
               915                        920                        925

GGG  CCC  GCA  CCT  TTC  GTC  CCC  CGC  GAG  CGC  GCC  TCA  GTG  GCC  CGC  TGG     3313
Gly  Pro  Ala  Pro  Phe  Val  Pro  Arg  Glu  Arg  Ala  Ser  Val  Ala  Arg  Trp
          930                        935                        940

CGC  CGG  CCC  AAG  GGC  GCG  GGG  CCG  CCG  GGG  GCG  GGC  CTG  GCC  GAC           3361
Arg  Arg  Pro  Lys  Gly  Ala  Gly  Pro  Pro  Gly  Gly  Ala  Gly  Leu  Ala  Asp
     945                        950                        955

GGC  TTC  CAC  CGC  TAC  TAC  GGC  CCC  ATC  GAG  CCG  CAG  GGC  CTA  GGC  CTC     3409
Gly  Phe  His  Arg  Tyr  Tyr  Gly  Pro  Ile  Glu  Pro  Gln  Gly  Leu  Gly  Leu
960                        965                        970                        975

GGC  CTG  GGC  GAA  GCG  CGC  GCG  GCA  CCG  CGG  GGC  GCA  GCC  GGG  CGC  CCG     3457
Gly  Leu  Gly  Glu  Ala  Arg  Ala  Ala  Pro  Arg  Gly  Ala  Ala  Gly  Arg  Pro
               980                        985                        990

CTG  TCC  CCG  CCG  GCC  GCT  CAG  CCC  CCG  CAG  AAG  CCG  CCG  GCC  TCC  TAT     3505
Leu  Ser  Pro  Pro  Ala  Ala  Gln  Pro  Pro  Gln  Lys  Pro  Pro  Ala  Ser  Tyr
          995                        1000                       1005

TTC  GCC  ATC  GTA  CGC  GAC  AAG  GAG  CCA  GCC  GAG  CCC  CCC  GCC  GGC  GCC     3553
Phe  Ala  Ile  Val  Arg  Asp  Lys  Glu  Pro  Ala  Glu  Pro  Pro  Ala  Gly  Ala
               1010                       1015                      1020

TTC  CCC  GGC  TTC  CCG  TCC  CCG  CCC  GCG  CCC  CCC  GCC  GCG  GCC  GCC  ACC     3601
Phe  Pro  Gly  Phe  Pro  Ser  Pro  Pro  Ala  Pro  Pro  Ala  Ala  Ala  Ala  Thr
          1025                       1030                       1035

GCC  GTC  GGG  CCG  CCA  CTC  TGC  CGC  TTG  GCC  TTC  GAG  GAC  GAG  AGC  CCG     3649
Ala  Val  Gly  Pro  Pro  Leu  Cys  Arg  Leu  Ala  Phe  Glu  Asp  Glu  Ser  Pro
```

-continued

```
        1040                    1045                    1050                    1055

CCG GCG CCC GCG CGG TGG CCG CGC TCG GAC CCC GAG AGC CAA CCC CTG      3697
Pro Ala Pro Ala Arg Trp Pro Arg Ser Asp Pro Glu Ser Gln Pro Leu
            1060                    1065                    1070

CTG GGG CCA GGC GCG GGC GGC GCG GGG GGC ACG GGG GGC GCA GGC GGA      3745
Leu Gly Pro Gly Ala Gly Gly Ala Gly Gly Thr Gly Gly Ala Gly Gly
            1075                    1080                    1085

GGA GCC CCG GCC GCT CCG CCC CCG TGC TTC GCC GCG CCG CCC CCG TGC      3793
Gly Ala Pro Ala Ala Pro Pro Pro Cys Phe Ala Ala Pro Pro Pro Cys
            1090                    1095                    1100

TTT TAC CTC GAT GTC GAC CAG TCG CCG TCG GAC TCG GAG GAC TCG GAG      3841
Phe Tyr Leu Asp Val Asp Gln Ser Pro Ser Asp Ser Glu Asp Ser Glu
            1105                    1110                    1115

AGC CTG GCC GGC GCG TCC CTG GCC GGC CTG GAT CCC TGG TGG TTC GCC      3889
Ser Leu Ala Gly Ala Ser Leu Ala Gly Leu Asp Pro Trp Trp Phe Ala
1120                    1125                    1130                    1135

GAC TTC CCT TAC CCG TAT GCC GAT CGC CTC GGG CSG CCC GCG GCA CGC      3937
Asp Phe Pro Tyr Pro Tyr Ala Asp Arg Leu Gly Xaa Pro Ala Ala Arg
                    1140                    1145                    1150

TAC GGA TTG GTC GAC AAA CTA GGG GGC TGG CTC GCC GGG AGC TGG GAC      3985
Tyr Gly Leu Val Asp Lys Leu Gly Gly Trp Leu Ala Gly Ser Trp Asp
            1155                    1160                    1165

TAC CTG CCT CCS CGC AGC GGT CGG GCC GCC TGG CAC TGT CGG CAC TGC      4033
Tyr Leu Pro Xaa Arg Ser Gly Arg Ala Ala Trp His Cys Arg His Cys
1170                    1175                    1180

GCC AGC CTG GAG CTG CTT CCG CCG CCG CGC CAT CTC AGC TGC TCG CAC      4081
Ala Ser Leu Glu Leu Leu Pro Pro Pro Arg His Leu Ser Cys Ser His
            1185                    1190                    1195

GAT GGC CTG GAC GGC GGC TGG TGG GCG CCA CCG CCT CCA CCC TGG GCC      4129
Asp Gly Leu Asp Gly Gly Trp Trp Ala Pro Pro Pro Pro Trp Ala
1200                    1205                    1210                    1215

GCC GGG CCC CTG CCC CGA CGC CGG GCC CGC TGC GGG TGC CCG CGG TCG      4177
Ala Gly Pro Leu Pro Arg Arg Arg Ala Arg Cys Gly Cys Pro Arg Ser
            1220                    1225                    1230

CAC CCG CAC CGC CCG CGG GCC TCG CAC CGC ACG CCC GCC GCT GCC GCG      4225
His Pro His Arg Pro Arg Ala Ser His Arg Thr Pro Ala Ala Ala Ala
            1235                    1240                    1245

CCC CAC CAC CAC AGG CAC CGG CGC GCC GCT GGG GGC TGG GAC CTC CCG      4273
Pro His His His Arg His Arg Arg Ala Ala Gly Gly Trp Asp Leu Pro
            1250                    1255                    1260

CCG CCC GCG CCC ACC TCG CGC TCG CTC GAG GAC CTC AGC TCG TGC CCT      4321
Pro Pro Ala Pro Thr Ser Arg Ser Leu Glu Asp Leu Ser Ser Cys Pro
            1265                    1270                    1275

CGC GCC GCC CCT GCG CGC AGG CTT ACC GGG CCC TCC CGC CAC GCT CGC      4369
Arg Ala Ala Pro Ala Arg Arg Leu Thr Gly Pro Ser Arg His Ala Arg
1280                    1285                    1290                    1295

AGG TGT CCG CAC GCC GCG CAC TGG GGG CCG CCG CTG CCT ACA GCT TCC      4417
Arg Cys Pro His Ala Ala His Trp Gly Pro Pro Leu Pro Thr Ala Ser
            1300                    1305                    1310

CAC CGG AGA CAC CGG GGC GGG GAC CTG GGC ACC GCC AGG GGC TCG GCG      4465
His Arg Arg His Arg Gly Gly Asp Leu Gly Thr Arg Arg Gly Ser Ala
            1315                    1320                    1325

CAC TTC TCT AGC CTC GAG TCC GAG GTA TGACGCGGCC CCGGGGGCCC           4512
His Phe Ser Ser Leu Glu Ser Glu Val
            1330                    1335

CACCGCCCCC TTGGTCAGCG CAGGCCACGG CCCGAGGGGG CGCCCGCAGT GGACAGGACC   4572

CGCGTGGGTT GGGAAGGAAA GCAGTGGAAC TGGCCGGACC CCGCCTGGAG CAGCGTCCTG   4632

CGCCCCCTGG TTCTGGAGGA ACCGCAAGCC GGAGAGGATT TGGTCCCTCA ACTATCACCC   4692
```

AGG 4695

( 2 ) INFORMATION FOR SEQ ID NO:58:

( i ) SEQUENCE CHARACTERISTICS:
        ( A ) LENGTH: 1336 amino acids
        ( B ) TYPE: amino acid
        ( D ) TOPOLOGY: linear ( i i ) MOLECULE TYPE: protein ( x i ) SEQUENCE DESCRIPTION: SEQ ID NO:58:

```
Met Arg Gly Ala Gly Gly Pro Arg Gly Pro Arg Gly Pro Ala Lys Met
 1               5                  10                  15

Leu Leu Leu Leu Ala Leu Ala Cys Ala Ser Pro Phe Pro Glu Glu Ala
             20                  25                  30

Pro Gly Pro Gly Gly Ala Gly Gly Pro Gly Gly Gly Leu Gly Gly Ala
             35                  40                  45

Arg Pro Leu Asn Val Ala Leu Val Phe Ser Gly Pro Ala Tyr Ala Ala
         50                  55                  60

Glu Ala Ala Arg Leu Gly Pro Ala Val Ala Ala Val Arg Ser Pro
 65                  70                  75                  80

Gly Leu Asp Val Arg Pro Val Ala Leu Val Leu Asn Gly Ser Asp Pro
                     85                  90                  95

Arg Ser Leu Val Leu Gln Leu Cys Asp Leu Leu Ser Gly Leu Arg Val
                 100                 105                 110

His Gly Val Val Phe Glu Asp Ser Arg Ala Pro Ala Val Ala Pro
                 115                 120                 125

Ile Leu Asp Phe Leu Ser Ala Gln Thr Ser Leu Pro Ile Val Ser Glu
         130                 135                 140

His Gly Gly Ala Ala Leu Val Leu Thr Pro Lys Glu Lys Gly Ser Thr
145                 150                 155                 160

Phe Leu His Leu Gly Ser Ser Pro Glu Gln Gln Leu Gln Val Ile Phe
                 165                 170                 175

Glu Val Leu Glu Glu Tyr Asp Trp Thr Ser Phe Val Ala Val Thr Thr
                 180                 185                 190

Arg Ala Pro Gly His Arg Ala Phe Leu Ser Tyr Ile Glu Val Leu Thr
             195                 200                 205

Asp Gly Ser Leu Val Gly Trp Glu His Arg Gly Ala Leu Thr Leu Asp
         210                 215                 220

Pro Gly Ala Gly Glu Ala Val Leu Ser Ala Gln Leu Arg Ser Val Ser
225                 230                 235                 240

Ala Gln Ile Arg Leu Leu Phe Cys Ala Arg Glu Glu Ala Glu Pro Val
                     245                 250                 255

Phe Arg Ala Ala Glu Glu Ala Gly Leu Thr Gly Ser Gly Tyr Val Trp
                 260                 265                 270

Phe Met Val Gly Pro Gln Leu Ala Gly Gly Gly Gly Ser Gly Ala Pro
             275                 280                 285

Gly Glu Pro Pro Leu Leu Pro Gly Gly Ala Pro Leu Pro Ala Gly Leu
         290                 295                 300

Phe Ala Val Arg Ser Ala Gly Trp Arg Asp Asp Leu Ala Arg Arg Val
305                 310                 315                 320

Ala Ala Gly Val Ala Val Val Ala Arg Gly Ala Gln Ala Leu Leu Arg
                     325                 330                 335

Asp Tyr Gly Phe Leu Pro Glu Leu Gly His Asp Cys Arg Ala Gln Asn
                 340                 345                 350
```

```
Arg  Thr  His  Arg  Gly  Glu  Ser  Leu  His  Arg  Tyr  Phe  Met  Asn  Ile  Thr
          355                      360                      365

Trp  Asp  Asn  Arg  Asp  Tyr  Ser  Phe  Asn  Glu  Asp  Gly  Phe  Leu  Val  Asn
     370                      375                      380

Pro  Ser  Leu  Val  Val  Ile  Ser  Leu  Thr  Arg  Asp  Arg  Thr  Trp  Glu  Val
385                           390                      395                      400

Val  Gly  Ser  Trp  Glu  Gln  Gln  Thr  Leu  Arg  Leu  Lys  Tyr  Pro  Leu  Trp
                    405                      410                      415

Ser  Arg  Tyr  Gly  Arg  Phe  Leu  Gln  Pro  Val  Asp  Asp  Thr  Gln  His  Leu
               420                      425                      430

Ala  Val  Ala  Thr  Leu  Glu  Glu  Arg  Pro  Phe  Val  Ile  Val  Glu  Pro  Ala
          435                      440                      445

Asp  Pro  Ile  Ser  Gly  Thr  Cys  Ile  Arg  Asp  Ser  Val  Pro  Cys  Arg  Ser
     450                      455                      460

Gln  Leu  Asn  Arg  Thr  His  Ser  Pro  Pro  Pro  Asp  Ala  Pro  Arg  Pro  Glu
465                      470                      475                      480

Lys  Arg  Cys  Cys  Lys  Gly  Phe  Cys  Ile  Asp  Ile  Leu  Lys  Arg  Leu  Ala
               485                      490                      495

His  Thr  Ile  Gly  Phe  Ser  Tyr  Asp  Leu  Tyr  Leu  Val  Thr  Asn  Gly  Lys
               500                      505                      510

His  Gly  Lys  Lys  Ile  Asp  Gly  Val  Trp  Asn  Gly  Met  Ile  Gly  Glu  Val
          515                      520                      525

Phe  Tyr  Gln  Arg  Ala  Asp  Met  Ala  Ile  Gly  Ser  Leu  Thr  Ile  Asn  Glu
     530                      535                      540

Glu  Arg  Ser  Glu  Ile  Val  Asp  Phe  Ser  Val  Pro  Phe  Val  Glu  Thr  Gly
545                      550                      555                      560

Ile  Ser  Val  Met  Val  Ala  Arg  Ser  Asn  Gly  Thr  Val  Ser  Pro  Ser  Ala
               565                      570                      575

Phe  Leu  Glu  Pro  Tyr  Ser  Pro  Ala  Val  Trp  Val  Met  Met  Phe  Val  Met
               580                      585                      590

Cys  Leu  Thr  Val  Val  Ala  Val  Thr  Val  Phe  Ile  Phe  Glu  Tyr  Leu  Ser
          595                      600                      605

Pro  Val  Gly  Tyr  Asn  Arg  Ser  Leu  Ala  Thr  Gly  Lys  Arg  Pro  Gly  Gly
     610                      615                      620

Ser  Thr  Phe  Thr  Ile  Gly  Lys  Ser  Ile  Trp  Leu  Leu  Trp  Ala  Leu  Val
625                      630                      635                      640

Phe  Asn  Asn  Ser  Val  Pro  Val  Glu  Asn  Pro  Arg  Gly  Thr  Thr  Ser  Lys
               645                      650                      655

Ile  Met  Val  Leu  Val  Trp  Ala  Phe  Phe  Ala  Val  Ile  Phe  Leu  Ala  Ser
               660                      665                      670

Tyr  Thr  Ala  Asn  Leu  Ala  Ala  Phe  Met  Ile  Gln  Glu  Glu  Tyr  Val  Asp
          675                      680                      685

Thr  Val  Ser  Gly  Leu  Ser  Asp  Arg  Lys  Phe  Gln  Arg  Pro  Gln  Glu  Gln
     690                      695                      700

Tyr  Pro  Pro  Leu  Lys  Phe  Gly  Thr  Val  Pro  Asn  Gly  Ser  Thr  Glu  Lys
705                      710                      715                      720

Asn  Ile  Arg  Ser  Asn  Tyr  Pro  Asp  Met  His  Ser  Tyr  Met  Val  Arg  Tyr
               725                      730                      735

Asn  Gln  Pro  Arg  Val  Glu  Glu  Ala  Leu  Thr  Gln  Leu  Lys  Ala  Gly  Lys
               740                      745                      750

Leu  Asp  Ala  Phe  Ile  Tyr  Asp  Ala  Ala  Val  Leu  Asn  Tyr  Met  Ala  Arg
          755                      760                      765

Lys  Asp  Glu  Gly  Cys  Lys  Leu  Val  Thr  Ile  Gly  Ser  Gly  Lys  Val  Phe
     770                      775                      780
```

```
Ala  Thr  Thr  Gly  Tyr  Gly  Ile  Ala  Leu  His  Lys  Gly  Ser  Arg  Trp  Lys
785            790                 795                      800

Arg  Pro  Ile  Asp  Leu  Ala  Leu  Leu  Gln  Phe  Leu  Gly  Asp  Asp  Glu  Ile
                    805                 810                      815

Glu  Met  Leu  Glu  Arg  Leu  Trp  Leu  Ser  Gly  Ile  Cys  His  Asn  Asp  Lys
               820                      825                      830

Ile  Glu  Val  Met  Ser  Ser  Lys  Leu  Asp  Ile  Asp  Asn  Met  Ala  Gly  Val
          835                      840                      845

Phe  Tyr  Met  Leu  Leu  Val  Ala  Met  Gly  Leu  Ser  Leu  Leu  Val  Phe  Ala
850                      855                      860

Trp  Glu  His  Leu  Val  Tyr  Trp  Arg  Leu  Arg  His  Cys  Leu  Gly  Pro  Thr
865                 870                      875                      880

His  Arg  Met  Asp  Phe  Leu  Leu  Ala  Phe  Ser  Arg  Gly  Met  Tyr  Ser  Cys
                    885                      890                      895

Cys  Ser  Ala  Glu  Ala  Ala  Pro  Pro  Ala  Lys  Pro  Pro  Pro  Pro  Pro  Pro
               900                 905                      910

Gln  Pro  Leu  Pro  Ser  Pro  Ala  Tyr  Pro  Ala  Pro  Gly  Pro  Ala  Pro  Gly
               915                 920                      925

Pro  Ala  Pro  Phe  Val  Pro  Arg  Glu  Arg  Ala  Ser  Val  Ala  Arg  Trp  Arg
          930                 935                      940

Arg  Pro  Lys  Gly  Ala  Gly  Pro  Pro  Gly  Gly  Ala  Gly  Leu  Ala  Asp  Gly
945                      950                      955                      960

Phe  His  Arg  Tyr  Tyr  Gly  Pro  Ile  Glu  Pro  Gln  Gly  Leu  Gly  Leu  Gly
                    965                      970                      975

Leu  Gly  Glu  Ala  Arg  Ala  Ala  Pro  Arg  Gly  Ala  Ala  Gly  Arg  Pro  Leu
               980                      985                      990

Ser  Pro  Pro  Ala  Ala  Gln  Pro  Pro  Gln  Lys  Pro  Pro  Ala  Ser  Tyr  Phe
               995                      1000                     1005

Ala  Ile  Val  Arg  Asp  Lys  Glu  Pro  Ala  Glu  Pro  Pro  Ala  Gly  Ala  Phe
          1010                      1015                     1020

Pro  Gly  Phe  Pro  Ser  Pro  Pro  Ala  Pro  Pro  Ala  Ala  Ala  Ala  Thr  Ala
1025                     1030                     1035                     1040

Val  Gly  Pro  Pro  Leu  Cys  Arg  Leu  Ala  Phe  Glu  Asp  Glu  Ser  Pro  Pro
                    1045                     1050                     1055

Ala  Pro  Ala  Arg  Trp  Pro  Arg  Ser  Asp  Pro  Glu  Ser  Gln  Pro  Leu  Leu
               1060                     1065                     1070

Gly  Pro  Gly  Ala  Gly  Gly  Ala  Gly  Gly  Thr  Gly  Gly  Ala  Gly  Gly  Gly
               1075                     1080                     1085

Ala  Pro  Ala  Ala  Pro  Pro  Pro  Cys  Phe  Ala  Ala  Pro  Pro  Pro  Cys  Phe
               1090                     1095                     1100

Tyr  Leu  Asp  Val  Asp  Gln  Ser  Pro  Ser  Asp  Ser  Glu  Asp  Ser  Glu  Ser
1105                     1110                     1115                     1120

Leu  Ala  Gly  Ala  Ser  Leu  Ala  Gly  Leu  Asp  Pro  Trp  Trp  Phe  Ala  Asp
                    1125                     1130                     1135

Phe  Pro  Tyr  Pro  Tyr  Ala  Asp  Arg  Leu  Gly  Xaa  Pro  Ala  Ala  Arg  Tyr
               1140                     1145                     1150

Gly  Leu  Val  Asp  Lys  Leu  Gly  Gly  Trp  Leu  Ala  Gly  Ser  Trp  Asp  Tyr
               1155                     1160                     1165

Leu  Pro  Xaa  Arg  Ser  Gly  Arg  Ala  Ala  Trp  His  Cys  Arg  His  Cys  Ala
               1170                     1175                     1180

Ser  Leu  Glu  Leu  Leu  Pro  Pro  Pro  Arg  His  Leu  Ser  Cys  Ser  His  Asp
1185                     1190                     1195                     1200

Gly  Leu  Asp  Gly  Gly  Trp  Trp  Ala  Pro  Pro  Pro  Pro  Pro  Trp  Ala  Ala
```

|  | 1205 | 1210 | 1215 |
|---|---|---|---|

Gly Pro Leu Pro Arg Arg Arg Ala Arg Cys Gly Cys Pro Arg Ser His
          1220                      1225                    1230

Pro His Arg Pro Arg Ala Ser His Arg Thr Pro Ala Ala Ala Ala Pro
       1235                    1240                    1245

His His His Arg His Arg Arg Ala Ala Gly Gly Trp Asp Leu Pro Pro
1250                  1255                    1260

Pro Ala Pro Thr Ser Arg Ser Leu Glu Asp Leu Ser Ser Cys Pro Arg
1265                 1270                1275                1280

Ala Ala Pro Ala Arg Arg Leu Thr Gly Pro Ser Arg His Ala Arg Arg
              1285                    1290                  1295

Cys Pro His Ala Ala His Trp Gly Pro Pro Leu Pro Thr Ala Ser His
              1300                    1305                  1310

Arg Arg His Arg Gly Gly Asp Leu Gly Thr Arg Arg Gly Ser Ala His
          1315                    1320                  1325

Phe Ser Ser Leu Glu Ser Glu Val
       1330                    1335

( 2 ) INFORMATION FOR SEQ ID NO:59:

( i ) SEQUENCE CHARACTERISTICS:
        ( A ) LENGTH: 71 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:59:

GGGTGGCGGC CGCAGAGCAC CTCCACCATC TCCTTGTCCT ACTCCAAGAT CTGGCCCTAG    60

TCCATGTTTG C    71

( 2 ) INFORMATION FOR SEQ ID NO:60:

( i ) SEQUENCE CHARACTERISTICS:
        ( A ) LENGTH: 71 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:60:

TGGTGGTCCC CAACCTGTAG GACTTGGTTC TGGAGGAGGA TCTGGTGTAG GCAAACATGG    60

ACTAGGGCCA G    71

( 2 ) INFORMATION FOR SEQ ID NO:61:

( i ) SEQUENCE CHARACTERISTICS:
        ( A ) LENGTH: 61 base pairs
        ( B ) TYPE: nucleic acid
        ( C ) STRANDEDNESS: both
        ( D ) TOPOLOGY: both ( i i ) MOLECULE TYPE: cDNA ( x i ) SEQUENCE DESCRIPTION: SEQ ID NO:61:

GTTGGGGACC ACCAGATGGA GGTAGAGCTG CACTTGTACG AAGAGCTCCA CAACCACCTG    60

G    61

( 2 ) INFORMATION FOR SEQ ID NO:62:

```
    ( i ) SEQUENCE CHARACTERISTICS:
            ( A ) LENGTH: 62 base pairs
            ( B ) TYPE: nucleic acid
            ( C ) STRANDEDNESS: both
            ( D ) TOPOLOGY: both ( i i ) MOLECULE TYPE: cDNA ( x i ) SEQUENCE DESCRIPTION: SEQ ID NO:62:

CGTGAGACGT    CAGACAAAGG    AGGCCCAGGT    GTAGGTGGTC    TACCAGGTGG    TTGTGGAGCT            60

CT                                                                                          62

( 2 ) INFORMATION FOR SEQ ID NO:63:

( i ) SEQUENCE CHARACTERISTICS:
            ( A ) LENGTH: 195 base pairs
            ( B ) TYPE: nucleic acid
            ( C ) STRANDEDNESS: both
            ( D ) TOPOLOGY: both ( i i ) MOLECULE TYPE: cDNA ( x i ) SEQUENCE DESCRIPTION: SEQ ID NO:63:

CCGCAGAGCA    CCTCCACCAT    CTCCTTGTCC    TACTCCAAGA    TCTGGCCCTA    GTCCATGTTT            60

GCCTACACCA    GATCCTCCTC    CAGAACCAAG    TCCTACAGGT    TGGGGACCAC    CAGATGGAGG           120

TAGAGCTGCA    CTTGTACGAA    GAGCTCCACA    ACCACCTGGT    AGACCACCTA    CACCTGGGCC           180

TCCTTTGTCT    GACGT                                                                       195
```

HUMAN N-METHYL-D-ASPARTATE RECEPTOR SUBUNITS, NUCLEIC ACIDS ENCODING SAME AND USES THEREFOR

This application is a division of U.S. Ser. No. 08/231,193, filed Apr. 20, 1994, and a continuation-in-part of U.S. Ser. No. 08/052,449, filed Apr. 20, 1993, now abandoned.

The present invention relates to nucleic acids and receptor proteins encoded thereby. Invention nucleic acids encode novel human N-methyl-D-aspartate (NMDA) receptor subunits. The invention also relates to methods for making such receptor subunits and for using the receptor proteins in assays designed to identify and characterize compounds which affect the function of such receptors, e.g., agonists and antagonists of NMDA receptors.

BACKGROUND OF THE INVENTION

The amino acid L-glutamate is a major excitatory neurotransmitter in the mammalian central nervous system. Anatomical, biochemical and electrophysiological analyses suggest that glutamatergic systems are involved in a broad array of neuronal processes, including fast excitatory synaptic transmission, regulation of neurotransmitter releases, long-term potentiation, learning and memory, developmental synaptic plasticity, hypoxic-ischemic damage and neuronal cell death, epileptiform seizures, as well as the pathogenesis of several neurodegenerative disorders. See generally, Monaghan et al., Ann. Rev. Pharmacol. Toxicol. 29:365–402 (1980). This extensive repertoire of functions, especially those related to learning, neurotoxicity and neuropathology, has stimulated recent attempts to describe and define the mechanisms through which glutamate exerts its effects.

Currently, glutamate receptor classification schemes are based on pharmacological criteria. Glutamate has been observed to mediate its effects through receptors that have been categorized into two main groups: ionotropic and metabotropic. Ionotropic glutamate receptors contain integral cation-specific, ligand-gated ion channels, whereas metabotropic glutamate receptors are G-protein-coupled receptors that transduce extracellular signals via activation of intracellular second messenger systems. Ionotropic receptors are further divided into at least two categories based on the pharmacological and functional properties of the receptors. The two main types of ionotropic receptors are N-methyl-D-aspartic acid (NMDA) and kainic acid (KA)/α-amino-3-hydroxy-5-methyl-isoxazole-4-propionic acid (AMPA), formerly called the quisqualic acid, or QUIS, receptor. While the metabotropic receptors bind to some of the same ligands that bind to ionotropic glutamate receptors, the metabotropic receptors alter synaptic physiology via GTP-binding proteins and second messengers such as cyclic AMP, cyclic GMP, diacylglycerol, inositol 1,4,5-triphosphate and calcium [Gundersen et al., Proc. R. Soc. London Ser. 221:127 (1984); Sladeczek et al., Nature 317:717 (1985); Nicoletti et al., J. Neurosci. 6:1905 (1986); Sugiyama et al. , Nature 325:531 (1987)].

The electrophysiological and pharmacological properties of the glutamate receptors have been studied using animal tissues and cell lines, as well as recombinantly produced non-human receptors, as the source of such receptors. The value of such studies for application to the development of human therapeutics has been limited by the availability of only non-human receptor subunits. Moreover, it is only recently that the characteristics and structure of glutamate receptors have been investigated at the molecular level. The majority of such investigation has, however, been carried out in non-human species. Because of the potential physiological and pathological significance of glutamate receptors, it would be desirable (for example, for drug screening assays) to have available human sequences (i.e., DNA, RNA, proteins) which encode representative members of the various glutamate receptor subtypes. The availability of such human sequences will also enable the investigation of receptor distribution in humans, the correlation of specific receptor modification with the occurrence of various disease states, etc.

BRIEF DESCRIPTION OF THE INVENTION

The present invention discloses novel nucleic acids encoding NMDA receptor protein subunits and the proteins encoded thereby. In a particular embodiment the novel nucleic acids encode NMDAR1 and NMDAR2 subunits of human NMDA receptors. More specifically, the invention nucleic acids encode NMDAR1, NMDAR2A, NMDAR2B, NMDAR2C and NMDAR2D subunits that contribute to the formation of NMDA-activated cation-selective ion channels. In addition to being useful for the production of NMDA receptor subunit proteins, these nucleic acids are also useful as probes, thus enabling those skilled in the art, without undue experimentation, to identify and isolate nucleic acids encoding related receptor subunits.

Functional glutamate receptors can be assembled, in accordance with the present invention, from a plurality of NMDA receptor subunit proteins of one type (homomeric) or from combinations of subunit proteins of different types (heteromeric).

In addition to disclosing novel NMDA receptor protein subunits, the present invention also comprises methods for using such receptor subunits to identify and characterize compounds which affect the function of such receptors, e.g., agonists, antagonists, and modulators of glutamate receptor function. The invention also comprises methods for determining whether unknown protein(s) are functional as NMDA receptor subunits.

BRIEF DESCRIPTION OF THE FIGURES

FIG. 1 is a schematic representation of various human NMDAR1 clones of the invention, with partial restriction maps of each clone. The clones are aligned and the differences in the DNAs (i.e., deletions and insertions), relative to clone NMDA10, are indicated. Translation initiation and termination sites are represented by a "V" and a "*", respectively. Insertions are marked as inverted triangles, deletions are indicated by spaces in the boxes. The numbers above the insertions and deletions refer to the number of nucleotides inserted or deleted relative to NMDA10.

FIG. 3 presents the entire nucleotide sequence of construct NMDAR1A (see Sequence ID No. 1) with the following information added for ease of comparison of the splice variations of the NMDAR1 subunit transcript: lowercase letters indicate 5' untranslated sequence and the 3' untranslated sequence of the NMDAR1 splice variant shown in Sequence ID No. 1 (in some of the other splice variants, this 3' untranslated sequence is actually coding sequence) ; uppercase letters indicate coding sequence; the translation initiation codon is identified by the word "START" whereas the three different translation termination codons (TGA) used in the different splice variants are identified by small boxes; significant restriction enzyme sites used in preparing full-length variant constructs are identified by name above the sites; the location of a 63-bp insertion (see Sequence ID No. 3) that exists in some of the variants is marked as "63 bp INSERT"; the nucleotide sequences that are deleted from some of the variants are boxed and labeled as "204 bp DELETION" "363 bp DELETION," and "1087 bp DELETION."

FIG. 4 is a schematic representation of various human NMDAR2C clones of the invention, with partial restriction maps of each clone. The clones are aligned and the differences in the DNAs relative to clone NMDA26 are indicated in the same manner as done in FIG. 1.

DETAILED DESCRIPTION OF THE INVENTION

Figure 2A:
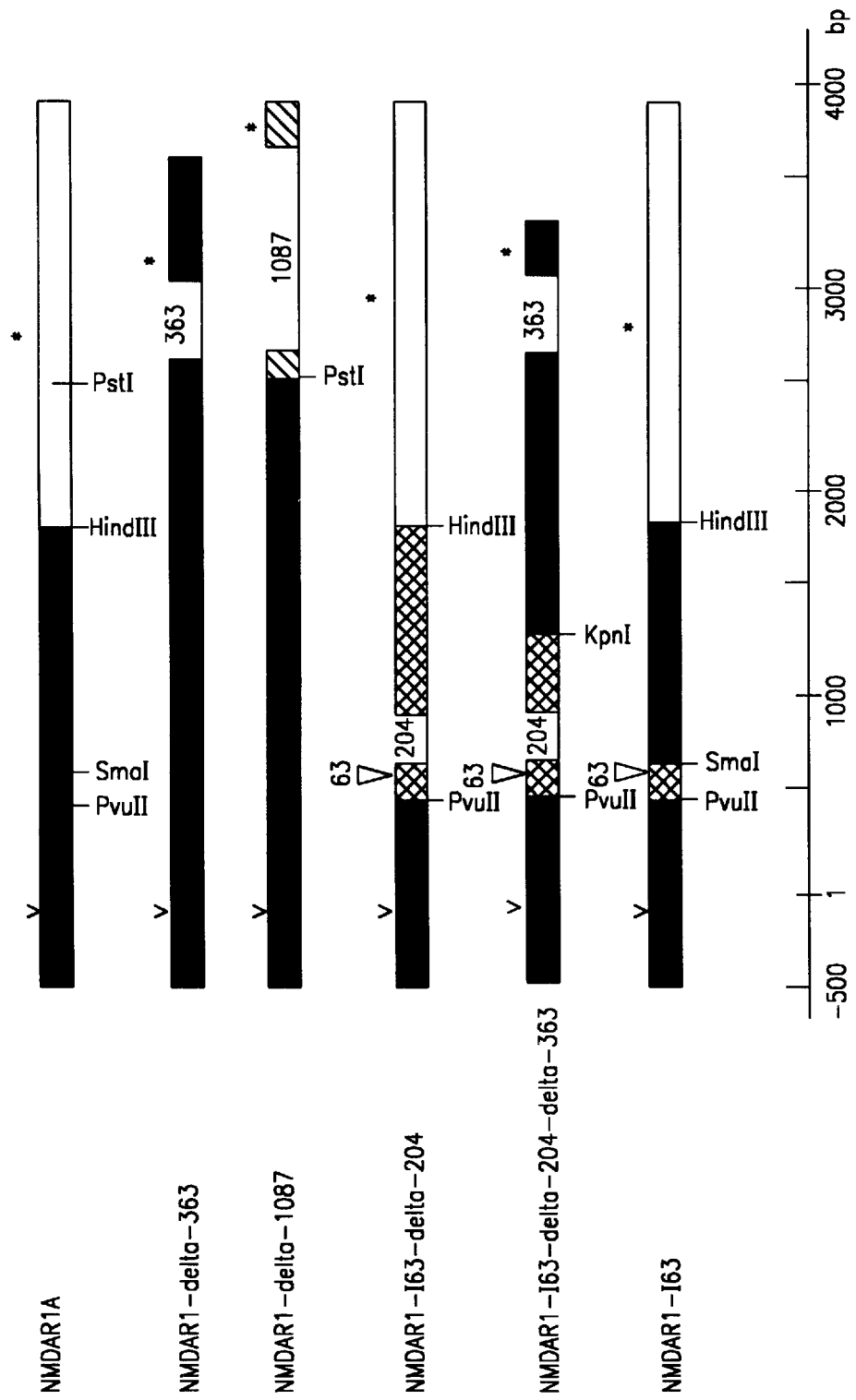
FIG. 2 is a schematic representation of cDNAs encoding full-length human NMDAR1 subunit subtypes of the invention, with partial restriction maps of each DNA. The full-length cDNAs are constructed by ligation of appropriate portions of the clones shown in FIG. 1. Regions of each full-length cDNA composed of nucleotide sequences corresponding to a particular clone are distinguished as solid, striped, cross-hatched or open boxes.

In accordance with the present invention, there are provided isolated nucleic acids encoding human N-methyl-D-aspartate (NMDA) receptor subunit(s). In one aspect of the present invention, nucleic acids encoding NMDA receptor subunit(s) of the NMDAR1 subtype are provided. In another aspect, nucleic acids encoding NMDA receptor subunit(s) of the NMDAR2 subtype are provided. In a further aspect, eukaryotic cells containing such nucleic acids, and eukaryotic cells expressing such nucleic acids are provided.

Also provided are protein(s) encoded by the above-described nucleic acids, as well as antibodies generated against the protein(s). In other aspects of the present invention, there are provided nucleic acid probes comprising at least NMDA receptor subunit-selective portions of the above-described nucleic acids.

As employed herein, the phrase "human N-methyl-D-aspartate (NMDA) receptor subunit(s)" refers to recombinantly produced (i.e., isolated or substantially pure) proteins which participate in the formation of a voltage-sensitive cation-selective selective channel activated by exposure to NMDA, and having at least one transmembrane domain, a large N-terminal extracellular domain, and the like, including variants thereof encoded by mRNA generated by alternative splicing of a primary transcript, and further including fragments thereof which retain one or more of the above properties.

Use of the phrase "recombinantly produced", "isolated" or "substantially pure" in the present specification and claims as a modifier of DNA, RNA, polypeptides or proteins means that the DNA, RNA, polypeptides or proteins so designated have been produced in such form by the hand of man, and thus are separated from their native in vivo cellular environment. As a result of this human intervention, the recombinant DNAs, RNAs, polypeptides and proteins of the invention are useful in ways that the DNAs, RNAs, polypeptides or proteins as they naturally occur are not, such as identification of selective drugs or compounds.

The term "functional", when used herein as a modifier of receptor protein(s) of the present invention, means that binding of NMDA (or NMDA-like) ligand to receptors comprising the protein(s) causes the receptor "ion channels" to open. This allows cations, particularly $Ca^{2+}$, as well as $Na^+$ and $K^+$, to move across the membrane. Stated another way, "functional" means that a signal is generated as a consequence of agonist activation of receptor protein(s).

As used herein, a splice variant refers to variant NMDA receptor subunit-encoding nucleic acid(s) produced by differential processing of primary transcript(s) of genomic DNA, resulting in the production of more than one type of mRNA. cDNA derived from differentially processed primary transcript will encode NMDA receptor subunits that have regions of complete amino acid identity and regions having different amino acid sequences. Thus, the same genomic sequence can lead to the production of multiple, related mRNAs and proteins. Both the resulting mRNAs and proteins are referred to herein as "splice variants".

Accordingly, also contemplated within the scope of the present invention are DNAs that encode NMDA receptor subunits as defined above, but that by virtue of degeneracy of the genetic code do not necessarily hybridize to the disclosed DNA under specified hybridization conditions. Such subunits also contribute to the formation of a functional receptor, as assessed by methods described herein or known to those of skill in the art, with one or more additional NMDA receptor subunits of the same or different type (the presence of additional subunits of a different type is optional when said subunit is an NMDAR1 subunit) . Typically, unless an NMDA receptor subunit is encoded by RNA that arises from alternative splicing (i.e., a splice variant), NMDA receptor subunit-encoding DNA and the NMDA receptor subunit encoded thereby share substantial sequence homology with at least one of the NMDA receptor subunit DNAs (and proteins encoded thereby) described herein. It is understood that DNA or RNA encoding a splice variant may share less than 90% overall sequence homology with the DNA or RNA provided herein, but include regions of nearly 100% homology to a DNA fragment described herein, and encode an open reading frame that includes start and stop codons and encodes a functional NMDA receptor subunit.

As employed herein, the phrase "NMDA receptor subunit (s) of the NMDAR1 subtype" refers to proteins which, by hydrophobicity analysis of deduced amino acid sequences, are believed to contain four or more putative transmembrane domains, preceded by a large extracellular N-terminal domain. The amino acid sequence typically contains possible phosphorylation sites for $Ca^{2+}$/calmodulin-dependent protein kinase type II and protein kinase C [see, for example, Kemp et al. (1990) Trends in Biological Science Vol. 15:342–346; Kishimoto et al. (1985) J. Biol. Chem. Vol. 260:12492–12499; Whittemore et al. (1993) Nature 364:70–73]. (These protein kinases reportedly play a crucial role in induction and maintenance of long term potentiation.)

The putative TMII segment (i.e., second transmembrane domain) is typically flanked by a glutamic acid residue at the extracellular side and a stretch of glutamic acid residues at the cytoplasmic side. This segment contains an asparagine residue believed to be responsible for high $Ca^{2+}$, permeability of the NMDAR channel.

For a summary of NMDAR properties, see Ben-Ari et al., in TINS 15:333–339 (1992), especially at p. 334.

Exemplary DNA sequences encoding human NMDAR1 subunits are represented by nucleotides which encode substantially the same amino acid sequence as set forth in Sequence ID Nos. 2, 20, 22, 24, 26, 28, 30, 32, 34, 36, 38 or 40. Presently preferred sequences encode substantially the same amino acid sequence as set forth in Sequence ID Nos. 2, 20, 22, 24, 26, 28 or 40.

Exemplary DNA can alternatively be characterized as those nucleotide sequences which encode a human NMDAR1 subunit and hybridize under high stringency conditions to substantially the entire sequence of any one of Sequence ID No. 1, nucleotides 320–3402 of Sequence ID No. 1, or Sequence ID Nos. 13, 15, 17, 19, 21, 23, 25, 27, 29, 31, 33, 35, 37 or 39, or substantial portions thereof (i.e., typically at least 25–30 nucleotides thereof); preferably exemplary DNA will hybridize under high stringency conditions to substantially the entire sequence of any one of Sequence ID Nos. 1, 19, 21, 23, 25, 27 or 39, or substantial portions thereof.

Stringency of hybridization is used herein to refer to conditions under which polynucleic acid hybrids are stable. As known to those of skill in the art, the stability of hybrids is reflected in the melting temperature ($T_m$) of the hybrids. $T_m$ can be approximated by the formula:

$$81.5° C. -16.6(log_{10}[Na^+])+0.41(\%G+C)-600/1,$$

where 1 is the length of the hybrids in nucleotides. $T_m$ decreases approximately 1°–1.5° C. with every 1% decrease in sequence homology. In general, the stability of a hybrid is a function of sodium ion concentration and temperature. Typically, the hybridization reaction is performed under conditions of lower stringency, followed by washes of varying, but higher, stringency. Reference to hybridization stringency relates to such washing conditions. Thus, as used herein:

(1) HIGH STRINGENCY conditions, with respect to fragment hybridization, refers to conditions that permit hybridization of only those nucleic acid sequences that form stable hybrids in 0.018M NaCl at 65° C. (i.e., if a hybrid is not stable in 0.018M NaCl at 65° C., it will not be stable under high stringency conditions, as contemplated herein). High stringency conditions can be provided, for example, by hybridization in 50% formamide, 5×Denhart's solution, 5×SSPE, 0.2% SDS at 42° C., followed by washing in 0.1×SSPE, and 0.1% SDS at 65° C.;

(2) MODERATE STRINGENCY conditions, with respect to fragment hybridization, refers to conditions equivalent to hybridization in 50% formamide, 5×Denhart's solution, 5×SSPE, 0.2% SDS at 42° C., followed by washing in 0.2×SSPE, 0.2% SDS, at 65° C.;

(3) LOW STRINGENCY conditions, with respect to Fragment hybridization, refers to conditions equivalent to hybridization in 10% formamide, 5×Denhart's solution, 6×SSPE, 0.2% SDS at 42° C., followed by washing in 1×SSPE, 0.2%. SDS, at 50° C.; and (4) HIGH STRINGENCY conditions, with respect to oligonucleotide (i.e., synthetic DNA ≦about 30 nucleotides in length) hybridization, refers to conditions equivalent to hybridization in 10% formamide, 5×Denhart's solution, 6×SSPE, 0.2% SDS at 42° C., followed by washing in 1×SSPE, and 0.2% SDS at 50° C.

It is understood that these conditions may be duplicated using a variety of buffers and temperatures and that they are not necessarily precise.

Denhart's solution and SSPE (see, e.g., Sambrook, Fritsch, and Maniatis, in: *Molecular Cloning, A Laboratory Manual*, Cold Spring Harbor Laboratory Press, 1989) are well known to those of skill in the art as are other suitable hybridization buffers. For example, SSPE is pH 7.4 phosphate-buffered 0.18M NaCl. SSPE can be prepared, for example, as a 20×stock solution by dissolving 175.3 g of NaCl, 27.6 g of $NaH_2PO_4$ and 7.4 g EDTA in 800 ml of water, adjusting the pH to 7.4, and then adding water to 1 liter. Denhart's solution (see, Denhart (1966) Biochem. Biophys. Res. Commun. 23:641) can be prepared, for example, as a 50×stock solution by mixing 5 g Ficoll (Type 400, Pharmacia LKB Biotechnology, INC., Piscataway, N.J.), 5 g of polyvinylpyrrolidone, 5 g bovine serum albumin (Fraction V; Sigma, St. Louis, Mo.) water to 500 ml and filtering to remove particulate matter.

Especially preferred sequences are those which have substantially the same nucleotide sequence as the coding sequences in any one of Sequence ID Nos. 1, 19, 21, 23, 25, 27, 29, 31, 33, 35, 37 or 39; with those having substantially the same sequence as the coding sequence in Sequence ID Nos. 1, 19, 21, 23, 25, 27 or 39 being most preferred.

As used herein, the phrase "substantial sequence homology" refers to nucleotide sequences which share at least about 90% identity, and amino acid sequences which typically share more than 95% amino acid identity (>99% amino acid identity when dealing with NMDAR1 subunits). It is recognized, however, that proteins (and DNA or mRNA encoding such proteins) containing less than the above-described level of homology arising as splice variants or that are modified by conservative amino acid substitutions (or substitution of degenerate codons) are contemplated to be within the scope of the present invention.

As used herein, the phrase "substantially the same" refers to the nucleotide sequences of DNA, the ribonucleotide sequences of RNA, or the amino acid sequences of protein, that have slight and non-consequential sequence variations from the actual sequences disclosed herein. Species that are "substantially the same" are considered to be equivalent to the disclosed sequences, and as such are within the scope of the appended claims. In this regard, "slight and non-consequential sequence variations" mean that sequences that are substantially the same as the DNA, RNA, or proteins disclosed and claimed herein, are functionally equivalent to the human-derived sequences disclosed and claimed herein. Functionally equivalent sequences will function in substantially the same manner to produce substantially the same compositions as the human-derived nucleic acid and amino acid compositions disclosed and claimed herein. In particular, functionally equivalent DNAs encode human-derived proteins that are the same as those disclosed herein or that have conservative amino acid variations, such as substitution of a non-polar residue for another non-polar residue or a charged residue for a similarly charged residue. These changes include those recognized by those of skill in the art as those that do not substantially alter the tertiary structure of the protein.

As employed herein, the phrase "NMDA receptor subunit (s) of the NMDAR2 subtype" refers to proteins which have a large putative extracellular domain at the amino-terminal region. Otherwise, the deduced structure of NMDAR2 subunits displays the same general characteristics as the NMDAR1 subunit structure. A notable typical exception is that the negatively charged glutamic acid residues that are generally present in the putative TMII segment of NMDAR1 subunits are generally absent from the TMII segment of NMDAR2. Instead, NMDAR2 subunits may contain a positively charged lysine residue in TMII. Unlike NMDAR1 subunits, NMDAR2 subunits generally do not form homomeric NMDA receptors. Moreover, the amino acid sequences of NMDAR1 and NMDAR2 subunits are generally less than 50% identical, with identities of less than 30% typically observed.

NMDAR2 subunits contemplated by the present invention include NMDAR2A, NMDAR2B, NMDAR2C and NMDAR2D types of subunits. Exemplary DNA sequences encoding human NMDAR2A subunits, or portions thereof, are represented by nucleotides which encode substantially the same amino acid sequence as set forth in Sequence ID No. 11, or substantially the same amino acid sequence as that encoded by the NMDAR2A-encoding portion of clone NMDA57, deposited with the ATCC under accession number 75442.

The deposited clone has been deposited at the American Type Culture Collection (ATCC), 12301 Parklawn Drive, Rockville, Md., U.S.A. 20852, under the terms of the Budapest Treaty on the International Recognition of Deposits of Microorganisms for Purposes of Patent Procedure and the Regulations promulgated under this Treaty. Samples of the deposited material are and will be available to industrial property offices and other persons legally entitled to receive them under the terms of the Treaty and Regulations and otherwise in compliance with the patent laws and regulations of the United States of America and all other nations or international organizations in which this application, or an application claiming priority of this application, is filed or in which any patent granted on any such application is granted. In particular, upon issuance of a U.S. patent based on this or any application claiming priority to or incorporating this application by reference thereto, all restriction upon availability of the deposited material will be irrevocably removed.

Exemplary human NMDAR2A subunit-encoding DNAs can alternatively be characterized as those nucleotide sequences which hybridize under high stringency conditions to substantially the entire sequence of Sequence ID No. 10, or substantial portions thereof (i.e., typically at least 25–30 nucleotides thereof), or the NMDAR2A-encoding portion of clone NMDA57 (ATCC accession No. 75442). Especially preferred sequences encoding human NMDAR2A subunits are those which have substantially the same nucleotide sequence as the coding sequence of Sequence ID No. 10, or those which contain substantially the same nucleotide sequence as the coding sequence in the NMDAR2A-encoding portion of clone NMDA57.

Exemplary DNA sequences encoding human NMDAR2B subunits are represented by nucleotides which encode substantially the same amino acid sequence as set forth in Sequence ID No. 56. Exemplary DNAs can alternatively be characterized as those nucleotide sequences which encode a human NMDAR2B subunit and hybridize under high stringency conditions to substantially the entire sequence of Sequence ID No. 55, or substantial portions thereof (i.e., typically at least 25–30 nucleotides thereof). Especially preferred NMDAR2B-encoding sequences are those which have substantially the same nucleotide sequence as the coding sequence in Sequence ID No. 55.

Exemplary DNA sequences encoding human NMDAR2C subunits are represented by nucleotides which encode substantially the same amino acid sequence as set forth in Sequence ID Nos. 6, 46, 48, 50, 52 or 54.

Exemplary DNAs can alternatively be characterized as those nucleotide sequences which encode a human NMDAR2C subunit and hybridize under high stringency conditions to substantially the entire sequence of any one of Sequence ID Nos. 5, 41, 43 or 44 or nucleotides 1–3025 of Sequence ID No. 5 or Sequence ID Nos. 45, 47, 49, 51 or 53, or substantial portions thereof (i.e., typically at least 25–30 nucleotides thereof); preferably exemplary DNA will hybridize under high stringency conditions to substantially the entire sequence of any one of Sequence ID Nos. 5, 45, 47 or 49, or substantial portions thereof.

Especially preferred NMDAR2C-encoding sequences are those which have substantially the same nucleotide sequence as the coding sequences in any one of Sequence ID Nos. 5, 45, 47, 49, 51 or 53; with those having substantially the same sequence as the coding sequences in Sequence ID Nos. 5, 45, 47, 49 being most preferred.

Exemplary DNA sequences encoding human NMDAR2D subunits are represented by nucleotides which encode substantially the same amino acid sequence as set forth in Sequence ID No. 58. Exemplary DNAs can alternatively be characterized as those nucleotide sequences which encode a human NMDAR2D subunit and hybridize under high stringency conditions to substantially the entire sequence of Sequence ID No. 57, or substantial portions thereof (i.e., typically at least 25–30 nucleotides thereof). Especially preferred NMDAR2D-encoding sequences are those which have substantially the same nucleotide sequence as the coding sequence in Sequence ID No. 57.

DNA encoding human NMDA receptor subunits may be isolated by screening suitable human cDNA or human genomic libraries under suitable hybridization conditions with DNA disclosed herein (including nucleotIdes derived from any of Sequence ID No. 1, nucleotides 320–3402 of Sequence ID No. 1, Sequence ID Nos. 13, 15, 17, 19, 21, 23, 25, 27, 29, 31, 33, 35, 37, 39, 5, 41, 43 or 44, nucleotides 1–3025 of Sequence ID No. 5 or Sequence ID Nos. 45, 47, 49, 51, 53, 10, 55 or 57). Suitable libraries can be prepared from neuronal tissue samples, e.g., hippocampus and cerebellum tissue, cell lines, and the like. For example, the library can be screened with a portion of DNA including substantially the entire subunit-encoding sequence thereof, or the library may be screened with a suitable probe.

As used herein, a probe is single-stranded DNA or RNA that has a sequence of nucleotides that includes at least 14 contiguous bases that are the same as (or the complement of) any 14 or more contiguous bases set forth in any of Sequence ID No. 1, nucleotides 320–3402 of Sequence ID No. 1, Sequence ID Nos. 13, 15, 17, 19, 21, 23, 25, 27, 29, 31, 33, 35, 37, 39, 5, 41, 43 or 44, nucleotides 1–3025 of Sequence ID No. 5 or Sequence ID Nos. 45, 47, 49, 51, 53, 10, 55 or 57. Preferred regions from which to construct probes include 5' and/or 3' coding sequences, sequences predicted to encode transmembrane domains, sequences predicted to encode cytoplasmic loops, signal sequences, NMDA binding sites, and the like.

Either the full-length cDNA clones or fragments thereof can be used as probes, preferably labeled with suitable label means for ready detection. When fragments are used as probes, preferably the DNA sequences will be from the carboxyl end-encoding portion of the DNA, and most preferably will include predicted transmembrane domain-encoding portions of the DNA sequence (the domains can be predicted based on hydropathy analysis of the deduced amino acid sequence using, for example, the method of Kyte and Doolittle (1982), *J. Mol. Biol.* Vol. 157:105). These probes can be used, for example, for the identification and isolation of additional members of the glutamate receptor family.

As a particular application of the invention sequences, genetic screening can be carried out using the nucleotide sequences of the invention as probes. Thus, nucleic acid samples from patients having neuropathological conditions suspected of involving alteration/modification of any one or more of the glutamate receptors can be screened with appropriate probes to determine if any abnormalities exist with respect to any of the endogenous glutamate receptors. Similarly, patients having a family history of disease states related to glutamate receptor dysfunction can be screened to determine if they are also predisposed to such disease states.

In accordance with another embodiment of the present invention, there is provided a method for identifying DNA encoding human N-methyl-D-aspartate (NMDA) receptor protein subunit(s), said method comprising:

contacting human DNA with a nucleic acid probe as described above, wherein said contacting is carried out under high stringency hybridization conditions, and identifying DNA(s) which hybridize to said probe.

After screening the library, positive clones are identified by detecting a hybridization signal; the identified clones are characterized by restriction enzyme mapping and/or DNA sequence analysis, and then examined, by comparison with the sequences set forth herein to ascertain whether they include DNA encoding a complete NMDA receptor subunit (i.e., if they include translation initiation and termination codons). If the selected clones are incomplete, they may be used to rescreen the same or a different library to obtain overlapping clones. If the library is genomic, then the overlapping clones may include exons and introns. If the library is a cDNA library, then the overlapping clones will include an open reading frame. In both instances, complete clones may be identified by comparison with the DNA and encoded proteins provided herein.

Complementary DNA clones encoding various human NMDA receptor subunits (e.g., NMDAR1, NMDAR2A, NMDAR2B, NMDAR2C, NMDAR2D) have been isolated. Each type of subunit appears to be encoded by a different gene. The DNA clones provided herein may be used to isolate genomic clones encoding each type of subunit and to isolate any splice variants by screening libraries prepared from different neural tissues. Nucleic acid amplification techniques, which are well known in the art, can be used to locate DNA encoding splice variants of human NMDA receptor subunits. This is accomplished by employing oligonucleotides based on DNA sequences surrounding divergent sequence(s) as primers for amplifying human RNA or genomic DNA. Size and sequence determinations of the amplification products can reveal the existence of splice variants. Furthermore, isolation of human genomic DNA sequences by hybridization can yield DNA containing multiple exons, separated by introns, that correspond to different splice variants of transcripts encoding human NMDA receptor subunits.

It has been found that not all subunits (and variants thereof) are expressed in all neural tissues or in all portions of the brain. Thus, in order to isolate cDNA encoding a particular subunit or splice variants thereof, it is preferable to screen libraries prepared from different neuronal or neural tissues. Preferred tissues to use as sources of nucleic acids for preparing libraries to obtain DNA encoding each subunit include: hippocampus to isolate human NMDAR1-encoding DNAs; hippocampus, cerebellum and fetal brain to isolate NMDAR2-encoding DNAs; and the like.

Once DNA encoding a subunit has been isolated, ribonuclease (RNase) protection assays can be employed to determine which tissues express mRNA encoding a particular NMDAR subunit subtype or variant. These assays provide a sensitive means for detecting and quantitating an RNA species in a complex mixture of total cellular RNA. The subunit DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualed by gel electrophorsis and autoradiography. In situ hybridization techniques can also be used to determine which tissues express mRNA encoding a particular NMDAR subunit. The labeled subunit DNAs are hybridized to different brain region slices to visualize subunit mRNA expression.

The distribution of expression of some human NMDA receptor subunits may differ from the distribution of such receptors in rat. For example, RNA encoding the rat NMDAR2C subunit is abundant in rat cerebellum, but is not abundant in rat hippocampus [see, e.g., Monyer et al., Science 256:1217–1221 (1992)]. Numerous human NMDAR2C clones were ultimately obtained, however, from a human hippocampus library. Thus, the distribution of some NMDA receptor subunits in humans and rats appears to be different.

The above-described nucleotide sequences can be incorporated into vectors for further manipulation. As used herein, vector (or plasmid) refers to discrete elements that are used to introduce heterologous DNA into cells for either expression or replication thereof. Selection and use of such vehicles are well within the skill of the artisan.

An expression vector includes vectors capable of expressing DNAs that are operatively linked with regulatory sequences, such as promoter regions, that are capable of effecting expression of such DNA fragments. Thus, an expression vector refers to a recombinant DNA or RNA construct, such as a plasmid, a phage, recombinant virus or other vector that, upon introduction into an appropriate host cell, results in expression of the cloned DNA. Appropriate expression vectors are well known to those of skill in the art and include those that are replicable in eukaryotic cells and/or prokaryotic cells and those that remain episomal or those which integrate into the host cell genome. Presently preferred plasmids for expression of invention NMDA receptor subunits in eukaryotic host cells, particularly mammalian cells, include cytomegalovirus (CMV) promoter-containing vectors such as pCMV-T7-2 or pCMV-T7-3 (see FIG. 6), pMMTVT7(+) or pMMTVT7(–) (modified versions of pMAMneo (Clontech, Palo Alto, Calif.), prepared as described herein), pcDNA1, and the like.

As used herein, a promoter region refers to a segment of DNA that controls transcription of DNA to which it i s operatively linked. The promoter region includes specific sequences that are sufficient for RNA polymerase recognition, binding and transcription initiation. This portion of the promoter region is referred to as the promoter. In addition, the promoter region includes sequences that modulate this re cognition, binding and transcription initiation activity of RNA polymerase. These sequences may be cis acting or may be responsive to trans acting factors. Promoters, depending upon the nature of the regulation, may be constitutive or regulated. Exemplary promoters contemplated for use in the practice of the present invention include the SV40 early promoter, the cytomegalovirus (CMV) promoter, the mouse mammary tumor virus (MMTV) steroid-inducible promoter, Moloney murine leukemia virus (MMLV) promoter, and the like.

As used herein, the term "operatively linked" refers to the functional relationship of DNA with regulatory and effector sequences of nucleotides, such as promoters, enhancers, transcriptional and translational stop sites, and other signal sequences. For example, operative linkage of DNA to a promoter refers to the physical and functional relationship between the DNA and the promoter such that the transcription of such DNA is initiated from the promoter by an RNA polymerase that specifically recognizes and binds to the promoter, and transcribes the DNA. In order to optimize expression and/or in vitro transcription, it may be necessary to remove, add or alter 5' and/or 3' untranslated portions of the clones to eliminate extra, potential inappropriate alternative translation initiation (i.e., start) codons or other sequences that may interfere with or reduce expression, either at the level of transcription or translation. Alternatively, consensus ribosome binding sites (see, for example, Kozak (1991) J. Biol. Chem. 266:19867–19870) can be inserted immediately 5' of the start codon and may enhance expression. Likewise, alternative codons, encoding the same amino acid, can be substituted for coding sequences of the NMDAR subunits in order to enhance transcription (e.g., the codon preference of the host cells can be adopted, the presence of G-C rich domains can be reduced, and the like). Furthermore, for potentially enhanced expression of NMDA receptor subunits in amphibian oocytes, the subunit coding sequence can optionally be incorporated into an expression construct wherein the 5'- and 3'-ends of the coding sequence are contiguous with Xenopus β-globin gene 5' and 3' untranslated sequences, respectively. For example, NMDA receptor subunit coding sequences can be incorporated into vector pSP64T (see Krieg and Melton (1984) in Nucleic Acids Research 12:7057–7070), a modified form of pSP64 (available from Promega, Madison, Wis.). The coding sequence is inserted between the 5' end of the β-globin gene and the 3' untranslated sequences located downstream of the SP6 promoter. In vitro transcripts can then be generated from the resulting vector. The desirability of (or need for) such modification may be empirically determined.

As used herein, expression refers to the process by which polynucleic acids are transcribed into mRNA and translated into peptides, polypeptides, or proteins. If the polynucleic acid is derived from genomic DNA, expression may, if an appropriate eukaryotic host cell or organism is selected, include splicing of the mRNA.

Particularly preferred vectors for transfection of mammalian cells are the pSV2dhfr expression vectors, which contain the SV40 early promoter, mouse dhfr gene, SV40 polyadenylation and splice sites and sequences necessary for maintaining the vector in bacteria, cytomegalovirus (CMV) promoter-based vectors such as pCMV-T7-2 and pCMV-T7-3 (described herein) or pCDNA1 (Invitrogen, San Diego, Calif.), and MMTV promoter-based vectors such as pMMTVT7(+) or pMMTVT7(-), described herein.

Full-length DNAs encoding human NMDA receptor subunits have been inserted into vectors pcDNA1, pMMTVT7(+), pCMV-T7-2 and pCMV-T7-3. pCMV-T7-2 is a pUC19-based mammalian cell expression vector containing the CMV promoter/enhancer, SV40 splice/donor sites located immediately downstream of the promoter, a T7 bacteriophage RNA polymerase promoter positioned downstream of the splice sites, followed by an SV40 polyadenylation signal and a polylinker between the T7 promoter and the polyadenylation signal. Placement of NMDA receptor subunit DNA between the CMV promoter and SV40 polyadenylation signal should provide for constitutive expression of the foreign DNA in a mammalian host cell transfected with the construct. Plasmid pCMV-T7-3 is identical to pCMV-T7-2 except that the order of restriction enzyme sites in the polylinker is reversed.

Vectors pMMTVT7(+) and pMMTVT7(-) were prepared by modifying vector pMAMneo (Clontech, Palo Alto, Calif.). pMAMneo is a mammalian expression vector that contains the Rous Sarcoma Virus (RSV) long terminal repeat (LTR) enhancer, linked to the dexamethasone-inducible mouse mammary tumor virus (MMTV)-LTR promoter, followed by SV40 splicing and polyadenylation sites. pMAMneo also contains the E. coli neo gene for selection of transformants, as well as the δ-lactamase gene (encoding a protein which imparts ampicillin-resistance) for propagation in E. coli.

Vector pMMTVT7(+) can be generated by modification of pMAMneo to remove the neo gene and insert the multiple cloning site and T7 and T3 promoters from pBluescript (Stratagene, La Jolla, Calif.). Thus, pMMTVT7(+) contains the RSV-LTR enhancer linked to the MMTV-LTR promoter, a T7 bacteriophage RNA polymerase promoter positioned downstream of the MMTV-LTR promoter, a polylinker positioned downstream of the T7 promoter, a T3 bacteriophage RNA polymerase promoter positioned downstream of the T7 promoter, and SV40 splicing and polyadenylation sites positioned downstream of the T3 promoter. The δ-lactamase gene (encoding a protein which imparts ampicillin-resistance) from pMAMneo is retained in pMMTVT7(+), although it is incorporated in the reverse orientation relative to the orientation in pMAMneo.

Vector pMMTVT7(-) is identical to pMMTVT7(+) except that the positions of the T7 and T3 promoters are switched, i.e., the T3 promoter in pMMTVT7(-) is located where the T7 promoter is located in pMMTVT7(+), and the T7 promoter in pMMTVT7(-) is located where the T3 promoter is located in pMMTVT7(+). Therefore, vectors pMMTVT7(+) and pMMTVT7(-) contain all of the regulatory elements required for expression of heterologous DNA in a mammalian host cell, wherein the heterologous DNA has been incorporated into the vectors at the polylinker. In addition, because the T7 and T3 promoters are located on either side of the polylinker, these plasmids can be used for synthesis of in vitro transcripts of heterologous DNA that has been subcloned into the vectors at the polylinker.

For inducible expression of human NMDA receptor subunit-encoding DNA in a mammalian cell, the DNA can be inserted into a plasmid such as pMMTVT7(+) or pMMTVT7(-). These plasmids contain the mouse mammary tumor virus (MMTV) promoter for steroid-inducible expression of operatively associated foreign DNA. If the host cell does not express endogenous glucocorticoid receptors required for uptake of glucocorticoids (i.e., inducers of the MMTV promoter) into the cell, it is necessary to additionally transfect the cell with DNA encoding the glucocorticoid receptor (ATCC accession no. 67200). For synthesis of in vitro transcripts, full-length human DNA clones encoding human NMDAR1, NMDAR2A, NMDAR2B, NMDAR2C and NMDAR2D can also be subcloned into pIBI24 (International Biotechnologies, Inc., New Haven, Conn.), pCMV-T7-2, pCMV-T7-3, pMMTVT7(+), pMMTVT7(-), pBluescript (Stratagene, La Jolla, Calif.) or pGEM7Z (Promega, Madison, Wis.).

In accordance with another embodiment of the present invention, there are provided cells containing the above-described polynucleic acids (i.e., DNA or mRNA). Such host cells as bacterial, yeast and mammalian cells can be used for replicating DNA and producing NMDA receptor subunit(s). Methods for assessing receptor expression and function are described in PCT Application Nos. PCT/US91/05625 and PCT/US92/11090, and in co-pending U.S. application Ser. Nos. 07/563,751 and 07/812,254. The subject matter of these documents is hereby incorporated by reference herein in their entirety.

Incorporation of cloned DNA into a suitable expression vector, transfection of eukaryotic cells with a plasmid vector or a combination of plasmid vectors, each encoding one or more distinct genes or with linear DNA, and selection of transfected cells are well known in the art (see, e.g., Sambrook et al. (1989) *Molecular Cloning: A Laboratory Manual*, Second Edition, Cold Spring Harbor Laboratory Press). Heterologous DNA may be introduced into host cells by any method known to those of skill in the art, such as transfection with a vector encoding the heterologous DNA by $CaPO_4$ precipitation (see, e.g., Wigler et al. (1979) Proc. Natl. Acad. Sci. 76:1373–1376) or lipofectamine (GISCO BRL #18324-012). Recombinant cells can then be cultured under conditions whereby the subunit(s) encoded by the DNA is (are) expressed. Preferred cells include mammalian cells (e.g., HEK293, CHO, BHKBI and Ltk⁻ cells, mouse monocyte macrophage P388D1 and J774A-1 cells (available from ATCC, Rockville, Md.), and the like), yeast cells (e.g., methylotrophic yeast cells, such as *Pichia pastoris*), bacterial cells (e.g., *Escherichia coli*), and the like.

While the DNA provided herein may be expressed in any eukaryotic cell, including yeast cells (such as, for example, *P. pastoris* (see U.S. Pat. Nos. 4,882,279, 4,837,148, 4,929,555 and 4,855,231), *Saccharomyces cerevisiae, Candida tropicalis, Hansenula polymorpha*, and the like), mammalian expression systems, including commercially available systems and other such systems known to those of skill in the art, for expression of DNA encoding the human NMDA receptor subunits provided herein are presently preferred. xenopus oocytes are preferred for expression of in vitro RNA transcripts of the DNA.

In preferred embodiments, human NMDAR subunit-encoding DNA is ligated into a vector, and introduced into suitable host cells to produce transformed cell lines that express a specific human NMDA receptor subtype, or specific combinations of subunits. The resulting cell lines can then be produced in quantity for reproducible quantitative analysis of the effects of known or potential drugs on receptor function. In other embodiments, mRNA may be produced by in vitro transcription of DNA encoding each subunit. This mRNA, either from a single subunit clone or from a combination of clones, can then be injected into Xenopus oocytes where the mRNA directs the synthesis of the human receptor subunits, which then form functional receptors. Alternatively, the subunit-encoding DNA can be directly injected into oocytes for expression of functional receptors. The transfected mammalian cells or injected oocytes may then be used in the methods of drug screening provided herein.

Eukaryotic cells in which DNA or RNA may be introduced include any cells that are transfectable by such DNA or RNA or into which such DNA or RNA may be injected. Preferred cells are those that can be transiently or stably transfected and also express the DNA and RNA. Presently most preferred cells are those that can form recombinant or heterologous human NMDA receptors comprising one or more subunits encoded by the heterologous DNA. Such cells may be identified empirically or selected from among those known to be readily transfected or injected.

Exemplary cells for introducing DNA include cells of mammalian origin (e.g., COS cells, mouse L cells, Chinese hamster ovary (CHO) cells, human embryonic kidney (HEK) cells (particularly HEK293 cells that can be frozen in liquid nitrogen and then thawed and regrown; for example, those described in U.S. Pat. No. 5,024,939 to Gorman (see, also, Stillman et al. (1985) Mol. Cell. Biol. 5:2051–2060)), African green monkey cells and other such cells known to those of skill in the art) , amphibian cells (e.g., *Xenopus laevis* oöcytes), yeast cells (e.g., *Saccharomyces cerevisiae, Pichia pastoris*) , and the like. Exemplary cells for expressing injected RNA transcripts include *Xenopus laevis* o öcytes. Cells that are preferred for transfection of DNA are known to those of skill in the art or may be empirically identified, and include HEK293 (which are available from ATCC under accession #CRL 1573); Ltk⁻ cells (which are available from ATCC under accession #CCL1.3); COS-7 cells (which are available from ATCC under accession #CRL 1651); and DG44 cells (dhfr⁻ CHO cells; see, e.g., Urlaub et al. (1986) Cell. Molec. Genet. 12: 555). Presently preferred cells include Ltk⁻ cells and DG44 cells.

DNA may be stably incorporated into cells or may be transiently expressed using methods known in the art. Stably transfected mammalian cells may be prepared by transfecting cells with an expression vector having a selectable marker gene (such as, for example, the gene for thymidine kinase, dihydrofolate reductase, neomycin resistance, and the like) , and growing the transfected cells under conditions selective for cells expressing the marker gene. To prepare transient transfectants, mammalian cells are transfected with a reporter gene (such as the *E. coil* β-galactosidase gene) to monitor transfection efficiency. Selectable marker genes are not included in the transient transfections because the transfectants are typically not grown under selective conditions, and are usually analyzed within a few days after transfection.

To produce such stably or transiently transfected cells, the cells should be transfected with a sufficient concentration of subunit-encoding nucleic acids to form human NMDA receptors that contain the human subunits encoded by heterologous DNA. The precise amounts and ratios of DNA encoding the subunits may be empirically determined and optimized for a particular combination of subunits, cells and assay conditions. Recombinant cells that express NMDA receptors containing subunits encoded only by the heterologous DNA or RNA are especially preferred.

Heterologous DNA may be maintained in the cell as an episomal element or may be integrated into chromosomal DNA of the cell. The resulting recombinant cells may then be cultured or subcultured (or passaged, in the case of mammalian cells) from such a culture or a subculture thereof. Methods for transfection, injection and culturing recombinant cells are known to the skilled artisan. Similarly, the human NMDA receptor subunits may be purified using protein purification methods known to those of skill in the art. For example, antibodies or other ligands that specifically bind to one or more of the subunits may be used for affinity purification and immunoprecipitation of the subunit or human NMDA receptors containing the subunits.

As used herein, heterologous or foreign DNA and RNA are used interchangeably and refer to DNA or RNA that does not occur naturally as part of the genome of the cell in which it is present or to DNA or RNA which is found in a location or locations in the genome that differ from that in which it occurs in nature. Typically, heterologous or foreign DNA and RNA refers to DNA or RNA that is not endogenous to the host cell and has been artificially introduced into the cell. Examples of heterologous DNA include DNA that encodes a human NMDA receptor subunit, DNA that encodes RNA or proteins that mediate or alter expression of endogenous DNA by affecting transcription, translation, or other regulatable biochemical processes, and the like. The cell that expresses heterologous DNA may contain DNA encoding the same or different expression products. Heterologous DNA need not be expressed and may be integrated into the host cell genome or maintained episomally.

Recombinant receptors on recombinant eukaryotic cell surfaces may contain one or more subunits encoded by the DNA or mRNA encoding human NMDA receptor subunits, or may contain a mixture of subunits encoded by the host cell and subunits encoded by heterologous DNA or mRNA. Recombinant receptors may be homomeric or may be a heteromeric combination of multiple subunits. Mixtures of DNA or mRNA encoding receptors from various species, such as rats and humans, may also be introduced into the cells. Thus, a cell can be prepared that expresses recombinant receptors containing only NMDAR1 subunits, or a combination of any one or more NMDAR1 and any one or more NMDAR2 subunits provided herein. For example, NMDAR1 subunits of the present invention can be co-expressed with NMDAR2A, NMDAR2B, NMDAR2C and/or NMDAR2D receptor subunits. Specific examples of heteromeric combinations of recombinant human NMDAR subunits that have been expressed in Xenopus oocytes include NMDAR1+NMDAR2A, NMDAR1+NMDAR2B, and NMDAR1+NMDAR2A+NMDAR2C (see Example 9).

The DNA, mRNA, vectors, receptor subunits, receptor subunit combinations and cells provided herein permit production of selected NMDA receptor subunits and specific combinations thereof, as well as antibodies to said receptor subunits. This provides a means to prepare synthetic or recombinant receptors and receptor subunits that are substantially free of contamination from many other receptor proteins whose presence can interfere with analysis of a single NMDA receptor subtype. The availability of desired receptor subtypes makes it possible to observe the effect of a drug substance on a particular receptor subtype or combination of NMDA receptor subunits, and to thereby perform initial in vitro screening of the drug substance in a test system that is specific for humans and specific for a human NMDA receptor subtype or combination of NMDA receptor subunits. The availability of specific antibodies makes it possible to identify the subunit combinations expressed in vivo. Such specific combinations can then be employed as preferred targets in drug screening.

The ability to screen drug substances in vitro to determine the effect of the drug on specific receptor compositions should permit the development and screening of receptor subtype-specific or disease-specific drugs. Also, testing of single receptor subunits or specific combinations of various types of receptor subunits with a variety of potential agonists or antagonists provides additional information with respect to the function and activity of the individual subunits and should lead to the identification and design of compounds that are capable of very specific interaction with one or more types of receptor subunits or receptor subtypes. The resulting drugs should exhibit fewer unwanted side effects than drugs identified by screening with cells that express a variety of receptor subtypes.

Further in relation to drug development and therapeutic treatment of various disease states, the availability of DNAs encoding human NMDA receptor subunits enables identification of any alterations in such genes (e.g., mutations) which may correlate with the occurrence of certain disease states. In addition, the creation of animal models of such disease states becomes possible, by specifically introducing such mutations into synthetic DNA sequences which can then be introduced into laboratory animals or in vitro assay systems to determine the effects thereof.

In another aspect, the invention comprises functional peptide fragments, and functional combinations thereof, encoded by the DNAs of the invention. Such functional peptide fragments can be produced by those skilled in the art, without undue experimentation, by eliminating some or all of the amino acids in the sequence not essential for the peptide to function as a glutamate receptor. A determination of the amino acids that are essential for glutamate receptor function is made, for example, by systematic digestion of the DNAs encoding the peptides and/or by the introduction of deletions into the DNAs. The modified (e.g., deleted or digested) DNAs are expressed, for example, by transcribing the DNA and then introducing the resulting mRNA into Xenopus oocytes, where translation of the mRNAs will occur. Functional analysis of the proteins thus expressed in the oocytes is accomplished by exposing the oocytes to ligands known to bind to and functionally activate glutamate receptors, and then monitoring the oocytes to see if the expressed fragments form ion channel (s). If ion channel(s) are detected, the fragments are functional as glutamate receptors.

The above-described method can be carried out in the presence of NMDAR1-like receptor subunits alone, or in the presence of combinations of NMDAR1-like and NMDAR2-like receptor subunits. Thus, for example, when the protein being tested is an NMDAR2-like receptor subunit, the additional subunit is preferably an NMDAR1-like subunit.

In accordance with still another embodiment of the present invention, there is provided a method for identifying compounds which bind to human N-methyl-D-aspartate (NMDA) receptor subunit(s), said method comprising employing receptor proteins of the invention in a competitive binding assay. Such an assay can accomodate the rapid screening of a large number of compounds to determine which compounds, if any, are capable of binding to NMDA receptors. Subsequently, more detailed assays can be carried out with those compounds found to bind, to further determine whether such compounds act as modulators, agonists or antagonists of invention receptors.

Another application of the binding assay of the invention is the assay of test samples (e.g., biological fluids) for the presence or absence of receptors of the present invention. Thus, for example, serum from a patient displaying symptoms related to glutamatergic pathway dysfunction can be assayed to determine if the observed symptoms are perhaps caused by over- or under-production of such receptor(s).

The binding assays contemplated by the present invention can be carried out in a variety of ways, as can readily be identified by those of skill in the art. For example, competitive binding assays can be employed, such as radioreceptor assays, and the like.

In accordance with a further embodiment of the present invention, there is provided a bioassay for identifying compounds which modulate the activity of human NMDA receptors of the invention, said bioassay comprising:

(a) exposing cells containing DNA encoding human NMDA receptor subunit(s), wherein said cells express functional NMDA receptors, to at least one compound whose ability to modulate the ion channel activity of said receptors is sought to be determined; and thereafter (b) monitoring said cells for changes in ion channel activity.

The above-described bioassay enables the identification of agonists and antagonists for human NMDA receptors. According to this method, recombinant NMDA receptors are contacted with an "unknown" or test substance (in the further presence of a known NMDA agonist, when antagonist activity is being tested), the ion channel activity of the known glutamate receptor is monitored subsequent to the contact with the "unknown" or test substance, and those substances which increase or decrease the ion channel response of the known glutamate receptor(s) are identified as functional ligands (i.e., modulators, agonists or antagonists) for human NMDA receptors.

In accordance with a particular embodiment of the present invention, recombinant human NMDA receptor-expressing mammalian cells or oocytes can be contacted with a test compound, and the modulating effect(s) thereof can then be evaluated by comparing the NMDA receptor-mediated response in the presence and absence of test compound, or by comparing the response of test cells, or control cells (i.e., cells that do not express NMDA receptors), to the presence of the compound.

As used herein, a compound or signal that "modulates the activity of an NMDA receptor" refers to a compound or signal that alters the activity of NMDA receptors so that activity of the NMDA receptor is different in the presence of the compound or signal than in the absence of the compound or signal. In particular, such compounds or signals include agonists and antagonists. The term agonist refers to a substance or signal, such as NMDA, that activates receptor function; and the term antagonist refers to a substance that interferes with receptor function. Typically, the effect of an antagonist is observed as a blocking of activation by an agonist. Antagonists include competitive and non-competitive antagonists. A competitive antagonist (or competitive blocker) interacts with or near the site specific for the agonist (e.g., ligand or neurotransmitter). A non-competitive antagonist or blocker inactivates the functioning of the receptor by interacting with a site other than the site that interacts with the agonist.

As understood by those of skill in the art, assay methods for identifying compounds that modulate human NMDA receptor activity (e.g., agonists and antagonists) generally require comparison to a control. One type of a "control" cell or "control" culture is a cell or culture that is treated substantially the same as the cell or culture exposed to the test compound, except the control culture is not exposed to test compound. For example, in methods that use voltage clamp electrophysiological procedures, the same cell can be tested in the presence and absence of test compound, by merely changing the external solution bathing the cell. Another type of "control" cell or "control" culture may be a cell or a culture of cells which is identical to the transfected cells, except the cells employed for the control culture do not express functional human NMDA receptor subunits. In this situation, the response of test cell to test compound is compared to the response (or lack of response) of receptor-negative (control) cell to test compound, when cells or cultures of each type of cell are exposed to substantially the same reaction conditions in the presence of compound being assayed.

In accordance with yet another embodiment of the present invention, the ion channel activity of human N-methyl-D-aspartate (NMDA) receptors can be modulated by contacting such receptors with an effective amount of at least one compound identified by the above-described bioassay.

In accordance with yet another embodiment of the present invention, there are provided antibodies generated against the above-described receptor proteins. Such antibodies can be employed for studying receptor tissue localization, subunit composition, structure of functional domains, as well as in diagnostic applications, therapeutic applications, and the like. Preferably, for therapeutic applications, the antibodies employed will be monoclonal antibodies.

The above-described antibodies can be prepared employing standard techniques, as are well known to those of skill in the art, using the invention receptor proteins or portions thereof as antigens for antibody production. Both anti-peptide and anti-fusion protein antibodies can be used [see, for example, Bahouth et al. (1991) *Trends Pharmacol Sci.* vol. 12:338–343; *Current Protocols in Molecular Biology* (Ausubel et al., eds.) John Wiley and Sons, New York (1989)]. Factors to consider in selecting portions of the NMDAR subunits for use as immunogen (as either a synthetic peptide or a recombinantly produced bacterial fusion protein) include antigenicity, accessibility (i.e., extracellular and cytoplasmic domains), uniqueness to the particular subunit, etc.

The availability of subunit-specific antibodies makes possible the application of the technique of immunohistochemistry to monitor the distribution and expression density of various subunits (e.g., in normal vs diseased brain tissue). Such antibodies could also be employed for diagnostic and therapeutic applications.

In accordance with still another embodiment of the present invention, there are provided methods for modulating the ion channel activity of receptor(s) of the invention by contacting said receptor(s) with an effective amount of the above-described antibodies.

The antibodies of the invention can be administered to a subject employing standard methods, such as, for example, by intraperitoneal, intramuscular, intravenous, or subcutaneous injection, implant or transdermal modes of administration, and the like. One of skill in the art can readily determine dose forms, treatment regiments, etc., depending on the mode of administration employed.

The invention will now be described in greater detail by reference to the following non-limiting examples.

EXAMPLE 1

Isolation of DNA Encoding Human NMDA Receptor NMDAR1 Subunits

A. cDNA Library Screening

RNA isolated from human hippocampus tissue was used as a template for the synthesis of oligo dT-primed and randomly primed, single-stranded cDNA according to standard procedures [see, for example, Maniatis et al. (1982) *Molecular Cloning: A Laboratory Manual*, Cold Spring Harbor Laboratory Press, Cold Spring Harbor, New York]. The single-stranded cDNA was converted to double-stranded cDNA, and EcoRI/SnaBI/XhoI adaptors were added to the ends thereof. The cDNAs were separated by size using agarose gel electrophoresis, and those that were >2.0 kb were ligated into EcoRI-digested $\lambda$g10 bacteriophage vectors. The resulting cDNA library was amplified by replication of each clone through limited infection of a bacterial host, and stored at $-70°$ C.

The amplified hippocampus oligo dT-primed cDNA library was later retrieved from storage and $1 \times 10^6$ recombinants were screened for hybridization to oligonucleotides corresponding to nucleotides 96–128 (SE7) and nucleotides 2576–2609 (SE8) of the rat NMDAR1A receptor cDNA (see Moriyoshi et al. (1991) *Nature* 354:31). Hybridization was performed at 42° C. in 6×SSPE, 5×Denhart's solution, 10% formamide, 0.2% SDS and 200 $\mu$g/ml herring sperm DNA. Washes were performed in 1×SSPE and 0.2% SDS at 50° C. Hybridizing clones (e.g. NMDA1–3) were identified. These clones hybridized to SE8 but not to SE7.

A randomly primed primary human hippocampus cDNA library (~$2 \times 10^5$ recombinants prepared by selecting only cDNAs >2.0 kb for inclusion in the library) was screened under the same conditions for hybridization to oligonucleotide SE8 and an oligonucleotide corresponding to nucleotides 129–141 of the rat NMDAR1 receptor cDNA (SE11). Five hybridizing clones, which hybridized to SE8 and not to SE11, were identified: NMDA5–7 and NMDA10–11.

B. Characterization of Clones

The clones were plaque purified and characterized by restriction enzyme mapping and DNA sequence analysis of the inserts. One of the clones, NMDA11 (see description of Sequence ID No. 13 in Summary of Sequences for a description of a portion of NMDA11), is a full-length cDNA (i.e., it contains translation initiation and termination codons) encoding a complete NMDAR1 subunit. The remaining clones are partial cDNAs. Clones NMDA2, NMDA3 (see Sequence ID No. 17), NMDA5, NMDA6, NMDA7 (see Sequence ID No. 15), and NMDA10 (which encodes a 3083 nucleotide sequence comprising nucleotides 320–3402 of Sequence ID No. 1) contain a translation termination codon but lack nucleotides at the 5' end of the coding sequence.

Characterization of the clones revealed that the isolated cDNAs correspond to different alternatively spliced forms of the human NMDAR1 subunit transcript. The four types of alternate splicing represented by the clones are depicted schematically in FIG. 1. Clone NMDA10 (which lacks 5' untranslated sequences as well as 60 nucleotides of the 5' end of the coding sequence) is used as a reference to which the other variants are compared.

Clone NMDA11 lacks 363 nucleotides (in the 3' portion of the clone) that are present in NMDA10. This 363-nucleotide deletion does not disrupt the reading frame of the transcript; however, it results in a different termination codon. The last 69 nucleotides of the coding sequence of NMDA11 correspond to 3' untranslated sequence of clone NMDA10 (i.e., nucleotides 3325–3393 of Sequence ID No. 1). Clone NMDA7 lacks the same 363-nucleotide sequence that is deleted from NMDA11; however, NMDA7 further lacks 204 nucleotides at the 5' end that are present in NMDA10 and NMDA11. This 204-nucleotide deletion also does not disrupt the reading frame of the transcript. Additionally, NMDA7 contains a 63-nucleotide in-frame insertion at the 5' end relative to NMDA10 and NMDA11. The last 69 base pairs of the coding sequence of NMDA7 correspond to 3' untranslated sequence of NMDA10 i.e., nucleotides 3325–3393 of Sequence ID No. 1). Clone NMDA3 lacks 1087 base pairs at the 3' end that are present in NMDA10. This 1087-base pair deletion does not disrupt the reading frame of the transcript; however it results in a different termination codon. The last 231 base pairs of the coding sequence of NMDA3 correspond to 3' untranslated sequence of clone NMDA10 (i.e., nucleotides 4049–4279 in Sequence ID No. 1).

EXAMPLE 2

Preparation of Full-Length NMDAR1 Subunit cDNA Constructs

Portions of clones NMDA10, NMDA11, NMDA7 and NMDA3 were ligated together to construct full-length cDNAs encoding variants of the NMDA receptor NMDAR1 subunit. The full-length NMDAR1 subunit cDNAs were incorporated into vector pcDNA1 (Invitrogen, San Diego, Calif.) for use in expressing the receptor subunits in mammalian host cells and for use in generating in vitro transcripts of the DNAs to be expressed in Xenopus oocytes.

Vector pcDNA1 is a pUC19-based plasmid that contains the following elements in the 5'-to-3' order: the cytomegalovirus (CMV) immediate early gene promoter/enhancer, the bacteriophage T7 RNA polymerase promoter, a polylinker, the bacteriophage SP6 RNA polymerase promoter, SV40 RNA processing (i.e., splice donor/acceptor) signals, SV40 polyadenylation signal, and the ColE1 origin and supF suppressor tRNA to permit maintenance of the vector in *Escherichia coli* strains with the P3 episome. This vector thus contains all the regulatory elements required for expression of heterologous DNA in a mammalian host cell, wherein the heterologous DNA has been incorporated into the vector at the polylinker. In addition, because the T7 and SP6 promoters are located on either side of the polylinker, this plasmid can be used for synthesis of in vitro transcripts of heterologous DNA that has been sublconed into the vector at the polylinker.

A. NMDAR1A

Figure 2B:
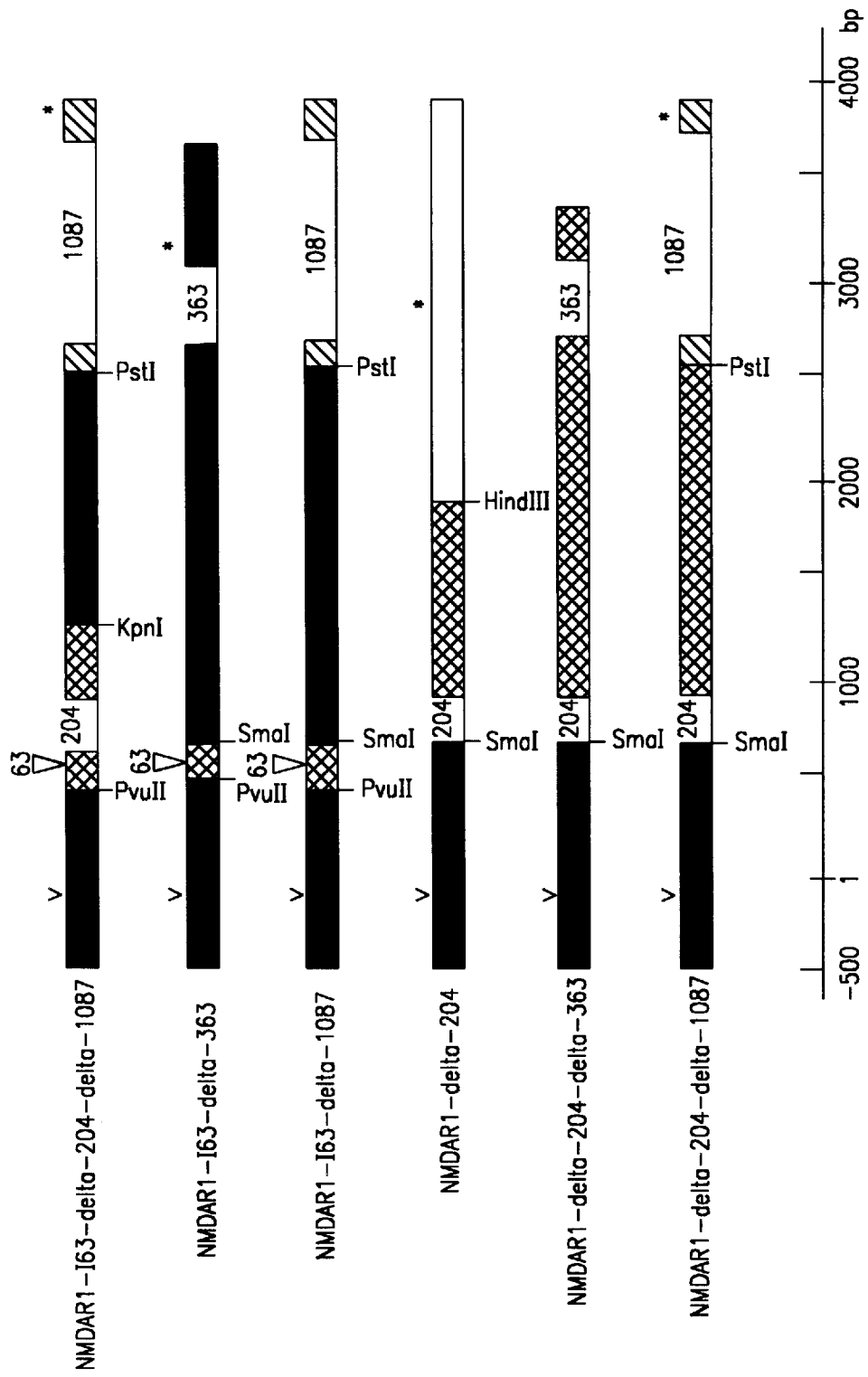

Full-length construct NMDAR1A was prepared by ligation of a 5' portion of NMDA11 (beginning 5' of the translation initiation codon and extending to the HindIII site in the middle of the clone) and a 3' portion of NMDA10 (beginning at the HindIII site in the middle of the clone and extending 3' of the translation termination codon) as depicted in FIG. 2. The two DNA fragments were joined in mammalian expression vector pcDNA1.

Initially, the strategy for generating the NMDAR1 construct involved a first step of separately subcloning the entire 4.0 kb EcoRI insert fragment of NMDA10 and the entire 4.0 kb SnaBI insert fragment of NMDA11 into pcDNA1; however, two attempts employing this cloning strategy were unsuccessful. It appeared that there may have been selection against *E. coli* hosts retaining the complete insert fragments since the surviving recombinant *E. coli* that were analyzed contained incomplete insert cDNAs from which nucleotides had been deleted. Therefore, it was necessary to prepare the full-length NMDAR1A construct in several steps by subcloning and combining various fragments of NMDA10 and NMDA11 in pcDNA1 as follows (see FIG. 3 for locations of restriction enzyme sites).

Clone NMDA10 was digested with BglII and EcoRI and the ~3.3 kb fragment containing nucleotides 1020–4298 of Sequence ID No. 1 was isolated and subcloned into BamHI/EcoRI-digested pcDNA1. The resulting plasmid was digested with HindIII and NheI and the fragment containing nucleotides 2137–4298 of Sequence ID No. 1 plus a portion of pcDNA1 was isolated.

Clone NMDA11 was digested with EcoRI and HindII and the ~2.1 kb fragment containing nucleotides 1–2136 of Sequence ID No. 1 was isolated and subcloned into EcoRI/HindIII-digested modified pcDNA1 (modified by deletion of the HindIII site located 5' of the EcoRI site in the polylinker and addition of a HindIII site into the polylinker at a position 3' of the EcoRI site). The resulting plasmid was digested with NheI and HindIII and the fragment containing nucleotides 1–2136 of Sequence ID No. 1 plus a portion of modified pcDNA1 was isolated. This NheI/HindIII fragment was then ligated to the HindIII/NheI fragment containing nucleotides 2137–4298 of Sequence ID No. 1 to generate the full-length construct NMDAR1A (see FIG. 2). The ligation mix was used to transform *E. coli* strain MC1061/P3. Because the NheI site in pcDNA1 occurs within the supF selection gene, only *E. coli* containing the correctly ligated, complete NMDAR1A plasmid (which has the complete, functional selection gene) were able to survive the selection process. This fragment subcloning strategy enabled selection of the desired correct NMDAR1A-containing E. coli host cells, even though the total number of such recombinant host cells was small.

In summary, construct NMDAR1A contains 261 base pairs of 5' untranslated sequence from NMDAR11 (nucleotides 1–261 of Sequence ID No. 1) and a complete coding sequence (nucleotides 262–3078 of Sequence ID No.1) for the NMDAR1A variant of the NMDAR1 subunit as well as 1220 base pairs of 3' untranslated sequence (nucleotides 3079–4298 of Sequence ID No. 1). The NMDAR1A-encoding sequence is operatively linked to the regulatory elements in pcDNA1 for expression in mammalian cells.

B. NMDAR1-Δ363

Full-length construct NMDAR1-Δ363 was prepared by ligation of a 5' portion of NMDA11 (beginning 5' of the translation initiation codon and extending to the HindIII site in the middle of the clone, i.e., nucleotides 1–2136 in Sequence ID No. 1) and a 3' portion of NMDA11 (beginning at the HindIII site in the middle of the clone and extending 3' of the translation termination codon, i.e., nucleotides 2137–2961 and 3325–4298 of Sequence ID No. 1). As described above, due to the difficulty in directly subcloning the entire 4.0 kb SnaBI NMDA11 insert into pcDNA1, it was necessary to generate the construct by ligating two fragments of the NMDA11 insert into pcDNA1 as follows (see FIG. 3 for locations of restriction enzyme sites).

To obtain the 5' NMDA11 fragment, clone NMDA11 was digested with EcoRI and HindIII and the ~2.2 kb fragment containing nucleotides 1–2136 of Sequence ID No. 1 was isolated and subcloned into EcoRI/HindIII-digested modified pcDNA1 (modified as described above). The resulting plasmid was digested with NheI and HindIII and the fragment containing nucleotides 1–2136 of Sequence ID No. 1 plus a portion of modified pcDNA1 was isolated.

To obtain the 3' NMDA11 fragment, clone NMDA11 was digested with BglII and EcoRI and the 3.0 kb fragment containing nucleotides 1020–2961 and 3325–4298 of Sequence ID No. 1 was isolated and subcloned into BamHI/EcoRI-digested pcDNA1. The resulting plasmid was digested with HindIII and NheI and the fragment containing nucleotides 2137–2961 and 3325–4298 of Sequence ID No. 1 plus a portion of pcDNA1 was isolated. This HindIII/NheI fragment was then ligated to the NheI/HindIII fragment containing nucleotides 1–2136 of Sequence ID No. 1 to generate NMDAR1-Δ363.

In summary, construct NMDAR1-Δ363 contains 261 base pairs of 5' untranslated sequence (nucleotides 1–261 of Sequence ID No. 1) and a complete coding sequence for the NMDAR1-Δ363 variant NMDAR1 subunit (nucleotides 262–2961 and 3325–3393 of Sequence ID No. 1) as well as 905 base pairs of 3' untranslated sequence (nucleotides 3394–4298 of Sequence ID No. 1). Thus, NMDAR1-Δ363 differs from NMDAR1 in that it lacks 363 nucleotides (nucleotides 2962–3324 of Sequence ID No. 1) that comprise the last 117 nucleotides of the coding sequence and the first 246 nucleotides of the 3' untranslated sequence of NMDAR1. The NMDAR1-Δ363 subunit variant-encoding sequence is operatively linked to the regulatory elements in pcDNA1 for expression in mammalian cells.

C. NMDAR1-Δ1087

Full-length construct NMDAR1-Δ1087 was prepared by replacing the 3' end of the NMDAR1 variant-encoding insert of NMDAR1-Δ363 with a fragment from the 3' end of clone NMDA3 (see FIG. 2). Plasmid NMDAR1-Δ363 was partially digested with PstI and completely digested with XbaI. There is a PstI site ~112 nucleotides upstream of the location of the 363-nucleotide deletion in NMDAR1-Δ363 and an XbaI site in the polylinker located downstream of the 3' untranslated sequence of NMDAR1-Δ363 (see FIG. 3). Thus, PstI/XbaI digestion of NMDAR1-Δ363 results in removal of a fragment containing nucleotides 2850–2961 and 3325–4298 of Sequence ID No. 1 from the vector. The larger fragment was isolated from the digest.

The insert of clone NMDA3 was cloned into the EcoRI restriction site(s) of pGEM (Promega, Madison, Wis.); and the resulting plasmid was digested with PstI and XbaI. The smaller fragment containing nucleotides 2850–2961 and 4049–4298 of Sequence ID No. 1 was isolated and ligated to the larger fragment from the PstI/XbaI digest of NMDAR1-Δ363. The resulting construct was designated NMDAR1-Δ1087.

In summary, NMDAR1-Δ1087 contains 261 base pairs of 5' untranslated sequence (nucleotides 1–261 in Sequence ID No. 1), the complete coding sequence for the NMDAR1-Δ1087 variant NMDAR1 subunit (nucleotides 262–2961 and 4049–4279 of Sequence ID No. 1) and 19 base pairs of 3' untranslated sequence (nucleotides 4280–4298 of Sequence ID No. 1). Thus, NMDAR1-Δ1087 differs from NMDAR1 in that it lacks 1087 nucleotides (nucleotides 2962–4048 of Sequence ID No. 1) that comprise the last 117 nucleotides of the coding sequence and the first 970 nucleotides of the 3' untranslated sequence of NMDAR1. The NMDAR1-Δ1087 subunit variant-encoding sequence is operatively linked to the regulatory elements in pcDNA1 for expression in mammalian cells.

D. NMDAR1-I63-Δ204

Full-length construct NMDAR1-I63-Δ204 was prepared by replacing a 1399-nucleotide fragment of construct NMDAR1A (i.e, nucleotides 738–2136 of Sequence ID No. 1) with the PvuII-HindIII fragment of NMDA7 (i.e., nucleotides 738–831 of sequence ID No. 1, plus nucleotides 1–63 of Sequence ID No. 3 and nucleotides 832–984 and 1189–2136 of Sequence ID No. 1), as depicted in FIG. 2. Because there are multiple PvuII sites in the NMDAR1 construct, a several-step process was required for construction of NMDAR1-I63-Δ204 as follows (see FIG. 3 for the location of restriction enzyme sites).

The ~2.2-kb EcoRI-HindIII fragment isolated from construct NMDAR1A and containing nucleotides 1–2136 of Sequence ID No. 1 was ligated with modified pcDNA1 (modified as described in Example 2A) that had been digested with EcoRI and HindIII. The resulting plasmid was digested with AvrII and self-ligated to remove two PvuII sites from a portion of the plasmid contributed by pcDNA1. The plasmid was then partially digested with PvuII and completely digested with HindIII. The digest was ligated with a 1258-nucleotide PvuII-HindIII fragment isolated from clone NMDA7. The resulting plasmid, designated NMDAR1-I63-Δ204-5', was digested with BamHI and HindIII and the ~2-kb fragment containing nucleotides 1–831 of Sequence ID No. 1, plus nucleotides 1–63 of Sequence ID No. 3 and nucleotides 832–984 and 1189–2136 of Sequence ID No. 1 was isolated and ligated to BamHI/HindIII-digested NMDAR1 to generate NMDAR1-I63-Δ204.

NMDAR1-I63-Δ204 contains 261 base pairs of 5' untranslated sequence (nucleotides 1–261 in Sequence ID No. 1), the complete coding sequence for the NMDAR1-I63-Δ204 variant NMDAR1 subunit (nucleotides 262–831 of Sequence ID No. 1 plus nucleotides 1–63 of Sequence ID No. 3 and nucleotides 832–984 and 1189–3078 of Sequence ID No. 1) and 1220 base pairs of 3' untranslated sequence (nucleotides 3079–4298 of Sequence ID No. 1). Thus NMDAR1-I63-Δ204 differs from NMDAR1 in that it contains 63 nucleotides that are not present in NMDAR1 (nucleotides 1–63 of Sequence ID No. 3) located between nt 831 and 832 of Sequence ID No. 1. Further, NMDAR1-I63-Δ204 lacks 204 nucleotides that are present in NMDAR1 (nucleotides 985–1188 of Sequence ID No. 1). The NMDAR1-I63-Δ204 subunit variant-encoding sequence is operatively linked to the regulatory elements in pcDNA1 for expression in mammalian cells.

E. NMDAR1-I63

Full-length construct NMDAR1-I63 can be described as NMDAR1 in which a 173-bp fragment (nucleotides 738–910 of Sequence ID No. 1) is replaced with the 236-bp PvuII-SmaI fragment of NMDA7 (nucleotides 738–831 of Sequence ID No. 1, plus nucleotides 1–63 of Sequence ID No. 3 and nucleotides 832–910 of Sequence ID No. 1). Because there are multiple PvuII sites in the NMDAR1 construct, a several-step process was required for construction of NMDAR1-I63 as follows. Plasmid NMDAR1-I63-Δ204-5' was partially digested with SmaI and completely digested with HindIII. The larger vector fragment was ligated with the 1226-bp SmaI/HindIII fragment isolated from NMDA11 (nucleotides 911–2136 of Sequence ID No. 1). The resulting vector was digested with BamHI and HindIII and the ~2.2-kb fragment containing nucleotides 1–831 of Sequence ID No. 1, plus nucleotides 1–63 of Sequence ID No. 3 and nucleotides 832–2136 of Sequence ID No. 1 was isolated and ligated to BamHI/HindIII-digested NMDAR1 to generate NMDAR1-I63.

NMDAR1-I63 contains 261 base pairs of 5' untranslated sequence (nucleotides 1–261 in Sequence ID No. 1), the complete coding sequence for the NMDAR1-I63 variant NMDAR1 subunit (nucleotides 262–831 of Sequence ID No. 1, plus nucleotides 1–63 of Sequence ID No. 3 and nucleotides 832–3078 of Sequence ID No. 1) and 1220 nucleotides of 3' untranslated sequence (nucleotides 3079–4298 of Sequence ID No. 1). Thus, NMDAR1-I63 differs from NMDAR1 in that it contains 63 nucleotides that are not present in NMDAR1 (nucleotides 1–63 of Sequence ID No. 3), located between nucleotides 831 and 832 of Sequence ID No. 1. The NMDAR1-I63 subunit variant-encoding sequence is operatively linked to the regulatory elements in pcDNA1 for expression in mammalian cells.

F. NMDAR1-I63-Δ204-Δ363

Full-length construct NMDAR1-I63-Δ204-Δ363 was prepared by replacing the 2861 nucleotide fragment from construct NMDAR1-I63-Δ204 (ie, nucleotldes 1438–4298 Sequence ID No. 1) with the KpnI-XbaI (polylinker site) fragment of NMDAR1-Δ363 (ie, nucleotides 1438–2961 and 3325–4298 of Sequence ID No. 1) as depicted in FIG. 2. The NMDAR1-I63-Δ204 was completely digested with XbaI then partially digested with KpnI due to the presence of two additional KpnI sites in the vector sequence. The resulting 5' NMDAR1-I63-Δ204 fragment, which includes the pcDNAI vector sequences, was ligated with the 3' KpnI-XbaI fragment from NMDAR1-Δ363 to generate NMDAR1-I63-Δ204-Δ363.

In summary, construct NMDAR1-I63-Δ204-Δ363 contains 261 base pairs of 5' untranslated sequence (nucleotides 1–261 in Sequence ID No. 1), the complete coding sequence for the NMDAR1-I63-Δ204-Δ363 variant NMDAR1A subunit (nucleotides 262–831 of Sequence ID No. 1, plus nucleotides 1–63 of Sequence ID No. 3, plus nucleotides 832–984, 1189–2961 and 3325–3393 of Sequence ID No. 1) as well as 905 base pairs of 3' untranslated sequence (nucleotides 3394–4298 of Sequence ID. No. 1). Thus, NMDAR1-I63-Δ204-Δ363 differs from NMDAR1A in that it contains 63 nucleotides that are not present in NMDAR1A (nucleotides 1–63 of Sequence ID No. 3) located between nucleotides 831 and 832 of Sequence ID No. 1. Further, NMDAR1-I63-Δ204-Δ363 lacks 204 nucleotides that are present in NMDAR1A (nucleotides 985–1188 of Sequence ID No. 1) and 363 nucleotides that are present in NMDAR1A (nucleotides 2962–3324 of Sequence ID No. 1) that comprise the last 117 nucleotides of the coding sequence and the first 246 nucleotides of the 3' untranslated sequence of NMDAR1A. The NMDAR1-I63-Δ204-Δ363 subunit variant encoding sequence is operatively linked to the regulatory elements in pcDNAI for expression in mammalian cells.

G. NMDAR1-I63-Δ204-Δ1087

Full-length construct NMDAR1-I63-Δ204-Δ1087 was prepared by replacing the 2861 nucleotide fragment from construct NMDAR1-I63-Δ204 (ie, nucleotides 1438–4298 Sequence ID. No. 1) with the KpnI-XbaI (polylinker site) fragment of NMDAR1-Δ1087 (ie, nucleotides 1438–2961 and 4049–4298 of Sequence ID No. 1) as depicted in FIG. 2. The NMDAR1-I63-Δ204 was completely digested with XbaI then partially digested with KpnI due to the presence of two additional KpnI sites in the vector sequence. The resulting 5' NMDAR1-I63-Δ204 fragment, which includes the pcDNAI vector sequences, was ligated with the 3' KpnI-XbaI fragment from NMDAR1-Δ1087 to generate NMDAR1-I63-Δ204-Δ1087.

In summary, construct NMDAR1-I63-Δ204-Δ1087 contains 261 base pairs of 5' untranslated sequence (nucleotides 1–261 in Sequence ID No. 1), the complete coding sequence for the NMDAR1-I63-Δ204-Δ363 variant NMDAR1A subunit (nucleotides 262–831 of Sequence ID No. 1, plus nucleotides 1–63 of Sequence ID No. 3, plus nucleotides 832–984, 1189–2961 and 4280–4298 of Sequence ID No. 1) as well as 19 base pairs of 3' untranslated sequence (nucleotides 4280-4298 of Sequence ID. No. 1). Thus, NMDAR1-I63-Δ204-Δ1087 differs from NMDAR1A in that it contains 63 nucleotides that are not present in NMDAR1A (nucleotides 1–63 of Sequence ID No. 3) located between nucleotides 831 and 832 of Sequence ID No. 1. Further, NMDAR1-I63-Δ204-Δ1087 lacks 204 nucleotides that are present in NMDAR1A (nucleotides 985–1188 of Sequence ID No. 1) and 1087 nucleotides that are present in NMDAR1A (nucleotides 2962–4048 of Sequence ID No. 1) that comprise the last 117 nucleotides of the coding sequence and the first 970 nucleotides of the 3' untranslated sequence of NMDAR1A. The NMDAR1-I63-Δ204-Δ1087 subunit variant encoding sequence is operatively linked to the regulatory elements in pcDNAI for expression in mammalian cells.

H. Additional Constructs Containing Full-Length cDNAs Encoding Variants of the NMDAR1 Subunit Additional full-length cDNAs encoding further possible NMDAR1 variants can be constructed using methods similar to those described in Examples 2A–G above. Specifically, the following constructs can be prepared by ligating portions of clones NMDA11, NMDA10, NMDA7 and NMDA3 as depicted in FIG. 2:

| NMDAR1-Δ204 | (Sequence ID No. 29) |
| NMDAR1-Δ204-Δ363 | (Sequence ID No. 31) |
| NMDAR1-I63-Δ363 | (Sequence ID No. 35) |

-continued

| NMDAR1-I63-Δ1087 | (Sequence ID No. 37) |
| NMDAR1-Δ204-Δ1087 | (Sequence ID No. 33) |

The full-length cDNAs can also be incorporated into mammalian expression vectors such as pcDNA1, as described in Examples 2A–G.

Several methods can be employed to determine which NMDAR1 subunit variants are actually expressed in various human tissues. For example, oligonucleotides specific for the nucleotide sequences located 5' and 3' of the insertions and deletions of the NMDAR1 transcripts described herein can be used to prime nucleic acid amplifications of RNA isolated from various tissues and/or cDNA libraries prepared from various tissues. The presence or absence of amplification products and the sizes of the products indicate which variants are expressed in the tissues. The products can also be characterized more thoroughly by DNA sequence analysis.

RNase protection assays can also be used to determine which variant transcripts are expressed in various tissues. These assays are a sensitive method for detecting and quantitating an RNA species in a complex mixture of total cellular RNA. A portion of the NMDAR1 subunit variant DNA is labeled and hybridized with cellular RNA. If complementary mRNA is present in the cellular RNA, a DNA-RNA hybrid results. The RNA sample is then treated with RNase, which degrades single-stranded RNA. Any RNA-DNA hybrids are protected from RNase degradation and can be visualizeded by gel electrophoresis and autoradiography.

Further information on possible splice variants of the NMDAR1 primary transcript can be obtained by isolation of genomic clones containing NMDAR1 subunit-encoding sequences (for example, by hybridization to the human NMDAR1 subunit cDNAs disclosed herein) and subsequent characterization of the resulting clones.

EXAMPLE 3

Isolation of DNA Encoding Human NMDA Receptor NMDAR2C Subunits

Degenerate oligonucleotides were synthesized based on two conserved regions of rat NMDAR2A, NMDAR2B and NMDAR2C DNAs that encode the putative first and fourth transmembrane domains. In rat NMDAR2A DNA, these regions are encoded by nucleotides 1669–1692 (oligo SE74) and 2437–2465 (olig SE75), respectively. [see monyer et al. (1992) *Science* 256:1217–1221]. These oligonucleotides were used to prime nucleic acid amplification of cDNAs prepared from RNA isolated from human hippocampus, cerebellum, and orbitofrontal tissue. Two products, a 795-bp and a 640-bp fragment, were detected when the reaction mixture was analyzed by gel electrophoresis and ethidium bromide staining. The 795-bp fragment amplified from the cerebellum cDNA was subcloned into PCR1000 (Invitrogen, San Diego, Calif.) and characterized by DNA sequence analysis, which revealed that it is ~86% similar to the rat NMDAR2A DNA sequence, ~78% similar to the rat NMDAR2B DNA sequence, and ~74% similar to the rat NMDAR2C DNA sequence. Thus, this plasmid was named pcrNMDAR2A.

The 795-bp insert from pcrNMDAR2A was used to screen 1×10⁶ recombinants of a human hippocampus cDNA library (prepared by using random primers to synthesize cDNAs from hippocampus tissue and selecting fragments >2.0 kb for insertion into λgt10 vectors) and a human cerebellum cDNA library (random-primed library size-selected for fragments >2.8 kb in λgt10). Hybridization was performed in 5×SSPE, 5×Denhart's solution, 50% deionized formamide, 0.2% SDS, 200 μg/ml sonicated, denatured herring sperm DNA at 42° C. Washes were performed in 1×SSPE, 0.2% SDS at 55° C. The probe hybridized to 11 plaques from the hippocampus library and 8 plaques from the cerebellum library.

DNA sequence analysis and/or restriction enzyme mapping of 15 of the hybridizing plaques that were purified surprisingly revealed that they were more similar to rat NMDAR2C DNA than to rat NMDAR2A DNA. All of the clones were partial cDNAs (i.e., they lacked a translation initiation and/or termination codon) and were designated as NMDAR2C cDNAs. Comparison of the clones revealed that the human NMDAR2C subunit transcript is differentially processed.

Clones NMDA26, NMDA24, NMDA22 and NMDA21 (see FIG. 4) represent four basic clones that were identified, all of which are believed to be splice variants. Clone NMDA26 (nucleotides 1–3025 of Sequence ID No. 5) is used as a reference to which the other variants can be compared. Clone NMDA24 (Sequence ID No. 44) contains a 24-bp sequence (see Sequence ID No. 7) that is not present in NMDA26. Clone NMDA22 (Sequence ID No. 43) lacks 15 bp that are present in NMDA26, and clone NMDA21 (Sequence ID No. 41) lacks 51 bp that are present in NMDA26. Clones NMDA22 and NMDA24 both contain an 11-bp sequence (Sequence ID No. 9) that is not present in NMDA26 (between nucleotides 1116–1117 of Sequence ID No. 5). Introduction of this sequence into these clones (between nucleotides 1116–1117 of Sequence ID No. 5) disrupts the reading frame of the transcript and introduces a premature translation termination (i.e., STOP) codon into the transcript.

Clones NMDA26 and NMDA27 (see FIG. 4) are partial NMDAR2C cDNAs that contain 5' untranslated sequence, a translation initiation codon and some of the coding sequence. Clone NMDA26 contains 188 base pairs of 5' untranslated sequence whereas clone NMDA27 contains ~1.1 kb of 5' untranslated sequence. The sequences of the 5' untranslated regions of these two clones are identical for the first 15 nucleotides proceeding 5' of the translation initiation codon. However, beginning with the 16th nucleotide 5' of the translation initiation codon, the sequences of the two clones diverge (compare nucleotides 116–191 of Sequence ID No. 5 to nucleotides 1–74 of Sequence ID No. 12).

EXAMPLE 4

Preparation of Full-length NMDAR2C Subunit cDNA Constructs

Figure 5:
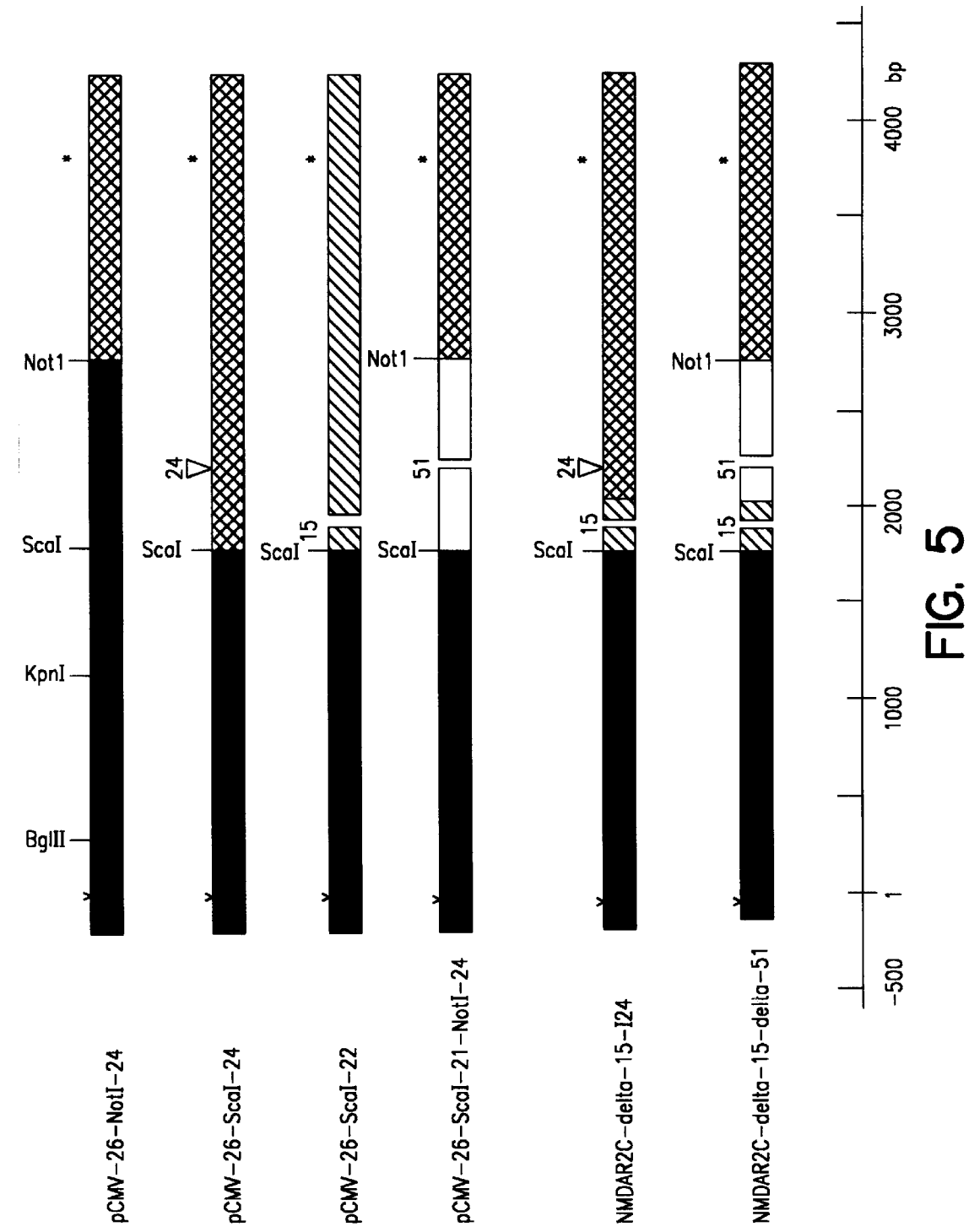
FIG. 5 is a schematic representation of full-length human NMDAR2C subunit subtypes of the invention, with partial restriction maps of each DNA. The full-length cDNAs are constructed by ligation of appropriate portions of the clones shown in FIG. 4. Regions of each full-length cDNA composed of nucleotide sequences corresponding to a particular clone are distinguished as solid, striped, cross-hatched or open boxes.

Portions of the partial NMDAR2C clones can be ligated in a variety of ways to generate constructs encoding full-length NMDAR2C subunit variants. The 5' end of each NMDAR2C cDNA can be contributed by NMDA26, whereas the 3' ends of the constructs are contributed by various combinations of clones NMDA21, NMDA22, and NMDA24. FIG. 5 depicts full-length NMDAR2C constructs and indicates the portions of the different clones that contribute to each construct.

For example, full-length constructs can be prepared using methods such as those described in Example 2 for preparing NMDAR1 constructs. Thus, clone inserts are transferred into a vector (e.g., pcDNA1) for ease of manipulation and then desired portions of the cDNAs are isolated by restriction enzyme digestion of the vectors. This can require several steps and/or partial digests if, for example, there are no unique restriction enzyme sites surrounding the desired portions of the cDNAs. The desired cDNA fragments are then ligated and incorporated into an expression plasmid such as pcDNA1 or pCMV-T7-2.

Figure 6A:
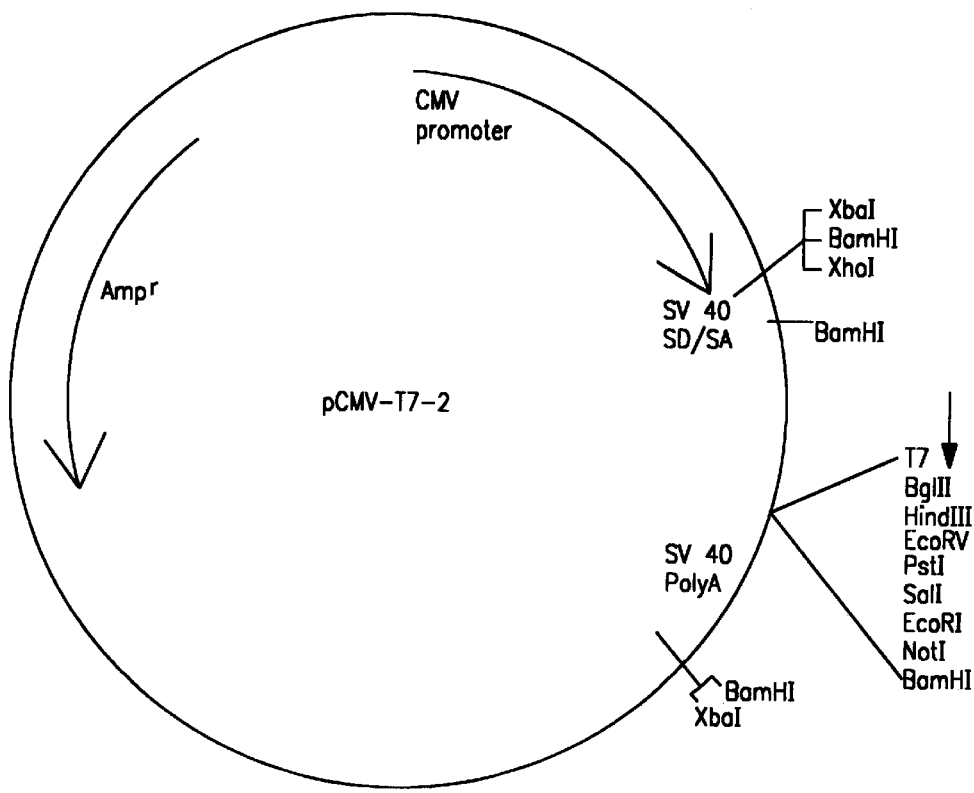
FIG. 6 presents restriction maps of CMV promoter-based vectors pCMV-T7-2 and pCMV-T7-3.
Figure 6B:
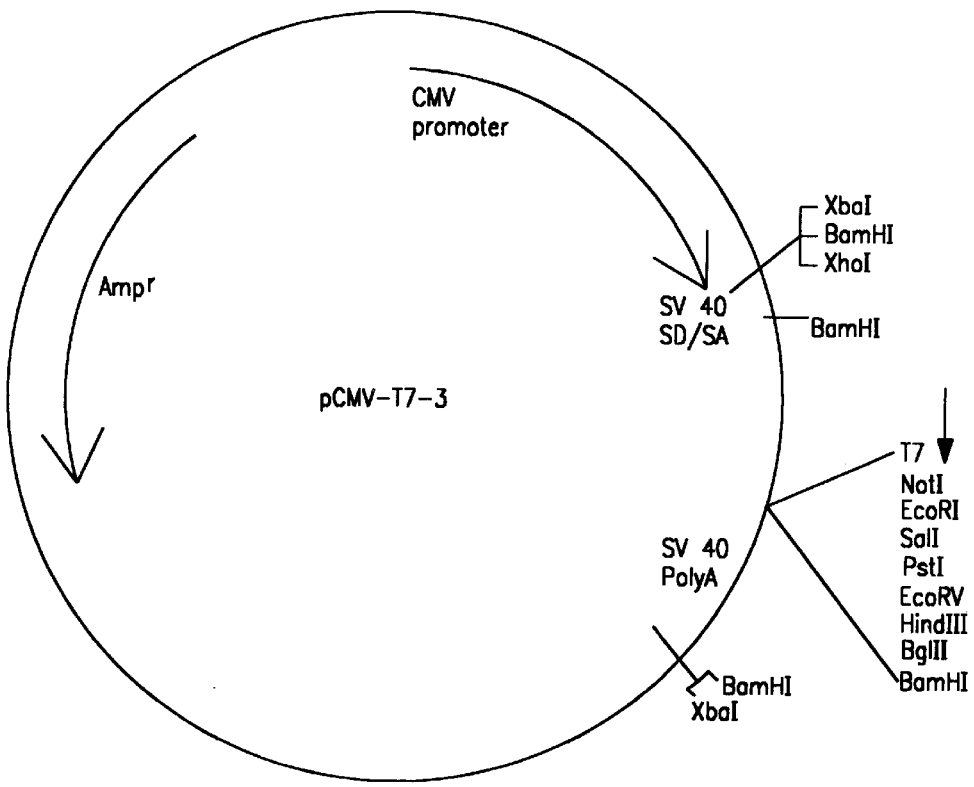

Plasmid pCMV-T7-2 (see FIG. 6) is a pUC19-based vector that contains a cytomegalovirus (CMV) promoter/enhancer, SV40 splice donor/splice acceptor sites located immediately downstream of the promoter, a T7 bacteriophage RNA polymerase promoter positioned downstream of the SV40 splice sites, an SV40 polyadenylation signal downstream of the T7 promoter, and a polylinker between the T7 promoter and the polyadenylation signal. This vector thus contains all the regulatory elements required for expression of heterologous DNA in a mammalian host cell, wherein the heterologous DNA has been incorporated into the vector at the polylinker. In addition, because the T7 promoter is located just upstream of the polylinker, this plasmid can be used for synthesis of in vitro transcripts of heterologous DNA that has been subcloned into the vector at the polylinker. Plasmid pCMV-T7-3, also depicted in FIG. 6, is identical to pCMV-T7-2 except that the order of the restriction enzyme sites in the polylinker is reversed. This plasmid can also be used for heterologous expression of NMDAR subunit DNA.

Construct pcDNA1-26-NotI-24-5'UT contains 188 base pairs of 5' untranslated sequence (nucleotides 1–188 of Sequence ID No. 5), the complete coding sequence of the first variant of the human NMDAR2C subunit (nucleotides 189–3899 of Sequence ID No. 5) and ~440 base pairs of 3' untranslated sequence (nucleotides 3900–4340 of Sequence ID No. 5). The NMDAR2C cDNA is contained within the polylinker of expression vector pcDNA1 for expression.

Construct pCMV-26-NotI-24 (Sequence ID No. 5) contains 49 base pairs of 5' untranslated sequence (nucleotides 140–188 of Sequence ID No. 5), the complete coding sequence of a first variant of the human NMDAR2C subunit (nucleotides 189–3899 of Sequence ID No. 5) and ~440 base pairs of 3' untranslated sequence (nuceotides 3900–4340 of Sequence ID No. 5). The NMDAR2C cDNA is contained within the polylinker of expression vector pCMV-T7-2 for expression.

Construct pCMV-26-ScaI-24 (Sequence ID No. 45) is identical to pCMV-26-NotI-24, except it contains 24-base pairs (Sequence ID No. 7) inserted between nucleotides 2350 and 2351 of Sequence ID No. 5.

Construct pCMV-26-ScaI-22 (Sequence ID No. 47) is identical to pCMV-26-NotI-24, except that it lacks 15-base pairs (nucleotides 1960-1974 of Sequence ID No. 5).

Construct pCMV-26-ScaI-21-NotI-24 (Sequence ID No. 49) is identical to pCMV-26-NotI-24, except that it lacks 51-base pairs (nucleotides 2351-2401 of Sequence ID No. 5).

Construct NMDAR2C-Δ15-I24 (Sequence ID No. 51) is identical to pCMV-26-NotI-24, except that it lacks 15-base pairs (i.e., nucleotides 1960–1974 of Sequence ID No. 5) and includes a 24-base pair sequence (i.e., Sequence ID No. 7; inserted between nucleotides 2350 and 2351 of Sequence ID No. 5).

Construct NMDAR2C-Δ15-Δ51 (Sequence ID No. 53) is identical to pCMV-26-NotI-24, except that it lacks 15-base pairs (i.e., nucleotides 1960–1974 of Sequence ID No. 5) and 51-base pairs (i.e., nucleotides 2351-2401 of Sequence ID No. 5).

Additional full-length NMDAR2C constructs can readily be prepared as described herein. For example, 5' untranslated sequence obtained from NMDA27 (instead of NMDA26) can be employed, and the 3' ends of the constructs can be contributed by various combinations of clones NMDA21, NMDA22, and NMDA24.

Several methods (e.g., nucleic acid amplification, RNase protection assays, etc.), as described in Example 2, can be employed to determine which NMDAR2C subunit variants are actually expressed in various human tissues.

Human NMDAR2C has 83.5% GC nucleotide content between nucleotides 2957 and 3166. To potentially enhance NMDAR2C subunit expression, the GC content in this region can be reduced while maintaining the native amino acid sequence. Synthetic DNAs can be made by oligonucleotide primer extension across this region. Four oligonucleotides, SE343 (Sequence ID No. 59), SE344 (Sequence ID No. 60), SE345 (Sequence ID No. 61), and SE346 (Sequence ID No. 62) were synthesized. These primers maintain the amino acid sequence of the human NMDAR2C receptor and some restriction sites, but lower the overall GC content of this region to 53.4%. The criteria for the modification of bases were: 1) to not have more than 4 guanine nucleotides in a row if at all possible, 2) to maintain the restriction cutting sites for NotI (nucleotides 2962–2969 of Sequence ID No. 5), AvaII (nucleotides 3069–3073 Sequence ID No.5), and AatII (nucleotides 3156–3161 of Sequence ID No. 5), 3) to reduce the secondary structure of the oligonucleotides as much as possible, 4) to not introduce any additional NotI, AvaII or AatII restriction sites into the sequence and 5) to have the basepair overlap between oligonucleotide pairs, {SE343 and SE344} or {SE345 and SE346} have a proposed melting temperature between 62°–66° C. The oligonucleotide pair SE343 and SE344 have complementary sequence from nucleotides 51–71 of Sequence ID Nos. 59 and 60. The oligonucleotide pair SE345 and SE346 have complementary sequence from nucleotides 42–61 of Sequence ID No. 61 and nucleotides 43–62 of Sequence ID No. 62, resepectively.

The primer pairs, {SE343 and SE344} and {SE345 and SE346}, are combined in a standard PCR reaction mixture, which contains 50 pmoles of each oligonucleotide, and are amplified according to the following PCR protocol:

Annealing temperature of 55° C. for 1 min, extension temperature of 72° C. for 2 min and melting temperature, 96° C. for 30 seconds for 30 cycles.

The resulting 121 bp PCR product from the primer pair SE343-SE344 is digested with NotI and AvaI, and the resulting 103 bp PCR product from the primer pair SE345-SE346 is digested with AvaI and AatII. These fragments are ligated into pCMV-NMDAR2C-26-NotI-24, which has been partially digested with both NotI and AatII due to the presence of additional NotI and/or AatII restriction sites in the vector sequence, to form pCMV-26-NotI-24-GCMOD. This construct, pCMV-26-NotI-24-GCMOD, contains nucleotides 140–2965 of Sequence ID No. 5, followed by the 195 nucleotides set forth in Sequence ID No. 63, and then nucleotides 3161 to 4340 of Sequence ID. No. 5.

EXAMPLE 5

Isolation of DNA Encoding Human NMDA Receptor NMDAR2A Subunits

Two human cDNA libraries were prepared using 5 different oligonucleotides (random and specific primers) to prime cDNA synthesis from RNA isolated from cerebellum tissue. The specific primer used for first-strand synthesis was SE162, nucleotides 904 to 929 of Sequence ID No. 10. cDNAs synthesized by random priming that ranged in size from 1.0–2.8 kb, and cDNAs synthesized by specific priming that ranged in size from 0.6–1.1 kb, were isolated and inserted into the λgt10 phage vector to generate the two libraries.

The random-primed library (3 x 106 recombinants) was screened for hybridization to the 795-base pair insert from pcrNMDAR2A (see Example 3) in 5X SSPE, 5×Denhart's solution, 50% deionized formamide, 0.2% SDS, 200 μg/ml sonicated, denatured herring sperm DNA at 42° C. Washes were performed in 1×SSPE, 0.2% SDS at 55° C. The probe hybridized to 11 plaques.

The specifically-primed library (6×10$^5$ recombinants) was screened for hybridization to oligonucleotide SE177 (nucleotides 859 to 884 of Sequence ID No. 10) in 6×SSPE, 5×Denhart's solution, 10% deionized formamide, 0.2% SDS, 200 μg/ml sonicated, denatured herring sperm DNA at 42° C. Washes were performed in 1×SSPE, 0.2% SDS at 50° C. The probe hybridized to 2 plaques.

Nine of the hybridizing plaques were purified and the inserts were characterized by restriction enzyme mapping and DNA sequence analysis. All clones contained partial cDNAs. Two of the clones, NMDA53 and NMDA54, contain the translation initiation codon and 320 base pairs and 88 base pairs, respectively, of 5' untranslated sequence. The sequences of four other clones, NMDA47, NMDA49, NMDA50 and NMDA51, along with those of NMDA53 and NMDA54, overlap to comprise ~70% of the human NMDAR2A subunit coding sequence (see nucleotides 1–3084 of Sequence ID No. 10).

To obtain clones containing the remaining ~1300 base pairs of 3' sequence needed to complete the NMDAR2A coding sequence, 6.6×10$^6$ recombinants of an additional human cDNA library (an amplified randomly primed cerebellum cDNA library with inserts ranging from 1.0–2.8 kb in length) were screened for hybridization to an oligonucleotide corresponding to the 3' end of clone NMDA51 (oligo SE171; nucleotide 3454 to 3479 of Sequence ID No. 10) using the same conditions as used for screening the specifically primed cerebellum cDNA library as described above. Four hybridizing plaques were purified and the inserts were characterized by DNA sequence analysis to determine if they contain the 3' end of the coding sequence and a translation termination codon. Two of the clones (NMDA57 and NMDA58, which were determined to be identical), contain a translation termination codon, as determined by DNA sequence analysis. Phage lysate containing clone NMDA57 were deposited under the provisions of the Budapest Treaty with the American Type Culture Collection (ATCC) on Apr. 13, 1993, and assigned Accession No. 75442.

EXAMPLE 6

Preparation of Full-Length NMDAR2A Subunit cDNA Constructs

Two separate constructs encoding a full-length NMDAR2A subunit (pCMV-hNMDAR2A-1(53) and pCMV-hNMDAR2A-2(54)) were prepared by ligating portions of the following partial NMDAR2A clones: NMDAR47, NMDAR50, NMDAR58 and either NMDAR53 or NMDAR54 (NMDA53 and NMDA54 differ only in the amount of 5' untranslated sequence contained in the clones. The inserts of clones NMDA47, NMDA50 and NMDA58 were isolated as EcoRI fragments and ligated with EcoRI-digested pCMV-T7-2 to create pNMDA47, pNMDA50 and pNMDA58, respectively. The inserts of clones NMDA53 and NMDA54 were isolated as XhoI fragments and ligated with SalI-digested pCMV-T7-2 to create pNMDA53 and pNMDA54, respectively.

pNMDA47 was digested with ScaI and NsiI to liberate an ~3,350-bp fragment containing a 3' portion of the β-lactamase gene, which encodes a protein which imparts ampicillin-resistance, and nucleotides 824–2415 of Sequence ID No. 10. This fragment was ligated with a ~2890-bp NsiI/ScaI fragment of pNMDA50 (containing a 5' portion of the β-lactamase gene and nucleotides 2416–3346 of Sequence ID No. 10) to generate pNMDA47+50.

The portion of pNMDA58 that encodes the 3' end of NMDAR2A contains two MscI sites. Because the 3' MscI site is cleaved in preference to the 5' MscI site, partial digestion of pNMDA58 was not an option. Thus, pNMDA58 was digested with ScaI/MscI, and the ~2020-bp fragment containing a 5' portion of the β-lactamase gene and a 3' portion of the insert (nucleotides 4751–4808 of Sequence ID No. 10) was isolated. This fragment was ligated to a ~4150-bp ScaI/MscI fragment of pNMDA47+50 (containing a 3' portion of the β-lactamase gene and nucleotides 824–3212 of Sequence ID No. 10) to generate pNMDA47+50+3'END58. This plasmid contained a complete δ-lactamase gene and nucleotides 824–3214 and 4751–4808 of Sequence ID No. 10. To add nucleotides 343–4750 of Sequence ID No. 10 to pNMDA47+50+ 3'END58, pNMDA58 was digested with MscI, and the isolated 1537-bp fragment consisting of nucleotides 3213–4750 of Sequence ID No. 10 was ligated to MscI-digested pNMDA47+50+3'END58. The resulting plasmid, pNMDA47+50+58, contained nucleotides 824–4808 of Sequence ID No. 10.

To generate two constructs containing identical NMDAR2A coding sequences but differing amounts of 51 untranslated sequence, pNMDA53 and pNMDA54 were digested with ScaI/EcoRI to liberate fragments containing a 3' portion of the β-lactamase gene and nucleotides 1–854 and 225–854 of Sequence ID No. 10, respectively. pNMDA47+50+58 was digested with ScaI/EcoRI (partial) and the 3954-bp fragment containing a 5' portion of the β-lactamase gene and nucleotides 855–4808 of Sequence ID No. 10 was separately ligated with the ScaI/EcoRI fragments of pNMDA53 and pNMDA54 to generate pCMV-hNMDAR2A-1(53) and pCMV-hNMDAR2A-2(54), respectively. These two constructs are identical except for the amount of 5' untranslated sequence contained in each. Both contain a full-length NMDAR2A-encoding sequence (nucleotides 311–4705 of Sequence ID No. 10) and 103 nucleotides of 3' untranslated sequence (nucleotides 4706–4808 of Sequence ID No. 10). pCMV-hDAR2A-1(53) contains 310 nucleotides of 5' untranslated sequence (nucleotides 1–310 of Sequence ID No. 10) , whereas pCMV-hNMDAR2A-2(54) contains 87 nt of 5' untranslated sequence (nucleotides 224–310 of Sequence ID No. 10). The NMDAR2A cDNA is operatively linked to the regulator elements of pCMV-T7-2 for expression in mammalian host cells.

There is no unique restriction site 3' of the NMDAR2A-specific DNA in pCMV-hNMDAR2A-1(53) that can be used to linearize the plasmid in order to prepare in vitro transcripts for injection into Xenopus oocytes. To make a construct that has a unique 3' restriction site (PCMV-hNMDAR2A-3(53)) , essentially the entire NMDAR2A-specific DNA of pCMV-hNMDAR2A-1(53) was transferred into vector pCMV-T7-3 as follows. pCMV-NMDAR2A-1 (53) was digested with NotI and the ~4.4-kb fragment was isolated and ligated with NotI-digested pCMV-T7-3 to generate pCMV-hNMDAR2A-3(53).

EXAMPLE 7

Isolation of DNA Encoding Human NMDA Receptor NMDAR2B Subunits

A human fetal brain λZAP cDNA library ($1 \times 10^6$ recombinants; Stratagene, La Jolla, Calif.) was screened for hybridization to a DNA fragment containing the entire rat NMDAR2B subunit coding sequence (see Monyer et al. (1992) Science 256:1217–1221). Hybridization was conducted in 50% deionized formamide, 5×Denhart's solution, 5×SSPE, 200 µg/ml sonicated, denatured herring sperm DNA and 0.2% SDS at 42° C. Washes were performed in 0.5×SSPE, 0.2% SDS at 65° C. One of the hybridizing clones excised from the human fetal brain library, NMDA81, containing a 5,435 bp insert and translation initiation and termination codons, encodes a full-length NMDAR2B subunit. This excised plasmid, which is in the pBluescript vector, was called pBS-hNMDAR2B.

NMDA81 was digested with EcoRI/EcoRV and the ~5.5-kbp fragment was isolated and ligated to EcoRI/EcoRV-digested pCMV-T7-3. The resulting construct, pCMVPL3-hNMDAR2B, contains the NMDAR2B coding sequence (nucleotides 210–4664 of Sequence ID No. 55), as well as 209 nucleotides of 5' untranslated sequence (nucleotides 1–209 of Sequence ID No. 55) and 339 nucleotides of 3' untranslated sequence (nucleotides 4665–5003 of Sequence ID No. 55). The NMDAR2B-encoding DNA in this construct is operatively linked to regulatory elements in pCMV-T7-3 for expression in mammalian host cells.

EXAMPLE 8

Isolation of DNA Encoding Human NMDA Receptor NMDAR2D subunits

A human fetal brain cDNA library ($1 \times 10^6$ recombinants; Stratagene, La Jolla, Calif.) was screened by subtraction screening methods for DNA encoding a human NMDAR2D receptor subunit. In this method, plaques were selected on the basis of weak or no hybridization to DNAs encoding human NMDAR2A, NMDAR2B and NMDAR2C subunits.

Initially, the library was screened for hybridization to pcrNMDAR2A (see Example 3) under low-stringency conditions (30% deionized formamide, 5×Denhart's solution, 5×SSPE, 200 ng/ml sonicated herring sperm DNA, 0.2% SDS at 42° C.). Washes were also performed using low-stringency conditions (2×SSPE, 0.2% SDS, 50° C.). The filters were stripped, then screened for hybridization to the pcrNMDAR2A fragment and to an ~1200 bp PstI fragment of DNA encoding a human NMDAR2B subunit (see Example 7) and an ~950 bp AccI fragment of DNA encoding a human NMDAR2C subunit (see Example 3) . These fragments contain DNA encoding all of the putative transmembrane domains of the subunits. Hybridization was performed under high-stringency conditions (50% deionized formamide, 5×Denhart's solution, 5×SSPE, 200 ng/ml sonicated herring sperm DNA, 0.2% SDS at 42° C.) as were washes (0.1×SSPE, 0.1% SDS, 65° C.).

Eighteen of the plaques that hybridized weakly to pcrNMDAR2A in the initial low stringency screening of the library hybridized only weakly or not at all to portions of DNA encoding human NMDAR2A, NMDAR2B and NMDAR2C subunits in the high stringency screening. The plaques were purified, and the insert fragments were characterized by DNA sequence analysis. One of the inserts, NMDA96, corresponds to the 3' half of the human NMDAR2D subunit gene coding sequence. The sequence of this clone is provided in Sequence ID No. 57.

To obtain clones containing the remaining ~2000 bp of 5' sequence needed to complete the NMDAR2D subunit coding sequence, the human fetal brain cDNA library was screened for hybridization to an ~831 bp SmaI fragment of the clone containing the 3' half of the NMDAR2D coding sequence under high stringency hybridization and washing with 0.5×SSPE, 0.2% SDS at 65° C. Nine hybridizing plaques were purified and analyzed by DNA sequencing, which revealed that none of the plaques contain DNA encoding a translation initiation codon and extending 3' to at least the 5' end of the clone containing the 3' half of the NMDAR2D coding sequence.

A human cDNA library was prepared using a specific oligonucleotide, SE296, to prime cDNA synthesis from RNA isolated from human fetal brain. The specific primer used for first-strand synthesis was SE296 (nucleotides 2920–2949 of Sequence ID No. 57). cDNAs synthesized by specific priming that were greater than 2.2 kb in size were isolated and inserted into the λZAPII phage vector to generate the library.

The specifically primed library ($1 \times 10^6$ recombinants) was screened for hybridization to the 831 bp SmaI fragment from NMDAR2D (nucleotides 2435–3265 of Sequence ID No. 57) in 5×SSPE, 5×Denhart's solution, 50% deionized formamide, 0.2% SDS, 200 µg/ml sonicated, denatured herring sperm DNA at 42° C. Washes were performed in 0.1×SSPE, 0.2% SDS at 65° C. One probe hybridized to 11 plaques.

Eleven of the hybridizing plaques were purified, and the inserts characterized by restriction enzyme mapping and DNA sequence analysis. Six of the clones (NMDA111, NMDA112, NMDA115, NMDA116, NMDA119 and NMDA121) contain the translation initiation codon and varying amounts of 5' untranslated sequence.

The sequences of these clones overlap with NMDA96 to constitute 100% of the human NMDAR2D subunit coding sequence (see nucleotides 485–4495 of Sequence ID No. 57).

The full-length hNMDAR2D construct was prepared using NMDA115 and NMDA96 cDNAs. NMDA115 and NMDA96 cDNAs are already in the pBlueScript vector, however the NMDA115 cDNA is in the sense orientation from the T7 promoter, while the NMDA96 cDNA is in the antisense orientation. For ease of subcloning the full-length construct, the NMDA96 cDNA was cloned into the sense orientation by digesting NMDA96 with EcoRI and screening the resulting clones for orientation (NMDAR96-T7). Within the complete human NMDAR2D sequence, there is a unique HindIII at nucleotides 2804 that was used to clone NMDA115 together with NMDA96. However, there is an additional HindIII site in the pBS polylinker at the 5' end of the NMDA115 cDNA. Therefore NMDA115 was fully digested with SpeI, a 3' polylinker site, and partially digested with HindIII. The resulting ~5.6 kb SpeI-HindIII fragment from pNMDA115 (pBS vector plus nucleotides 397–2804 of Sequence ID No. 57) was ligated with the 1.7 kb HindIII-SpeI fragment (nucleotides 2805–4651 of Sequence ID No. 57) from NMDA96-T7 to form pBS-hNMDAR2D. In vitro transcripts were prepared for co-injection into Xenopus oocytes to test for alteration of NMDAR1A currents.

The complete NMDAR2D insert is then transfered into the pMMTV-T7+ mammalian expression vector as a ~4.7 kb EcoRV/SpeI fragment. The EcoRV and SpeI restriction sites are in the multiple cloning region of the pBluscript vector.

In summary, construct NMDAR2D contains 88 base pairs of 5' untranslated sequence (nucleotides 397–484 in Sequence ID No. 57), the complete coding sequence for the NMDAR2D subunit (nucleotides 484–4495 of Sequence ID No. 57) as well as 200 base pairs of 3' untranslated sequence (nucleotides 4496–4695 of Sequence ID No. 57). The NMDAR2D subunit encoding sequence is operatively linked to the regulatory elements in pMMTV-T7 for expression in mammalian cells.

EXAMPLE 9

Expression of Recombinant Human NMDA Receptor Subunits on Oocytes

Xenopus oocytes were injected with in vitro transcripts prepared from constructs containing DNA encoding human NMDA receptor NMDAR1 and NMDAR2 subunits. Electrophysiological measurements of the oocyte transmembrane currents were made using the two-electrode voltage clamp technique (see e.g., Stuhmer (1992) Meth. Enzymol. 207:319–339).

A. Preparation of in vitro Transcripts

Recombinant capped transcripts of NMDA receptor subunit cDNAs contained in constructs NMDAR1A, NMDAR1-I63, NMDAR1-I63-Δ204, NMDAR1-Δ1087, NMDAR1-Δ363, and pCMV-26-NotI-24 were synthesized from linearized plasmids using the mCAP RNA Capping Kit (Cat. #200350, Stratagene, Inc., La Jolla, Calif.). For experiments in which NMDAR2A or NMDAR2B and NMDAR1 or NMDAR1-I63 transcripts were co-injected into Xenopus oocytes, the transcripts were synthesized from linearized constructs NMDAR1A, NMDAR1-I63, pCMV-hNMDAR2A-3(53), pCMV-26-NotI-24 and pBS-hNMDAR2B using mMessage mMachine (Ambion, catalog #1344, Austin, Tex.) The mass of each synthesized transcript was determined by UV absorbance and the integrity of each transcript was determined by electrophoresis through an agarose gel.

B. Electrophysiology

Xenopus oocytes were injected with 12.5–50 ng of one or more NMDA receptor subunit transcripts per oocyte. The preparation and injection of oocytes were carried out as described by Dascal [(1987) Crit. Rev. Biochem. 22:317–387]. Two-to-six days following mRNA injection, the oocytes were examined using the two-electrode voltage clamp technique. The cells were bathed in Ringer's solution (115 mM NaCl, 2.5 mM KCl, 1.8 mM $CaCl_2$, 10 mM HEPES, pH 7.3), and the membrane potential was clamped at −80 to −100 mV. Drugs were applied by pipetting 6.0 μl aliquots of drug-containing solution directly into the bath, or by using gravity-feed into a Warner Instruments chamber (volume=110 μl) at a flow rate of 8 ml/min. The data were sampled at 2–5 Hz with a Labmaster data acquisition board in a PC-386 using AXOTAPE version 1.2 (Axon Instruments, Foster City, Calif.) software. The data were exported to a laser printer or plotted using Sigmaplot version 5.0.

NMDA agonists, i.e., 10–30 μM glycine (gly) and 10–100 μM glutamate (glu) or 100–1000 μM NMDA, were applied to the bath. If a current response was observed, the agonists were washed from the bath and 0.1–1.0 mM $MgCl_2$ or 1 μM MK801 (Research Biochemicals, Inc., Natick, Mass.) (NMDA receptor antagonists) were applied before a second agonist application in order to determine whether the current was blocked by antagonists. Alternatively, $MgCl_2$ or MK-801 were applied during agonist-induced current flow. The results of multiple recordings are summarized in Table 1.

TABLE 1

Electrophysiological Analysis of Oocytes Injected with NMDA Receptor Subunit Transcripts

| Transcript (ng injected) | No. Oocytes Responding | Agonists | Peak Current Amplitude |
| --- | --- | --- | --- |
| NMDAR1A (12.5) | 6 of 8[a] | 10 μM gly + 10 μM glu | 3–40 nA* |
| NMDAR1A (12.5) | 2 of 2[a] | 10 μM gly + 100 μM NMDA | 3–8 nA |
| NMDAR1A (12.5) | 0 of 9[a] | 10 μM gly + 10 μM glu | |
| NMDAR1A (50) | 0 of 1[a] | 20 μM gly + 20 μM glu | |
| NMDAR1A (40) | 4 of 10 | 10 μM gly + 10 μM glu | 21.3 ± 20.9 nA* |
| NMDAR1A (40) | 1 of 5 | 10 μM gly + 100 μM NMDA | 24 nA* |
| NMDAR1A (40) | 1 of 1 | 10 μM gly + 100 μM NMDA | 15.4 nA |
| NMDAR1A (30) | 4 of 9 | 10 μM gly + 50 μM glu | 10.6 ± 11.7 nA* |
| NMDAR1A (30) | 0 of 8 | 10–20 μM gly + 10–100 μM glu | |
| NMDAR1A (30) | 1 of 4 | 20 μM gly + 100 μM NMDA | 10.5 nA |
| NMDAR1A (25–50) | 3 of 3 | 30 μM gly + 100 μM glu | 3–10 nA |
| NMDAR1-I63 (12.5) | 1 of 5[a] | 10 μM gly + 10 μM glu | ~30 nA* |
| NMDAR1-I63 (50) | 0 of 4[a] | 10 μM gly + 10 μM glu | |
| NMDAR1-I63 (40) | 4 of 5 | 10 μM gly + 10 μM glu | 13.4 ± 7.1 nA[+] |
| NMDAR1-I63 (40) | 3 of 3 | 10 μM gly + 20 μM glu | 17.4 ± 3.7 nA[+] |
| NMDAR1-I63 (40) | 1 of 1 | 10 μM gly + 100 μM glu | 28 nA |
| NMDAR1-I63 (40) | 1 of 1 | 10 μM gly + 10 μM NMDA | 1.4 nA[+] |
| NMDAR1-I63 (25–50) | 3 of 3 | 10 μM gly + 100 μM glu | 3–5 nA |
| NMDAR1-I63 (40) | 7 of 10 | 10 μM gly + 100 μM NMDA | 8.1 ± 3.0 nA[+] |
| NMDAR1-I63 (40) | 1 of 2 | 10 μM gly + 1000 μM NMDA | 16.4 nA[+] |
| NMDAR1-I63-Δ204 (12.5) | 0 of 8[a] | 10 μM gly + 10 μM glu | |
| NMDAR1-I63-Δ204 (50) | 1 of 5[a] | 20 μM gly + 20 μM glu | ~50 nA |
| NMDAR1-Δ1087 (50) | 3 of 13 | 10 μM gly + 10 μM glu | 4–11 nA* |
| NMDAR1A (39) + pCMV-26-NotI-24 (39) | 1 of 5 | 10 μM gly + 50 μM glu | 10 nA |
| NMDAR1A (30) + pCMV-26-NotI-24 (30) | 0 of 7 | 10 μM gly + 20 μM glu | |

TABLE 1-continued

Electrophysiological Analysis of Oocytes Injected with
NMDA Receptor Subunit Transcripts

| Transcript (ng injected) | No. Oocytes Responding | Agonists | Peak Current Amplitude |
|---|---|---|---|
| NMDAR1A (32) + pCDNA1-26-NotI-24-5'UT (50) | 4 of 5 | 10 μM gly + 10 μM glu | 15.8 ± 2.6 μA |
| NMDAR1A (25–50) + pCMV-hNMDAR2A-3(53) (25–50) | 16 of 29 | 30 μM gly + 100 μM glu | 40 nA–3.4 μA |
| NMDAR1-I63 (25–50) + pCMV-hNMDAR2A-3(53) (25–50) | 6 of 11 | 10 μM gly + 100 μM glu | 10–100 nA |
| NMDAR1A (25) + pBS-hNMDAR2B (25) | 4 of 5 | 30 μM gly + 30 μM glu | >100 nA |
| NMDAR1A (50) + pCMV-hNMDAR2A-3 (50) + pCMV-26-NotI-24 (50) | 15 of 22 | 100 μM NMDA + 30 μM gly or 100 μM NMDA + 100 μM gly | 137.7 nA 1340.1 nA |

<sup>a</sup>Oocytes were unhealthy (i.e., the holding current was large)
*The agonist-induced currents in at least 1 cell were blocked by 100 μM MgCl$_2$.
<sup>+</sup>The agonist-induced currents in at least 1 cell were blocked by 1.0 'μM MK801.

Analysis of the results shown in Table 1 indicates that, in general, the NMDA agonist-induced currents were blocked by either MgCl$_2$ or MK801.

Oocytes injected with transcripts (12.5 to 65 ng) of the NMDAR-1 subunit-encoding inserts of constructs NMDAR1A, NMDAR1-I63 or NMDAR1-Δ363 were further analyzed to evaluate human NMDA receptor sensitivity to glutamate and NMDA. The two-electrode voltage clamp methods described above were used to measure current in the cells.

To determine glutamate and NMDA sensitivity of the recombinant human NMDA receptors, various concentrations of glutamate (0.1–100 μM) or NMDA (3–1000 μM) were applied to the bath (in the presence of 10–30 μM glycine) and the current response was recorded. The bath was flushed between agonist applications. Intermediate test applications of 10 μM glycine plus 10 μM glutamate were included in the experiments to monitor the receptors for run-down (i.e., inactivation of receptors that have been repeatedly activated during prolonged electrophysiological recording). The data were used to generate dose-response curves from which EC$_{50}$ values for the two agonists were calculated. Glycine sensitivity was determined in the same manner except that various concentrations (0.1–100 μM) of glycine were co-applied with 100 μM NMDA.

The EC$_{50}$ values determined for glutamate stimulation of NMDA receptors expressed in oocytes injected with NMDAR1A, NMDAR1-I63 or NMDAR1-Δ363 transcripts were 0.4, 0.6 and 0.5 μM, respectively. The EC$_{50}$ values determined for NMDA stimulation of NMDA receptors expressed in oocytes injected with NMDAR1A, NMDAR1-I63 or NMDAR1-Δ363 transcripts were 6.3, 10.9 and 11.9 μM, respectively.

There was a marked potentiation of the current magnitude in response to glutamate and glycine in oocytes co-injected with in vitro transcripts of pCMV-hNMDAR2A-3(53) and NMDAR1A or NMDAR1-I63 compared to the currents recorded in oocytes injected with transcripts of either NMDAR1A or NMDAR1-I63 alone. Similarly, there was a marked potentiation of the current magnitude in response to glutamate and glycine in oocytes co-injected with in vitro transcripts of NMDAR1A and pBS-hNMDAR2B compared to the currents recorded in oocytes injected with only the NMDAR1A transcript.

To investigate the pharmacological properties of human NMDA receptors generated by coexpression of the human NMDAR1A, NMDAR2A and NMDAR2C subunits, oocytes were co-injected with 50 ng each of in vitro transcripts prepared from the NMDAR1A, pCMV-hNMDAR2A-3, and pCMV-26-NotI-24 (NMDAR2C) constructs. The sensitivity of the recombinant heteromeric receptors to glycine and NMDA was determined as described above. The EC$_{50}$ for glycine activation of inward currents in these recombinant oocytes was calculated from the dose-response curve to be 0.87±0.24 μM (mean±S.D. of 4 oocytes), which was significantly different than the EC$_{50}$ calculated for glycine sensitivity of oocytes injected with 50 ng each of in vitro transcripts of NMDAR1A and pCMV-hNMDAR2A-3 alone (1.9+0.26 μM, ; p=0.0002, one-tailed t-test) . The sensitivity to NMDA also increased when human NMDAR2C was co-expressed with human NMDAR1A and NMDAR2A subunits. The EC$_{50}$ for NMDA was shifted from 30.2+9.4 μM for oocytes co-injected with 50 ng each of in vitro transcripts of NMDAR1A and pCMV-hNMDAR2A-3 to 11.9+5.2 μM for oocytes co-injected with 50 ng each of in vitro transcripts of NMDAR1A, pCMV-hNMDAR2A-3 and pCMV-26-NotI-24 (mean±S.D. of 4 oocytes).

EXAMPLE 10

Recombinant Expression of Human NMDA Receptor Subunits in Mammalian Cells

Mammalian cells, such as human embryonic kidney (HEK293) cells can be transiently and/or stably transfected with DNA encoding human NMDA receptor subunits (e.g., DNA encoding an NMDAR1 subunit or DNA encoding an NMDAR1 subunit and DNA encoding an NMDAR2 subunit such as pCMV-26-NotI-24, pCMV-hNMDAR2A-3(53) or pCMVPL3-hNMDAR2B). Transfectants are analyzed for expression of NMDA receptors using various assays, e.g., northern blot hybridization, electrophysiological recording of cell currents, Ca$^{2+}$-sensitive fluorescent indicator-based assays and [$^3$H]-MK801 binding assays.

A. Transient Transfection of HEK Cells

Two transient transfections were performed. In one transfection, HEK 293 cells were transiently transfected with DNA encoding an NMDAR1 (construct NMDAR1A)

subunit. In another transfection, HEK 293 cells were transiently co-transfected with DNA encoding NMDAR1 (construct NMDAR1A) and NMDAR2C (pCMV-26-NotI-24) subunits. In both transfections, ~2×10⁶ HEK cells were transiently transfected with 19 μg of the indicated plasmid(s) according to standard $CaPO_4$ transfection procedures [Wigler et al. (1979) *Proc. Natl. Acad. Sci. USA* 76:1373–1376]. In addition, 1 μg of plasmid pCMVβgal (Clontech Laboratories, Palo Alto, Calif.), which contains the *Escherichia coli* β-galactosidase gene fused to the CMV promoter, were co-transfected as a reporter gene for monitoring the efficiency of transfection. The transfectants were analyzed for β-galactosidase expression by direct staining of the product of a reaction involving β-galactosidase and the X-gal substrate [Jones (1986) *EMBO* 5:3133–3142]. Transfectants can also be analyzed for β-galactosidase expression by measurement of β-galacrosidase activity [Miller (1972) in *Experiments in Molecular Genetics*, pp.352–355, Cold Spring Harbor Press].

The efficiency of these transfections of HEK cells was typical of standard efficiencies (i.e., ~50%).

B. Stable Transfection of Mammalian Cells

Mammalian cells, such as HEK 293 cells, can be stably transfected using the calcium phosphate transfection procedure [*Current Protocols in Molecular Biology*, Vol. 1, Wiley Inter-Science, Supplement 14, Unit 9.1.1–9.1.9 (1990)]. Ten-cm plates, each containing 1–2×10⁶ cells, are transfected with 10 ml of DNA/calcium phosphate precipitate in media containing approximately 19 μg of NMDA receptor subunit-encoding DNA and 1 μg of DNA encoding a selectable marker, for example, neomycin-resistance gene (i.e., pSv2neo) . After ~14 days of growth in media containing typically 1 μg/ml G418, colonies form and are individually isolated using cloning cylinders. The isolates are then subjected to limiting dilution and screened to identify those that express NMDA receptors using, for example, methods described below.

C. Analysis of Transfectants

1. Northern Blot Hybridization Analysis

Total RNA was isolated from ~1×10⁷ HEK cells co-transfected with NMDAR1 and pCMV-26-NotI-24, and 5–10 μg of RNA was used for northern hybridization analysis. Fragments from human neuronal NMDAR subunit-encoding plasmids were randomly primed and labeled with ³²P-dCTP Klenow incorporation and used as probes. The northern blot hybridization and wash conditions were as follows:

hybridization in 5×SSPE, 5×Denhart's solution, 50% formamide, at 42° C. followed by washing in 0.2× SSPE, 0.1% SDS, at 65° C.

Results of these studies revealed the transfectants expressed detectable levels of NMDAR1 and NMDAR2C mRNA of the appropriate size (based on the size of the cDNAs).

2. Fluorescent Indicator-Based Assays

Activation of ligand-gated NMDA receptors by agonists leads to an influx of cations (both monovalent and divalent), including $Ca^{2+}$, through the receptor channel. Calcium entry into the cell through the channel can in turn induce release of calcium contained in intracellular stores. Monovalent cation entry into the cell through the channel can also result in an increase in cytoplasmic calcium levels through depolarization of the membrane and subsequent activation of voltage-dependent calcium channels. Therefore, methods of detecting transient increases in intracellular calcium concentration can be applied to the analysis of functional NMDA receptor expression. One method for measuring intracellular calcium levels relies on calcium-sensitive fluorescent indicators.

Calcium-sensitive indicators, such as fluo-3 (Catalog No. F-1241, Molecular Probes, Inc., Eugene, Oreg.) are available as acetoxymethyl esters which are membrane permeable. When the acetoxymethyl ester form of the indicator enters a cell, the ester group is removed by cytosolic esterases, thereby trapping the free indicator in the cytosol. Interaction of the free indicator with calcium results in increased fluorescence of the indicator; therefore, an increase in the intracellular $Ca^{2+}$ concentration of cells containing the indicator can be expressed directly as an increase in fluorescence. An automated fluorescence detection system for assaying NMDA receptors has been described in commonly assigned pending U.S. patent application No. 07/812,254 and corresponding PCT Patent Application No. US92/11090, incorporated by reference herein in their entirety.

Mammalian cells that have been transfected with DNA encoding NMDAR1 or NMDAR1 and NMDAR2 subunits can be analyzed for expression of functional recombinant NMDA receptors using the automated fluorescent indicator-based assay. The assay procedure is as follows.

Untransfected mammalian host cells (or host cells transiently transfected with pCMV-T7-2) and mammalian cells that have been transfected with NMDAR1 ±NMDAR2 subunit DNA are plated in the wells of a 96-well microtiter dish (Nunc Catalog No. 1-6708, available through Alameda Industries, Escondido, Calif.) that has been precoated with poly-L-lysine at a density of 2.5×10⁵ cells/well and loaded with fluo-3 by incubation for 2 hours at 20° C. in a medium containing 20 μM fluo-3, 0.2% Pluronic F-127 in HES (125 mM NaCl, 5 mM KCl, 1.8 mM $CaCl_2$, 0.62 mM $MgCl_2$, 20 mM glucose, 20 mM HEPES, pH 7.4). The cells are then washed with assay buffer (i.e. HBS). The microtiter dish is then placed into a fluorescence plate reader (e.g., Fluoroskan II, Lab Products International, Ltd., Raleigh, N.C.) and the basal fluorescence of each well is measured and recorded before addition of 10 μM glycine and 10 μM glutamate to the wells. The fluorescence of the wells is monitored repeatedly (75 readings at 0.63-sec intervals) following addition of agonist.

The fluorescence of the untransfected host cells preferably will not change after addition of glycine and glutamate, i.e., the host cells should not express endogenous excitatory amino acid receptors. The fluorescence of mammalian cells transfected with NMDAR1 ±NMDAR2 subunit DNA will increase after addition of glycine and glutamate if a sufficient number of functional NMDA receptors are expressed at the cell surface, and fluorescence readings are taken rapidly.

The resting potential of the membrane of some mammalian host cells may be relatively positive (e.g., –35 mV). Because activation of some NMDA receptors may be significantly reduced at relatively positive potentials, it may be necessary to lower the resting potential of the membrane of cells transfected with human NMDA receptor subunit-encoding DNAs prior to assaying the cells for NMDA receptor activity using the fluorescent indicator-based assay. This may be accomplished by adding valinomycin (~10 μM) to the transfected cells prior to adding NMDA receptor agonists to initiate the assay.

3. NMDA Receptor Ligand Binding Assays

Mammalian cells transfected with NMDAR1±NMDAR2 subunit DNAs can be analyzed for [³H]-MK801 binding. An additional ligand-binding assay for NMDA receptors using ³H-CGP39653 is also described below. Rat brain membranes are included in the binding assays as a positive control.

a. Preparation of Membranes i. Buffy Coat Homogenate from Rat Cerebral Cortex

Buffy coat membranes are prepared from rat brain cortices as described by Jones et al. [(1989) *J. Pharmacol. Meth.* 21:161]. Briefly, cortices from ten freshly thawed frozen rat brains are dissected and weighed. The tissue is homogenized in 20 volumes of 0.32M ice-cold sucrose in a glass homogenizing tube using a Teflon pestle. The suspension is centrifuged at 1,000×g for 10 minutes at 4° C. The supernatant is decanted and centrifuged at 20,000×g for 20 minutes at 4° C. The pellet is resuspended in 20 volumes of ice-cold distilled water with a Polytron for 30 sec at setting 6. The suspension is centrifuged at 8,000×g for 20 minutes at 4° C. The buffy coat pellet is rinsed gently with supernatant and then recentrifuged at 48,000×g for 20 minutes at 4° C. The pellet is resuspended in 20 volumes of ice-cold distilled water with a Polytron and centrifuged again at 48,000×g for 20 minutes. The wash step is repeated once more. The final suspension is divided into aliquots, centrifuged. Each pellet can be stored frozen at −20° C. for 12 hrs or more before use.

ii. Membranes from Transfected and Untransfected Mammalian Cells

In order to prepare membranes from transfected and untransfected mammalian cells, the cells are scraped from the tissue culture plates, and the plates are rinsed with 5 ml of PBS (phosphate-buffered saline: 137 mM NaCl, 2.7 mM KCl, 10 mM $Na_2HPO_4$, 1.7 mM $KH_2PO_4$). The cells are centrifuged at low speed in a table-top centrifuge, and the cell pellet is rinsed with PBS. The cell pellet is resuspended in 20 ml of 10 mM Hepes buffer, pH 7.4, using a Polytron at setting 3–6 for 30 seconds. The cell suspension is centrifuged at 48,000×g for 20 minutes at 4° C. The supernatant is discarded, and the pellet is kept frozen for 12 hrs or more at −20° C.

b. [³H]-MK801 Binding to NMDA Receptors

The binding of [³H]-MK801 to NMDA receptors is carried out as described by Wong et al. [(1986) *Proc. Natl. Acad. Sci. USA* 83:7104], with a few minor changes. Thus, on the day of the assay, the rat brain and mammalian cell (transfected and untransfected) membrane pellets are resuspended in 50 volumes of 10 mM Hepes buffer, pH 7.4, using a 10-ml syringe and a 21-gauge needle, and incubated for 20 minutes at 37° C. The supernatant is centrifuged at 48,000×g for 20 minutes at 4° C. The pellet is resuspended in 2 ml of 10 mM Hepes, pH 7.4 and centrifuged as described above. The wash step is repeated once more, and the pellet is resuspended in 10 ml of 10 mM Hepes, pH 7.4. The protein concentration is determined using the Biorad Bradford reagent. The pellet is finally resuspended in the assay buffer (10 mM Hepes, pH 7.4) at 1 mg/ml.

For binding studies, the membrane suspension is incubated in duplicate with 2.5 nM [³H]-MK801 (New England Nuclear, Boston, Mass.) in a total volume of 0.5 ml assay buffer (10 mM Hepes, pH 7.4) in the presence and absence of 10 μM glutamate and 10 μM glycine for 60 or 120 min at 23° C. Bound radioactivity is separated from free radioactivity by rapid filtration through Whatman GF/C filters which are presoaked for 2–3 hrs in 0.05% polyethylenimine. The filters are washed twice with 3 ml ice-cold assay buffer. The filters are dried and transferred to scintillation vials, each containing 10 ml of scintillation fluid. The vials are vortexed, and the radioactivity is measured in a Beckman scintillation counter. The nonspecific binding observed in the presence of 10 μM MK801 is subtracted from the total binding in order to determine the specific binding.

Rat brain cortical buffy coat membranes displayed specific saturable binding of [³H]-MK801. In the presence of glycine and glutamate, the ratio of total-to-nonspecific binding (S:N ratio) was 28:1, whereas in the absence of glutamate and glycine the S:N ratio was 5:1. Thus, the binding of MK801 to rat NMDA receptors is potentiated by glutamatergic agonists. Scatchard analysis of [³H]-MK801 binding to rat brain membranes indicated that the sensitivity of the assay was 90 fmoles of receptor.

c. [³H]-CGP39653 Binding to NMDA Receptors

The binding of [³H]-CGP39653 to rat brain membranes is carried out as described by Sills et al. [(1991) *Eur. J. Pharmacol.* 192:19]. The buffy coat membrane pellet is resuspended in 50 volumes of 5 mM Tris-HCl containing 10 mM EDTA, pH 7.7, and incubated for 10 min. at 37° C. The supernatant is centrifuged at 48,000×g for 10 min. at 4° C. The wash step is repeated once and the pellet is resuspended in 10 ml of 5 mM Tris-HCl containing 10 mM EDTA, pH 7.7. This rat brain membrane suspension is incubated in duplicate or triplicate with 2.0 nM [³H]-CGP39653 (New England Nuclear) in a total volume of 0.5 ml assay buffer (5 mM Tris-HCl, pH 7.7) for 60 min at 0° C. Nonspecific binding is determined in the presence of 100 μM glutamate. Bound radioactivity is separated from the free by vacuum filtration through GF/C filters which are presoaked for 2–3 hrs in 0.05% polyethylenimine, using the filtration manifold. Unbound radioactivity is removed with two washes of 3 ml each of ice-cold buffer. The filters are dried and transferred to scintillation vials, each containing 10 ml of scintillation fluid. The vials are vortexed, and the radioactivity is measured in a Beckman scintillation counter. The nonspecific binding observed in the presence of 100 μM glutamate is subtracted from the total binding to determine the specific binding.

[³H]-CGP39653 binding was first measured as a function of membrane concentration. Specific binding increased linearly with increasing membrane concentration up to 200 μg of protein in the presence of 2 nM [³H]-CGP39653.

Saturation analysis of [³H]-CGP39653 binding was carried out by incubating 150 μg of rat buffy coat homogenate with increasing concentrations of [³H]-CGP39653 for 60 min at 4° C. Scatchard analysis indicated a single class of binding sites with a $B_{max}$ value of 0.69±0.09 pmoles/mg and a $K_d$ value of 12.3±0.12 nM.

While the invention has been described in detail with reference to certain preferred embodiments thereof, it will be understood that modifications and variations are within the spirit and scope of that which is described and claimed.

Summary of Sequences

Sequence ID No. 1 is a nucleotide sequence encoding a human N-methyl-D-aspartate (NMDA) receptor subunit, NMDAR1A, and the deduced amino acid sequence thereof.

Clone NMDA10 encodes a 3083 nucleotide sequence comprising nucleotides 320–3402 of Sequence ID No. 1. Thus, this sequence encoded by the NMDA10 clone differs from Sequence ID No. 1 in that it does not contain the 319 5' nucleotides, nor the 896 3' nucleotides thereof.

Sequence ID No. 13 is a 3155 nucleotide sequence encoded by clone NMDA11, comprising nucleotides 1–2961, plus nucleotides 3325–3518 of Sequence ID No. 1. Thus, Sequence ID No. 13 differs from Sequence ID No. 1 by the deletion of 363 nucleotides from the 3' portion thereof (i.e., by the deletion of nucleotides 2962–3324 of Sequence ID No. 1), and further by the lack of the 781 terminal 3' nucleotides of Sequence ID No. 1.

Sequence ID No. 15 is a 2542 nucleotide sequence encoded by clone NMDA7, comprising nucleotides 556–831 of Sequence ID No. 1, plus an additional 63 nucleotides (set forth in Sequence ID No. 3) and nucleotides 832–984, 1189–2961 and 3325–3599 of Sequence ID No. 1. Thus, Sequence ID No. 15 differs from Sequence ID No. 1 in that it does not contain the 555 5'-most nucleotides thereof, it does not contain the 204 nucleotides set forth as nucleotides 985–1188 of Sequence ID No. 1, it does not contain the 363 3' nucleotides set forth as nucleotides 2962–3324 of Sequence ID No. 1, and it does not contain the 700 3'-most nucleotides of Sequence ID No. 1, while it does contain an additional 63 nucleotides (Sequence ID No. 3) inserted between nucleotides 831 and 832 of Sequence ID No. 1.

Sequence ID No. 17 is a 593 nucleotide sequence encoded by clone NMDA3, comprising nucleotides 2617–2961, plus nucleotides 4049–4298 of Sequence ID No. 1. Thus, Sequence ID No. 17 differs from Sequence ID No. 1 in that it does not contain the 2616 5' nucleotides thereof, and by the deletion of 1087 nucleotides from the 3' portion thereof (i.e., by the deletion of nucleotides 2962–4048 of Sequence ID No. 1).

Sequence ID No. 19 is a nucleotide sequence encoding human NMDA receptor subunit NMDAR1-Δ363, comprising nucleotides 1–2961, plus nucleotides 3325–4298 of Sequence ID No. 1. Thus, Sequence ID No. 19 differs from Sequence ID No. 1 in that it does not contain the 363 nucleotides set forth as nucleotides 2962–3324 of Sequence ID No. 1.

Sequence ID No. 21 is a nucleotide sequence encoding human NMDA receptor subunit NMDAR1-Δ1087, comprising nucleotides 1–2961, plus nucleotides 4049–4298 of Sequence ID No. 1. Thus, Sequence ID No. 21 differs from Sequence ID No. 1 in that it does not contain the 1087 nucleotides set forth as nucleotides 2962–4048 of Sequence ID No. 1.

Sequence ID No. 23 is a nucleotide sequence encoding human NMDA receptor subunit NMDAR1-I63. Sequence ID No. 23 is the same as Sequence ID No. 1, further comprising an additional 63 nucleotides (set forth in Sequence ID No. 3) inserted between nucleotides 831 and 832 of Sequence ID No. 1.

Sequence ID No. 25 is a nucleotide sequence encoding human NMDA receptor subunit NMDAR1-I63-Δ204. Sequence ID No. 25 is the same as Sequence ID No. 23, except Sequence ID No. 25 does not contain the 204 nucleotides set forth as nucleotides 985–1188 of Sequence ID No. 1.

Sequence ID No. 27 is a nucleotide sequence encoding human NMDA receptor subunit NMDAR1-I63-Δ204-Δ363. Sequence ID No. 27 is the same as Sequence ID No. 25, except Sequence ID No. 27 does not contain the 363 nucleotides set forth as nucleotides 2962–3324 of Sequence ID No. 1.

Sequence ID No. 29 is a nucleotide sequence encoding human NMDA receptor subunit NMDAR1-Δ204. Sequence ID No. 29 is the same as Sequence ID No. 1, except Sequence ID No. 29 does not contain the 204 nucleotides set forth as nucleotides 985–1188 of Sequence ID No. 1.

Sequence ID No. 31 is a nucleotide sequence encoding human NMDA receptor subunit NMDAR1-Δ204-Δ363. Sequence ID No. 31 differs from Sequence ID No. 1 in that Sequence ID No. 31 does not contain the 204 nucleotides set forth as nucleotides 985–1188 of Sequence ID No. 1, nor the 363 nucleotides set forth as nucleotides 2962–3324 of Sequence ID No. 1.

Sequence ID No. 33 is a nucleotide sequence encoding human NMDA receptor subunit NMDAR1-Δ204-Δ1087. Sequence ID No. 33 differs from Sequence ID No. 1 in that Sequence ID No. 33 does not contain the 204 nucleotides set forth as nucleotides 985–1188 of Sequence ID No. 1, nor the 1087 nucleotides set forth as nucleotides 2962–4048 of Sequence ID No. 1.

Sequence ID No. 35 is a nucleotide sequence encoding human NMDA receptor subunit NMDAR1-I63-Δ363. Sequence ID No. 35 is the same as Sequence ID No. 23 except Sequence ID No. 35 does not contain the 363 nucleotides set forth as nucleotides 2962–3324 of Sequence ID No. 1.

Sequence ID No. 37 is a nucleotide sequence encoding human NMDA receptor subunit NMDAR1-I63-Δ1087. Sequence No. 37 is the same as Sequence ID No. 23 except Sequence ID No. 37 does not contain the 1087 nucleotides set forth as nucleotides 2962–4048 of Sequence ID No. 1.

Sequence ID No. 39 is a nucleotide sequence encoding human NMDA receptor subunit NMDAR1-I63-Δ204-Δ1087. Sequence ID No. 39 is the same as Sequence ID No. 25, except Sequence ID No. 39 does not contain the 1087 nucleotides set forth as nucleotides 2962–4048 of Sequence ID No. 1.

Sequence ID No. 2 is the amino acid sequence of the NMDA receptor subunit set forth in Sequence ID No. 1.

Sequence ID No. 14 is the amino acid sequence of an NMDA receptor subunit encoded by the nucleotide sequence of Sequence ID No. 13.

Sequence ID No. 16 is the amino acid sequence of a portion of an NMDA receptor subunit as encoded by the nucleotide sequence of Sequence ID No. 15.

Sequence ID No. 18 is the amino acid sequence of a portion of an NMDA receptor subunit as encoded by the nucleotide sequence of Sequence ID No. 17.

Sequence ID No. 20 is the amino acid sequence of an NMDA receptor subunit encoded by the nucleotide sequence of Sequence ID No. 19.

Sequence ID No. 22 is the amino acid sequence of an NMDA receptor subunit encoded by the nucleotide sequence of Sequence ID No. 21.

Sequence ID No. 24 is the amino acid sequence of an NMDA receptor subunit encoded by the nucleotide sequence of Sequence ID No. 23.

Sequence ID No. 26 is the amino acid sequence of an NMDA receptor subunit encoded by the nucleotide sequence of Sequence ID No. 25.

Sequence ID No. 28 is the amino acid sequence of an NMDA receptor subunit encoded by the nucleotide sequence of Sequence ID No. 27.

Sequence ID No. 30 is the amino acid sequence of an NMDA receptor subunit encoded by the nucleotide sequence of Sequence ID No. 29.

Sequence ID No. 32 is the amino acid sequence of an NMDA receptor subunit encoded by the nucleotide sequence of Sequence ID No. 31.

Sequence ID No. 34 is the amino acid sequence of an NMDA receptor subunit encoded by the nucleotide sequence of Sequence ID No. 33.

Sequence ID No. 36 is the amino acid sequence of an NMDA receptor subunit encoded by the nucleotide sequence of Sequence ID No. 35.

Sequence ID No. 38 is the amino acid sequence of an NMDA receptor subunit encoded by the nucleotide sequence of Sequence ID No. 37.

Sequence ID No. 40 is the amino acid sequence of an NMDA receptor subunit encoded by the nucleotide sequence of Sequence ID No. 39.

Sequence ID No. 3 is a nucleotide sequence encoding the 63 nucleotide insert present in Sequence ID Nos. 15, 23, 25, 27, 35, 37 and 39.

Sequence ID No. 4 is the 21 amino acid sequence encoded by the insert set forth in Sequence ID No. 3.

Sequence ID No. 5 is a nucleotide sequence of a clone (pCMV-26-NotI-24) encoding a human N-methyl-D-aspartate (NMDA) receptor subunit, NMDAR2C, and the deduced amino acid sequence thereof.

Sequence ID No. 41 is a 2026 nucleotide sequence encoded by clone NMDA21, comprising nucleotides 931–2350, and 2402–3307 of Sequence ID No. 5. Thus, Sequence ID No. 41 differs from Sequence ID No. 5 in that it does not contain the 930 5' nucleotides thereof, nor the 51 nucleotides located at position 2351–2401 of Sequence ID No. 5, nor the 1061 3' nucleotides of Sequence ID No. 5.

Sequence ID No. 43 is a 3698 nucleotide sequence encoded by clone NMDA22, comprising nucleotides 367–1300 of Sequence ID No. 5, plus an additional 11 nucleotides (set forth as Sequence ID No. 9), and nucleotides 1301–1959 and 1975–4068 of Sequence ID No. 5. Thus, Sequence ID No. 43 differs from Sequence ID No. 5 by the lack of the 366 5'-most nucleotides, by the insertion of 11 nucleotides between nucleotides 1300 and 1301 of Sequence ID No. 5, and further by the lack of the 15 nucleotides of Sequence ID No. 5 from residue 1960 to residue 1974.

Sequence ID No. 44 is a 3243 nucleotide sequence encoded by clone NMDA24, comprising nucleotides 861–1300 of Sequence ID No. 5, plus an additional 11 nucleotides (Sequence ID No. 9), nucleotides 1301–2350 of Sequence ID No. 5, an additional 24 nucleotides (set forth as Sequence ID No. 7) and nucleotides 2351–4068 of Sequence ID No. 5. Thus, Sequence ID No. 44 differs from Sequence ID No. 5 in that it does not contain the 860 5'-most nucleotides thereof, while it does contain an additional 11 nucleotides (Sequence ID No. 9) inserted between nucleotides 1300 and 1301, plus an additional 24 nucleotides (Sequence ID No. 7) inserted between nucleotides 2350 and 2351 of Sequence ID No. 5.

Nucleotides 1–3025 of Sequence ID No. 5 are a 3025 nucleotide sequence encoded by clone NMDA26. Thus, this sequence differs from Sequence ID No. 5 in that it does not contain the 1043 3'-terminal nucleotides thereof.

Sequence ID No. 45 is a nucleotide sequence encoding human NMDA receptor subunit pCMV-26-ScaI-24, which differs from Sequence ID No. 5 only in the insertion of 24 nucleotides (Sequence ID No. 7) between nucleotides 2350 and 2351 of Sequence ID No. 5.

Sequence ID No. 47 is a nucleotide sequence encoding human NMDA receptor subunit pCMV-26-ScaI-22, which differs from Sequence ID No. 5 only in the deletion of nucleotides 1960–1974 of Sequence ID No. 5.

Sequence ID No. 49 is a nucleotide sequence encoding human NMDA receptor subunit pCMV-26-ScaI-21-NotI-24, which differs from Sequence ID No. 5 only in the deletion of nucleotides 2351–2401 of Sequence ID No. 5.

Sequence ID No. 51 is a nucleotide sequence encoding human NMDA receptor subunit NMDAR2C-Δ15-I24. Sequence ID No. 51 is the same as Sequence ID No. 47, except Sequence ID No. 51 further contains the 24 nucleotide insert set forth in Sequence ID No. 7, positioned between nucleotides 2350 and 2351 of Sequence ID No. 5.

Sequence ID No. 53 is a nucleotide sequence encoding human NMDA receptor subunit NMDAR2C-Δ15-Δ51.

Sequence ID No. 53 is the same as Sequence ID No. 49, except Sequence ID No. 53 does not contain the 15 nucleotides set forth as nucleotides 1960–1974 of Sequence ID No. 5.

Sequence ID No. 6 is the amino acid sequence of the NMDA receptor subunit set forth in Sequence ID No. 5.

Sequence ID No. 42 is the amino acid sequence of a portion of an NMDA receptor subunit as encoded by the nucleotide sequence of Sequence ID No. 41.

The amino acid sequence of a portion of an NMDA receptor subunit as encoded by the nucleotide sequence of Sequence ID No. 43 is set forth in Sequence ID No. 43.

The amino acid sequence of a portion of an NMDA receptor subunit as encoded by the nucleotide sequence of Sequence ID No. 44 is set forth in Sequence ID No. 44.

Sequence ID No. 46 is the amino acid sequence of an NMDA receptor subunit encoded by the nucleotide sequence of Sequence ID No. 45.

Sequence ID No. 48 is the amino acid sequence of an NMDA receptor subunit encoded by the nucleotide sequence of Sequence ID No. 47.

Sequence ID No. 50 is the amino acid sequence of an NMDA receptor subunit encoded by the nucleotide sequence of Sequence ID No. 49.

Sequence ID No. 52 is the amino acid sequence of an NMDA receptor subunit encoded by the nucleotide sequence of Sequence ID No. 51.

Sequence ID No. 54 is the amino acid sequence of an NMDA receptor subunit encoded by the nucleotide sequence of Sequence ID No. 53.

Sequence ID No. 7 is a nucleotide sequence encoding the 24 nucleotide insert present in Sequence ID Nos. 44, 45 and 51.

Sequence ID No. 8 is the 7 amino acid sequence encoded by nucleotides 2–22 of the insert set forth in Sequence ID No. 7. Because the insert is introduced within a codon, the insert itself only encodes 7 amino acids. The terminal residues of the nucleotide insert participate in forming codons with adjacent sequence at the site of insertion.

Sequence ID No. 9 is a nucleotide sequence encoding the 11 nucleotide insert present in Sequence ID Nos. 43 and 44.

Sequence ID No. 10 is a nucleotide sequence encoding a human N-methyl-D-aspartate (NMDA) receptor subunit, NMDAR2A.

Sequence ID No. 11 is the amino acid sequence of an NMDA receptor subunit as encoded by the nucleotide sequence set forth in Sequence ID No. 10.

Sequence ID No. 12 is the nucleotide sequence of 71 nucleotides of 5' untranslated sequence of clone NMDA27, plus the initiation codon (nucleotides 72–74) of said clone.

Sequence ID No. 55 is a nucleotide sequence of a clone encoding a human N-methyl-D-aspartate (NMDA) receptor subunit, NMDAR2B.

Sequence ID No. 56 is the amino acid sequence of the NMDA receptor subunit set forth in Sequence ID No. 55.

Sequence ID No. 57 is a nucleotide sequence of a clone encoding a human N-methyl-D-aspartate (NMDA) receptor subunit, NMDAR2D.

Sequence ID No. 58 is the amino acid sequence of the NMDA receptor subunit set forth in Sequence ID No. 57.

Sequence ID Nos. 59–62 are four synthetic oligonucleotides used in the preparation of an NMDAR2C clone (pCMV-26-NotI-24-GCMOD) having reduced GC nucleotide content between nucleotides 2957 and 3166.

Sequence ID No. 63 is the nucleotide sequence of the 195 basepair insert of NMDAR2C clone pCMV-26-NotI-24-GCMOD (replacing nucleotides 2966–3160 of Sequence ID No. 5).

That which is claimed is:

1. An isolated DNA fragment, comprising a sequence of nucleotides that encodes a human N-methyl-D-aspartate (NMDA) receptor subunit selected from the group consisting of:

(a) a DNA fragment, comprising a sequence of nucleotides that encodes an human N-methyl-D-aspartate receptor type 2C subunit (NMDAR2C) and that hybridizes under conditions of high stringency to DNA comprising the sequence of nucleotides set forth in any one of SEQ ID Nos. 5, 45, 47, 49, 51, or 53, wherein the sequence that encodes the NMDAR2C subunit comprises a sequence of nucleotides that has at least about 90% sequence identity with the coding portion of any one of the sequences of nucleotides set forth in any one of SEQ ID Nos. 5, 45, 47, 49, 51, or 53, (b) a DNA fragment that encodes an NMDA receptor subunit and that comprises the coding portion of the sequence of nucleotides set forth in any one of SEQ ID No. 5, 45, 47, 49, 51, or 53, and (c) a DNA fragment that encodes an NMDA receptor subunit and that comprises a sequence of nucleotides that encodes an NMDA receptor subunit that is encoded by the sequence of nucleotides comprising any one of those set forth in SEQ ID Nos. 5, 45, 47, 49, 51 or 53 or the NMDA receptor subunit-encoding DNA in the clone NMDA57 deposited under ATCC accession No. 75442.

2. The DNA fragment of claim 1 that encodes an NMDAR2C subunit that comprises the sequence of amino acids set forth in SEQ ID No. 6.

3. The DNA fragment of claim 1, wherein the NMDA receptor subunit comprises the sequence of amino acids set forth in any one of SEQ ID Nos. 6, 46, 48, 50, 52 or 54.

4. The DNA fragment of claim 1, comprising a sequence of nucleotides that encodes an NMDAR2C receptor subunit and that hybridizes under high stringency conditions to DNA comprising the sequences of nucleotides set forth in any one of Sequence ID Nos. 5, 45, 47, 49, 51 or 53.

5. Isolated mRNA that encodes an NMDA receptor encoded by the DNA fragment of claim 1.

6. An amphibian oocyte comprising the mRNA of claim 5.

7. A eukaryotic cell, comprising the DNA fragment of claim 1.

8. A cell of claim 7 that comprises a functional heterologous NMDA receptor.

9. An isolated DNA fragment of claim 1, comprising the coding portion of the sequence of nucleotides set forth in any one of Sequence ID Nos. 5, 45, 47, 49, 51 or 53.

10. An isolated DNA fragment of claim 1, comprising the coding portion of the sequence of nucleotides set forth in Sequence ID No. 5.

11. An isolated DNA fragment of claim 1, comprising a sequence of nucleotides that encodes an NMDAR2 receptor subunit and hybridizes under conditions of high stringency to DNA comprising the sequence of nucleotides set forth in any one of SEQ ID Nos. 5, 45, 47, 49, 51 or 53.

12. An isolated DNA fragment of claim 1, comprising a sequence of nucleotides that encodes an NMDAR2 receptor subunit that is encoded by the sequence of nucleotides set forth in any one of SEQ ID Nos. 5, 45, 47, 49, 51 or 53.

13. The DNA fragment of claim 1, comprising the coding portion of the sequence of nucleotides set forth in SEQ ID No. 47.

14. The DNA fragment of claim 1, comprising the coding portion of the sequence of nucleotides set forth in SEQ ID No. 51.

15. The DNA fragment of claim 1, comprising the coding portion of the sequence of nucleotides set forth in SEQ ID No. 45.

16. The DNA fragment of claim 1, comprising the coding portion of the sequence of nucleotides set forth in SEQ ID No. 53.

17. An isolated DNA fragment of claim 1 that encodes a splice variant of an NMDAR2C subunit, wherein the NMDAR2C subunit comprises any one of SEQ ID Nos. 5, 47, 51 or 53.

18. A DNA fragment, comprising the sequence of nucleotides set forth in SEQ ID No. 63.

19. A DNA fragment, comprising the coding portion of the sequence of nucleotides set forth in SEQ ID No. 45.

20. An isolated DNA fragment, comprising the sequence of nucleotides set forth in SEQ ID No. 41.

21. An isolated DNA fragment, comprising the sequence of nucleotides set forth in SEQ ID No. 43.

22. An isolated DNA fragment, comprising the sequence of nucleotides set forth in SEQ ID No. 44.

23. An isolated DNA fragment, comprising nucleotides 1–3025 of the sequence of nucleotides set forth in SEQ ID No. 5.

24. A DNA fragment, comprising the coding portion of the sequence of nucleotides set forth in SEQ ID No. 49.

25. An isolated DNA fragment, comprising a sequence of nucleotides that encodes a human NMDAR2C receptor subunit that hybridizes under conditions of high stringency to DNA comprising the sequence of nucleotides set forth in SEQ ID No. 5 and that comprises a sequence of nucleotides that has at least about 70% identity to the sequence of nucleotides set forth in any one of SEQ ID Nos. 5, 45, 47, 49, 51 or 53.

* * * * *

UNITED STATES PATENT AND TRADEMARK OFFICE
CERTIFICATE OF CORRECTION

PATENT NO.: 5,849,895

DATED: Dec 15, 1998

INVENTOR(S): Dagget and Lu

It is certified that error appears in the above-identified patent and that said Letters Patent is hereby corrected as shown below:

Delete claim 1 and replace with the following claim:

1) An isolated DNA fragment, comprising a sequence of nucleotides that encodes a human N-methyl-D-aspartate receptor subunit selected from the group consisting of:

(a) a DNA fragment, comprising a sequence of nucleotides that encodes a human N-methyl-D-aspartate receptor 2C subunit (NMDAR2C) and that hybridizes under conditions of high stringency to DNA comprising the sequence of nucleotides set forth in any one of SEQ ID Nos. 5, 45, 47, 49, 51, or 53, wherein the sequence that encodes the NMDAR2C subunit comprises a sequence of nucleotides that has at least about 90% sequence identity with the coding portion of any one of the sequences of nucleotides set forth in any one of SEQ ID Nos. 5, 45, 47, 49, 51, or 53, (b) a DNA fragment that encodes an NMDA receptor subunit and that comprises the coding portion of the sequence of nucleotides set forth in any one of SEQ ID Nos. 5, 45, 47, 49, 51, or 53, (c) a DNA fragment that encodes an NMDA receptor subunit and that comprises a sequence of nucleotides that encodes an NMDA receptor subunit that is encoded by the sequence of nucleotides comprising any one of those set forth in SEQ ID Nos. 5, 45, 47, 49, 51, or 53.

Signed and Sealed this

Nineteenth Day of October, 1999

Attest:

Q. TODD DICKINSON

*Attesting Officer*  *Acting Commissioner of Patents and Trademarks*

UNITED STATES PATENT AND TRADEMARK OFFICE
CERTIFICATE OF CORRECTION

PATENT NO.   : 5,849,895
DATED        : December 15, 1998
INVENTOR(S)  : Daggett, et. al.

It is certified that error appears in the above-identified patent and that said Letters Patent is hereby corrected as shown below:

Column 2, lines 64 to 67, and at column 3, lines 1 and 2, please delete "lowercase letters indicate 5' untranslated sequence and the 3' untranslated sequence of the NMDAR1 splice variant shown in Sequence ID No. 1 (in some of the other splice variants, this 3' untranslated sequence is actually coding sequence); uppercase letters indicate coding sequence;"

Signed and Sealed this

Thirtieth Day of November, 1999

Attest:

Q. TODD DICKINSON

Attesting Officer

Acting Commissioner of Patents and Trademarks